(12) United States Patent
Sawyer et al.

(10) Patent No.: US 11,786,218 B2
(45) Date of Patent: Oct. 17, 2023

(54) BURST ULTRASOUND RECONSTRUCTION WITH SIGNAL TEMPLATES AND RELATED METHODS AND SYSTEMS

(71) Applicant: CALIFORNIA INSTITUTE OF TECHNOLOGY, Pasadena, CA (US)

(72) Inventors: Daniel P. Sawyer, Pasadena, CA (US); Arash Farhadi, Pasadena, CA (US); Avinoam D. Bar-Zion, Pasadena, CA (US); Mikhail Shapiro, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 16/736,581

(22) Filed: Jan. 7, 2020

(65) Prior Publication Data

US 2020/0237346 A1 Jul. 30, 2020

Related U.S. Application Data

(60) Provisional application No. 62/895,553, filed on Sep. 4, 2019, provisional application No. 62/825,612, filed on Mar. 28, 2019, provisional application No. 62/789,295, filed on Jan. 7, 2019.

(51) Int. Cl.
*A61B 8/08* (2006.01)

(52) U.S. Cl.
CPC ............ *A61B 8/5207* (2013.01); *A61B 8/481* (2013.01); *A61B 8/5246* (2013.01)

(58) Field of Classification Search
CPC ..... A61B 8/5207; A61B 8/5246; A61B 8/481; A61B 8/085; A61B 8/5223
See application file for complete search history.

(56) References Cited

U.S. PATENT DOCUMENTS

| | | | |
|---|---|---|---|
| 5,558,092 | A | 9/1996 | Unger et al. |
| 5,824,309 | A | 10/1998 | Dassarma et al. |
| 7,498,024 | B2 | 3/2009 | Fang et al. |
| 9,107,949 | B2 | 8/2015 | Ju |
| 10,493,172 | B2 | 12/2019 | Lakshmanan et al. |

(Continued)

FOREIGN PATENT DOCUMENTS

| | | |
|---|---|---|
| CN | 105232045 A | 1/2016 |
| EP | 3908656 A1 | 11/2021 |

(Continued)

OTHER PUBLICATIONS

EPO Communication pursuant to Rules 161(2) and 162 EPC for EP Application No. 20739042 filed on Jul. 14, 2021 on behalf of California Institute of Technology dated Aug. 18, 2021 3 pages.

(Continued)

*Primary Examiner* — Joseph M Santos Rodriguez
*Assistant Examiner* — Kaitlyn E Sebastian
(74) *Attorney, Agent, or Firm* — Steinfl + Bruno LLP

(57) ABSTRACT

The application of a step function increase in acoustic pressure during ultrasound imaging using gas vesicle contrast, along with capturing successive frames of ultrasound imaging and extracting time-series vectors for pixels of the frames, allows for improved imaging down to even the cell level. Template vectors can be used to implement signal separation of the time-series vectors to improve detection.

22 Claims, 11 Drawing Sheets

Specification includes a Sequence Listing.

(56) References Cited

U.S. PATENT DOCUMENTS

| | | | |
|---|---|---|---|
| 10,955,496 B2 | 3/2021 | Lu et al. | |
| 11,118,210 B2 | 9/2021 | Bourdeau et al. | |
| 11,446,523 B2 | 9/2022 | Bar-Zion et al. | |
| 11,504,438 B2 | 11/2022 | Lakshmanan et al. | |
| 2002/0115717 A1 | 8/2002 | Gervais et al. | |
| 2003/0147812 A1* | 8/2003 | Ueberle | A61B 8/481 |
| | | | 424/9.52 |
| 2003/0157025 A1 | 8/2003 | Unger et al. | |
| 2004/0204922 A1* | 10/2004 | Beadle | G06K 9/624 |
| | | | 702/189 |
| 2004/0265393 A1 | 12/2004 | Unger et al. | |
| 2005/0058605 A1 | 3/2005 | Schneider et al. | |
| 2006/0025683 A1 | 2/2006 | Hoffmann | |
| 2006/0058618 A1* | 3/2006 | Nishiura | A61B 8/0883 |
| | | | 600/407 |
| 2006/0216810 A1* | 9/2006 | Ju | A61K 49/223 |
| | | | 435/243 |
| 2010/0069757 A1* | 3/2010 | Yoshikawa | A61B 5/02007 |
| | | | 600/454 |
| 2010/0239170 A1* | 9/2010 | Asnis | G06K 9/3241 |
| | | | 382/190 |
| 2012/0020878 A1 | 1/2012 | Qi | |
| 2014/0288411 A1 | 9/2014 | Shapiro et al. | |
| 2014/0288412 A1 | 9/2014 | Schwartz | |
| 2014/0288421 A1 | 9/2014 | Shapiro et al. | |
| 2016/0220672 A1 | 8/2016 | Chalasani et al. | |
| 2018/0028693 A1* | 2/2018 | Lakshmanan | A61K 49/0093 |
| 2018/0030501 A1* | 2/2018 | Bourdeau | C07K 14/32 |
| 2018/0038922 A1* | 2/2018 | Lu | A61B 8/5261 |
| 2020/0164095 A1 | 5/2020 | Lakshmanan et al. | |
| 2020/0237346 A1 | 7/2020 | Sawyer et al. | |
| 2020/0291409 A1 | 9/2020 | Farhadi et al. | |
| 2020/0306564 A1 | 10/2020 | Bar-Zion et al. | |
| 2021/0060185 A1 | 3/2021 | Lakshmanan et al. | |
| 2021/0301298 A1 | 9/2021 | Bourdeau et al. | |

FOREIGN PATENT DOCUMENTS

| | | |
|---|---|---|
| WO | 2007/014162 A2 | 2/2007 |
| WO | 2012/038950 A1 | 3/2012 |
| WO | 2018/043716 A1 | 3/2018 |
| WO | 2018/069788 A1 | 4/2018 |
| WO | 2020/146367 A1 | 7/2020 |
| WO | 2020/146379 A1 | 7/2020 |
| WO | 2020/198728 A1 | 10/2020 |
| WO | 2021/041934 A1 | 3/2021 |

OTHER PUBLICATIONS

International Preliminary Report on Patentability for International Application No. PCT/US2020/012557 filed on Jan. 7, 2020, on behalf of California Institute of Technology, dated Jul. 22, 2021. 8 Pages.

International Preliminary Report on Patentability for International Application No. PCT/US2020/012572 filed on Jan. 7, 2020, on behalf of California Institute of Technology, dated Jul. 22, 2021. 8 Pages.

International Preliminary Report on Patentability for International PCT Application No. PCT/US2020/025608 filed on Mar. 29, 2020 filed on behalf of California Institute of Technology, dated Sep. 28, 2021. 7 Pages.

Notice of Allowance for U.S. Appl. No. 16/656,417, filed Oct. 17, 2019, on behalf of California Institute of Technology, dated Sep. 3, 2021. 9 Pages.

Restriction Requirement for U.S. Appl. No. 16/736,683, filed Jan. 7, 2020 on behalf of California Institute of Technology dated Sep. 14, 2021 8 pages.

International Search Report and Written Opinion for PCT App. No. PCT/US2020/048572 filed on Aug. 28, 2020, on behalf of California Institute of Technology, dated Dec. 29, 2020. 11 Pages.

Lakshmanan, A et al., "Acoustic Biosensors for Ultrasound Imaging of Enzyme Activity", Nature Chemical Biology, 16, pp. 988-996 (Jul. 13, 2020), 23 pages.

Notice of Allowance for U.S. Appl. No. 15/663,600, filed Jul. 28, 2017 on behalf of California Institute of Technology, dated Dec. 11, 2020. 13 Pages.

Notice of Allowance for U.S. Appl. No. 15/663,635, filed Jul. 28, 2017 on behalf of California Institute of Technology dated Jan. 26, 2021. 15 pages.

Abdul Rahman, H.S., et al., "Fast and robust three-dimensional best path phase unwrapping algorithm". Applied Optics, 2007. 46(26): p. 6623-6635.

Ahrens, E.T. et al., "Tracking immune cells in vivo using magnetic resonance imaging". Nature Reviews: Immunology, 2013. 13(10): p. 755-763. 19 pages.

Altschul, et al, Gapped BLAST and PSI-BLAST: a new generation of protein database search programs. Nucleic Acids Res., 1997. 25(17): 3389-3402. p. 14.

Archer, E.J., et al., "Engineered E. coli that detect and respond to gut inflammation through nitric oxide sensing". ACS synthetic biology, 2012. 1(10): p. 451-457.

Atanasijevic, T., et al., "Calcium-sensitive MRI contrast agents based on superparamagnetic iron oxide nanoparticies and calmodulin". Proceedings of the National Academy of Sciences, 2006. 103(40): p. 14707-14712.

Barrett, T. et al., "MRI of Tumor Angiogenesis", Journal of Magnetic Resonance Imaging 26, pp. 235-249, (2007), 15 pages.

Bar-Zion, A. et al. Acoustically Detonated Biomolecules for Genetically Encodable Inertial Cavitation. bioRxiv 620567 (2019) 11 pages.

Beard, P. "Biomedical photoacoustic imaging."*Interface Focus*1, 602-631(2011).

Belkaid, Y. et al., "Role of the microbiota in immunity and inflammation". Cell, 2014. 157(1): p. 121-141.

Blanco, E., et al., "Principles of nanoparticle design for overcoming biological barriers to drug delivery". Nature biotechnology, 2015. 33(9): p. 941-951.

Bourdeau, R.W., et al., "Acoustic Reporter Genes for Non-Invasive Imaging of Microorganisms in Mammalian Hosts." Nature 553, 86-90, (Jan. 2018). 19 pages.

Bowen, C.V., et al., Application of the static dephasing regime theory to superparamagnetic iron-oxide loaded cells. Magnetic Resonance in Medicine, 2002. 48(1): p. 52-61.

Braat, H., et al., "A phase I trial with transgenic bacteria expressing interleukin-10 in Crohn's disease". Clinical gastroenterology and hepatology, 2006. 4(6): p. 754-759.

Brock, R., "The uptake of arginine-rich cell-penetrating peptides: putting the puzzle Together". Bioconjugate chemistry, 2014. 25(5): p. 863-868.

Brooks, et al., "On T2-shortening by weakly magnetized particles: The chemical exchange model". Magnetic Resonance in Medicine, 2001. 45(6): p. 1014-1020.

Buchholz, B., et al., "The distribution of the outer gas vesicle protein, GvpC, on the Anabaena gas vesicle, and its ratio to GvpA". Microbiology, 1993. 139(10): p. 2353-2363.

Buchler, et al., "On schemes of combinatorial transcription logic", Proceedings of the National Academy of Sciences, 2003. 100(9): p. 5136-5141.

Burns, P.N., "Harmonic imaging with ultrasound contrast agents". Clin. Radiol., 1996. 51: p. 50-55.

Caldwell et al. "A *Zoogloea* sp. associated with blooms of Anabaena fiosaquae" Canadian Journal of Microbiology, NRC Research Press. Aug. 1978. vol. 24, No. 8. pp. 922-931. (Abstract Only) 2 pages.

Calvo, et al, Upstream open reading frames cause widespread reduction of protein expression and are polymorohic among humans. Proc Natl Acad Sci U S A, 2009. 106(18): p. 7507-7512.

Caravan, P., et al., "Gadolinium(III) Chelates as MRI Contrast Agents: Structure, Dynamics, and Applications", Chemical Reviews, 1999. 99(9): p. 2293-2352.

Cherin, E., et al., "Acoustic Behavior of Halobacterium salinarum Gas Vesicles in the High-Frequency Range: Experiments and Modeling". Ultrasound in Medicine & Biology, 2017. 43(5): p. 1016-1030.

(56) References Cited

OTHER PUBLICATIONS

Choi, J.J., et al., Noninvasive, transcranial and localized opening of the blood-brain barrier using focused ultrasound in mice. Ultrasound in Medicine & Biology, 2007. 33(1): p. 95-104.
Chu, et al., "A bright cyan-excitable orange fluorescent protein facilitates dual-emission microscopy and enhances bioluminescence imaging in vivo". Nat Biotech 34, 760-767 (2016). 29 pages.
Church C. "Frequency , pulse length , and the mechanical index. "*Acoustics Research Letters Online*162-168, 1-8(2005).
Claesen, J., et al., "Synthetic microbes as drug delivery systems". ACS synthetic biology, 2014. 4(4): p. 358-364.
Cohen, B., et al., "Ferritin as an Endogenous MRI Reporter for Noninvasive Imaging of Gene Expression in C6 Glioma Tumors". Neoplasia, 2005. 7(2): p. 109-117.
Cohen, B., et al., "MRI detection of transcriptional regulation of gene expression in transgenic mice". Nat Med, 2007. 13(4): p. 498-503.
Corrected Notice of Allowability for U.S. Appl. No. 15/613,104, filed Jun. 2, 2017 on behalf of California Institute of Technology dated Sep. 9, 2019 10 pages.
Cosgrove, D., et al., "Clinical Uses of Microbubbles in Diagnosis and Treatment." Med. Biol. Eng. Comput. 47, 813-826, (2009), 14 pages.
Courbet, A., et al., "Detection of pathological biomarkers in human clinical samples via amplifying genetic switches and logic gates". Science translational medicine, 2015. 7(289): p. 289ra83-289ra83. Abstract Only.
Coussios, C. et al., "Applications of Acoustics and Cavitation to Noninvasive Therapy and Drug Delivery." *Annu. Rev. Fluid Mech.* (2008) 40, 395-420. 28 pages.
Cunningham, C.H., et al., "Positive contrast magnetic resonance imaging of cells labeled with magnetic nanoparticies". Magnetic Resonance in Medicine, 2005. 53(5): p. 999-1005.
Dang, L. H. et al., "Combination bacteriolytic therapy for the treatment of experimental tumors." *Proc. Natl. Acad. Sci. U. S. A*.98, 26, 15155-60(2001).
Daniel, C., et al., "Bioluminescence imaging study of spatial and temporal persistence of Lactobacillus plantarum and Lactococcus lactis in living mice". Applied and environmental microbiology, 2013. 79(4): p. 1086-1094.
Daniel, C., et al., "Recombinant lactic acid bacteria as mucosal biotherapeutic agents". Trends in biotechnology, 2011. 29(10): p. 499-508.
Danino, T., et al., "In vivo gene expression dynamics of tumor-targeted bacteria". ACS synthetic biology, 2012. 1(10): p. 465-470.
Danino, T., et al., "Programmable probiotics for detection of cancer in urine". Science translational medicine, 2015. 7(289): p. 289ra84-289ra84. 28 pages.
Dassarma, et al.,"An improved genetic system for bioengineering buoyant gas vesicle nanoparticies from Haloarchaea". BMC Biotechnol. 2013, 13, 112. 10 pgs.
Dassarma, P., et al., "Bioengineering Novel Floating Nanoparticles for Protein and Drug Delivery." Materials Today: Proceedings: Advances in Functional Materials (Conference 2015), 3(2), 206-210, (2016). 8 pages.
Davila, M. L. et al. "Efficacy and Toxicity Management of 19-28z CAR T Cell Therapy in B Cell Acute Lymphoblastic Leukemia". 6(224), *Sci Transl Med*(2014). 23 pages.
Dawson, P.E. et al., "Synthesis of proteins by native chemical ligation". Science, 1994. 266(5186): p. 776-780.
Del Vecchio, D and Muarray, R.M. "Biomolecular Feedback Systems" bfs-pupss. Jun. 13, 2014. 280 pages.
Derrien, M., et al., "Fate, activity, and impact of ingested bacteria within the human gut microbiota". Trends in microbiology, vol. 23, No. 6, 2015, pp. 354-366.
Din, M.O., et al., "Synchronized cycles of bacterial lysis for in vivo delivery". Nature, 2016. 536(7614): p. 81-85.
Donaldson, G.P., et al., "Gut biogeography of the bacterial microbiota". Nature Reviews Microbiology, vol. 14, 2015, pp. 20-32.

Errico, C., et al., "Ultrafast ultrasound localization microscopy for deep super-resolution vascular imaging". Nature, 2015. 527(7579): p. 499-502.
Evbuomwan, O.M., et al., "CEST and PARACEST Agents for Molecular Imaging, in The Chemistry of Molecular Imaging". 2014, John Wiley & Sons, Inc. p. 225-243.
Farhadi, A., et al., Recombinantly Expressed Gas Vesicles as Nanoscale Contrast Agents for Ultrasound and Hyperpolarized MRI. AIChE J, 2018. 64(8): p. 2927-2933.
Farhadi A. et al., "Ultrasound imaging of gene expression in mammalian cells" Science 365, 1469-1475, Sep. 2019, 43 pages.
Ferrara, K., et al., "Ultrasound Microbubble Contrast Agents: Fundamentals and Application to Gene and Drug Delivery." Annu. Rev. Biomed. Eng. 9, 415-447, (2017). 35 pages.
Final Office Action for U.S. Appl. No. 15/663,635, filed Jul. 28, 2017 on behalf of California Institute of Technology dated Oct. 24, 2019 27 pages.
Fischbach, M.A., et al., "Cell-based therapeutics: the next pillar of medicine". Science translational medicine, 2013. 5(179): p. 179ps7-179ps7.
Fischer, et al., "Average protein density is a molecular-weight-dependent function". Protein Science, 2004. 13(10): p. 2825-2828.
Forbes N. S., et al., "Sparse initial entrapment of systemically injected *Salmonella typhimurium* leads to heterogeneous accumulation within tumors."*Cancer Res.* 63, 5188-5193 (2003).
Foster, et al., "Advances in ultrasound biomicroscopy". Ultrasound in medicine & biology 26, 1-27 (2000).
Foster, F.S., et al., "Principles and applications of ultrasound backscatter microscopy". Ultrasonics, Ferroelectrics and Frequency Control, IEEE Transactions on, 1993. 40(5): p. 608-617.
Foucault, M.-L., et al., "In vivo bioluminescence imaging for the study of intestinal colonization by *Escherichia coli* in mice". Applied and environmental microbiology, 2010. 76(1): p. 264-274.
Genove, G., et al., "A new transgene reporter for in vivo magnetic resonance imaging". Nat Med. 2005. 11 (43): p. 450-454.
Gilad, A.A., et al., "Artificial reporter gene providing MRI contrast based on proton exchange". Nat Biotech, 2907. 25(2): p. 217-219.
Gilad, A.A., et al., "Developing MR reporter genes: promises and pitfalls". NMR in Biomedicine, 2007. 20(3): p. 275-290.
Gilad, A.A., et al., "MRI Reporter Genes". Journal of Nuclear Medicine. 2008. 49(12): p. 1905-1908.
Gillis, et al., "On T2-shortening by strongly magnetized spheres: A partial refocusing model". Magnetic Resonance in Medicine, 2002. 47(2): p. 257-263.
Gillis, et al., "Transverse relaxation of solvent protons induced by magnetized spheres: Application to ferritin, erythrocytes, and magnetite". Magnetic Resonance in Medicine, 1987. 5(4): p. 323-345.
Gorbach, S.L., "Chapter 95: Microbiology of the Gastrointestinal Tract", Medical Microbiology, 4th Edition, Editor: Samuel Baron, University of Texas Medical Branch at Galveston, Galveston, TX (1996). 10 pages.
Griffiths, et al., "The homologies of gas vesicle proteins", Journal of General Microbiology (1992), 138, 1243-1250.
Haacke, E.M. et al., "Susceptibility-Weighted Imaging: Technical Aspects and Clinical Applications," Part 1. American Journal of Neuroradiology 30 (1), pp. 19-30, (Jan. 2009), 29 pages.
Hayes, et al., "Complete amino acid sequence of cyanobacterial gas-vesicle protein indicates a 70-residue molecule that corresponds in size to the crystallographic unit cell". Biochemical Journal, 1986. 236(1): p. 31-36.
Hayes, et al., "The gvpA/C cluster of Anabaena flos-aquae has multiple copies of a gene encoding GvpA", Archives of microbiology, 1995. 164(1): p. 50-57.
Hayes, P., et al., "Gas vesicles are strengthened by the outersurface protein, GvpC". Archives of microbiology, 1992. 157(3): p. 229-234.
Häcker, G. et al., "Activation of the immune system by bacterial CpG-DNA," *Immunology*105, 245-251 (2002).
He, et al, "Biophysical mechanisms of phase contrast in gradient echo MRI". Proceedings of the National Academy of Sciences, 2009. 106(32): p. 13558-13563.
Holland C. et al., "An Improved Theory for the Prediction of Microcavitation Thresholds." 204-208 *IEEE* (1989).

(56) References Cited

OTHER PUBLICATIONS

Huang, H. et al. "A G-Quadruplex-Containing RNA Activates Fiourescence in a GFP-Like Flourophore", Nat Chem Biol., Aug. 2014, 10 (8); 686-691. 22 pages.
Hung, A.H., et al., "Magnetic Barcode Imaging for Contrast Agents." Magnetic Resonance in Medicine, 77(3), 970-978, (2017). 9 pages.
International Search Report for International Application No. PCT/US2020/012557 filed on Jan. 7, 2020 on behalf of California Institute of Technology dated May 1, 2020 5 pages.
International Search Report for International Application No. PCT/US2020/012572 filed on Jan. 7, 2020 on behalf of California Institute of Technology dated May 6, 2020 4 pages.
Jackson, H. J. et al., "Driving CAR T—cells forward." *Nat. Rev. Clin. Oncl.* 13, 370-383 (2016). 31 pages.
Jaffer, F.A. et al., "Molecular and Cellular Imaging of Atherosclerosis", Emerging Applications. Journal of the American College of Cardiology, vol. 47, No. 7, pp. 1328-1338, (2006), 11 pages.
Jang, M. J. et al., "NeuroCa: integrated framework for systematic analysis of spatiotemporal neuronal activity patterns from large-scale optical recording data."*Neurophotonics*2(3), 035003 (2015). 16 pages.
Jensen, et al., "NMR relaxation in tissues with weak magnetic inhomogeneities". Magnetic Resonance in Medicine, 2000. 44(1): p. 144-156.
Jolesz, F.A., "MRI-Guided Focused Ultrasound Surgery". Annual Review of Medicine, 2009. 60(1): p. 417-430.
Karlin, et al., "Applications and statistics for multiple high-scoring segments in molecular sequences",. Proceedings of the National Academy of Sciences, 1993. 90(12): p. 5873-5877.
Karlin, et al., "Methods for assessing the statistical significance of molecular sequence features by using general scoring schemes", Proceedings of the National Academy of Sciences, 1990. 87(6): p. 2264-2268.
Kaufmann, B.A., et al., "Molecular Imaging with Targeted Contrast Ultrasound." Current Opinion in Biotechnology 18(1), 11-16, (2007). 6 pages.
Kinsman, et al., "Genes encoding proteins homologous to halobacterial Gvps N, J, K, F & L are located downstream of gvpC in the cyanobacterium Anabaena flos-aquae", DNA Sequence, 1997. 7(2): p. 97-106.
Kinsman, R., et al., "GvpCs with reduced numbers of repeating sequence elements bind to and strengthen cyanobacterial gas vesicles". Molecular microbiology, 1995. 17(1): p. 147-154.
Kislukhin, A.A., et al., "Paramagnetic fluorinated nanoemulsions for sensitive cellular fluorine-19 magnetic resonance imaging". Nat Mater, 2016. 15(6): 662-668. 19 pages.
Klumpp, S., et al., "Bacterial growth: global effects on gene expression, growth feedback and proteome partition". Current opinion in biotechnology, 2014. 28: p. 96-102.
Koehne G. et al., "Serial in vivo imaging of the targeted migration of human HSV-TK-transduced antigen-specific lymphocytes." *Nature Biotechnology*vol. 21, 405-413 (Apr. 2003).
Kotula, J.W., et al., "Programmable bacteria detect and record an environmental signal in the mammalian gut". Proceedings of the National Academy of Sciences, 2014. 111(13): p. 4838-4843.
Kunth, M. et al., "Protein Nanostructures Produce Self-Adjusting Hyperpolarized Magnetic Resonance Imaging Contrast through Physical Gas Partitioning." *ACS Nano* (2018). 12, 10989-10948. doi:10.1021/acsnano.8b04222.
Kwan, J. J. et al. "Ultrasound-Propelled Nanocups for Drug Delivery." *Small Journal*11, No. 39, 5305-5314 (2015).
Lakshmanan, A., et al., "Molecular Engineering of Acoustic Protein Nanostructures". ACS Nano, 2016. 10(8): p. 7314-7322.
Lakshmanan, A., et al., Preparation of biogenic gas vesicle nanostructures for use as contrast agents for ultrasound and MRI. Nat Protoc, 2017. 12(10): p. 2050-2080.
Lecoq, J. et al., "An Infrared Fluorescent Protein for Deeper Imaging", Nat Biotech, vol. 29, No. 8, pp. 715-716 (2011), 2 pages.
Lee, J.-H., et al., "Artificially engineered magnetic nanoparticles for ultra-sensitive molecular imaging", Nat Med, 2007. 13(1): p. 95-99.

Li, et al., "Gas vesicle genes identified in Bacillus megaterium and functional expression in *Escherichia coli*", J Bacteriol, 1998. 180(9): p. 2450-2458.
Li, Z. et al., "Comparison of Reporter Gene and Iron Particle Labeling for Tracking Fate of Human Embryonic Stem Cells and Differentiated Endothelial Cells in Living Subjects", Stem Cells 26 (4), pp. 864-873, (2008), 21 pages.
Lu, G.J., et al., Acoustically modulated magnetic resonance imaging of gas-filled protein nanostructures. Nat Mater, 2018. 17(5): p. 456-463. 15 pages.
Mani, V., et al., "Gradient echo acquisition for superparamagnetic particles with positive contrast (GRASP): Sequence characterization in membrane and glass superparamagnetic iron oxide phantoms at 1.5T and 3T". Magnetic Resonance in Medicine, 2006. 55(1): p. 126-135.
Maresca D, et al ., "Nonlinear X-Wave Ultrasound Imaging of Acoustic Biomolecules" *Phys Rev X*vol. 8,(2018). 041002-1 to 041002-12. 12 pages.
Maresca D, et al., "Biomolecular Ultrasound and Sonogenetics" *Annu Rev Chem Biomol Eng*vol. 9, 229-252 (Jun. 2018). 29 pages.
Maresca, D., et al., "Imaging microvasculature with contrast-enhanced ultraharmonic Ultrasound". Ultrasound in medicine & biology, 2014. 40(6): p. 1318-1328.
Maresca, D., et al., "Nonlinear Ultrasound Imaging of Nanoscale Acoustic Biomolecules". Applied Physics Letters, 2017. 110(7).
Matsumoto, et al., "T2 relaxation induced by clusters of superparamagnetic nanoparticles: Monte Carlo simulations". Magnetic Resonance Imaging, 2008. 26(7): p. 994-998.
McMahon, M.T., et al., "New "multicolor" polypeptide diamagnetic chemical exchange saturation transfer (DIACEST) contrast agents for MRI". Magnetic Resonance in Medicine, 2008. 60(4): p. 803-812.
Meeker, D., Finite element method magnetics. FEMM, 2015. 4: p. 32.
Milenic D. E. et al., "Antibody-Targeted Radiation Cancer Therapy." *Nature*3,(2004). 488-498.
Milo, R., et al., "BioNumbers—the database of key numbers in molecular and cell biology". Nucleic Acids Research, 2010. 38(suppl 1): p. D750-D753.
Mowat, A.M., et al., "Regional specialization within the intestinal immune system". Nature Reviews Immunology, vol. 14, 2014, 667-685.
Myers, et al., "Optimal alignments in linear space", Computer applications in the biosciences: CABIOS, 1988. 4(1): p. 11-17.
Natarajan, S, "NS3 protease from flavivirus as a target for designing antiviral inhibitors against dengue virus", Genetics and Molecular Biology, 33, 2, 214-219 (2010).
Needleman, et al., "A general method applicable to the search for similarities in the amino acid sequence of two proteins", Journal of molecular biology, 1970. 48(3): p. 443-453.
Ngamdee et al. "Competition between Burkholderia pseudomallei and B. thailandesis" *BMC Microbiology, BioMed Central*.2015. vol. 15, No. 56. 15 pages.
Nilsson, B.L., et al., "Chemical synthesis of proteins". Annu. Rev. Biophys. Biomol. Struct., 2005. 34: p. 91-118.
Non-Final Office Action for U.S. Appl. No. 15/663,635, filed Jul. 28, 2017, on behalf of California Institute of Technology, dated Jan. 2, 2019. 29 pages.
Notice of Allowance for U.S. Appl. No. 15/613,104, filed Jun. 2, 2017 on behalf of California Institute of Technology dated Jul. 18, 2019 15 pages.
Ntziachristos, V., et al., "Looking and Listening to Light: the Evolution of Whole-Body Photonic Imaging." Nature Biotechnology, 23(3), 313-320, (2005). 8 pages.
Ntziachristos, V. "Going deeper than microscopy: the optical imaging frontier in biology." *Nature Methods*7, No. 8, 603-614 (2010).
Pearson, et al., "Improved tools for biological sequence comparison", Proceedings of the National Academy of Sciences, 1988. 85(8): p. 2444-2448.
Perez, J.M., et al., "Magnetic relaxation switches capable of sensing molecular interactions". Nat Biotech, 2002. 20(8): p. 816-820.

(56) References Cited

OTHER PUBLICATIONS

Pfeifer, Felicitas. "Distribution, formation and regulation of gas vesicles" *Nature Reviews—Microbiology, Macmillan Publishers Ltd.*Oct. 2012. vol. 10. pp 705-715. 11 pages.

Piraner, D. I. et al. Going Deeper: Biomolecular Tools for Acoustic and Magnetic Imaging and Control of Cellular Function. Biochemistry 56, 5202-5209 (2017).

Puderbach, M. et al. "MR Imaging of the Chest: A Practical Approach at 1.5 T." European Journal of Radiology 64, 345-355, (2007). 13 pages.

Purnick, P.E. and R. Weiss, "The second wave of synthetic biology: from modules to systems." *Nat Rev Mol Cell Biol*,2009. 10(6): p. 410-422.

Qin et al. "Bacterial abundance and diversity in pond water supplied with different feeds" *Nature—Scientific Reports, Nature Publishing Group*.Oct. 19, 2016. vol. 6, No. 35232. pp 1-13. 13 pages.

Ramnarine, et al, "Construction and geometric stability of physiological flow rate wall-less stenosis phantoms." *Ultrasound in medicine & biology*27, 245-250 (2001).

Ramsay, J.P., et al., "A quorum-sensing molecule acts as a morphogen controlling gas vesicle organelle biogenesis and adaptive flotation in an enterobacterium." *Proc Natl Acad Sci U S A*,2011. 108(36): p. 14932-14937.

Reits, E.A., et al., "From fixed to FRAP: measuring protein mobility and activity in living cells". Nature cell biology, 2001. 3(6): p. E145-E147.

Restriction Requirement for U.S. Appl. No. 15/613,104, filed Jun. 2, 2017 on behalf of California Institute of Technology, dated Feb. 21, 2019. 9 pages.

Restriction Requirement for U.S. Appl. No. 15/663,600, filed Jul. 28, 2017 on behalf of California Institute of Technology, dated Dec. 27, 2019. 7 pages.

Rodriguez, P.L., et al., "Minimal" Self"peptides that inhibit phagocytic clearance and enhance delivery of nanoparticies". Science, 2013. 339(6122): p. 971-975.

Romero, P.A., et al., "Exploring protein fitness landscapes by directed evolution". Nature Reviews Molecular Cell Biology, 2009. 10(12): p. 866-876.

Rose, A.B., Intron-mediated regulation of gene expression. Curr Top Microbiol Immunol, 2008. 326: p. 277-290.

Round, J.L. et al., "The gut microbiota shapes intestinal immune responses during health and disease". Nature Reviews Immunology, 2009, 9(5): p. 313-323.

Ruoslahti, E., "RGD and other recognition sequences for integrins". Annual review of cell and developmental biology, 1996. 12(1): p. 697-715.

Ryan, R. M. et al. "Bacterial delivery of a novel cytolysin to hypoxic areas of solid tumors." Gene Ther.16, 329-339 (2009).

Santos E. B. et al., "Sensitive in vivo imaging of T cells using a membrane-bound Gaussia princeps luciferase", *Nat Med.*vol. 15, No. 3, 338-344 (Mar. 2009).

Savage, D. C. "Microbial ecology of the gastrointestinal tract." *Annual review of microbiology*31, 107-133 (1977).

Schechter, et al, On the active site of proteases. 3. Mapping the active site of papain; specific peptide inhibitors of papain. Biochem Biophys Res Commun., 1968 32(5): p. 898-902.

Schechter, et al, On the size of the active site in proteases. I. Papain. Biochem Biophys Res Commun., 1967. 27(2): p. 157-162.

Schindelin, J., et al., "Fiji: an open-source platform for biological-image analysis". *Nat Meth*, 2012. 9(7): p. 676-682.

Schneider, C. et al., "NIH Image to ImageJ: 25 years of image analysis." *Nat. Methods*9(7), 671-675 (2012). 12 pages.

Schweser, F., et al., "Quantitative imaging of intrinsic magnetic tissue properties using MRI signal phase: An approach to in vivo brain iron metabolism?", NeuroImage, 2011. 54(4): p. 2789-2807.

Shaner, N.C., et al., "A bright monomeric green fluorescent protein derived from Branchiostoma lanceolatum". Nat Meth, 2013. 10(5): p. 407-409.

Shaner, N.C., et al., "Improved monomeric red, orange and yellow fluorescent proteins derived from *Discosoma* sp. red fluorescent protein". Nature biotechnology, 2004. 22(12): p. 1567-1572.

Shaner, N.C., et al., "Improving the photostability of bright monomeric orange and red fluorescent proteins". Nature methods, 2008. 5(6): p. 545-551.

Shapiro, M.G., et al., "Biogenic gas nanostructures as ultrasonic molecular reporters". Nature nanotechnology, 2014. 9(4): p. 311-316.

Shapiro, M.G., et al., "Directed evolution of a magnetic resonance imaging contrast agent for noninvasive imaging of dopamine". Nat Biotech, 2010. 28(3): p. 264-270.

Shapiro, M.G., et al., "Genetically encoded reporters for hyperpolarized xenon magnetic resonance imaging", Nat Chem, 2014. 6(7): p. 629-634.

Shapiro, M.G., et al., "Protein Nanoparticies Engineered to Sense Kinase Activity in MRI". Journal of the American Chemical Society, 2009. 131(7): p. 2484-2486.

Silva-Rocha, et al., "Mining logic gates in prokaryotic transcriptional regulation networks", FEBS letters, 2008. 582(8): p. 1237-1244.

Simon, G. L. & Gorbach, S. L. intestinal flora in health and disease. Gastroenterology 86, 174-193 (1984).

Simon, R.D., "Morphology and Protein Composition of Gas Vesicles from Wild Type and Gas Vacuole Defective Strains of Halobacterium salinarium Strain 5". Microbiology, 1981. 125(1): p. 103-111.

Smith, et ai., "Comparison of biosequences", Advances in applied mathematics, 1981. 2(4): p. 482-489.

Smith TF, et al., identification of common molecular subsequences. J Mol Biol, 1981. 147(1): 195-197. p. 3.

Smith-Bindman, et al., "Use of diagnostic imaging studies and associated radiation exposure for patients enrolled in large integrated health care systems", 1996-2010. JAMA 307, 2400-2409 (2012).

Sprinzak, D., et al., "Reconstruction of genetic circuits". Nature, 2005. 438 (7067): p. 443-448.

Sremac, M., et al., "Recombinant Gas Vesicles from *Halobacterium* sp. Displaying SIV Peptides Demonstrate Biotechnology Potential as a Pathogen Peptide Delivery Vehicle", BMC Biotechnology 8(9), (2008). 14 pages.

Srivastava, A.K., et al., "Advances in using MRI probes and sensors for in vivo cell tracking as applied to regenerative medicine". Disease Models and Mechanisms, 2015. 8(4): p. 323-336.

Steidler, L., et al., "Treatment of murine colitis by Lactococcus lactis secreting interleukin-10". Science, 2000. 289(5483): p. 1352-1355.

Stuber, M., et al., "Positive contrast visualization of iron oxide-labeled stem cells using inversion-recovery with ON-resonant water suppression (IRON)". Magnetic Resonance in Medicine, 2007. 58(5): p. 1072-1077.

Szymczak A. L. et al., "Development of 2A peptide-based strategies in the design of multicistronic vectors." *Expert Opin Biol*Th 5 (5), 627-638 (2005).

Tang, J., et al., "SWIM: Susceptibility Mapping as a Means to Visualize Veins and Quantify Oxygen Saturation, in Susceptibility Weighted Imaging in MRI". 2011, John Wiley & Sons, Inc. p. 461-485.

Taratula, et al., "Functionalized 129Xe contrast agents for magnetic resonance imaging". Current Opinion in Chemical Biology, 2010. 14(1): p. 97-104.

Tashiro, et al., "Molecular genetic and physical analysis of gas vesicles in buoyant enterobacteria", Environmental microbiology, 2016. 18(4): p. 1264-1276.

Terreno, E., et al., "Challenges for Molecular Magnetic Resonance Imaging". Chemical Reviews, 2010. 110(5): p. 3019-3042.

Tsien R. Y., "Imagining imaging's future" *Nature Reviews Molecular Cell Biology*, Ss16-Ss21 (Sep. 2003).

Tsien, R. Y. The Green Fluorescent Protein. Annual Review of Biochemistry 67, 509-544 (1998).

Van Keulen, G., et al., "Gas vesicles in actinomycetes: old buoys in novel habitats?", Trends in microbiology, 2005. 13(8): p. 350-354.

Walsby, A. E."Gas Vesicles." *Annu. Rev. Plant Physiol.*26, 427-439 (1975).

(56) References Cited

OTHER PUBLICATIONS

Walsby, A. E. "The pressure relationships of gas vacuoles." *Proc. R. Soc. London. Ser. B. Biol. Sci.*178, 301-326 (1971).
Walsby, A.E., "Cyanobacteria: planktonic gas-vacuolate forms", The Prokaryotes, a Handbook on Habitats, Isolation, and Identification of Bacteria, 2013. 1: p. 224-235.
Walsby, A.E., et al., "The gas-permeability coefficient of the cyanobacterial gas vesicle wall". Journal of General Microbiology, 1992. 138: p. 837-845.
Walsby, A.E., Gas vesicles. Microbiol. Rev., 1994. 58(1): p. 94-144.
Walsby, A.E., "Gas-vacuolate bacteria (apart from cyanobacteria)", in The Prokaryotes. 1981, Springer. p. 441-447.
Walsby, et al., "Average thickness of the gas vesicle wall in Anabaena flos-aquae". Journal of Molecular Biology, 1979. 129(2): p. 279-285.
Walsby, et al., "Gas vesicle proteins". Biochem. J. 1989, 264, 313-322.
Wang, et al., "Quantitative susceptibility mapping (QSM): Decoding MRI data for a tissue magnetic biomarker". Magnetic Resonance in Medicine, 2015. 73(1): p. 82-101.
Wang, Y., et al., "The role of microbiome in central nervous system disorders". Brain, behavior, and immunity, 2014. 38: p. 1-12.
Watanabe et al. "Distribution and identification of proteolytic *Bacillus* spp. in paddy field soil under rice cultivation" Canadian Journal of Microbiology, NRC Research Press. Jul. 1993. vol. 39. No. 7. pp. 674-680. (Abstract Only) 2 pages.
Weissleder, R., et al., "Ultrasmall superparamagnetic iron oxide: characterization of a new class of contrast agents for MR imaging", Radiology, 1990. 175(2): p. 489-493.
Wells, J.M., et al., "Mucosal delivery of therapeutic and prophylactic molecules using lactic acid bacteria". Nature Reviews Microbiology, 2008. 6(5): p. 349-362.
Woese, C.R., Bacterial evolution. Microbiological reviews, 1987. 51(2): p. 221.
Written Opinion for International Apolication No. PCT/US2020/012572 filed on Jan. 7, 2020 on behalf of California Institute of Technology dated May 6, 2020 6 pages.
Written Opinion for International Application No. PCT/US2020/012557 filed on Jan. 7, 2020 on behalf of California Institute of Technology dated May 1, 2020 6 pages.
Yablonskiy, D.A., et al., "Theory of NMR signal behavior in magnetically inhomogeneous tissues: The static dephasing regime". Magnetic Resonance in Medicine, 1994. 32(6): p. 749-763.
Yi, et al., "Identifying clusters of functionally related genes in genomes", Bioinformatics, 2007. 23(9): p. 1053-1060.
Yurist-Doutsch, S., et al., "Gastrointestinal microbiota-mediated control of enteric pathogens". Annual review of genetics, 2014. 48: p. 361-382.
Zabow, G., et al., "Koretsky, Shape-changing magnetic assemblies as highsensitivity NMR-readable nanoprobes". Nature, 2015. 520 (7545): p. 73-U157.
Zakeri, B., et al., "Peptide tag forming a rapid covalent bond to a protein, through engineering a bacterial adhesin". Proc. Natl. Acad. Sci. U. S. A., 2012. 109(12): p. E690-7.
Zhang, H. F. et al., "Imaging of hemoglobin oxygen saturation variations in single vessels in vivo using photoacoustic microscopy." *Appl. Phys. Lett.*90, 5-7 (2007).
Zhang, S., et al., "PARACEST Agents: Modulating MRI Contrast via Water Proton Exchange". Accounts of Chemical Research, 2003. 36(10): p. 783-790.
Zordan, R.E., et al., "Avoiding the ends: internal epitope tagging of proteins using transposon Tn7". Genetics, 2015. 200(1): p. 47-58.
Zurkiya, O., et al., "Off-resonance saturation as a means of generating contrast with superparamagnetic nanoparticles". Magnetic Resonance in Medicine, 2006. 56(4): p. 726-732.
Non-Final Office Action for U.S. Appl. No. 16/656,417, filed Oct. 17, 2019 on behalf of California Institute of Technology dated Mar. 23, 2021 20 pages.

Notice of Allowance for U.S. Appl. No. 15/663,635, filed Jul. 28, 2017, on behalf of California Institute of Technology, dated May 27, 2021. 10 pages.
Notice of Allowability for U.S. Appl. No. 16/833,637, filed Mar. 29, 2020, on behalf of California Institute of Technology, dated Aug. 17, 2022. 9 Pages.
Notice of Allowability for U.S. Appl. No. 167833,637, filed Mar. 29, 2020 on behalf of California Institute of Technology dated Jun. 13, 2022 6 pages.
Notice of Allowance for U.S. Appl. No. 16/656,417, filed Oct. 17, 2019 on behalf of California Institute of Technology dated Jun. 27, 2022 9 pages.
Notice of Allowance for U.S. Appl. No. 16/833,637, filed Mar. 29, 2020 on behalf of California Institute of Technology dated May 16, 2022 12 pages.
Aguilera et al., "Systemic in vivo distribution of activatable cell penetrating peptides is superior to cell penetrating peptides." Integr Biol (Camb). 2009. 1(5-6): p. 371-381. 22 pages.
Baker, T.A. et al., "ClpXP, an ATP-powered unfolding and protein-degradation machine." Biochimica et Biophysica Acta (BBA)-Molecular Cell Research, 2012. 1823(1): p. 15-28. 33 pages.
Blum-Oehler, G., et al., "Development of strain-specific PCR reactions for the detection of the probiotic *Escherichia coli* strain Nissle 1917 in fecal samples." Research in Microbiology, 2002. 154(1): p. 59-66.
Cameron, D.E. and Collins, J.J., "Tunable protein degradation in bacteria." Nature Biotechnology 2014. 32 (12): p. 1276-1281. 19 pages.
Cha-Molstad et al., "Modulation of SQSTM1/p62 activity by N-terminal arginylation of the endoplasmic reticulum chaperone HSPA5/GRP78/BiP." Autophagy, 2016. 12(2): p. 426-428.
Chassin H. et al., "A modular degron library for synthetic circuits in mammalian cells." Nature Communications 2019. 10: 2013. 11 pages.
Datsenko, K.A. et al., "One-step inactivation of chromosomal genes in *Escherichia coli* K-12 using PCR products." Proceedings of the National Academy of Sciences, 2000. 97(12): p. 6640-6645.
Drag, M. et al., "Emerging principles in protease-based drug discovery." Nature Reviews Drug Discovery 9 (9), 690-701, (2010). 27 pages.
Elowitz, M.B. and S. Leibler, A synthetic oscillatory network of transcriptional regulators. Nature, 2000. 403(6767): p. 335-338.
Fernandez-Rodriguez, J. et al., "Post-translational control of genetic circuits using Potyvirus proteases." Nucleic Acids Research 44, No. 13, 6493-6502 (2016).
Gao, X.J. et al., "Programmable protein circuits in living cells." Science 361, 1252-1258 (2018).
Gardner, T.S. et al., "Construction of a genetic toggle switch in *Escherichia coli*." Nature, 2000. 403(6767): p. 339-342. 4 pages.
Geva-Zatorsky, N., et al., "In vivo imaging and tracking of host-microbiota interactions via metabolic labeling of gut anaerobic bacteria." Nature Medicine, 2015. 21(9): p. 1091-1100. 27 pages.
Goll, D.E., et al., "The calpain system." Physiological Reviews, 2003. 83(3): p. 731-801.
Heim, R. et al., "Engineering green fluorescent protein for improved brightness, longer wavelengths and fluorescence resonance energy transfer." Current Biology 6, 178-182 (1996).
Khalil, A.S. et al., "Synthetic biology: applications come of age." Nature Reviews Genetics, 2010. 11(5): p. 367-379.
Lakshmanan, et al., "Acoustic biosensors for ultrasound imaging of enzyme activity," Supplementary Information in Nature Chemical Biology. Jul. 13, 2020. 3 Pages.
Lin, M.Z. et al., "Genetically encoded indicators of neuronal activity." Nature Neuroscience 19, No. 9, 1142-1153 (2016).
Lopez-Otin, C. et al., "Proteases: multifunctional enzymes in life and disease." Journal of Biological Chemistry 283, No. 45, 30433-7 (2008).
Machtaler, S., et al., "Assessment of inflammation in an acute on chronic model of inflammatory bowel disease with ultrasound molecular imaging." Theranostics, 2015. 5(11): p. 1175-1186.

(56) References Cited

OTHER PUBLICATIONS

Mark Welch, J.L., et al., "Spatial organization of a model 15-member human gut microbiota established in gnotobiotic mice." Proceedings of the National Academy of Sciences, 2017. 114(43): p. E9105-E9114.

Mitra, R.D. et al., "Fluorescence resonance energy transfer between blue emitting and red-shifted excitation derivatives of the green fluorescent protein." Gene 173, 13-17 (1996).

Miyawaki, A. et al., "Molecular spies for bioimaging-fluorescent protein-based probes." Molecular Cell 58, 632-643 (2015).

Muradali, D. et al., "US of gastrointestinal tract disease." Radiographics, 2015. 35(1): p. 50-68.

Ong, I.L.H. et al., "Recent developments in protease activity assays and sensors." Analyst 142, 1867-1881 (2017).

Ono, Y. et al., "Calpain research for drug discovery: challenges and potential." Nature Reviews Drug Discovery, 2016. 15(12): p. 854-876. 34 pages.

Ono, Y. et al., "Calpains—an elaborate proteolytic system." Biochimica et Biophysica Acta (BBA)-Proteins and Proteomics, 2012. 1824(1): p. 224-236.

Palmer, A.E. et al., "Design and application of genetically encoded biosensors." Trends in Biotechnology 29 (3), 144-152 (2011). 18 pages.

Parks, T.D., et al., "Release of proteins and peptides from fusion proteins using a recombinant plant virus proteinase." Analytical Biochemistry, 1994. 216(2): p. 413-417.

Pfeifer, F., "Distribution, formation and regulation of gas vesicles", Nat. Rev. Microbiol., 2012. 10(10): p. 705-15.

Phan, J., et al., "Structural basis for the substrate specificity of tobacco etch virus protease." Journal of Biological Chemistry, 2002. 277(52): p. 50564-50572.

Rodriguez, E.A. et al. "The growing and glowing toolbox of fluorescent and photoactive proteins." Trends in Biochemical Sciences 42 (2), 111-129 (2017). 31 pages.

Sauer, R.T. and Baker, T.A., "AAA+ Proteases: ATP-Fueled Machines of Protein Destruction." Annual Review of Biochemistry, 2011. 80: p. 587-612. 31 pages.

Sauer, R.T., et al., "Sculpting the proteome with AAA(+) proteases and disassembly machines." Cell, 2004. 119(1): p. 9-18. 21 pages.

Sonnenborn, U. et al., "The non-pathogenic *Escherichia coli* strain Nissle 1917—features of a versatile probiotic." Microbial Ecology in Health and Disease, 2009. 21(3-4):p. 122-158.

Stein, V. et al. "Protease-based synthetic sensing and signal amplification." Proceedings of the National Academy of Sciences 111, No. 45, 15934-15939 (2014).

St-Pierre, F., et al., "One-step cloning and chromosomal integration of DNA." ACS synthetic biology, 2013. 2(9): p. 537-541.

Suzuki, S., et al., "Development of an artificial calcium-dependent transcription factor to detect sustained intracellular calcium elevation." ACS Synthetic Biology, 2014. 3(10): p. 717-722.

Tigges, M., et al., "A tunable synthetic mammalian oscillator." Nature," 2009. 457(7227): p. 309-312.

Turk, B., et al., "Protease signaling: the cutting edge." The EMBO Journal 31, 1630-1643 (2012).

Yin, L. et al., "Quantitatively Visualizing Tumor-Related Protease Activity in Vivo Using a Ratiometric Photoacoustic Probe." J. Am. Chem. Soc., 2019. 141(7): p. 3265-3273.

International Preliminary Report on Patentability for International Application No. PCT/US2020/048572 filed on Aug. 28, 2020 on behalf of California Institute of Technology dated Mar. 1, 2022. 7 pages.

Non-Final Office Action for U.S. Appl. No. 16/833,637, filed Mar. 29, 2020 on behalf of California Institute of Technology dated Jan. 25, 2022. 26 pages.

Non-Final Office Action issued for U.S. Appl. No. 16/736,683, filed Jan. 7, 2020, on behalf of California Institute of Technology, dated Apr. 8, 2022. 36 Pages.

Notice of Allowance for U.S. Appl. No. 16/656,417, filed Oct. 17, 2019, on behalf of California Institute of Technology, dated Dec. 8, 2021. 7 Pages.

Notice of Allowance for U.S. Appl. No. 16/656,417, filed Oct. 17, 2019, on behalf of California Institute of Technology, dated Mar. 31, 2022. 19 Pages.

International Search Report and Written Opinion for PCT App. No. PCT/US2020/025608 filed on Mar. 29, 2020 on behalf of California Institute of Technology, dated Jul. 17, 2020. 13 Pages.

Non-Final Office Action for U.S. Appl. No. 15/663,600, filed Jul. 28, 2017 on behalf of California Institute of Technology, dated Jun. 23, 2020. 26 pages.

Non-Final Office Action for U.S. Appl. No. 15/663,635, filed Jul. 28, 2017 on behalf of California Institute of Technology dated May 29, 2020 24 pages.

Corrected Notice of Allowability for U.S. Appl. No. 16/656,417, filed Oct. 17, 2019, on behalf of California Institute of Technology. dated Oct. 20, 2022. 4 Pages.

Extended European Search Report for EP Application No. 20739042.8 filed on Jan. 7, 2020 on behalf of California Institute of Technology dated Sep. 5, 2022 10 pages.

Notice of Allowability for U.S. Appl. No. 16/656,417, filed Oct. 17, 2019, on behalf of California Institute of Technology. dated Sep. 29, 2022. 4 pages.

Restriction Requirement issued for U.S. Appl. No. 17/006,591, filed Aug. 28, 2020, on behalf of California Institute of Technology. dated Sep. 8, 2022. 12 Pages.

Notice of Allowance issued for U.S. Appl. No. 16/736,683, filed Jan. 7, 2020, on behalf of California Institute of Technology. dated Jan. 6, 2023. 11 Pages.

Aguino, Carmen F. et al; "Single component biohybrid light-emitting diodes using a white-emitting fused protein." ACS Omega (2018) 3, p. 15829-15836.

Cesaratto, Francesca et al; "Engineered tobacco etch virus (TEV) protease active in the secretory pathway of mammalian cells." J. Biotech. (2015) 212, p. 159-166.

Herrmann, Joerg et al; "Ubiquitin and ubiquitin-like proteins in protein regulation." Circulation Research (May 2007) 100, p. 1276-1291.

Lux, Jacques et al; "Thrombin-activatable microbubbles as potential ultrasound contrast agents for the detection of acute thrombosis." ACS Appl. Mater. Interfaces (Nov. 2017) 9(43), p. 37587-37596. 22 pages.

Non-Final Office Action issued for U.S. Appl. No. 17/006,591, filed Aug. 28, 2020, on behalf of California Institute of Technology. dated Apr. 14, 2023. 39 Pages.

To, Tsz-Leung et al; "Rationally designed fluorogenic protease reporter visualizes spatiotemporal dynamics of apoptosis in vivo." PNAS (Mar. 2015) 112(11), p. 3338-3343.

Notice of Allowance for U.S. Appl. No. 17/816,373, filed Jul. 29, 2022 on behalf of California Institute of Technology, dated Jun. 8, 2023. 13 pages.

Notice of Allowance issued for U.S. Appl. No. 16/736,683, filed Jan. 7, 2020, on behalf of California Institute of Technology. dated May 31, 2023. 11 Pages.

\* cited by examiner

SEQUENCE LISTING

```
<160> NUMBER OF SEQ ID NOS: 365

<210> SEQ ID NO 1
<211> LENGTH: 48
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (16)..(16)
<223> OTHER INFORMATION: Xaa can be any naturally occurring amino acid

<400> SEQUENCE: 1

Ser Ser Ser Leu Ala Glu Val Leu Asp Arg Ile Leu Asp Lys Gly Xaa
1               5                   10                  15

Val Ile Asp Ala Trp Ala Arg Val Ser Leu Val Gly Ile Glu Ile Leu
            20                  25                  30

Thr Ile Glu Ala Arg Val Val Ile Ala Ser Val Asp Thr Tyr Leu Arg
        35                  40                  45

<210> SEQ ID NO 2
<211> LENGTH: 6
<212> TYPE: PRT
<213> ORGANISM: Artificial Sequence
<220> FEATURE:
<223> OTHER INFORMATION: Synthetic Polypeptide
```

```
<400> SEQUENCE: 2

Leu Asp Arg Ile Leu Asp
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 3

Arg Ile Leu Asp Lys Gly Xaa Val Ile Asp Ala Trp Ala Arg Val Ser
1               5                   10                  15

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 4

Asp Thr Tyr Leu Arg
1               5

<210> SEQ ID NO 5
<211> LENGTH: 125
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (59)..(60)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
```

```
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid

<400> SEQUENCE: 5

Arg Ala Leu Xaa Tyr Leu Gln Ala Gly Tyr Xaa Val His Xaa Arg Gly
1               5                   10                  15

Pro Ala Gly Thr Gly Lys Thr Thr Leu Ala Met His Leu Ala Xaa Xaa
            20                  25                  30

Leu Xaa Arg Pro Val Met Leu Ile Xaa Gly Asp Asp Glu Phe Xaa Thr
        35                  40                  45

Ser Asp Leu Ile Gly Ser Glu Ser Gly Tyr Xaa Xaa Lys Lys Val Val
50                  55                  60

Asp Asn Tyr Ile His Ser Val Val Lys Val Glu Asp Glu Leu Arg Gln
65                  70                  75                  80

Asn Trp Val Asp Asn Arg Leu Thr Xaa Ala Cys Arg Glu Gly Phe Thr
                85                  90                  95

Leu Val Tyr Asp Glu Phe Asn Arg Ser Arg Pro Glu Xaa Asn Asn Val
            100                 105                 110

Leu Leu Ser Val Leu Glu Glu Lys Ile Leu Xaa Leu Pro
        115                 120                 125

<210> SEQ ID NO 6
<211> LENGTH: 308
<212> TYPE: PRT
<213> ORGANISM: Artificial Sequence
<220> FEATURE:
<223> OTHER INFORMATION: Synthetic Polypeptide

<400> SEQUENCE: 6

Met Thr Val Leu Thr Asp Lys Arg Lys Lys Gly Ser Gly Ala Phe Ile
1               5                   10                  15

Gln Asp Asp Glu Thr Lys Glu Val Leu Ser Arg Ala Leu Ser Tyr Leu
            20                  25                  30

Lys Ser Gly Tyr Ser Ile His Phe Thr Gly Pro Ala Gly Gly Gly Lys
        35                  40                  45

Thr Ser Leu Ala Arg Ala Leu Ala Lys Lys Arg Lys Arg Pro Val Met
50                  55                  60

Leu Met His Gly Asn His Glu Leu Asn Asn Lys Asp Leu Ile Gly Asp
65                  70                  75                  80

Phe Thr Gly Tyr Thr Ser Lys Lys Val Ile Asp Gln Tyr Val Arg Ser
                85                  90                  95

Val Tyr Lys Lys Asp Glu Gln Val Ser Glu Asn Trp Gln Asp Gly Arg
            100                 105                 110

Leu Leu Glu Ala Val Lys Asn Gly Tyr Thr Leu Ile Tyr Asp Glu Phe
        115                 120                 125

Thr Arg Ser Lys Pro Ala Thr Asn Asn Ile Phe Leu Ser Ile Leu Glu
    130                 135                 140

Glu Gly Val Leu Pro Leu Tyr Gly Val Lys Met Thr Asp Pro Phe Val
145                 150                 155                 160

Arg Val His Pro Asp Phe Arg Val Ile Phe Thr Ser Asn Pro Ala Glu
                165                 170                 175
```

```
Tyr Ala Gly Val Tyr Asp Thr Gln Asp Ala Leu Leu Asp Arg Leu Ile
            180                 185                 190

Thr Met Phe Ile Asp Tyr Lys Asp Ile Asp Arg Glu Thr Ala Ile Leu
            195                 200                 205

Thr Glu Lys Thr Asp Val Glu Glu Asp Glu Ala Arg Thr Ile Val Thr
            210                 215                 220

Leu Val Ala Asn Val Arg Asn Arg Ser Gly Asp Glu Asn Ser Ser Gly
225                 230                 235                 240

Leu Ser Leu Arg Ala Ser Leu Met Ile Ala Thr Leu Ala Thr Gln Gln
                245                 250                 255

Asp Ile Pro Ile Asp Gly Ser Asp Glu Asp Phe Gln Thr Leu Cys Ile
            260                 265                 270

Asp Ile Leu His His Pro Leu Thr Lys Cys Leu Asp Glu Glu Asn Ala
            275                 280                 285

Lys Ser Lys Ala Glu Lys Ile Ile Leu Glu Glu Cys Lys Asn Ile Asp
            290                 295                 300

Thr Glu Glu Lys
305

<210> SEQ ID NO 7
<211> LENGTH: 255
<212> TYPE: PRT
<213> ORGANISM: Artificial Sequence
<220> FEATURE:
<223> OTHER INFORMATION: Synthetic Polypeptide

<400> SEQUENCE: 7

Met Ser Glu Thr Asn Glu Thr Gly Ile Tyr Ile Phe Ser Ala Ile Gln
1               5                   10                  15

Thr Asp Lys Asp Glu Glu Phe Gly Ala Val Glu Val Glu Gly Thr Lys
            20                  25                  30

Ala Glu Thr Phe Leu Ile Arg Tyr Lys Asp Ala Ala Met Val Ala Ala
            35                  40                  45

Glu Val Pro Met Lys Ile Tyr His Pro Asn Arg Gln Asn Leu Leu Met
    50                  55                  60

His Gln Asn Ala Val Ala Ala Ile Met Asp Lys Asn Asp Thr Val Ile
65                  70                  75                  80

Pro Ile Ser Phe Gly Asn Val Phe Lys Ser Lys Glu Asp Val Lys Val
                85                  90                  95

Leu Leu Glu Asn Leu Tyr Pro Gln Phe Glu Lys Leu Phe Pro Ala Ile
            100                 105                 110

Lys Gly Lys Ile Glu Val Gly Leu Lys Val Ile Gly Lys Lys Glu Trp
            115                 120                 125

Leu Glu Lys Lys Val Asn Glu Asn Pro Glu Leu Glu Lys Val Ser Ala
    130                 135                 140

Ser Val Lys Gly Lys Ser Glu Ala Ala Gly Tyr Tyr Glu Arg Ile Gln
145                 150                 155                 160

Leu Gly Gly Met Ala Gln Lys Met Phe Thr Ser Leu Gln Lys Glu Val
                165                 170                 175

Lys Thr Asp Val Phe Ser Pro Leu Glu Glu Ala Ala Glu Ala Ala Lys
            180                 185                 190

Ala Asn Glu Pro Thr Gly Glu Thr Met Leu Leu Asn Ala Ser Phe Leu
            195                 200                 205

Ile Asn Arg Glu Asp Glu Ala Lys Phe Asp Glu Lys Val Asn Glu Ala
    210                 215                 220
```

His Glu Asn Trp Lys Asp Lys Ala Asp Phe His Tyr Ser Gly Pro Trp
225                 230                 235                 240

Pro Ala Tyr Asn Phe Val Asn Ile Arg Leu Lys Val Glu Glu Lys
                245                 250                 255

<210> SEQ ID NO 8
<211> LENGTH: 72
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid

<400> SEQUENCE: 8

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Val Arg Val
                20                  25                  30

Ser Leu Val Gly Ile Glu Leu Leu Ala Ile Glu Ala Arg Xaa Val Ile
            35                  40                  45

Ala Ser Val Glu Thr Tyr Leu Lys Tyr Ala Glu Ala Val Gly Leu Thr
        50                  55                  60

Xaa Ser Ala Ala Val Pro Ala Xaa
65                  70

<210> SEQ ID NO 9
<211> LENGTH: 71
<212> TYPE: PRT
<213> ORGANISM: Aphanizomenon-flos-aquae

<400> SEQUENCE: 9

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Val Arg Val
                20                  25                  30

Ser Leu Val Gly Ile Glu Leu Leu Ala Ile Glu Ala Arg Ile Val Ile
            35                  40                  45

Ala Ser Val Glu Thr Tyr Leu Lys Tyr Ala Glu Ala Val Gly Leu Thr
        50                  55                  60

Gln Ser Ala Ala Val Pro Ala
65                  70

<210> SEQ ID NO 10
<211> LENGTH: 72
<212> TYPE: PRT
<213> ORGANISM: Aphanothece-halophytica

<400> SEQUENCE: 10

Met Ala Val Glu Lys Thr Asn Ser Ser Ser Leu Gly Glu Val Val
1               5                   10                  15

Asp Arg Ile Leu Asp Lys Gly Val Val Val Asp Leu Trp Val Arg Val
                20                  25                  30

Ser Leu Val Gly Ile Glu Leu Leu Ala Val Glu Ala Arg Val Val Val
            35                  40                  45

Ala Ser Val Glu Thr Tyr Leu Lys Tyr Ala Gly Ala Val Gly Leu Thr
    50                  55                  60

Ser Ser Ala Ala Val Pro Ala Glu
65                  70

<210> SEQ ID NO 11
<211> LENGTH: 71
<212> TYPE: PRT
<213> ORGANISM: Anabaena-flos-aquae

<400> SEQUENCE: 11

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Val Arg Val
            20                  25                  30

Ser Leu Val Gly Ile Glu Leu Leu Ala Ile Glu Ala Arg Ile Val Ile
            35                  40                  45

Ala Ser Val Glu Thr Tyr Leu Lys Tyr Ala Gly Ala Val Gly Leu Thr
    50                  55                  60

Gln Ser Ala Ala Val Pro Ala
65                  70

<210> SEQ ID NO 12
<211> LENGTH: 70
<212> TYPE: PRT
<213> ORGANISM: Ancylobacter-aquaticus

<400> SEQUENCE: 12

Met Ala Val Glu Lys Ile Asn Ala Ser Ser Leu Ala Glu Val Val
1               5                   10                  15

Asp Arg Ile Leu Asp Lys Gly Val Val Val Asp Ala Trp Val Arg Val
            20                  25                  30

Ser Leu Val Gly Ile Glu Leu Leu Ala Val Glu Ala Arg Val Val Val
            35                  40                  45

Ala Gly Val Asp Thr Tyr Leu Lys Tyr Ala Glu Ala Val Gly Leu Thr
    50                  55                  60

Ala Ser Ala Gln Ala Ala
65                  70

<210> SEQ ID NO 13
<211> LENGTH: 70
<212> TYPE: PRT
<213> ORGANISM: Aquabacter-spiritensis

<400> SEQUENCE: 13

Met Ala Val Glu Lys Ile Asn Ala Ser Ser Leu Ala Glu Val Val
1               5                   10                  15

Asp Arg Ile Leu Asp Lys Gly Val Val Val Asp Ala Trp Val Arg Val
            20                  25                  30

Ser Leu Val Gly Ile Glu Leu Leu Ala Val Glu Ala Arg Val Val Val
            35                  40                  45

Ala Gly Val Asp Thr Tyr Leu Lys Tyr Ala Glu Ala Val Gly Leu Thr
    50                  55                  60

Ala Gly Ala Gln Ala Ala
65                  70

-continued

```
<210> SEQ ID NO 14
<211> LENGTH: 72
<212> TYPE: PRT
<213> ORGANISM: Arthrospira-sp-PCC-8005

<400> SEQUENCE: 14

Met Ala Val Glu Lys Val Asn Ser Ser Ser Leu Ala Glu Val Ile
1               5                   10                  15

Asp Arg Ile Leu Asp Lys Gly Ile Val Ile Asp Ala Trp Val Arg Val
                20                  25                  30

Ser Leu Val Gly Ile Glu Leu Ser Val Glu Ala Arg Val Val Ile
        35                  40                  45

Ala Ser Val Glu Thr Tyr Leu Lys Tyr Ala Glu Ala Val Gly Leu Thr
    50                  55                  60

Ala Gln Ala Ala Val Pro Ser Val
65                  70

<210> SEQ ID NO 15
<211> LENGTH: 71
<212> TYPE: PRT
<213> ORGANISM: Calothrix-sp-strain-PCC-7601

<400> SEQUENCE: 15

Met Ala Val Glu Lys Thr Asn Ser Ser Ser Leu Ala Glu Val Ile
1               5                   10                  15

Asp Arg Ile Leu Asp Lys Gly Ile Val Val Asp Ala Trp Val Arg Val
                20                  25                  30

Ser Leu Val Gly Ile Glu Leu Leu Ala Ile Glu Ala Arg Ile Val Ile
        35                  40                  45

Ala Ser Val Glu Thr Tyr Leu Lys Tyr Ala Glu Ala Val Gly Leu Thr
    50                  55                  60

Gln Ser Ala Ala Val Pro Ala
65                  70

<210> SEQ ID NO 16
<211> LENGTH: 72
<212> TYPE: PRT
<213> ORGANISM: Dactylococcopsis-salina-PCC-8305

<400> SEQUENCE: 16

Met Ala Val Glu Lys Thr Asn Ser Ser Ser Leu Gly Glu Val Val
1               5                   10                  15

Asp Arg Ile Leu Asp Lys Gly Val Val Val Asp Leu Trp Val Arg Val
                20                  25                  30

Ser Leu Val Gly Ile Glu Leu Leu Ala Val Glu Ala Arg Val Val Ile
        35                  40                  45

Ala Ser Val Glu Thr Tyr Leu Lys Tyr Ala Glu Ala Val Gly Leu Thr
    50                  55                  60

Ser Ser Ala Ala Val Pro Ala Glu
65                  70

<210> SEQ ID NO 17
<211> LENGTH: 71
<212> TYPE: PRT
<213> ORGANISM: Dolichospermum-circinale-AWQC131C

<400> SEQUENCE: 17

Met Ala Val Glu Lys Thr Asn Ser Ser Ser Leu Ala Glu Val Ile
1               5                   10                  15
```

-continued

Asp Arg Ile Leu Asp Lys Gly Ile Val Ile Asp Ala Trp Val Arg Val
            20                  25                  30

Ser Leu Val Gly Ile Glu Leu Leu Ala Ile Glu Ala Arg Ile Val Ile
        35                  40                  45

Ala Ser Val Glu Thr Tyr Leu Lys Tyr Ala Glu Ala Val Gly Leu Thr
    50                  55                  60

Gln Ser Ala Ala Val Pro Ala
65                  70

<210> SEQ ID NO 18
<211> LENGTH: 71
<212> TYPE: PRT
<213> ORGANISM: Dolichospermum-lemmermannii

<400> SEQUENCE: 18

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Val Arg Val
            20                  25                  30

Ser Leu Val Gly Ile Glu Leu Leu Ala Ile Glu Ala Arg Ile Val Ile
        35                  40                  45

Ala Ser Val Glu Thr Tyr Leu Lys Tyr Ala Glu Ala Val Gly Leu Thr
    50                  55                  60

Gln Ser Ala Ala Val Pro Ala
65                  70

<210> SEQ ID NO 19
<211> LENGTH: 70
<212> TYPE: PRT
<213> ORGANISM: Enhydrobacter-aerosaccus

<400> SEQUENCE: 19

Met Ala Val Glu Lys Met Asn Ala Ser Ser Leu Ala Glu Val Val
1               5                   10                  15

Asp Arg Ile Leu Asp Lys Gly Ile Val Ile Asp Ala Trp Val Arg Val
            20                  25                  30

Ser Leu Val Gly Ile Glu Leu Leu Ala Val Glu Ala Arg Val Val Val
        35                  40                  45

Ala Gly Val Asp Thr Tyr Leu Lys Tyr Ala Glu Ala Val Gly Leu Thr
    50                  55                  60

Ala Gly Ala Glu Ala Ala
65                  70

<210> SEQ ID NO 20
<211> LENGTH: 72
<212> TYPE: PRT
<213> ORGANISM: Lyngbya-confervoides-BDU141951

<400> SEQUENCE: 20

Met Ala Val Glu Lys Val Asn Ser Ser Ser Leu Ala Glu Val Val
1               5                   10                  15

Asp Arg Ile Leu Asp Lys Gly Ile Val Val Asp Ala Trp Val Arg Val
            20                  25                  30

Ser Leu Val Gly Ile Glu Leu Leu Ala Ile Glu Ala Arg Val Val Ile
        35                  40                  45

Ala Ser Val Glu Thr Tyr Leu Lys Tyr Ala Glu Ala Val Gly Leu Thr
    50                  55                  60

Ala Gln Ala Ala Val Pro Ala Ser

<210> SEQ ID NO 21
<211> LENGTH: 73
<212> TYPE: PRT
<213> ORGANISM: Nostoc-punctiforme-PCC-73102

<400> SEQUENCE: 21

Met Ala Val Glu Lys Val Asn Ser Ser Ser Leu Ala Glu Val Ile
1               5                   10                  15

Asp Arg Ile Leu Asp Lys Gly Ile Val Ile Asp Ala Trp Val Arg Val
            20                  25                  30

Ser Leu Val Gly Ile Glu Leu Leu Ser Ile Glu Ala Arg Ile Val Ile
            35                  40                  45

Ala Ser Val Glu Thr Tyr Leu Arg Tyr Ala Glu Ala Val Gly Leu Thr
        50                  55                  60

Ser Gln Ala Ala Val Pro Ser Ala Ala
65                  70

<210> SEQ ID NO 22
<211> LENGTH: 71
<212> TYPE: PRT
<213> ORGANISM: Nostoc-sp-PCC-7120

<400> SEQUENCE: 22

Met Ala Val Glu Lys Thr Asn Ser Ser Ser Leu Ala Glu Val Ile
1               5                   10                  15

Asp Arg Ile Leu Asp Lys Gly Ile Val Val Asp Ala Trp Val Arg Val
            20                  25                  30

Ser Leu Val Gly Ile Glu Leu Leu Ala Ile Glu Ala Arg Ile Val Ile
            35                  40                  45

Ala Ser Val Glu Thr Tyr Leu Lys Tyr Ala Glu Ala Val Gly Leu Thr
        50                  55                  60

Gln Ser Ala Ala Met Pro Ala
65                  70

<210> SEQ ID NO 23
<211> LENGTH: 71
<212> TYPE: PRT
<213> ORGANISM: Microchaete-diplosiphon

<400> SEQUENCE: 23

Met Ala Val Glu Lys Thr Asn Ser Ser Ser Leu Ala Glu Val Ile
1               5                   10                  15

Asp Arg Ile Leu Asp Lys Gly Ile Val Val Asp Ala Trp Val Arg Val
            20                  25                  30

Ser Leu Val Gly Ile Glu Leu Leu Ala Ile Glu Ala Arg Ile Val Ile
            35                  40                  45

Ala Ser Val Glu Thr Tyr Leu Lys Tyr Ala Glu Ala Val Gly Leu Thr
        50                  55                  60

Gln Ser Ala Ala Val Pro Ala
65                  70

<210> SEQ ID NO 24
<211> LENGTH: 71
<212> TYPE: PRT
<213> ORGANISM: Microcystis-aeruginosa-NIES-843

<400> SEQUENCE: 24

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Ala Arg Val
            20                  25                  30

Ser Leu Val Gly Ile Glu Leu Leu Ala Ile Glu Ala Arg Val Val Ile
        35                  40                  45

Ala Ser Val Glu Thr Tyr Leu Lys Tyr Ala Glu Ala Val Gly Leu Thr
    50                  55                  60

Gln Ser Ala Ala Val Pro Ala
65              70

<210> SEQ ID NO 25
<211> LENGTH: 71
<212> TYPE: PRT
<213> ORGANISM: Microcystis-aeruginosa-NIES-843

<400> SEQUENCE: 25

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Ala Arg Val
            20                  25                  30

Ser Leu Val Gly Ile Glu Leu Leu Ala Ile Glu Ala Arg Val Val Ile
        35                  40                  45

Ala Ser Val Glu Thr Tyr Leu Lys Tyr Ala Glu Ala Val Gly Leu Thr
    50                  55                  60

Gln Ser Ala Ala Val Pro Ala
65              70

<210> SEQ ID NO 26
<211> LENGTH: 71
<212> TYPE: PRT
<213> ORGANISM: Microcystis-aeruginosa-NIES-843

<400> SEQUENCE: 26

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Ala Arg Val
            20                  25                  30

Ser Leu Val Gly Ile Glu Leu Leu Ala Ile Glu Ala Arg Val Val Ile
        35                  40                  45

Ala Ser Val Glu Thr Tyr Leu Lys Tyr Ala Glu Ala Val Gly Leu Thr
    50                  55                  60

Gln Ser Ala Ala Val Pro Ala
65              70

<210> SEQ ID NO 27
<211> LENGTH: 71
<212> TYPE: PRT
<213> ORGANISM: Microcystis-flos-aquae-TF09

<400> SEQUENCE: 27

Met Ala Val Glu Lys Thr Asn Ser Ser Ser Leu Ala Glu Val Ile
1               5                   10                  15

Asp Arg Ile Leu Asp Lys Gly Ile Val Ile Asp Ala Trp Ala Arg Val
            20                  25                  30

Ser Leu Val Gly Ile Glu Leu Leu Ala Ile Glu Ala Arg Val Val Ile
        35                  40                  45

Ala Ser Val Glu Thr Tyr Leu Lys Tyr Ala Glu Ala Val Gly Leu Thr

Gln Ser Ala Ala Val Pro Ala
65                  70

<210> SEQ ID NO 28
<211> LENGTH: 72
<212> TYPE: PRT
<213> ORGANISM: Phormidium-tenue-NIES-30

<400> SEQUENCE: 28

Met Ala Val Glu Lys Val Asn Ser Ser Ser Leu Ala Glu Val Val
1               5                   10                  15

Asp Arg Ile Leu Asp Lys Gly Ile Val Ile Asp Ala Trp Val Arg Val
            20                  25                  30

Ser Leu Val Gly Ile Glu Leu Leu Ala Ile Glu Ala Arg Val Val Ile
                35                  40                  45

Ala Ser Val Asp Thr Tyr Leu Lys Tyr Ala Glu Ala Val Gly Leu Thr
            50                  55                  60

Ala Gln Ala Ala Val Pro Ala Ala
65                  70

<210> SEQ ID NO 29
<211> LENGTH: 72
<212> TYPE: PRT
<213> ORGANISM: Planktothrix-agardhii

<400> SEQUENCE: 29

Met Ala Val Glu Lys Val Asn Ser Ser Ser Leu Ala Glu Val Ile
1               5                   10                  15

Asp Arg Ile Leu Asp Lys Gly Ile Val Ile Asp Ala Trp Val Arg Val
            20                  25                  30

Ser Leu Val Gly Ile Glu Leu Leu Ser Ile Glu Ala Arg Ile Val Ile
                35                  40                  45

Ala Ser Val Glu Thr Tyr Leu Lys Tyr Ala Glu Ala Val Gly Leu Thr
            50                  55                  60

Ala Gln Ala Ala Val Pro Ser Val
65                  70

<210> SEQ ID NO 30
<211> LENGTH: 72
<212> TYPE: PRT
<213> ORGANISM: Planktothrix-rubescens

<400> SEQUENCE: 30

Met Ala Val Glu Lys Val Asn Ser Ser Ser Leu Ala Glu Val Ile
1               5                   10                  15

Asp Arg Ile Leu Asp Lys Gly Ile Val Ile Asp Ala Trp Val Arg Val
            20                  25                  30

Ser Leu Val Gly Ile Glu Leu Leu Ser Ile Glu Ala Arg Ile Val Ile
                35                  40                  45

Ala Ser Val Glu Thr Tyr Leu Lys Tyr Ala Glu Ala Val Gly Leu Thr
            50                  55                  60

Ala Gln Ala Ala Val Pro Ser Val
65                  70

<210> SEQ ID NO 31
<211> LENGTH: 72
<212> TYPE: PRT
<213> ORGANISM: Pseudanabaena-galeata-PCC-6901

<400> SEQUENCE: 31

Met Ala Val Glu Lys Val Asn Ser Ser Ser Leu Ala Glu Val Ile
1               5                   10                  15

Asp Arg Ile Leu Asp Lys Gly Ile Val Ile Asp Ala Trp Val Arg Val
            20                  25                  30

Ser Leu Val Gly Ile Glu Leu Ser Ile Glu Ala Arg Val Val Ile
        35                  40                  45

Ala Ser Val Glu Thr Tyr Leu Lys Tyr Ala Glu Val Gly Leu Thr
    50                  55                  60

Ala Ser Ala Ala Val Pro Ala Ala
65                  70

<210> SEQ ID NO 32
<211> LENGTH: 70
<212> TYPE: PRT
<213> ORGANISM: Stella-vacuolata

<400> SEQUENCE: 32

Met Ala Val Glu Lys Ile Asn Ala Ser Ser Leu Ala Glu Val Val
1               5                   10                  15

Asp Arg Ile Leu Asp Lys Gly Val Val Asp Ala Trp Val Arg Val
            20                  25                  30

Ser Leu Val Gly Ile Glu Leu Leu Ala Val Glu Ala Arg Val Val Val
        35                  40                  45

Ala Gly Val Asp Thr Tyr Leu Lys Tyr Ala Glu Ala Val Gly Leu Thr
    50                  55                  60

Ala Gly Ala Gln Thr Ala
65                  70

<210> SEQ ID NO 33
<211> LENGTH: 75
<212> TYPE: PRT
<213> ORGANISM: Trichodesmium-erythraeum-IMS101

<400> SEQUENCE: 33

Met Ala Val Glu Lys Val Asn Ser Ser Ser Leu Ala Glu Val Ile
1               5                   10                  15

Asp Arg Ile Leu Asp Lys Gly Val Val Asp Ala Trp Ile Arg Leu
            20                  25                  30

Ser Leu Val Gly Ile Glu Leu Leu Thr Ile Glu Ala Arg Ile Val Val
        35                  40                  45

Ala Ser Val Glu Thr Tyr Leu Lys Tyr Ala Glu Val Gly Leu Thr
    50                  55                  60

Thr Leu Ala Ala Ala Pro Gly Glu Ala Ala Ala
65                  70              75

<210> SEQ ID NO 34
<211> LENGTH: 72
<212> TYPE: PRT
<213> ORGANISM: Trichodesmium-erythraeum-IMS101

<400> SEQUENCE: 34

Met Ala Val Glu Lys Val Asn Ser Ser Ser Leu Ala Glu Val Ile
1               5                   10                  15

Asp Arg Ile Leu Asp Lys Gly Val Val Asp Ala Trp Val Arg Leu
            20                  25                  30

Ser Leu Val Gly Ile Glu Leu Leu Thr Ile Glu Ala Arg Ile Val Ile

```
                 35                  40                  45
Ala Ser Val Glu Thr Tyr Leu Lys Tyr Ala Glu Ala Val Gly Leu Thr
        50                  55                  60

Thr Leu Ala Ala Glu Pro Ala Ala
65                  70

<210> SEQ ID NO 35
<211> LENGTH: 71
<212> TYPE: PRT
<213> ORGANISM: Tolypothrix-sp.-PCC-7601

<400> SEQUENCE: 35

Met Ala Val Glu Lys Thr Asn Ser Ser Ser Leu Ala Glu Val Ile
1               5                   10                  15

Asp Arg Ile Leu Asp Lys Gly Ile Val Val Asp Ala Trp Val Arg Val
            20                  25                  30

Ser Leu Val Gly Ile Glu Leu Leu Ala Ile Glu Ala Arg Ile Val Ile
        35                  40                  45

Ala Ser Val Glu Thr Tyr Leu Lys Tyr Ala Glu Ala Val Gly Leu Thr
        50                  55                  60

Gln Ser Ala Ala Val Pro Ala
65                  70

<210> SEQ ID NO 36
<211> LENGTH: 71
<212> TYPE: PRT
<213> ORGANISM: Tolypothrix-sp.-PCC-7601

<400> SEQUENCE: 36

Met Ala Val Glu Lys Thr Asn Ser Ser Ser Leu Ala Glu Val Ile
1               5                   10                  15

Asp Arg Ile Leu Asp Lys Gly Ile Val Val Asp Ala Trp Val Arg Val
            20                  25                  30

Ser Leu Val Gly Ile Glu Leu Leu Ala Ile Glu Ala Arg Ile Val Ile
        35                  40                  45

Ala Ser Val Glu Thr Tyr Leu Lys Tyr Ala Glu Ala Val Gly Leu Thr
        50                  55                  60

Gln Ser Ala Ala Val Pro Ala
65                  70

<210> SEQ ID NO 37
<211> LENGTH: 78
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 37

Met Ala Gln Pro Asp Ser Ser Ser Leu Ala Glu Val Leu Asp Arg Val
1               5                   10                  15

Leu Asp Lys Gly Val Val Val Asp Val Trp Ala Arg Xaa Ser Leu Val
            20                  25                  30

Gly Ile Glu Ile Leu Thr Val Glu Ala Arg Val Val Ala Ala Ser Val
```

35                  40                  45

Asp Thr Phe Leu His Tyr Ala Glu Glu Ile Ala Lys Ile Glu Gln Ala
         50                  55                  60

Glu Leu Thr Ala Gly Ala Glu Ala Xaa Pro Ala Pro Glu Ala
65                  70                  75

<210> SEQ ID NO 38
<211> LENGTH: 76
<212> TYPE: PRT
<213> ORGANISM: Halobacterium-salinarum

<400> SEQUENCE: 38

Met Ala Gln Pro Asp Ser Ser Gly Leu Ala Glu Val Leu Asp Arg Val
1               5                   10                  15

Leu Asp Lys Gly Val Val Asp Val Trp Ala Arg Val Ser Leu Val
            20                  25                  30

Gly Ile Glu Ile Leu Thr Val Glu Ala Arg Val Val Ala Ala Ser Val
            35                  40                  45

Asp Thr Phe Leu His Tyr Ala Glu Glu Ile Ala Lys Ile Glu Gln Ala
         50                  55                  60

Glu Leu Thr Ala Gly Ala Glu Ala Ala Pro Glu Ala
65                  70                  75

<210> SEQ ID NO 39
<211> LENGTH: 79
<212> TYPE: PRT
<213> ORGANISM: Halobacterium-salinarum

<400> SEQUENCE: 39

Met Ala Gln Pro Asp Ser Ser Ser Leu Ala Glu Val Leu Asp Arg Val
1               5                   10                  15

Leu Asp Lys Gly Val Val Asp Val Trp Ala Arg Ile Ser Leu Val
            20                  25                  30

Gly Ile Glu Ile Leu Thr Val Glu Ala Arg Val Val Ala Ala Ser Val
            35                  40                  45

Asp Thr Phe Leu His Tyr Ala Glu Glu Ile Ala Lys Ile Glu Gln Ala
         50                  55                  60

Glu Leu Thr Ala Gly Ala Glu Ala Pro Glu Pro Ala Pro Glu Ala
65                  70                  75

<210> SEQ ID NO 40
<211> LENGTH: 76
<212> TYPE: PRT
<213> ORGANISM: Halobacterium-salinarum-NRC-1

<400> SEQUENCE: 40

Met Ala Gln Pro Asp Ser Ser Gly Leu Ala Glu Val Leu Asp Arg Val
1               5                   10                  15

Leu Asp Lys Gly Val Val Asp Val Trp Ala Arg Val Ser Leu Val
            20                  25                  30

Gly Ile Glu Ile Leu Thr Val Glu Ala Arg Val Val Ala Ala Ser Val
            35                  40                  45

Asp Thr Phe Leu His Tyr Ala Glu Glu Ile Ala Lys Ile Glu Gln Ala
         50                  55                  60

Glu Leu Thr Ala Gly Ala Glu Ala Ala Pro Glu Ala
65                  70                  75

<210> SEQ ID NO 41

```
<211> LENGTH: 79
<212> TYPE: PRT
<213> ORGANISM: Halobacterium-salinarum-NRC-1

<400> SEQUENCE: 41

Met Ala Gln Pro Asp Ser Ser Leu Ala Glu Val Leu Asp Arg Val
1               5                   10                  15

Leu Asp Lys Gly Val Val Asp Val Trp Ala Arg Ile Ser Leu Val
            20                  25                  30

Gly Ile Glu Ile Leu Thr Val Glu Ala Arg Val Val Ala Ser Val
        35                  40                  45

Asp Thr Phe Leu His Tyr Ala Glu Glu Ile Ala Lys Ile Glu Gln Ala
    50                  55                      60

Glu Leu Thr Ala Gly Ala Glu Ala Pro Glu Pro Ala Pro Glu Ala
65                  70                  75

<210> SEQ ID NO 42
<211> LENGTH: 78
<212> TYPE: PRT
<213> ORGANISM: Haloferax-mediterranei-ATCC-33500

<400> SEQUENCE: 42

Met Val Gln Pro Asp Ser Ser Leu Ala Glu Val Leu Asp Arg Val
1               5                   10                  15

Leu Asp Lys Gly Val Val Asp Val Trp Ala Arg Ile Ser Leu Val
            20                  25                  30

Gly Ile Glu Ile Leu Thr Val Glu Ala Arg Val Val Ala Ala Ser Val
        35                  40                  45

Asp Thr Phe Leu His Tyr Ala Glu Glu Ile Ala Lys Ile Glu Gln Ala
    50                  55                      60

Glu Leu Thr Ala Gly Ala Glu Ala Ala Pro Thr Pro Glu Ala
65                  70                  75

<210> SEQ ID NO 43
<211> LENGTH: 78
<212> TYPE: PRT
<213> ORGANISM: Halogeometricum-borinquense-DSM-11551

<400> SEQUENCE: 43

Met Ala Gln Pro Asp Ser Ser Leu Ala Glu Val Leu Asp Arg Val
1               5                   10                  15

Leu Asp Lys Gly Val Val Asp Val Trp Ala Arg Val Ser Leu Val
            20                  25                  30

Gly Ile Glu Ile Leu Thr Val Glu Ala Arg Val Val Ala Ala Ser Val
        35                  40                  45

Asp Thr Phe Leu His Tyr Ala Glu Glu Ile Ala Lys Ile Glu Gln Ala
    50                  55                      60

Glu Leu Thr Ala Thr Ala Glu Ala Ala Pro Thr Pro Glu Ala
65                  70                  75

<210> SEQ ID NO 44
<211> LENGTH: 76
<212> TYPE: PRT
<213> ORGANISM: Halopenitus-persicus-strain-DC30

<400> SEQUENCE: 44

Met Ala Gln Pro Asp Ser Ser Gly Leu Ala Glu Val Leu Asp Arg Val
1               5                   10                  15

Leu Asp Lys Gly Val Val Val Asp Val Trp Ala Arg Val Ser Leu Val
```

```
            20                  25                  30

Gly Ile Glu Ile Leu Thr Val Glu Ala Arg Val Val Ala Ala Ser Val
            35                  40                  45

Asp Thr Phe Leu His Tyr Ala Glu Glu Ile Ala Lys Ile Glu Gln Ala
        50                  55                  60

Glu Leu Thr Ala Gly Ala Glu Ala Ala Pro Glu Ala
65                  70                  75

<210> SEQ ID NO 45
<211> LENGTH: 72
<212> TYPE: PRT
<213> ORGANISM: Haloquadratum-walsbyi-C23

<400> SEQUENCE: 45

Met Ala Gln Pro Asp Ser Ser Ser Leu Ala Glu Val Leu Asp Arg Val
1               5                   10                  15

Leu Asp Lys Gly Ile Val Val Asp Thr Phe Ala Arg Ile Ser Leu Val
            20                  25                  30

Gly Ile Glu Ile Leu Thr Val Glu Ala Arg Val Val Ala Ser Val
            35                  40                  45

Asp Thr Phe Leu His Tyr Ala Glu Glu Ile Ala Lys Ile Glu Gln Ala
        50                  55                  60

Glu Leu Thr Ala Gly Ala Glu Ala
65                  70

<210> SEQ ID NO 46
<211> LENGTH: 78
<212> TYPE: PRT
<213> ORGANISM: Halorubrum-vacuolatum-strain-DSM-8800

<400> SEQUENCE: 46

Met Ala Gln Pro Asp Ser Ser Ser Leu Ala Glu Val Leu Asp Arg Val
1               5                   10                  15

Leu Asp Lys Gly Val Val Val Asp Val Tyr Ala Arg Leu Ser Leu Val
            20                  25                  30

Gly Ile Glu Ile Leu Thr Val Glu Ala Arg Val Val Ala Ala Ser Val
            35                  40                  45

Asp Thr Phe Leu His Tyr Ala Glu Glu Ile Ala Lys Ile Glu Gln Ala
        50                  55                  60

Glu Leu Thr Ala Gly Ala Glu Ala Ala Pro Thr Pro Glu Ala
65                  70                  75

<210> SEQ ID NO 47
<211> LENGTH: 95
<212> TYPE: PRT
<213> ORGANISM: Halopiger-xanaduensis

<400> SEQUENCE: 47

Met Ala Gln Pro Gln Arg Arg Pro Asp Ser Ser Ser Leu Ala Glu Val
1               5                   10                  15

Leu Asp Arg Ile Leu Asp Lys Gly Val Val Ile Asp Val Trp Ala Arg
            20                  25                  30

Ile Ser Val Val Gly Ile Glu Leu Leu Thr Ile Glu Ala Arg Val Val
            35                  40                  45

Val Ala Ser Val Asp Thr Phe Leu His Tyr Ala Glu Glu Ile Ala Lys
        50                  55                  60

Ile Glu Gln Ala Thr Ala Glu Gly Asp Leu Glu Glu Leu Glu Glu Leu
65                  70                  75                  80
```

Glu Val Glu Pro Arg Pro Glu Ser Ser Pro Gln Ser Ala Ala Glu
            85                  90                  95

<210> SEQ ID NO 48
<211> LENGTH: 95
<212> TYPE: PRT
<213> ORGANISM: Natrialba-magadii-ATCC-43099

<400> SEQUENCE: 48

Met Ala Gln Pro Gln Arg Arg Pro Asp Ser Ser Leu Ala Glu Val
1               5                   10                  15

Leu Asp Arg Val Leu Asp Lys Gly Val Val Ile Asp Ile Trp Ala Arg
            20                  25                  30

Val Ser Val Val Gly Ile Glu Leu Leu Thr Val Glu Ala Arg Val Val
        35                  40                  45

Val Ala Ser Val Asp Thr Phe Leu His Tyr Ala Glu Glu Ile Ala Lys
    50                  55                  60

Ile Glu Gln Ala Thr Ala Glu Gly Asp Leu Glu Asp Leu Glu Glu Leu
65                  70                  75                  80

Glu Val Glu Pro Arg Pro Glu Ser Ser Pro Lys Ser Ala Thr Glu
            85                  90                  95

<210> SEQ ID NO 49
<211> LENGTH: 94
<212> TYPE: PRT
<213> ORGANISM: Natrinema-pellirubrum-DSM-15624

<400> SEQUENCE: 49

Met Ala Gln Pro Gln Arg Arg Pro Asp Ser Ser Ser Leu Ala Glu Val
1               5                   10                  15

Leu Asp Arg Val Leu Asp Lys Gly Val Val Ile Asp Val Trp Ala Arg
            20                  25                  30

Ile Ser Val Val Gly Ile Glu Leu Leu Thr Ile Glu Ala Arg Val Val
        35                  40                  45

Val Ala Ser Val Asp Thr Phe Leu His Tyr Ala Glu Glu Ile Ala Lys
    50                  55                  60

Ile Glu Gln Ala Thr Ala Glu Gly Asp Leu Asp Glu Leu Glu Glu Leu
65                  70                  75                  80

Glu Val Glu Pro Arg Pro Glu Ser Ser Pro Lys Ser Ala Glu
            85                  90

<210> SEQ ID NO 50
<211> LENGTH: 95
<212> TYPE: PRT
<213> ORGANISM: Natronobacterium-gregoryi-SP2

<400> SEQUENCE: 50

Met Ala Gln Pro Gln Arg Arg Pro Asp Ser Ser Leu Ala Glu Val
1               5                   10                  15

Leu Asp Arg Ile Leu Asp Lys Gly Val Val Ile Asp Val Trp Ala Arg
            20                  25                  30

Val Ser Val Val Gly Ile Glu Leu Leu Thr Ile Glu Ala Arg Val Val
        35                  40                  45

Val Ala Ser Val Asp Thr Phe Leu His Tyr Ala Glu Glu Ile Ala Lys
    50                  55                  60

Ile Glu Gln Ala Thr Ala Glu Gly Asp Leu Glu Asp Leu Glu Glu Leu
65                  70                  75                  80

```
Glu Val Glu Pro Arg Pro Glu Ser Ser Pro Gln Ser Ala Thr Glu
                85                  90                  95
```

<210> SEQ ID NO 51
<211> LENGTH: 74
<212> TYPE: PRT
<213> ORGANISM: Methanosaeta-thermophila

<400> SEQUENCE: 51

```
Met Val Thr Ser Thr Pro Asp Ser Ser Leu Ala Glu Val Leu Asp
1               5                   10                  15

Arg Ile Leu Asp Lys Gly Ile Val Val Asp Val Trp Ala Arg Val Ser
                20                  25                  30

Leu Val Gly Ile Glu Ile Leu Thr Val Glu Ala Arg Val Val Ala
            35                  40                  45

Ser Val Asp Thr Phe Leu His Tyr Ser Glu Glu Met Ala Lys Ile Glu
            50                  55                  60

Gln Ala Ala Ile Ala Ala Ala Pro Ser Ala
65                  70
```

<210> SEQ ID NO 52
<211> LENGTH: 76
<212> TYPE: PRT
<213> ORGANISM: Methanosaeta-thermophila

<400> SEQUENCE: 52

```
Met Val Thr Ser Thr Pro Asp Ser Ser Leu Ala Glu Val Leu Asp
1               5                   10                  15

Arg Ile Leu Asp Lys Gly Ile Val Val Asp Val Trp Ala Arg Val Ser
                20                  25                  30

Leu Val Gly Ile Glu Ile Leu Thr Val Glu Ala Arg Val Val Ala
            35                  40                  45

Ser Val Asp Thr Phe Leu His Tyr Ser Glu Glu Met Ala Lys Ile Glu
            50                  55                  60

Gln Ala Ala Ile Ala Ala Ala Pro Gly Val Pro Ala
65                  70                  75
```

<210> SEQ ID NO 53
<211> LENGTH: 76
<212> TYPE: PRT
<213> ORGANISM: Methanosarcina-barkeri-3

<400> SEQUENCE: 53

```
Met Val Ser Gln Ser Pro Asp Ser Ser Leu Ala Glu Val Leu Asp
1               5                   10                  15

Arg Ile Leu Asp Lys Gly Ile Val Val Asp Val Trp Ala Arg Val Ser
                20                  25                  30

Leu Val Gly Ile Glu Ile Leu Ala Ile Glu Ala Arg Val Val Ala
            35                  40                  45

Ser Val Asp Thr Phe Leu His Tyr Ala Glu Glu Ile Thr Lys Ile Glu
            50                  55                  60

Ile Ala Ala Lys Glu Glu Lys Pro Ala Ile Ala Ala
65                  70                  75
```

<210> SEQ ID NO 54
<211> LENGTH: 76
<212> TYPE: PRT
<213> ORGANISM: Methanosarcina-vacuolata

<400> SEQUENCE: 54

Met Val Ser Gln Ser Pro Asp Ser Ser Leu Ala Glu Val Leu Asp
1               5                   10                  15

Arg Ile Leu Asp Lys Gly Ile Val Val Asp Thr Trp Ala Arg Val Ser
                20                  25                  30

Leu Val Gly Ile Glu Ile Leu Ala Ile Glu Ala Arg Val Val Ala
            35                  40                  45

Ser Val Asp Thr Phe Leu His Tyr Ala Glu Glu Ile Thr Lys Ile Glu
        50                  55                  60

Ile Ala Ala Arg Glu Glu Lys Pro Val Ile Ala Ala
65                  70                  75

<210> SEQ ID NO 55
<211> LENGTH: 76
<212> TYPE: PRT
<213> ORGANISM: Methanosarcina-vacuolata

<400> SEQUENCE: 55

Met Val Ser Gln Ser Pro Asp Cys Ser Leu Ala Glu Val Leu Asp
1               5                   10                  15

Arg Ile Leu Asp Lys Gly Ile Val Val Asp Thr Trp Ala Arg Val Ser
                20                  25                  30

Leu Val Gly Ile Glu Ile Leu Ala Ile Glu Ala Arg Val Val Ala
            35                  40                  45

Ser Val Asp Thr Phe Leu His Tyr Ala Glu Glu Ile Thr Lys Ile Glu
        50                  55                  60

Ile Ala Ala Arg Glu Glu Lys Pro Val Ile Ala Ala
65                  70                  75

<210> SEQ ID NO 56
<211> LENGTH: 87
<212> TYPE: PRT
<213> ORGANISM: Haladaptatus-paucihalophilus-DX253

<400> SEQUENCE: 56

Met Val Gln Ala Glu Pro Asn Ser Ser Leu Ala Asp Val Leu Asp
1               5                   10                  15

Arg Ile Leu Asp Lys Gly Val Val Ile Asp Val Trp Ala Arg Ile Ser
                20                  25                  30

Val Val Gly Ile Glu Val Leu Thr Val Glu Ala Arg Val Val Ala
            35                  40                  45

Ser Val Asp Thr Phe Leu His Tyr Ala Lys Glu Met Ala Lys Leu Glu
        50                  55                  60

Arg Ala Ser Ser Glu Asp Glu Ile Asp Phe Glu Gln Val Glu Val Ala
65                  70                  75                  80

Ser Pro Glu Ala Ser Thr Ser
                85

<210> SEQ ID NO 57
<211> LENGTH: 73
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (34)..(34)

<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid

<400> SEQUENCE: 57

```
Met Ser Ile Gln Lys Ser Thr Xaa Ser Ser Leu Ala Glu Val Ile
1               5                   10                  15

Asp Arg Ile Leu Asp Lys Gly Ile Val Ile Asp Ala Phe Ala Arg Val
            20                  25                  30

Ser Xaa Val Gly Ile Glu Ile Leu Thr Ile Glu Ala Arg Val Val Ile
        35                  40                  45

Ala Ser Val Asp Thr Trp Leu Arg Tyr Ala Glu Ala Val Gly Leu Leu
    50                  55                  60

Asp Val Glu Glu Gly Leu Pro Arg Xaa
65                  70
```

<210> SEQ ID NO 58
<211> LENGTH: 86
<212> TYPE: PRT
<213> ORGANISM: Bacillus-megaterium

<400> SEQUENCE: 58

```
Met Ser Ile Gln Lys Ser Thr Asp Ser Ser Leu Ala Glu Val Ile
1               5                   10                  15

Asp Arg Ile Leu Asp Lys Gly Ile Val Ile Asp Ala Phe Ala Arg Val
            20                  25                  30

Ser Leu Val Gly Ile Glu Ile Leu Thr Ile Glu Ala Arg Val Val Ile
        35                  40                  45

Ala Ser Val Asp Thr Trp Leu Arg Tyr Ala Glu Ala Val Gly Leu Leu
    50                  55                  60

Thr Asp Lys Val Glu Glu Gly Leu Pro Gly Arg Thr Glu Arg
65                  70                  75                  80

Gly Ala Gly Leu Ser Phe
                85
```

<210> SEQ ID NO 59
<211> LENGTH: 88
<212> TYPE: PRT
<213> ORGANISM: Bacillus-megaterium

<400> SEQUENCE: 59

```
Met Ser Ile Gln Lys Ser Thr Asn Ser Ser Leu Ala Glu Val Ile
1               5                   10                  15

Asp Arg Ile Leu Asp Lys Gly Ile Val Ile Asp Ala Phe Ala Arg Val
            20                  25                  30

Ser Val Val Gly Ile Glu Ile Leu Thr Ile Glu Ala Arg Val Val Ile
        35                  40                  45

Ala Ser Val Asp Thr Trp Leu Arg Tyr Ala Glu Ala Val Gly Leu Leu
    50                  55                  60

Arg Asp Asp Val Glu Glu Asn Gly Leu Pro Glu Arg Ser Asn Ser Ser
65                  70                  75                  80

Glu Gly Gln Pro Arg Phe Ser Ile
                85
```

<210> SEQ ID NO 60
<211> LENGTH: 72
<212> TYPE: PRT

<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid

<400> SEQUENCE: 60

Met Ala Lys Val Gln Lys Ser Thr Asp Ser Ser Ser Leu Ala Glu Val
1               5                   10                  15

Val Asp Arg Ile Leu Asp Lys Gly Ile Val Ile Asp Ala Trp Xaa Lys
            20                  25                  30

Val Ser Leu Val Gly Ile Glu Leu Leu Ser Ile Glu Ala Arg Val Val
        35                  40                  45

Ile Ala Ser Val Glu Thr Tyr Leu Lys Tyr Ala Glu Ala Ile Gly Leu
    50                  55                  60

Thr Ala Xaa Ala Ala Ala Pro Ala
65                  70

<210> SEQ ID NO 61
<211> LENGTH: 73
<212> TYPE: PRT
<213> ORGANISM: Burkholderia-sp-Bp5365

<400> SEQUENCE: 61

Met Ala Lys Val Gln Lys Ser Thr Asp Ser Ser Ser Leu Ala Glu Val
1               5                   10                  15

Val Asp Arg Ile Leu Asp Lys Gly Ile Val Ile Asp Val Trp Ala Lys
            20                  25                  30

Val Ser Leu Val Gly Ile Glu Leu Leu Ser Ile Glu Ala Arg Val Val
        35                  40                  45

Ile Ala Ser Val Glu Thr Tyr Leu Lys Tyr Ala Glu Ala Ile Gly Leu
    50                  55                  60

Thr Ala Thr Ala Ala Ala Pro Thr Ala
65                  70

<210> SEQ ID NO 62
<211> LENGTH: 72
<212> TYPE: PRT
<213> ORGANISM: Desulfobacterium-vacuolatum-DSM-3385

<400> SEQUENCE: 62

Met Ala Lys Val Gln Lys Thr Thr Asp Ser Ser Ser Leu Ala Glu Val
1               5                   10                  15

Val Asp Arg Ile Leu Asp Lys Gly Ile Val Val Asp Ala Trp Ala Lys
            20                  25                  30

Ile Ser Leu Val Gly Ile Glu Leu Ile Ser Ile Glu Ala Arg Val Val
        35                  40                  45

Ile Ala Ser Val Glu Thr Tyr Leu Lys Tyr Ala Glu Ala Ile Gly Leu
    50                  55                  60

Thr Ala Ala Ala Ala Ala Pro Ala
65                  70

<210> SEQ ID NO 63
<211> LENGTH: 72
<212> TYPE: PRT

```
<213> ORGANISM: Desulfomonile-tiedjei-DSM-6799

<400> SEQUENCE: 63

Met Ala Lys Ile Ala Lys Ser Thr Asp Ser Ser Leu Ala Glu Val
1               5                   10                  15

Val Asp Arg Ile Leu Asp Lys Gly Ile Val Ile Asp Ala Trp Ala Lys
            20                  25                  30

Val Ser Leu Val Gly Ile Glu Leu Ser Val Glu Ala Arg Val Val
        35                  40                  45

Ile Ala Ser Val Glu Thr Tyr Leu Lys Tyr Ala Glu Ala Ile Gly Leu
    50                  55                  60

Thr Ala Ser Ala Ala Pro Ala
65                  70

<210> SEQ ID NO 64
<211> LENGTH: 72
<212> TYPE: PRT
<213> ORGANISM: Isosphaera-pallida-ATCC-43644

<400> SEQUENCE: 64

Met Ala Lys Val Thr Lys Ser Thr Asp Ser Ser Leu Ala Glu Val
1               5                   10                  15

Val Asp Arg Ile Leu Asp Lys Gly Ile Val Ile Asp Ala Phe Ala Lys
            20                  25                  30

Val Ser Leu Val Gly Ile Glu Leu Ser Val Glu Ala Arg Val Val
        35                  40                  45

Ile Ala Ser Val Glu Thr Tyr Leu Lys Tyr Ala Glu Ala Ile Gly Leu
    50                  55                  60

Thr Ala Ser Ala Ala Thr Pro Ala
65                  70

<210> SEQ ID NO 65
<211> LENGTH: 72
<212> TYPE: PRT
<213> ORGANISM: Lamprocystis-purpurea-DSM-4197

<400> SEQUENCE: 65

Met Ala Lys Val Ala Asn Ser Thr Asp Ser Ser Leu Ala Glu Val
1               5                   10                  15

Val Asp Arg Ile Leu Asp Lys Gly Ile Val Ile Asp Ala Trp Ile Lys
            20                  25                  30

Val Ser Leu Val Gly Ile Glu Leu Leu Ala Ile Glu Ala Arg Ile Val
        35                  40                  45

Ile Ala Ser Val Glu Thr Tyr Leu Lys Tyr Ala Glu Ala Ile Gly Leu
    50                  55                  60

Thr Ala Pro Ala Ala Ala Pro Ala
65                  70

<210> SEQ ID NO 66
<211> LENGTH: 72
<212> TYPE: PRT
<213> ORGANISM: Lamprocystis-purpurea-DSM-4197

<400> SEQUENCE: 66

Met Ala Lys Val Ala Asn Ser Thr Asp Ser Ser Leu Ala Glu Val
1               5                   10                  15

Val Asp Arg Ile Leu Asp Lys Gly Ile Val Ile Asp Ala Trp Leu Lys
            20                  25                  30
```

```
Val Ser Leu Val Gly Ile Glu Leu Ala Val Glu Ala Arg Val Val
            35                  40                  45

Ile Ala Ser Val Glu Thr Tyr Leu Lys Tyr Ala Glu Ala Ile Gly Leu
    50                  55                  60

Thr Ala Pro Ala Ala Ala Pro Ala
65                  70

<210> SEQ ID NO 67
<211> LENGTH: 72
<212> TYPE: PRT
<213> ORGANISM: Legionella-drancourtii-LLAP12

<400> SEQUENCE: 67

Met Ala Lys Val Gln Lys Ser Thr Asp Ser Ser Leu Ala Glu Val
1               5                   10                  15

Ile Asp Arg Ile Leu Asp Lys Gly Ile Val Ile Asp Val Trp Ala Lys
                20                  25                  30

Val Ser Leu Val Gly Ile Glu Leu Leu Ser Ile Glu Ala Arg Val Val
            35                  40                  45

Ile Ala Ser Val Glu Thr Tyr Leu Lys Tyr Ala Glu Ala Ile Gly Leu
    50                  55                  60

Thr Ala Thr Ala Ser His Pro Ala
65                  70

<210> SEQ ID NO 68
<211> LENGTH: 72
<212> TYPE: PRT
<213> ORGANISM: Psychromonas-Ingrahamii

<400> SEQUENCE: 68

Met Ala Asn Val Gln Lys Thr Thr Asp Ser Ser Gly Leu Ala Glu Val
1               5                   10                  15

Ile Asp Arg Ile Leu Asp Lys Gly Ile Val Ile Asp Ala Phe Val Lys
                20                  25                  30

Val Ser Leu Val Gly Ile Glu Leu Leu Ser Ile Glu Ala Arg Val Val
            35                  40                  45

Ile Ala Ser Val Glu Thr Tyr Leu Lys Tyr Ala Glu Ala Ile Gly Leu
    50                  55                  60

Thr Ala Ser Ala Ala Thr Pro Ala
65                  70

<210> SEQ ID NO 69
<211> LENGTH: 72
<212> TYPE: PRT
<213> ORGANISM: Psychromonas-Ingrahamii

<400> SEQUENCE: 69

Met Ala Asn Val Gln Lys Ser Thr Asp Ser Ser Gly Leu Ala Glu Val
1               5                   10                  15

Val Asp Arg Ile Leu Glu Lys Gly Ile Val Ile Asp Ala Phe Val Lys
                20                  25                  30

Val Ser Leu Val Gly Ile Glu Leu Leu Ser Ile Glu Ala Arg Val Val
            35                  40                  45

Ile Ala Ser Val Glu Thr Tyr Leu Lys Tyr Ala Glu Ala Ile Gly Leu
    50                  55                  60

Thr Ala Ser Ala Ala Thr Pro Ala
65                  70
```

-continued

<210> SEQ ID NO 70
<211> LENGTH: 72
<212> TYPE: PRT
<213> ORGANISM: Serratia-39006

<400> SEQUENCE: 70

Met Ala Lys Val Gln Lys Ser Thr Asp Ser Ser Leu Ala Glu Val
1               5                   10                  15

Val Asp Arg Ile Leu Asp Lys Gly Ile Val Ile Asp Ala Trp Val Lys
            20                  25                  30

Val Ser Leu Val Gly Ile Glu Leu Leu Ser Ile Glu Ala Arg Val Val
        35                  40                  45

Ile Ala Ser Val Glu Thr Tyr Leu Lys Tyr Ala Glu Ala Ile Gly Leu
    50                  55                  60

Thr Ala Ser Ala Ala Thr Pro Ala
65                  70

<210> SEQ ID NO 71
<211> LENGTH: 72
<212> TYPE: PRT
<213> ORGANISM: Thiocapsa-rosea-strain-DSM-235-Ga0242571-11

<400> SEQUENCE: 71

Met Ala Lys Val Ala Asn Ser Thr Asp Ser Ser Ser Leu Ala Glu Val
1               5                   10                  15

Val Asp Arg Ile Leu Asp Lys Gly Ile Val Ile Asp Ala Trp Val Lys
            20                  25                  30

Val Ser Leu Val Gly Ile Glu Leu Leu Ala Ile Glu Ala Arg Val Val
        35                  40                  45

Ile Ala Ser Val Glu Thr Tyr Leu Lys Tyr Ala Glu Ala Ile Gly Leu
    50                  55                  60

Thr Ala Pro Ala Ala Ala Pro Ala
65                  70

<210> SEQ ID NO 72
<211> LENGTH: 70
<212> TYPE: PRT
<213> ORGANISM: Bradyrhizobium-oligotrophicum-S58

<400> SEQUENCE: 72

Met Ala Ile Glu Lys Ala Thr Ser Ser Ser Leu Ala Glu Val Ile
1               5                   10                  15

Asp Arg Ile Leu Asp Lys Gly Val Val Ile Asp Ala Phe Val Arg Val
            20                  25                  30

Ser Leu Val Gly Ile Glu Leu Leu Ser Ile Glu Leu Arg Ala Val Val
        35                  40                  45

Ala Ser Val Glu Thr Trp Leu Lys Tyr Ala Glu Ala Ile Gly Leu Val
    50                  55                  60

Ala Gln Pro Met Pro Ala
65                  70

<210> SEQ ID NO 73
<211> LENGTH: 71
<212> TYPE: PRT
<213> ORGANISM: Desulfotomaculum-acetoxidans-DSM-771

<400> SEQUENCE: 73

Met Ala Val Lys His Ser Val Ala Ser Ser Ser Leu Val Glu Val Ile
1               5                   10                  15

```
Asp Arg Ile Leu Glu Lys Gly Ile Val Ile Asp Ala Trp Ala Arg Val
            20                  25                  30

Ser Leu Val Gly Ile Glu Leu Leu Ala Ile Glu Ala Arg Val Val Val
        35                  40                  45

Ala Ser Val Asp Thr Phe Leu Lys Tyr Ala Glu Ala Ile Gly Leu Thr
    50                  55                  60

Lys Phe Ala Ala Val Pro Ala
65                  70

<210> SEQ ID NO 74
<211> LENGTH: 67
<212> TYPE: PRT
<213> ORGANISM: Octadecabacter-antarcticus-307

<400> SEQUENCE: 74

Met Ala Val Asn Lys Met Asn Ser Ser Ser Leu Ala Glu Val Val
1               5                   10                  15

Asp Arg Ile Leu Asp Lys Gly Val Val Ile Asp Ala Trp Val Arg Val
            20                  25                  30

Ser Leu Val Gly Ile Glu Leu Ile Ala Val Glu Ala Arg Val Val Ile
        35                  40                  45

Ala Gly Val Asp Thr Tyr Leu Lys Tyr Ala Glu Ala Val Gly Leu Thr
    50                  55                  60

Ala Glu Ala
65

<210> SEQ ID NO 75
<211> LENGTH: 67
<212> TYPE: PRT
<213> ORGANISM: Octadecabacter-arcticus-238

<400> SEQUENCE: 75

Met Ala Val Ser Lys Met Asn Ser Ser Ser Leu Ala Glu Val Val
1               5                   10                  15

Asp Arg Ile Leu Asp Lys Gly Val Val Ile Asp Ala Trp Val Arg Val
            20                  25                  30

Ser Leu Val Gly Ile Glu Leu Ile Ala Val Glu Ala Arg Val Val Ile
        35                  40                  45

Ala Gly Val Asp Thr Tyr Leu Lys Tyr Ala Glu Ala Val Gly Leu Thr
    50                  55                  60

Ala Glu Ala
65

<210> SEQ ID NO 76
<211> LENGTH: 68
<212> TYPE: PRT
<213> ORGANISM: Pelodictyon-luteolum-DSM-273

<400> SEQUENCE: 76

Met Ala Val Glu Lys Thr Ile Gly Ser Ser Leu Val Glu Val Ile
1               5                   10                  15

Asp Arg Ile Leu Asp Lys Gly Val Val Val Asp Ala Trp Val Arg Met
            20                  25                  30

Ser Leu Val Gly Ile Glu Leu Leu Ala Ile Glu Ala Arg Val Val Val
        35                  40                  45

Ala Ser Val Glu Thr Tyr Leu Lys Tyr Ala Glu Ala Ile Gly Leu Thr
    50                  55                  60

Ala Lys Ala Ala
```

<210> SEQ ID NO 77
<211> LENGTH: 68
<212> TYPE: PRT
<213> ORGANISM: Pelodictyon-luteolum-DSM-273

<400> SEQUENCE: 77

Met Ala Val Glu Lys Thr Ile Gly Ser Ser Leu Val Glu Val Ile
1               5                   10                  15

Asp Arg Ile Leu Asp Lys Gly Val Val Val Asp Ala Trp Val Arg Val
            20                  25                  30

Ser Leu Val Gly Ile Glu Leu Leu Ala Ile Glu Ala Arg Val Val Val
        35                  40                  45

Ala Ser Val Glu Thr Tyr Leu Lys Tyr Ala Glu Ala Ile Gly Leu Thr
    50                  55                  60

Ala Lys Ala Ala
65

<210> SEQ ID NO 78
<211> LENGTH: 68
<212> TYPE: PRT
<213> ORGANISM: Pelodictyon-phaeoclathratiforme

<400> SEQUENCE: 78

Met Ser Val Glu Lys Thr Ile Gly Ser Ser Leu Val Glu Val Ile
1               5                   10                  15

Asp Arg Ile Leu Asp Lys Gly Val Val Val Asp Ala Trp Val Arg Val
            20                  25                  30

Ser Leu Val Gly Ile Glu Leu Leu Ala Ile Glu Ala Arg Val Val Val
        35                  40                  45

Ala Ser Val Glu Thr Tyr Leu Lys Tyr Ala Glu Ala Ile Gly Leu Thr
    50                  55                  60

Ala Lys Ala Ala
65

<210> SEQ ID NO 79
<211> LENGTH: 70
<212> TYPE: PRT
<213> ORGANISM: Rhodobacter-capsulatus-SB-1003

<400> SEQUENCE: 79

Met Ala Ile Glu Lys Ser Leu Ala Ser Ala Ser Ile Ala Glu Val Ile
1               5                   10                  15

Asp Arg Val Leu Asp Lys Gly Ile Val Val Asp Ala Phe Val Arg Ile
            20                  25                  30

Ser Leu Val Gly Ile Glu Leu Leu Ala Ile Glu Leu Arg Ala Val Val
        35                  40                  45

Ala Ser Val Glu Thr Trp Leu Lys Tyr Ala Glu Ala Ile Gly Leu Thr
    50                  55                  60

Val Asp Pro Gln Thr Pro
65                  70

<210> SEQ ID NO 80
<211> LENGTH: 70
<212> TYPE: PRT
<213> ORGANISM: Rhodobacter-sphaeroides

<400> SEQUENCE: 80

```
Met Ala Ile Glu Lys Ser Val Ala Ser Ile Ala Glu Val Ile
1               5                   10                  15

Asp Arg Ile Leu Asp Lys Gly Val Val Ile Asp Ala Phe Val Arg Val
            20                  25                  30

Ser Leu Val Gly Ile Glu Leu Ile Ala Ile Glu Val Arg Ala Val Val
            35                  40                  45

Ala Ser Ile Glu Thr Trp Leu Lys Tyr Ala Glu Ala Val Gly Leu Thr
    50                  55                  60

Val Asp Pro Ala Thr Thr
65              70
```

<210> SEQ ID NO 81
<211> LENGTH: 245
<212> TYPE: PRT
<213> ORGANISM: Anabaena-flos-aquae

<400> SEQUENCE: 81

```
Met Ser Ile Pro Leu Tyr Leu Tyr Gly Ile Phe Pro Asn Thr Ile Pro
1               5                   10                  15

Glu Thr Leu Glu Leu Glu Gly Leu Asp Lys Gln Pro Val His Ser Gln
            20                  25                  30

Val Val Asp Glu Phe Cys Phe Leu Tyr Ser Glu Ala Arg Gln Glu Lys
            35                  40                  45

Tyr Leu Ala Ser Arg Arg Asn Leu Leu Thr His Glu Lys Val Leu Glu
    50                  55                  60

Gln Thr Met His Ala Gly Phe Arg Val Leu Leu Pro Leu Arg Phe Gly
65                  70                  75                  80

Leu Val Val Lys Asp Trp Glu Thr Ile Met Ser Gln Leu Ile Asn Pro
                85                  90                  95

His Lys Asp Gln Leu Asn Gln Leu Phe Gln Lys Leu Ala Gly Lys Arg
            100                 105                 110

Glu Val Ser Ile Lys Ile Phe Trp Asp Ala Lys Ala Glu Leu Gln Thr
            115                 120                 125

Met Met Glu Ser His Gln Asp Leu Lys Gln Gln Arg Asp Asn Met Glu
130                 135                 140

Gly Lys Lys Leu Ser Met Glu Glu Val Ile Gln Ile Gly Gln Leu Ile
145                 150                 155                 160

Glu Ile Asn Leu Leu Ala Arg Lys Gln Ala Val Ile Glu Val Phe Ser
                165                 170                 175

Gln Glu Leu Asn Pro Phe Ala Gln Glu Ile Val Val Ser Asp Pro Met
            180                 185                 190

Thr Glu Glu Met Ile Tyr Asn Ala Ala Phe Leu Ile Pro Trp Glu Ser
            195                 200                 205

Glu Ser Glu Phe Ser Glu Arg Val Glu Val Ile Asp Gln Lys Phe Gly
    210                 215                 220

Asp Arg Leu Arg Ile Arg Tyr Asn Asn Phe Thr Ala Pro Tyr Thr Phe
225                 230                 235                 240

Ala Gln Leu Asp Ser
                245
```

<210> SEQ ID NO 82
<211> LENGTH: 268
<212> TYPE: PRT
<213> ORGANISM: Ancylobacter-aquaticus-strain-UV5

<400> SEQUENCE: 82

Met Ser Ala Thr Leu Ser Ala Pro Gly Thr Ala Asn Val Ala Val Glu
1               5                   10                  15

Ala Thr Ala Ala Ala Asp Gly Lys Tyr Leu Tyr Gly Ile Ile Glu Ala
            20                  25                  30

Pro Ala Pro Ala Thr Phe Asp Val Pro Ala Ile Gly Gly Arg Gly Asp
            35                  40                  45

Val Val His Thr Ile Ala Leu Gly Arg Leu Ala Ala Val Val Ser Asn
        50                  55                  60

Ser Pro Arg Ile Asp Tyr Asp Asn Ser Arg Arg Asn Met Leu Ala His
65                  70                  75                  80

Thr Lys Val Leu Glu Ala Val Met Ala Arg His Thr Leu Leu Pro Val
                85                  90                  95

Cys Phe Gly Thr Val Gly Ser Asp Ala Glu Val Ile Ile Glu Lys Ile
            100                 105                 110

Leu Arg Glu Arg Arg Asp Glu Leu Ala Gly Leu Leu Gly Gln Met His
            115                 120                 125

Gly Arg Met Glu Leu Gly Leu Lys Ala Ser Trp Arg Glu Glu Ile Ile
        130                 135                 140

Phe Glu Glu Val Leu Ala Glu Asn Pro Ala Ile Arg Lys Leu Arg Asp
145                 150                 155                 160

Ala Leu Val Gly Arg Ser Pro Asp Gln Ser His Tyr Glu Arg Ile Gln
                165                 170                 175

Leu Gly Glu Arg Ile Gly Gln Ala Leu Gln Arg Lys Arg Gln Asp Asp
            180                 185                 190

Glu Glu Arg Ile Leu Glu Arg Val Arg Pro Phe Val His Lys Thr Arg
        195                 200                 205

Leu Asn Lys Leu Ile Gly Asp Arg Met Val Ile Asn Ala Ala Phe Leu
210                 215                 220

Val Asp Ala Ala Val Glu Ser Arg Leu Asp Ala Ser Ile Arg Ala Met
225                 230                 235                 240

Asp Glu Glu Trp Gly Gly Arg Leu Ala Phe Lys Tyr Val Gly Pro Val
                245                 250                 255

Pro Pro Tyr Asn Phe Val Thr Ile Thr Ile His Trp
            260                 265

<210> SEQ ID NO 83
<211> LENGTH: 245
<212> TYPE: PRT
<213> ORGANISM: Aphanizomenon-flos-aquae-NIES-81

<400> SEQUENCE: 83

Met Asn Thr Gly Leu Tyr Leu Tyr Gly Ile Phe Pro Asp Pro Ile Pro
1               5                   10                  15

Glu Thr Val Asp Leu Gln Gly Leu Asp Lys Gln Ser Val His Ser Gln
            20                  25                  30

Val Val Asp Gly Phe Ser Phe Leu Tyr Ser Asp Ala Cys Gln Glu Lys
        35                  40                  45

Tyr Leu Ala Ser Arg Arg Asn Leu Leu Thr His Glu Lys Val Leu Glu
    50                  55                  60

Gln Ala Met His Glu Gly Phe Val Leu Leu Pro Leu Arg Phe Gly
65                  70                  75                  80

Leu Val Val Lys Asp Trp Glu Thr Ile Gln Lys Gln Leu Ile Glu Pro
                85                  90                  95

Tyr Lys Glu Gln Leu Asn Glu Leu Phe Gln Lys Leu Ala Gly Gln Arg
            100                 105                 110

-continued

```
Glu Val Ser Ile Lys Ile Leu Trp Asp Ser Lys Ser Glu Leu Gln Ala
            115                 120                 125

Met Met Glu Ser Asn Gln Asp Leu Lys Gln Gln Arg Asp Asn Met Glu
130                 135                 140

Gly Lys Lys Leu Lys Met Glu Glu Ile Ile Gln Ile Gly Gln Leu Ile
145                 150                 155                 160

Glu Ser Asn Leu Ala Ala Arg Lys Gln Thr Val Ile Gln Glu Phe Phe
                165                 170                 175

Asn Asn Leu His Pro Leu Ala Lys Glu Ile Ile Glu Ser Glu Pro Met
                180                 185                 190

Thr Glu Glu Met Ile Tyr Asn Ala Ala Phe Leu Ile Pro Trp Glu Thr
            195                 200                 205

Glu Ser Val Phe Ser Glu Arg Val Glu Ala Ile Asp Arg Lys Phe Gly
            210                 215                 220

Asp Arg Leu Arg Ile Arg Tyr Asn Asn Phe Thr Ala Pro Tyr Thr Phe
225                 230                 235                 240

Ala Gln Leu Ala Ser
                245
```

<210> SEQ ID NO 84
<211> LENGTH: 245
<212> TYPE: PRT
<213> ORGANISM: Aphanothece-halophytica-strain-PCC-7418

<400> SEQUENCE: 84

```
Met Ala Glu Gly Phe Tyr Leu Tyr Gly Ile Phe Pro Pro Gly Pro
1               5                   10                  15

Gln Thr Ile Ala Val Gln Gly Leu Asp Lys Gln Pro Ile Phe Ser His
                20                  25                  30

Thr Val Glu Gly Phe Thr Phe Leu Tyr Ser Glu Ala Gln Gln Ser Arg
            35                  40                  45

Tyr Leu Ala Ser Arg Arg Asn Leu Ile Thr His Thr Lys Val Leu Glu
50                  55                  60

Glu Ala Met Glu Gln Gly Phe Arg Thr Leu Leu Pro Leu Gln Phe Gly
65                  70                  75                  80

Leu Val Val Pro Asp Trp Glu Ser Val Ser Gln Asp Leu Leu Gln His
                85                  90                  95

Gln Ser Glu Thr Leu Gln Leu Leu Phe Gln Arg Leu Glu Gly Lys Arg
            100                 105                 110

Glu Val Ser Leu Lys Ile Tyr Trp Glu Thr Asp Ala Glu Leu Asn Ala
            115                 120                 125

Leu Leu Glu Glu Asn Pro Asp Leu Lys Ala Arg Arg Asp Asn Leu Glu
130                 135                 140

Gly Lys Asn Leu Ser Met Asp Glu Val Ile Gln Ile Gly Gln Ala Leu
145                 150                 155                 160

Glu Gln Ala Met Glu Arg Arg Lys Gln Glu Val Ile Thr Arg Phe Glu
                165                 170                 175

Asp Ala Leu Ile Pro Phe Ala Val Glu Thr Gln Glu Asn Asp Val Leu
                180                 185                 190

Thr Glu Thr Met Ile Tyr Asn Thr Ala Phe Leu Ile Pro Trp Glu Ser
            195                 200                 205

Glu Pro Glu Phe Gly Glu Ala Val Glu Thr Val Asp Ala Glu Phe Ala
            210                 215                 220

Pro Arg Leu Lys Ile Arg Tyr Asn Asn Phe Thr Pro Pro Tyr Asn Phe
```

```
                   225                 230                 235                 240

Val Glu Leu Arg Glu
                245

<210> SEQ ID NO 85
<211> LENGTH: 261
<212> TYPE: PRT
<213> ORGANISM: Aquabacter-spiritensis-strain-DSM-9035

<400> SEQUENCE: 85

Met Met Gln Thr Asp Thr Leu Ala Pro Ala Glu Thr Val Ala Glu Gly
1               5                   10                  15

Lys Tyr Leu Tyr Cys Leu Ile Asp Ala Pro Ala Pro Asp Thr Phe Ala
                20                  25                  30

Ser Pro Gly Ile Gly Gly Arg Gly Asp Val Val His Thr Ile Thr Val
            35                  40                  45

Gly Arg Leu Ala Ala Val Val Ser Asp Ser Pro Arg Ile Glu Tyr Glu
        50                  55                  60

Asn Ser Arg Arg Asn Met Met Ala His Thr Lys Val Leu Glu Glu Val
65                  70                  75                  80

Met Ala Arg His Thr Met Leu Pro Val Cys Phe Gly Thr Val Ala Thr
                85                  90                  95

Gly Pro Asp Pro Ile Ser Gly Lys Ile Leu Glu Gly Arg Arg Asp Glu
                100                 105                 110

Leu Val Gly Leu Leu Glu Gln Met Arg Gly Arg Leu Glu Leu Gly Leu
            115                 120                 125

Lys Ala Thr Trp Arg Glu Asp Val Ile Phe Ala Glu Ile Leu Gln Glu
        130                 135                 140

Asn Pro Ala Ile Ala Lys Leu Arg Asp Ser Leu Val Gly Arg Ser Pro
145                 150                 155                 160

Glu Lys Ser His Phe Glu Arg Ile Arg Leu Gly Glu Met Ile Gly Gln
                165                 170                 175

Ala Met Glu Arg Lys Arg Arg Asp Asp Glu Glu Arg Ile Leu Glu Arg
                180                 185                 190

Val Arg Pro Phe Val His Lys Thr Lys Leu Asn Lys Pro Ile Gly Asp
            195                 200                 205

Arg Met Ile Leu Asn Ala Ala Val Leu Val Glu Ala Ala Arg Glu Ala
        210                 215                 220

Gly Leu Asp Gln Ala Val Arg Gln Met Asp Ala Glu Trp Gly Ala Arg
225                 230                 235                 240

Leu Ser Phe Lys Tyr Val Gly Pro Val Pro Pro Tyr Asn Phe Val Thr
                245                 250                 255

Ile Thr Ile His Trp
            260

<210> SEQ ID NO 86
<211> LENGTH: 255
<212> TYPE: PRT
<213> ORGANISM: Bacillus-megaterium

<400> SEQUENCE: 86

Met Ser Glu Thr Asn Glu Thr Gly Ile Tyr Ile Phe Ser Ala Ile Gln
1               5                   10                  15

Thr Asp Lys Asp Glu Glu Phe Gly Ala Val Glu Val Glu Gly Thr Lys
                20                  25                  30

Ala Glu Thr Phe Leu Ile Arg Tyr Lys Asp Ala Ala Met Val Ala Ala
```

```
            35                  40                  45
Glu Val Pro Met Lys Ile Tyr His Pro Asn Arg Gln Asn Leu Leu Met
 50                  55                  60

His Gln Asn Ala Val Ala Ala Ile Met Asp Lys Asn Asp Thr Val Ile
 65                  70                  75                  80

Pro Ile Ser Phe Gly Asn Val Phe Lys Ser Lys Glu Asp Val Lys Val
                 85                  90                  95

Leu Leu Glu Asn Leu Tyr Pro Gln Phe Glu Lys Leu Phe Pro Ala Ile
                100                 105                 110

Lys Gly Lys Ile Glu Val Gly Leu Lys Val Ile Gly Lys Lys Glu Trp
            115                 120                 125

Leu Glu Lys Lys Val Asn Glu Asn Pro Glu Leu Glu Lys Val Ser Ala
130                 135                 140

Ser Val Lys Gly Lys Ser Glu Ala Ala Gly Tyr Tyr Glu Arg Ile Gln
145                 150                 155                 160

Leu Gly Gly Met Ala Gln Lys Met Phe Thr Ser Leu Gln Lys Glu Val
                165                 170                 175

Lys Thr Asp Val Phe Ser Pro Leu Glu Glu Ala Ala Glu Ala Ala Lys
            180                 185                 190

Ala Asn Glu Pro Thr Gly Glu Thr Met Leu Leu Asn Ala Ser Phe Leu
        195                 200                 205

Ile Asn Arg Glu Asp Glu Ala Lys Phe Asp Lys Val Asn Glu Ala
    210                 215                 220

His Glu Asn Trp Lys Asp Lys Ala Asp Phe His Tyr Ser Gly Pro Trp
225                 230                 235                 240

Pro Ala Tyr Asn Phe Val Asn Ile Arg Leu Lys Val Glu Lys
                245                 250                 255

<210> SEQ ID NO 87
<211> LENGTH: 258
<212> TYPE: PRT
<213> ORGANISM: Bradyrhizobium-oligotrophicum-S58

<400> SEQUENCE: 87

Met Ser Asn Gln Pro Ile Tyr Val Tyr Gly Leu Ile Arg Ala Glu Asp
 1               5                  10                  15

His Gln Pro Leu Ala Val Arg Ala Val Gly Asp Ser Glu Gln Pro Val
            20                  25                  30

Asn Ile Ile Gly Ser Gly Asn Val Ala Leu Val Ser Thr Ile Asp
         35                  40                  45

Leu Pro Glu Ile Met Pro Thr Arg Arg His Met Leu Ala His Thr Lys
 50                  55                  60

Val Leu Glu Ala Ala Met Ala Asn Gly Pro Val Leu Pro Met Arg Phe
 65                  70                  75                  80

Gly Ile Ile Val Pro Asn Pro Ala Thr Leu Leu Arg Val Ile Gly Phe
                 85                  90                  95

Arg His Gln Glu Leu Arg Ala Arg Leu Asp Glu Ile Asp Gly Arg Ile
            100                 105                 110

Glu Val Ala Leu Lys Ala Ser Trp Asp Glu Gln Phe Met Trp Arg Gln
        115                 120                 125

Leu Ala Ser Glu His Pro Asp Leu Ala Val Ser Gly Arg Thr Met Met
    130                 135                 140

Gly Arg Gly Glu Gln Gln Ser Tyr Tyr Asp Arg Ile Glu Leu Gly Arg
145                 150                 155                 160
```

Ala Ile Gly Ala Ala Leu Glu Glu Arg Arg Thr Ala Ala Arg Leu Gln
            165                 170                 175

Leu Leu Gln Thr Val Thr Pro Phe Ala Val Gln Val Lys Glu Leu Thr
        180                 185                 190

Pro Val Asp Asp Ala Met Phe Ala His Leu Ala Leu Leu Val Glu Lys
        195                 200                 205

Gly Ala Glu Pro Ser Leu Tyr Gln Thr Val Glu Ala Leu Glu Arg Ser
        210                 215                 220

Asn Asp Ser Gly Leu Lys Phe Arg Tyr Val Ala Pro Ile Pro Pro Tyr
225                 230                 235                 240

Asn Phe Val Ala Val Thr Leu Asp Trp Glu Gln His Glu Gln Ala Pro
            245                 250                 255

Arg Arg

<210> SEQ ID NO 88
<211> LENGTH: 249
<212> TYPE: PRT
<213> ORGANISM: Artificial Sequence
<220> FEATURE:
<223> OTHER INFORMATION: Synthetic Polypeptide

<400> SEQUENCE: 88

Met Asn Ser Arg Asn Gly Ala Arg Tyr Leu Tyr Ala Val Gln His Ala
1               5                   10                  15

Arg Asp Val Pro Ala Ser Leu Pro Ala Gly Ile Gly Ala Ala Val
            20                  25                  30

Arg Ala Leu Thr Asp Gly Asp Val Ala Ala Ile Val Ser Asp Thr Gly
        35                  40                  45

Leu Ala Lys Val Arg Pro Glu Arg Arg His Leu Leu Ala His His Thr
 50                  55                  60

Val Ile Gln Ser Leu Ala Ala Gly Thr Val Leu Pro Val Ala Phe
65                  70                  75                  80

Gly Thr Ile Ala Thr Ser Glu Val Ala Leu Arg Arg Met Leu Arg Lys
                85                  90                  95

His Arg Asn Ala Leu Ala Gly Glu Leu Ala Arg Leu Val Asp His Val
            100                 105                 110

Glu Met Ser Val Arg Leu Asn Trp Asp Val Thr Asp Leu Phe Arg His
        115                 120                 125

Leu Ile Asp Val Arg Pro Asp Leu Lys Ala Ala Arg Asp Ala Met Leu
130                 135                 140

Ala Leu Gly Ser Ala Val Thr Arg Asp Lys Ile Glu Leu Gly Ser
145                 150                 155                 160

Arg Phe Glu Arg Val Leu Asn Glu Glu Arg Ala Arg His Ala Ala Leu
                165                 170                 175

Val Asp Glu Ala Leu Asp Ala Cys Cys Lys Glu Ile Arg Arg Asp Pro
            180                 185                 190

Pro Arg His Glu Thr Glu Ile Leu His Leu Thr Cys Leu Val Arg His
        195                 200                 205

Ala Glu Leu Gly Arg Phe Glu Ser Gly Val Ala Ala Ser Arg Glu
        210                 215                 220

Leu Asp Asp Ser Leu Val Leu Lys Tyr Ser Gly Pro Cys Pro Pro His
225                 230                 235                 240

His Phe Val Asn Leu Asn Met Ser Leu
                245

-continued

<210> SEQ ID NO 89
<211> LENGTH: 260
<212> TYPE: PRT
<213> ORGANISM: Artificial Sequence
<220> FEATURE:
<223> OTHER INFORMATION: Synthetic Polypeptide

<400> SEQUENCE: 89

Met Glu Arg Asp Gly Lys Tyr Ile Tyr Cys Ile Ile Gly Ala Asp Cys
1               5                   10                  15

Glu Cys Asp Phe Gly Pro Ile Gly Ile Gly Gly Arg Gly Asp Leu Val
            20                  25                  30

Ser Thr Ile Gly Phe Glu Gly Ile Ser Met Val Val Ser Asp His Pro
        35                  40                  45

Leu Asn Arg Phe Val Val Asp Pro Asp Gly Ile Leu Ala His Gln Arg
    50                  55                  60

Val Ile Glu Ala Val Met Lys Glu His Glu Ser Val Ile Pro Val Arg
65                  70                  75                  80

Phe Gly Thr Val Ala Ala Thr Pro Asp Glu Ile Arg Asn Leu Leu Asp
                85                  90                  95

Arg Arg Tyr Gly Glu Leu Ser Glu Leu Leu Leu Arg Leu Arg Asn Lys
            100                 105                 110

Val Glu Phe Asn Val Thr Gly Arg Trp His Asp Met Ala Ala Ile Tyr
        115                 120                 125

Lys Glu Val Glu Arg Thr His Pro Glu Ile Lys Glu Gln Arg Ala Arg
    130                 135                 140

Ile Glu Ser Met Arg Asp Gly Asp Gly Glu Ala Leu Lys Gln Ser Leu
145                 150                 155                 160

Ile Leu Asp Thr Gly His Gln Ile Glu Ala Ala Leu Glu Val Met Lys
                165                 170                 175

Glu Glu Lys Phe Asp Ala Val Ala Ser Leu Phe Arg Lys Thr Ala Met
            180                 185                 190

Ala Ser Lys Met Asn Arg Thr Thr Ser Pro Asp Met Phe Met Asn Ala
        195                 200                 205

Ala Phe Leu Ile Asp Arg Gly Arg Glu Val Glu Phe Asp Gly Ile Met
    210                 215                 220

Glu Ile Leu Gly Gln Lys Asp Ala Asp Arg Cys Asp Tyr Arg Tyr Ser
225                 230                 235                 240

Gly Pro Leu Ala Ile Phe Asn Phe Val Asp Leu Arg Ile Leu Pro Glu
                245                 250                 255

Lys Trp Glu Leu
            260

<210> SEQ ID NO 90
<211> LENGTH: 259
<212> TYPE: PRT
<213> ORGANISM: Artificial Sequence
<220> FEATURE:
<223> OTHER INFORMATION: Synthetic Polypeptide

<400> SEQUENCE: 90

Met Ala His Glu Ala Ala Glu Gln Asp Gly Leu Tyr Ile Tyr Gly Ile
1               5                   10                  15

Ile Asn Asn Ser Gly Glu Leu Asp Phe Gly Pro Ile Gly Ile Gly Gly
            20                  25                  30

Arg Glu Glu Arg Val Tyr Ala Val Ile His Asn Asp Ile Ala Ala Val
        35                  40                  45

```
Val Ser Arg Thr Val Val Lys Glu Phe Glu Pro Arg Ala Asn Met
 50                  55                  60

Ile Ala His Gln Lys Val Leu Glu Ala Val Met Val Ser His Ala Val
 65                  70                  75                  80

Leu Pro Val Arg Phe Ser Thr Val Ser Pro Gly His Asp Asp Met Lys
                 85                  90                  95

Val Glu Lys Ile Leu Glu Glu Asp Tyr Leu Arg Leu Lys Lys Leu Leu
            100                 105                 110

Val Lys Met Glu Gly Lys Lys Glu Met Gly Leu Lys Val Met Ala Asn
        115                 120                 125

Glu Glu Lys Val Tyr Glu Ser Ile Ile Thr Gly Tyr Asp Asn Ile Arg
130                 135                 140

Tyr Leu Arg Asp Lys Leu Ile Asn Leu Pro Pro Glu Lys Thr His Tyr
145                 150                 155                 160

Gln Arg Val Lys Ile Gly Glu Leu Val Ala Ala Leu Glu Lys Glu
                165                 170                 175

Val Gly Thr Tyr Lys Asp Ala Val Leu Asp Ala Leu Ser Pro Ile Ala
                180                 185                 190

Glu Glu Val Lys Val Asn Asp Ser Tyr Gly Ser Met Met Val Leu Asn
                195                 200                 205

Ala Ala Phe Leu Ile Arg Thr Ala Arg Glu Glu Phe Asp Arg Ala
210                 215                 220

Val Asn Ala Leu Asp Asp Arg Tyr His Asp Met Met Thr Phe Lys Tyr
225                 230                 235                 240

Val Gly Thr Leu Pro Pro Tyr Asn Phe Val Asn Ile Ser Ile Asn Ile
                245                 250                 255

Lys Gly Arg

<210> SEQ ID NO 91
<211> LENGTH: 343
<212> TYPE: PRT
<213> ORGANISM: Artificial Sequence
<220> FEATURE:
<223> OTHER INFORMATION: Synthetic Polypeptide

<400> SEQUENCE: 91

Met Asn Gln Ser Ile Tyr Ile Tyr Gly Ile Val Asn Glu Pro Ala Leu
 1               5                  10                  15

Ala Ala Ser Phe Val Glu Thr Asp Pro Asp Ile Tyr Ala Val Ala Ser
                 20                  25                  30

Met Gly Cys Ser Ala Ile Val Glu Asn Arg Pro Ala Ile Asp Leu Gly
             35                  40                  45

Glu Leu Asp Arg Glu Ser Leu Ala Arg Met Leu Leu Gln His Gln Gln
 50                  55                  60

Thr Leu Glu Arg Leu Met Glu Ser Gly Met Gln Leu Ile Pro Leu Lys
 65                  70                  75                  80

Leu Gly Thr Phe Val Ser Ser Ala Ala Asp Ala Ala Cys Ile Ile Glu
                 85                  90                  95

Asp Gly Tyr Asn Leu Ile Glu Arg Ile Phe Arg Glu Thr Glu Asp Ala
            100                 105                 110

His Glu Leu Glu Val Val Lys Trp Ser Ser Phe Ala Asp Leu Leu
        115                 120                 125

Gln Glu Val Val Ser Glu Gly Asp Val Gln Glu Leu Lys Arg Glu Val
130                 135                 140

Glu Ala Arg Gln Ser Ser Ser Thr Glu Asp Ala Ile Ala Val Gly Arg
```

```
            145                 150                 155                 160
        Leu Ile Lys Glu Lys Ile Asp Arg Arg Asn Ala Ala Leu Ser Ala Ser
                        165                 170                 175

Val Leu Arg Gln Leu Gly Glu Arg Ala Ser Gln Ser Lys Arg His Glu
                        180                 185                 190

Thr Met Asp Asp Glu Met Val Leu Asn Ala Ala Phe Leu Val Asn Arg
                        195                 200                 205

Gly Asp Val Asp Ala Phe Val Ala Thr Val Glu Ala Leu Asp Ser Gln
                        210                 215                 220

Tyr Leu Asn Ala Leu His Phe Arg Ile Val Gly Pro Leu Pro Cys Tyr
        225                 230                 235                 240

Ser Phe Tyr Thr Leu Glu Val Thr Ala Leu Phe Glu Glu Phe Ile Ala
                        245                 250                 255

Glu Lys Arg Ala Val Leu Gly Leu Asp Ala Arg Ser Cys Glu Ala Asp
                        260                 265                 270

Val Lys Lys Ala Tyr His Ala Lys Ala Lys Val Ala His Pro Asp Val
                        275                 280                 285

His Val Pro Ala Gly Ala Asn Asn Gly Ala Asp Phe Thr Val Leu Asn
                        290                 295                 300

Glu Ala Tyr Met Thr Leu His Asp Tyr Tyr Ser Ala Leu Arg Asn Ser
        305                 310                 315                 320

Ala Ser Ser Arg His Gly His Glu Gly Gln Asp Ser Ser Ser Val Val
                        325                 330                 335

Phe Ser Val Lys Ile Leu Asn
                        340

<210> SEQ ID NO 92
<211> LENGTH: 245
<212> TYPE: PRT
<213> ORGANISM: Artificial Sequence
<220> FEATURE:
<223> OTHER INFORMATION: Synthetic Polypeptide

<400> SEQUENCE: 92

Met Thr Glu Gly Phe Tyr Leu Tyr Gly Ile Phe Pro Pro Gly Pro
        1               5                   10                  15

Lys Thr Ile Glu Thr Gln Gly Leu Asp Lys Gln Pro Ile Phe Ser His
                        20                  25                  30

Thr Val Glu Gly Phe Thr Phe Leu Tyr Ser Glu Ala Gln Gln Ser Arg
                        35                  40                  45

Tyr Leu Ala Ser Arg Arg Asn Leu Ile Thr His Thr Lys Val Leu Glu
        50                  55                  60

Glu Ala Met Glu Asn Gly Ser Arg Thr Leu Leu Pro Leu Gln Phe Gly
        65                  70                  75                  80

Leu Ile Val Pro Asp Trp Glu Thr Val Val Gln Asp Leu Leu Gln His
                        85                  90                  95

Gln Ala Glu Ser Leu His Phe Leu Glu Lys Leu Glu Gly Lys Arg
                        100                 105                 110

Glu Val Ser Leu Lys Ile Tyr Trp Glu Thr Asn Ala Glu Leu Asn Ala
                        115                 120                 125

Leu Leu Glu Glu Asn Pro Ala Leu Lys Ala Arg Arg Asp Asn Leu Glu
                        130                 135                 140

Gly Lys Gln Leu Ser Met Asp Glu Val Ile Gln Ile Gly Gln Ala Leu
        145                 150                 155                 160

Glu Gln Glu Met Glu Gly Arg Lys Gln Asp Ile Ile Ser Arg Phe Glu
```

```
            165                 170                 175
Glu Val Leu Ile Pro Phe Ala Phe Glu Ile Lys Glu Asn Asp Val Leu
                180                 185                 190

Thr Glu Thr Met Ile Tyr Asn Thr Ala Phe Leu Ile Asn Trp Asp Ala
            195                 200                 205

Glu Ser Asp Phe Gly Glu Gln Leu Glu Ala Ile Asp Ala Glu Phe Ser
210                 215                 220

Pro Arg Leu Lys Ile Arg Tyr Asn Asn Phe Thr Pro Tyr Asn Phe
225                 230                 235                 240

Val Glu Leu Arg Glu
            245

<210> SEQ ID NO 93
<211> LENGTH: 252
<212> TYPE: PRT
<213> ORGANISM: Desulfobacterium vacuolatum_DSM 3385

<400> SEQUENCE: 93

Met Ser Lys Lys Asn Leu Lys Arg Asn Gly Arg Tyr Leu Tyr Ala Ile
1               5                   10                  15

Ile Glu Ala Ser Glu Lys Thr Phe Gly Ser Ile Gly Met Asp Gly
            20                  25                  30

Ser Asp Val Tyr Leu Ile Val Glu Asp Lys Thr Ala Ala Val Val Ser
            35                  40                  45

Asp Val Pro Asn Lys Lys Ile Arg Pro Gln Arg Lys Asn Ile Ala Ala
        50                  55                  60

His His Ala Val Leu Asn Lys Ile Met Glu Glu Ile Thr Pro Leu Pro
65                  70                  75                  80

Met Ala Phe Gly Ile Ile Ala Asp Gly Glu Gln Ala Ile Arg Lys Ile
                85                  90                  95

Leu Ala Asp Asn Arg Asp Val Phe Arg Glu Gln Phe Ala Thr Val Ser
            100                 105                 110

Gly Lys Val Glu Met Gly Met Arg Ile Ser Tyr Asp Val Pro Asn Ile
        115                 120                 125

Phe Glu Tyr Phe Ile Ser Thr Asp Ser Glu Ile Arg Ala Ala Arg Asp
    130                 135                 140

Gln Tyr Phe Gly Gly Asn Arg Glu Pro Ser Gln Glu Ala Lys Leu Glu
145                 150                 155                 160

Leu Gly Arg Met Phe Asn Arg Gln Leu Asn Ala Asn Arg Glu Glu Tyr
                165                 170                 175

Thr Asn Gln Val Ile Glu Ile Leu Asp Asp Tyr Cys Asp Ile Lys
            180                 185                 190

Glu Asn Lys Cys Arg Asn Glu Gln Glu Val Thr Ser Leu Ala Cys Leu
        195                 200                 205

Ile Asn Arg Ser Asp Gln Lys Arg Phe Glu Glu Gly Val Phe Glu Ser
    210                 215                 220

Ala Arg His Phe Asp Asn Asn Phe Ser Phe Glu Tyr Asn Gly Pro Trp
225                 230                 235                 240

Ser Pro His Asn Phe Val Asn Ile Leu Ile Glu Leu
                245                 250

<210> SEQ ID NO 94
<211> LENGTH: 255
<212> TYPE: PRT
<213> ORGANISM: Desulfomonile tiedjei DSM 6799
```

<400> SEQUENCE: 94

Met Glu Lys Ala Thr Ile Lys Thr Thr Gly Ser Asn Gly Arg Tyr Leu
1               5                   10                  15

Tyr Ala Val Val Pro Gly Ser Gln Glu Arg Val Tyr Gly Cys Leu Gly
            20                  25                  30

Ile Asn Gly Gly Asn Val Tyr Thr Ile Ala Ala Lys Asp Val Ala Ala
        35                  40                  45

Val Val Ser Asp Val Pro His Gln Lys Ile Arg Pro Glu Arg Arg His
50                  55                  60

Phe Ala Ala His Gln Ala Val Leu Lys Arg Val Met Leu Asp Gly Asp
65                  70                  75                  80

Leu Leu Pro Met Ser Phe Gly Ile Ile Ser Gln Gly Pro Lys Ala Val
                85                  90                  95

Arg Ala Ile Leu Ser Arg Asn Asn Lys Ser Val Gln Gln Leu Lys
            100                 105                 110

Arg Ile Ser Gly Lys Ala Glu Met Gly Ile Lys Val Thr Trp Asp Val
            115                 120                 125

Pro Asn Ile Phe Glu Tyr Phe Ile Asp Val Asn Arg Glu Leu Arg Glu
        130                 135                 140

Ala Arg Asn Lys Leu Val Gln Pro Asn Tyr Leu Pro Thr Gln Gln Glu
145                 150                 155                 160

Lys Ile Glu Ile Gly Arg Met Phe Glu Glu Ile Leu Asn Leu Glu Arg
                165                 170                 175

Glu Arg His Thr Lys Gln Val Glu Arg Val Met Ser Lys Arg Cys Ser
            180                 185                 190

Glu Ile Lys Arg Ser Lys Cys Arg Thr Glu Ile Glu Val Met Asn Leu
        195                 200                 205

Ser Cys Leu Val Asp Arg Thr Leu Leu Ser Asp Phe Glu Ala Gly Val
210                 215                 220

Leu Glu Ala Ala Ser His Phe Asp Asp Ser Phe Ala Phe Asp Phe Asn
225                 230                 235                 240

Gly Pro Trp Ala Pro His Asn Phe Val Asp Leu Glu Ile Asp Val
                245                 250                 255

<210> SEQ ID NO 95
<211> LENGTH: 250
<212> TYPE: PRT
<213> ORGANISM: Desulfotomaculum acetoxidans_DSM 771

<400> SEQUENCE: 95

Met Ser Thr Gly Arg Tyr Val Tyr Cys Val Ile Asn Ser Ile Glu Pro
1               5                   10                  15

Leu Thr Phe Met Ser Gly Pro Val Gly Asn Glu Pro Glu Gly Val Phe
            20                  25                  30

Thr Val His Tyr Lys Glu Leu Ala Ala Val Ser Gln Ser Ser Glu
        35                  40                  45

Glu Lys Tyr Asn Val Cys Arg Glu Asn Thr Ile Ala His Gln Lys Val
    50                  55                  60

Leu Glu Glu Val Leu Val Ser His Pro Leu Pro Val Arg Phe Gly
65                  70                  75                  80

Thr Val Ala Gln Asn Glu Glu Ile Val Lys Lys Phe Leu Leu Gln Glu
                85                  90                  95

Arg Tyr Ala Glu Leu Arg Ser Met Leu His Asn Val Thr Gly Lys Val
            100                 105                 110

```
Gln Met Gly Leu Lys Val Leu Trp Thr Asp Met Lys Thr Val Tyr Gln
            115                 120                 125

Glu Ile Val Glu Glu Asn Pro Gln Ile Lys Asn Leu Lys Lys Lys Leu
    130                 135                 140

Glu Ser Lys Pro Ala Glu Thr Ile His Tyr Glu Met Ile Asp Leu Gly
145                 150                 155                 160

Gln Met Val Asn Gln Ala Leu Leu Arg Lys Glu Lys Gln Lys Glu
                165                 170                 175

Met Val Leu Lys Pro Leu Gln Lys Ile Ala Leu Glu Thr Lys Glu Ser
            180                 185                 190

Phe Leu Tyr Gly Asp Gln Met Phe Val Asn Ala Asp Phe Leu Ile Ser
            195                 200                 205

Arg Ser Ser Leu Asp Asp Phe Asn Ala Lys Val Asn Glu Leu Gly Glu
            210                 215                 220

Phe Phe Asn Glu Gln Ala Leu Phe Lys Tyr Ile Gly Pro Leu Pro Pro
225                 230                 235                 240

Tyr Asn Phe Val Thr Leu Tyr Val Asn Phe
                245                 250

<210> SEQ ID NO 96
<211> LENGTH: 357
<212> TYPE: PRT
<213> ORGANISM: Desulfotomaculum acetoxidans_DSM 771

<400> SEQUENCE: 96

Met Val Lys Asn His Asn Thr Asp His Leu Lys Glu Leu Tyr Ile Tyr
1               5                   10                  15

Gly Leu Ile Gly Gly Thr Pro Phe Lys Asp Glu Leu Glu Lys Ile Ser
            20                  25                  30

Val Ile Gln Glu Asn Thr Pro Ile Tyr Gly Val Trp His Lys Asn Ile
        35                  40                  45

Gly Phe Ala Val Ser Ala Ala Pro Asp Tyr Pro Leu Lys Asp Leu Ser
    50                  55                  60

Lys Glu Ser Ile Ile Gln Leu Phe Val Asp His Gln Gln Val Leu Glu
65                  70                  75                  80

Cys Leu Arg Gln Lys Phe Ser Leu Ile Pro Val Lys Leu Gly Thr Val
                85                  90                  95

Leu Glu Ser Val Thr Glu Ala Ala Ala Val Leu Ala Asn Asn Glu Glu
            100                 105                 110

Lys Phe Asn Asp Leu Leu Asn Tyr Leu Lys Asp Lys Val Glu Leu Asn
        115                 120                 125

Leu Ser Val Ser Trp Asn Asp Leu Asn Glu Val Val Ala Lys Ile Gly
    130                 135                 140

Glu Glu Asp Glu Val Lys Lys Leu Lys Gln Ser Leu Leu Ala Gln Glu
145                 150                 155                 160

Gln Val Ser Gln Glu Asp Leu Ile Lys Ile Gly Lys Ile Ile Ser Phe
                165                 170                 175

Gln Met Gln Gln Lys Lys Gln Ala Ala Arg Glu Tyr Ile Ile Ser Glu
            180                 185                 190

Leu Arg Asn Leu Trp Glu Asp Tyr Phe Ile Asn Glu Val Val Asp Glu
        195                 200                 205

Asn Ser Ile Leu Asn Leu Thr Leu Leu Ala Ile Thr Gly Lys Val Asp
    210                 215                 220

Asp Val Asn Lys Lys Ile Glu Tyr Leu Asn Gln Ile Tyr Arg Asp Ser
225                 230                 235                 240
```

```
Leu Asp Phe Ser Leu Thr Lys Ser Leu Leu Pro Gln Gly Phe Ser Thr
                245                 250                 255

Val Ser Ile Lys Lys Ile Thr Met Asp Gln Leu Leu Ala Lys Asp
            260                 265                 270

Ile Leu Lys Leu Pro Asp Thr Ala Ser Leu Gln Asp Ile Asn Ala Ala
            275                 280                 285

Arg Arg Ala Leu Leu His Cys Tyr His Pro Asp Lys Asn Asp His Ala
        290                 295                 300

Ala Val Asn Lys Val Gln Glu Ile Asn Ala Ala Tyr Lys Leu Leu Glu
305                 310                 315                 320

Glu Tyr Cys Gln Glu Asn Ser Ser Asp Phe Asn Val Asp Leu Ile Thr
                325                 330                 335

Asp Tyr Tyr Ile Met Lys Val Ile Lys Ala Asp Lys Ser Asn Val Asn
            340                 345                 350

Ser Met Asn Met Glu
            355

<210> SEQ ID NO 97
<211> LENGTH: 252
<212> TYPE: PRT
<213> ORGANISM: Dolichospermum circinale

<400> SEQUENCE: 97

Met Asn Thr Asp Leu Ala His Lys Asn Phe Gly Leu Tyr Leu Tyr Gly
1               5                   10                  15

Ile Phe Pro Asp Thr Ile Pro Glu Thr Leu Glu Ile Lys Gly Leu Asp
            20                  25                  30

Gly Lys Ser Val His Ser Gln Val Val Asp Gly Phe Thr Phe Leu Tyr
        35                  40                  45

Ser Gln Ala Cys Gln Glu Lys Tyr Leu Ala Ser Arg Arg Asn Leu Leu
    50                  55                  60

Ala His Glu Arg Val Leu Glu Gln Thr Met His Glu Gly Phe His Val
65                  70                  75                  80

Leu Leu Pro Leu Arg Phe Gly Leu Val Val Lys Asp Trp Glu Thr Ile
                85                  90                  95

Met Ser Gln Leu Ile Asn Pro His Lys Glu Gln Leu His Lys Leu Phe
            100                 105                 110

Glu Lys Leu Ala Gly Gln Arg Glu Val Ser Ile Lys Ile Leu Trp Asp
        115                 120                 125

Ala Lys Ala Glu Leu Gln Ala Met Met Glu Ser Asn His Asp Leu Arg
    130                 135                 140

Gln Gln Arg Asp Asn Met Glu Gly Lys Lys Leu Ser Met Glu Glu Val
145                 150                 155                 160

Ile Gln Ile Gly Gln Leu Ile Glu Ser Asn Leu Gln Ala Arg Lys Gln
                165                 170                 175

Ala Val Ile Glu Val Phe Thr Arg Glu Leu Asn Pro Leu Ala Gln Glu
            180                 185                 190

Ile Val Val Ser Glu Pro Met Thr Glu Met Ile Tyr Asn Ala Ala
        195                 200                 205

Phe Leu Ile Pro Trp Asp Ser Glu Pro Leu Phe Ser Glu Arg Val Glu
    210                 215                 220

Ser Ile Asp Gln Lys Phe Gly Asn Arg Leu Arg Ile Arg Tyr Asn Asn
225                 230                 235                 240

Phe Thr Ala Pro Tyr Thr Phe Ala Leu Leu Asp Ser
```

-continued

<210> SEQ ID NO 98
<211> LENGTH: 277
<212> TYPE: PRT
<213> ORGANISM: Enhydrobacter aerosaccus strain ATCC 27094

<400> SEQUENCE: 98

Met Asn Pro Pro Glu Ala Tyr Ile Ala Gly Arg Thr Ala Ala Lys Ser
1               5                   10                  15

Val Glu Asp Arg Lys Ala Arg Pro Gln Asp Leu Ala Glu Gly Lys Tyr
            20                  25                  30

Val Tyr Ala Ile Ile Ala Cys Asp Glu Pro Arg Glu Phe Lys Asn Arg
        35                  40                  45

Gly Ile Gly Glu Arg Gly Asp Lys Val His Thr Ile Asn His Arg Gln
    50                  55                  60

Met Ala Ala Val Val Ser Asp Ser Pro Thr Ile Asp Tyr Glu Arg Ser
65                  70                  75                  80

Arg Arg Asn Met Met Ala His Thr Val Val Leu Glu Glu Val Met Lys
                85                  90                  95

Glu Phe Asp Leu Leu Pro Leu Arg Phe Gly Thr Val Ala Ser Ser Ala
            100                 105                 110

Glu Ser Val Glu Arg Gln Leu Leu Val Pro Arg Tyr Gly Glu Leu Ser
        115                 120                 125

Ala Met Leu Glu Lys Met Arg Gly Arg Ser Glu Phe Gly Leu Lys Ala
    130                 135                 140

Phe Trp His Glu Gly Val Ala Phe Gly Glu Ile Val Arg Glu Asn Ala
145                 150                 155                 160

Arg Val Arg Lys Leu Arg Asp Ala Leu Gln Gly Arg Ser Leu Glu Glu
                165                 170                 175

Ser Tyr Tyr Gln Arg Ile Gln Leu Gly Glu Glu Val Glu Lys Ala Leu
            180                 185                 190

Thr Ala Ile Arg Ala Arg Asp Glu Glu Leu Ile Leu Ser Arg Leu Arg
        195                 200                 205

Pro Phe Met Arg Asp Ile Arg Thr Asn Lys Ile Ile Ser Asp Arg Met
    210                 215                 220

Val Leu Asn Ala Ala Phe Leu Val Glu Arg Gly Asp Val Pro Ala Leu
225                 230                 235                 240

Asp Glu Ala Ile Arg Gln Leu Asp Gln Glu Phe Ser Glu Arg Leu Met
                245                 250                 255

Phe Lys Tyr Val Gly Pro Val Pro Tyr Asn Phe Val Asn Ile Ala
            260                 265                 270

Ile Asn Trp Glu Arg
        275

<210> SEQ ID NO 99
<211> LENGTH: 279
<212> TYPE: PRT
<213> ORGANISM: Isosphaera pallida_ATCC-43644

<400> SEQUENCE: 99

Met Arg Asn Ala Pro Pro Thr Arg Pro Gly Ser Val Thr Pro Ala Ser
1               5                   10                  15

Pro Gly Lys Pro Val Ile Asp Gly Pro Ala Arg Tyr Leu Tyr Ala Phe
            20                  25                  30

Thr His Asp Leu Pro Glu Gly Pro Leu Ala Asp Leu Glu Gly Leu Pro

```
            35                  40                  45
Gly Ala Arg Val Val Val Ala Asp Gly Arg Val Ala Val Val
 50                  55                  60

Ser Pro Cys Pro Leu Gly Lys Val Arg Pro Glu Arg Gln Val Ala
 65                  70                  75                  80

Gly His His His Val Leu Lys His Leu Gln Asp Thr Leu Gly Lys Ala
                     85                  90                  95

Ile Leu Pro Ala Ser Phe Gly Met Val Ala Asp Ser Glu Glu Asp Leu
                100                 105                 110

Arg Ala Leu Leu Arg His His Ser Ala Ala Ile Ala Glu Gly Leu Val
                115                 120                 125

Arg Val Gln Gly Lys Val Glu Met Thr Val Lys Leu Arg Trp Ala Pro
    130                 135                 140

Asp Asn Val Ala Gln Ala Val Leu Gly Arg Asp Pro Glu Leu Arg Gln
145                 150                 155                 160

Leu Arg Asp Gln Leu Tyr Ser Asn Gly Gln Thr Pro Thr Arg Asp Gln
                165                 170                 175

Ser Leu Asp Leu Gly Arg Arg Phe His His Ala Leu Glu Arg Gln Arg
                180                 185                 190

Asp His Tyr Ala Ala Tyr Leu Arg Ala Ala Leu Ser Pro Leu Leu Ser
                195                 200                 205

Glu Leu Val Glu Asp Leu Arg Asp Glu Arg Asp Leu Val His Trp
    210                 215                 220

Ala Cys Leu Ile Glu Asn Gln Arg Arg Ala Gly Phe Glu Ala Ala Leu
225                 230                 235                 240

Asp Arg Leu Ala Glu Glu Leu Glu Asp Leu Val Leu Glu Leu Thr
                    245                 250                 255

Gly Pro Trp Pro Pro His His Phe Val Asp Leu Asp Leu Asp Asp
                260                 265                 270

His Asp Asp Asp Glu Glu Glu
        275

<210> SEQ ID NO 100
<211> LENGTH: 258
<212> TYPE: PRT
<213> ORGANISM: Legionella drancourtii LLAP12

<400> SEQUENCE: 100

Met Asp Ser Thr Ser Lys Lys Pro Ala Ala Ser Asn Leu Tyr Leu Tyr
  1               5                  10                  15

Ala Ile Ala Ser Val Asn Glu Asn Gln Glu Pro Ile Ser Phe His Gly
                 20                  25                  30

Ile Glu Glu Gln Pro Ile Asp Leu Val Pro Tyr Lys Asp Ile Met Leu
             35                  40                  45

Val Val Ser Asn Leu Ser Lys Lys Val Arg Pro Glu Arg Lys Asn
 50                  55                  60

Val Ala Val His His Ala Val Leu Asn His Leu Met Lys His Asn Thr
 65                  70                  75                  80

Ser Met Leu Pro Ile Arg Phe Gly Met Ile Ala Asp Asn Arg Lys Glu
                 85                  90                  95

Val Gln Arg Leu Leu Thr Ile Asn Tyr Asp Met Leu His Thr Lys Leu
                100                 105                 110

Lys Met Met Ala Gly Arg Val Glu Met Gly Val Ser Leu Ser Trp Asp
            115                 120                 125
```

Val Pro Asn Ile Phe Glu Tyr Leu Leu Asn Arg His Ser Gln Leu Arg
130                 135                 140

Glu Thr Arg Asp Lys Leu Leu Ala Asn Pro Ala His Glu Pro Ser Arg
145                 150                 155                 160

Asp Glu Lys Ile Glu Ile Gly Ala Leu Phe Ser Gln Ile Leu Asp Glu
            165                 170                 175

Glu Arg Glu Val Tyr Thr Asp Thr Ile Leu Ser Leu Ser Pro Val
            180                 185                 190

Cys Cys Asp Val Val Lys Ser Thr Tyr Arg Asn Asp Thr Glu Ile Met
        195                 200                 205

Asn Ile Phe Cys Leu Ile Ser Ala Ala Arg Arg Asp Glu Phe Glu Glu
210                 215                 220

Lys Ile Ile Glu Ala Ser Thr Ile Leu Asp Asp Asn Phe Val Ile Lys
225                 230                 235                 240

Tyr Thr Gly Pro Trp Pro Pro His Asn Phe Ser Lys Leu Asn Leu Ser
                245                 250                 255

Leu Glu

<210> SEQ ID NO 101
<211> LENGTH: 247
<212> TYPE: PRT
<213> ORGANISM: Lyngbya confervoides BDU141951

<400> SEQUENCE: 101

Met Pro Gln Leu Leu Tyr Leu Tyr Gly Ile Phe Pro Ala Pro Gly Pro
1               5                   10                  15

Gln Asp Leu Glu Val Gln Gly Leu Asp Gln Gln Pro Ile His Thr His
            20                  25                  30

Ile Ile Asp Glu Phe Val Phe Leu Tyr Ser Val Ala Gln Gln Glu Arg
        35                  40                  45

Tyr Leu Ala Ser Arg Lys Asn Leu Leu Gly His Glu Arg Val Leu Glu
50                  55                  60

Ala Ala Met Lys Val Gly Tyr Arg Thr Leu Leu Pro Leu Gln Phe Gly
65                  70                  75                  80

Leu Ile Ile Glu Thr Trp Asp Arg Val Ile Lys Glu Leu Ile Thr Pro
                85                  90                  95

Arg Gly Asp Ala Leu Lys Arg Leu Phe Ala Lys Leu Glu Gly Arg Arg
            100                 105                 110

Glu Val Ser Val Lys Leu Leu Trp Gly Pro Asp Ala Glu Leu Asn Gln
        115                 120                 125

Leu Met Glu Glu Asp Ala Gly Leu Arg Ala Glu Arg Asp Arg Leu Glu
130                 135                 140

Gly Gln Gln Leu Ser Met Asp Gln Ile Val Asp Ile Gly Gln Ala Ile
145                 150                 155                 160

Glu Thr Ala Met Thr Glu Arg Lys Asp Val Ile Asn Ala Phe Arg
            165                 170                 175

Gln Arg Leu Asn Ala Leu Ala Ile Glu Val Leu Glu Asn Asp Pro Leu
        180                 185                 190

Thr Asp Ala Met Ile Tyr Asn Thr Ala Tyr Leu Ile Pro Trp Glu Asp
        195                 200                 205

Glu Val Lys Phe Ser Gln Ala Ile Glu Glu Leu Asp Glu Gln Phe Glu
210                 215                 220

Asp Arg Leu Arg Ile Arg Tyr Asn Asn Phe Thr Ala Pro Tyr Asn Phe
225                 230                 235                 240

Ala Gln Leu Asp Gln Leu Ser
            245

<210> SEQ ID NO 102
<211> LENGTH: 244
<212> TYPE: PRT
<213> ORGANISM: Microcystis aeruginosa NIES-843

<400> SEQUENCE: 102

Met Thr Val Gly Leu Tyr Leu Tyr Gly Ile Phe Pro Glu Pro Val Pro
1               5                   10                  15

Asp Gly Leu Val Leu Gln Gly Ile Asp Asn Glu Pro Val His Ser Glu
            20                  25                  30

Met Ile Glu Gly Phe Ser Phe Leu Tyr Ser Ala Ala His Lys Glu Lys
        35                  40                  45

Tyr Leu Ala Ser Arg Arg Tyr Leu Ile Cys His Glu Lys Val Leu Glu
    50                  55                  60

Thr Val Met Glu Ala Gly Phe Thr Thr Leu Leu Pro Leu Arg Phe Gly
65                  70                  75                  80

Leu Val Ile Lys Thr Trp Glu Ser Val Thr Glu Gln Leu Ile Ser Pro
                85                  90                  95

Tyr Lys Thr Gln Leu Lys Glu Leu Phe Ala Lys Leu Ser Gly Gln Arg
            100                 105                 110

Glu Val Ser Ile Lys Ile Phe Trp Asp Asn Gln Trp Glu Leu Gln Ala
        115                 120                 125

Ala Leu Glu Ser Asn Pro Lys Leu Lys Gln Glu Arg Asp Ala Met Met
    130                 135                 140

Gly Lys Asn Leu Asn Met Glu Glu Ile Ile His Ile Gly Gln Leu Ile
145                 150                 155                 160

Glu Ala Thr Val Leu Gln Arg Lys Gln Asp Ile Ile Gln Val Phe Arg
                165                 170                 175

Asp Gln Leu Asn His Arg Ala Gln Glu Val Ile Glu Ser Asp Pro Met
            180                 185                 190

Thr Asp Asp Met Ile Tyr Asn Ala Ala Tyr Leu Ile Pro Trp Glu Gln
        195                 200                 205

Glu Pro Glu Phe Ser Gln Asn Val Glu Ala Ile Asp Gln Gln Phe Gly
    210                 215                 220

Asp Arg Leu Arg Ile Arg Tyr Asn Asn Leu Thr Ala Pro Tyr Thr Phe
225                 230                 235                 240

Ala Gln Leu Val

<210> SEQ ID NO 103
<211> LENGTH: 247
<212> TYPE: PRT
<213> ORGANISM: Nostoc punctiforme ATCC 29133

<400> SEQUENCE: 103

Met Ser Phe Tyr Ile Tyr Gly Ile Leu Thr Leu Pro Ala Pro Gln Asn
1               5                   10                  15

Leu Asn Leu Glu Gly Leu Asp Arg Gln Pro Val Gln Ile Lys Ile Leu
            20                  25                  30

Asp Asp Phe Ala Val Ile Tyr Ser Glu Ala Gln Gln Glu Arg Tyr Leu
        35                  40                  45

Ala Ser Arg Arg Asn Leu Leu Ser His Glu Lys Val Leu Glu Glu Ile
    50                  55                  60

Met Gln Ala Gly Asp Arg Tyr Leu Leu Pro Val Gln Phe Gly Leu Leu

```
            65                  70                  75                  80
Val Ser Ser Trp Glu Thr Val Ser Gln Gln Leu Ile Arg Pro His Gln
                85                  90                  95

Glu Glu Leu Thr Gln Leu Leu Ala Lys Leu Ser Gly Cys Arg Glu Val
            100                 105                 110

Ser Val Lys Val Phe Trp Asp Thr Glu Ala Glu Ile Gln Gly Leu Leu
            115                 120                 125

Ala Glu His Pro Asn Leu Lys Thr Glu Arg Asp Lys Leu Val Gly Gln
            130                 135                 140

Pro Leu Ser Met Glu Arg Val Ile Gln Ile Gly Gln Val Ile Glu Gln
145                 150                 155                 160

Gly Met Ser Asp Arg Lys Gln Gly Ile Ile Asp Val Phe Lys Gly Thr
                165                 170                 175

Leu Asn Ser Ile Ala Ile Glu Val Val Glu Asn Thr Pro Gln Val Asp
            180                 185                 190

Thr Met Ile Tyr Asn Ser Ala Tyr Leu Ile Pro Trp Glu Ala Glu Ser
            195                 200                 205

Gln Phe Ser Glu His Val Glu Ser Leu Asp Arg Gln Phe Glu Asn Arg
            210                 215                 220

Leu Arg Ile Arg Tyr Asn Asn Phe Thr Ala Pro Tyr Asn Phe Ala Arg
225                 230                 235                 240

Leu Arg Leu Thr Thr Ser Asn
                245

<210> SEQ ID NO 104
<211> LENGTH: 244
<212> TYPE: PRT
<213> ORGANISM: Nostoc sp. PCC 7120

<400> SEQUENCE: 104

Met Ser Ser Gly Leu Tyr Leu Tyr Gly Ile Phe Pro Asp Pro Ile Pro
1               5                   10                  15

Glu Thr Val Thr Leu Gln Gly Leu Asp Ser Gln Leu Val Tyr Ser Gln
            20                  25                  30

Ile Ile Asp Gly Phe Thr Phe Leu Tyr Ser Glu Ala Lys Gln Glu Lys
            35                  40                  45

Tyr Leu Ala Ser Arg Arg Asn Leu Ile Ser His Glu Lys Val Leu Glu
        50                  55                  60

Gln Ala Met His Ala Gly Phe Arg Thr Leu Leu Pro Leu Arg Phe Gly
65                  70                  75                  80

Leu Val Val Lys Asn Trp Glu Thr Val Val Thr Gln Leu Leu Gln Pro
                85                  90                  95

Tyr Lys Ala Gln Leu Arg Glu Leu Phe Gln Lys Leu Ala Gly Arg Arg
            100                 105                 110

Glu Val Ser Val Lys Ile Phe Trp Asp Ser Lys Ala Glu Leu Gln Ala
            115                 120                 125

Met Met Asp Ser His Gln Asp Leu Lys Gln Lys Arg Asp Gln Met Glu
            130                 135                 140

Gly Lys Ala Leu Ser Met Glu Glu Val Ile His Ile Gly Gln Leu Ile
145                 150                 155                 160

Glu Ser Asn Leu Leu Ser Arg Lys Glu Ser Ile Ile Gln Val Phe Phe
                165                 170                 175

Asp Glu Leu Lys Pro Leu Ala Asp Glu Val Ile Glu Ser Asp Pro Met
            180                 185                 190
```

```
Thr Glu Asp Met Ile Tyr Asn Ala Ala Phe Leu Ile Pro Trp Glu Asn
            195                 200                 205

Glu Ser Ile Phe Ser Gln Gln Val Glu Ser Ile Asp His Lys Phe Asp
        210                 215                 220

Glu Arg Leu Arg Ile Arg Tyr Asn Asn Phe Thr Ala Pro Tyr Thr Phe
225                 230                 235                 240

Ala Gln Ile Ser

<210> SEQ ID NO 105
<211> LENGTH: 264
<212> TYPE: PRT
<213> ORGANISM: Octadecabacter antarcticus 307

<400> SEQUENCE: 105

Met Lys Arg Glu Val Val Arg Met Thr Asp Glu Asn Thr Ile Asn Ser
1               5                   10                  15

Lys Tyr Leu Tyr Ala Ile Ile Lys Cys Arg Glu Gln Arg Glu Phe Ile
            20                  25                  30

Ala Arg Gly Ile Gly Glu Arg Gly Asp Ala Val His Thr Ile Ala Tyr
        35                  40                  45

Lys Gly Leu Ala Ala Val Val Ser Asp Ser Pro Val Met Glu Tyr Asp
    50                  55                  60

Gln Ser Arg Arg Asn Met Met Ala His Thr Ala Val Leu Glu Glu Leu
65                  70                  75                  80

Met Glu Glu Phe Thr Leu Leu Pro Val Arg Phe Asn Thr Val Ala Pro
                85                  90                  95

Glu Ala Gly Ala Ile Glu Glu Arg Leu Leu Val Pro Arg His Glu Glu
            100                 105                 110

Phe Thr Gln Leu Leu Gly Gln Ile Asp Lys Arg Val Glu Leu Gly Ile
        115                 120                 125

Lys Ala Phe Trp His Asp Gly Met Ile Phe Glu Glu Val Leu Arg Glu
130                 135                 140

Asn Asp Ser Ile Arg Lys Met Arg Asp Ala Leu Glu Gly Lys Ser Val
145                 150                 155                 160

Asp Gly Ser Tyr Tyr Glu Arg Ile Gln Leu Gly Glu Lys Ile Glu Gln
                165                 170                 175

Ala Met Ile Lys Lys Arg Val Glu Asp Glu Glu Ile Ile Leu Ser Arg
            180                 185                 190

Ile Arg Gln His Val His Lys Ser Arg Ser Asn Lys Thr Ile Gly Asp
        195                 200                 205

Arg Met Val Leu Asn Gly Ala Phe Leu Val Asp Ala Asn Lys Glu Ser
    210                 215                 220

Asp Phe Asp Lys Ala Val Gln Leu Leu Asp Gln Asp Leu Gly Asn Arg
225                 230                 235                 240

Leu Met Phe Lys Tyr Val Gly Pro Val Pro Pro Tyr Asn Phe Val Asn
                245                 250                 255

Ile Val Val Asn Trp Gly Val Val
            260

<210> SEQ ID NO 106
<211> LENGTH: 356
<212> TYPE: PRT
<213> ORGANISM: Octadecabacter antarcticus 307

<400> SEQUENCE: 106

Met Thr Val Val Ala Glu Glu Asn Met Thr Gly Ser Val Gly Leu Tyr
```

```
                1               5                   10                  15
        Val Cys Ala Ile Val Ala Glu Trp Glu Ser Asn Ser Ala Leu Ile Lys
                        20                  25                  30
        Cys Ala Asn Glu Ala Gln Gly Glu Ile Gln Leu Ile Gly Gln Gly Gly
                        35                  40                  45
        Ile Thr Ala Val Val Met Val Pro Pro Glu Asp Gln Pro Val Ser Arg
                        50                  55                  60
        Asp Arg Gln Glu Leu Val Arg Gln Leu Val His Gln Gln Leu Val
        65                      70                  75                  80
        Glu Arg Phe Thr Glu Ile Ala Pro Val Leu Pro Val Lys Phe Gly Thr
                        85                  90                  95
        Leu Ala Pro Asp Arg Glu Ser Val Glu Leu Gly Leu Glu Arg Gly Arg
                        100                 105                 110
        Glu Lys Phe Phe Thr Ala Phe Gly Gly Leu Ser Gly Lys Thr Gln Phe
                        115                 120                 125
        Glu Ile Thr Val Thr Trp Asp Val Ala Asp Val Phe Ala Lys Ile Ala
                        130                 135                 140
        Lys Leu Pro Ala Val Val Lys Leu Lys Val Asp Leu Val Ala Thr Ser
        145                     150                 155                 160
        Glu Ser Asp Arg Pro Ile Asn Leu Asp Arg Val Gly Arg Leu Val Lys
                        165                 170                 175
        Glu Thr Leu Asp His Gln Arg Ala Gln Thr Gly Lys Val Leu Leu Asp
                        180                 185                 190
        Ala Leu Leu Pro Leu Gly Val Asp Ser Ile Val Asn Pro Ile Leu Asn
                        195                 200                 205
        Asp Ser Ile Val Leu Asn Leu Ala Leu Leu Val Asp Thr Asp Gln Ala
                        210                 215                 220
        Asp Ala Leu Asp Arg Cys Leu Asp Glu Leu Asp Ser Thr Phe His Gly
        225                     230                 235                 240
        Ala Leu Ser Phe Arg Cys Val Gly Pro Met Pro Pro His Ser Phe Ala
                        245                 250                 255
        Thr Val Glu Ile Asn Tyr Ile Glu Pro Thr Gln Val Ser His Ala Cys
                        260                 265                 270
        Cys Val Leu Glu Leu Asp Ala Ala His Asn Phe Glu Glu Ile Arg Ser
                        275                 280                 285
        Ala Tyr His Arg Leu Ala Arg Gln Thr Gln Gln Asp Ile Ala Pro Asp
                        290                 295                 300
        Val Val Asp Asn Lys Ser Ser Val Gly Ile Ala Val Leu Asn
        305                     310                 315                 320
        Asp Ala Tyr Lys Thr Leu Leu Ser Phe Val Asp Ala Gly Gly Pro Val
                        325                 330                 335
        Val Val Ser Val Gln Arg Gln Glu Asp Ala Tyr Ala Thr Asp Ile Pro
                        340                 345                 350
        Ser Ser Gly Gly
                355

<210> SEQ ID NO 107
<211> LENGTH: 257
<212> TYPE: PRT
<213> ORGANISM: Octadecabacter arcticus 238

<400> SEQUENCE: 107

Met Thr Asp Glu Lys Lys Val Asn Ser Lys Tyr Leu Tyr Ala Ile Ile
        1               5                   10                  15
```

```
Gln Cys Arg Glu Pro Arg Glu Leu Lys Ala Arg Gly Ile Gly Glu Arg
             20                  25                  30

Gly Asp Val Val His Thr Val Val His Lys Gly Leu Ala Ala Val Val
         35                  40                  45

Ser Asp Ser Pro Val Met Glu Tyr Asp Gln Ser Arg Arg Asn Met Met
 50                  55                  60

Ala His Thr Ala Val Leu Glu Leu Met Glu Phe Thr Leu Leu
 65                  70                  75                  80

Pro Val Arg Phe Asn Thr Val Ala Pro Glu Ala Val Ala Ile Glu Glu
             85                  90                  95

Arg Leu Leu Val Pro Arg His Asp Glu Phe Thr Gln Leu Leu Gly Gln
             100                 105                 110

Ile Asp Lys Arg Val Glu Leu Gly Leu Lys Ala Phe Trp His Asp Gly
             115                 120                 125

Met Ile Phe Gly Glu Val Leu Arg Glu Asn Asp Ser Ile Arg Lys Met
 130                 135                 140

Arg Asp Ser Leu Lys Gly Gln Ser Val Asp Gly Ser Tyr Tyr Glu Arg
145                 150                 155                 160

Ile Gln Leu Gly Glu Lys Ile Glu Lys Ala Leu Thr Glu Lys Arg Leu
             165                 170                 175

Glu Asp Glu Glu Met Ile Leu Ser Arg Ile Arg Pro His Val His Lys
             180                 185                 190

Ser Arg Ser Asn Lys Thr Ile Gly Asp Arg Met Val Leu Asn Gly Ala
             195                 200                 205

Phe Leu Val Asp Ala Glu Lys Glu Ser Lys Phe Asp Glu Ala Val Gln
 210                 215                 220

Ser Leu Asp Gln Asp Leu Ser Asp Arg Leu Met Phe Lys Tyr Val Gly
225                 230                 235                 240

Pro Val Pro Pro Tyr Asn Phe Val Asn Ile Val Asn Trp Gly Glu
             245                 250                 255

Ser

<210> SEQ ID NO 108
<211> LENGTH: 360
<212> TYPE: PRT
<213> ORGANISM: Octadecabacter arcticus 238

<400> SEQUENCE: 108

Met Arg Ala Gln Lys Val Ile Pro Ala Ala Glu Glu Asn Ile Ser Gly
 1               5                  10                  15

Asn Val Gly Leu Tyr Val Cys Ala Ile Val Ala Glu Arg Val Ser Cys
             20                  25                  30

Ser Ala Leu Ile Gln Cys Ala Asn Asp Ala Pro Gly Glu Ile Gln Leu
         35                  40                  45

Ile Gly His Gly Asp Phe Thr Ala Val Val Met Val Pro Glu Lys Asp
 50                  55                  60

Gln Leu Val Ser Pro Asp Arg Lys Glu Leu Met Gln Gln Leu Leu Val
 65                  70                  75                  80

His Gln Gln Leu Ile Glu Lys Phe Met Glu Ile Ala Pro Val Leu Pro
             85                  90                  95

Val Lys Phe Ala Thr Leu Ala Pro Asn Arg Glu Ser Val Glu Leu Gly
             100                 105                 110

Leu Glu Val Gly Ser Glu Lys Phe Ser Ala Ala Phe Asn Ser Leu Ser
             115                 120                 125
```

```
Gly Lys Val Gln Phe Glu Val Ile Val Thr Trp Asp Val Ala Glu Val
    130                 135                 140

Phe Ala Glu Ile Ala Lys Glu Pro Ala Val Ala Lys Leu Lys Val Asp
145                 150                 155                 160

Leu Ala Ala Met Pro Glu Ser Tyr Gly Ser Val Ser Leu Glu Gln Leu
                165                 170                 175

Gly Lys Leu Val Lys Glu Thr Leu Glu Leu Arg Arg Ala Glu Thr Gly
                180                 185                 190

Lys Val Leu Leu Asp Ala Leu Val Gln Val Gly Val Asp Asn Val Val
                195                 200                 205

Asn Ser Ile Leu Asp Asp Ser Ile Ile Leu Asn Leu Ala Leu Leu Val
210                 215                 220

Glu Ala Lys Arg Ala Asp Ala Phe Asp Arg Cys Leu Asp Glu Leu Asp
225                 230                 235                 240

Ser Thr Tyr His Gly Ala Leu Thr Phe Arg Cys Val Gly Pro Leu Pro
                245                 250                 255

Pro His Ser Phe Ala Thr Val Glu Ile Thr Tyr Leu Glu Pro Ala Lys
                260                 265                 270

Val Thr Glu Ala Cys Asp Ile Leu Glu Leu Asp Val Ala Arg Ser Thr
                275                 280                 285

Glu Glu Val Arg Ser Ala Tyr His Arg Leu Ala Arg Lys Ser His Pro
290                 295                 300

Asp Ile Val Pro Asp Val Ala Val Gly Glu Thr Ala Ser Val Ser Met
305                 310                 315                 320

Ala Val Leu Thr Asp Ala Tyr Lys Thr Leu Leu Ser Phe Val Gly Ala
                325                 330                 335

Gly Gly Ser Val Val Val Ser Val Gln Arg Gln Glu Ala Ser Tyr Ala
                340                 345                 350

Ala Asp Ile Ile Ser Ser Ala Gly
                355                 360

<210> SEQ ID NO 109
<211> LENGTH: 258
<212> TYPE: PRT
<213> ORGANISM: Pelodictyon phaeoclathratiforme

<400> SEQUENCE: 109

Met Asp Ile Glu Thr Thr Lys Glu Gly Arg Tyr Ile Tyr Gly Ile Ile
1               5                   10                  15

Arg Asn Ser Glu Phe Ile Asp Phe Gly Gln Ile Gly Ile Gly Lys Arg
                20                  25                  30

Asn Asp Arg Val Tyr Gly Val Ile Tyr Lys Asp Ile Cys Ala Val Val
                35                  40                  45

Ser Ser Thr Pro Ile Ile Gln Tyr Glu Ala Arg Arg Ala Asn Met Ile
            50                  55                  60

Ala His Gln Lys Val Leu Glu Glu Val Met Lys Arg Phe Asn Val Leu
65                  70                  75                  80

Pro Val Arg Phe Ser Thr Ile Ser Pro His Asp Asn Asp Ala Ile
                85                  90                  95

Ile Lys Ile Leu Ile Thr Asp Tyr Ser Arg Phe Asp Glu Leu Leu Ile
                100                 105                 110

Lys Met Lys Gly Lys Lys Glu Leu Gly Leu Lys Val Met Ala Asp Glu
                115                 120                 125

Thr Arg Ile Tyr Glu Asn Ile Ile Gln Lys Tyr Asp Asn Ile Arg Ser
                130                 135                 140
```

Leu Arg Asp Lys Leu Leu Asn Gln Pro Ala Asp Lys Ile His Tyr Gln
145                 150                 155                 160

Arg Val Lys Ile Gly Glu Met Val Ala Asp Ala Leu Lys Lys Glu Ile
                165                 170                 175

Glu Ser Tyr Lys Gln Gln Ile Leu Asp Ile Leu Ser Pro Ile Ala Glu
            180                 185                 190

Asp Ile Lys Ile Thr Asp Asn Tyr Gly Asn Leu Met Ile Leu Asn Ala
                195                 200                 205

Ala Phe Leu Ile Lys Glu Val Lys Glu Ser Glu Phe Asp Asp Ser Val
            210                 215                 220

Asn Lys Leu Asp Glu Lys Tyr Gly Asn Ile Met Thr Phe Lys Tyr Val
225                 230                 235                 240

Gly Thr Leu Pro Pro Tyr Asn Phe Val Asn Leu Ser Ile Asn Thr Lys
                245                 250                 255

Gly Val

<210> SEQ ID NO 110
<211> LENGTH: 257
<212> TYPE: PRT
<213> ORGANISM: Pelodictyon phaeoclathratiforme

<400> SEQUENCE: 110

Met Glu Lys Asp Gly Lys Tyr Val Tyr Cys Ile Ile Ala Ser Thr Tyr
1               5                   10                  15

Glu Cys Asn Phe Gly Ala Ile Gly Ile Gly Gly Arg Gly Asp Leu Val
                20                  25                  30

Asn Thr Ile Gly Phe Gln Gly Leu Ser Met Val Val Ser Asp His Pro
            35                  40                  45

Leu Asn His Phe Val Leu Asn Pro Asp Asn Ile Leu Ala His Gln Arg
        50                  55                  60

Val Ile Glu Val Val Met Ser Gln Phe Asn Ser Val Ile Pro Val Arg
65                  70                  75                  80

Phe Gly Thr Val Ala Ala Thr Pro Asp Glu Ile Arg Asn Leu Leu Asp
                85                  90                  95

Arg Arg Tyr Gly Glu Leu Ser Glu Leu Leu Glu Arg Phe Glu Asn Lys
                100                 105                 110

Val Glu Tyr Asn Leu Lys Ala Ser Trp Arg Cys Met Ile Asp Ile Tyr
            115                 120                 125

Lys Glu Ile Asp Lys Glu His Val Glu Leu Lys Gln Leu Arg Arg Glu
130                 135                 140

Ile Glu Gly Leu Lys Asp Glu Glu Lys Arg Lys Leu Leu Ile Val Glu
145                 150                 155                 160

Ala Gly His Ile Ile Glu Asn Glu Leu Gln Lys Lys Glu Val
                165                 170                 175

Ala Tyr Glu Ile Val Thr Tyr Leu Arg Lys Thr Val Val Ala His Lys
            180                 185                 190

His Asn Lys Thr Thr Gly Glu Ala Met Phe Met Asn Thr Ala Phe Leu
        195                 200                 205

Leu Asn Lys Gly Arg Glu Val Glu Phe Asp Asn Ile Met Asn Asp Leu
        210                 215                 220

Gly Glu Gln Tyr Lys Asp Arg Ser Asp Tyr Tyr Tyr Thr Gly Pro Leu
225                 230                 235                 240

Pro Ile Phe Asn Phe Ile Asp Leu Arg Ile Leu Pro Glu Lys Trp Glu
                245                 250                 255

Leu

```
<210> SEQ ID NO 111
<211> LENGTH: 339
<212> TYPE: PRT
<213> ORGANISM: Pelodictyon phaeoclathratiforme

<400> SEQUENCE: 111
```

| | | | | | | | | | | | | | | |
|---|---|---|---|---|---|---|---|---|---|---|---|---|---|---|

Met Asp Arg Gln Gly Ile Tyr Ile Tyr Gly Phe Ile Pro Asn His Tyr
 1               5                  10                  15

Leu Thr Asp Ile Lys Thr Ile Leu Ile Glu Ser Gly Ile Tyr Ser Ile
            20                  25                  30

Glu Tyr Gly Ser Ile Ala Ala Leu Val Ser Asp Thr Met Val Asp Asp
        35                  40                  45

Ile Glu Tyr Leu Asn Arg Glu Asp Leu Ala Tyr Leu Leu Val Asp His
    50                  55                  60

Gln Lys Lys Ile Glu Leu Ile Met Ser Thr Gly Cys Ser Thr Ile Ile
65                  70                  75                  80

Pro Met Gln Leu Gly Thr Ile Val Asn Ser Gly Asn Asp Val Ile Lys
                85                  90                  95

Ile Val Lys Asn Gly Leu Arg Ile Ile Asn Lys Thr Phe Asp Asp Ile
            100                 105                 110

Ala Asp Ile Gln Glu Phe Asp Leu Val Val Met Trp Asn Asn Phe Pro
        115                 120                 125

Asp Leu Ile Lys Lys Ile Ser Asp Thr Pro Gln Ile Arg Ile Met Lys
    130                 135                 140

Glu Glu Ile Ala Asn Lys Gly Ser Tyr Asp Gln Ala Asp Ser Ile Asn
145                 150                 155                 160

Ile Gly Lys Ile Ile Lys Lys Ile Asp Glu Lys Asn Ser Lys Val
                165                 170                 175

Asn Leu Asp Ile Met Asn Ser Leu Ser Ser Leu Cys Ile Cys Val Lys
            180                 185                 190

Lys His Glu Ser Met Asn Asp Glu Met Pro Leu Asn Ser Ala Phe Leu
        195                 200                 205

Ile Lys Lys Asp Lys Glu Asn Ser Phe Ile Glu Met Val Asn Gln Leu
    210                 215                 220

Asp Ile Lys Tyr Glu Asn Leu Leu Arg Tyr Lys Ile Val Gly Pro Leu
225                 230                 235                 240

Pro Cys Tyr Ser Phe Tyr Thr Leu Glu Ser Lys Leu Leu Asn Lys Lys
                245                 250                 255

Glu Ile Glu Lys Ala Glu Lys Ile Leu Gly Ile Asp Ala Tyr Lys Ser
            260                 265                 270

Glu Ser Asp Ile Lys Lys Ala Tyr Arg Ala Lys Ala His Ala His
        275                 280                 285

Pro Asp Lys Asn Asn Thr Ile Ser Ala Ile Asp Asn Asp Phe Ile
        290                 295                 300

Glu Ile Asn Lys Ala Tyr Gln Ile Leu Leu Glu Tyr Ser Ser Val Phe
305                 310                 315                 320

Lys Asp Ser Pro Asp His Lys Pro Asp Glu Pro Phe Tyr Leu Val Lys
                325                 330                 335

Ile Lys Lys

```
<210> SEQ ID NO 112
<211> LENGTH: 244
```

-continued

```
<212> TYPE: PRT
<213> ORGANISM: Phormidium tenue NIES-30

<400> SEQUENCE: 112
```

Met Ala Asp Arg Tyr Tyr Leu Tyr Gly Ile Phe Pro Ala Pro Gly Pro
1               5                   10                  15

Ala Glu Leu Pro Leu Met Gly Leu Asp Glu Gln Val Val Gln Ala Gln
            20                  25                  30

Gln Leu Gly Asp Phe Thr Phe Leu Tyr Ser Leu Ala Cys Gln Lys Arg
        35                  40                  45

Tyr Leu Ser Ser Arg Lys Asn Leu Leu Gly His Glu Lys Val Leu Glu
50                  55                  60

Ala Ala Met Glu Gln Gly His Arg Thr Leu Leu Pro Leu Gln Phe Gly
65                  70                  75                  80

Leu Ile Val Glu Ser Trp Asn Gln Val Gln Asp Leu Val Thr Pro
                85                  90                  95

Tyr Ala Glu Asp Leu Thr Gln Leu Phe Gly Arg Leu Asn Gly Cys Arg
            100                 105                 110

Glu Val Ser Ile Lys Val Gln Trp Glu Pro Ser Thr Glu Leu Glu Met
        115                 120                 125

Met Met Ala Glu Asn Ala Asp Leu Arg Ala Gln Arg Asp Gln Leu Glu
130                 135                 140

Gly Thr Gln Leu Gly Met Glu Gln Val Ile Phe Ile Gly Gln Gln Ile
145                 150                 155                 160

Glu Ser Ala Leu Glu Glu Arg Lys Gln Gly Ile Val Asp Gln Phe Arg
            165                 170                 175

Gln Ala Leu Ser Pro Leu Ala Lys Asp Val Leu Glu Asn Ala Pro Gln
        180                 185                 190

Thr Asp Val Met Ile Tyr Asn Ala Ala Phe Leu Ile Pro Trp Glu Ser
            195                 200                 205

Glu Ala Glu Phe Ser Gln Ala Val Asp Ala Ile Asp Ser Thr Phe Gly
210                 215                 220

Asp Arg Leu Arg Ile Arg Tyr Asn Asn Phe Thr Ala Pro Tyr Asn Phe
225                 230                 235                 240

Ala Gln Leu Asn

```
<210> SEQ ID NO 113
<211> LENGTH: 245
<212> TYPE: PRT
<213> ORGANISM: Planktothrix agardhii str. 7805

<400> SEQUENCE: 113
```

Met Gly Asn Gly Leu Tyr Leu Tyr Gly Ile Leu Pro Thr Asn Arg Val
1               5                   10                  15

Arg Pro Leu Ala Leu His Gly Leu Asp Lys Gln Pro Ile Gln Thr His
            20                  25                  30

Pro Val Asp Glu Phe Ser Phe Leu Tyr Ser Glu Thr Gln Gln Glu Arg
        35                  40                  45

Tyr Leu Ala Ser Arg Arg Asn Leu Leu Gly His Glu Asp Val Leu Glu
50                  55                  60

Lys Val Met Gln His Gly Tyr Arg Ser Val Leu Pro Leu Gln Phe Gly
65                  70                  75                  80

Leu Ile Val Lys Asp Trp Asp His Val Lys Ala Gln Leu Ile Ile Pro
                85                  90                  95

Tyr Gln Asp Arg Leu Lys Glu Leu Phe His Lys Leu Glu Gly Lys Arg

```
                  100                 105                 110
Glu Val Gly Val Lys Ile Phe Trp Glu Glu Thr Glu Glu Leu Asp Leu
            115                 120                 125

Leu Met Thr Glu Asn Gln Glu Leu Arg Glu Lys Arg Asp Ser Leu Glu
130                 135                 140

Gly Lys Arg Leu Ser Met Asp Glu Ile Ile Gly Ile Gly Gln Glu Ile
145                 150                 155                 160

Glu Arg Ala Met Gln Asp Arg Gln Gln Gly Ile Ile Asp Lys Phe Gln
                165                 170                 175

Gln Ile Leu Asn Pro Leu Ala Gln Glu Ile Val Glu Asn Asp Asn Leu
            180                 185                 190

Thr Ser Ala Met Ile Tyr Asn Ala Ala Tyr Leu Ile Pro Trp Asp Ile
        195                 200                 205

Glu Pro Gln Phe Gly Asp Lys Ile Glu Glu Leu Asp His His Phe Asn
    210                 215                 220

Asn Arg Leu Arg Ile Arg Tyr Asn Asn Phe Thr Ala Pro Phe Asn Phe
225                 230                 235                 240

Ala Gln Leu Asn Pro
            245

<210> SEQ ID NO 114
<211> LENGTH: 268
<212> TYPE: PRT
<213> ORGANISM: Psychromonas ingrahamii 37

<400> SEQUENCE: 114

Met Ala Glu Asn Lys Lys Val Arg Lys Ser Ser Lys Val Ile
1               5                   10                  15

Ala Lys Pro Lys Val Ile Tyr Ala Ile Thr Ala Gly Gly Leu Gln Asp
            20                  25                  30

Leu Gly Asn Leu Val Gly Ile Asn Lys Ser Asp Ile Tyr Thr Ile Glu
        35                  40                  45

Lys Glu Ser Ile Ser Phe Val Val Ser Asp Leu Ser Pro Ser Ser Pro
    50                  55                  60

Arg Pro Arg Pro Asp Arg Arg Asn Ile Met Ala His Asn Glu Ile Leu
65                  70                  75                  80

Lys Gln Leu Met Ser Lys Thr Ser Val Leu Pro Val Arg Phe Gly Thr
                85                  90                  95

Val Ala Thr Gly Glu Arg Ala Val Asn Arg Phe Cys Ser Gln Tyr Asn
            100                 105                 110

Ala Gln Leu Leu Glu Gln Leu Asp Arg Val Gln Asp Arg Val Glu Met
        115                 120                 125

Gly Ile Lys Val Thr Trp Asn Val Pro Asn Ile Tyr Asp Tyr Phe Val
    130                 135                 140

Asp Asn His Ser Glu Leu Arg Glu Glu Arg Asp Arg Val Tyr Asp Gly
145                 150                 155                 160

Asn Lys Asn Pro Arg Arg Asp Asp Arg Ile Asn Leu Gly His Met Tyr
                165                 170                 175

Asp Ala Leu Val Thr Glu Ala Arg Leu Ser His Gln Thr Asp Leu Glu
            180                 185                 190

Glu Ile Ile Leu Pro Gly Cys Asp Glu Ile His Ser Ile Pro Pro Lys
        195                 200                 205

Asp Glu Lys Val Val Val Asn Leu Ala Cys Leu Val Gln Arg Ala Asp
    210                 215                 220
```

```
Leu Glu Val Phe Glu Arg Val Val Glu Ala Gly Lys Thr Leu Asp
225                 230                 235                 240

Asn Thr Tyr Asp Ile Glu Leu Asn Gly Pro Trp Ala Pro His Asn Phe
            245                 250                 255

Val Glu Leu Asp Leu Lys Thr Met Thr Gly Arg Arg
            260                 265
```

<210> SEQ ID NO 115
<211> LENGTH: 273
<212> TYPE: PRT
<213> ORGANISM: Serratia sp. ATCC 39006

<400> SEQUENCE: 115

```
Met Met Ser Ile Asp Lys Ser Arg Asn His Arg Ala Lys Val Leu Tyr
1               5                   10                  15

Ala Leu Cys Val Ser Asp Asp Ser Thr Pro Asn Tyr Lys Ile Arg Gly
            20                  25                  30

Leu Glu Ala Ala Pro Val Tyr Ser Ile Asp Gln Asp Gly Leu Arg Ala
        35                  40                  45

Val Val Ser Asp Thr Leu Ser Thr Arg Leu Arg Pro Glu Arg Arg Asn
50                  55                  60

Ile Thr Ala His Gln Ala Val Leu His Lys Leu Thr Glu Glu Gly Thr
65                  70                  75                  80

Val Leu Pro Met Arg Phe Gly Val Ile Ala Arg Asn Ala Glu Ala Val
            85                  90                  95

Lys Asn Leu Leu Val Ala Asn Gln Asp Thr Ile Arg Glu His Phe Glu
        100                 105                 110

Arg Leu Asp Gly Cys Val Glu Met Gly Leu Arg Val Ser Trp Asp Val
        115                 120                 125

Thr Asn Ile Tyr Glu Tyr Phe Val Ala Thr Tyr Pro Val Leu Ser Glu
    130                 135                 140

Thr Arg Asp Glu Ile Trp Asn Gly Asn Ser Asn Ala Asn Asn His Arg
145                 150                 155                 160

Glu Glu Lys Ile Arg Leu Gly Asn Leu Tyr Glu Ser Leu Arg Ser Gly
                165                 170                 175

Asp Arg Lys Glu Ser Thr Glu Lys Val Lys Glu Val Leu Leu Asp Tyr
            180                 185                 190

Cys Glu Glu Ile Ile Glu Asn Pro Val Lys Lys Glu Lys Asp Val Met
        195                 200                 205

Asn Leu Ala Cys Leu Val Ala Arg Glu Arg Met Asp Glu Phe Ala Lys
    210                 215                 220

Gly Val Phe Glu Ala Ser Lys Leu Phe Asp Asn Val Tyr Leu Phe Asp
225                 230                 235                 240

Tyr Thr Gly Pro Trp Ala Pro His Asn Phe Val Thr Leu Asp Leu His
                245                 250                 255

Ala Pro Thr Ala Lys Lys Lys Thr Leu Thr Arg Ala Gly Thr Leu Ser
            260                 265                 270

Asp
```

<210> SEQ ID NO 116
<211> LENGTH: 260
<212> TYPE: PRT
<213> ORGANISM: Stella vacuolata_ATCC-43931

<400> SEQUENCE: 116

```
Met Gln Thr Glu Ala Leu Ala Pro Ala Ala Val Ala Ala Glu Gly Lys
```

```
1               5                   10                  15
Tyr Leu Tyr Cys Ile Ile Asp Ala Pro Ala Pro Ala Thr Phe Ala Ser
            20                  25                  30

Pro Gly Ile Gly Gly Arg Gly Asp Val Val His Thr Leu Ala Val Gly
            35                  40                  45

Arg Leu Ala Ala Val Val Ser Asp Thr Pro Arg Ile Glu Tyr Glu Asn
            50                  55                  60

Ser Arg Arg Asn Met Met Ala His Thr Lys Val Leu Glu Glu Val Met
65                  70                  75                  80

Ala His His Thr Leu Leu Pro Val Cys Phe Gly Thr Val Gly Ser Gly
            85                  90                  95

Asp Asp Val Ile Ala Glu Lys Ile Leu Glu Gly Arg Arg Glu Glu Leu
            100                 105                 110

Ser Arg Leu Leu Glu Glu Met Arg Gly Arg Val Glu Leu Gly Leu Lys
            115                 120                 125

Ala Thr Trp Arg Glu Glu Val Ile Phe Ala Glu Val Leu Asp Glu Asp
            130                 135                 140

Pro Ala Val Arg Lys Leu Arg Asp Ser Leu Val Gly Arg Ser Pro Glu
145                 150                 155                 160

Lys Ser His Phe Glu Arg Ile Arg Leu Gly Glu Leu Ile Gly Gln Ala
            165                 170                 175

Leu Leu Arg Lys Arg Arg Asp Glu Glu Arg Ile Leu Asp Arg Val
            180                 185                 190

Arg Pro Phe Val Arg Lys Thr Lys Leu Asn Lys Pro Ile Gly Asp Arg
            195                 200                 205

Met Ile Leu Asn Ala Ala Phe Leu Val Glu Thr Ala Arg Glu Ala Ala
210                 215                 220

Leu Asp Gln Ser Val Arg Glu Met Asp Ala Asp Trp Gly Ala Arg Leu
225                 230                 235                 240

Ser Phe Lys Tyr Val Gly Pro Val Pro Pro Tyr Asn Phe Val Thr Ile
            245                 250                 255

Thr Ile His Trp
            260

<210> SEQ ID NO 117
<211> LENGTH: 254
<212> TYPE: PRT
<213> ORGANISM: Thiocapsa rosea strain DSM 235 Ga0242571_11

<400> SEQUENCE: 117

Met Gln Gln Ala Lys Arg Gln Asp Val Ala Gly Arg Tyr Ile Tyr
1               5                   10                  15

Ala Ile Ile Pro Asp Arg Gly Asp His Ser Leu Gly Ile Gly Leu
            20                  25                  30

Asp Glu Ser Glu Val Tyr Thr Ile Gly Asp Gly Arg Val Ala Ala Val
            35                  40                  45

Val Ser Asp Leu Ser Gly Gly Arg Ile Arg Pro Gln Arg Arg Asn Met
50                  55                  60

Ala Ala His Gln Glu Val Leu Lys Gln Val Leu Arg Glu Val Ser Pro
65                  70                  75                  80

Leu Pro Ala Ala Phe Gly Leu Met Ala Asp Asp Glu Ala Ala Ile Ile
            85                  90                  95

Arg Ile Leu Lys Asp Asn Gln Asp Ala Phe Leu Asn Gln Leu Glu Arg
            100                 105                 110
```

Val Asp Gly Ser Leu Glu Met Gly Leu Arg Met Ser Trp Asp Val Pro
115                 120                 125

Asn Ile Phe Glu Tyr Phe Val Gly Ala His Pro Glu Leu Gln Glu Leu
130                 135                 140

Arg Asp Asp Phe Phe Arg Asp Gly Ser Asn Leu Thr Gln Asp Gln Met
145                 150                 155                 160

Ile Thr Leu Gly Arg Ser Phe Glu Arg Leu Leu Glu Gln Asp Arg Glu
                165                 170                 175

Glu Tyr Thr Glu Gln Val Glu Ser Val Met Arg Ser Cys Cys Arg Glu
                180                 185                 190

Ile Lys Arg Asn Lys Cys Arg Thr Glu Lys Glu Val Leu His Leu Ala
                195                 200                 205

Cys Leu Val Asp Arg Asp Ala Ala Gly Arg Phe Glu Gln Val Val Leu
210                 215                 220

Gln Ala Ala Arg Pro Phe Asp Asn Asn Tyr Ala Phe Asp Phe Asn Gly
225                 230                 235                 240

Pro Trp Ala Pro His Asn Phe Val Glu Met Asp Ile His Val
                245                 250

<210> SEQ ID NO 118
<211> LENGTH: 244
<212> TYPE: PRT
<213> ORGANISM: Tolypothrix sp. PCC 7601

<400> SEQUENCE: 118

Met Asp Ala Gly Leu Tyr Leu Tyr Gly Ile Phe Ser Asp Pro Ile Pro
1               5                   10                  15

Pro Thr Val Ser Leu Lys Gly Leu Asp Ser Gln Pro Val Tyr Ser Gln
                20                  25                  30

Val Ile Glu Gly Phe Thr Phe Leu Tyr Ser Asp Ala Lys Gln Glu Lys
                35                  40                  45

Tyr Leu Ala Ser Arg Arg Asn Leu Ile Ser His Glu Lys Val Leu Glu
50                  55                  60

Gln Ala Met Gln Glu Gly Phe Arg Thr Leu Leu Pro Leu Arg Phe Gly
65                  70                  75                  80

Leu Val Val Lys Asn Trp Glu Thr Val Ile Ser Gln Leu Ile Gln Pro
                85                  90                  95

Cys Glu Arg Gln Leu Arg Asp Leu Phe Gln Lys Leu Ala Gly Lys Arg
                100                 105                 110

Glu Val Ser Val Lys Ile Leu Trp Asp Thr Lys Ala Glu Leu Gln Ala
                115                 120                 125

Met Met Gln Ser Asn Pro Asp Leu Lys Gln Lys Arg Asp Gln Met Glu
130                 135                 140

Gly Lys Asn Leu Ser Met Glu Glu Val Ile Glu Ile Gly Gln Leu Ile
145                 150                 155                 160

Glu Ser Asn Leu Gln Gln Arg Lys Glu Ala Val Ile Lys Thr Phe Phe
                165                 170                 175

Asp Glu Leu Lys Pro Leu Ala Glu Glu Val Val Glu Ser Glu Pro Met
                180                 185                 190

Met Glu Glu Met Ile Tyr Asn Ala Ala Phe Leu Ile Pro Trp Asp Gln
                195                 200                 205

Glu Ala Leu Phe Ser Gln Arg Val Glu Ala Ile Asp Lys Lys Phe Gly
210                 215                 220

Asp Arg Leu Arg Ile Arg Tyr Asn Asn Phe Thr Ala Pro Tyr Thr Phe
225                 230                 235                 240

Ala Gln Ile Ser

<210> SEQ ID NO 119
<211> LENGTH: 266
<212> TYPE: PRT
<213> ORGANISM: Trichodesmium erythraeum IMS101

<400> SEQUENCE: 119

Met Glu Phe Gly Phe Tyr Val Tyr Gly Leu Ile Gln Glu Lys Gly Lys
1               5                   10                  15

Met Asp Glu Ser Lys Asp Glu Ser Lys Asn Gly Leu Lys Gly Ser Asn
            20                  25                  30

Glu Ser Lys Asp Glu Leu Lys Gly Leu Asp Lys Glu Asp Val Lys Ile
        35                  40                  45

Gln Asp Val Asp Glu Phe Ala Val Leu Tyr Ser Ile Ala Lys Lys Glu
    50                  55                  60

Arg Tyr Leu Ala Ser Arg Arg Asn Leu Ile Thr His Glu Lys Val Leu
65                  70                  75                  80

Glu Ser Ala Met Glu Ala Gly Tyr Arg Asn Leu Leu Pro Met Gln Phe
                85                  90                  95

Gly Leu Val Val Ser Glu Trp Glu Lys Phe Ser Gln Asp Phe Thr Lys
            100                 105                 110

Pro Cys Glu Gln Gln Ile His Asp Leu Phe Thr Lys Leu Lys Asn Asn
        115                 120                 125

Arg Glu Val Gly Ile Lys Ile Tyr Trp Glu Pro Asp Ala Glu Leu Glu
    130                 135                 140

Lys Leu Leu Glu Asn Asp Lys Asp Leu Lys Glu Glu Arg Asp Ser Leu
145                 150                 155                 160

Lys Asp Lys Lys Leu Thr Met Asp Gln Val Ile Asp Ile Gly Gln Lys
                165                 170                 175

Ile Glu Gln Gly Met Asn Glu Arg Lys Gln Asn Ile Ile Glu Ile Phe
            180                 185                 190

Gln Glu Thr Leu Asn Lys Met Ala Ile Glu Val Ile Glu Asn Glu Val
        195                 200                 205

Gln Thr Glu Lys Met Ile Tyr Asn Ala Ala Tyr Leu Ile Pro Trp Asp
    210                 215                 220

Gln Glu Glu Asp Phe Gly Glu Lys Val Glu Thr Ile Asp Ser Lys Leu
225                 230                 235                 240

Cys Glu Arg Gly Asn Phe Thr Ile Arg Tyr Asn Ser Phe Thr Ala Pro
                245                 250                 255

Tyr Asn Phe Ala Arg Ile Arg Gln Gln Asp
            260                 265

<210> SEQ ID NO 120
<211> LENGTH: 334
<212> TYPE: PRT
<213> ORGANISM: Ancylobacter aquaticus strain UV5

<400> SEQUENCE: 120

Met Thr Asp Leu Leu Val Phe Ala Val Val Pro Ala Asp Arg Phe Asp
1               5                   10                  15

Pro Ala Ile Leu Ala Glu Gly Asp Gly Leu Pro Pro Gly Leu Arg Ala
            20                  25                  30

Ile Ala Ala Gly Pro Leu Ala Val Val Gly Ala Ala Pro Glu Gly
        35                  40                  45

Gly Leu Lys Gly Arg Glu Arg Ser Ala Leu Leu Pro Trp Leu Leu Ala
    50                  55                  60

Ser Gln Lys Val Met Glu Arg Leu Leu Ala Asn Ala Pro Val Leu Pro
65                  70                  75                  80

Val Ala Leu Gly Thr Val Val Glu Asp Glu Gly Arg Val Arg His Met
                85                  90                  95

Leu Asp Ala Gly Ala Ala Ile Leu Gly Glu Gly Phe Gln Ala Val Gly
                100                 105                 110

Asp Gly Ile Glu Met Asn Leu Ser Val Leu Trp His Leu Asp Thr Val
            115                 120                 125

Val Ala Arg Leu Leu Pro Gly Val Ala Pro Glu Leu Arg Gln Ala Ala
130                 135                 140

Ala Gly Gly Asp Ala Ile Glu Arg Gln Ala Leu Gly Val Val Leu Ala
145                 150                 155                 160

Gly Leu Val Ser Ala Glu Arg Arg Ala Arg Ala Arg Val Ile Glu
                165                 170                 175

Ala Leu Gln Ala Val Thr Arg Asp Phe Ala Ile Gly Glu Pro Thr Glu
            180                 185                 190

Pro Gly Gly Val Val Asn Leu Ala Leu Leu Val Asp Arg Ala Ala Glu
        195                 200                 205

Glu Ala Leu Gly Ala Ala Leu Glu Ala Leu Asp Ala Glu Phe Asp Gly
    210                 215                 220

Ala Leu Thr Phe Arg Leu Val Gly Leu Pro Pro Tyr Ser Phe Ala
225                 230                 235                 240

Ser Val Gln Val His Leu Ser Pro Ala Ala Val Cys Gly Ala Arg
                245                 250                 255

Ala Ala Leu Gly Val Glu Pro Asp Ala Ser Pro Glu Thr Val Lys Ala
                260                 265                 270

Ala Tyr Arg Arg Ala Ala Arg Glu Thr His Pro Asp Leu Val Pro Met
            275                 280                 285

Gly Gly Glu Asp Glu Glu Ala Pro Glu Ala Thr Ala Asp Glu Thr Ser
        290                 295                 300

Arg Phe Val Val Leu Ser Asp Ala Tyr Arg Val Leu Glu Gly Glu His
305                 310                 315                 320

Ala Pro Val Ser Leu Arg Arg Leu Asp Ser Val Leu Thr Glu
                325                 330

<210> SEQ ID NO 121
<211> LENGTH: 255
<212> TYPE: PRT
<213> ORGANISM: Ancylobacter aquaticus strain UV5

<400> SEQUENCE: 121

Met Leu Tyr Val Tyr Ala Ile Thr Ala Asp Tyr Ala Ala Gly Ala Asn
1               5                   10                  15

His Leu Leu Pro Ala Lys Gly Ile Val Pro Gly Val Pro Val Gln Arg
            20                  25                  30

Phe Gly Thr Gly Ala Leu Gly Ala Val Ala Ser Pro Val Pro Val Thr
        35                  40                  45

Val Phe Gly Lys Glu Ala Leu His Ala Leu Leu Asp Asp Ala Asp Trp
    50                  55                  60

Thr Arg Ala Arg Ile Leu Ala His Gln Arg Val Val Ser Ser Leu Leu
65                  70                  75                  80

Pro Leu Ala Thr Val Leu Pro Leu Lys Phe Gly Thr Leu Val Ala Gly
                85                  90                  95

```
Glu Ala Ser Leu Ala Ala Ala Leu Thr Ser Gln His Asp Ala Leu Asp
                100                 105                 110

Ala Thr Val Ala Arg Leu Arg Gly Ala Arg Glu Trp Gly Val Lys Leu
            115                 120                 125

Phe Phe Glu Ala Pro Thr Arg Thr Ile Arg Ala Glu Glu Pro Val Gly
        130                 135                 140

Ala Gly Ala Gly Leu Ala Phe Phe Arg Arg Lys Lys Glu Glu Gln Glu
145                 150                 155                 160

Thr Arg Ala Ala Ala Glu Ala Ala Leu Asp Arg Cys Val Ala Ala Ser
                165                 170                 175

His Arg Arg Leu Ala Ser His Ala Arg Ala Ala Val Ala Asn Pro Leu
            180                 185                 190

Gln Pro Pro Glu Leu His Gly His Pro Gly Thr Met Gly Leu Asn Gly
        195                 200                 205

Ala Tyr Leu Val Ala Ala Glu Asn Glu Ala Ala Trp Arg Val Cys Phe
    210                 215                 220

Ser Glu Leu Glu Gln Ala Tyr Ala Ala Leu Gly Ala Arg Tyr Val Arg
225                 230                 235                 240

Thr Gly Pro Trp Ala Ala Tyr Asn Phe Thr Gly Gly Gly Leu Val
                245                 250                 255

<210> SEQ ID NO 122
<211> LENGTH: 337
<212> TYPE: PRT
<213> ORGANISM: Aquabacter spiritensis strain DSM 9035

<400> SEQUENCE: 122

Met Ser Gly Leu Leu Val Phe Ala Ile Val Pro Ala Asp Arg Ile Glu
1               5                   10                  15

Pro Gly Leu Leu Ala Pro Ala Glu Gly Leu Pro Pro Gly Leu Glu Thr
            20                  25                  30

Val Val Ala Ala Gly Phe Ala Ala Ile Val Gly Thr Ala Pro Glu Gly
        35                  40                  45

Gly Leu Lys Gly Arg Asp Arg Gly Ser Leu Leu Pro Trp Leu Leu Ala
    50                  55                  60

Ser Gln Lys Val Ile Glu Arg Leu Met Ala Arg Gly Pro Val Leu Pro
65                  70                  75                  80

Ala Ala Leu Gly Ser Val Leu Glu Asp Glu Ser Arg Val Arg His Met
                85                  90                  95

Leu Val Cys Gly Gln Ala Ala Leu Ala Ala Phe Glu Thr Leu Asn
            100                 105                 110

Gly Cys Trp Gln Thr Asp Leu Ser Val Arg Trp Asp Leu Ser Arg Thr
        115                 120                 125

Val Ala His Leu Met Thr Glu Leu Pro Pro Gly Leu Arg Ala Ala Ala
    130                 135                 140

Glu Thr Gly Asp Glu Thr Ala Arg Arg Ser Leu Gly Ala Ala Leu Ala
145                 150                 155                 160

Gly Leu Val Ala Gly Glu Arg Arg Ile Gln Ser Arg Ile Gly Ala
                165                 170                 175

Val Leu Gly Ala Val Ala Arg Asp Leu Ile Val Ser Asp Pro Val Glu
            180                 185                 190

Pro Glu Gly Val Val Gly Val Ala Leu Leu Val Asp Ala Pro Ala Ser
        195                 200                 205

Ala Gln Val Asp Ala Ala Leu Asp Arg Leu Asp Gly Glu Phe Glu Gly
```

Arg Leu Thr Phe Arg Leu Val Gly Pro Leu Ala Pro Tyr Ser Phe Ala
225                 230                 235                 240

Thr Val Gln Ile His Leu Gly Pro Ala Ala Gly Leu Ala Gly Ala His
            245                 250                 255

Ala Glu Leu Gly Leu Glu Ala Gly Ala Pro Leu Glu Ala Val Lys Ala
            260                 265                 270

Ala Tyr His Arg Leu Ile Val Gly Leu His Pro Asp Leu Val Pro His
            275                 280                 285

Gly Ser Pro Gly Asp Ala Asp Asp Ala Ala Ser Gly Lys Gly Gly
290                 295                 300

Arg Ala Ala Arg Phe Ala Ala Val Thr Ala Ala Tyr Arg Thr Leu Gln
305                 310                 315                 320

Ala Glu His Ala Pro Val Ser Leu Arg Arg Gln Asp Gly Leu Ser Pro
            325                 330                 335

Gly

<210> SEQ ID NO 123
<211> LENGTH: 257
<212> TYPE: PRT
<213> ORGANISM: Aquabacter spiritensis strain DSM 9035

<400> SEQUENCE: 123

Met Leu Tyr Val Tyr Ala Ile Thr Ala Asp His Pro Gly Pro His Asp
1               5                   10                  15

Ala Gly Ser Leu Pro Gly Glu Gly Ile Val Pro Gly Ala Pro Val Arg
            20                  25                  30

Leu Leu Pro Phe Gly Asp Leu Ala Ala Ala Val Ser Pro Val Ser Ala
            35                  40                  45

Val Asp Phe Gly Pro Glu Ala Leu Pro Ala Arg Leu Gln Asp Val Asp
50                  55                  60

Trp Thr Gly Gln Arg Val Leu Ala His Gln Arg Val Val Asp Ser Leu
65                  70                  75                  80

Val Asp Val Ala Thr Val Leu Pro Met Lys Phe Cys Thr Leu Phe Ser
                85                  90                  95

Gly Ala Ala Ala Leu Arg Ala Ala Leu Ala Asp Asn Arg Ala Ala Leu
            100                 105                 110

Glu Ala Thr Val Val Arg Leu Arg Gly Ala Arg Glu Trp Gly Val Lys
            115                 120                 125

Leu Phe Trp Glu Ala Pro Pro Ala Glu Pro Ala Pro Val Glu Arg Gly
130                 135                 140

Pro Gly Ala Gly Ala Ala Phe Phe Gln Arg Lys Arg Asp Ala Gln Arg
145                 150                 155                 160

Leu Arg Ala Glu Ala Glu Ala Leu Ala His Gly Val Ala Glu Ser
            165                 170                 175

His Arg Arg Leu Ala Ala Arg Ala Arg Ala Ala Val Ala Asn Pro Val
            180                 185                 190

Gln Pro Ala Ala Val His Arg Arg Gly Glu Met Ala Leu Asn Gly
            195                 200                 205

Ala Tyr Leu Val Pro Arg Ala Asp Glu Ala Ala Trp Arg Glu Ser Leu
            210                 215                 220

Ala Glu Leu Glu Arg Thr Tyr Ala Gly Ala Gly Ile Arg Tyr Glu Leu
225                 230                 235                 240

Thr Gly Pro Trp Gly Pro Tyr Asn Phe Thr Gly Gly Gly Leu Ala Gly

Ser

<210> SEQ ID NO 124
<211> LENGTH: 334
<212> TYPE: PRT
<213> ORGANISM: Bradyrhizobium oligotrophicum S58

<400> SEQUENCE: 124

Met Thr Met Asn Leu Val Gly Ile Thr Thr Pro Asp Val Ala Gly Ala
1               5                   10                  15

Ile Ala Ala Ala Gly Gly Arg Leu Ala Asp Val Glu Thr Arg Ala Val
            20                  25                  30

Glu Ala Gly Gly Leu Val Ala Leu Leu Ala Leu Ser Lys Ala Pro Phe
        35                  40                  45

Trp His Val Leu Arg Arg Ser Arg Thr Ala Leu Arg Ser Met Leu Thr
    50                  55                  60

Ala Gln Arg Ile Leu Glu Ala Ala Val Tyr Gly Pro Leu Leu Pro
65                  70                  75                  80

Ala Arg Pro Gly Thr Leu Ile Arg Asn Asp Ala Glu Ala Cys Met Leu
                85                  90                  95

Leu Arg Ser Gln Cys Arg His Leu Ala Glu Gly Leu Arg Leu His Gly
            100                 105                 110

Thr Ser Arg Gln Tyr Gln Ile Thr Ile Ser Trp Asp Pro Val Ala Ala
        115                 120                 125

Leu Ala Ala Arg Arg Asp His Gln Asp Leu Val Glu Ala Ala Ala Ala
130                 135                 140

Ser Ala Asp Gly Ala Ala Asp Lys Ala Ala Ser Met Ile Gln Arg Phe
145                 150                 155                 160

Met Ser Asp Gln Gln Ala Arg Phe Glu Ala Glu Ala Met Arg Ala Leu
                165                 170                 175

Ala Ala Val Ala Glu Asp Val Ile Thr Leu Pro Val Asn Gln Pro Asp
            180                 185                 190

Met Leu Met Asn Ala Val Val Leu Leu Ala Pro Gly Ala Glu Pro Glu
        195                 200                 205

Leu Glu Arg Val Leu Glu Ala Leu Asp Arg Gly Leu Arg Gly Lys Asn
    210                 215                 220

Leu Ile Arg Leu Ile Gly Pro Leu Pro Pro Val Ser Phe Ala Ala Val
225                 230                 235                 240

Ser Ile Glu Arg Pro Gly Arg Gln Arg Ile Ala Ala Ala Arg Arg Leu
                245                 250                 255

Leu Gly Ile Gly Glu Ala Thr Arg Thr Cys Asp Leu Arg Arg Ala Tyr
            260                 265                 270

Leu Asp Lys Ala His Ala His His Pro Asp Thr Gly Gly His Ala Ala
        275                 280                 285

Asp Ala Ser Ile Val Gly Ala Ala Ala Glu Ala Phe Arg Leu Leu Ala
    290                 295                 300

Arg Val Ala Glu Ala Arg Ala Ser Ala Gly Gln Asp Val Ile Leu
305                 310                 315                 320

Val Asp Ile Arg Arg Gln Asp Gln Gln Arg Ser Leu Ser Thr
                325                 330

<210> SEQ ID NO 125
<211> LENGTH: 253
<212> TYPE: PRT

<213> ORGANISM: Bradyrhizobium oligotrophicum S58

<400> SEQUENCE: 125

| | | | | | | | | | | | | | | |
|---|---|---|---|---|---|---|---|---|---|---|---|---|---|---|
| Met | Ser | Lys | Ala | Asn | Leu | Gly | Ile | Gly | Leu | Val | His | Gly | Val | Thr |
| 1 | | | | 5 | | | | | 10 | | | | | 15 |
| Ala | Gln | Ser | Ala | Ala | Leu | Leu | Pro | Gln | Ile | Val | Asp | Ala | Phe | Asp | Ala |
| | | | 20 | | | | | 25 | | | | | 30 | | |
| Thr | Glu | Ile | Ile | Val | Val | Asn | Thr | Glu | Gln | Gln | Ala | Leu | Leu | Ile | Ser |
| | | | 35 | | | | | 40 | | | | | 45 | | |
| Asp | Ile | Pro | Gln | Tyr | Leu | Arg | Gly | His | Val | Glu | Ala | Asp | Thr | Leu | Phe |
| | 50 | | | | | 55 | | | | | 60 | | | | |
| Ser | Asp | Pro | Ala | Arg | Ile | Ser | Thr | Leu | Ala | Met | Lys | His | His | Arg | Ile |
| 65 | | | | | 70 | | | | | 75 | | | | | 80 |
| Leu | Gln | Ala | Ala | Ala | Val | Val | Thr | Asp | Val | Val | Pro | Val | Arg | Leu | Gly |
| | | | | 85 | | | | | 90 | | | | | 95 | |
| Thr | Leu | Val | Arg | Gly | Pro | Ser | Gly | Ala | Arg | Asp | Leu | Leu | Asn | Arg | Glu |
| | | | 100 | | | | | 105 | | | | | 110 | | |
| Ala | Val | Arg | Phe | Ala | Gly | His | Leu | Val | Thr | Ile | His | Asn | Ala | Leu | Glu |
| | | | 115 | | | | | 120 | | | | | 125 | | |
| Phe | Ser | Val | Arg | Ile | Leu | Pro | Thr | Glu | Gln | Pro | Ser | Arg | Arg | Val | Ala |
| | 130 | | | | | 135 | | | | | 140 | | | | |
| Arg | Pro | Val | Pro | Ser | Ser | Gly | Arg | Asp | Tyr | Leu | Arg | Ile | Arg | Arg | Asp |
| 145 | | | | | 150 | | | | | 155 | | | | | 160 |
| Glu | Arg | Cys | Gly | Gln | Arg | Pro | Ala | Val | Val | Asp | Ile | Thr | Leu | Gln | Glu |
| | | | | 165 | | | | | 170 | | | | | 175 | |
| Leu | Ala | Ser | Arg | Ala | Val | Ala | Ile | Arg | Glu | Arg | Gln | Ser | Ala | Ser | Arg |
| | | | 180 | | | | | 185 | | | | | 190 | | |
| Ser | Gly | Gly | Arg | Thr | Pro | Ala | Leu | Ala | Glu | Ala | Ala | Phe | Leu | Val | Asp |
| | | | 195 | | | | | 200 | | | | | 205 | | |
| Arg | His | Ala | Leu | Ala | Ala | Phe | Asp | Asp | Cys | Ala | Gly | Arg | Ile | Glu | Arg |
| | 210 | | | | | 215 | | | | | 220 | | | | |
| Gln | Ile | Ala | Glu | Asn | Gly | Leu | Ala | Leu | Asp | Ile | Phe | Gly | Pro | Trp | Pro |
| 225 | | | | | 230 | | | | | 235 | | | | | 240 |
| Ala | Tyr | Ser | Phe | Val | Asp | Gly | Ala | Arg | Glu | Asn | Leu | Gly | | | |
| | | | | 245 | | | | | 250 | | | | | | |

<210> SEQ ID NO 126
<211> LENGTH: 214
<212> TYPE: PRT
<213> ORGANISM: Bradyrhizobium oligotrophicum S58

<400> SEQUENCE: 126

| | | | | | | | | | | | | | | | |
|---|---|---|---|---|---|---|---|---|---|---|---|---|---|---|---|
| Met | Ser | Ser | Pro | Arg | Leu | Ile | Gly | Leu | Leu | Ala | Ala | Asp | Asp | Val | Pro |
| 1 | | | | 5 | | | | | 10 | | | | | 15 | |
| Ala | Asp | Leu | Ala | Asp | Gln | Ile | Met | Ser | Cys | Gly | Pro | Val | Ala | Ala | Ala |
| | | | 20 | | | | | 25 | | | | | 30 | | |
| Ile | Arg | Phe | Ala | Pro | Ala | Ala | Ser | Ser | Glu | Ser | Leu | Asp | His |
| | | | 35 | | | | | 40 | | | | | 45 | | |
| His | Ala | Ala | Val | Val | Ala | Trp | Cys | Arg | Arg | Ala | Ala | Phe | Leu | Pro | Ser |
| | 50 | | | | | 55 | | | | | 60 | | | | |
| Arg | Ala | Gly | Ile | Pro | Ile | Ser | Pro | Glu | Leu | Leu | Gln | Ser | Ile | Ala | Arg |
| 65 | | | | | 70 | | | | | 75 | | | | | 80 |
| Ser | Ala | Trp | Tyr | His | Arg | Ser | Thr | Ile | Glu | His | Ile | Glu | Gly | Arg | Val |
| | | | | 85 | | | | | 90 | | | | | 95 | |
| Glu | Ile | Ser | Val | Glu | Leu | Glu | Arg | Arg | Asp | Gly | Val | Arg | Asp | Gly | Gly |

```
            100                 105                 110
Ile Asp Gly Gly Gly Arg Ala Tyr Leu Arg Ala Thr Ala His Asp Leu
        115                 120                 125

Arg Ala Cys Glu Val Gly Val Ala Thr Ala Ala Asn Leu Leu Ala Met
    130                 135                 140

Tyr Ser Glu Arg Ala Asp Ala Asp Leu Ile Ala Arg Thr Ala Pro Leu
145                 150                 155                 160

Pro Ala Ile Arg Leu Arg Ala Ser Val Leu Val Arg Arg Ala Val Ala
                165                 170                 175

Pro Arg Leu Ala Arg Gln Phe Asp Ser Met Leu Ser Ala Ile Ser Asp
            180                 185                 190

Arg Leu Val Cys Arg Val Thr Gly Pro Trp Pro Pro Tyr Ser Phe Ser
        195                 200                 205

Thr Ile Arg Glu Pro Ser
    210

<210> SEQ ID NO 127
<211> LENGTH: 252
<212> TYPE: PRT
<213> ORGANISM: Burkholderia thailandensis sp. Bp5365 strain MSMB43

<400> SEQUENCE: 127

Met Val Trp Leu Thr Tyr Ala Val Leu Thr Pro Lys Arg Ser Ile Thr
1               5                   10                  15

Leu Pro Pro Gly Val Ala Gly Ala Arg Leu Glu Ile Val Asp Gly Ala
            20                  25                  30

His Leu Arg Thr Ile Val Ser Glu His Pro Arg Ala Pro Ser Ala Thr
        35                  40                  45

Ile Pro Ser Ala Leu Asp Phe Gly Gln Thr Val Ala Ala Leu Phe Arg
    50                  55                  60

His Gly Ala Ile Val Pro Met Arg Phe Pro Thr Cys Leu Asp Ser Lys
65                  70                  75                  80

Gln Ala Val Arg Asp Trp Leu Asp Asp Glu Ser Asp Met Tyr Arg Asp
                85                  90                  95

Leu Leu Gln Arg Ile Asp Gly Cys Val Glu Met Gly Leu Arg Phe Arg
            100                 105                 110

Leu Pro Glu Ala Pro Arg Ala Gln Pro Arg Pro Gln Ala Gly Gly Pro
        115                 120                 125

Gly His Ala Tyr Leu Ala Ala Arg Gly Ala Pro Asn Ser Val Ala Arg
    130                 135                 140

Ser His Gly Glu Arg Ile Ala Ala Val Leu Arg Asn Leu Tyr Arg Asp
145                 150                 155                 160

Trp Arg Phe Asp Gly Leu Val Glu Gly Phe Val Ser Leu Ser Phe Leu
                165                 170                 175

Val Arg Gln Thr Thr Leu Asp Asp Phe Val Asp Arg Cys Arg Gln Ala
            180                 185                 190

Ala Arg Glu Thr Ala Phe Pro Leu Tyr Met Ser Gly Pro Trp Pro Pro
        195                 200                 205

Tyr Ser Phe Ala Thr Asp Glu Arg Ser Ser Ala Pro Glu Pro His Arg
    210                 215                 220

Ala Leu Arg Leu Met Arg Arg Pro Ser Thr Ala Val Ser Ile Ser Ala
225                 230                 235                 240

Asn Val Ala Ala Pro Glu Lys Lys Asp Ser Ala Arg
                245                 250
```

<210> SEQ ID NO 128
<211> LENGTH: 257
<212> TYPE: PRT
<213> ORGANISM: Desulfobacterium vacuolatum-DSM 3385

<400> SEQUENCE: 128

```
Met Thr Leu His Leu Leu Tyr Cys Val Phe Ser Ser Gly Glu Met Glu
1               5                   10                  15

Lys Thr Arg Lys Leu Val Pro Pro Gly Ile Asp Gly Glu Pro Val His
            20                  25                  30

Glu Ile Cys Ser Asn Lys Ile Ser Gly Val Val Ser Thr Leu Gly Lys
        35                  40                  45

Pro Pro Asp Thr His Val Lys Ser Leu Leu Ala Tyr His Gly Val Ile
    50                  55                  60

Asp Ser Tyr His Gln Asn Arg Thr Val Ile Pro Met Arg Phe Ala Ala
65                  70                  75                  80

Val Phe Arg Thr Tyr Ala His Met Ile Thr Ala Leu Asn Asn Asn Glu
                85                  90                  95

Lys Ser Tyr Leu Leu Gln Leu Lys Arg Leu His Asp Cys Thr Glu Met
            100                 105                 110

Cys Val Arg Phe Ile Ser Asn Ser Pro Cys Cys Val Lys Lys Lys Glu
        115                 120                 125

Pro Ala Ile Ser Pro Lys Lys Ile Ser Gly Thr Thr Phe Leu Gln Gln
    130                 135                 140

Arg Lys Ala Met Tyr Glu Gln Gln Asn Arg Leu Pro Pro Glu Ile His
145                 150                 155                 160

Glu Lys Thr Arg Asp Ile Leu Gln His Phe Arg Gly Leu Tyr Met Glu
                165                 170                 175

Phe Lys Gln Glu Ser Gln Pro Leu Glu Lys Asp Cys Pro Ser Leu Ser
            180                 185                 190

Leu Gln Gly Ala Glu Lys Thr Asp Gly Asn Ala Leu Leu Ile Ser Leu
        195                 200                 205

Phe Phe Leu Ile Ser Lys Lys Asn Ile Ser Leu Phe Arg Ser Arg Phe
    210                 215                 220

Gln Asn Ile Cys Gly Ser Ser Gly Arg His Met Met Asn Gly Pro
225                 230                 235                 240

Trp Pro Pro Phe Asn Phe Ile Asn Thr Glu Ser Asn Leu Thr Asp Pro
                245                 250                 255

Ser
```

<210> SEQ ID NO 129
<211> LENGTH: 265
<212> TYPE: PRT
<213> ORGANISM: Desulfomonile tiedjei DSM 6799

<400> SEQUENCE: 129

```
Met Leu Gly Ser Leu Ala Ala Ile Gln Phe Leu Ser Ile Ser Ser Tyr
1               5                   10                  15

Gly Ala Asp Glu Met Lys Phe Leu Met Tyr Cys Ile Phe Thr Glu Asn
            20                  25                  30

Ser Ile Glu Pro Pro His Ser Leu Val Gly Val Asn Arg Ser Pro Val
        35                  40                  45

Arg Ile Ile Ser Cys Asp Gly Leu Ala Ala Val Ser Val Ile Thr
    50                  55                  60

Gln Lys Glu Ile Pro Arg Asp Pro Ala Thr Gly Leu Asp Tyr His Lys
```

```
            65                  70                  75                  80
Val Ile Gln Trp Phe His Glu Arg Ile Gly Val Ile Pro Leu Arg Leu
                85                  90                  95
Gly Thr Cys Leu Gly His Glu Ser Asp Val Val Gln Leu Leu His Ser
                100                 105                 110
His Gly Ala Arg Tyr Lys Ser Leu Leu Lys Glu Leu Asp Gly Cys Val
                115                 120                 125
Glu Met Gly Ile Arg Val Ile His Asp Arg Pro Gly Pro Gln Glu Leu
        130                 135                 140
Ala Ser Lys Ser Pro Phe Ile Ser Arg Phe Asn Gly Thr Glu Ser Gly
145                 150                 155                 160
Thr Asp Tyr Leu Met Arg Arg Lys Val Leu Phe Asp Ala Asp Glu Phe
                165                 170                 175
Ala Ile Ser Arg Asn Arg Glu Ile Val Glu Arg Tyr His Ser Pro Phe
                180                 185                 190
Thr Gly Leu Tyr Val Ser Phe Lys Ala Gln Thr Ser Lys Phe Ser Pro
                195                 200                 205
Leu Gly Thr Asp Arg Asn Ser Val Leu Thr Ser Leu Tyr Phe Leu Ile
        210                 215                 220
Pro Arg Gln Ser Ala Asp Ser Phe Arg Ala Ile Tyr Gly Asp Leu Arg
225                 230                 235                 240
Ser Gly Leu His Glu Arg Ile Met Leu Ser Gly Pro Trp Pro Tyr
                245                 250                 255
Asn Phe Val Leu Pro Glu Asp Cys Leu
                260                 265

<210> SEQ ID NO 130
<211> LENGTH: 279
<212> TYPE: PRT
<213> ORGANISM: Enhydrobacter aerosaccus strain ATCC 27094

<400> SEQUENCE: 130

Met Glu Gly His Arg Ile Tyr Ile Tyr Gly Ile Val Arg Asp Ala Ala
1               5                   10                  15
Asp Gly Gly Pro Ala Pro Val Pro Pro Val Ala Gly Leu Asp Gly Gly
                20                  25                  30
Ala Leu Arg Ala Ile Ala Gly Tyr Gly Leu Ala Ala Ile Ala Ser Ala
                35                  40                  45
Val Asp Leu Ser Lys Ala Gly Ile Pro Phe Glu Glu Gln Leu Lys Asp
        50                  55                  60
Pro Asp Arg Ala Thr Ala Leu Val Leu Glu His His Arg Val Leu Gln
65                  70                  75                  80
Gln Ala Ile Asp Ala Gln Thr Val Leu Pro Met Arg Phe Gly Ala Leu
                85                  90                  95
Phe Gln Asp Asp Arg Gly Val Thr Asp Ala Leu Glu Lys Asn Arg Cys
                100                 105                 110
Gly Leu Met Asp Ala Leu Gly Arg Ile Asp Gly Ala Arg Glu Trp Gly
                115                 120                 125
Val Lys Ile Phe Cys Asp Arg Ala Val Ala Arg Gln Leu Ser Ala
        130                 135                 140
Thr Ser Ala Val Val Gln Ala Ala Glu Lys Glu Leu Ser Gly Leu Ala
145                 150                 155                 160
Glu Gly Arg Ala Phe Phe Leu Arg Arg Leu Glu Arg Leu Arg Thr
                165                 170                 175
```

```
Glu Glu Thr Asp Arg Ala Val Ala His Glu Val Asp Val Ser Arg Gln
            180                 185                 190

Ala Leu Cys Glu Leu Ala Arg Ala Ser Ala Pro Leu Lys Leu Gln Pro
        195                 200                 205

Ala Ala Val His Gly Arg Gly Glu Asp Met Val Trp Asn Gly Ala Phe
    210                 215                 220

Leu Val Pro Arg Ser Gly Glu Arg Phe Leu Ser Arg Leu Glu Val
225                 230                 235                 240

Val Val Gln Ser Arg Ser Asp Leu Gly Leu His Tyr Glu Val Thr Gly
                245                 250                 255

Pro Trp Pro Pro Phe Ser Phe Val Asp Gly Gln Leu Gly Gly Gly
                260                 265                 270

Asp Ala Cys Pro Asp Gly Ala
        275
```

<210> SEQ ID NO 131
<211> LENGTH: 278
<212> TYPE: PRT
<213> ORGANISM: Octadecabacter antarcticus 307

<400> SEQUENCE: 131

```
Met Arg Ser Ala Thr Ser Ile Val Tyr Ala Tyr Gly Val Leu Thr Asn
1               5                   10                  15

Cys Ser Asp Ile Ala Leu Asp Met Pro Arg Ser Asp Leu Ala Gly Leu
            20                  25                  30

Val Lys Asn Gly Pro Leu Arg Ile Leu Pro Phe Gly Asn Ile Ala Ala
        35                  40                  45

Val Val Cys Asp Phe Val Leu Pro Asn Gly Ser Asp Leu Glu Thr Leu
50                  55                  60

Leu Glu Asp Ser Arg Ser Ala Glu Arg Leu Ile Leu Asn His His Gln
65                  70                  75                  80

Val Leu Ser Tyr Ile Val Ser Gln His Thr Ile Leu Pro Leu Arg Phe
                85                  90                  95

Gly Ala Ala Phe Thr Glu Asp Ala Gly Val Ile Ala Ala Leu Gly Gly
            100                 105                 110

Arg Cys Ser Glu Leu Gln Lys Ala Leu Gly Arg Ile Asp Gly Ala Leu
        115                 120                 125

Glu Trp Gly Val Lys Thr Phe Cys Asp Arg Lys Leu Leu Lys Gln Arg
    130                 135                 140

Val Arg Gly Thr Gly Ser Glu Ile Ser Asp Leu Glu Ser Glu Ile Ala
145                 150                 155                 160

Lys Gln Gly Glu Gly Lys Ala Phe Phe Leu Arg Arg Arg Lys Glu Arg
                165                 170                 175

Leu Ile Leu Glu Glu Val Glu Glu Ile Leu Glu Gln Cys Val Val Gly
            180                 185                 190

Thr Gln Glu Gln Leu Glu Pro Ser Val Ile Glu Glu Ala Leu Val Lys
        195                 200                 205

Leu Gln Pro Pro Thr Val His Gly His Glu His Asp Met Leu Ser Asn
    210                 215                 220

Ile Ser Tyr Leu Ile Ala Arg Gly Thr Glu Asp Ala Phe Met Gln Ser
225                 230                 235                 240

Leu Glu Asp Leu Arg Leu Ala His Ala Pro Tyr Gly Leu Glu Tyr Gln
                245                 250                 255

Met Asn Gly Pro Trp Pro Ala Tyr Ser Phe Ser Asp Gln Gln Leu Glu
            260                 265                 270
```

Gly Gly Val Asn Asp Gln
        275

<210> SEQ ID NO 132
<211> LENGTH: 278
<212> TYPE: PRT
<213> ORGANISM: Octadecabacter arcticus 238

<400> SEQUENCE: 132

Met Ser Ser Ala Thr Ser Ile Val Tyr Val Tyr Gly Val Leu Thr Asn
1               5                   10                  15

Cys Ser Asp Leu Val Leu Asp Phe Pro Pro Gly Asp Leu Ala Gly Ile
            20                  25                  30

Val Glu Ser Gly Pro Leu Arg Ile Leu Pro Phe Gly Asp Ile Gly Ala
        35                  40                  45

Leu Val Cys Asp Phe Ile Leu Pro Asp Gly Ser Asp Leu Lys Thr Ile
    50                  55                  60

Leu Glu Asp Ser Arg Ser Ala Glu Arg Met Ile Leu Asn His His Leu
65                  70                  75                  80

Val Leu Ala Asp Met Val Ser Arg Tyr Thr Ile Leu Pro Leu Arg Phe
                85                  90                  95

Gly Ala Val Phe Ala Glu Asp Ala Gly Val Ile Ala Ala Leu Gly Gly
            100                 105                 110

Arg Tyr Ser Thr Leu Gln Lys Glu Leu Asp Arg Ile Asp Gly Ala Ile
        115                 120                 125

Glu Trp Gly Val Lys Ser Phe Cys Asn Arg Lys Met Phe Ser Glu Cys
    130                 135                 140

Val Ala Glu Thr Val Ser Glu Ile Ser Val Leu Glu Lys Glu Ile Ala
145                 150                 155                 160

Asp Gln Gly Glu Gly Lys Ala Phe Phe Leu Arg Arg Arg Ile Gln Arg
                165                 170                 175

Leu Ile Leu Asp Glu Val Glu Lys Thr Leu Glu Gln Cys Leu Val Gly
            180                 185                 190

Ala Gln Asp Gln Leu Lys Ser Arg Ala Ile Glu Glu Thr Leu Val Lys
        195                 200                 205

Leu Gln Pro Pro Thr Val His Gly His Lys His Glu Met Val Ser Asn
    210                 215                 220

Arg Ser Tyr Leu Ile Ala Arg Gly Ala Glu Asp Ala Phe Met Gln Ser
225                 230                 235                 240

Leu Asp Asp Leu Arg Val Val Tyr Ala Pro Phe Gly Phe Asp Tyr Gln
                245                 250                 255

Ile Asn Gly Pro Trp Pro Ala Tyr Ser Phe Ser Asp Gln Gln Leu Gly
            260                 265                 270

Gly Gly Val Asn Asp Lys
        275

<210> SEQ ID NO 133
<211> LENGTH: 261
<212> TYPE: PRT
<213> ORGANISM: Rhodobacter capsulatus SB 1003

<400> SEQUENCE: 133

Met Gly His Tyr Leu Tyr Gly Leu Leu Ala Pro Pro Ala Arg Gly Thr
1               5                   10                  15

Leu Ala Gln Met Gln Ala Ala Ala Ala Gly Val Thr Ser Leu Gly Gly
            20                  25                  30

Pro Val Ala Leu Ser Ala Val Glu Gly Met Leu Leu Val His Cys Pro
        35                    40                    45

Cys Asp Leu Ala Glu Ile Ser Gln Thr Arg Arg Asn Met Leu Ala His
  50                      55                  60

Thr Arg Met Leu Glu Ala Leu Met Pro Leu Ala Thr Cys Leu Pro Val
65                    70                    75                  80

Arg Phe Gly Val Ile Ala Gln Asp Leu Ala Glu Val Ala Arg Met Ile
                85                    90                  95

His Glu Arg Arg Ala Glu Leu Val Gly His Ala Gln Arg Leu Leu Asp
            100                 105                110

Pro Val Glu Ile Gly Leu Arg Val Arg Phe Pro Arg Asp Arg Ala Leu
            115                 120                125

Ala Gln Leu Met Ala Glu Thr Pro Asp Phe Val Ala Glu Arg Asp Arg
130                    135                    140

Leu Met Gly Gln Gly Ala Gly Ala His Phe Ala Arg Ala Asp Phe Gly
145                    150                    155                160

Arg Arg Leu Ala Glu Ala Leu Asp Ala Arg Arg Thr Arg Asp Gln Lys
            165                 170                175

Arg Leu Leu Ala Ala Leu Arg Pro His Val Arg Asp His Val Leu Arg
        180                    185                    190

Ala Pro Glu Glu Asp Val Glu Val Leu Arg Ala Glu Phe Leu Ile Pro
            195                 200                205

Ala Ala Gly Val Asp Ala Phe Ser Arg Ile Ala His Asp Leu Ala Ala
210                    215                    220

Ala Leu Gly Phe Ala Gly Ala Ala Glu Pro Glu Leu Gln Val Ile Gly
225                    230                    235                240

Pro Ala Pro Pro Tyr His Phe Leu Ser Leu Ser Leu Ala Phe Asp Asn
                245                 250                255

Thr Ser Glu Ala Ala
            260

<210> SEQ ID NO 134
<211> LENGTH: 316
<212> TYPE: PRT
<213> ORGANISM: Rhodobacter capsulatus SB 1003

<400> SEQUENCE: 134

Met Ala His Glu Ile Ile Ala Ile Leu Pro Cys Glu Ala Ala Gln Leu
1                  5                    10                  15

Pro Ser Gly Leu Thr Gly Val Val Gly Arg Gly Ala Thr Ala Val Leu
            20                    25                  30

Ala Pro Ala Pro Gly Trp Ala Glu Arg Leu Thr Gly Gly Pro Lys Gln
                35                    40                  45

Thr Ala Val Arg His His Ser Arg Leu Glu Ala Leu Met Ala Met Gly
  50                      55                  60

Ser Val Leu Pro Phe Ala Ala Gly Ile Ala Cys Thr Pro Glu Glu Ala
65                    70                    75                  80

Ala Leu Leu Leu Arg Leu Asp Ala Pro Leu Ile Ala Arg Leu Ala Ala
                85                    90                  95

Glu Ile Gly Pro Arg Arg His Phe Gln Leu Ala Leu Asp Trp Asp Glu
            100                 105                110

Ser Arg Val Leu Ala Ala Phe Arg Asp Ser Pro Glu Leu Ala Pro Leu
            115                 120                125

Phe Ser Gly Ala Ala Val Thr Pro Glu Ala Leu Arg Gln Ala Ile Thr

```
            130                 135                 140
Ala Leu Ala Asp Arg Leu Ser Ala Thr Ala Leu Arg Leu Leu Asp Pro
145                 150                 155                 160

Val Ala Glu Asp Pro Val Glu Gln Pro Arg Ala Pro Gly Cys Leu Leu
                165                 170                 175

Asn Leu Val Phe Leu Leu Arg Pro Glu Asp Glu Pro Arg Leu Asp Ala
                180                 185                 190

Ala Leu Gln Ala Ile Asp Ala Leu Trp Ser Glu Gly Leu Arg Leu Arg
                195                 200                 205

Leu Ile Gly Pro Ser Ala Pro Ile Ser His Ala Leu Val Asp Ile Asp
210                 215                 220

Arg Ala Asp Val Ala Ala Leu Ala Ala Ala Asp Leu Leu Lys Val
225                 230                 235                 240

Ala Pro Glu Ala Gly Pro Glu Ala Val Thr Glu Ala Ala Lys Ala Ala
                245                 250                 255

Leu Arg Ser Pro Asp Leu Ala Ala Asn Ala Ala Glu Gln Ile Arg Ala
                260                 265                 270

Ala Ala Arg Leu Leu Leu Arg Ala Gly Asp Ile Ala Ala Leu Gly Leu
                275                 280                 285

Ser Gly Ala Ala Thr Leu Pro His Leu Val His Leu Arg Pro Gly Gly
                290                 295                 300

Arg Lys Ser Gly Leu Thr Ser Ser Gly Glu Ala Ala
305                 310                 315

<210> SEQ ID NO 135
<211> LENGTH: 231
<212> TYPE: PRT
<213> ORGANISM: Rhodobacter capsulatus SB 1003

<400> SEQUENCE: 135

Met Thr Gly Leu Ala Leu His Gly Phe Val Ser Pro Asp Gly Trp Ser
1               5                   10                  15

Ala Ala Ala Ala Pro Pro Ala Arg Cys Ala Val Val Leu Gly Gly Val
                20                  25                  30

Ala Ala Leu Val Ser Glu Ala Gly Asp Ala Leu Asp Thr Pro Glu Thr
                35                  40                  45

Ala Gln Ala Ala Ala Leu Ala His His Ala Leu Ile Ser Ala Trp His
                50                  55                  60

Arg Arg Gly Pro Val Leu Pro Val Arg Leu Gly Thr Val Phe Ser Ser
65                  70                  75                  80

Gln Ala Ala Leu Gln Thr Ala Leu Ala Pro Lys Ala Ala Gln Leu Arg
                85                  90                  95

Ala Ala Leu Asp Ala Leu Ala Asp Lys Glu Glu Met Val Leu Thr Ile
                100                 105                 110

Val Pro Ala Ala Arg Pro Pro Asp Leu Pro Pro Ala Ala Thr Gly
                115                 120                 125

Ala Asp Trp Leu Arg Ala Arg Lys Ala Val Arg Asp Arg Gly Gln Ala
                130                 135                 140

Arg Gln Thr Asp Arg Gln Gln Thr Leu Ala Gly Leu Gln Asp Ala Leu
145                 150                 155                 160

Arg Ala Gln Gly Val Ala Ser Leu Ala Ala Pro Ala Pro Arg Glu Gly
                165                 170                 175

Gly Ser Arg Trp His Leu Leu Ile Ala Arg Asp Asp Gly Ala Gly Leu
                180                 185                 190
```

```
Asp Arg Trp Leu Ala Ala Gln Ala Asp Arg Phe Asp Ala Ala Gly Leu
            195                 200                 205

Asp Leu Thr Leu Asp Gly Pro Trp Pro Pro Tyr Arg Phe Ala Ala Glu
    210                 215                 220

Ile Leu Glu Ala Leu Asp Gly
225                 230

<210> SEQ ID NO 136
<211> LENGTH: 220
<212> TYPE: PRT
<213> ORGANISM: Rhodobacter capsulatus SB 1003

<400> SEQUENCE: 136

Met Ser Glu Pro Arg Ile Ser Gly Leu Ala Pro Trp Arg Ala Asp Leu
1               5                   10                  15

Pro Asp Val Ile Gly Cys His Gly Gly Trp Val Leu Met Gly Ala Ala
            20                  25                  30

Ala Asp Glu Thr Pro Glu Ala Arg Leu Arg Arg Gln Val Gly Trp Cys
        35                  40                  45

Arg Ala Ala Val Asp Val Leu Pro Leu Ser Pro Arg Leu Ala Pro Thr
    50                  55                  60

Arg Ala Glu Ala Glu Arg Leu Val Ala Thr Arg Gly Pro Asp Leu Glu
65                  70                  75                  80

Arg Ala His Arg His Ile Arg Gly Arg Leu Gln Val Ile Val Gln Leu
                85                  90                  95

Glu Met Cys Arg Thr Asp Leu Gly Leu Val Arg Arg Glu Ile Ser Gly
            100                 105                 110

Gly Arg Ser Trp Leu Gln Asp Arg Ala Glu Arg Ala Thr Arg Glu Ala
        115                 120                 125

Arg Ala Asn Ala Asp Phe Glu Ala Gln Val Arg Arg Val Val Arg Ala
    130                 135                 140

Leu Phe Pro Arg Glu Gly Gln Val Val Thr Leu Ala Pro Ser Gly Thr
145                 150                 155                 160

Ala Gly Gln Leu Arg Leu Arg Arg Ala Val Leu Val Pro Arg Ala Gly
                165                 170                 175

Leu Gln Ala Phe Ala Ala Ala Leu Ser Ala Asp Leu Asp Arg Asp Gly
            180                 185                 190

Arg Gly Gly Leu Trp Asp Val Ile Ala Pro Leu Pro Pro Leu Ala Phe
        195                 200                 205

Ala Ala Leu Glu Ala Gly Pro Gly Gly Ala Val Thr
    210                 215                 220

<210> SEQ ID NO 137
<211> LENGTH: 254
<212> TYPE: PRT
<213> ORGANISM: Rhodobacter sphaeroides 2.4.1

<400> SEQUENCE: 137

Met Ile Tyr Leu Tyr Gly Leu Leu Glu Glu Pro Ala Ser Gly His Glu
1               5                   10                  15

Val Leu Ala Gly Met Ala Gly Val Thr Gly Pro Ile Ala Leu Ala Arg
            20                  25                  30

Leu Pro Gly Gly Ile Leu Ile Tyr Ser Ser Ala Thr Glu Ala Asp Ile
        35                  40                  45

Leu Pro Arg Arg Arg Leu Leu Leu Ala His Thr Arg Val Leu Glu Ala
    50                  55                  60
```

```
Ala Ala Trp Phe Gly Asn Leu Leu Pro Met Arg Phe Gly Met Met Ala
 65                  70                  75                  80

Ser Thr Leu Ala Glu Val Ala Ala Met Leu Ala Ser Arg Leu Thr Glu
                 85                  90                  95

Leu Cys Ala Ala Phe Asp Arg Val Arg Gly Arg Val Glu Leu Gly Leu
            100                 105                 110

Arg Leu Ser Phe Pro Arg Glu Pro Ala Leu Ala Thr Leu Ala Thr
        115                 120                 125

Ala Pro Asp Leu Ala Ala Glu Arg Ala Arg Leu Leu Ala Leu Arg Arg
130                 135                 140

Pro Asp Pro Met Ala Gln Ala Glu Phe Gly Arg Arg Leu Ala Glu Arg
145                 150                 155                 160

Leu Asp Ala Arg Arg Gly Glu Thr Gln Arg Leu Leu Phe Gln Ser Leu
                165                 170                 175

Arg Pro Leu Trp Val Asp His Arg Leu Arg Val Pro Asp Ser Asp Val
            180                 185                 190

Gln Val Ile Ala Val Asp Val Leu Val Glu Asp Gly Ala Gln Asp Arg
        195                 200                 205

Leu Ala Ala Ala Leu Val Lys Ala Ala Ala Asp Cys Ser Phe Ala Pro
210                 215                 220

Thr Ala Glu Pro Ser Val Arg Val Ile Gly Pro Val Pro Leu Phe Asn
225                 230                 235                 240

Phe Val Asp Leu Val Leu Ser Pro Arg Arg Glu Glu Val Ala
                245                 250

<210> SEQ ID NO 138
<211> LENGTH: 291
<212> TYPE: PRT
<213> ORGANISM: Rhodobacter sphaeroides 2.4.1

<400> SEQUENCE: 138

Met Arg Leu Arg Glu Val Val Ala Val Leu Glu Gly His Pro Pro Ser
1               5                   10                  15

Val Leu Pro Glu Gly Thr Glu Ala Ile Cys Glu Ala Gly Leu Thr Ala
                20                  25                  30

Ile Leu Gly Met Pro Pro Gly Leu Leu Ser Gly Arg Arg Ala Leu Leu
            35                  40                  45

Glu His Ala Ala Cys Arg Gln Ala Val Leu Glu Arg Leu Met Ala Phe
    50                  55                  60

Gly Thr Val Leu Pro Val Leu Thr Gly Asn Cys Leu Thr Pro Ala Glu
65                  70                  75                  80

Ala Ala Ala Ala Leu Ala Ala Asn Ser Pro Arg Leu Arg Gln Glu Leu
                85                  90                  95

Arg Arg Leu Ala Gly Arg Val Gln Phe Gln Val Leu Val Gln Trp His
            100                 105                 110

Ala Ala Leu Val Pro Lys Arg Thr Asp Pro Asp Glu Thr Ala Glu Asp
        115                 120                 125

Leu Arg Leu Arg Phe Thr His Arg Ile Ala Asp Ala Leu Ala Arg Val
130                 135                 140

Ala Glu Arg His Val Asn Leu Pro Leu Arg Glu Asp Met Leu Ala Asn
145                 150                 155                 160

Gln Ala Leu Leu Leu Leu Gln Thr Arg Thr Asp Asp Leu Asp Arg Ser
                165                 170                 175

Leu Glu Gln Ile Asp Ala Leu Trp Thr Glu Gly Leu Arg Ile Arg Arg
            180                 185                 190
```

```
Ile Gly Pro Ser Pro Val Ser Phe Ala Ser Leu Asn Phe Arg Arg
        195                 200                 205

Val Ser Ser Ala Ala Ile Arg Arg Ala Arg His Arg Phe Asp Leu Glu
    210                 215                 220

Gly Pro Val Asp Pro Ile Arg Leu Arg Ala Leu Arg Arg Asp Leu Leu
225                 230                 235                 240

Leu Arg Ala Ser Glu Ala Glu Arg Ala Glu Ile Leu Ala Ala Ala
                245                 250                 255

Val Leu Asp Leu Leu Thr Arg Cys Ala Ala Ser Gly Gly Asp Leu His
                260                 265                 270

Leu Val Arg Ile Trp Ser Glu Gly Gln Ala Val Pro Ser Asp Leu Glu
            275                 280                 285

Asp Ala Ala
    290

<210> SEQ ID NO 139
<211> LENGTH: 232
<212> TYPE: PRT
<213> ORGANISM: Rhodobacter sphaeroides 2.4.1

<400> SEQUENCE: 139

Met Ser Gly Leu Leu Leu Gly Val Val Ser Gly Leu Gly Ile Ser
1               5                   10                  15

Pro Ala Ile Thr Ser Pro His Leu Arg Leu Asp Gly Asp Gly Tyr Ala
            20                  25                  30

Ala Ile Leu Leu Ser Leu Asp Arg Leu Pro Pro Asp Pro Ala Ser Pro
        35                  40                  45

Asp Trp Ala Val Gln Ala Ala Leu Ala Gln Asn Ala Ile Leu Ser Ala
    50                  55                  60

Tyr Ala Ala Thr Glu Asp Val Leu Pro Val Ala Leu Gly Ala Ala Phe
65                  70                  75                  80

Thr Gly Ile Ala Ala Val Lys Arg His Leu Asp Ala Glu Arg Ala Thr
                85                  90                  95

Leu Asp Ala Gly Met Glu Arg Leu Ala Gly Arg Ala Glu Tyr Val Ala
            100                 105                 110

Gln Leu Ile Ala Glu Gln Val Ala Asp Gly Ala Ala Pro Ala Pro Ala
        115                 120                 125

Ser Gly Ser Ala Phe Leu Lys Ala Arg Ser Ala Arg His Glu Gln Arg
    130                 135                 140

Arg His Leu Ala Arg Glu Arg Thr Gly Phe Ala Arg Ala Thr Ala Glu
145                 150                 155                 160

Glu Leu Ala Ser Leu Ser Cys Ser Ala Ser Ala Arg Pro Leu Lys Pro
                165                 170                 175

Asp Gly Pro Leu Leu Asp Leu Ser Leu Leu Val Ala Arg Asp Arg Val
            180                 185                 190

Pro Gly Leu Leu Glu Ala Ala Glu Ala Ser Ser Arg Ala Gly Ser Arg
        195                 200                 205

Leu Ala Leu Ser Val Arg Leu Ile Gly Pro Cys Ala Pro Phe Ser Phe
    210                 215                 220

Leu Pro Glu Thr Arg Gly His Asp
225                 230

<210> SEQ ID NO 140
<211> LENGTH: 169
<212> TYPE: PRT
```

<213> ORGANISM: Rhodobacter sphaeroides 2.4.1

<400> SEQUENCE: 140

```
Met Ala Gly Asp Ala Arg Ser Arg Val Arg Leu His Leu Ala Met
1               5                   10                  15

Arg Asp Cys Glu Thr Phe Leu Pro Phe Pro Ala Ala Thr Ile Ala
                20                  25                  30

Val Asp Glu Ala Ile Ala Trp Cys Gly Arg Arg Thr Asn Ala Leu Ala
            35                  40                  45

Glu Glu Ile Asp Arg Phe Ser Arg Gln Arg Gln Leu Thr Val Ser Ala
        50                  55                  60

Arg Leu Ile Ala Pro Leu Leu Pro Asp Ala Ala Ser Gly Ala Gly
65                  70                  75                  80

Trp Leu Arg Ala Arg Arg Asp Ala Ser Ala His Gln Ala Arg Leu Arg
                85                  90                  95

Thr Val Leu Met Gln Ile Met Ser Leu Leu Gly Glu Val Arg Cys Ile
            100                 105                 110

Pro Gly Arg Leu Gln Asp Glu Val Gln Val Asn Leu Leu Val Pro Ala
        115                 120                 125

Ala Glu Thr His Pro Val Leu His Glu Leu Arg Glu Arg Leu Arg Val
    130                 135                 140

Gly Asp Ala Leu Trp Ser Ala Cys Thr Val Thr Gly Pro Trp Pro Pro
145                 150                 155                 160

Tyr Ala Phe Ile Ser Trp Glu Thr Ala
                165
```

<210> SEQ ID NO 141
<211> LENGTH: 260
<212> TYPE: PRT
<213> ORGANISM: Rhodococcus hoagii 103S

<400> SEQUENCE: 141

```
Met Ser Glu Gln Glu Ser Ala Pro Asp Gly Gly Pro Val Val Tyr
1               5                   10                  15

Val Tyr Gly Leu Val Pro Ala Asp Val Glu Val Lys Glu Asp Ala Thr
                20                  25                  30

Gly Ile Gly Ser Pro Pro Arg Pro Leu Lys Ile Val His His Glu Asp
            35                  40                  45

Val Ala Ala Leu Val Ser Glu Ile Asp Pro Asp Thr Pro Leu Gly Ser
        50                  55                  60

Ser Asp Asp Leu Arg Ala His Ala Ala Val Leu Asp Ser Thr Ala Thr
65                  70                  75                  80

Val Ala Pro Val Leu Pro Leu Arg Phe Gly Ala Val Leu Thr Asp Thr
                85                  90                  95

Asp Ala Val Val Ala Glu Leu Leu Glu Pro Tyr Arg Asp Glu Phe His
            100                 105                 110

Glu Ala Leu Glu Gln Leu Glu Gly Lys Val Glu Phe Val Val Lys Gly
        115                 120                 125

Lys Tyr Val Glu Asp Ala Ile Leu Arg Glu Ile Leu Ala Asp Asp Pro
    130                 135                 140

Glu Ala Ala Arg Leu Arg Asp Val Val Arg Glu Gln Pro Glu Asp Thr
145                 150                 155                 160

Thr Arg Asp Glu Arg Leu Ala Leu Gly Glu Arg Ile Ser Gln Ala Leu
                165                 170                 175

Thr Ala Lys Arg Glu Gln Asp Thr Gly Arg Ile Val Glu Ala Leu Gln
```

```
                    180                 185                 190
Pro Ala Ala Thr Ala Val Ala Pro Arg Glu Pro Thr Asp Asp Glu Glu
                195                 200                 205

Ala Gly Ser Val Ala Val Leu Ile Ser Ala Asp Gly Val Asp Glu Leu
    210                 215                 220

Asp Lys Ala Val Ala Arg Leu Ile Asp Asp Trp Gln Gly Arg Val Glu
225                 230                 235                 240

Val Thr Val Thr Gly Pro Leu Ala Ala Tyr Asp Phe Val Lys Thr Arg
                245                 250                 255

Ala Pro Gly Thr
            260

<210> SEQ ID NO 142
<211> LENGTH: 259
<212> TYPE: PRT
<213> ORGANISM: Rhodococcus hoagii 103S

<400> SEQUENCE: 142

Met Thr Pro Asp Asp Gly Val Trp Val Tyr Ala Val Thr Gly Asp Gly
1               5                   10                  15

Ser Phe Pro Gly Gly Ile Ser Gly Ile Arg Gly Val Ala Gly Glu Glu
            20                  25                  30

Leu Arg Thr Val Thr Asp Ser Gly Phe Thr Ala Val Val Gly Thr Val
        35                  40                  45

Arg Leu Asp Thr Phe Gly Glu Glu Ala Leu Arg Arg Asn Leu Glu Asp
    50                  55                  60

Leu Asp Trp Leu Ala Asp Thr Ala Arg Arg His Asp Ala Val Val Ala
65                  70                  75                  80

Ala Ile Cys Ala Gly Gly Ala Thr Val Pro Leu Arg Leu Ala Thr Val
                85                  90                  95

Tyr Phe Asp Asp Asp Arg Val Arg Thr Met Leu Arg Asp Asn Ala Glu
            100                 105                 110

Gln Leu Gly Glu Ala Leu Gln Gln Ile Ala Asp Arg Ser Glu Trp Gly
        115                 120                 125

Val Arg Ala Tyr Leu Glu Arg Pro Arg Ser Glu Pro Arg Asp Ala Arg
    130                 135                 140

Glu Lys Thr Gly Arg Pro Ser Gly Thr Ala Tyr Leu Met Gln Arg Arg
145                 150                 155                 160

Ala Gln Val Ala Ala Arg Glu Gln Ala Glu Ser Ala Ala Gly Arg Arg
                165                 170                 175

Ala Asp Glu Ile Phe Ala Glu Leu Ala Arg Trp Ala Val Ala Gly Val
            180                 185                 190

Arg Gln Pro Pro Ser Pro Pro Asp Leu Ala Gly Arg Arg Ser Gln Glu
        195                 200                 205

Ile Leu Asn Thr Ser Phe Leu Val Asp Asn Gly Arg His Arg Glu Phe
    210                 215                 220

Val Thr Ala Val Glu Glu Leu Asp Ala Arg Leu Ser Asp Val Asp Leu
225                 230                 235                 240

Val Leu Thr Gly Pro Trp Pro Pro Tyr Ser Phe Thr Ser Val Glu Ala
                245                 250                 255

Ser Ala Arg

<210> SEQ ID NO 143
<211> LENGTH: 222
<212> TYPE: PRT
```

<213> ORGANISM: Serratia sp. ATCC 39006

<400> SEQUENCE: 143

Met Ser Leu Leu Leu Tyr Gly Ile Val Ala Glu Asp Thr Gln Leu Ala
1               5                   10                  15

Leu Glu Pro Asp Gly Ser Pro His Ala Gly Glu Glu Pro Met Gln Leu
            20                  25                  30

Val Lys Ala Ala Thr Leu Ala Ala Leu Val Lys Pro Cys Glu Ala Asp
        35                  40                  45

Val Ser Arg Glu Pro Ala Ala Ala Leu Ala Phe Gly Gln Gln Ile Met
    50                  55                  60

His Val His Gln Gln Thr Thr Ile Ile Pro Ile Arg Tyr Gly Cys Val
65                  70                  75                  80

Leu Ala Asp Glu Asp Ala Val Thr Gln His Leu Leu Asn His Glu Ala
                85                  90                  95

His Tyr Gln Thr Gln Leu Val Glu Leu Glu Asn Cys Asp Glu Met Gly
            100                 105                 110

Ile Arg Leu Ser Leu Ala Ser Ala Glu Asp Asn Ala Val Thr Thr Pro
        115                 120                 125

Gln Ala Ser Gly Leu Asp Tyr Leu Arg Ser Arg Lys Leu Ala Tyr Ala
    130                 135                 140

Val Pro Glu His Ala Glu Arg Gln Ala Ala Leu Leu Asn Asn Ala Phe
145                 150                 155                 160

Thr Gly Leu Tyr Arg Arg His Cys Ala Glu Ile Ser Met Phe Asn Gly
                165                 170                 175

Gln Arg Thr Tyr Leu Leu Ser Tyr Leu Val Pro Arg Thr Gly Leu Gln
            180                 185                 190

Ala Phe Arg Asp Gln Phe Asn Thr Leu Ala Asn Asn Met Thr Asp Ile
        195                 200                 205

Gly Val Ile Ser Gly Pro Trp Pro Pro Tyr Asn Phe Ala Ser
    210                 215                 220

<210> SEQ ID NO 144
<211> LENGTH: 362
<212> TYPE: PRT
<213> ORGANISM: Stella vacuolata-ATCC-43931

<400> SEQUENCE: 144

Met Ser Gly Leu Leu Val Phe Ala Ile Val Pro Ala Asp Gly Ile Glu
1               5                   10                  15

Pro Gly Ile Leu Ala Pro Arg Glu Glu Leu Pro Ala Asn Leu Arg Ala
            20                  25                  30

Val Ala Ala Asp Gly Phe Ala Ala Val Val Gly Ala Ala Pro Glu Gly
        35                  40                  45

Gly Leu Lys Gly Arg Asp Arg Ser Val Leu Leu Pro Arg Leu Leu Ala
    50                  55                  60

Ser Gln Lys Val Ile Glu Arg Leu Met Ala Arg Gly Pro Val Leu Pro
65                  70                  75                  80

Val Thr Leu Gly Thr Val Leu Glu Asp Glu Ala Arg Val Arg His Met
                85                  90                  95

Leu Ala Ala Gly Ala Pro Met Leu Glu Ala Phe Gly Thr Leu Gly
            100                 105                 110

Asp Cys Trp Gln Met Asp Leu Ser Val Arg Trp Asp Leu Asn Gln Val
        115                 120                 125

Val Ala Arg Leu Met Gly Glu Val Pro Gly Asp Val Arg Ala Ala Ala

```
            130                 135                 140
Gly Ser Gly Asp Glu Ala Ala Arg Arg Ala Leu Gly Glu Ala Leu Ala
145                 150                 155                 160

Gly Leu Ala Ala Gly Glu Arg Arg Val Gln Ser Arg Leu Ala Ala
                165                 170                 175

Ala Leu Arg Asp Val Ala Arg Asp Leu Ile Val Ser Glu Pro Val Glu
                180                 185                 190

Pro Glu Ser Val Val Asp Ile Ala Ile Leu Val Glu Arg Pro Ala Leu
            195                 200                 205

Ala Glu Val Glu Ala Ala Leu Asp Arg Leu Asp Ala Glu Phe Glu Gly
        210                 215                 220

Arg Leu Lys Phe Arg Leu Val Gly Pro Leu Ala Pro His Ser Phe Ala
225                 230                 235                 240

Thr Val Gln Val His Leu Ala Pro Glu Ala Ala Leu Ala Gly Ala Cys
                245                 250                 255

Ala Glu Leu Gly Val Glu Arg Gly Ala Gly Leu Gln Asp Val Lys Val
                260                 265                 270

Ala Tyr His Arg Ala Leu Val Arg Phe His Pro Asp Leu Ala Pro His
            275                 280                 285

Gly Asp Asp Gly Gly Pro Glu Asp His Asp Gly Gly Glu Gly Arg
        290                 295                 300

Ala Ser Arg Leu Leu Thr Val Thr Ala Ala Tyr Arg Ala Leu Gln Ala
305                 310                 315                 320

Glu His Ala Pro Ile Ser Leu Arg Arg Gln Asp Gly Ile Ala Val Asn
                325                 330                 335

Gln Glu Gln Asp Ala Ser Ala Ala Met Gly Gln Gln Arg Gly Ile Val
                340                 345                 350

Pro Gly Arg Glu Leu Gln Ala Leu Arg Met
            355                 360

<210> SEQ ID NO 145
<211> LENGTH: 258
<212> TYPE: PRT
<213> ORGANISM: Stella vacuolata-ATCC-43931

<400> SEQUENCE: 145

Met Leu Tyr Val Tyr Ala Ile Ala Ala Asp His Pro Asp Pro Asp Asn
1               5                   10                  15

Ala Met Phe Gly Gly Glu Gly Ile Val Pro Asp Ala Pro Val Arg Leu
                20                  25                  30

Leu Gln Leu Gly Asp Leu Ala Val Ala Ala Ser Leu Val Ser Ala Ala
            35                  40                  45

Asp Phe Ala Ala Asp Ala Leu Arg Ala His Leu Glu Asp Ala Arg Trp
        50                  55                  60

Thr Ala Leu Arg Val Leu Ala His Gln Arg Val Val Asp Ser Leu Leu
65                  70                  75                  80

Pro His Ala Thr Val Leu Pro Met Lys Phe Cys Thr Leu Phe Ser Gly
                85                  90                  95

Glu Ala Ala Leu Lys Gln Ala Leu Ala His Asn Arg Ala Ala Leu Gln
                100                 105                 110

Ala Thr Val Glu Arg Leu Arg Gly Ala Arg Glu Trp Gly Val Lys Leu
            115                 120                 125

Tyr Trp Glu Ala Pro Arg Asn Pro Ala Pro Ser Ala Gly Gln Gly
        130                 135                 140
```

Glu Ala Gly Ala Gly Ala Phe Phe Gln Arg Lys Arg Asp Gln Gln
145                 150                 155                 160

Arg Gln Arg Ala Glu Ala Glu Ala Ala Val Ala Arg Cys Val Ala Ala
            165                 170                 175

Ser His Arg Arg Leu Ala Asp Ala Ala Arg Ala Ala Val Ala Asn Pro
        180                 185                 190

Val Gln Pro Pro Ala Val His Arg Gln Pro Gly Glu Met Ala Leu Asn
    195                 200                 205

Gly Ala Tyr Leu Val Ala Arg Ala Ala Glu Pro Ala Trp Arg Glu Val
210                 215                 220

Leu Ala Glu Leu Glu Arg Thr His Ala Asp Gly Gly Ile Arg Tyr Glu
225                 230                 235                 240

Leu Thr Gly Pro Trp Gly Pro Tyr Asn Phe Thr Gly Ser Gly Leu Val
                245                 250                 255

Gly Ser

<210> SEQ ID NO 146
<211> LENGTH: 253
<212> TYPE: PRT
<213> ORGANISM: Thiocapsa rosea strain DSM 235 Ga0242571-11

<400> SEQUENCE: 146

Met Ser Asp Arg Pro Arg Pro Met Leu His Cys Ile Leu Arg Ser Pro
1               5                   10                  15

Pro Gly Ser Ile Ala Arg Ala Glu Ala Gly Leu Arg Trp Ile Glu Arg
            20                  25                  30

Asp Gly Leu Ala Ala Leu Val Ala Asp Arg Glu Pro Ser Glu Ile Ala
        35                  40                  45

Gly Ala Ser Ser Val Gly Leu Gln Arg Tyr Ala Asp Ile Val Ala Glu
    50                  55                  60

Ile His Ala Cys Ala Ala Val Ile Pro Val Arg Phe Gly Cys Leu Leu
65                  70                  75                  80

Ala Gly Asp Glu Ala Val Gly Lys Leu Leu His Arg Ser Arg Asp Arg
                85                  90                  95

Leu His Gly Leu Leu Asp Gln Val Gly Asp Cys Leu Glu Phe Gly Ile
            100                 105                 110

Arg Leu Leu Leu Pro Ala Asp Ala Pro Ala Ala Thr Asp Asp Asp Ala
        115                 120                 125

Ala Pro Arg Leu His Ala Asn Ala Pro Ser Asp Pro Arg Ala Asp Pro
    130                 135                 140

Asp Met Gly Pro Gly Leu Ser His Leu Leu Ala Ile Arg His Arg Leu
145                 150                 155                 160

Asp Val Glu Ala Ser Leu Ala Arg Ala Arg Glu Ala Arg Glu Val
                165                 170                 175

Ile Lys Gly Arg Val Ala Gly Arg Phe Arg Glu Val Arg Glu Glu Leu
            180                 185                 190

Gly Gln Ile Asp Gly Arg Ser Leu Leu Ser Leu Tyr Phe Leu Val Pro
        195                 200                 205

Arg Glu Gln Gly Glu His Phe Val Glu Cys Leu Arg Gln Asp Ala Ser
    210                 215                 220

Ser Leu Arg Gly Thr Gly Leu Leu Thr Gly Pro Trp Pro Tyr Asn
225                 230                 235                 240

Phe Val Gly Ala Ile Asp Asp Asp Ile Arg Ser Leu Asp
                245                 250

<210> SEQ ID NO 147
<211> LENGTH: 119
<212> TYPE: PRT
<213> ORGANISM: Anabaena-flos-aquae

<400> SEQUENCE: 147

Met Leu Thr Lys Leu Leu Leu Pro Ile Met Gly Pro Leu Asn Gly
1               5                   10                  15

Val Val Trp Ile Ala Glu Gln Ile Gln Glu Arg Thr Asn Thr Glu Phe
            20                  25                  30

Asp Ala Gln Glu Asn Leu His Lys Gln Leu Leu Ser Leu Gln Leu Ser
        35                  40                  45

Phe Asp Ile Gly Glu Ile Gly Glu Glu Phe Glu Ile Gln Glu Glu
    50                  55                  60

Glu Ile Leu Leu Lys Ile Gln Ala Leu Glu Glu Glu Ala Arg Leu Glu
65                  70                  75                  80

Leu Glu Ala Glu Gln Glu Glu Ala Arg Leu Glu Leu Glu Ala Glu Gln
                85                  90                  95

Glu Asp Phe Glu Tyr Pro Pro Gln Phe Thr Ala Glu Val Asn Lys Asp
            100                 105                 110

Gln His Leu Val Leu Leu Pro
            115

<210> SEQ ID NO 148
<211> LENGTH: 88
<212> TYPE: PRT
<213> ORGANISM: Bacillus-megaterium

<400> SEQUENCE: 148

Val Leu His Lys Leu Val Thr Ala Pro Ile Asn Leu Val Val Lys Ile
1               5                   10                  15

Gly Glu Lys Val Gln Glu Glu Ala Asp Lys Gln Leu Tyr Asp Leu Pro
            20                  25                  30

Thr Ile Gln Gln Lys Leu Ile Gln Leu Gln Met Met Phe Glu Leu Gly
        35                  40                  45

Glu Ile Pro Glu Glu Ala Phe Gln Glu Lys Glu Asp Glu Leu Leu Met
    50                  55                  60

Arg Tyr Glu Ile Ala Lys Arg Arg Glu Ile Glu Gln Trp Gly Glu Leu
65                  70                  75                  80

Thr Gln Lys Arg Asn Glu Glu Ser
                85

<210> SEQ ID NO 149
<211> LENGTH: 83
<212> TYPE: PRT
<213> ORGANISM: Ancylobacter aquaticus strain UV5

<400> SEQUENCE: 149

Met Gly Met Leu Thr Asp Val Val Phe Ala Pro Ala Val Gly Pro Leu
1               5                   10                  15

Lys Gly Val Leu Trp Leu Ala Arg Ile Ile Ala Glu Gln Ala Glu Arg
            20                  25                  30

Thr Leu Tyr Asp Glu Gly Val Ile Arg Ala Ala Leu Leu Asp Leu Glu
        35                  40                  45

Gln Gln Leu Glu Ala Gly Glu Ile Asp Glu Asp Ala Tyr Glu Thr Gln
    50                  55                  60

Glu Thr Val Leu Leu Glu Arg Leu Lys Ile Ala Arg Glu Arg Met Arg

```
                65                  70                  75                  80
Ser Gly Leu

<210> SEQ ID NO 150
<211> LENGTH: 122
<212> TYPE: PRT
<213> ORGANISM: Aphanizomenon flos-aquae NIES-81

<400> SEQUENCE: 150

Met Leu Thr Lys Leu Leu Leu Pro Ile Met Gly Pro Leu Asn Gly
1               5                   10                  15

Leu Val Trp Ile Gly Glu Gln Ile Gln Glu Arg Thr Asn Thr Glu Phe
            20                  25                  30

Asp Ala Gln Glu Asn Leu His Lys Gln Leu Leu Asn Leu Gln Leu Ser
        35                  40                  45

Phe Asp Ile Gly Glu Ile Ser Glu Glu Asp Phe Glu Ile Gln Glu Glu
    50                  55                  60

Glu Leu Leu Leu Lys Ile Gln Ala Leu Glu Glu Glu Ala Arg Leu Glu
65                  70                  75                  80

Leu Glu Leu Ala Glu Glu Ala Arg Leu Glu Leu Glu Leu Glu Gln
                85                  90                  95

Glu Glu Glu Glu Asp Phe Val Val Lys Pro Gln Leu Thr Thr Glu Ile
            100                 105                 110

Asp Arg Asp Lys Asp Leu Val Leu Pro
        115                 120

<210> SEQ ID NO 151
<211> LENGTH: 86
<212> TYPE: PRT
<213> ORGANISM: Aphanothece halophytica (strain PCC 7418)

<400> SEQUENCE: 151

Met Val Phe Lys Leu Leu Leu Pro Ile Thr Gly Pro Ile Glu Gly
1               5                   10                  15

Val Thr Trp Leu Gly Glu Gln Ile Leu Glu Arg Ala Asn Gln Glu Leu
            20                  25                  30

Asp Glu Lys Glu Asn Leu Asn Lys Arg Leu Leu Ser Leu Gln Leu Ser
        35                  40                  45

Leu Asp Leu Gly Glu Ile Ser Glu Glu Tyr Asp Glu Gln Glu Glu
    50                  55                  60

Glu Ile Leu Leu Ala Met Gln Ala Met Glu Asp Glu Glu Asn Asn Gln
65                  70                  75                  80

Ala Glu Glu Glu Thr Asp
                85

<210> SEQ ID NO 152
<211> LENGTH: 83
<212> TYPE: PRT
<213> ORGANISM: Aquabacter spiritensis strain DSM 9035

<400> SEQUENCE: 152

Met Ser Leu Val Thr Asp Val Leu Phe Ala Pro Ala Val Gly Pro Leu
1               5                   10                  15

Lys Gly Val Leu Trp Leu Ala Arg Leu Ile Ala Glu Gln Ala Glu Arg
            20                  25                  30

Thr Leu Tyr Asp Glu Asp Val Leu Arg Ala Ala Leu Leu Asp Leu Glu
        35                  40                  45
```

Gln Arg Phe Glu Ala Gly Glu Ile Ser Glu Ala Asp Tyr Glu Thr Glu
        50                  55                  60

Glu Asp Ile Leu Leu Ala Arg Leu Lys Ile Ala Arg Glu Arg Met Arg
 65                  70                  75                  80

Ser Gly Leu

<210> SEQ ID NO 153
<211> LENGTH: 82
<212> TYPE: PRT
<213> ORGANISM: Bradyrhizobium oligotrophicum S58

<400> SEQUENCE: 153

Met Leu Phe Gln Ile Leu Thr Ser Pro Val Ser Gly Pro Phe Arg Met
 1               5                  10                  15

Val Ser Trp Ile Gly Gly Ala Ile Arg Asp Ala Val Asp Thr Lys Met
                20                  25                  30

Asn Asp Pro Ala Glu Ile Lys Arg Ala Leu Ala Leu Glu Gln Gln
            35                  40                  45

Leu Glu Ala Gly Ser Leu Ser Glu Gln Asp Tyr Glu Arg Met Glu Met
        50                  55                  60

Glu Leu Ile Glu Arg Leu Gln Ser Ser Leu Arg His Gly Ser Gly Asn
 65                  70                  75                  80

Gly Gly

<210> SEQ ID NO 154
<211> LENGTH: 75
<212> TYPE: PRT
<213> ORGANISM: Burkholderia thailandensis sp. Bp5365 strain MSMB43

<400> SEQUENCE: 154

Met Phe Ile Leu Asp Asn Leu Leu Ala Ala Pro Ile Lys Gly Met Phe
 1               5                  10                  15

Trp Ile Phe Glu Glu Ile Ala Gln Ala Ala Glu Glu Thr Ile Ala
                20                  25                  30

Asp Ile Glu Met Ile Lys Ala Ala Leu Val Glu Leu Tyr Arg Glu Leu
            35                  40                  45

Glu Ser Gly Gln Ile Asp Glu Thr Glu Phe Glu Thr Arg Glu Arg Ala
50 55 60

Leu Leu Asp Arg Leu Asp Ser Leu Glu Thr Ser
65 70 75

<210> SEQ ID NO 155
<211> LENGTH: 78
<212> TYPE: PRT
<213> ORGANISM: Chlorobium luteolum DSM 273

<400> SEQUENCE: 155

Met Phe Ile Leu Asp Asp Ile Leu Leu Ala Pro Leu Ser Gly Met Val
1 5 10 15

Phe Leu Gly Arg Lys Ile Asn Glu Ile Val Gln Asn Glu Met Ser Asp
20 25 30

Glu Gly Ala Val Lys Glu Gln Leu Met Lys Leu Gln Phe Arg Phe Glu
35 40 45

Met Asp Glu Leu Ser Glu Glu Glu Tyr Asp Arg Leu Glu Asp Glu Leu
50 55 60

Leu Ser Thr Leu Ala Glu Ile Arg Ala Gln Lys Glu Asn Arg
65 70 75

<210> SEQ ID NO 156
<211> LENGTH: 83
<212> TYPE: PRT
<213> ORGANISM: Dactylococcopsis salina PCC 8305

<400> SEQUENCE: 156

Met Val Phe Lys Leu Leu Leu Pro Ile Thr Gly Pro Ile Glu Gly
1               5                   10                  15

Ile Thr Trp Leu Gly Glu Gln Ile Leu Glu Arg Ala Asp Gln Glu Leu
            20                  25                  30

Asp Ser Lys Glu Asn Leu Asn Lys Arg Leu Leu Ser Leu Gln Leu Ser
        35                  40                  45

Leu Asp Leu Gly Glu Ile Ser Glu Glu Tyr Asp Glu Gln Glu Glu
    50                  55                  60

Glu Ile Leu Leu Ala Met Gln Ala Met Glu Asp Glu Asn Glu Glu
65                  70                  75                  80

Glu Glu Ser

<210> SEQ ID NO 157
<211> LENGTH: 77
<212> TYPE: PRT
<213> ORGANISM: Desulfobacterium vacuolatum_DSM 3385

<400> SEQUENCE: 157

Met Phe Leu Val Asp Asp Ile Leu Phe Phe Pro Ala Lys Ser Leu Val
1               5                   10                  15

Trp Val Phe Arg Glu Leu His Asn Ala Val Gln Gln Glu Lys Thr Asn
            20                  25                  30

Glu Ser Asp Ala Leu Thr Thr Glu Leu Ser Glu Leu Tyr Met Met Leu
        35                  40                  45

Glu Thr Gly Lys Ile Thr Glu Glu Glu Phe Asp Glu Arg Glu Glu Gln
    50                  55                  60

Ile Leu Asp Arg Leu Asp Glu Ile Gln Glu Arg Asp Gln
65                  70                  75

<210> SEQ ID NO 158
<211> LENGTH: 86
<212> TYPE: PRT
<213> ORGANISM: Desulfomonile tiedjei DSM 6799

<400> SEQUENCE: 158

Met Glu Arg Tyr Thr Met Phe Leu Leu Asp Asp Ile Leu Phe Leu Pro
1               5                   10                  15

Met Asn Gly Val Leu Trp Ile Cys Asn Glu Ile His Asp Ala Ala Glu
            20                  25                  30

Gln Glu Leu His Asn Glu Ser Asp Ala Ile Thr Ala Gln Leu Gln Lys
        35                  40                  45

Leu Tyr Thr Leu Leu Glu Ala Gly Asp Ile Gly Glu Ser Glu Phe Asp
    50                  55                  60

Val Leu Glu Ala Glu Leu Leu Asp Arg Leu Asp Ala Ile Gln Glu Arg
65                  70                  75                  80

Gly Ala Leu Leu Glu Ala
                85

<210> SEQ ID NO 159
<211> LENGTH: 83
<212> TYPE: PRT
<213> ORGANISM: Desulfotomaculum acetoxidans_DSM 771

<400> SEQUENCE: 159

Met Leu Gly Lys Leu Leu Leu Ser Pro Ile Leu Gly Pro Val Met Gly
1               5                   10                  15

Val Lys Phe Ile Ala Glu Lys Ile Lys Gln Gln Ala Asp Gln Glu Leu
            20                  25                  30

Tyr Asp Lys Ser Lys Ile Lys Gln Asp Leu Met Glu Leu Gln Ile Lys
        35                  40                  45

Leu Glu Leu Glu Glu Ile Thr Glu Glu Tyr Tyr Leu Gln Arg Glu Glu
    50                  55                  60

Glu Leu Leu Val Arg Leu Asp Glu Leu Ala Ser Met Glu Thr Glu Glu
65                  70                  75                  80

Glu Glu Val

<210> SEQ ID NO 160
<211> LENGTH: 129
<212> TYPE: PRT
<213> ORGANISM: Dolichospermum circinale

<400> SEQUENCE: 160

Met Leu Thr Gln Leu Leu Leu Pro Ile Met Gly Pro Leu Asn Gly
1               5                   10                  15

Val Val Trp Ile Ala Glu Gln Ile Gln Glu Arg Thr Asn Thr Glu Phe
            20                  25                  30

Asp Ala Gln Glu Asn Leu His Lys Gln Leu Leu Ser Leu Gln Leu Ser
        35                  40                  45

Phe Asp Ile Gly Glu Ile Ser Glu Glu Phe Glu Ile Gln Glu Glu
    50                  55                  60

Glu Ile Leu Leu Lys Ile Gln Ala Leu Glu Glu Ala Arg Leu Glu
65                  70                  75                  80

Leu Glu Ala Glu Gln Glu Glu Ala Arg Leu Glu Leu Glu Ala Glu Gln
                85                  90                  95

Glu Gln Ala Arg Leu Glu Leu Glu Ala Glu Gln Glu Leu Glu Asn
            100                 105                 110

Gln Pro Gln Leu Thr Pro Lys Ile Asp Thr Tyr Arg His Leu Val Lys
        115                 120                 125

Leu

<210> SEQ ID NO 161
<211> LENGTH: 81
<212> TYPE: PRT
<213> ORGANISM: Enhydrobacter aerosaccus strain ATCC 27094

<400> SEQUENCE: 161

Met Gly Met Leu Ala Arg Leu Leu Thr Leu Pro Val Ser Ala Pro Val
1               5                   10                  15

Gly Gly Val Leu Trp Ile Ala Arg Lys Ile Glu Glu Ala Asn Ala
            20                  25                  30

Glu Arg Trp Asp Arg Asn Lys Ile Thr Gly Ala Leu Ser Glu Leu Glu
        35                  40                  45

Leu Glu Leu Asp Leu Gly Ala Ile Asp Val Glu Tyr Asp Ala Arg
    50                  55                  60

Glu Ala Val Leu Leu Gln Lys Leu Lys Glu Leu Gln Glu Val Glu Asn
65                  70                  75                  80

Asp

<210> SEQ ID NO 162
<211> LENGTH: 103
<212> TYPE: PRT
<213> ORGANISM: Isosphaera pallida_ATCC-43644

<400> SEQUENCE: 162

Met Phe Leu Val Asp Asp Ile Leu Leu Ala Pro Ala His Ser Leu Met
1               5                   10                  15

Phe Leu Leu Arg Glu Ile His Gln Ala Ala Leu Glu Glu Leu Arg Arg
            20                  25                  30

Asp Ala Gln Lys Val Arg Glu Glu Leu Ala Glu Cys Tyr Arg Ala Leu
        35                  40                  45

Glu Thr Gly Ala Leu Thr Asp Glu Glu Phe Ala Ser Leu Glu Thr Asp
    50                  55                  60

Leu Leu Asp Arg Leu Asp Ala Leu Glu Glu Leu Ala Arg Phe Asn Ser
65                  70                  75                  80

Asp Glu Asp Asp Asp Pro Glu Asp Glu Asp Trp Asp Val Glu Asp Asp
                85                  90                  95

Asp Pro Ala Glu Ala Val Trp
            100

<210> SEQ ID NO 163
<211> LENGTH: 77
<212> TYPE: PRT
<213> ORGANISM: Legionella drancourtii LLAP12

<400> SEQUENCE: 163

Met Leu Leu Leu Gly Ser Ile Leu Met Ala Pro Val His Gly Leu Met
1               5                   10                  15

Ala Ile Phe Glu Lys Ile Lys Glu Ala Val Asp Glu Glu Lys Gln His
            20                  25                  30

Asp Ile Glu Arg Ile Lys Ser Glu Leu Met Ala Leu Tyr Thr Lys Leu
        35                  40                  45

Glu Ser Gly Glu Leu Ser Glu Ala Asp Phe Glu Lys Gln Glu Lys Ile
    50                  55                  60

Leu Leu Asp Lys Leu Asp Ser Leu Glu Asp Glu Asp Asp
65                  70                  75

<210> SEQ ID NO 164
<211> LENGTH: 86
<212> TYPE: PRT
<213> ORGANISM: Microcystis aeruginosa NIES-843

<400> SEQUENCE: 164

Met Phe Leu Asp Leu Leu Phe Leu Pro Val Thr Gly Pro Ile Gly Gly
1               5                   10                  15

Leu Ile Trp Ile Gly Glu Lys Ile Gln Glu Arg Ala Asp Ile Glu Tyr
            20                  25                  30

Asp Glu Ala Glu Asn Leu His Lys Leu Leu Ser Leu Gln Leu Ser
        35                  40                  45

Tyr Asp Met Gly Asn Ile Ser Glu Glu Phe Glu Ile Gln Glu Glu
    50                  55                  60

Glu Leu Leu Leu Lys Ile Gln Ala Leu Glu Glu Glu Ala Glu Asn
65                  70                  75                  80

Glu Ser Glu Ser Ser Leu
            85

```
<210> SEQ ID NO 165
<211> LENGTH: 84
<212> TYPE: PRT
<213> ORGANISM: Nostoc punctiforme ATCC 29133

<400> SEQUENCE: 165

Met Val Leu Arg Phe Leu Leu Leu Pro Ile Thr Gly Pro Leu Met Gly
1               5                   10                  15

Val Thr Trp Leu Gly Glu Lys Ile Leu Glu Gln Ala Ser Thr Glu Ile
            20                  25                  30

Asp Asp Lys Glu Asn Leu Ser Lys Gln Leu Leu Ala Leu Gln Leu Ala
        35                  40                  45

Phe Asp Met Gly Glu Ile Pro Glu Glu Phe Glu Ile Gln Glu Glu
    50                  55                  60

Ala Leu Leu Leu Ala Ile Leu Glu Ala Glu Gln Glu Glu Arg Asp Gln
65                  70                  75                  80

Thr Gln Glu Tyr

<210> SEQ ID NO 166
<211> LENGTH: 125
<212> TYPE: PRT
<213> ORGANISM: Nostoc sp. PCC 7120

<400> SEQUENCE: 166

Met Leu Gly Lys Ile Leu Leu Leu Pro Val Met Gly Pro Ile Asn Gly
1               5                   10                  15

Leu Met Trp Ile Gly Glu Gln Ile Gln Glu Arg Thr Asn Thr Glu Phe
            20                  25                  30

Asp Ala Gln Glu Asn Leu His Lys Gln Leu Leu Ser Leu Gln Leu Lys
        35                  40                  45

Phe Asp Met Gly Glu Ile Ser Glu Glu Phe Asp Ile Gln Glu Glu
    50                  55                  60

Glu Ile Leu Leu Lys Ile Gln Ala Leu Glu Ala Glu Glu Arg Leu Asn
65                  70                  75                  80

Ala Glu Ser Glu Glu Asp Asp Asp Leu Asp Val Gln Pro Ile Phe Ile
                85                  90                  95

Leu Ala Ser Glu Glu Asn Pro Val Tyr Gln Asp Gln Ser Arg Phe Ser
                100                 105                 110

Glu Glu Tyr Glu Asp Lys Glu Asp Leu Val Leu Ser Pro
            115                 120                 125

<210> SEQ ID NO 167
<211> LENGTH: 84
<212> TYPE: PRT
<213> ORGANISM: Octadecabacter antarcticus 307

<400> SEQUENCE: 167

Met Gly Ile Ile Leu Asn Thr Leu Met Ser Pro Leu Ile Gly Pro Met
1               5                   10                  15

Lys Gly Val Phe Trp Val Ala Glu Gln Ile Lys Asp Gln Thr Asp Ala
            20                  25                  30

Glu Ile Tyr Asp Asp Ser Lys Ile Leu Val Glu Leu Ser Glu Leu Glu
        35                  40                  45

Leu Leu Leu Asp Leu Glu Lys Ile Glu Leu Lys Asp Phe Glu Ala Lys
    50                  55                  60

Glu Asp Val Leu Leu Lys Arg Leu Gln Glu Ile Arg Lys Ala Lys Lys
65                  70                  75                  80
```

Asn Asp Ser Val

<210> SEQ ID NO 168
<211> LENGTH: 84
<212> TYPE: PRT
<213> ORGANISM: Octadecabacter arcticus 238

<400> SEQUENCE: 168

Met Ser Ile Ile Leu Asn Thr Leu Met Gly Pro Leu Ile Gly Pro Met
1               5                   10                  15

Lys Gly Leu Leu Trp Val Ala Glu Gln Ile Lys Asp Gln Ala Asp Ala
            20                  25                  30

Glu Leu Tyr Asp Asp Ser Lys Ile Leu Val Ala Leu Ser Glu Leu Glu
        35                  40                  45

Leu Ser Phe Asp Leu Glu Gln Ile Glu Leu Lys Glu Phe Glu Ala Gln
    50                  55                  60

Glu Asp Val Leu Leu Gln Arg Leu Gln Ala Ile Arg Lys Ala Lys Gln
65                  70                  75                  80

Asn Asp Thr Asp

<210> SEQ ID NO 169
<211> LENGTH: 78
<212> TYPE: PRT
<213> ORGANISM: Pelodictyon phaeoclathratiforme

<400> SEQUENCE: 169

Met Phe Ile Leu Asp Asp Ile Leu Phe Ala Pro Leu Asn Gly Leu Ile
1               5                   10                  15

Phe Ile Ala Lys Lys Ile Asn Asp Val Val Glu Lys Glu Thr Ser Asp
            20                  25                  30

Glu Gly Val Val Lys Glu Arg Leu Met Ala Leu Gln Leu Arg Phe Glu
        35                  40                  45

Leu Asp Glu Ile Asp Glu Val Glu Tyr Asp Arg Glu Glu Asp Glu Leu
    50                  55                  60

Leu Gln Lys Leu Glu Arg Ile Arg Leu Asn Lys Gln Asn Gln
65                  70                  75

<210> SEQ ID NO 170
<211> LENGTH: 81
<212> TYPE: PRT
<213> ORGANISM: Phormidium tenue NIES-30

<400> SEQUENCE: 170

Met Leu Phe Lys Leu Leu Phe Ala Pro Val Leu Gly Pro Ile Glu Gly
1               5                   10                  15

Ile Ser Trp Val Ala Asn Lys Leu Leu Glu Gln Ala Asp Val Pro Thr
            20                  25                  30

Asn Asp Leu Glu Ser Leu Gln Lys Gln Leu Leu Ala Leu Gln Leu Ala
        35                  40                  45

Phe Asp Met Gly Glu Val Ala Glu Asp Phe Glu Ile Gln Glu Glu
    50                  55                  60

Glu Ile Leu Leu Ala Ile Gln Ala Ile Glu Asp Glu Asp Glu Asp
65                  70                  75                  80

Glu

<210> SEQ ID NO 171
<211> LENGTH: 85
<212> TYPE: PRT

-continued

```
<213> ORGANISM: Planktothrix agardhii str. 7805

<400> SEQUENCE: 171

Met Ile Leu Arg Leu Leu Ser Pro Ile Thr Ala Pro Phe Glu Gly
1               5                   10                  15

Val Ile Trp Ile Gly Glu Gln Leu Leu Glu Arg Ala Glu Ala Glu Leu
            20                  25                  30

Asp Asp Lys Glu Asn Leu Gly Lys Arg Leu Leu Ala Leu Gln Leu Ala
        35                  40                  45

Phe Asp Met Gly Asp Ile Pro Glu Glu Asp Phe Glu Val Gln Glu Glu
    50                  55                  60

Glu Leu Leu Leu Gln Ile Gln Ala Leu Glu Asp Glu Ala Asn Gln Glu
65                  70                  75                  80

Asn Asp Glu Ile Asp
                85

<210> SEQ ID NO 172
<211> LENGTH: 149
<212> TYPE: PRT
<213> ORGANISM: Psychromonas ingrahamii 37

<400> SEQUENCE: 172

Met Phe Ile Leu Asp Asp Ile Leu Leu Ala Pro Tyr Ser Gly Ile Lys
1               5                   10                  15

Trp Leu Phe Lys Glu Ile Gln Arg Gln Ala Gln Glu Glu Leu Asp Gly
            20                  25                  30

Glu Ala Asp Arg Ile Thr Thr Asp Leu Thr Asn Leu Tyr Arg Gln Phe
        35                  40                  45

Glu Ser Asn Glu Ile Thr Glu Gln Phe Glu Glu Arg Glu Thr Val
    50                  55                  60

Leu Leu Asp Arg Leu Asp Glu Leu Gln Glu Glu Ser Asn Leu Leu Asp
65                  70                  75                  80

Glu Glu Tyr Asp Glu Glu Tyr Glu Asp Asp Glu Glu Tyr Glu Asp
                85                  90                  95

Asp Asp Glu Glu Tyr Glu Asp Asp Glu Glu Tyr Glu Asp Asp
            100                 105                 110

Glu Glu Tyr Glu Asp Asp Lys Asn Asp Lys Asp Lys Asn Asp Asp
        115                 120                 125

His Asp Asn Asp Asp Asp Glu Asn Lys Asp Glu Asn Asp Lys Tyr
    130                 135                 140

Asn Asp Glu Glu Arg
145

<210> SEQ ID NO 173
<211> LENGTH: 85
<212> TYPE: PRT
<213> ORGANISM: Rhodobacter capsulatus SB 100

<400> SEQUENCE: 173

Met Gly Leu Leu Arg Lys Leu Leu Ala Pro Val Glu Leu Pro Ile
1               5                   10                  15

Thr Gly Ala Leu Trp Ile Val Glu Lys Ile Ala Glu Thr Ala Glu Ser
            20                  25                  30

Glu Leu Thr Asp Pro Gly Thr Val Arg Arg Leu Leu Arg Gly Leu Glu
        35                  40                  45

Gln Gln Leu Glu Ala Gly Glu Ile Thr Glu Glu Glu Tyr Glu Phe Ala
    50                  55                  60
```

-continued

Glu Ile Leu Leu Asp Arg Leu Lys Arg Gly Gln Ala Ala Glu Ala
 65                  70                  75                  80

Arg Ser Gly Gly Pro
                85

<210> SEQ ID NO 174
<211> LENGTH: 77
<212> TYPE: PRT
<213> ORGANISM: Rhodobacter sphaeroides 2.4.1

<400> SEQUENCE: 174

Met Gly Leu Leu Thr Ser Leu Leu Thr Leu Pro Phe Arg Gly Pro Phe
  1               5                  10                  15

Asp Gly Thr Leu Trp Ile Ala Ala Arg Ile Gly Glu Ala Ala Glu Gln
             20                  25                  30

Ser Trp Asn Asp Pro Ala Ala Leu Arg Ala Ala Leu Val Glu Ala Glu
         35                  40                  45

Arg Gln Leu Leu Ala Gly Glu Leu Ser Glu Glu Thr Tyr Asp Ala Ile
     50                  55                  60

Glu Leu Asp Leu Leu Glu Arg Leu Lys Gly Thr Ala Arg
 65                  70                  75

<210> SEQ ID NO 175
<211> LENGTH: 83
<212> TYPE: PRT
<213> ORGANISM: Rhodococcus hoagii 103S

<400> SEQUENCE: 175

Met Gly Leu Phe Ser Ala Ile Phe Gly Leu Pro Leu Ala Pro Val Arg
  1               5                  10                  15

Gly Val Val Trp Ile Gly Glu Val Val Arg Arg Gln Val Glu Glu Glu
             20                  25                  30

Thr Thr Ser Pro Ala Ala Met Arg Arg Asp Leu Glu Ala Ile Glu Glu
         35                  40                  45

Gly Arg Arg Ser Gly Glu Ile Ser Glu Asp Glu Ala Ala Gln Ala Glu
     50                  55                  60

Asp Glu Ile Leu His Arg Val Thr Arg Arg Asp Ala Gly Ala Ser
 65                  70                  75                  80

Gly Glu Glu

<210> SEQ ID NO 176
<211> LENGTH: 138
<212> TYPE: PRT
<213> ORGANISM: Serratia sp. ATCC 39006

<400> SEQUENCE: 176

Met Leu Leu Ile Asp Asp Ile Leu Phe Ser Pro Val Lys Gly Val Met
  1               5                  10                  15

Trp Ile Phe Arg Gln Ile His Glu Leu Ala Glu Asp Glu Leu Ala Gly
             20                  25                  30

Glu Ala Asp Arg Ile Arg Glu Ser Leu Thr Asp Leu Tyr Met Leu Leu
         35                  40                  45

Glu Thr Gly Gln Ile Thr Glu Asp Glu Phe Glu Gln Gln Glu Ala Val
     50                  55                  60

Leu Leu Asp Arg Leu Asp Ala Leu Asp Glu Glu Asp Met Leu Gly
 65                  70                  75                  80

Asp Glu Pro Gly Asp Asp Glu Asp Asp Glu Tyr Glu Glu Asp Asp Asp

```
                85                  90                  95
Glu Glu Asp Asp Asp Glu Glu Asp Asp Asp Glu Asp Asp Asp
            100                 105                 110

Glu Asp Asp Asp Asp Glu Glu Asp Asp Asp Asp Glu Asp Asp
            115                 120                 125

Asp Glu Asp Glu Pro Glu Gly Thr Thr Lys
            130                 135

<210> SEQ ID NO 177
<211> LENGTH: 83
<212> TYPE: PRT
<213> ORGANISM: Stella vacuolata_ATCC-43931

<400> SEQUENCE: 177

Met Gly Leu Val Thr Asn Val Ala Phe Ala Pro Val Val Gly Pro Leu
1               5                   10                  15

Lys Gly Val Leu Trp Leu Ala Arg Leu Ile Ala Asp Gln Ala Glu Arg
            20                  25                  30

Thr Leu Tyr Asp Glu Asp Leu Val Arg Ala Ala Leu Leu Asp Leu Glu
        35                  40                  45

Gln Arg Leu Asp Ala Gly Gln Ile Ser Glu Ala Asp Tyr Asp Ala Glu
    50                  55                  60

Glu Glu Ile Leu Leu Ala Arg Leu Lys Ile Ala Arg Glu Arg Met Arg
65                  70                  75                  80

Ser Gly Leu

<210> SEQ ID NO 178
<211> LENGTH: 98
<212> TYPE: PRT
<213> ORGANISM: Thiocapsa rosea strain DSM 235 Ga0242571_11

<400> SEQUENCE: 178

Met Leu Ile Val Asp Asp Leu Leu Ala Ala Pro Phe Lys Gly Ile Ile
1               5                   10                  15

Trp Val Phe Glu Glu Ile His Lys Ser Ala Thr Ala Glu Gln Arg Ala
            20                  25                  30

Arg Arg Asp Glu Ile Met Ala Ala Leu Ser Ala Leu Tyr Arg Ala Leu
        35                  40                  45

Glu Gln Gly Glu Ile Thr Asp Asp Thr Phe Asp Thr Arg Glu Gln Ala
    50                  55                  60

Leu Leu Asp Glu Leu Asp Ala Leu Asp Ala Arg Glu Asp Ala Asn Glu
65                  70                  75                  80

Leu Gly Ser Asp Glu Asp Glu Asp Leu Asp Gly Ala Gly Glu Asp
            85                  90                  95

Ala Ser

<210> SEQ ID NO 179
<211> LENGTH: 132
<212> TYPE: PRT
<213> ORGANISM: Tolypothrix sp. PCC 7601

<400> SEQUENCE: 179

Met Glu Val Met Ile Met Leu Gly Lys Ile Leu Leu Phe Pro Val Met
1               5                   10                  15

Gly Pro Ile Ser Gly Leu Met Trp Ile Gly Glu Gln Ile Gln Glu Arg
            20                  25                  30

Thr Asp Thr Glu Phe Asp Ala Gln Glu Asn Leu His Lys Gln Leu Leu
```

```
            35                  40                  45
Ser Leu Gln Leu Ser Phe Asp Ile Gly Glu Ile Ser Glu Glu Asp Phe
 50                  55                  60

Glu Glu Gln Glu Glu Glu Leu Leu Lys Ile Gln Ala Leu Glu Glu
 65                  70                  75                  80

Glu Lys Ala Arg Leu Glu Ala Glu Ser Ile Glu Asp Glu Asp Glu
                 85                  90                  95

Val Glu Pro Thr Tyr Phe Ile Ala Glu Val Glu Glu Asp Lys Val Leu
                100                 105                 110

Ala Glu Ala Phe Arg Gly Asn Lys Lys Tyr Glu Asp Asn Glu Asn Leu
                115                 120                 125

Val Leu Ser Pro
            130

<210> SEQ ID NO 180
<211> LENGTH: 85
<212> TYPE: PRT
<213> ORGANISM: Trichodesmium erythraeum IMS101

<400> SEQUENCE: 180

Met Leu Leu Arg Leu Leu Thr Leu Pro Ile Ser Gly Pro Leu Glu Gly
 1               5                  10                  15

Val Thr Trp Leu Gly Lys Lys Leu Gln Glu Gln Val Asp Thr Glu Ile
                20                  25                  30

Asp Glu Thr Glu Asn Leu Ser Lys Lys Leu Leu Thr Leu Gln Leu Ala
                35                  40                  45

Phe Asp Met Gly Glu Ile Ser Glu Glu Asp Phe Glu Ser Gln Glu Glu
 50                  55                  60

Glu Leu Leu Leu Ala Ile Gln Ala Leu Glu Glu Gln Lys Leu Lys Glu
 65                  70                  75                  80

Glu Glu Glu Asp Ala
                 85

<210> SEQ ID NO 181
<211> LENGTH: 248
<212> TYPE: PRT
<213> ORGANISM: Anabaena-flos-aquae

<400> SEQUENCE: 181

Met Leu Pro Thr Arg Pro Gln Thr Asn Ser Ser Arg Thr Ile Asn Thr
 1               5                  10                  15

Ser Thr Gln Gly Ser Thr Leu Ala Asp Ile Leu Glu Arg Val Leu Asp
                20                  25                  30

Lys Gly Ile Val Ile Ala Gly Asp Ile Ser Ile Ser Ile Ala Ser Thr
                35                  40                  45

Glu Leu Val His Ile Arg Ile Arg Leu Leu Ile Ser Ser Val Asp Lys
 50                  55                  60

Ala Lys Glu Met Gly Ile Asn Trp Trp Glu Ser Asp Pro Tyr Leu Ser
 65                  70                  75                  80

Thr Lys Ala Gln Arg Leu Val Glu Glu Asn Gln Gln Leu Gln His Arg
                85                  90                  95

Leu Glu Ser Leu Glu Ala Lys Leu Asn Ser Leu Thr Ser Ser Ser Val
                100                 105                 110

Lys Glu Glu Ile Pro Leu Ala Ala Asp Val Lys Asp Asp Leu Tyr Gln
                115                 120                 125

Thr Ser Ala Lys Ile Pro Ser Pro Val Asp Thr Pro Ile Glu Val Leu
```

```
                130                 135                 140
Asp Phe Gln Ala Gln Ser Ser Gly Gly Thr Pro Pro Tyr Val Asn Thr
145                 150                 155                 160

Ser Met Glu Ile Leu Asp Phe Gln Ala Gln Thr Ser Ala Glu Ser Ser
                165                 170                 175

Ser Pro Val Gly Ser Thr Val Glu Ile Leu Asp Phe Gln Ala Gln Thr
                180                 185                 190

Ser Glu Glu Ser Ser Pro Val Val Ser Thr Val Glu Ile Leu Asp
                195                 200                 205

Phe Gln Ala Gln Thr Ser Glu Glu Ser Ser Pro Val Gly Ser Thr
210                 215                 220

Val Glu Ile Leu Asp Phe Gln Ala Gln Thr Ser Glu Glu Ile Pro Ser
225                 230                 235                 240

Ser Val Asp Pro Ala Ile Asp Val
                245

<210> SEQ ID NO 182
<211> LENGTH: 100
<212> TYPE: PRT
<213> ORGANISM: Bacillus-megaterium

<400> SEQUENCE: 182

Met Ala Val Glu His Asn Met Gln Ser Ser Thr Ile Val Asp Val Leu
1               5                   10                  15

Glu Lys Ile Leu Asp Lys Gly Val Val Ala Gly Asp Ile Thr Val
            20                  25                  30

Gly Ile Ala Asp Val Glu Leu Leu Thr Ile Lys Ile Arg Leu Ile Val
            35                  40                  45

Ala Ser Val Asp Lys Ala Lys Glu Ile Gly Met Asp Trp Trp Glu Asn
50                  55                  60

Asp Pro Tyr Leu Ser Ser Lys Gly Ala Asn Asn Lys Ala Leu Glu Glu
65                  70                  75                  80

Glu Asn Lys Met Leu His Glu Arg Leu Lys Thr Leu Glu Glu Lys Ile
                85                  90                  95

Glu Thr Lys Arg
            100

<210> SEQ ID NO 183
<211> LENGTH: 120
<212> TYPE: PRT
<213> ORGANISM: Ancylobacter aquaticus strain UV5

<400> SEQUENCE: 183

Met Asn Glu Gln Arg Met Glu His Ser Leu Gln Ala Val Gly Leu Ala
1               5                   10                  15

Asp Ile Leu Glu Arg Val Leu Asp Lys Gly Ile Val Ile Ala Gly Asp
            20                  25                  30

Ile Thr Ile Ser Leu Val Glu Val Glu Leu Leu Asn Ile Arg Leu Arg
            35                  40                  45

Leu Val Val Ala Ser Val Asp Arg Ala Met Ser Met Gly Ile Asn Trp
50                  55                  60

Trp Gln Ser Asp Pro His Leu Asn Ser His Ala Arg Glu Leu Ala Glu
65                  70                  75                  80

Glu Asn Lys Leu Leu Arg Glu Arg Leu Asp Arg Leu Glu Ala Ala Val
                85                  90                  95

Val Pro Ser Ala Leu Pro Ala Asp Ala Ala Leu Glu Pro Ser Leu Ala
```

```
                    100                 105                 110

Gly Glu Asp Ala Arg His Gly Gly
        115                 120

<210> SEQ ID NO 184
<211> LENGTH: 72
<212> TYPE: PRT
<213> ORGANISM: Ancylobacter aquaticus strain UV5

<400> SEQUENCE: 184

Met Pro Ser Arg His Ser Gly Glu Ile Ala Val Ala Asp Leu Leu Asp
1               5                   10                  15

Arg Ala Leu His Lys Gly Leu Val Val Trp Gly Glu Ala Thr Ile Ser
            20                  25                  30

Val Ala Gly Val Asp Leu Val Tyr Leu Gly Leu Lys Leu Leu Leu Thr
        35                  40                  45

Ser Thr Asp Thr Val Asn Arg Met Arg Glu Ala Ala Asn Ala Pro Pro
    50                  55                  60

Asp Glu Arg His Leu His Ala Asp
65                  70

<210> SEQ ID NO 185
<211> LENGTH: 157
<212> TYPE: PRT
<213> ORGANISM: Aphanizomenon flos-aquae NIES-81

<400> SEQUENCE: 185

Val Thr Ser Thr Pro Ile Leu Pro Thr Arg Pro Gln Thr Asn Ser Ser
1               5                   10                  15

Arg Ala Ile Asn Thr Ser Thr Gln Gly Ser Thr Leu Ala Asp Ile Leu
            20                  25                  30

Glu Arg Val Leu Asp Lys Gly Ile Val Ile Ala Gly Asp Ile Ser Ile
        35                  40                  45

Ser Ile Ala Ser Thr Glu Leu Ile His Ile Arg Ile Arg Leu Leu Ile
    50                  55                  60

Ala Ser Val Asp Lys Ala Lys Glu Met Gly Ile Asn Trp Trp Glu Thr
65                  70                  75                  80

Asp Pro Tyr Leu Ser Thr Lys Ala Gln Arg Leu Val Glu Glu Asn Gln
                85                  90                  95

Gln Leu Gln Asn Arg Leu Glu Asn Leu Glu Ser Gln Ile Asn Leu Leu
            100                 105                 110

Thr Ser Ala Lys Val Gln Glu Gln Ile Ser Leu Val Glu Thr Thr Glu
        115                 120                 125

Asp Asn Thr His Gln Thr Thr Glu Asp Asn Thr His Gln Thr His Glu
    130                 135                 140

Glu Ser Ile Pro Leu Pro Ile Asp Ser Gln Leu Asp Val
145                 150                 155

<210> SEQ ID NO 186
<211> LENGTH: 128
<212> TYPE: PRT
<213> ORGANISM: Aphanothece halophytica (strain PCC 7418)

<400> SEQUENCE: 186

Met Val Asn Pro Asn Thr Asn Lys Pro Lys Ser Tyr Gln Ser Lys Gly
1               5                   10                  15

Ile Thr Asn Ser Thr Gln Ser Ser Ser Leu Ala Asp Ile Leu Glu Arg
            20                  25                  30
```

Val Leu Asp Lys Gly Ile Val Ile Ala Gly Asp Ile Thr Val Ser Val
         35                  40                  45

Gly Ser Thr Glu Leu Leu Ser Ile Arg Ile Arg Leu Leu Val Ser Ser
     50                  55                  60

Val Asp Lys Ala Arg Glu Leu Gly Ile Asn Trp Trp Glu Gly Asp Pro
 65                  70                  75                  80

Tyr Leu Ser Ser Gln Ala Asn Leu Leu Lys Glu Glu Asn Gln Ala Leu
                 85                  90                  95

Gln Asn Arg Leu Glu Asn Met Glu Ala Glu Leu Arg Arg Leu Lys Gly
             100                 105                 110

Glu Thr Asn Pro Glu Pro Ser Phe Leu Ser Glu Ser Glu Asp Asn Ser
         115                 120                 125

<210> SEQ ID NO 187
<211> LENGTH: 114
<212> TYPE: PRT
<213> ORGANISM: Aquabacter spiritensis strain DSM 9035

<400> SEQUENCE: 187

Met Ser Glu Gln Arg Met Glu His Ser Leu Gln Ala Val Gly Leu Ala
1               5                   10                  15

Asp Ile Leu Glu Arg Val Leu Asp Lys Gly Ile Val Ile Ala Gly Asp
             20                  25                  30

Ile Ser Ile Ser Leu Val Glu Val Asp Leu Leu Asn Ile Arg Leu Arg
             35                  40                  45

Leu Val Val Ala Ser Val Asp Arg Ala Met Ser Met Gly Ile Asn Trp
         50                  55                  60

Trp Gln Ser Asp Pro His Leu Asn Ser His Ala Arg Gln Leu Glu Glu
 65                  70                  75                  80

Glu Asn Arg Leu Leu Arg Glu Arg Leu Asp Arg Leu Glu Ala Ala Leu
                 85                  90                  95

Ala Pro Pro Glu Gly Gly Met Leu Arg Ala Glu Val Glu Val Ala His
             100                 105                 110

Gly Gly

<210> SEQ ID NO 188
<211> LENGTH: 78
<212> TYPE: PRT
<213> ORGANISM: Aquabacter spiritensis strain DSM 9035

<400> SEQUENCE: 188

Met Pro Asp Pro Glu Pro Ile Ile Pro Arg Thr Ser Gly Asp Val Ala
1               5                   10                  15

Leu Ala Asp Leu Leu Asp Arg Ala Leu His Lys Gly Leu Val Leu Trp
             20                  25                  30

Gly Glu Ala Thr Ile Ser Val Ala Gly Val Asp Leu Val Tyr Leu Gly
             35                  40                  45

Leu Lys Val Leu Leu Ala Ser Thr Asp Thr Ala Asn Arg Met Arg Asp
         50                  55                  60

Ala Ala Ala Ala Ser Ala Ala Gly Ser His Leu Pro Gly Gly
 65                  70                  75

<210> SEQ ID NO 189
<211> LENGTH: 127
<212> TYPE: PRT
<213> ORGANISM: Arthrospira platensis NIES-39

<400> SEQUENCE: 189

Met Thr Leu Gln Ser Arg Ser Ser Pro Gln Arg Gly Val Pro Met
1               5                   10                  15

Ser Thr Ser Gly Ser Ser Leu Ala Asp Ile Leu Glu Arg Val Leu Asp
            20                  25                  30

Lys Gly Ile Val Ile Ala Gly Asp Ile Ser Val Ser Val Gly Ser Thr
        35                  40                  45

Glu Leu Leu Ser Ile Arg Ile Arg Leu Leu Ile Ala Ser Val Asp Lys
50                  55                  60

Ala Lys Glu Ile Gly Ile Asn Trp Trp Glu Ser Asp Pro Tyr Leu Ser
65                  70                  75                  80

Ser Gln Ala Gln Gln Leu Ser Gln Ser Asn Gln Leu Leu Glu Glu
                85                  90                  95

Val Lys Arg Leu Gln Glu Glu Val Arg Ser Leu Lys Ala Leu Thr Ser
            100                 105                 110

Gln Ser Ser Gln Pro Val Thr Pro Pro Asn Ser Glu Asn Asp Asp
        115                 120                 125

<210> SEQ ID NO 190
<211> LENGTH: 119
<212> TYPE: PRT
<213> ORGANISM: Bradyrhizobium oligotrophicum S58

<400> SEQUENCE: 190

Met Thr Phe Thr Val His Gln Pro Thr Gly Gly Asp Arg Leu Ala Asp
1               5                   10                  15

Ile Leu Glu Arg Val Leu Asp Lys Gly Ile Val Val Ala Gly Asp Val
            20                  25                  30

Thr Ile Ser Leu Val Gly Ile Glu Leu Leu Asn Ile Lys Ile Arg Leu
        35                  40                  45

Ile Val Ala Thr Val Asp Arg Ala Leu Glu Leu Gly Ile Asn Trp Trp
    50                  55                  60

Glu Ala Asp Pro Arg Leu Thr Thr Arg Ala Ser Glu Leu Ser Val Glu
65                  70                  75                  80

Asn Glu Glu Leu Lys Lys Arg Leu Ala Leu Leu Glu Ala Asp Ala Gly
                85                  90                  95

Arg Asn Gln Arg Pro Arg Lys Arg Arg Val Arg Ser Ile Ala Ala Thr
            100                 105                 110

Ser Gly Ala Ser His Glu Arg
        115

<210> SEQ ID NO 191
<211> LENGTH: 81
<212> TYPE: PRT
<213> ORGANISM: Bradyrhizobium oligotrophicum S58

<400> SEQUENCE: 191

Met Thr Tyr Arg Ala Asp Leu Asp Tyr Leu Pro Ala Ala Ser Ser
1               5                   10                  15

Glu Gly Ser Leu Leu Glu Leu Leu Asp His Leu Leu Asp Arg Gly Val
            20                  25                  30

Leu Leu Trp Gly Glu Leu Arg Ile Ser Val Ala Asp Val Glu Leu Ile
        35                  40                  45

Glu Val Gly Leu Lys Leu Met Leu Ala Ser Ala Arg Thr Ala Asp Arg
    50                  55                  60

Trp Arg Gln Thr Thr Thr Gln Arg Ala Ser Ile Ala Pro Gly Asp Cys

```
65                  70                  75                  80

Pro

<210> SEQ ID NO 192
<211> LENGTH: 74
<212> TYPE: PRT
<213> ORGANISM: Burkholderia thailandensis sp. Bp5365 strain MSMB43

<400> SEQUENCE: 192

Met Arg Ser Ala Asp Gly Glu Pro Val Ser Ala Glu Leu Ala Gln Arg
1               5                   10                  15

Leu Ser Leu Cys Glu Ser Leu Asp Arg Ile Leu Asn Lys Gly Ala Val
            20                  25                  30

Ile Ser Ala Gln Val Val Val Ser Val Ala Asp Val Asp Leu Leu Tyr
        35                  40                  45

Leu His Leu Arg Leu Leu Leu Thr Ser Val Glu Thr Ala Leu Val Gly
    50                  55                  60

Arg Ala Met Pro Arg Glu Glu Ala Ser Arg
65                  70

<210> SEQ ID NO 193
<211> LENGTH: 89
<212> TYPE: PRT
<213> ORGANISM: Burkholderia thailandensis sp. Bp5365 strain MSMB43

<400> SEQUENCE: 193

Met Ala Asp Leu Leu Glu Arg Val Leu Asp Lys Gly Val Val Ile Thr
1               5                   10                  15

Gly Asp Ile Arg Ile Asn Leu Val Asp Val Glu Leu Leu Thr Ile Arg
            20                  25                  30

Ile Arg Leu Leu Val Cys Ser Val Asp Lys Ala Lys Glu Leu Gly Ile
        35                  40                  45

Asp Trp Trp Asn Ala Asp Thr Phe Phe Leu Gly Pro Asp Arg Gly Gln
    50                  55                  60

Ser Ala Leu Pro Gly Arg Ala Ser Ala Val Asp Val Ala Ala Gly Ser
65                  70                  75                  80

Ala Val His Ala Asp Ala Ala His Arg
                85

<210> SEQ ID NO 194
<211> LENGTH: 97
<212> TYPE: PRT
<213> ORGANISM: Chlorobium luteolum DSM 273

<400> SEQUENCE: 194

Met Pro Glu Leu Lys His Ala Val Asn Ala Thr Gly Leu Ala Asp Ile
1               5                   10                  15

Leu Glu Arg Val Leu Asp Lys Gly Ile Val Ile Ala Gly Asp Ile Lys
            20                  25                  30

Ile Gln Ile Ala Asp Ile Asp Leu Leu Thr Ile Lys Ile Arg Leu Met
        35                  40                  45

Val Ala Ser Val Asp Lys Ala Ile Glu Met Gly Ile Asn Trp Trp Gln
    50                  55                  60

Glu Asp Pro Tyr Leu Ser Thr Gly Ala Lys Thr Ser Glu Gln Thr Arg
65                  70                  75                  80

Leu Leu Gly Glu Ile Asn Gln Arg Ile Glu Lys Leu Glu Ser Ile Asn
                85                  90                  95
```

Arg

<210> SEQ ID NO 195
<211> LENGTH: 69
<212> TYPE: PRT
<213> ORGANISM: Chlorobium luteolum DSM 273

<400> SEQUENCE: 195

Met Gln Glu Asp Leu Tyr Thr Ala Asn Arg Gln Val Thr Leu Leu Asp
1               5                   10                  15

Ile Leu Asp Arg Val Leu Asn Lys Gly Val Val Ile Ser Gly Asp Ile
            20                  25                  30

Ile Ile Ser Val Ala Gly Ile Asp Leu Val Tyr Val Gly Leu Arg Val
        35                  40                  45

Leu Leu Ser Ser Val Glu Thr Met Glu Arg Leu Asp Ala Ala Arg Ala
    50                  55                  60

Glu Gly Leu Gln Gln
65

<210> SEQ ID NO 196
<211> LENGTH: 68
<212> TYPE: PRT
<213> ORGANISM: Chlorobium luteolum DSM 273

<400> SEQUENCE: 196

Met Ala Val Glu Lys Thr Ile Gly Ser Ser Ser Leu Val Glu Val Ile
1               5                   10                  15

Asp Arg Ile Leu Asp Lys Gly Val Val Val Asp Ala Trp Val Arg Val
            20                  25                  30

Ser Leu Val Gly Ile Glu Leu Leu Ala Ile Glu Ala Arg Val Val Val
        35                  40                  45

Ala Ser Val Glu Thr Tyr Leu Lys Tyr Ala Glu Ala Ile Gly Leu Thr
    50                  55                  60

Ala Lys Ala Ala
65

<210> SEQ ID NO 197
<211> LENGTH: 68
<212> TYPE: PRT
<213> ORGANISM: Chlorobium luteolum DSM 273

<400> SEQUENCE: 197

Met Ala Val Glu Lys Thr Ile Gly Ser Ser Ser Leu Val Glu Val Ile
1               5                   10                  15

Asp Arg Ile Leu Asp Lys Gly Val Val Val Asp Ala Trp Val Arg Val
            20                  25                  30

Ser Leu Val Gly Ile Glu Leu Leu Ala Ile Glu Ala Arg Val Val Val
        35                  40                  45

Ala Ser Val Glu Thr Tyr Leu Lys Tyr Ala Glu Ala Ile Gly Leu Thr
    50                  55                  60

Ala Lys Ala Ala
65

<210> SEQ ID NO 198
<211> LENGTH: 130
<212> TYPE: PRT
<213> ORGANISM: Dactylococcopsis salina PCC 8305

<400> SEQUENCE: 198

Met Val Asn Ser Asn Thr Asn Gln Pro Lys Ser Tyr Gln Ser Lys Gly
1               5                   10                  15

Ile Thr Asn Ser Thr Gln Ser Ser Ser Leu Ala Asp Ile Leu Glu Arg
            20                  25                  30

Val Leu Asp Lys Gly Ile Val Ile Ala Gly Asp Ile Ser Val Ser Val
        35                  40                  45

Gly Ser Thr Glu Leu Leu Thr Ile Arg Ile Arg Leu Leu Ile Ser Ser
    50                  55                  60

Val Asp Arg Ala Arg Glu Ile Gly Ile Asn Trp Trp Glu Ser Asp Pro
65                  70                  75                  80

Tyr Leu Ser Ser Gln Ala His Leu Met Lys Glu Glu Asn Gln Ala Leu
                85                  90                  95

Gln Ser Arg Leu Glu Asn Met Glu Ala Glu Leu Arg Arg Leu Lys Gly
            100                 105                 110

Glu Thr Asn Leu Asp Gln Ser Ser Leu Gly Glu Ser Asp Gln Arg Ser
        115                 120                 125

Leu Gln
130

<210> SEQ ID NO 199
<211> LENGTH: 74
<212> TYPE: PRT
<213> ORGANISM: Desulfobacterium vacuolatum_DSM 3385

<400> SEQUENCE: 199

Met Ala Tyr Ile Asp Ile Asp Asn Asp Ala Ser Lys Gln Ile Ser Ile
1               5                   10                  15

Cys Glu Ala Leu Asp Arg Val Leu Asn Lys Gly Ala Val Ile Thr Gly
            20                  25                  30

Glu Leu Thr Ile Ser Val Ala Asp Ile Asp Leu Ile Tyr Leu Ser Leu
        35                  40                  45

Gln Ala Val Leu Thr Ser Val Glu Thr Ala Arg His Met Phe Asp Ser
    50                  55                  60

Gln Ile Asn Asp Ala Val Lys Glu Val Lys
65                  70

<210> SEQ ID NO 200
<211> LENGTH: 105
<212> TYPE: PRT
<213> ORGANISM: Desulfobacterium vacuolatum_DSM 3385

<400> SEQUENCE: 200

Met Pro Ile Gln Arg Thr Ala Gln His Ser Ile Glu Ser Thr Asn Ile
1               5                   10                  15

Ala Asp Leu Leu Glu Arg Val Leu Asp Lys Gly Ile Val Ile Ala Gly
            20                  25                  30

Asp Ile Lys Ile Ser Leu Val Asp Ile Glu Leu Leu Ser Ile Gln Leu
        35                  40                  45

Arg Leu Val Ile Cys Ser Val Asp Lys Ala Lys Glu Met Gly Met Asp
    50                  55                  60

Trp Trp Val Asn Asn Pro Val Phe Met Pro Asn Lys Gly Thr Gln Asn
65                  70                  75                  80

Asp Glu Ile Ala Asp Thr Leu Thr Lys Ile Asn Ser Arg Leu Glu His
                85                  90                  95

Leu Glu Lys Ala Thr Ile Ser Gly Ser
            100                 105

<210> SEQ ID NO 201
<211> LENGTH: 73
<212> TYPE: PRT
<213> ORGANISM: Desulfomonile tiedjei DSM 6799

<400> SEQUENCE: 201

Met Met Asp Glu Glu His Val Ser Leu Cys Glu Ala Leu Asp Arg
1               5                   10                  15

Val Leu Asn Lys Gly Ala Val Ile Ala Gly Glu Val Thr Ile Ser Val
        20                  25                  30

Ala Asn Val Asp Leu Ile Tyr Leu Gly Leu Gln Val Val Leu Ala Ser
            35                  40                  45

Val Asp Thr Ile Arg Gly Lys Arg Asn Glu Leu Leu Arg His Asp Val
    50                  55                  60

Gly Leu His Leu Thr Ala Asp Asn Ala
65                  70

<210> SEQ ID NO 202
<211> LENGTH: 81
<212> TYPE: PRT
<213> ORGANISM: Desulfomonile tiedjei DSM 6799

<400> SEQUENCE: 202

Met Ser Ile Gln Ala Ser Thr Arg His Ser Ile Gln Ser Thr Asn Leu
1               5                   10                  15

Ala Asp Leu Leu Glu Arg Val Leu Asp Lys Gly Val Val Ile Ala Gly
            20                  25                  30

Asp Ile Lys Ile Lys Leu Val Asp Val Glu Leu Leu Thr Ile Gln Ile
            35                  40                  45

Arg Leu Val Val Cys Ser Val Asp Lys Ala Lys Glu Met Gly Met Asp
    50                  55                  60

Trp Trp Thr Asn Asn Pro Ala Phe Gln Pro Ala Leu Ala Gln Ile Ser
65                  70                  75                  80

Glu

<210> SEQ ID NO 203
<211> LENGTH: 123
<212> TYPE: PRT
<213> ORGANISM: Desulfotomaculum acetoxidans_DSM 771

<400> SEQUENCE: 203

Met Gly Pro Gln Met Gly Pro Ile Lys Ser Thr Gly Asn Leu Ser Leu
1               5                   10                  15

Leu Asp Val Ile Asp Arg Ile Leu Asp Lys Gly Leu Val Ile Asn Ala
            20                  25                  30

Asp Ile Ser Val Ser Ile Val Gly Val Glu Leu Leu Gly Ile Lys Ile
            35                  40                  45

Lys Ala Ala Val Ala Ser Phe Glu Thr Ala Ala Lys Tyr Gly Leu Gln
    50                  55                  60

Phe Pro Thr Gly Thr Glu Ile Asn Glu Lys Val Ser Glu Ala Ala Lys
65                  70                  75                  80

Gln Leu Lys Glu Ile Cys Pro Cys Gly Lys Lys Ser Gly Arg Asp
            85                  90                  95

Glu Leu Leu His Glu Gly Cys Pro Trp Cys Gly Trp Ile Ser Ala Arg
            100                 105                 110

Ala Leu Arg Leu Glu Thr Glu His Ser Gln Arg
        115                 120

-continued

<210> SEQ ID NO 204
<211> LENGTH: 78
<212> TYPE: PRT
<213> ORGANISM: Desulfotomaculum acetoxidans_DSM 771

<400> SEQUENCE: 204

Met Leu Pro Ile Arg Glu Glu Arg Ala Thr Leu Thr Asp Leu Leu Asp
1               5                   10                  15

Arg Val Leu Asp Lys Gly Leu Leu Asn Ala Asp Ile Leu Ile Ser
            20                  25                  30

Val Ala Gly Val Pro Leu Ile Gly Ile Thr Leu Lys Ala Ala Ile Ala
        35                  40                  45

Gly Met Glu Thr Met Lys Lys Tyr Gly Leu Leu Ile Asp Trp Asp Gln
    50                  55                  60

Glu Ser Arg Leu Ala Glu Arg Arg Leu Arg Ser Ser Arg His
65                  70                  75

<210> SEQ ID NO 205
<211> LENGTH: 108
<212> TYPE: PRT
<213> ORGANISM: Enhydrobacter aerosaccus strain ATCC 27094

<400> SEQUENCE: 205

Met Ala Val Thr Asn Gly Arg Met Glu His Ser Ile Gln Gly Ser Ser
1               5                   10                  15

Leu Ala Asp Ile Leu Asp Arg Ile Leu Asp Lys Gly Ile Val Ile Ala
            20                  25                  30

Gly Asp Val Thr Ile Ser Leu Val Gly Val Glu Leu Leu Asn Ile Arg
        35                  40                  45

Leu Arg Leu Leu Val Ala Ser Val Asp Lys Ala Ile Glu Met Gly Ile
    50                  55                  60

Asn Trp Trp Glu Ala Asp Pro Tyr Leu Thr Ser Gln Thr Lys Ala Ser
65                  70                  75                  80

Ser Glu Gln Thr Glu Leu Leu Gln Gln Arg Leu Glu Arg Ile Glu Gly
                85                  90                  95

Leu Leu Ala Gly Gln Ala Thr Lys Glu Gln Pro Leu
            100                 105

<210> SEQ ID NO 206
<211> LENGTH: 74
<212> TYPE: PRT
<213> ORGANISM: Enhydrobacter aerosaccus strain ATCC 27094

<400> SEQUENCE: 206

Met Pro Val Gln Thr Ala His Asp Gly Glu Leu Ala Leu Ala Asp Leu
1               5                   10                  15

Leu Asp Arg Ala Leu Asn Lys Gly Val Val Leu Trp Gly Asp Ala Thr
            20                  25                  30

Ile Ser Leu Ala Gly Val Glu Leu Val Tyr Val Gly Leu Arg Val Leu
        35                  40                  45

Val Ala Ser Cys Ser Thr Met Glu Lys Tyr Arg Ser Ser Pro Arg Lys
    50                  55                  60

Gly Ser Met Pro Ile Ala Arg Gly Glu Ser
65                  70

<210> SEQ ID NO 207
<211> LENGTH: 98

```
<212> TYPE: PRT
<213> ORGANISM: Isosphaera pallida_ATCC-43644

<400> SEQUENCE: 207

Met Ile Val Cys Ser Ser Thr Pro Glu Arg Ile Gly Pro Pro Met
1               5                   10                  15

Asn Leu Pro Pro His His Ala Pro Trp Cys Tyr Asp Ser Pro Asp
            20                  25                  30

Leu Glu Thr Leu Pro Leu Asp Pro Ala Glu Arg Ile Ala Leu Cys Glu
        35                  40                  45

Val Leu Asp Arg Val Leu Asn Lys Gly Val Val Ile His Gly Glu Ile
50                  55                  60

Thr Ile Ser Val Ala Gly Val Asp Leu Val Tyr Leu Gly Leu Asn Leu
65                  70                  75                  80

Leu Leu Thr Ser Val Glu Thr Ala Gln Ser Trp Lys Phe Arg Gly Met
                85                  90                  95

Ile Glu

<210> SEQ ID NO 208
<211> LENGTH: 171
<212> TYPE: PRT
<213> ORGANISM: Isosphaera pallida_ATCC-43644

<400> SEQUENCE: 208

Met Ala Ile Thr Arg Ser Ser Arg Pro Asp Val Thr His Ser Thr Ser
1               5                   10                  15

Gly Ala Thr Leu Ala Asp Val Leu Glu Arg Val Leu Asp Lys Gly Leu
            20                  25                  30

Val Ile Ala Gly Asp Ile Lys Ile Lys Leu Val Asp Val Glu Leu Leu
        35                  40                  45

Thr Ile Gln Ile Arg Leu Val Val Ala Ser Val Asp Lys Ala Arg Glu
50                  55                  60

Met Gly Leu Asp Trp Trp Thr Arg Ser Pro Glu Leu Ser Leu Ala
65                  70                  75                  80

Ala Thr Thr Cys Pro Ala Leu Thr Pro Pro Lys Gln Glu Ala Thr Pro
                85                  90                  95

Pro Ala Thr Arg Ile Gln Ala Pro Thr Glu Ser Ala Gln Thr Thr Pro
            100                 105                 110

Asp Gln Ser His Pro Ser Asp Pro Ser Ala Ser Asn Ile Asp Glu Val
        115                 120                 125

Ala Glu Leu Arg Arg His Ile Glu Leu Met Gln Leu Arg Asp Glu Ala
    130                 135                 140

Arg Gln Arg Ala His Arg Glu Glu Leu Ala Ala Leu Arg Ala Gln Leu
145                 150                 155                 160

Thr Arg Leu Thr Glu Leu Leu Asp Ser Pro Arg
                165                 170

<210> SEQ ID NO 209
<211> LENGTH: 61
<212> TYPE: PRT
<213> ORGANISM: Legionella drancourtii LLAP12

<400> SEQUENCE: 209

Met Ile Ile Glu Asp Lys Pro Val Ser Leu Cys Glu Thr Leu Asp Arg
1               5                   10                  15

Val Leu Asn Lys Gly Val Val Val Ala Gly Thr Val Thr Ile Ser Val
            20                  25                  30
```

```
Ala Asp Val Asp Leu Leu Tyr Leu Asp Leu His Cys Leu Leu Ser Ser
            35                  40                  45

Met Lys Gly Met Asn Leu Ile Gly Ser Glu Arg Glu Arg
    50                  55                  60

<210> SEQ ID NO 210
<211> LENGTH: 106
<212> TYPE: PRT
<213> ORGANISM: Legionella drancourtii LLAP12

<400> SEQUENCE: 210

Met Glu Leu Gln Lys Ser Pro Thr His Ser Ile Gly Ser Thr Thr Ile
1               5                   10                  15

Ala Asp Leu Leu Glu Arg Ile Leu Asp Lys Gly Ile Val Ile Ala Gly
            20                  25                  30

Asp Ile Lys Val Asn Leu Val Gln Val Glu Leu Leu Thr Ile Gln Ile
            35                  40                  45

Arg Leu Leu Ile Cys Ser Val Asp Lys Ala Lys Glu Ile Gly Met Asp
    50                  55                  60

Trp Trp Thr His Gln Asn Asp Val Gln Ser Lys Asn Gly Ser Met Pro
65                  70                  75                  80

Ile Gln Glu Tyr Val Thr Gln Met Glu Glu Arg Leu Lys Asn Leu Glu
                85                  90                  95

Asn Thr Leu Ala Ser Ser Lys Asn Ala Ile
            100                 105

<210> SEQ ID NO 211
<211> LENGTH: 114
<212> TYPE: PRT
<213> ORGANISM: Lyngbya confervoides BDU141951

<400> SEQUENCE: 211

Met Thr Gly Gln Ser Leu Ser Arg Ser Ser Ala Asn Arg Gln Met
1               5                   10                  15

Ala Thr Ala Thr Gln Gly Ser Thr Leu Val Asp Val Leu Glu Arg Val
            20                  25                  30

Leu Asp Lys Gly Ile Val Ile Ala Gly Asp Ile Ser Val Ser Val Gly
            35                  40                  45

Ser Thr Glu Leu Leu Thr Ile Arg Ile Arg Leu Leu Val Ala Ser Val
    50                  55                  60

Asp Lys Ala Arg Glu Met Gly Ile Asn Trp Trp Glu Asn Asp Pro Tyr
65                  70                  75                  80

Leu Ser Ala Arg Ser Gln Glu Leu Leu Thr Ala Asn Glu Gln Leu Gln
                85                  90                  95

Ser Arg Ile Glu Ser Leu Glu Gln Glu Leu Lys Ser Leu Arg Ser Gln
            100                 105                 110

Glu Asp

<210> SEQ ID NO 212
<211> LENGTH: 136
<212> TYPE: PRT
<213> ORGANISM: Microcystis aeruginosa NIES-843

<400> SEQUENCE: 212

Met Thr Ser Ser Thr Phe Ala Gly Ser Leu Arg Asn Gln Ser Asn Asn
1               5                   10                  15

Ser Leu Lys Thr Ala Thr Gln Gly Ser Ser Leu Ala Asp Ile Leu Glu
```

```
                 20                  25                  30

Arg Val Leu Asp Lys Gly Ile Val Ile Ala Gly Asp Ile Ser Val Ser
             35                  40                  45

Ile Ala Ser Thr Glu Leu Ile Asn Ile Arg Ile Arg Leu Leu Ile Ala
         50                  55                  60

Ser Val Asp Lys Ala Arg Glu Met Gly Ile Asn Trp Trp Glu Gly Asp
 65                  70                  75                  80

Pro Tyr Leu His Ser Gln Ser Gln Ala Leu Leu Ala Glu Asn Arg Glu
                 85                  90                  95

Leu Ser Leu Arg Leu Gln Thr Leu Glu Thr Glu Leu Glu Thr Leu Lys
            100                 105                 110

Ser Leu Thr Gln Leu Ser Ala Met Glu Ser His Asp Thr Ser Pro Asn
        115                 120                 125

Asp Glu Ala His Ser Ser Asp Ala
    130                 135

<210> SEQ ID NO 213
<211> LENGTH: 116
<212> TYPE: PRT
<213> ORGANISM: Nostoc punctiforme ATCC 29133

<400> SEQUENCE: 213

Met Ser Thr Asn Thr Asn Arg Gly Ala Ile Thr Thr Ser Thr Gln Gly
 1               5                  10                  15

Ser Thr Leu Ala Asp Ile Leu Glu Arg Val Leu Asp Lys Gly Ile Val
                20                  25                  30

Ile Ala Gly Asp Ile Ser Ile Ser Val Gly Ser Thr Glu Leu Leu Asn
             35                  40                  45

Ile Arg Ile Arg Leu Leu Ile Ser Ser Val Asp Lys Ala Lys Glu Ile
         50                  55                  60

Gly Ile Asn Trp Trp Glu Ser Asp Pro Tyr Leu Asn Ser Gln Thr Arg
 65                  70                  75                  80

Thr Leu Leu Ala Thr Asn Gln Gln Leu Gln Glu Arg Leu Ala Ser Leu
                 85                  90                  95

Glu Thr Glu Leu Gln Ser Leu Lys Ala Leu Asn Pro Ile Asn His Gln
            100                 105                 110

Asn Ala Gly Asp
        115

<210> SEQ ID NO 214
<211> LENGTH: 148
<212> TYPE: PRT
<213> ORGANISM: Nostoc sp. PCC 7120

<400> SEQUENCE: 214

Met Thr Thr Thr Pro Ile His Pro Thr Arg Pro Gln Thr Asn Ser Asn
 1               5                  10                  15

Arg Val Ile Pro Thr Ser Thr Gln Gly Ser Thr Leu Ala Asp Ile Leu
                20                  25                  30

Glu Arg Val Leu Asp Lys Gly Ile Val Ile Ala Gly Asp Ile Ser Ile
             35                  40                  45

Ser Ile Ala Ser Thr Glu Leu Ile His Ile Arg Ile Arg Leu Leu Ile
         50                  55                  60

Ser Ser Val Asp Lys Ala Arg Glu Met Gly Ile Asn Trp Trp Glu Asn
 65                  70                  75                  80

Asp Pro Tyr Leu Ser Ser Lys Ser Gln Arg Leu Val Glu Glu Asn Gln
```

```
            85                  90                  95
Gln Leu Gln Gln Arg Leu Glu Ser Leu Glu Thr Gln Leu Arg Leu Leu
            100                 105                 110

Thr Ser Ala Ala Lys Glu Glu Thr Thr Leu Thr Ala Asn Asn Pro Glu
            115                 120                 125

Asp Leu Gln Pro Met Tyr Glu Val Asn Ser Gln Glu Gly Asp Asn Ser
130                 135                 140

Gln Leu Glu Ala
145

<210> SEQ ID NO 215
<211> LENGTH: 112
<212> TYPE: PRT
<213> ORGANISM: Octadecabacter antarcticus 307

<400> SEQUENCE: 215

Met Asn Asp Gly Lys Met Glu His Ser Leu Asn Ala Thr Asn Leu Ala
1               5                   10                  15

Asp Ile Leu Glu Arg Val Leu Asp Lys Gly Ile Val Ile Ala Gly Asp
            20                  25                  30

Val Thr Ile Ser Leu Val Gly Val Glu Leu Leu Asn Ile Lys Leu Arg
        35                  40                  45

Leu Leu Ile Ala Ser Val Asp Lys Ala Met Glu Met Gly Ile Asn Trp
    50                  55                  60

Trp Ala His Asp Pro Phe Leu Thr Ala Gly Ala Gln Ala Pro Ala Val
65                  70                  75                  80

Ala Asp Pro Ala Met Leu Glu Arg Met Asp Arg Leu Glu Ala Ala Leu
                85                  90                  95

Ala Thr Ala Leu Ala Ser Asn Gln Thr Thr Pro Met Lys Gly His Lys
            100                 105                 110

<210> SEQ ID NO 216
<211> LENGTH: 74
<212> TYPE: PRT
<213> ORGANISM: Octadecabacter antarcticus 307

<400> SEQUENCE: 216

Met Thr Asn Lys Ala Gln Gly Gly Gln Asp Leu Ala Leu Ala Asp Leu
1               5                   10                  15

Leu Asp Arg Ala Leu Ser Thr Gly Val Val Ile Trp Gly Glu Ala Thr
            20                  25                  30

Ile Ser Leu Ala Gly Val Asp Leu Val Tyr Val Gly Leu Lys Val Leu
        35                  40                  45

Val Ala Ser Val Asp Ala Ala Glu Arg Met Lys Ala Ala Ser Leu Val
    50                  55                  60

Asp Arg Pro Thr Asp Arg Gly Gln Gln Ile
65                  70

<210> SEQ ID NO 217
<211> LENGTH: 113
<212> TYPE: PRT
<213> ORGANISM: Octadecabacter arcticus 238

<400> SEQUENCE: 217

Met Asn Asn Gly Lys Met Glu His Ser Leu Asp Ala Thr Asn Leu Ala
1               5                   10                  15

Asp Ile Leu Glu Arg Val Leu Asp Lys Gly Ile Val Ile Ala Gly Asp
            20                  25                  30
```

Val Thr Ile Ser Leu Val Gly Val Glu Leu Leu Asn Ile Lys Leu Arg
         35                  40                  45

Leu Leu Ile Ala Ser Val Asp Lys Ala Met Glu Met Gly Ile Asn Trp
 50                  55                  60

Trp Ala His Asp Pro Tyr Leu Thr Ala Gly Ala Gln Ala Pro Val Gly
 65                  70                  75                  80

Val Asp Pro Ala Met Leu Glu Arg Met Asp Arg Leu Glu Ala Ala Leu
                 85                  90                  95

Ala Lys Ala Leu Ala Ser Asn Gln Thr Thr Pro Ala Glu Gly Gln Ser
             100                 105                 110

Ser

<210> SEQ ID NO 218
<211> LENGTH: 72
<212> TYPE: PRT
<213> ORGANISM: Octadecabacter arcticus 238

<400> SEQUENCE: 218

Met Thr Asn Glu Thr Gln Gly Gly Gln Asp Leu Ala Leu Ala Asp Leu
 1               5                  10                  15

Leu Asp Arg Ala Leu Ser Thr Gly Val Val Ile Trp Gly Glu Ala Thr
                 20                  25                  30

Ile Ser Leu Ala Gly Val Asp Leu Val Tyr Val Gly Leu Lys Val Leu
             35                  40                  45

Val Ala Ser Val Asp Ala Ala Gln Arg Met Lys Asp Ala Ser Leu Val
 50                  55                  60

Asp Arg Pro Thr Asp Gly Gly Gln
 65                  70

<210> SEQ ID NO 219
<211> LENGTH: 99
<212> TYPE: PRT
<213> ORGANISM: Pelodictyon phaeoclathratiforme

<400> SEQUENCE: 219

Met Pro Glu Leu Lys His Ala Val Asn Ala Thr Gly Leu Ala Asp Ile
 1               5                  10                  15

Leu Glu Arg Val Leu Asp Lys Gly Ile Val Ile Ala Gly Asp Ile Lys
                 20                  25                  30

Ile Gln Ile Ala Asp Ile Asp Leu Leu Thr Ile Lys Ile Arg Leu Leu
             35                  40                  45

Ile Ala Ser Val Asp Lys Ala Met Glu Met Gly Ile Asn Trp Trp Gln
 50                  55                  60

Glu Asp Thr Tyr Leu Ser Thr Lys Ala Lys Asp Lys Glu Gln Gln Leu
 65                  70                  75                  80

Leu Arg Asp Asp Leu Gln Gln Arg Ile Glu Lys Leu Glu Ala Leu Thr
                 85                  90                  95

Lys Ile Thr

<210> SEQ ID NO 220
<211> LENGTH: 66
<212> TYPE: PRT
<213> ORGANISM: Pelodictyon phaeoclathratiforme

<400> SEQUENCE: 220

Met Gln Asp Glu Phe Tyr Ser Lys Asn Lys Glu Ile Thr Ile Leu Asp
 1               5                  10                  15

Val Leu Asp Arg Val Leu Thr Lys Gly Val Ile Thr Gly Asp Ile
            20                  25                  30

Val Ile Ser Val Ala Asp Ile Asp Leu Val Tyr Val Gly Leu Arg Leu
            35                  40                  45

Leu Leu Ser Ser Val Glu Thr Met Glu Lys Asn Lys Gln Asn Ser Ile
50                      55                  60

Lys Met
65

<210> SEQ ID NO 221
<211> LENGTH: 101
<212> TYPE: PRT
<213> ORGANISM: Phormidium tenue NIES-30

<400> SEQUENCE: 221

Met Ala Thr Ala Thr Gln Gly Ser Ser Leu Val Asp Val Ile Glu Arg
1               5                   10                  15

Val Leu Asp Lys Gly Ile Val Ile Ala Gly Asp Ile Ser Val Ser Val
            20                  25                  30

Gly Ser Thr Glu Leu Leu Ser Ile Arg Ile Arg Leu Ile Ile Ser Ser
            35                  40                  45

Val Asp Lys Ala Arg Glu Ile Gly Ile Asn Trp Trp Glu Ser Asp Pro
50                      55                  60

Tyr Leu Ser Ser Arg Thr Asn Glu Leu Leu Glu Ala Asn Gln Gln Leu
65                  70                  75                  80

Gln Ser Arg Leu Glu Thr Leu Gly Ala Glu Leu Lys Ala Leu Arg Ser
                85                  90                  95

Ala Glu Pro Val Ser
            100

<210> SEQ ID NO 222
<211> LENGTH: 125
<212> TYPE: PRT
<213> ORGANISM: Planktothrix agardhii str. 7805

<400> SEQUENCE: 222

Met Asn Ser Gln Gln Leu Pro Ser Asn Ile Gln Arg Gly Val Pro Thr
1               5                   10                  15

Ser Thr Gln Gly Ser Ser Leu Ala Asp Ile Leu Glu Arg Val Leu Asp
            20                  25                  30

Lys Gly Ile Val Ile Ala Gly Asp Ile Ser Val Ser Val Gly Ser Thr
            35                  40                  45

Glu Leu Leu Asn Ile Arg Ile Arg Leu Leu Ile Ala Ser Val Asp Lys
50                      55                  60

Ala Arg Glu Ile Gly Ile Asn Trp Trp Glu Ser Asp Pro Tyr Leu Ser
65                  70                  75                  80

Ser Gln Thr Lys Val Leu Thr Glu Ser Asn Gln Gln Leu Leu Glu Gln
                85                  90                  95

Val Lys Phe Leu Gln Glu Glu Val Lys Ala Leu Lys Ala Leu Leu Pro
                100                 105                 110

Gln Glu Asn Gln Pro Asn Pro Ile Ser Asp Pro His Lys
            115                 120                 125

<210> SEQ ID NO 223
<211> LENGTH: 121
<212> TYPE: PRT
<213> ORGANISM: Planktothrix rubescens

<400> SEQUENCE: 223

```
Met Asn Ser Gln Gln Arg Pro Ser Asn Ile Gln Arg Gly Val Pro Thr
1               5                   10                  15

Ser Thr Gln Gly Ser Ser Leu Ala Asp Ile Leu Glu Arg Val Leu Asp
            20                  25                  30

Lys Gly Ile Val Ile Ala Gly Asp Ile Ser Val Ser Val Gly Ser Thr
        35                  40                  45

Glu Leu Leu Asn Ile Arg Ile Arg Leu Leu Ile Ala Ser Val Asp Lys
50                  55                  60

Ala Arg Glu Ile Gly Ile Asn Trp Trp Glu Ser Asp Pro Tyr Leu Ser
65                  70                  75                  80

Ser Gln Thr Lys Val Leu Thr Glu Ser Asn Gln Glu Leu Leu Glu Gln
                85                  90                  95

Val Lys Leu Leu Gln Glu Val Lys Ala Leu Lys Ala Leu Leu Pro
            100                 105                 110

Gln Glu Asn Gln Pro Lys Glu Met Glu
            115                 120
```

<210> SEQ ID NO 224
<211> LENGTH: 72
<212> TYPE: PRT
<213> ORGANISM: Psychromonas ingrahamii 37

<400> SEQUENCE: 224

```
Met Ala Asn Val Gln Lys Ser Thr Asp Ser Ser Gly Leu Ala Glu Val
1               5                   10                  15

Val Asp Arg Ile Leu Glu Lys Gly Ile Val Ile Asp Ala Phe Val Lys
            20                  25                  30

Val Ser Leu Val Gly Ile Glu Leu Leu Ser Ile Glu Ala Arg Val Val
        35                  40                  45

Ile Ala Ser Val Glu Thr Tyr Leu Lys Tyr Ala Glu Ala Ile Gly Leu
50                  55                  60

Thr Ala Ser Ala Ala Thr Pro Ala
65                  70
```

<210> SEQ ID NO 225
<211> LENGTH: 74
<212> TYPE: PRT
<213> ORGANISM: Psychromonas ingrahamii 37

<400> SEQUENCE: 225

```
Met Pro Met Ala Asn Val Ser Ile Asn Pro Glu Leu Thr Ala Gln Glu
1               5                   10                  15

Cys Glu Lys Ile Ser Leu Cys Asp Ala Leu Asp Arg Ile Ile Asn Lys
            20                  25                  30

Gly Val Val Ile His Gly Glu Ile Thr Ile Ser Val Ala Asn Val Asp
        35                  40                  45

Leu Ile Ser Leu Gly Val Arg Leu Ile Leu Ser Asn Val Glu Thr Arg
50                  55                  60

Glu Gln Ser Asn Thr Pro Lys Glu Glu Val
65                  70
```

<210> SEQ ID NO 226
<211> LENGTH: 101
<212> TYPE: PRT
<213> ORGANISM: Psychromonas ingrahamii 37

<400> SEQUENCE: 226

Met Ala Thr Gly Lys Pro Gln Ser Met Thr His Ser Val Lys Ser Thr
1               5                   10                  15

Thr Val Ala Asp Leu Leu Glu Arg Ile Leu Asp Lys Gly Ile Val Val
            20                  25                  30

Thr Gly Asp Ile Lys Ile Lys Leu Val Asp Val Glu Leu Leu Thr Val
        35                  40                  45

Glu Leu Arg Leu Val Ile Cys Ser Val Asp Lys Ala Val Glu Met Gly
    50                  55                  60

Met Asp Trp Trp Asn Asn Asn Pro Ala Phe Ala Pro Gln Ala Pro Ala
65              70                  75                  80

Gln Glu Gly Glu Leu Ser Ser Ile Glu Lys Arg Leu Glu Lys Ile Glu
                85                  90                  95

Lys Ala Leu Val Lys
            100

<210> SEQ ID NO 227
<211> LENGTH: 151
<212> TYPE: PRT
<213> ORGANISM: Rhodobacter capsulatus SB 1003

<400> SEQUENCE: 227

Met Gly Tyr Arg Ser Ala Ser Gln Pro Glu Gly Leu Ala Asp Val Leu
1               5                   10                  15

Glu Arg Ile Leu Asp Lys Gly Ile Val Ile Ala Gly Asp Val Ser Val
            20                  25                  30

Ser Leu Val Gly Ile Glu Leu Leu Thr Ile Arg Leu Arg Leu Leu Ile
        35                  40                  45

Ala Thr Val Asp Lys Ala Arg Glu Met Gly Ile Asp Trp Trp Ser His
    50                  55                  60

Asp Pro Tyr Leu Asn Gly Arg Leu Arg Pro Gly Glu Pro Ala Pro Glu
65              70                  75                  80

Thr Glu Thr Glu Thr Ala Ala Leu Arg Asp Arg Leu Ala Gln Leu Glu
                85                  90                  95

Ala Gln Leu Ser Ala Leu Gly Ala Gln Val Gly Ala Ala Pro Ala Leu
            100                 105                 110

Ala Glu Pro Ala Leu Arg Gly Leu Ala Ala Gly Ser Ser Ala Leu
        115                 120                 125

Cys Ala Ala Pro Glu Ala Ser Ser Ala Asp Val Val Gln Pro Val Phe
    130                 135                 140

Arg Arg Tyr Lys Glu Ala Pro
145                 150

<210> SEQ ID NO 228
<211> LENGTH: 69
<212> TYPE: PRT
<213> ORGANISM: Rhodobacter capsulatus SB 1003

<400> SEQUENCE: 228

Met Asp Asp Arg Phe Ser Leu Arg Leu Phe Gly Pro Glu Glu Val Phe
1               5                   10                  15

Asp Ala Pro Ser Gly Gly Leu Ala Asp Leu Leu Asp Gly Leu Leu Gly
            20                  25                  30

His Gly Ile Val Leu His Gly Asp Leu Trp Leu Thr Val Ala Asp Val
        35                  40                  45

Glu Leu Val Tyr Val Gly Leu Ser Ala Val Leu Ala Ser Pro Glu Ala

```
                50                  55                  60
Leu Arg Ser His Glu
 65

<210> SEQ ID NO 229
<211> LENGTH: 104
<212> TYPE: PRT
<213> ORGANISM: Rhodobacter sphaeroides 2.4.1

<400> SEQUENCE: 229

Met Ser Phe Gln Met Gln Ser Pro Leu Gln Asp Ser Leu Ala Asp
  1               5                  10                  15

Val Leu Glu Arg Ile Leu Asp Lys Gly Ile Val Ile Ala Gly Asp Ile
                 20                  25                  30

Ser Ile Ser Leu Val Gly Ile Glu Leu Leu Thr Ile Arg Leu Arg Leu
             35                  40                  45

Leu Val Ala Thr Val Asp Lys Ala Arg Glu Met Gly Ile Asn Trp Trp
         50                  55                  60

Glu Ser Asp Pro Arg Leu Cys Ile Thr Gln Ala Pro Ala Ser Asp Gly
 65                  70                  75                  80

Ser Ala Ala Leu Leu Asp Arg Leu Glu Arg Ile Glu Thr Gln Ile Gly
                 85                  90                  95

Gln Leu Ala Ala Ala Arg Glu Gly
            100

<210> SEQ ID NO 230
<211> LENGTH: 74
<212> TYPE: PRT
<213> ORGANISM: Rhodobacter sphaeroides 2.4.1

<400> SEQUENCE: 230

Met Thr Asp Ser Ala Pro Thr Leu Gln Phe Ala Thr Ala Glu Glu Ala
  1               5                  10                  15

Leu Gln Ser Ser Glu Thr Arg Leu Val Asp Val Val Asp Ala Leu Leu
                 20                  25                  30

Ser Gln Gly Ile Ala Ile Arg Gly Glu Leu Trp Leu Thr Ile Ala Asp
             35                  40                  45

Val Asp Leu Val Phe Leu Gly Leu Asp Leu Leu Leu Ala Asn Pro Asp
         50                  55                  60

Arg Leu Gln Cys Arg Val Pro Asp Ala Ala
 65                  70

<210> SEQ ID NO 231
<211> LENGTH: 137
<212> TYPE: PRT
<213> ORGANISM: Rhodococcus hoagii 103S

<400> SEQUENCE: 231

Met Thr Arg Ser Gly Ser Gly Ala Asn Tyr Pro Gln Gln Tyr Ser Gln
  1               5                  10                  15

Gly Leu Gly Gly Ala Gly His Glu Pro Ala Asn Leu Gly Asp Ile Leu
                 20                  25                  30

Glu Arg Val Leu Asp Lys Gly Ile Val Ile Ala Gly Asp Ile Arg Val
             35                  40                  45

Asn Leu Leu Asp Ile Glu Leu Leu Thr Ile Lys Leu Arg Leu Val Ile
         50                  55                  60

Ala Ser Leu Glu Thr Ala Arg Glu Val Gly Ile Asp Trp Trp Glu His
 65                  70                  75                  80
```

```
Asp Pro Trp Leu Ser Gly Asn Asn Arg Asp Leu Glu Leu Glu Asn Glu
                 85                  90                  95

Arg Leu Arg Ala Arg Ile Glu Ala Leu Glu Ser Gly Glu Arg Arg Val
            100                 105                 110

Ala Asp Val Thr Asp Pro His Arg Ala Val Gln Pro Ala Glu Ser Pro
        115                 120                 125

Ala Ala Glu Val Arg Asp Asp Ala
    130                 135

<210> SEQ ID NO 232
<211> LENGTH: 65
<212> TYPE: PRT
<213> ORGANISM: Serratia sp. ATCC 39006

<400> SEQUENCE: 232

Met Pro Val Asn Lys Gln Tyr Gln Asp Glu Gln Gln Gln Val Ser Leu
1               5                   10                  15

Cys Glu Ala Leu Asp Arg Val Leu Asn Lys Gly Val Val Ile Val Ala
            20                  25                  30

Asp Ile Thr Ile Ser Val Ala Asn Ile Asp Leu Ile Tyr Leu Ser Leu
        35                  40                  45

Gln Ala Leu Val Ser Ser Val Glu Ala Lys Asn Arg Leu Pro Gly Arg
    50                  55                  60

Glu
65

<210> SEQ ID NO 233
<211> LENGTH: 110
<212> TYPE: PRT
<213> ORGANISM: Serratia sp. ATCC 39006

<400> SEQUENCE: 233

Met Ser Gly Asn Lys Lys Leu Thr His Ser Thr Asp Ser Thr Thr Val
1               5                   10                  15

Ala Asp Leu Leu Glu Arg Leu Leu Asp Lys Gly Val Val Ile Ser Gly
            20                  25                  30

Asp Ile Arg Ile Arg Leu Val Glu Val Glu Leu Leu Thr Leu Glu Ile
        35                  40                  45

Arg Leu Leu Ile Cys Ser Val Asp Lys Ala Val Glu Met Gly Leu Asp
    50                  55                  60

Trp Trp Ser Gly Asn Pro Ala Phe Asp Ser Arg Ala Arg Val Ser Ser
65                  70                  75                  80

Ser Ala Pro Ala Pro Glu Leu Glu Glu Arg Leu Gln Arg Leu Glu Ala
                85                  90                  95

Arg Leu Glu Ala Ala Pro Ser Val Ile Glu Glu Thr His Leu
            100                 105                 110

<210> SEQ ID NO 234
<211> LENGTH: 123
<212> TYPE: PRT
<213> ORGANISM: Stella vacuolata_ATCC-43931

<400> SEQUENCE: 234

Met Ser Gly Gln Arg Met Glu His Ser Val Gln Ala Val Gly Leu Ala
1               5                   10                  15

Asp Ile Leu Glu Arg Val Leu Asp Lys Gly Ile Val Ile Ala Gly Asp
            20                  25                  30
```

-continued

```
Ile Ser Ile Ser Leu Val Glu Val Glu Leu Leu Thr Ile Arg Leu Arg
            35                  40                  45

Leu Val Val Ala Ser Val Asp Arg Ala Met Ser Met Gly Ile Asn Trp
 50                  55                  60

Trp Gln Ser Asp Pro Asn Leu Asn Ser His Ala Arg Gln Leu Glu Glu
 65                  70                  75                  80

Asp Asn Arg Leu Leu Arg Glu Arg Leu Asp Arg Leu Glu Ala Ala Leu
                85                  90                  95

Ala Leu Pro Glu Met Ala Gly Glu Arg Leu Ala Asp Ala Gly Gln Gly
            100                 105                 110

Gly Gly Ala Glu Gln Gly Val Thr His Gly Arg
        115                 120

<210> SEQ ID NO 235
<211> LENGTH: 78
<212> TYPE: PRT
<213> ORGANISM: Stella vacuolata_ATCC-43931

<400> SEQUENCE: 235

Met Ser Asp Pro Glu Pro Ile Ile Pro Arg Thr Ser Gly Asp Ile Ala
 1               5                  10                  15

Leu Ala Asp Leu Leu Asp Arg Ala Leu His Lys Gly Leu Val Leu Trp
                20                  25                  30

Gly Glu Ala Thr Ile Ser Val Ala Gly Val Asp Leu Val Tyr Leu Gly
            35                  40                  45

Leu Lys Val Leu Val Ala Ser Thr Glu Thr Ala Asp Arg Met Arg Ala
 50                  55                  60

Ala Ala Ala Ser Gln Ser Ala Asp Pro Lys Val Arg Ala Gly
 65                  70                  75

<210> SEQ ID NO 236
<211> LENGTH: 71
<212> TYPE: PRT
<213> ORGANISM: Thiocapsa rosea strain DSM 235 Ga0242571_11

<400> SEQUENCE: 236

Met Met Leu Ala Ile Gly Glu His Pro Asp Cys Pro Glu Glu Ile Gln
 1               5                  10                  15

Arg Val Ser Leu Cys Glu Ala Leu Asp Arg Ile Leu Asn Lys Gly Ala
                20                  25                  30

Val Val Ser Gly Glu Leu Thr Ile Ala Val Ala Asn Val Asp Leu Leu
            35                  40                  45

Tyr Leu Ser Leu Gln Leu Val Ile Thr Ser Val Glu Thr Ala Lys Arg
 50                  55                  60

Glu Met Leu Tyr Val Arg His
 65                  70

<210> SEQ ID NO 237
<211> LENGTH: 116
<212> TYPE: PRT
<213> ORGANISM: Thiocapsa rosea strain DSM 235 Ga0242571_11

<400> SEQUENCE: 237

Met Ser Val Gln Arg Ser Thr Leu Thr His Ser Thr Asn Ser Thr Ser
 1               5                  10                  15

Val Ala Asp Leu Leu Glu Arg Val Leu Asp Lys Gly Ile Val Ile Ala
                20                  25                  30

Gly Asp Ile Arg Ile Lys Leu Val Asp Ile Glu Leu Leu Thr Ile Gln
```

```
                35                  40                  45
Leu Arg Leu Val Ile Cys Ser Val Asp Lys Ala Arg Glu Met Gly Ile
 50                  55                  60

Asp Trp Trp Ser Asp Asn Ala Met Phe Lys Gly Leu Ser Ser Gln Ala
 65                  70                  75                  80

Ser Ala Ala Ser Leu Pro Gly Thr Ala Ala Ser Gly Ile Glu Asp
                 85                  90                  95

Arg Leu Ala Arg Leu Glu Ser Leu Val Lys Gln Ser Ala Ala Ala
                100                 105                 110

Glu Thr Val Leu
        115

<210> SEQ ID NO 238
<211> LENGTH: 121
<212> TYPE: PRT
<213> ORGANISM: Tolypothrix sp. PCC 7601

<400> SEQUENCE: 238

Met Ala Asp Ile Leu Glu Arg Val Leu Asp Lys Gly Ile Val Ile Ala
 1               5                  10                  15

Gly Asp Ile Ser Val Ser Ile Ala Ser Thr Glu Leu Leu His Ile Arg
                20                  25                  30

Ile Arg Leu Leu Ile Ser Ser Val Asp Lys Ala Lys Glu Leu Gly Ile
                35                  40                  45

Asn Trp Trp Glu Asn Asp Pro Tyr Leu Ser Ser Lys Ser Gln Arg Leu
 50                  55                  60

Val Glu Glu Asn Gln Gln Leu Gln Gln Arg Leu Glu Ser Leu Glu Ala
 65                  70                  75                  80

Gln Leu Arg Ser Leu Thr Ala Ala Lys Ile Asn Asn Pro Glu Leu Phe
                 85                  90                  95

Pro Val Asn Ala Glu Asp Asn Gly Gln Ser Asp Glu Glu Asn Val Pro
                100                 105                 110

Leu Pro Met Asn Tyr Gln Pro Asn Asp
                115                 120

<210> SEQ ID NO 239
<211> LENGTH: 54
<212> TYPE: PRT
<213> ORGANISM: Trichodesmium erythraeum IMS101

<400> SEQUENCE: 239

Met Phe Ile Arg Val Asp Phe Leu Leu Asp Lys Gly Val Ile Val Asp
 1               5                  10                  15

Ala Trp Val Arg Leu Ser Leu Val Val Ile Glu Leu Leu Thr Ile Glu
                20                  25                  30

Ala Lys Ile Val Ile Ala Ser Val Glu Ala Tyr Leu Lys Tyr Ser Glu
                35                  40                  45

Ala Phe Cys Phe Asn Tyr
        50

<210> SEQ ID NO 240
<211> LENGTH: 75
<212> TYPE: PRT
<213> ORGANISM: Trichodesmium erythraeum IMS101

<400> SEQUENCE: 240

Met Ala Val Glu Lys Val Asn Ser Ser Ser Ser Leu Ala Glu Val Ile
 1               5                  10                  15
```

```
Asp Arg Ile Leu Asp Lys Gly Val Val Asp Ala Trp Ile Arg Leu
            20                  25                  30

Ser Leu Val Gly Ile Glu Leu Leu Thr Ile Glu Ala Arg Ile Val Val
        35                  40                  45

Ala Ser Val Glu Thr Tyr Leu Lys Tyr Ala Gly Ala Val Gly Leu Thr
 50                  55                  60

Thr Leu Ala Ala Ala Pro Gly Glu Ala Ala Ala
 65                  70                  75

<210> SEQ ID NO 241
<211> LENGTH: 72
<212> TYPE: PRT
<213> ORGANISM: Trichodesmium erythraeum IMS101

<400> SEQUENCE: 241

Met Ala Val Glu Lys Val Asn Ser Ser Ser Leu Ala Glu Val Ile
 1               5                  10                  15

Asp Arg Ile Leu Asp Lys Gly Val Val Asp Ala Trp Val Arg Leu
            20                  25                  30

Ser Leu Val Gly Ile Glu Leu Leu Thr Ile Glu Ala Arg Ile Val Ile
        35                  40                  45

Ala Ser Val Glu Thr Tyr Leu Lys Tyr Ala Gly Ala Val Gly Leu Thr
 50                  55                  60

Thr Leu Ala Ala Glu Pro Ala Ala
 65                  70

<210> SEQ ID NO 242
<211> LENGTH: 103
<212> TYPE: PRT
<213> ORGANISM: Trichodesmium erythraeum IMS101

<400> SEQUENCE: 242

Met Lys Thr Ser Ala Asn Ile Ala Thr Ser Ala Ser Gly Asn Gly Leu
 1               5                  10                  15

Ala Asp Val Leu Glu Arg Val Leu Asp Lys Gly Val Val Ile Ala Gly
                20                  25                  30

Asp Ile Ser Val Ser Ile Ala Ser Thr Glu Leu Leu Asn Ile Lys Ile
            35                  40                  45

Arg Leu Leu Ile Ser Ser Val Glu Arg Ala Lys Glu Ile Gly Ile Asn
 50                  55                  60

Trp Trp Glu Ser Asp Pro Tyr Phe Ser Ser Gln Asn Asn Ser Leu Val
 65                  70                  75                  80

Gln Ala Asn Glu Lys Leu Leu Glu Arg Val Ala Ser Leu Glu Ser Glu
                85                  90                  95

Ile Lys Ala Leu Arg Ser Asn
            100

<210> SEQ ID NO 243
<211> LENGTH: 104
<212> TYPE: PRT
<213> ORGANISM: Trichodesmium erythraeum IMS101

<400> SEQUENCE: 243

Met Lys Thr Ser Ala Asn Ile Ala Lys Ser Ala Gly Gly Asp Ser Leu
 1               5                  10                  15

Ala Asp Val Leu Glu Arg Val Leu Asp Lys Gly Ile Val Ile Ala Gly
                20                  25                  30
```

```
Asp Ile Ser Val Ser Ile Ala Ser Thr Glu Leu Leu Asn Ile Lys Ile
            35                  40                  45

Arg Leu Leu Ile Ser Ser Val Glu Arg Ala Lys Glu Ile Gly Ile Asn
 50                  55                  60

Trp Trp Glu Ser Asp Pro Ser Leu Ser Ser Gln Asn Asn Ser Leu Val
 65                  70                  75                  80

Gln Val Asn Gln Lys Leu Leu Glu Arg Val Ala Ser Leu Glu Ser Glu
                85                  90                  95

Ile Glu Ala Leu Lys Tyr Ser Gln
            100

<210> SEQ ID NO 244
<211> LENGTH: 155
<212> TYPE: PRT
<213> ORGANISM: Anabaena-flos-aquae

<400> SEQUENCE: 244

Met Val Cys Thr Pro Ala Glu Asn Phe Asn Asn Ser Leu Thr Ile Ala
 1               5                  10                  15

Ser Lys Pro Lys Asn Glu Ala Gly Leu Ala Pro Leu Leu Leu Thr Val
            20                  25                  30

Leu Glu Leu Val Arg Gln Leu Met Glu Ala Gln Val Ile Arg Arg Met
            35                  40                  45

Glu Glu Asp Leu Leu Ser Glu Pro Asp Leu Glu Arg Ala Ala Asp Ser
 50                  55                  60

Leu Gln Lys Leu Glu Gln Ile Leu His Leu Cys Glu Met Phe Glu
 65                  70                  75                  80

Val Asp Pro Ala Asp Leu Asn Ile Asn Leu Gly Glu Ile Gly Thr Leu
                85                  90                  95

Leu Pro Ser Ser Gly Ser Tyr Tyr Pro Gly Gln Pro Ser Ser Arg Pro
            100                 105                 110

Ser Val Leu Glu Leu Leu Asp Arg Leu Leu Asn Thr Gly Ile Val Val
            115                 120                 125

Asp Gly Glu Ile Asp Leu Gly Ile Ala Gln Ile Asp Leu Ile His Ala
            130                 135                 140

Lys Leu Arg Leu Val Leu Thr Ser Lys Pro Ile
145                 150                 155

<210> SEQ ID NO 245
<211> LENGTH: 94
<212> TYPE: PRT
<213> ORGANISM: Bacillus-megaterium

<400> SEQUENCE: 245

Met Gln Pro Val Ser Gln Ala Asn Gly Arg Ile His Leu Asp Pro Asp
 1               5                  10                  15

Gln Ala Glu Gln Gly Leu Ala Gln Leu Val Met Thr Val Ile Glu Leu
            20                  25                  30

Leu Arg Gln Ile Val Glu Arg His Ala Met Arg Arg Val Glu Gly Gly
            35                  40                  45

Thr Leu Thr Asp Glu Gln Ile Glu Asn Leu Gly Ile Ala Leu Met Asn
 50                  55                  60

Leu Glu Glu Lys Met Asp Glu Leu Lys Glu Val Phe Gly Leu Asp Ala
 65                  70                  75                  80

Glu Asp Leu Asn Ile Asp Leu Gly Pro Leu Gly Ser Leu Leu
            85                  90
```

<210> SEQ ID NO 246
<211> LENGTH: 101
<212> TYPE: PRT
<213> ORGANISM: Ancylobacter aquaticus strain UV5

<400> SEQUENCE: 246

Met Thr Ala Pro Cys Thr Ala Glu Thr Leu Glu Asn Ala Leu Arg Gly
1               5                   10                  15

Arg Ile Asp Ile Asp Pro Glu Lys Val Glu Gln Gly Leu Val Lys Leu
            20                  25                  30

Val Leu Met Leu Val Glu Thr Val Arg Gln Val Val Glu Arg Gln Ala
        35                  40                  45

Ile Arg Arg Val Glu Gly Gly Thr Leu Thr Glu Glu Thr Glu Arg
    50                  55                  60

Leu Gly Leu Ala Leu Met Arg Leu Glu Gly Lys Met Ala Glu Leu Arg
65                  70                  75                  80

Leu His Phe Gly Leu Glu Asp Gly Asp Leu Asp Leu Lys Leu Gln Leu
                85                  90                  95

Pro Leu Gly Glu Leu
            100

<210> SEQ ID NO 247
<211> LENGTH: 169
<212> TYPE: PRT
<213> ORGANISM: Aphanizomenon flos-aquae NIES-81

<400> SEQUENCE: 247

Met Val Tyr Ser Pro Val Glu Asn Ser Asn Asp Phe Leu Asn Val Ile
1               5                   10                  15

Pro Val Glu Asn Ser Asn Glu Phe Leu Asn Thr Ser Pro Lys Lys Lys
            20                  25                  30

Ser Asn Ser Glu Thr Gly Leu Ala Pro Leu Leu Thr Val Leu Glu
        35                  40                  45

Leu Ile Arg Gln Leu Met Glu Ala Gln Ile Ile Arg Arg Met Glu Glu
    50                  55                  60

Asp Leu Leu Ser Glu Ser Asp Leu Glu Arg Thr Ala Glu Ser Leu Gln
65                  70                  75                  80

Lys Leu Glu Glu Gln Ile Leu Asn Leu Cys Gln Ile Phe Asp Ile Asp
                85                  90                  95

Pro Ala Asp Leu Asn Ile Asn Leu Gly Asp Phe Gly Ser Leu Leu Pro
            100                 105                 110

Ala Ser Gly Ser Tyr Tyr Pro Gly Glu Thr Gly Asn Arg Pro Ser Ile
        115                 120                 125

Leu Glu Leu Leu Asp Arg Leu Leu Asn Thr Gly Ile Val Val Asp Gly
    130                 135                 140

Glu Ile Asp Ile Gly Val Ala Gln Leu Asp Leu Ile His Ala Lys Leu
145                 150                 155                 160

Arg Leu Val Leu Thr Ser Lys Pro Ile
                165

<210> SEQ ID NO 248
<211> LENGTH: 157
<212> TYPE: PRT
<213> ORGANISM: Aphanothece halophytica (strain PCC 7418)

<400> SEQUENCE: 248

Met Ser Ala Asp Glu Ser Asn Leu Ser Gln Val Asn Leu Asn Pro Ala

```
             1               5                  10                 15
            Thr Ser Asn Ser Asp Ala Gly Leu Ala Pro Leu Leu Thr Val Thr
                       20                  25                 30

Glu Leu Ile Arg Gln Leu Met Glu Ala Gln Val Ile Arg Arg Met Asp
                        35                  40                 45

Gly Gly Leu Leu Asn Glu Glu Leu Asp Arg Ala Gly Asp Ser Leu
             50                  55                  60

Gln Arg Leu Glu Ala Glu Ile Ile Arg Leu Cys Glu Ile Phe Glu Ile
             65                  70                  75                 80

Asp Pro Lys Asp Leu Asn Val Asp Leu Gly Glu Leu Gly Thr Leu Met
                            85                  90                 95

Pro Lys Asn Gly Gly Tyr Tyr Pro Gly Glu Ser Ser Asp Asp Pro Ser
                       100                 105                110

Ile Leu Glu Leu Leu Asp Arg Ile Leu His Lys Gly Val Val Ile Asp
                       115                 120                125

Gly Asn Leu Asp Leu Gly Ile Ala Gln Leu Ser Leu Ile Gln Ala Arg
             130                 135                 140

Leu His Leu Val Leu Thr Ser Gln Pro Ile Asn Gly Lys
             145                 150                 155

<210> SEQ ID NO 249
<211> LENGTH: 105
<212> TYPE: PRT
<213> ORGANISM: Aquabacter spiritensis strain DSM 9035

<400> SEQUENCE: 249

Met Thr Gly Phe Ala Gly Gly Pro Ala Val Thr Glu Thr Leu Glu Ser
             1               5                  10                 15

Val Leu Gln Gly Arg Val Asp Ile Asp Pro Glu Arg Val Glu Gln Gly
                        20                  25                 30

Leu Val Lys Leu Val Leu Met Val Glu Thr Leu Arg Gln Val Ile
                        35                  40                 45

Glu Arg Gln Ala Ile Arg Arg Val Glu Ala Gly Ala Leu Thr Asp Glu
             50                  55                  60

Glu Ile Glu Arg Leu Gly Leu Thr Leu Leu Arg Leu Glu Glu Lys Met
             65                  70                  75                 80

Ala Glu Leu Arg Val Gln Phe Asn Leu Ser Glu Ala Asp Leu Ser Leu
                        85                  90                 95

Lys Leu Arg Leu Pro Leu Gly Glu Leu
                       100                 105

<210> SEQ ID NO 250
<211> LENGTH: 119
<212> TYPE: PRT
<213> ORGANISM: Bradyrhizobium oligotrophicum S58

<400> SEQUENCE: 250

Met Ser Ala Ser Ser His Ser Glu Ala Pro Gly Leu Arg Leu Gln Leu
             1               5                  10                 15

Gly Asp Leu Asp Thr Ala Leu Ala Ala Val Phe Thr Asp Ala Ala Pro
                        20                  25                 30

Asn Gly Ser Ile Asn Leu Asp Pro Asp Lys Ile Glu His Asp Leu Ala
                        35                  40                 45

Arg Leu Val Leu Thr Leu Ile Glu Phe Leu Arg Arg Leu Leu Glu Leu
             50                  55                  60

Gln Ala Ile Arg Arg Met Glu Ala Asn Glu Leu Ser Glu Asp Glu Glu
```

```
            65                  70                  75                  80
Glu Arg Val Gly Leu Ala Leu Met Arg Ala Ala Gln Val Ser Arg
                    85                  90                  95

Leu Ala Arg Glu Leu Gly Val Asp Pro Arg Glu Leu Asn Leu Gln Leu
                100                 105                 110

Gly Pro Leu Gly Arg Leu Leu
            115

<210> SEQ ID NO 251
<211> LENGTH: 120
<212> TYPE: PRT
<213> ORGANISM: Burkholderia thailandensis sp. Bp5365 strain MSMB43

<400> SEQUENCE: 251

Met Asn Ala Pro His Ala Ala Val Ser Asp Ala Ala Leu Ala
1               5                   10                  15

Ala Ala Leu Glu Gln Ala Leu Ala Gln Gln Gln Ala Pro Pro Arg
                20                  25                  30

Ala Thr Gln Arg Phe Asp Val Ala Thr Ala Ser Ala Gly Asn Gly Leu
                35                  40                  45

Ala Lys Leu Val Leu Ala Leu Met Lys Leu Leu His Glu Leu Leu Glu
            50                  55                  60

Arg Gln Ala Leu Arg Arg Ile Glu Ala Gly Ser Leu Asn Asp Asp Glu
65                  70                  75                  80

Ile Glu Arg Leu Gly Leu Ala Leu Met Arg Gln Ala Glu Ile Glu
                    85                  90                  95

Arg Leu Ala Ala Gln Phe Gly Phe Thr Asp Ala Asp Leu Asn Leu Asp
                100                 105                 110

Leu Gly Pro Leu Gly Arg Leu Phe
            115                 120

<210> SEQ ID NO 252
<211> LENGTH: 114
<212> TYPE: PRT
<213> ORGANISM: Chlorobium luteolum DSM 273

<400> SEQUENCE: 252

Met His Glu Asp Lys Val Gln Phe Gln Ala Ser Ser Val Glu Glu Ala
1               5                   10                  15

Leu Arg Gln Leu Glu Gly Met Lys Gln Gly Lys Glu Ser Arg Ile Glu
                20                  25                  30

Ala Asn Pro Asp Asn Val Glu Ser Gly Leu Ala Arg Leu Val Leu Thr
            35                  40                  45

Leu Ile Glu Leu Leu Arg Lys Leu Met Glu Lys Gln Ala Met Arg Arg
        50                  55                  60

Ile Asp Gly Gly Ser Leu Asp Glu Ala Gln Ile Asp Glu Leu Gly Glu
65                  70                  75                  80

Thr Leu Met Lys Leu Glu Met Lys Met Asp Glu Leu Lys Lys Thr Phe
                    85                  90                  95

Asn Leu Thr Asp Ser Asp Leu Asn Leu Asn Leu Gly Pro Leu Gly Asp
                100                 105                 110

Leu Met

<210> SEQ ID NO 253
<211> LENGTH: 156
<212> TYPE: PRT
<213> ORGANISM: Dactylococcopsis salina PCC 8305
```

<400> SEQUENCE: 253

Met Ser Glu Glu Ser Asn Leu Ser Arg Val Asp Leu Asn Pro Ala
1               5                   10                  15

Ser Ser Asn Ser Asp Ala Gly Leu Ala Pro Leu Leu Leu Thr Val Thr
            20                  25                  30

Glu Leu Ile Arg Gln Leu Met Glu Ala Gln Val Ile Arg Arg Met Asp
            35                  40                  45

Ala Glu Leu Leu Thr Glu Ala Glu Leu Asp Arg Ala Gly Glu Ser Leu
    50                  55                  60

Gln Arg Leu Glu Glu Glu Ile Leu Arg Leu Cys Glu Ile Phe Asp Val
65                  70                  75                  80

Asp Pro Ala Asp Leu Asn Val His Leu Gly Glu Leu Gly Thr Leu Leu
                85                  90                  95

Pro Lys Glu Gly Gly Tyr Tyr Pro Gly Glu Thr Ser Asp Gln Pro Ser
            100                 105                 110

Ile Leu Glu Leu Leu Asp Arg Val Leu His Thr Gly Val Val Ile Asp
        115                 120                 125

Gly Asn Leu Asp Leu Gly Ile Ala Gln Leu Asn Leu Ile Gln Ala Lys
130                 135                 140

Leu His Leu Val Leu Thr Ser Gln Pro Ile Asn Asn
145                 150                 155

<210> SEQ ID NO 254
<211> LENGTH: 128
<212> TYPE: PRT
<213> ORGANISM: Desulfobacterium vacuolatum_DSM 3385

<400> SEQUENCE: 254

Met Ile Lys Asp Pro Glu Ala Lys Asp Phe Lys Ile Glu Ser Asp Ser
1               5                   10                  15

Ile Asp Ala Phe Ala Arg Val Met His Ala Asp Thr Ser Ser Cys Ser
            20                  25                  30

Ser Ser Ser Val Thr Ala Gly Gln Arg Gln Arg Leu Lys Ile Asp
        35                  40                  45

Glu Glu Asn Ile Lys Asn Gly Leu Ala Gln Leu Val Met Thr Leu Ile
50                  55                  60

Lys Leu Leu His Glu Leu Leu Glu Arg Gln Ala Ile Arg Arg Ile Glu
65                  70                  75                  80

Ser Gly Ser Leu Asp Asp Asp Gln Ile Glu Arg Leu Gly Leu Thr Leu
                85                  90                  95

Met Gln Gln Cys Glu Glu Ile Asp Arg Leu Arg Lys Leu Phe Asp Leu
            100                 105                 110

Glu Glu Glu Asp Leu Asn Leu Asp Leu Gly Pro Leu Gly Lys Leu Leu
        115                 120                 125

<210> SEQ ID NO 255
<211> LENGTH: 121
<212> TYPE: PRT
<213> ORGANISM: Desulfomonile tiedjei DSM 6799

<400> SEQUENCE: 255

Met Asn Pro Met Asn Ile Ala Lys Val Glu Ser Asp Ser Leu Gly Asp
1               5                   10                  15

Phe Ala Glu Ile Met Gln Thr Asp Trp Ile Ser Ser Leu His Ser Asp
            20                  25                  30

```
Lys Glu Glu Lys Arg Leu Asn Leu Asn Gln Asp Ser Val Lys Asn Gly
            35                  40                  45

Leu Gly Gln Leu Val Leu Thr Leu Val Lys Leu Leu His Asp Leu Leu
    50                  55                  60

Glu Arg Gln Ala Ile Arg Arg Met Glu Ala Gly Thr Leu Thr Asp Thr
65                  70                  75                  80

Glu Ile Asp Arg Leu Gly Thr Thr Leu Met Met Gln Ala Gln Glu Ile
                85                  90                  95

Glu Arg Leu Arg Ser Glu Phe Gly Leu Glu Glu Glu Asp Leu Asn Leu
            100                 105                 110

Asp Leu Gly Pro Leu Gly Lys Leu Leu
            115                 120
```

```
<210> SEQ ID NO 256
<211> LENGTH: 104
<212> TYPE: PRT
<213> ORGANISM: Desulfotomaculum acetoxidans_DSM 771

<400> SEQUENCE: 256

Met Tyr Ile Asp Ile Ser Glu Gly Ser Leu Lys Gln Gly Val Leu Gly
1               5                   10                  15

Leu Leu Leu Ala Leu Val Glu Ile Ile Lys Asp Ala Leu Lys Ile Gln
            20                  25                  30

Ala Leu Lys Arg Ile Glu Gly Asp Ser Leu Thr Glu Asp Glu Ile Glu
        35                  40                  45

Arg Leu Gly Asn Ala Leu His Glu Leu Glu Glu Ala Leu Val Glu Ile
    50                  55                  60

Glu Met Glu His Asn Leu Gln Asn Val Val Gln Asn Ile Arg Glu Gly
65                  70                  75                  80

Leu Asp Asn Val Val Asn Glu Val Val Asp Thr Phe Asn Pro Glu Arg
                85                  90                  95

Trp Ile Ala Glu Asn Glu Phe Asn
            100
```

```
<210> SEQ ID NO 257
<211> LENGTH: 155
<212> TYPE: PRT
<213> ORGANISM: Dolichospermum circinale

<400> SEQUENCE: 257

Met Leu Ser Thr Pro Ala Asp Asn Phe Asp Glu Ser Leu Thr Thr Val
1               5                   10                  15

Ser Lys Ser Lys Asn Glu Ala Gly Leu Ala Pro Leu Leu Leu Thr Val
            20                  25                  30

Leu Glu Leu Leu Arg Gln Leu Met Glu Ala Gln Val Ile Arg Arg Met
        35                  40                  45

Glu Asp Asn Leu Leu Ser Glu Ser Glu Leu Glu Arg Ala Ala Asp Ser
    50                  55                  60

Ile Gln Lys Leu Glu Glu Gln Ile Leu His Leu Cys Glu Thr Phe Glu
65                  70                  75                  80

Val Asp Pro Ala Glu Leu Asn Ile Asn Leu Gly Asp Phe Gly Thr Leu
                85                  90                  95

Leu Pro Gln Ser Gly Ser Tyr Tyr Pro Gly Glu Thr Gly Ser Arg Pro
            100                 105                 110

Ser Val Leu Glu Leu Leu Asp Arg Leu Leu Asn Thr Gly Val Val Leu
        115                 120                 125
```

```
Asp Gly Glu Ile Asp Leu Gly Leu Ala Gln Leu Asp Leu Ile His Ala
    130                 135                 140

Lys Leu Arg Leu Val Leu Thr Ser Lys Pro Ile
145                 150                 155

<210> SEQ ID NO 258
<211> LENGTH: 94
<212> TYPE: PRT
<213> ORGANISM: Enhydrobacter aerosaccus strain ATCC 27094

<400> SEQUENCE: 258

Met Thr Lys Leu Leu Glu Ala Lys Thr Val Asp Pro Asp Lys Ala Gly
1               5                   10                  15

Asp Asp Leu Val Lys Leu Val Leu Ala Leu Val Glu Thr Leu Arg Gln
                20                  25                  30

Leu Val Glu Arg Gln Ala Ile Arg Arg Val Asp Ser Gly Val Leu Asn
            35                  40                  45

Asp Asp Glu Val Glu Arg Leu Gly Leu Ala Leu Leu Arg Leu Glu Glu
        50                  55                  60

Lys Met Ser Glu Leu Lys Ala His Phe Gly Phe Gly Asp Glu Glu Leu
65                  70                  75                  80

Thr Leu Lys Leu Gly Ser Leu Gly Glu Leu Ala Arg Asp Val
                85                  90

<210> SEQ ID NO 259
<211> LENGTH: 146
<212> TYPE: PRT
<213> ORGANISM: Isosphaera pallida_ATCC-43644

<400> SEQUENCE: 259

Met Ser Asp Ser Leu Phe Glu Val Arg Ser Pro Ser Ala Ala Pro Pro
1               5                   10                  15

Ser Pro Val Asn Pro Gly Val Ala Asp Glu Trp Thr Ala Val Leu Lys
                20                  25                  30

Asp Trp Asp Thr Leu Thr Ala Gln Leu Arg Gln Ala Thr Ala Pro Pro
            35                  40                  45

Asn Ala Glu Asn Ser Ala Arg Ser His Ala Thr Thr Gly Arg Ile Asp
        50                  55                  60

Leu Asp Pro Glu Gln Val Gly Asp Gly Leu Ala Lys Leu Val Leu Thr
65                  70                  75                  80

Leu Leu Glu Leu Ile Arg Gln Leu Leu Glu Arg Gln Ala Ile Arg Arg
                85                  90                  95

Leu Asp Ala Gly Ser Leu Asp His Glu Gln Thr Glu Arg Leu Gly Leu
            100                 105                 110

Thr Leu Met Arg Leu Ala Gln Arg Met Glu Glu Leu Lys Thr His Phe
        115                 120                 125

Gly Leu Gln Gly Glu Asp Leu Asn Leu Asp Leu Gly Pro Leu Gly Lys
    130                 135                 140

Leu Leu
145

<210> SEQ ID NO 260
<211> LENGTH: 98
<212> TYPE: PRT
<213> ORGANISM: Legionella drancourtii LLAP12

<400> SEQUENCE: 260

Met Asn Asp Lys Arg Glu Glu Asp Asn Ala Leu Pro Gln Arg Ile Asn
```

```
                1               5                   10                  15
        Leu Gln Pro Asp Asp Val Lys Asn Gly Leu Gly Lys Leu Val Leu Ile
                        20                  25                  30

Leu Ile Gln Leu Ile His Glu Leu Leu Glu Arg Gln Ala Ile Gly Arg
                        35                  40                  45

Ile Glu Ala Gly Asp Leu Ser Asp Glu Gln Ile Asp Arg Leu Gly Ile
                50                  55                  60

Thr Leu Met Lys Gln Ala Glu Glu Ile Asp Lys Leu Arg Glu Val Phe
        65                  70                  75                  80

Gly Leu Thr Gln Glu Asp Leu Asn Leu Asp Leu Gly Pro Leu Gly Lys
                        85                  90                  95

Leu Leu

<210> SEQ ID NO 261
<211> LENGTH: 157
<212> TYPE: PRT
<213> ORGANISM: Microcystis aeruginosa NIES-843

<400> SEQUENCE: 261

Met Thr Leu Ala Cys Thr Pro Tyr Asp Ser Asp Asn Gln Ala Leu Leu
        1               5                   10                  15

Thr Arg Pro Glu Ser Asn Ser Gln Ala Gly Leu Ala Pro Leu Leu Leu
                        20                  25                  30

Thr Val Glu Leu Val Arg Gln Leu Leu Glu Ala Gln Ile Ile Arg
                        35                  40                  45

Arg Met Glu Lys Gly Val Leu Ser Glu Ser Asp Leu Asp Arg Ala Ala
                50                  55                  60

Glu Ser Ile Gln Lys Leu Gln Glu Gln Ile Leu Tyr Leu Cys Glu Ile
        65                  70                  75                  80

Phe Glu Val Glu Pro Glu Glu Leu Asn Val His Leu Gly Glu Phe Gly
                        85                  90                  95

Thr Leu Leu Pro Glu Ala Gly Ser Tyr Tyr Pro Gly Glu Glu Gly Ile
                        100                 105                 110

Lys Pro Ser Val Leu Glu Leu Val Asp Arg Leu Leu Asn Thr Gly Val
                        115                 120                 125

Val Val Glu Gly Asn Val Asp Leu Gly Leu Ala Gln Leu Asp Leu Ile
                        130                 135                 140

His Leu Lys Leu Arg Leu Val Leu Thr Ser Gln Pro Val
        145                 150                 155

<210> SEQ ID NO 262
<211> LENGTH: 144
<212> TYPE: PRT
<213> ORGANISM: Nostoc punctiforme ATCC 29133

<400> SEQUENCE: 262

Met Gln Ala Ile Ser Lys Ser Lys Gly Ser Asp Ser Gly Leu Ala Pro
        1               5                   10                  15

Leu Leu Leu Thr Val Val Glu Leu Ile Arg Gln Leu Met Glu Ala Gln
                        20                  25                  30

Val Ile Arg Arg Met Asp Ala Gly Thr Leu Asn Asp Ser Glu Leu Asp
                        35                  40                  45

Arg Ala Ala Glu Ser Leu Gln Lys Leu Glu Gln Gln Val Val Gln Leu
                50                  55                  60

Cys Glu Ile Phe Asp Ile Asp Pro Ala Asp Leu Asn Ile Asn Leu Gly
        65                  70                  75                  80
```

-continued

```
Glu Met Gly Asn Leu Leu Pro Gln Ser Gly Gly Tyr Tyr Pro Gly Glu
                 85                  90                  95

Thr Ser Ser Gln Pro Ser Ile Leu Glu Leu Leu Asp Arg Leu Leu Asn
            100                 105                 110

Thr Gly Val Val Val Glu Gly Asp Leu Asp Leu Gly Leu Ala Gln Leu
            115                 120                 125

Ser Leu Val His Ala Lys Leu Arg Leu Val Leu Thr Ser Lys Pro Leu
        130                 135                 140

<210> SEQ ID NO 263
<211> LENGTH: 155
<212> TYPE: PRT
<213> ORGANISM: Nostoc sp. PCC 7120

<400> SEQUENCE: 263

Met Val Cys Thr Pro Val Glu Lys Ser Pro Asn Leu Leu Pro Thr Thr
1               5                  10                  15

Ser Lys Ala Asn Ser Lys Ala Gly Leu Ala Pro Leu Leu Leu Thr Val
             20                  25                  30

Val Glu Leu Ile Arg Gln Leu Met Glu Ala Gln Val Ile Arg Arg Met
         35                  40                  45

Glu Gln Asp Cys Leu Ser Glu Ser Glu Leu Glu Gln Ala Ser Glu Ser
     50                  55                  60

Leu Gln Lys Leu Glu Glu Gln Val Leu Asn Leu Cys His Ile Phe Glu
65                  70                  75                  80

Ile Glu Pro Ala Asp Leu Asn Ile Asn Leu Gly Asp Val Gly Thr Leu
                 85                  90                  95

Leu Pro Ser Pro Gly Ser Tyr Tyr Pro Gly Glu Ile Gly Asn Lys Pro
            100                 105                 110

Ser Val Leu Glu Leu Leu Asp Arg Leu Leu Asn Thr Gly Ile Val Val
        115                 120                 125

Asp Gly Glu Ile Asp Leu Gly Leu Ala Gln Leu Asn Leu Ile His Ala
    130                 135                 140

Lys Leu Arg Leu Val Leu Thr Ser Arg Pro Leu
145                 150                 155

<210> SEQ ID NO 264
<211> LENGTH: 132
<212> TYPE: PRT
<213> ORGANISM: Octadecabacter antarcticus 307

<400> SEQUENCE: 264

Met Lys Thr Thr Ser Asp Ser Gln Phe Asp Ser Met Lys Lys Ile Leu
1               5                  10                  15

Thr Asp Ser Ser Lys Glu Asp Ser Ala Ser Cys Asp Pro Thr Asp Leu
             20                  25                  30

Leu Pro Asn Lys Ser Leu Pro Pro Ser Leu Ser Thr Ser Pro Glu Thr
         35                  40                  45

Ala Ala Asp Asp Leu Val Lys Leu Val Leu Ala Val Ile Asp Thr Val
     50                  55                  60

Arg Gln Val Met Glu Lys Gln Ala Ile Arg Arg Val Glu Ser Gly Ala
65                  70                  75                  80

Leu Ala Glu Ala Glu Ile Glu Arg Leu Gly Leu Thr Leu Met Arg Leu
                 85                  90                  95

Glu Ala Arg Met Val Glu Leu Lys Ser His Phe Gly Leu Ser Asn Glu
            100                 105                 110
```

```
Asp Leu Asn Leu His Phe Gly Thr Val Gln Asp Leu Lys Asp Ile Leu
        115                 120                 125

Asn Asp Glu Glu
    130

<210> SEQ ID NO 265
<211> LENGTH: 132
<212> TYPE: PRT
<213> ORGANISM: Octadecabacter arcticus 238

<400> SEQUENCE: 265

Met Lys Thr Gln Asn Asp Thr Gln Phe Asp Ser Met Lys Lys Ile Leu
1               5                   10                  15

Thr Asp Ser Gly Gly Gly Asp Pro Asn Pro Asn Gly Ser Pro Asp Gln
            20                  25                  30

Thr Gln His Ala Ser Leu Pro Ser Asn Leu Ser Thr Asp Pro Glu Thr
        35                  40                  45

Ala Ala Asp Asp Leu Val Lys Leu Val Leu Ala Val Ile Asp Thr Val
    50                  55                  60

Arg Gln Val Met Glu Arg Gln Ala Ile Arg Arg Val Asp Ser Gly Ala
65                  70                  75                  80

Leu Ala Asp Glu Glu Ile Glu Arg Leu Gly Leu Thr Leu Met Arg Leu
                85                  90                  95

Glu Glu Arg Met Ala Asp Leu Lys Ser His Phe Gly Leu Ser Asn Glu
            100                 105                 110

Asp Leu Asn Leu Asn Phe Gly Thr Val Gln Asp Leu Lys Asp Ile Leu
        115                 120                 125

Asn Asp Glu Glu
    130

<210> SEQ ID NO 266
<211> LENGTH: 114
<212> TYPE: PRT
<213> ORGANISM: Pelodictyon phaeoclathratiforme

<400> SEQUENCE: 266

Met Asp Ser Asp Lys Ile Leu Tyr Tyr Ala Gly Ser Ala Asp Glu Ile
1               5                   10                  15

Ile Glu Glu Leu Glu Lys Leu Lys Pro Gly Ile Gln Gly Arg Ile Asn
            20                  25                  30

Ala Thr Pro Asp Asn Val Glu Ser Gly Leu Ala Lys Leu Val Leu Thr
        35                  40                  45

Leu Ile Glu Leu Ile Arg Lys Leu Ile Glu Lys Gln Ala Met Arg Arg
    50                  55                  60

Ile Asp Gly Asn Ser Leu Ser Glu Ser Gln Ile Glu Glu Leu Gly Glu
65                  70                  75                  80

Thr Leu Met Lys Leu Glu Lys Lys Met Glu Glu Leu Lys Gly Ile Phe
                85                  90                  95

Asn Leu Thr Asp Lys Asp Leu Asn Leu Asn Leu Gly Pro Leu Gly Asp
            100                 105                 110

Leu Met

<210> SEQ ID NO 267
<211> LENGTH: 156
<212> TYPE: PRT
<213> ORGANISM: Phormidium tenue NIES-30
```

<400> SEQUENCE: 267

Met Thr Ser Glu Asn Ala Glu Pro Asp Leu Ser Thr Thr Leu Ala Leu
1               5                   10                  15

Gln Pro Pro Ala Lys Thr Asp Ala Gly Leu Ala Pro Leu Leu Leu Thr
            20                  25                  30

Val Ile Glu Leu Val Arg Gln Leu Met Glu Ala Gln Val Ile Arg Arg
        35                  40                  45

Met Glu Ser Gly Asp Leu Asp Asp Asn Asp Leu Glu Arg Ala Ala Asp
    50                  55                  60

Ser Leu Arg Lys Leu Glu Glu Gln Val Val Ser Met Cys Glu Ile Phe
65                  70                  75                  80

Asp Val Asp Pro Ala Asp Leu Asn Ile Asp Leu Gly Glu Ile Gly Thr
                85                  90                  95

Leu Leu Pro Lys Glu Gly Asn Tyr Tyr Pro Gly Gln Lys Asn Gln Asn
            100                 105                 110

Pro Thr Ile Leu Glu Leu Leu Asp Arg Leu Leu Asp Thr Gly Val Val
        115                 120                 125

Val Glu Gly Asp Val Asp Leu Gly Met Ala Gln Leu Asn Leu Ile His
    130                 135                 140

Ala Lys Leu Arg Leu Val Leu Thr Ser Lys Pro Ile
145                 150                 155

<210> SEQ ID NO 268
<211> LENGTH: 153
<212> TYPE: PRT
<213> ORGANISM: Planktothrix agardhii str. 7805

<400> SEQUENCE: 268

Met Ser Ser Glu Pro Ser Ile Glu Thr Ile Ile Thr Pro Lys Ser
1               5                   10                  15

Ser Arg Lys Asp Ala Gly Leu Ala Pro Leu Val Leu Thr Leu Val Glu
            20                  25                  30

Leu Ile Arg Gln Leu Met Glu Ala Gln Val Ile Arg Arg Met Glu Gly
        35                  40                  45

Asn Thr Leu Ser Glu Glu Glu Leu Asp Arg Ala Ala Gln Ser Leu Gln
    50                  55                  60

Gln Leu Glu Ile Gln Val Leu Lys Leu Cys Glu Ile Phe Glu Ile Asp
65                  70                  75                  80

Pro Thr Asp Leu Asn Ile Glu Leu Ser Glu Phe Gly Thr Leu Leu Pro
                85                  90                  95

Lys Ser Gly Ser Tyr Tyr Pro Gly Glu Asn Thr Gln Asn Pro Ser Ile
            100                 105                 110

Leu Glu Leu Leu Asp Arg Leu Met Asn Thr Gly Ile Val Val Glu Gly
        115                 120                 125

Ser Val Asp Leu Gly Leu Ala Gln Leu Asn Leu Ile His Ala Lys Leu
    130                 135                 140

Arg Leu Val Leu Thr Ser Lys Pro Leu
145                 150

<210> SEQ ID NO 269
<211> LENGTH: 110
<212> TYPE: PRT
<213> ORGANISM: Psychromonas ingrahamii 37

<400> SEQUENCE: 269

Met Pro Phe Glu His Phe Lys Ser Asn Asn Gln Ala Asp Val Asn Ser

-continued

```
                1               5                  10                  15
Asp Thr Lys Pro Ala Ala Ser Val Gly Gly Leu Asn Leu Glu Ser Asp
                    20                  25                  30
Asp Leu Lys Asn Gly Leu Gly Arg Leu Val Leu Thr Leu Val Lys Leu
                    35                  40                  45
Leu His Glu Leu Leu Glu Arg Gln Ala Leu Arg Arg Met Asp Ala Gly
                    50                  55                  60
Ser Leu Gln Asp Glu Ile Glu Arg Leu Gly Leu Ala Phe Met Lys
 65                 70                  75                  80
Gln Ala Glu Glu Ile Asp Arg Leu Arg Lys Glu Phe Gly Leu Glu Val
                    85                  90                  95
Glu Asp Leu Asn Leu Asp Leu Gly Pro Leu Gly Arg Leu Leu
                    100                 105                 110
```

<210> SEQ ID NO 270
<211> LENGTH: 112
<212> TYPE: PRT
<213> ORGANISM: Rhodobacter capsulatus SB 1003

<400> SEQUENCE: 270

```
Met Ser Ala Ala Met His Leu Glu Leu Gly Asp Val Asp Ala Val Leu
 1               5                  10                  15
Ser Gln Ala Ala Arg Ser Leu Ala Ala Gly Gly Arg Leu Thr Leu Asp
                    20                  25                  30
Pro Glu Arg Val Glu Gln Asp Leu Ala Arg Leu Val Leu Gly Ile Val
                    35                  40                  45
Glu Leu Leu Arg Lys Leu Met Glu Leu Gln Ala Ile Arg Arg Met Glu
                    50                  55                  60
Ala Gly Ser Leu Thr Pro Glu Gln Glu Glu Thr Leu Gly Leu Thr Leu
 65                 70                  75                  80
Met Arg Ala Glu Ala Ala Leu His Glu Val Ala Ala Lys Phe Gly Leu
                    85                  90                  95
Gln Pro Ala Asp Leu Ile Leu Asp Leu Gly Pro Leu Gly Arg Ser Val
                    100                 105                 110
```

<210> SEQ ID NO 271
<211> LENGTH: 110
<212> TYPE: PRT
<213> ORGANISM: Rhodobacter sphaeroides 2.4.1

<400> SEQUENCE: 271

```
Met Thr Tyr Pro Phe Pro Pro Leu Leu Leu Arg Asp Asp Arg Leu Pro
 1               5                  10                  15
Pro Thr Glu Ala Pro Val Thr Ala Pro Arg Ile Ala Leu Asp Pro Asp
                    20                  25                  30
Arg Leu Glu His Asp Leu Ala Arg Ile Leu Leu Gly Leu Met Glu Met
                    35                  40                  45
Leu Arg Gln Ile Met Glu Leu Gln Ala Ile Arg Arg Met Glu Ala Gly
                    50                  55                  60
Ser Leu Ser Glu Ser Gln Gln Glu Gln Leu Gly Thr Thr Leu Met Arg
 65                 70                  75                  80
Ala Glu Ala Ala Ile His Glu Met Ala Ala Arg Phe Gly Leu Thr Pro
                    85                  90                  95
Ala Asp Leu Ser Leu Asp Leu Gly Pro Leu Gly Arg Thr Ile
                    100                 105                 110
```

```
<210> SEQ ID NO 272
<211> LENGTH: 91
<212> TYPE: PRT
<213> ORGANISM: Rhodococcus hoagii 103S

<400> SEQUENCE: 272

Met Arg Arg Arg Ile Asp Ser Asp Pro Glu Ser Val Glu Arg Gly Leu
1               5                   10                  15

Val Ala Leu Val Leu Thr Leu Val Glu Leu Leu Arg Gln Leu Met Glu
            20                  25                  30

Arg Gln Ala Leu Arg Arg Val Asp Ala Gly Asp Leu Ser Asp Asp Gln
        35                  40                  45

Ile Glu Arg Ile Gly Thr Thr Leu Met Leu Leu Glu Glu Lys Met Glu
50                  55                  60

Glu Leu Arg Glu His Phe Gly Leu Glu Pro Glu Asp Leu Asn Ile Asp
65                  70                  75                  80

Leu Gly Pro Leu Gly Pro Leu Leu Ala Glu Asp
                85                  90

<210> SEQ ID NO 273
<211> LENGTH: 115
<212> TYPE: PRT
<213> ORGANISM: Serratia sp. ATCC 39006

<400> SEQUENCE: 273

Met Thr Thr Asn Gln Leu Ser His His Ser Pro Val Phe Gly Pro Thr
1               5                   10                  15

Ser Pro Ala Ile Gln Arg Pro Ile Thr Glu Ala Asn Arg His Lys Ile
            20                  25                  30

Asp Ile Asp Gly Glu Arg Val Arg Asp Gly Leu Ala Gln Leu Val Leu
        35                  40                  45

Thr Leu Val Lys Leu Leu His Glu Leu Leu Glu Arg Gln Ala Ile Arg
50                  55                  60

Arg Met Asp Ser Gly Ser Leu Ser Asp Glu Glu Val Glu Arg Leu Gly
65                  70                  75                  80

Leu Ala Leu Met Arg Gln Ala Glu Glu Leu Thr His Leu Cys Asp Val
                85                  90                  95

Phe Gly Phe Lys Asp Asp Asp Leu Asn Leu Asp Leu Gly Pro Leu Gly
            100                 105                 110

Arg Leu Leu
        115

<210> SEQ ID NO 274
<211> LENGTH: 105
<212> TYPE: PRT
<213> ORGANISM: Stella vacuolata_ATCC-43931

<400> SEQUENCE: 274

Met Thr Gly Phe Leu Asn Gly Pro Ala Asp Val Glu Thr Leu Glu Thr
1               5                   10                  15

Ala Leu Arg Gly Arg Val Asp Ile Asp Pro Glu Arg Val Glu Gln Gly
            20                  25                  30

Leu Val Lys Leu Val Leu Met Val Val Glu Thr Leu Arg Gln Val Ile
        35                  40                  45

Glu Arg Gln Ala Ile Arg Arg Val Glu Ser Gly Ser Leu Thr Asp Asp
50                  55                  60

Glu Val Glu Arg Leu Gly Leu Thr Leu Met Arg Leu Glu Glu Lys Met
65                  70                  75                  80
```

Asp Gln Leu Arg Arg Gln Phe Asp Leu Gly Glu Glu Asp Leu Ser Met
            85                  90                  95

Arg Leu Arg Leu Pro Leu Gln Glu Leu
            100                 105

<210> SEQ ID NO 275
<211> LENGTH: 127
<212> TYPE: PRT
<213> ORGANISM: Thiocapsa rosea strain DSM 235 Ga0242571_11

<400> SEQUENCE: 275

Met Ser Asp Thr Arg Thr Gly Thr Ala Pro Ser Ser Ala Ala Ser Ala
1               5                   10                  15

Ala Pro Asp Thr Ser Thr Leu Gln Arg Ala Asn Leu Leu Ala Asp Leu
            20                  25                  30

Leu Glu Thr Lys Val Ala Ala Ala Gly Arg Arg Ile Asp Ile Asp Pro
        35                  40                  45

Glu Arg Val Gln Arg Gly Leu Gly Gln Leu Val Leu Thr Val Val Lys
    50                  55                  60

Leu Leu His Val Leu Leu Glu Arg Gln Ala Ile Arg Arg Val Asp Gly
65                  70                  75                  80

Gly Asp Leu Asp Glu Asp Glu Ile Glu Gln Leu Gly Leu Ala Leu Met
            85                  90                  95

Arg Gln Ser Glu Glu Ile Glu Arg Leu Arg Arg Leu Leu Gly Leu Glu
            100                 105                 110

Glu Gln Asp Leu Asn Leu Asp Leu Gly Pro Leu Gly Lys Leu Phe
        115                 120                 125

<210> SEQ ID NO 276
<211> LENGTH: 160
<212> TYPE: PRT
<213> ORGANISM: Tolypothrix sp. PCC 7601

<400> SEQUENCE: 276

Met Ala Met Val Cys Thr Pro Ser Glu Asn Ser Asn Asp Leu Leu Ala
1               5                   10                  15

Thr Asn Ser Lys Ala Asn Asn Gln Ala Gly Leu Val Pro Leu Leu Leu
            20                  25                  30

Thr Val Val Glu Leu Ile Arg Gln Leu Met Glu Ala Gln Val Ile Arg
        35                  40                  45

Arg Met Glu Glu Glu Cys Leu Ser Glu Ser Asp Leu Glu Arg Ala Ala
    50                  55                  60

Glu Ser Leu Gln Lys Leu Glu Glu Gln Val Leu Asn Leu Cys Gln Ile
65                  70                  75                  80

Phe Glu Ile Asp Pro Ala Asp Leu Asn Ile His Leu Gly Glu Leu Gly
            85                  90                  95

Ser Leu Leu Pro Ala Ala Gly Ser Tyr Tyr Pro Gly Glu Thr Gly Asn
            100                 105                 110

Thr Pro Ser Val Leu Glu Leu Leu Asp Arg Leu Leu Asn Thr Gly Val
        115                 120                 125

Val Val Asp Gly Glu Leu Asp Leu Gly Val Ala Gln Leu Asn Leu Ile
    130                 135                 140

His Ala Lys Leu Arg Leu Val Leu Thr Ser Lys Pro Leu Asn Thr Lys
145                 150                 155                 160

<210> SEQ ID NO 277

```
<211> LENGTH: 153
<212> TYPE: PRT
<213> ORGANISM: Trichodesmium erythraeum IMS101

<400> SEQUENCE: 277

Met Ser Leu Glu Asn Ser Pro Glu Ser Leu Ile Val Pro Ile Asp
1               5                   10                  15

Lys Ser Lys Ser Asn Pro Glu Ala Gly Leu Ala Pro Leu Leu Leu Thr
            20                  25                  30

Val Ile Glu Leu Leu Arg Glu Leu Met Gln Ala Gln Val Ile Arg Arg
        35                  40                  45

Met Asp Ala Gly Ile Leu Ser Asp Glu Gln Leu Glu Arg Ala Ala Glu
50                  55                  60

Gly Leu Arg Gln Leu Glu Glu Gln Val Ile Lys Leu Cys Lys Val Phe
65                  70                  75                  80

Asp Ile Pro Thr Glu Asp Leu Asn Leu Asp Leu Gly Glu Ile Gly Thr
                85                  90                  95

Leu Leu Pro Lys Ser Gly Glu Tyr Tyr Pro Gly Glu Lys Ser Glu Asn
            100                 105                 110

Pro Ser Val Leu Glu Leu Leu Asp Arg Ile Leu Asn Thr Gly Val Val
        115                 120                 125

Leu Asp Gly Thr Val Asp Leu Gly Leu Ala Glu Leu Asp Leu Ile His
130                 135                 140

Ala Arg Leu Arg Leu Val Leu Thr Ala
145                 150

<210> SEQ ID NO 278
<211> LENGTH: 231
<212> TYPE: PRT
<213> ORGANISM: Ancylobacter aquaticus strain UV5

<400> SEQUENCE: 278

Met Leu Tyr Leu Tyr Ala Ile Leu Glu Ser Pro Pro Gln Lys Pro
1               5                   10                  15

Leu Pro Pro Gly Ile Gly Gly Ala Ala Pro Leu Phe Val Glu Ser His
            20                  25                  30

Ala Leu Val Cys Ala Ala Ser Glu Ala Ala Asp Ala Ala Ile Ala Arg
        35                  40                  45

Glu Pro Ser Gln Ile Trp Arg His Gln Glu Val Val Ala Ala Leu Met
50                  55                  60

Glu Gly Arg Pro Val Leu Pro Leu Arg Phe Gly Thr Val Val Glu Asp
65                  70                  75                  80

Ser Ala Ala Cys Leu Arg Leu Ala Arg His His Ala Glu Leu Ser
            85                  90                  95

Ala Gln Leu Asp Arg Val Arg His Cys Val Glu Phe Ala Leu Arg Val
            100                 105                 110

Ala Gly Leu Ser Glu Leu Ala Asp Pro Gly Leu Asp Pro Asn Ala Thr
        115                 120                 125

Pro Ala Gly Leu Gly Pro Gly Ala Ser His Leu Arg Thr Leu Val Arg
130                 135                 140

Arg Glu Arg Gly Trp Pro Val Ser Ser Ala Ala Phe Pro His Asp Thr
145                 150                 155                 160

Leu Thr Ala His Ala Ala Ser Arg Leu Leu Trp Ala Arg Ser Pro Ser
                165                 170                 175

Gln Pro Asp Leu Arg Ala Ser Phe Leu Val Gln Arg Arg Ser Ala Ser
            180                 185                 190
```

Ala Phe Leu Asp Asp Val Asn Ala Leu Gln Arg Leu Arg Pro Asp Leu
            195                 200                 205

Gly Ile Thr Val Thr Gly Pro Trp Pro Pro Tyr Ser Phe Ser Asp Pro
210                 215                 220

Asp Leu Ser Gly Gly Arg Glu
225                 230

<210> SEQ ID NO 279
<211> LENGTH: 223
<212> TYPE: PRT
<213> ORGANISM: Aphanothece halophytica (strain PCC 7418)

<400> SEQUENCE: 279

Met Leu Tyr Thr Tyr Cys Phe Leu Phe Ser Pro Glu Lys Thr Leu Ser
1               5                   10                  15

Leu Pro Gln Gly Phe Lys Gly Asp Leu Gln Met Ile Glu Lys Gly Ala
            20                  25                  30

Ile Ala Ala Val Val Glu Pro Asn Leu Pro Lys Ala Glu Leu Glu Glu
        35                  40                  45

Asp Asp Gln Lys Leu Val Gln Ala Val Val His His Asp Trp Val Ile
50                  55                  60

Cys Glu Leu Phe Arg Gly Leu Thr Val Leu Pro Leu Arg Phe Gly Thr
65                  70                  75                  80

Tyr Phe Arg Gly Glu Ala Asp Leu Arg Ser His Leu Ala Ala Tyr Glu
                85                  90                  95

Glu Ser Tyr Gln Gln Lys Leu Thr Ala Leu Thr Gly Lys Val Glu Val
            100                 105                 110

Thr Leu Lys Leu Thr Pro Ile Pro Phe Ser Glu Glu Gly Ser Ser Ser
        115                 120                 125

Thr Ala Lys Gly Lys Ala Tyr Leu Gln Ala Lys Lys Gln Arg Tyr Gln
130                 135                 140

Gln Gln Ser Asn Tyr Gln Thr Gln Gln Glu Ala Leu Glu Lys Leu
145                 150                 155                 160

Gln Glu Glu Ile Lys Lys Thr Tyr Pro Gln Leu Ile His Asp Glu Pro
                165                 170                 175

Lys Glu Asn Thr Glu Arg Phe Tyr Leu Leu Ile Asp Ser His Ser Phe
            180                 185                 190

Ser Val Phe Gly Glu Lys Met Glu Gln Trp Lys Gln Phe Leu Ser Ser
        195                 200                 205

Trp Ser Ile Glu Ile Ser Asp Pro Leu Pro Pro Tyr His Phe Leu
210                 215                 220

<210> SEQ ID NO 280
<211> LENGTH: 226
<212> TYPE: PRT
<213> ORGANISM: Aquabacter spiritensis strain DSM 9035

<400> SEQUENCE: 280

Met Leu Tyr Leu Tyr Ala Val Leu Glu Ala Pro Pro Ala Arg Ser
1               5                   10                  15

Leu Pro Pro Gly Ile Gly Gly Ala Pro His Phe Ile Glu Ala Phe
            20                  25                  30

Glu Leu Val Cys Ala Ala Ser Glu Thr Pro Asn Arg Ser Val Ala Pro
        35                  40                  45

Glu Pro Ala Glu Val Trp Arg His Gln Gln Val Val Glu Ala Leu Ile
50                  55                  60

Asp Arg Ala Pro Ala Leu Pro Leu Arg Phe Gly Thr Leu Val Glu Asp
65                  70                  75                  80

Ala Ser Ala Cys Arg Arg Leu Leu Thr Arg His Arg Asp Ala Leu Gly
            85                  90                  95

Ala Gln Leu Gly Arg Val Arg His Cys Val Glu Phe Ala Leu Arg Val
        100                 105                 110

Ser Gly Leu Pro Glu Glu Val Ala Pro Asp Pro Gly Ile Gly Gly Gly
    115                 120                 125

Pro Gly Thr Ser Tyr Leu Arg Thr Leu Ala Arg Arg Glu Ala Gly Trp
130                 135                 140

Pro Pro Ser Thr Ala Val Phe Pro His Asp Gly Leu Ala Ala His Ala
145                 150                 155                 160

Ala Glu Arg Leu Leu Trp Ala Arg Ser Thr Ser Gln Pro Asp Leu Arg
                165                 170                 175

Ala Ser Phe Leu Val Arg Lys Pro Asn Val Ala Ala Phe Leu Ala Asp
            180                 185                 190

Val Ser Ala Leu Gln Arg Val Arg Pro Asp Leu Gly Ile Thr Cys Thr
        195                 200                 205

Gly Pro Trp Pro Pro Tyr Ser Phe Ser Asp Pro Asp Leu Ser Gly Val
    210                 215                 220

Ser Pro
225

<210> SEQ ID NO 281
<211> LENGTH: 269
<212> TYPE: PRT
<213> ORGANISM: Bacillus-megaterium

<400> SEQUENCE: 281

Met Gly Glu Leu Leu Tyr Leu Tyr Gly Leu Ile Pro Thr Lys Glu Ala
1               5                   10                  15

Ala Ala Ile Glu Pro Phe Pro Ser Tyr Lys Gly Phe Asp Gly Glu His
            20                  25                  30

Ser Leu Tyr Pro Ile Ala Phe Asp Gln Val Thr Ala Val Val Ser Lys
        35                  40                  45

Leu Asp Ala Asp Thr Tyr Ser Glu Lys Val Ile Gln Glu Lys Met Glu
    50                  55                  60

Gln Asp Met Ser Trp Leu Gln Glu Lys Ala Phe His His His Glu Thr
65                  70                  75                  80

Val Ala Ala Leu Tyr Glu Glu Phe Thr Ile Ile Pro Leu Lys Phe Cys
                85                  90                  95

Thr Ile Tyr Lys Gly Glu Glu Ser Leu Gln Ala Ala Ile Glu Ile Asn
            100                 105                 110

Lys Glu Lys Ile Glu Asn Ser Leu Thr Leu Leu Gln Gly Asn Glu Glu
        115                 120                 125

Trp Asn Val Lys Ile Tyr Cys Asp Asp Thr Glu Leu Lys Lys Gly Ile
    130                 135                 140

Ser Glu Thr Asn Glu Ser Val Lys Ala Lys Gln Glu Ile Ser His
145                 150                 155                 160

Leu Ser Pro Gly Arg Gln Phe Phe Glu Lys Lys Ile Asp Gln Leu
                165                 170                 175

Ile Glu Lys Glu Leu Glu Leu His Lys Asn Lys Val Cys Glu Ile
            180                 185                 190

His Asp Lys Leu Lys Glu Leu Ser Leu Tyr Asp Ser Val Lys Lys Asn

```
        195                 200                 205

Trp Ser Lys Asp Val Thr Gly Ala Ala Glu Gln Met Ala Trp Asn Ser
    210                 215                 220

Val Phe Leu Leu Pro Ser Leu Gln Ile Thr Lys Phe Val Asn Glu Ile
225                 230                 235                 240

Glu Glu Leu Gln Gln Arg Leu Glu Asn Lys Gly Trp Lys Phe Glu Val
                245                 250                 255

Thr Gly Pro Trp Pro Pro Tyr His Phe Ser Ser Phe Ala
            260                 265

<210> SEQ ID NO 282
<211> LENGTH: 266
<212> TYPE: PRT
<213> ORGANISM: Burkholderia thailandensis sp. Bp5365 strain MSMB43

<400> SEQUENCE: 282

Met Asn Asp Ala Leu Tyr Leu Phe Cys Phe Ala Arg Ala Glu Pro Leu
1               5                   10                  15

Ala Pro Ala Trp Ala Lys Arg Ala Pro Gly Glu Pro Arg Leu Gln Leu
            20                  25                  30

Leu His Glu Gly Asn Leu Ala Ala Val Leu Cys Asp Val Ser Arg Ser
        35                  40                  45

Glu Phe Ala Gly Ala Asp Ala Glu Arg Arg Leu Ala Asp Pro Ala Trp
    50                  55                  60

Ile Ala Gly Arg Val Ala Val His Ala Ala Ala Ile Glu Trp Thr Met
65                  70                  75                  80

Arg Tyr Ser Pro Val Ile Pro Ala Gln Phe Gly Thr Leu Phe Ser Gly
                85                  90                  95

Ala Gly Arg Val Ile Ala Leu Met Glu Ser Cys His Ala His Ile Gly
            100                 105                 110

Arg Val Leu Asp His Val Glu Gly Lys Thr Glu Trp Ala Val Lys Gly
        115                 120                 125

Trp Leu Asp Arg Gln Ala Ala Ala Asp Ser Gln Ala Ala Leu Leu Arg
    130                 135                 140

Ala Asp Glu Pro Glu Ser Ala Ala Arg Thr Ala Gly Ala Arg Tyr Leu
145                 150                 155                 160

Arg Glu Arg Gln Leu Gln Ala Arg Ala Gly Gln Asn Leu Arg Asp Trp
                165                 170                 175

Leu Glu Gln Ser Val Pro Pro Ile Ser Ala Arg Leu Gln Arg His Ala
            180                 185                 190

Val Glu Met Cys Ser Arg Pro Cys Arg Ala Ser Asp Ser Glu His Glu
        195                 200                 205

Ile Val Ala Asn Trp Ala Phe Leu Val Arg Asn Arg Asp Val Pro Ala
    210                 215                 220

Phe Arg Arg Gln Ala Glu Ala Ile Asp Ala Glu Phe Ala Thr Trp Gly
225                 230                 235                 240

Leu His Phe Asp Phe Ser Gly Pro Trp Pro Pro Tyr Ser Phe Cys Ala
                245                 250                 255

Pro Leu Thr Glu Glu Thr Thr Trp Ser Gly
            260                 265

<210> SEQ ID NO 283
<211> LENGTH: 292
<212> TYPE: PRT
<213> ORGANISM: Chlorobium luteolum DSM 273
```

<400> SEQUENCE: 283

```
Met Pro Cys Arg Leu Thr Val Thr Trp Lys Ser Leu Arg Thr Ala Gly
1               5                   10                  15

Leu Leu Pro Thr Ala Lys Gly Ile Gln Gly Arg Thr Glu Arg Met Ala
            20                  25                  30

Gln Asn Ile Leu Tyr Val Tyr Cys Ile Val Arg Gln Leu Pro Gly Ala
        35                  40                  45

Asp Ile Val Ala Arg Tyr Pro Asp Leu Val Phe Ile Glu Ala Gly Ser
    50                  55                  60

Ala Tyr Val Ala Ala Lys Tyr Val Ser Pro Leu Glu Tyr Ser Asp Ala
65                  70                  75                  80

Ser Met Lys Leu Lys Leu Ala Asp Glu Glu Trp Leu Asp Arg Asn Ala
                85                  90                  95

Arg Glu His Leu Ser Val Asn Val Met Ile Met Ala Gln Gln Thr Ile
            100                 105                 110

Ile Pro Phe Asn Phe Gly Thr Ile Phe Lys Ser Arg Glu Ser Leu Ser
        115                 120                 125

Gly Phe Leu Gly Asp Tyr Gly Arg Lys Leu Asp Glu Ser Phe Asp Ala
    130                 135                 140

Leu Glu Gly Arg Glu Glu Trp Ala Val Lys Ala Tyr Cys Asn Glu Ser
145                 150                 155                 160

Phe Leu Leu Lys Asn Leu His Leu Glu Ser Pro Ala Ile Ala Ala Ile
                165                 170                 175

Glu Gln Glu Ile Gln Ala Ala Ser Pro Gly Lys Ala Tyr Leu Leu Lys
            180                 185                 190

Lys Lys Lys Glu Ala Met Ser Ala Ser Ala Leu Glu Gly Val His Gln
        195                 200                 205

Gly His Ala Lys Ala Val Trp Gly Glu Leu Ala Ala Leu Ser Lys Glu
    210                 215                 220

His Val Leu Asn Arg Leu Ile Pro Glu Asp Val Ser Gly Val Asp Gly
225                 230                 235                 240

Arg Met Ile Val Asn Gly Val Phe Leu Ile Ala Asn Thr Asp Val Gly
                245                 250                 255

Ala Phe Ile Arg Thr Thr Glu Asp Leu Gly Glu Arg Tyr Arg Asp Ala
            260                 265                 270

Gly Val Phe Leu Asp Val Thr Gly Pro Trp Pro Tyr Asp Phe Val
        275                 280                 285

Asp Ile Pro Tyr
    290
```

<210> SEQ ID NO 284
<211> LENGTH: 225
<212> TYPE: PRT
<213> ORGANISM: Dactylococcopsis salina PCC 8305

<400> SEQUENCE: 284

```
Met Leu Tyr Thr Tyr Cys Leu Ile Ala Ser Ser Pro Ser Ala Leu Ser
1               5                   10                  15

Leu Pro Ser Gly Phe Arg Gly Glu Leu Gln Leu Ile Lys Gln Gly Ala
            20                  25                  30

Ile Ala Ala Ile Val Glu Ala Glu Leu Pro Leu Glu Glu Leu Glu Glu
        35                  40                  45

Asn Asp Gln Lys Leu Ile Gln Ala Val Ile His His Asp Ala Val Ile
    50                  55                  60
```

```
Cys Glu Ile Phe Gln Gln Ile Pro Leu Leu Pro Leu Arg Phe Gly Thr
 65                  70                  75                  80

Tyr Phe Pro Thr Glu Lys Asp Leu Leu Glu His Leu Asp Phe Lys Ala
                 85                  90                  95

Glu Lys Tyr Gln Lys Lys Leu Gln Glu Ile Gln Asp Lys Val Glu Leu
            100                 105                 110

Thr Leu Lys Leu Thr Pro Leu Pro Phe Ser Thr Glu Asn Ala Ser Pro
        115                 120                 125

Met Glu Lys Gln Gly Lys Asn Tyr Leu Lys Ala Lys Lys Gln Arg Tyr
130                 135                 140

Gln Glu Gln Thr Asn Tyr Gln Ser Gln Gln Ala Glu Leu Asn Gln
145                 150                 155                 160

Leu Gln Thr Gln Ile Asn Gln Asp Tyr Pro Gln Phe Ile His Gly Glu
                165                 170                 175

Pro Lys Glu Asn Ile Glu Arg Phe Tyr Leu Leu Ile Lys Glu Arg Asp
            180                 185                 190

Arg Ser Val Phe Ser Glu Gln Leu Glu Gln Trp Lys Lys Asp Phe Pro
        195                 200                 205

Thr Trp Thr Ile Glu Val Ser Asp Pro Leu Pro Pro Tyr His Phe Ile
    210                 215                 220

Glu
225

<210> SEQ ID NO 285
<211> LENGTH: 269
<212> TYPE: PRT
<213> ORGANISM: Desulfobacterium vacuolatum-DSM 3385

<400> SEQUENCE: 285

Met Glu Lys Lys Lys Ala Val Tyr Leu Tyr Cys Val Thr Arg Ala Asn
 1               5                  10                  15

Lys Phe Asn Ala Pro Gly Ile Thr Gly Ile Asp Ala Asn Thr Pro Val
                 20                  25                  30

Cys Phe Glu His Leu Glu Asn Phe Val Ala Val Tyr Asn Ile Ile Pro
            35                  40                  45

Leu Asn Thr Phe Val Gly Thr Ser Ala Glu Glu Asn Met Lys Asn Ile
 50                  55                  60

Asp Trp Ile Gly Pro Arg Ala Met Arg His Glu Asn Val Ile Glu Arg
 65                  70                  75                  80

Met Met Gln Glu Ser Ser Val Tyr Pro Ala Arg Phe Ala Thr Leu Phe
                 85                  90                  95

Ser Ser Met Glu Asn Leu Arg Glu Thr Leu His Leu Lys Ser Gly Leu
            100                 105                 110

Ile Ser Arg Phe Leu Asn Gln Thr Gln His Lys Cys Glu Tyr Ser Leu
        115                 120                 125

Lys Gly Phe Ile Asn Arg Lys Gln Leu Leu Glu Phe Leu Ile Lys Thr
130                 135                 140

Lys Phe Lys Gln Glu Lys Lys Gln Leu Asp Gly Leu Ser Pro Gly Lys
145                 150                 155                 160

Lys Tyr Phe Ala Gln His Gln Phe Asn Lys Val Leu Glu Thr Gly Ile
                165                 170                 175

Asn Gln Trp Ile Lys Arg Arg Cys Gly Ile Phe Leu Asp His Leu Thr
            180                 185                 190

Lys Arg Asn Pro Glu Val Ser Pro Arg Glu Leu Phe Thr Glu Lys Thr
        195                 200                 205
```

Glu Lys Asn Asn Leu Glu Met Met Phe Asn Leu Ala Phe Leu Ile His
    210                 215                 220

Asn Asp Ser Lys Ser Ala Phe Leu Gln Glu Ile Ser Gln Ala Glu Lys
225                 230                 235                 240

Glu Phe Ser Gln Thr Gly Ile Ser Leu Val Val Ser Gly Pro Trp Ala
                245                 250                 255

Pro Tyr Ser Phe Cys Lys Thr Thr Arg Gly Glu Gly Leu
                260                 265

<210> SEQ ID NO 286
<211> LENGTH: 268
<212> TYPE: PRT
<213> ORGANISM: Desulfomonile tiedjei DSM 6799

<400> SEQUENCE: 286

Met Ser Asn Val Leu Tyr Leu Phe Cys Leu Ala Arg Thr Gly Leu Val
1               5                   10                  15

Asp His Ile Glu Gly Thr Gly Ile Thr Gly Thr Glu Asp Leu Ile Leu
            20                  25                  30

Lys Asn Phe Ser Gly Val Thr Ala Val Thr Cys Glu Val Pro Glu Asp
        35                  40                  45

Asp Phe Ser Gly Glu Ser Ala Glu Ile Lys Leu Gln Asp Leu Ala Trp
    50                  55                  60

Val Gly Pro Arg Ala Val Arg His Asp Arg Ile Ile Glu Glu Ile Met
65                  70                  75                  80

Gln Tyr Ser Pro Val Phe Pro Ala Pro Phe Gly Ser Leu Phe Ser Ser
                85                  90                  95

Glu Lys Arg Leu Gly Thr Leu Ile Glu Ser Asn Ile Asp Ala Ile Arg
            100                 105                 110

Glu Phe Leu Asp His Thr Ala Asp Lys Gln Glu Trp Ser Val Lys Gly
        115                 120                 125

Leu Val Cys Lys Ser Lys Ala Val Asp Glu Ile Phe Thr Gly Lys Leu
    130                 135                 140

Lys Ile Leu Ser Glu Thr Leu Ser Ser Ser Pro Ala Gly Met Arg Tyr
145                 150                 155                 160

Phe Lys Glu Arg Gln Met Arg Ser Glu Ala Glu Lys Glu Leu Ser Gly
                165                 170                 175

Lys Val Lys Ala Ala Cys Thr Val Val Gly Glu Lys Leu Leu Ala Cys
            180                 185                 190

Ser Asn Asn Phe Arg Gln Arg Lys Asn Ile Ser Phe Gly Lys Ala Glu
        195                 200                 205

Gly Asp Lys Gln Leu Val Val Asn Trp Ala Phe Leu Val Asp His Ser
    210                 215                 220

Arg Ile Ser Tyr Phe Leu Asp Gln Val Glu His Ala Asn Ser Asn Tyr
225                 230                 235                 240

Gln Ala Gly Gly Leu Ala Phe Cys Ser Gly Pro Trp Pro Tyr
                245                 250                 255

Ser Phe Cys Pro Ser Leu His Met Glu Pro Thr Arg
            260                 265

<210> SEQ ID NO 287
<211> LENGTH: 259
<212> TYPE: PRT
<213> ORGANISM: Desulfotomaculum acetoxidans-DSM 771

<400> SEQUENCE: 287

```
Met Asn Leu Ile Asp Asp Cys Lys Ala Lys Tyr Ile Tyr Cys Ile Gly
1               5                   10                  15

Glu Asn Pro Gly Asn Trp Pro Ser Glu Val Met Gly Val Glu Gly Ser
            20                  25                  30

Leu Val Tyr His Val Val Tyr Arg Asp Ile Ala Ala Val Val His Asp
        35                  40                  45

Cys Ala Glu Gln Pro Tyr Asn Ser Asp Asn Asn Lys Val Ile Asp
50                  55                  60

Trp Val Leu Gly His Gln Leu Val Val Asp Lys Ala Cys Ser Cys Tyr
65              70                  75                  80

Ser Ser Val Leu Pro Phe Thr Phe Asn Ser Ile Val Lys Gly Lys Glu
                85                  90                  95

Asp Leu Ser Ser His Glu Ile Leu Val Asn Trp Leu Glu Asp Asn Tyr
            100                 105                 110

Asp Asn Phe Lys Leu Lys Leu Gly Lys Ile Lys Gly Lys Lys Glu Tyr
        115                 120                 125

Ser Val Gln Leu Phe Leu Asp Lys Gln Val Ser Leu Ser Leu Leu Gln
    130                 135                 140

Ser Glu Ser Asp Ile Leu Glu Leu Gln Val Glu Leu Leu Gly Ser Ala
145                 150                 155                 160

Lys Gly Lys Ala Tyr Phe Val Gln Glu Lys Ile Asn Lys Lys Ile Gly
                165                 170                 175

Glu Leu Met Ala Asn Arg Ala Asp Ser Tyr Cys Arg Gln Phe Tyr His
            180                 185                 190

Glu Ile Ser Ser Val Val Ser Glu Cys Lys Leu Cys Lys Leu Lys Gln
        195                 200                 205

Ala Gly Arg Asn Glu Ile Met Ile Ile Asn Leu Val Cys Leu Ala Gly
    210                 215                 220

Asp Asn Glu Val Glu Val Leu Gly Asp Val Leu Glu Lys Ile Lys Ser
225                 230                 235                 240

Asn Asp Ile Ala Ile Lys Ile Lys Phe Ser Gly Pro Trp Pro Ala Tyr
                245                 250                 255

Ser Phe Val

<210> SEQ ID NO 288
<211> LENGTH: 240
<212> TYPE: PRT
<213> ORGANISM: Enhydrobacter aerosaccus strain ATCC 27094

<400> SEQUENCE: 288

Met Leu Tyr Val Tyr Gly Ile Ala Asp Asn Ala Phe Glu Val Leu Arg
1               5                   10                  15

Gly Ala Gly Leu Leu Asn Ser Asp Val Phe Ala Val Pro Ala Gly Cys
            20                  25                  30

Leu Ala Ala Ala Ala Ser Lys Leu Ala Gln Gly Gly Ile Glu Thr Thr
        35                  40                  45

Pro Gln Gly Val Trp Arg His Glu Gln Val Leu Arg Gln Leu Met Gln
    50                  55                  60

Asp His Ala Val Leu Pro Leu Arg Phe Gly Thr Ile Cys Arg Asp Arg
65              70                  75                  80

Glu Thr Leu Thr Asp Arg Leu Met Glu Ala Ser Asp Asp Leu Val Arg
                85                  90                  95

Gly Leu Gly Arg Val Arg Gly Lys Val Glu Ile Ala Leu Arg Ile Val
            100                 105                 110
```

```
Asp Glu Arg Glu His Glu Ala His Pro Val Pro Ser Glu Thr Pro Thr
            115                 120                 125

Val Asp Ala Ile Gly Gly Arg Gly Thr Ala Tyr Leu Arg Ala Arg
    130                 135                 140

Arg Arg His His Ala Ala Glu Met Gly Arg Glu Ala Arg Ala Glu Arg
145                 150                 155                 160

Val Gly Lys Met Leu Ser Ala Tyr Ile Asp Val Gly Ala Glu Asp Leu
                165                 170                 175

Val Cys Ser Val Ala Pro Glu Gly Asp His Ala Val Ser Val Ser Cys
            180                 185                 190

Leu Leu Gly Arg Asp Gln Leu Ala Thr Leu Gln Ala Ala Leu Glu Arg
            195                 200                 205

Phe Gln Ser Asp His Pro Ala Ile Gly Leu Ser Trp Thr Gly Pro Trp
            210                 215                 220

Thr Pro Tyr Ser Phe Val Ala Pro Ser Leu Phe Gly Val Gly Leu Pro
225                 230                 235                 240

<210> SEQ ID NO 289
<211> LENGTH: 266
<212> TYPE: PRT
<213> ORGANISM: Legionella drancourtii LLAP12

<400> SEQUENCE: 289

Met Asn Lys Ala Leu Tyr Leu Phe Cys Leu Thr Pro Ala Ser Asp Leu
1               5                   10                  15

Pro Met Met Glu Gly Glu Leu Leu Pro Asn Phe Ser Pro Leu Phe Ile
                20                  25                  30

His Pro Phe Gln Thr Phe Asn Ala Ile Leu Ser Trp Val Pro Ala Lys
            35                  40                  45

Glu Tyr Gln Glu Gln Ser Thr Asp Ser Asn Leu Ile Asn Thr Glu Glu
    50                  55                  60

Phe Met Gln Arg Val Phe Phe His Glu Leu Val Val Glu Lys Ile Met
65                  70                  75                  80

Arg Asp Glu Ala Val Phe Pro Ile Gly Phe Gly Thr Leu Phe Ser Ser
                85                  90                  95

Ile Ala Ser Leu Glu Glu Gln Ile Leu Thr His Gln Thr Leu Ile Ser
                100                 105                 110

Ser Cys Leu Ala Asn Leu Asn Gln Lys Asp Glu Tyr Ala Val Arg Val
            115                 120                 125

Tyr Leu Asn Gln Asp Lys Ala Leu Glu Ser Leu Leu Ser Val Met Leu
    130                 135                 140

Gln Glu Arg Glu Ser Ser Trp Ala Ser Ser Pro Gly Val Gln Tyr
145                 150                 155                 160

Leu Lys Lys Gln Gln Leu His Asn Glu Ile Gln Arg Asn Leu Asn Gln
                165                 170                 175

His Leu Gly Gly Met Leu Asp Glu Val Leu Ser Met Phe Gln Arg His
            180                 185                 190

Ala Thr Asp Phe Lys Ser Arg Glu Asn Thr Ala Gln Ser Ser Asp Ile
            195                 200                 205

His Gly Thr Ser Ile Leu His Trp Ala Phe Leu Ile Pro Arg Val Val
            210                 215                 220

Ser Ser Ile Phe Lys Glu Gln Val Asp Leu Met Asn Ala Lys Tyr Asn
225                 230                 235                 240

Pro Phe Gly Leu His Phe Val Leu Thr Gly Pro Trp Pro Ala Tyr Ser
```

-continued

```
                245                 250                 255
Phe Cys Thr Leu Gln Ser Val Glu Ala Pro
            260                 265

<210> SEQ ID NO 290
<211> LENGTH: 240
<212> TYPE: PRT
<213> ORGANISM: Lyngbya confervoides BDU141951

<400> SEQUENCE: 290

Met Arg Trp His Arg Ser Glu Ala Val Ile Ser Tyr Cys Asp Leu Ser
1               5                   10                  15

Met Ile Tyr Leu Tyr Ala Leu Cys Pro Asn Ser Thr Glu Thr Asn Asn
            20                  25                  30

Leu Pro Glu Gly Ile Gly Thr Ala Gln Val Glu Val Leu Thr Val Gly
        35                  40                  45

Thr Leu Gly Ala Val Ile Glu Arg Asp Val Asp Ile Ala Gln Ile Gln
    50                  55                  60

Lys Asp Asp Ala Gln Leu Met Ala Ala Val Leu Ala His Asp Arg Ile
65                  70                  75                  80

Leu Ser His Leu Phe Thr Tyr Ser Pro Leu Pro Leu Arg Phe Gly
                85                  90                  95

Thr Gln Phe Ser Asn Ser Glu Ala Val Thr Thr Phe Leu Lys Thr Gln
            100                 105                 110

Gly Glu Thr Tyr Arg Gln Lys Leu Ser His Leu Gln Asp Arg Ala Glu
        115                 120                 125

Tyr Leu Val Lys Leu Ile Pro Gln Pro Leu Asp Leu Pro Ala Ile Ala
    130                 135                 140

Ser Asp Leu Lys Gly Arg Glu Tyr Phe Leu Ala Lys Lys Gln Arg Leu
145                 150                 155                 160

Gln Asp His Thr Ala Ala Leu Asn Gln Gln Ala Asp Glu Leu Gln Thr
                165                 170                 175

Phe Leu Thr Asp Leu Ala Thr Gln Asp Ile Pro Leu Val Arg Ser Ala
            180                 185                 190

Pro Gln Asp His Glu Glu Arg Leu His Val Leu Leu Ser Arg Asp Thr
        195                 200                 205

Asp Thr Thr Glu Gln Val Ile Met Thr Trp Gln Glu Gln Leu Pro Asn
    210                 215                 220

Trp Gln Val Val Cys Ser Glu Pro Leu Pro Pro Tyr His Phe Ala Ala
225                 230                 235                 240

<210> SEQ ID NO 291
<211> LENGTH: 240
<212> TYPE: PRT
<213> ORGANISM: Octadecabacter antarcticus 307

<400> SEQUENCE: 291

Met Lys Arg Leu Tyr Val Tyr Gly Ile Val Gly Ala Thr Ser Phe Asp
1               5                   10                  15

Asp Pro Leu Pro Asn Gly His Asp Glu Ala Ser Val Phe Ala Leu Val
            20                  25                  30

Ser Gly Asp Ile Ala Val Ala Ser Phe Val Glu Ser Ala Val
        35                  40                  45

Glu Ala Ser Ala Ala Asn Val Trp Leu His Asp Asn Val Leu Ser Ala
    50                  55                  60

Leu Met Thr Arg Tyr Ala Val Leu Pro Met Arg Phe Gly Thr Ile Ala
```

```
            65                   70                  75                  80
Val Gly Ala Thr Gln Leu Leu Glu Gly Ile Val Lys Arg Gln Lys Gln
                    85                  90                  95

Leu Met Lys Asp Leu Met Arg Leu Asn Glu Asn Val Glu Ile Ala Leu
                   100                 105                 110

His Ile Ser Gly Lys Asn Trp Glu Lys Val Asn Gln Lys Val Thr Lys
                   115                 120                 125

Lys Asn Thr Asp Gln Ala Ile Thr Gln Gly Thr Ala Tyr Leu Leu Gly
                   130                 135                 140

Arg Gln Gln Ser Leu Tyr Gly Ser Asp Lys Thr Gln Leu Leu Val Gln
145                    150                 155                 160

Asn Val Arg Arg Ala Ile Arg Ser Gly Leu Asp Pro Leu Met Lys Asp
                   165                 170                 175

Val Ile Trp Pro Ile Asp Lys Pro Gln Ala Leu Pro Phe Lys Ala Ser
                   180                 185                 190

Cys Leu Ile Asn Arg Asn Asp Val Ala Ser Phe Val Gln Ile Val Asn
                   195                 200                 205

Asp Ile Ala Ala Gln Asn Leu Asp Ala Arg Val Thr Cys Thr Gly Pro
                   210                 215                 220

Trp Ala Pro Tyr Ser Phe Val Gly Lys Ser Gly Val Glu Gly Glu Thr
225                    230                 235                 240

<210> SEQ ID NO 292
<211> LENGTH: 240
<212> TYPE: PRT
<213> ORGANISM: Octadecabacter arcticus 238

<400> SEQUENCE: 292

Met Thr Lys Leu Tyr Val Tyr Gly Ile Val Gly Ala Thr His Phe Asp
1                   5                   10                  15

Val Lys Leu Pro Asn Gly His Asp Glu Ala Pro Val Phe Ala Ile Val
                    20                  25                  30

Ser Gly Asp Leu Ala Val Ala Val Ser Ser Leu Glu Arg Ser Ala Val
                    35                  40                  45

Glu Ala Ser Ala Ala Asn Val Trp Leu His Glu Asn Val Leu Ser Ala
                    50                  55                  60

Leu Met Glu Gly His Ala Val Leu Pro Met Arg Phe Gly Thr Ile Ala
65                  70                  75                  80

Thr Gly Ala Ala Gln Leu Leu Gly Asp Ile Val Lys Arg Arg Gly Gln
                    85                  90                  95

Leu Met Lys Asp Leu Thr Arg Leu Asp Gly Lys Val Glu Ile Ala Leu
                   100                 105                 110

Arg Ile Ser Gly Lys Asn Arg Glu Lys Val Glu Gln Arg Ile Ala Gly
                   115                 120                 125

Gln Ile Val Asp Thr Asn Val Thr Gln Gly Val Ala Tyr Leu Gln Glu
                   130                 135                 140

Lys Gln Gln Asn Leu Tyr Gly Ser Phe Tyr Thr Gln Ser Ser Val Gln
145                    150                 155                 160

Cys Ala Arg Arg Ala Ile Arg Ser Gln Leu Asp Pro Phe Ile Val Glu
                   165                 170                 175

Ala Ile Trp Pro Thr Asp Glu Pro Gln Met Leu Pro Phe Arg Ala Ser
                   180                 185                 190

Cys Leu Ile Lys Lys Gly Asp Ile Ala Arg Phe Val Gln Thr Val Asp
                   195                 200                 205
```

```
Asp Val Val Lys Val Ser Asp Ile Arg Val Thr Cys Thr Gly Pro
    210             215                 220
Trp Ala Pro Tyr Ser Phe Val Gly Gln Ser Gly Ser Glu Ala Glu Thr
225                 230                 235                 240
```

<210> SEQ ID NO 293
<211> LENGTH: 266
<212> TYPE: PRT
<213> ORGANISM: Pelodictyon phaeoclathratiforme

<400> SEQUENCE: 293

```
Met Val Ala Ile Gln Glu Arg Leu Ile Tyr Ile Phe Cys Val Thr Ser
1               5                   10                  15
Glu Pro Pro Leu Leu Gln Gln Tyr Gln Leu Gln Lys Gly Ile Cys Val
                20                  25                  30
Val Asp Val Asp Gly Leu Phe Val Thr Thr Met Asp Val Thr Asp Asn
            35                  40                  45
Asp Phe Ala Glu Asn Gln Leu Gln Ser Asn Leu Ser Asp Val Val Trp
        50                  55                  60
Leu Asp Thr Lys Val Arg Glu His Leu Asp Val Ile Thr Ser Ile Met
65                  70                  75                  80
Gln His Val Lys Ser Leu Ile Pro Phe Asn Phe Gly Thr Leu Tyr Lys
                85                  90                  95
Ser Glu Ser Ser Leu Met Gln Phe Ile Ile Lys Tyr Ala Glu Glu Phe
            100                 105                 110
Lys Lys Asn Leu Val Tyr Leu Glu Glu Lys Glu Glu Trp Ala Val Lys
        115                 120                 125
Leu Tyr Cys Asn Lys Asn Lys Ile Val Glu Asn Ile Thr His Leu Ser
130                 135                 140
Lys Lys Val Ser Asp Ile Asn Ala Leu Ile Gln Asn Ser Ser Ile Gly
145                 150                 155                 160
Lys Ala Tyr Ile Leu Gly Lys Lys Asn Glu Ile Ile Glu Asn Glu
                165                 170                 175
Ile Ile Asn Ile Tyr Asn Thr Tyr Ser Lys Lys Ile Phe Thr Lys Phe
            180                 185                 190
Ser Ile Leu Ser Glu Glu Phe Arg Phe Asn Pro Ile Pro Asn Asn Glu
        195                 200                 205
Thr Leu Glu Lys Glu Asp Asp Met Ile Leu Asn Val Val Leu Leu Leu
210                 215                 220
Asn Lys Ala Asn Val Glu Ser Phe Ile Glu Thr Ser Asp Gln Leu Ile
225                 230                 235                 240
Ile Gln His Gln Asn Ile Gly Leu Asn Ile Glu Ile Thr Gly Pro Trp
                245                 250                 255
Pro Cys Tyr Ser Phe Ile Asn Ile Ser His
            260                 265
```

<210> SEQ ID NO 294
<211> LENGTH: 249
<212> TYPE: PRT
<213> ORGANISM: Pelodictyon phaeoclathratiforme

<400> SEQUENCE: 294

```
Met Pro Leu Ile Ile Tyr Ala Ile Phe Asp Ser Ile Asn Tyr Ile Asp
1               5                   10                  15
Ser Phe Ser Ser Tyr Val Asp Ala Ile Ser Leu Lys Ser Lys Ile Lys
                20                  25                  30
```

```
Leu Glu Ile Ile Ser Thr Ser Thr Leu Ser Ala Ile Val Ser Arg Thr
             35                  40                  45

Thr Asp Glu Lys Lys Gln Ala Cys Gln Asn Asp Val Met Ile Tyr Ala
 50                  55                  60

Thr Ile Ile Gly Asp Ile Ala Ala Lys Tyr Ser Ile Leu Pro Met Arg
 65                  70                  75                  80

Tyr Gly Ser Ile Val Ser Ser Pro Phe Asp Val Thr Glu Leu Leu Lys
                     85                  90                  95

Asn His Asn Glu Thr Phe Val Thr Ile Ile Lys Lys Ile Thr Asp Lys
                100                 105                 110

Glu Glu Tyr Ser Leu Arg Ile Leu Tyr Ser His Gln Asp Lys Glu Lys
            115                 120                 125

Asn Asn Ile Glu Asp Leu Phe Asp Leu Pro Gln Asn Val Pro Asp Ile
130                 135                 140

Leu His Gly Asn Thr Asp Ser Lys Lys Tyr Leu Leu Asn Lys Tyr Ile
145                 150                 155                 160

Lys His Leu Ser Glu Glu Lys Arg Leu Gln Tyr Ile Asp Lys Ile Gln
                165                 170                 175

Ser Ile Val Ala Cys Asn Leu Gln Lys Ile Thr Asp Leu Ile Val Tyr
            180                 185                 190

Asn Lys Gln Thr Thr Thr Gly Phe Ile Val Asp Ala Val Phe Met Ile
        195                 200                 205

Glu Arg Ser Lys Lys Ser Glu Leu Leu Asp Leu Val Ile Gln Met Gln
210                 215                 220

Thr Leu Phe Ser Glu His Asn Val Val Leu Ser Gly Pro Trp Pro Pro
225                 230                 235                 240

Tyr Asn Phe Ser Asn Ile Asn Ile Gly
                245

<210> SEQ ID NO 295
<211> LENGTH: 270
<212> TYPE: PRT
<213> ORGANISM: Psychromonas ingrahamii 37

<400> SEQUENCE: 295

Met Lys Asn Ser Asn His Ser Gly Leu Asp Pro Asn Gln Ala Leu Tyr
 1               5                  10                  15

Leu Tyr Cys Phe Val His Ala Asp Ser Ile Gln Ser Val Thr Ser Gln
             20                  25                  30

Ala Ile Glu Lys Asp Ser Pro Val Phe Ile Tyr Gln Trp Gln Asp Ile
         35                  40                  45

Ala Ala Val Leu Ser His Val Pro Thr Ser Tyr Phe Thr Gly Tyr Asp
 50                  55                  60

Asp Glu Glu Pro Glu Gln Thr Ile Ala Arg Ile Leu Pro Arg Thr Gln
 65                  70                  75                  80

Leu His Glu Gln Val Ile Glu Glu Val Met Arg Gln Ser Pro Val Phe
                 85                  90                  95

Pro Ala Gln Phe Gly Thr Leu Phe Ser Ser Gln Glu Ser Leu Glu Gln
                100                 105                 110

Glu Ile Ser Gln Gln Tyr Leu Ala Ile Thr His Thr Leu Lys Glu Val
            115                 120                 125

Ser Gly Ser Val Glu Trp Ala Val Lys Gly Val Leu Asp Arg Gly Val
130                 135                 140

Ala Glu Lys Ala Leu Tyr Ser Gln Gln Leu Thr Glu Gln Gln Asn Ser
145                 150                 155                 160
```

```
Leu Ser Ser Ser Pro Gly Met Arg His Leu Gln Glu Gln Arg Leu Arg
            165                 170                 175

Arg Glu Thr Gln Ser Lys Leu Asn Ser Trp Leu His Gln Leu Tyr Thr
        180                 185                 190

Asp Ile Ala Thr Pro Leu Ser Glu Leu Ser Gly Asp Phe Phe Gln Arg
        195                 200                 205

Lys Ile Pro Ser Ser Ile Glu Glu Gly Lys Glu Val Ile Leu Asn Trp
        210                 215                 220

Ala Phe Leu Val Pro Glu Ser Ala Gly Asp Asp Phe His Ala Gln Ile
225                 230                 235                 240

Asp Lys Leu Asn Gln Arg Leu Asn Ser Phe Gly Leu Val Ile Gln Cys
                245                 250                 255

Ser Gly Pro Trp Pro Pro Tyr Ser Phe Cys Asn Gln Ser Ser
                260                 265                 270

<210> SEQ ID NO 296
<211> LENGTH: 270
<212> TYPE: PRT
<213> ORGANISM: Psychromonas ingrahamii 37

<400> SEQUENCE: 296

Met Lys Asn Ser Asn His Ser Gly Leu Asp Pro Asn Gln Ala Leu Tyr
1               5                   10                  15

Leu Tyr Cys Phe Val His Ala Asp Ser Ile Gln Ser Val Thr Ser Gln
            20                  25                  30

Ala Ile Glu Lys Asp Ser Pro Val Phe Ile Tyr Gln Trp Gln Asp Ile
        35                  40                  45

Ala Ala Val Leu Ser His Val Pro Thr Ser Tyr Phe Thr Gly Tyr Asp
    50                  55                  60

Asp Glu Glu Pro Glu Gln Thr Ile Ala Arg Ile Leu Pro Arg Thr Gln
65                  70                  75                  80

Leu His Glu Gln Val Ile Glu Glu Val Met Arg Gln Ser Pro Val Phe
                85                  90                  95

Pro Ala Gln Phe Gly Thr Leu Phe Ser Ser Gln Glu Ser Leu Glu Gln
            100                 105                 110

Glu Ile Ser Gln Gln Tyr Leu Ala Ile Thr His Thr Leu Lys Glu Val
        115                 120                 125

Ser Gly Ser Val Glu Trp Ala Val Lys Gly Val Leu Asp Arg Gly Val
    130                 135                 140

Ala Glu Lys Ala Leu Tyr Ser Gln Gln Leu Thr Glu Gln Gln Asn Ser
145                 150                 155                 160

Leu Ser Ser Ser Pro Gly Met Arg His Leu Gln Glu Gln Arg Leu Arg
                165                 170                 175

Arg Glu Thr Gln Ser Lys Leu Asn Ser Trp Leu His Gln Leu Tyr Thr
            180                 185                 190

Asp Ile Ala Thr Pro Leu Ser Glu Leu Ser Gly Asp Phe Phe Gln Arg
        195                 200                 205

Lys Ile Pro Ser Ser Ile Glu Glu Gly Lys Glu Val Ile Leu Asn Trp
    210                 215                 220

Ala Phe Leu Val Pro Glu Ser Ala Gly Asp Asp Phe His Ala Gln Ile
225                 230                 235                 240

Asp Lys Leu Asn Gln Arg Leu Asn Ser Phe Gly Leu Val Ile Gln Cys
                245                 250                 255

Ser Gly Pro Trp Pro Pro Tyr Ser Phe Cys Asn Gln Ser Ser
```

<210> SEQ ID NO 297
<211> LENGTH: 262
<212> TYPE: PRT
<213> ORGANISM: Serratia sp. ATCC 39006

<400> SEQUENCE: 297

Met Thr Met Asn Thr Glu Ala Gln Thr Glu Gln Ala Ile Tyr Leu Tyr
1               5                   10                  15

Gly Leu Thr Leu Pro Asp Leu Ala Ala Pro Pro Ile Leu Gly Val Asp
            20                  25                  30

Asn Gln His Pro Ile Asn Thr His Gln Cys Ala Gly Leu Asn Ala Val
        35                  40                  45

Ile Ser Pro Val Ala Leu Ser Asp Phe Thr Gly Glu Lys Gly Glu Asp
    50                  55                  60

Asn Val Gln Asn Val Thr Trp Leu Thr Pro Arg Ile Cys Arg His Ala
65                  70                  75                  80

Gln Ile Ile Asp Ser Leu Met Ala Gln Gly Pro Val Tyr Pro Leu Pro
                85                  90                  95

Phe Gly Thr Leu Phe Ser Ser Gln Asn Ala Leu Glu Gln Glu Met Lys
            100                 105                 110

Ser Arg Ala Thr Asp Val Phe Val Ser Leu Arg Arg Ile Thr Gly Cys
        115                 120                 125

Gln Glu Trp Ala Leu Glu Ala Thr Leu Asp Arg Lys Gln Ala Val Asp
    130                 135                 140

Val Leu Phe Thr Glu Gly Leu Asp Ser Gly Arg Phe Cys Leu Pro Glu
145                 150                 155                 160

Ala Ile Gly Arg Arg His Leu Glu Glu Gln Lys Leu Arg Arg Arg Leu
                165                 170                 175

Thr Thr Glu Leu Ser Asp Trp Leu Ala His Ala Leu Thr Ala Met Gln
            180                 185                 190

Asn Glu Leu His Pro Leu Val Arg Asp Phe Arg Ser Arg Arg Leu Leu
        195                 200                 205

Asp Asp Lys Ile Leu His Trp Ala Tyr Leu Leu Pro Val Glu Asp Val
    210                 215                 220

Ala Ala Phe Gln Gln Gln Val Ala Asp Ile Val Glu Arg Tyr Glu Ala
225                 230                 235                 240

Tyr Gly Phe Ser Phe Arg Val Thr Gly Pro Trp Ala Ala Tyr Ser Phe
                245                 250                 255

Cys Gln Pro Asp Glu Ser
            260

<210> SEQ ID NO 298
<211> LENGTH: 226
<212> TYPE: PRT
<213> ORGANISM: Stella vacuolata-ATCC-43931

<400> SEQUENCE: 298

Met Leu Tyr Leu Tyr Ala Val Leu Glu Ala Leu Pro Ala Ala Arg Thr
1               5                   10                  15

Leu Pro Ala Gly Ile Gly Gly Gly Glu Leu Leu Phe Val Glu Ala Phe
            20                  25                  30

Glu Leu Val Cys Ala Ala Ser Glu Thr Pro Glu Arg Ala Ile Ala Pro
        35                  40                  45

Glu Pro Thr Gln Val Trp Arg His Gln Gln Val Val Glu Ala Leu Ile

```
            50                  55                  60
Asp Cys Ala Ala Ala Leu Pro Leu Arg Phe Gly Thr Leu Val Glu Asp
 65                  70                  75                  80

Ala Val Ala Cys Arg Arg Leu Leu Thr Arg His Arg Glu Ala Leu Cys
                 85                  90                  95

Ala Gln Leu Asp Arg Val Arg His Cys Val Glu Phe Ala Leu Arg Val
                100                 105                 110

Ser Gly Leu Arg Glu Glu Val Gly Ser Asp His Val Ile Gly Gly Gly
            115                 120                 125

Pro Gly Val Ser Tyr Met Arg Ala Leu Ala Arg Arg Glu Ala Ser Trp
        130                 135                 140

Pro Pro Ser Thr Gly Thr Phe Pro His Asp Gly Leu Ala Ala His Ala
145                 150                 155                 160

Ala Asp Arg Leu Leu Trp Ser Arg Ser Ala Ser Gln Pro Asp Leu Arg
                165                 170                 175

Ala Ser Phe Leu Val Leu Lys Pro Asn Val Ala Ala Phe Leu Ala Asp
                180                 185                 190

Val Ser Ala Leu Gln Arg Met Arg Pro Asp Leu Gly Ile Thr Cys Thr
            195                 200                 205

Gly Pro Trp Pro Pro Tyr Ser Phe Ser Asp Pro Asp Leu Ser Gly Met
        210                 215                 220

Ser Pro
225

<210> SEQ ID NO 299
<211> LENGTH: 250
<212> TYPE: PRT
<213> ORGANISM: Thiocapsa rosea strain DSM 235 Ga0242571-11

<400> SEQUENCE: 299

Met Asp Ala Phe Tyr Cys Phe Cys Phe Ala Pro Ala Cys Leu Ala Ser
  1               5                  10                  15

Asp Leu Arg Phe Asp Asp Cys Gly Trp Glu Asp Pro Ile Glu Ile Arg
                 20                  25                  30

Arg Leu Ala Gly Leu Asp Val Ile Leu Ser Arg Val Pro Leu Gly Arg
             35                  40                  45

Phe Ala Gly Ala Glu Ala Glu Gln Arg Leu Ala Asp Leu Glu Trp Leu
         50                  55                  60

Val Pro Arg Ala Gln Ala His Asp Arg Val Ile Thr Arg Thr Met Glu
 65                  70                  75                  80

Arg Ser Thr Val Phe Pro Leu Thr Phe Ala Thr Leu Phe Ser Ser Leu
                 85                  90                  95

Pro Ala Leu Ala Leu Glu Val Ala Ala Arg Arg Ala Leu Leu Asp
                100                 105                 110

Phe Phe Glu Arg Met Ala Gly Arg Glu Glu Trp Ala Val Lys Val Ser
            115                 120                 125

Met Asp Arg Glu Arg Val Ile Ala Thr Arg Met Gln Ser Leu Tyr Pro
        130                 135                 140

Glu Gly Gly Asp Val Pro Ala Gly Gly Arg Gly Tyr Leu Leu Lys Gln
145                 150                 155                 160

Arg Arg Arg Gly Glu Ala Glu Gln Ala Ile Gly Pro Trp Leu Lys Gly
                165                 170                 175

Gln Ile Gly Cys Leu Asp Glu Ala Leu Arg Pro Ser Cys Glu Thr Leu
            180                 185                 190
```

```
Leu Ile Arg Pro Leu Arg Asp Glu Met Val Ala Ser Arg Ala Cys Leu
            195                 200                 205

Val Ala Arg Asp Leu Gly Pro Ser Leu Ser Glu Ala Ile Glu Arg Ser
    210                 215                 220

Arg Glu Ala Phe Ala Asp Gln Gly Leu Asp Leu His Cys Ser Gly Pro
225                 230                 235                 240

Trp Pro Leu Tyr Ser Phe Cys Gly Thr Pro
                245                 250

<210> SEQ ID NO 300
<211> LENGTH: 225
<212> TYPE: PRT
<213> ORGANISM: Trichodesmium erythraeum IMS101

<400> SEQUENCE: 300

Met Ser Tyr Tyr Val Tyr Gly Phe Leu Tyr Leu Pro Glu Ser Cys Leu
1               5                   10                  15

Ala Leu Pro Lys Gly Met Glu Lys Glu Val Glu Leu Val Pro Tyr Gln
            20                  25                  30

Asn Ile Ala Ala Val Val Glu Ala Asn Val Ser Ile Glu Ala Ile Gln
        35                  40                  45

Glu Thr Glu Glu Lys Leu Leu Glu Ala Ile Leu Ala His Asp Arg Val
    50                  55                  60

Val Arg Glu Ile Phe Gln Gln Val Ser Met Leu Pro Leu Arg Phe Gly
65                  70                  75                  80

Asn Ala Phe Ala Leu Arg Glu Asn Ile Ile Asn Asp Leu Gln Asn Asn
                85                  90                  95

Gln Gln Gln Tyr Leu Asn Ile Leu Thr Lys Leu Gln Gln Ala Glu
            100                 105                 110

Tyr Thr Ile Thr Phe Thr Pro Val Ser Tyr Pro Ser Thr Leu Glu Val
            115                 120                 125

Ser Lys Val Arg Gly Lys Ala Tyr Leu Leu Ala Lys Lys Gln Gln Phe
    130                 135                 140

Glu Gln Gln Gln Ala Phe Gln Thr Lys Gln Arg Gln Gln Trp Glu Asn
145                 150                 155                 160

Ile Arg Gln Leu Ile Phe Lys Asn Tyr Pro Lys Ala Val Phe Arg Asp
                165                 170                 175

Ser Thr Glu Ser Lys Ile Lys Gln Val His Leu Leu Ala Asn Arg Asp
            180                 185                 190

Ala Arg Val Ile Thr Thr Glu Glu Leu Ser Thr Trp Gln Thr Glu Cys
        195                 200                 205

Ser Tyr Trp Gln Ile Thr Leu Ser Glu Gln Leu Pro Pro Tyr His Phe
    210                 215                 220

Val
225

<210> SEQ ID NO 301
<211> LENGTH: 335
<212> TYPE: PRT
<213> ORGANISM: Anabaena-flos-aquae

<400> SEQUENCE: 301

Met Thr Thr Thr Lys Val Asn His Lys Arg Ala Val Leu Arg Leu Arg
1               5                   10                  15

Pro Gly Gln Phe Val Val Thr Pro Ala Ile Glu Arg Val Ala Ile Arg
            20                  25                  30
```

```
Ala Leu Arg Tyr Leu Lys Ser Gly Phe Pro Val His Leu Arg Gly Pro
         35                  40                  45

Ala Gly Thr Gly Lys Thr Thr Leu Ala Met His Leu Ala Asn Cys Leu
 50                  55                  60

Asp Arg Pro Val Met Leu Leu Phe Gly Asp Asp Gln Phe Lys Ser Ser
 65                  70                  75                  80

Asp Leu Ile Gly Ser Glu Ser Gly Tyr Thr His Lys Lys Val Leu Asp
                 85                  90                  95

Asn Tyr Ile His Ser Val Val Lys Leu Glu Asp Glu Phe Lys Gln Asn
             100                 105                 110

Trp Val Asp Ser Arg Leu Thr Leu Ala Cys Arg Glu Gly Phe Thr Leu
             115                 120                 125

Val Tyr Asp Glu Phe Asn Arg Ser Arg Pro Glu Val Asn Asn Val Leu
         130                 135                 140

Leu Ser Ala Leu Glu Glu Lys Ile Leu Ser Leu Pro Pro Ser Ser Asn
145                 150                 155                 160

Gln Pro Glu Tyr Leu Ser Val Asn Pro Gln Phe Arg Val Ile Phe Thr
                 165                 170                 175

Ser Asn Pro Glu Glu Tyr Ala Gly Val His Ser Thr Gln Asp Ala Leu
             180                 185                 190

Met Asp Arg Leu Val Thr Ile Ser Met Pro Glu Pro Asp Glu Ile Thr
         195                 200                 205

Gln Thr Glu Ile Leu Ile Gln Lys Thr Asn Ile Asp Arg Glu Ser Ala
     210                 215                 220

Asn Phe Ile Val Arg Leu Val Lys Ser Phe Arg Leu Ala Thr Gly Ala
225                 230                 235                 240

Glu Lys Thr Ser Gly Leu Arg Ser Cys Leu Met Ile Ala Lys Val Cys
                 245                 250                 255

Ala Asp Asn Asn Ile Pro Val Thr Thr Glu Ser Leu Asp Phe Pro Asp
             260                 265                 270

Ile Ala Ile Asp Ile Leu Phe Asn Arg Ser His Leu Ser Met Ser Glu
         275                 280                 285

Ser Thr Asn Ile Phe Leu Glu Leu Leu Asp Lys Phe Ser Ala Glu Glu
     290                 295                 300

Leu Glu Ile Leu Asn Asn Arg Val Thr Gly Asp Asn Asp Phe Leu Ile
305                 310                 315                 320

Asp Asn Ser Gln Phe Val Ser Gln Gln Leu Ala Gly Gln Pro Asn
                 325                 330                 335

<210> SEQ ID NO 302
<211> LENGTH: 357
<212> TYPE: PRT
<213> ORGANISM: Ancylobacter aquaticus strain UV5

<400> SEQUENCE: 302

Met Thr Ser Glu Ala Ala Ser Lys Asp Pro Ile Ser Leu Leu Ser Gly
 1               5                  10                  15

Phe Gly Ala Gly Ala Ala Ser Ser Gly Pro Lys Ala Gly Gly Arg Ser
                 20                  25                  30

Thr Pro Ser Ala Leu Thr Pro Arg Pro Arg Thr Gly Phe Val Glu Ala
             35                  40                  45

Glu Gln Val Arg Asp Leu Thr Arg Arg Gly Leu Gly Phe Leu Asn Ala
         50                  55                  60

Gly Tyr Pro Leu His Phe Arg Gly Pro Ala Gly Thr Gly Lys Thr Thr
 65                  70                  75                  80
```

```
Leu Ala Leu His Val Ala Ala Gln Leu Gly Arg Pro Val Ile Ile Ile
                85                  90                  95

Thr Gly Asp Asn Glu Leu Gly Thr Ala Asp Leu Val Gly Ser Gln Arg
            100                 105                 110

Gly Tyr His Tyr Arg Lys Val Val Asp Gln Phe Ile His Asn Val Thr
        115                 120                 125

Lys Leu Glu Glu Thr Ala Asn Gln His Trp Thr Asp His Arg Leu Thr
130                 135                 140

Thr Ala Cys Arg Glu Gly Phe Thr Leu Val Tyr Asp Glu Phe Thr Arg
145                 150                 155                 160

Ser Arg Pro Glu Thr His Asn Val Leu Leu Gly Val Phe Glu Glu Arg
                165                 170                 175

Met Leu Phe Leu Pro Ala Gln Ala Arg Glu Glu Cys Tyr Ile Lys Val
            180                 185                 190

His Pro Glu Phe Arg Ala Ile Phe Thr Ser Asn Pro Gln Glu Tyr Ala
        195                 200                 205

Gly Val His Ala Ser Gln Asp Ala Leu Ala Asp Arg Leu Ala Thr Ile
210                 215                 220

Asp Val Asp Tyr Pro Asp Arg Ala Met Glu Leu Ala Val Ala Ser Ala
225                 230                 235                 240

Arg Thr Gly Met Pro Glu Ala Ser Ala Ala Arg Ile Ile Asp Leu Val
                245                 250                 255

Arg Ala Phe Arg Ala Ser Gly Asp Tyr Gln Gln Thr Pro Thr Met Arg
            260                 265                 270

Ala Gly Leu Met Ile Ala Arg Val Ala Gln Glu Gly Phe Glu Val
        275                 280                 285

Ser Val Asp Asp Pro Arg Phe Val Gln Leu Cys Ser Asp Ala Leu Glu
290                 295                 300

Ser Arg Ile Phe Ser Gly Gln Arg Ala Glu Glu Val Ala Arg Glu Gln
305                 310                 315                 320

Arg Arg Ala Ala Leu His Ala Leu Ile Asp Thr His Cys Pro Ser Ala
                325                 330                 335

Ala Lys Pro Arg Ala Arg Arg Ala Gly Gly Ala Val Arg Ala Ser Ile
            340                 345                 350

Glu Gly Ala Gln Ser
        355

<210> SEQ ID NO 303
<211> LENGTH: 359
<212> TYPE: PRT
<213> ORGANISM: Aphanizomenon flos-aquae NIES-81

<400> SEQUENCE: 303

Met Thr Lys Thr Asn His Lys Arg Ala Val Leu Arg Val Arg Pro Gly
1               5                   10                  15

Gln Phe Val Val Thr Pro Ala Ile Glu Gln Val Ala Ile Arg Ala Leu
            20                  25                  30

Leu Tyr Leu Lys Ser Gly Phe Pro Ile His Leu Arg Gly Pro Ala Gly
        35                  40                  45

Thr Gly Lys Thr Thr Leu Ala Leu His Leu Ala His Cys Leu Asp Arg
    50                  55                  60

Pro Val Met Leu Leu Phe Gly Asp Asp Glu Phe Lys Ser Ser Asp Leu
65                  70                  75                  80

Ile Gly Ser Glu Ser Gly Tyr Thr His Lys Lys Leu Leu Asp Asn Tyr
```

```
                            85                  90                  95
Ile His Ser Val Val Lys Val Glu Asp Glu Phe Lys Gln Asn Trp Val
                100                 105                 110

Asp Ser Arg Leu Thr Leu Ala Cys Arg Glu Gly Phe Thr Leu Val Tyr
                115                 120                 125

Asp Glu Phe Asn Arg Ser Arg Pro Glu Val Asn Asn Val Leu Leu Ser
                130                 135                 140

Ala Leu Glu Glu Lys Ile Leu Ser Leu Pro Pro Ser Ser Asn Gln Pro
145                 150                 155                 160

Glu Tyr Leu Ser Val Ser Pro Gln Phe Arg Ala Ile Phe Thr Ser Asn
                165                 170                 175

Pro Glu Glu Tyr Cys Gly Val His Ser Thr Gln Asp Ala Leu Met Asp
                180                 185                 190

Arg Leu Val Thr Ile Asn Met Pro Glu Pro Asp Glu Ile Thr Gln Thr
                195                 200                 205

Glu Ile Leu Ile Gln Lys Thr Asn Ile Gln Lys Glu Ser Ala His Leu
                210                 215                 220

Ile Val Arg Leu Val Lys Ser Phe Arg Ile Ala Thr Gly Ala Glu Lys
225                 230                 235                 240

Thr Ser Gly Leu Arg Ser Cys Leu Met Ile Ala Lys Val Cys Ala Asp
                245                 250                 255

Asn Asn Leu Val Ala Glu Pro Glu Asn Ser Phe Phe Gln Glu Ile Ala
                260                 265                 270

Met Glu Ile Leu Ser Asn Arg Thr His Leu Ser Val Asn Glu Ser Thr
                275                 280                 285

Asp Ile Phe Leu Asp Val Ile Ser Gln Phe Ser Asn Lys Glu Ile Glu
                290                 295                 300

Ile Leu Asn Asp Ala Glu Leu Gly Ser Leu Pro Thr Met Asp Thr Leu
305                 310                 315                 320

Ala Asn Thr Asp Leu Gly Asn Asp Val Pro Leu Glu Lys Glu Ala Ser
                325                 330                 335

Asp Tyr Val Ile Gln Gln Lys Asn Asn Glu Phe Lys Gly Phe Gln Lys
                340                 345                 350

Pro Ser Thr Lys Val Leu Asn
                355

<210> SEQ ID NO 304
<211> LENGTH: 337
<212> TYPE: PRT
<213> ORGANISM: Aphanothece halophytica (strain PCC 7418)

<400> SEQUENCE: 304

Met Thr Thr Val Leu His Ala Arg Pro Lys Gly Phe Val Ser Thr Pro
1               5                   10                  15

Thr Ile Asp Arg Ile Ser Arg Arg Ala Trp Arg Tyr Leu Gln Ser Gly
                20                  25                  30

Phe Ser Ile His Leu Arg Gly Pro Ala Gly Thr Gly Lys Thr Thr Leu
                35                  40                  45

Ala Met His Leu Ala Asp Leu Leu Asn Arg Pro Ile Met Leu Leu Tyr
                50                  55                  60

Gly Asp Asp Glu Phe Lys Ser Thr Asp Leu Ile Gly Ser Asn Thr Gly
65                  70                  75                  80

Tyr Thr Arg Lys Lys Val Val Asp Asn Tyr Ile His Ser Val Val Lys
                85                  90                  95
```

Glu Glu Asp Glu Leu Arg Gln Gln Trp Val Asp Ser Arg Leu Thr Met
            100                 105                 110

Ala Cys Arg Glu Gly Phe Thr Leu Val Tyr Asp Glu Phe Asn Arg Ser
        115                 120                 125

Pro Pro Glu Val Asn Asn Val Leu Leu Ser Ala Leu Glu Glu Lys Leu
    130                 135                 140

Leu Val Leu Pro Pro Asp Ser His Arg Ser Glu Tyr Val Arg Val Ser
145                 150                 155                 160

Pro Asn Phe Arg Ala Ile Phe Thr Ser Asn Pro Glu Glu Tyr Trp Gly
                165                 170                 175

Val His Gly Thr Gln Asp Ala Leu Leu Asp Arg Val Val Thr Ile Asn
            180                 185                 190

Val Pro Glu Pro Asp Leu Glu Thr Gln Arg Glu Ile Ile Val Gln Lys
        195                 200                 205

Val Gly Ile Asn Ala Asp Asp Gly Asp Met Ile Val Asn Phe Val Arg
    210                 215                 220

Asn Phe Arg Asp Arg Ala Glu Met Glu Asn Ser Ser Gly Leu Arg Ser
225                 230                 235                 240

Cys Leu Met Ile Ala Gln Val Cys His Gln His Glu Ile Pro Val Gln
                245                 250                 255

Thr Ser Asn Glu Asp Phe Gln Asp Ile Cys Tyr Asp Ile Leu Thr Ser
            260                 265                 270

Arg Cys Pro Leu Ser Thr Gln Glu Ser Ile Ser Leu Leu Glu Gln Leu
        275                 280                 285

Phe Arg Glu Tyr Glu Leu Glu Leu Val Val Asp Glu Asp Glu Asp
    290                 295                 300

Val Pro Ser Val Ile Val Glu Gly Glu Thr Glu Asp Leu Ser Ser Asp
305                 310                 315                 320

Glu Lys Pro His Leu Arg Leu Ser His Pro Phe Gly Asn Thr Glu Asn
                325                 330                 335

Asp

<210> SEQ ID NO 305
<211> LENGTH: 364
<212> TYPE: PRT
<213> ORGANISM: Aquabacter spiritensis strain DSM 9035

<400> SEQUENCE: 305

Met Ser Thr Glu Pro Ala Pro Leu Val Ser Pro Ser Gln Asp Val Glu
1               5                   10                  15

Thr Thr Pro Gln Arg Pro Ala Arg Pro Glu Pro Ala Glu Ala Leu Ala
            20                  25                  30

Val Gly Tyr Arg Leu Ser Ala Arg Pro Ala Ser Pro Ala Thr Leu Thr
        35                  40                  45

Pro Arg Pro Arg Ala Asp Phe Val Glu Thr Asp Gln Val Lys Asp Leu
    50                  55                  60

Thr Arg Arg Gly Leu Gly Phe Leu Arg Ala Gly Tyr Pro Leu His Phe
65                  70                  75                  80

Arg Gly Pro Ala Gly Thr Gly Lys Thr Thr Leu Ala Leu His Val Ala
                85                  90                  95

Ala Gln Leu Gly Arg Pro Val Ile Val Ile Thr Gly Asp Asn Glu Leu
            100                 105                 110

Gly Thr Ala Asp Leu Val Gly Ser Gln Arg Gly Tyr His Tyr Arg Lys
        115                 120                 125

```
Val Val Asp Gln Phe Ile His Asn Val Thr Lys Leu Glu Glu Thr Ala
    130                 135                 140

Asn Gln Arg Trp Thr Asp His Arg Leu Thr Thr Ala Cys Arg Glu Gly
145                 150                 155                 160

Tyr Thr Leu Val Tyr Asp Glu Phe Thr Arg Ser Arg Pro Glu Thr His
                165                 170                 175

Asn Val Leu Leu Gly Val Phe Glu Glu Lys Ile Leu Phe Leu Pro Ala
                180                 185                 190

Gln Ala Arg Glu Glu Cys Tyr Ile Arg Val His Pro Asp Phe Arg Ala
            195                 200                 205

Ile Phe Thr Ser Asn Pro Gln Glu Tyr Ala Gly Val His Ala Ser Gln
    210                 215                 220

Asp Ala Leu Ala Asp Arg Leu Ala Thr Ile Asp Val Asp Tyr Pro Asp
225                 230                 235                 240

Arg Gly Met Glu Leu Ala Val Ala Ser Ala Arg Thr Gly Leu Gly Glu
                245                 250                 255

Thr Glu Ala Ala Arg Ile Ile Asp Leu Val Arg Ala Phe Arg Ala Ser
                260                 265                 270

Gly Asp Tyr Gln Gln Thr Pro Thr Met Arg Ala Ser Leu Met Ile Ala
            275                 280                 285

Arg Val Ala Ala Gln Glu Gly Leu Arg Val Ser Ile Asp Asp Pro Gly
290                 295                 300

Phe Val Gln Leu Cys Met Asp Ala Leu Glu Ser Arg Met Phe Ser Gly
305                 310                 315                 320

Ala Arg Leu Glu Ala Ala Thr Arg Glu Thr Ser Arg Ala Ala Leu Leu
                325                 330                 335

Ala Leu Leu Ala Val His Cys Pro Ser Glu Ala Pro Ile Val Arg Val
                340                 345                 350

Thr Ala Ala Arg Arg Ala Lys Lys Ala Asp Ala Ser
                355                 360

<210> SEQ ID NO 306
<211> LENGTH: 394
<212> TYPE: PRT
<213> ORGANISM: Arthrospira platensis NIES-39

<400> SEQUENCE: 306

Met Thr Thr Val Leu Arg Ala Val Pro Lys Gly Phe Val Asn Thr Pro
1               5                   10                  15

Ala Ile Glu Arg Ile Thr Val Arg Ala Leu Arg Tyr Leu Gln Ser Gly
            20                  25                  30

Phe Ser Val His Leu Arg Gly Pro Ala Gly Thr Gly Lys Thr Thr Leu
        35                  40                  45

Ala Leu His Leu Ala Asp Leu Leu Asn Arg Pro Ile Met Leu Ile Phe
    50                  55                  60

Gly Asp Asp Glu Leu Lys Ser Ser Asp Met Ile Gly Asn Gln Thr Gly
65                  70                  75                  80

Tyr Thr Arg Lys Lys Val Val Asp Asn Phe Ile His Ser Val Val Lys
                85                  90                  95

Leu Glu Asp Ser Leu Lys Gln Asn Trp Ile Asp Ser Arg Leu Thr Leu
            100                 105                 110

Ala Cys Arg Glu Gly Phe Thr Leu Val Tyr Asp Glu Phe Asn Arg Ser
        115                 120                 125

Arg Pro Glu Val Asn Asn Val Leu Leu Ser Ala Leu Glu Glu Lys Leu
    130                 135                 140
```

Leu Val Leu Pro Pro Asn Asn Ser Arg Ser Glu Tyr Ile Arg Val Asn
145                 150                 155                 160

Pro His Phe Arg Ala Ile Phe Thr Ser Asn Pro Glu Glu Tyr Cys Gly
                165                 170                 175

Val Tyr Ser Thr Gln Asp Ala Leu Leu Asp Arg Leu Ile Thr Met Asn
            180                 185                 190

Met Pro Glu Pro Asp Glu Ala Thr Gln Gln Glu Ile Leu Ile Gln Lys
        195                 200                 205

Val Ala Val Thr Pro Glu Glu Ala Gln Thr Ile Val Thr Leu Val Gln
    210                 215                 220

Gln Phe Arg Glu Ala Thr His Ala Ile Ala Pro Ser Lys Ile Gln Thr
225                 230                 235                 240

Val Ala Arg Gln Gln Thr Asn Ala Asp Lys Ala Ser Gly Leu Arg Pro
                245                 250                 255

Ser Leu Met Leu Ala Arg Ile Cys Gln Glu His Asn Ile Pro Ile Val
            260                 265                 270

Pro Ile Asp Pro Asp Phe Gln Glu Val Cys Arg Asp Ile Leu Leu Ser
        275                 280                 285

Arg Ala Ile Gly Asp Ile Thr Glu Leu Glu Ser Arg Leu His Gln Ile
    290                 295                 300

Phe Asp His Leu Ser Gly Leu Glu Asn Asp Gln Ile Ile Ala Leu Pro
305                 310                 315                 320

Pro Arg Glu Glu Leu Thr Thr Ser Ser Val Pro Asn Asn Leu Ser Asp
                325                 330                 335

Thr Glu Gln Lys Ile Tyr Thr Tyr Ile Lys Asp Ser Asp Gly Ala Arg
            340                 345                 350

Val Ser Glu Ile Glu Ile Ala Leu Gly Leu Asn Arg Val Gln Thr Thr
        355                 360                 365

Asp Ala Leu Arg Ser Leu Leu Arg Lys Ser Tyr Leu Thr Gln Gln Asp
    370                 375                 380

Asn Arg Leu Phe Val Val Tyr Glu Gly Asp
385                 390

<210> SEQ ID NO 307
<211> LENGTH: 308
<212> TYPE: PRT
<213> ORGANISM: Bacillus-megaterium

<400> SEQUENCE: 307

Met Thr Val Leu Thr Asp Lys Arg Lys Lys Gly Ser Gly Ala Phe Ile
1               5                   10                  15

Gln Asp Asp Glu Thr Lys Glu Val Leu Ser Arg Ala Leu Ser Tyr Leu
            20                  25                  30

Lys Ser Gly Tyr Ser Ile His Phe Thr Gly Pro Ala Gly Gly Gly Lys
        35                  40                  45

Thr Ser Leu Ala Arg Ala Leu Ala Lys Lys Arg Lys Arg Pro Val Met
    50                  55                  60

Leu Met His Gly Asn His Glu Leu Asn Asn Lys Asp Leu Ile Gly Asp
65                  70                  75                  80

Phe Thr Gly Tyr Thr Ser Lys Lys Val Ile Asp Gln Tyr Val Arg Ser
                85                  90                  95

Val Tyr Lys Lys Asp Glu Gln Val Ser Glu Asn Trp Gln Asp Gly Arg
            100                 105                 110

Leu Leu Glu Ala Val Lys Asn Gly Tyr Thr Leu Ile Tyr Asp Glu Phe

```
            115                 120                 125
Thr Arg Ser Lys Pro Ala Thr Asn Asn Ile Phe Leu Ser Ile Leu Glu
130                 135                 140

Glu Gly Val Leu Pro Leu Tyr Gly Val Lys Met Thr Asp Pro Phe Val
145                 150                 155                 160

Arg Val His Pro Asp Phe Arg Val Ile Phe Thr Ser Asn Pro Ala Glu
                165                 170                 175

Tyr Ala Gly Val Tyr Asp Thr Gln Asp Ala Leu Leu Asp Arg Leu Ile
            180                 185                 190

Thr Met Phe Ile Asp Tyr Lys Asp Ile Asp Arg Glu Thr Ala Ile Leu
        195                 200                 205

Thr Glu Lys Thr Asp Val Glu Glu Asp Glu Ala Arg Thr Ile Val Thr
210                 215                 220

Leu Val Ala Asn Val Arg Asn Arg Ser Gly Asp Glu Asn Ser Ser Gly
225                 230                 235                 240

Leu Ser Leu Arg Ala Ser Leu Met Ile Ala Thr Leu Ala Thr Gln Gln
                245                 250                 255

Asp Ile Pro Ile Asp Gly Ser Asp Glu Asp Phe Gln Thr Leu Cys Ile
            260                 265                 270

Asp Ile Leu His His Pro Leu Thr Lys Cys Leu Asp Glu Glu Asn Ala
        275                 280                 285

Lys Ser Lys Ala Glu Lys Ile Ile Leu Glu Glu Cys Lys Asn Ile Asp
290                 295                 300

Thr Glu Glu Lys
305

<210> SEQ ID NO 308
<211> LENGTH: 351
<212> TYPE: PRT
<213> ORGANISM: Bradyrhizobium oligotrophicum S58

<400> SEQUENCE: 308

Met Leu Arg Ser Asp Arg Ala Ala Ile Ala Gly Gly Gln Arg Gly Ser
1               5                   10                  15

Arg Ala Gln Gly Asp Ala Val Ala Arg Asn Asp Ala Ala Ala Gly Ser
                20                  25                  30

Arg Ala Ala Ile Ala Gln Ile Ser Pro Arg Pro Asp Ala Asp Asn Ala
            35                  40                  45

Ala Leu Ser Pro Ala Pro Arg Thr Asp Leu Phe Glu Asn Pro Gln Leu
        50                  55                  60

Ala Ser Met Ala Ala Arg Ala Leu Thr Tyr Leu Asn Ala Gly Ile Pro
65                  70                  75                  80

Val His Leu Arg Gly Pro Ala Gly Thr Gly Lys Thr Thr Met Ala Met
                85                  90                  95

Gln Leu Ala Ala Arg Leu Gly Arg Pro Val Val Leu Leu Thr Gly Asp
            100                 105                 110

Asp Gly Leu Thr Ala Ala His Leu Val Gly Arg Glu Ile Gly Thr Lys
        115                 120                 125

Ser Arg Gln Val Val Asp Arg Tyr Val His Ser Val Arg Arg Val Glu
130                 135                 140

Thr Glu Thr Ser Ser Met Trp Cys Asp Ala Val Leu Ala Gln Ala Val
145                 150                 155                 160

Val Glu Gly Leu Thr Phe Val Tyr Asp Glu Phe Thr Arg Ser Pro Pro
                165                 170                 175
```

```
Gln Ala Asn Asn Pro Leu Leu Ser Val Val Glu Glu Arg Ile Leu Ile
            180                 185                 190

Phe Pro Ala Gly Ser Arg Lys Glu Arg Leu Val His Ala His Pro Glu
        195                 200                 205

Phe Arg Ala Ile Leu Thr Ser Asn Pro Glu Glu Tyr Ala Gly Val Ser
    210                 215                 220

Arg Pro Gln Asp Ala Leu Leu Asp Arg Leu Ile Thr Phe Asp Leu Asp
225                 230                 235                 240

Asp Tyr Asp Arg Glu Thr Glu Ile Gly Ile Val Ser Asn Arg Thr Gly
                245                 250                 255

Leu Ala Tyr Ala Glu Ala Gly Val Ile Val Asp Leu Val Arg Gly Val
            260                 265                 270

Arg Arg Trp Pro Lys Ala His His Pro Pro Ser Met Arg Ser Ala Ile
        275                 280                 285

Met Ile Ala Arg Ile Val Ala Arg Glu Leu Ile Thr Pro Ser Val Asp
    290                 295                 300

Asp Pro Arg Phe Val Arg Leu Cys Leu Asp Val Leu Ala Ala Lys Ala
305                 310                 315                 320

Lys Pro Thr Asp Arg Asp Asp Arg Asp Arg Phe Ala Ala Thr Leu Leu
                325                 330                 335

Arg Leu Met Asn Asn His Cys Pro Ala Gly Ala Ile Asp Gly Gly
            340                 345                 350

<210> SEQ ID NO 309
<211> LENGTH: 287
<212> TYPE: PRT
<213> ORGANISM: Burkholderia thailandensis sp. Bp5365 strain MSMB43

<400> SEQUENCE: 309

Met Glu Ala Ser Ala Glu Phe Val Gln Thr Pro Ala Val Arg Asn Leu
1               5                   10                  15

Thr Glu Arg Ala Leu Thr Tyr Leu Gly Ala Gly Tyr Gly Val His Leu
            20                  25                  30

Ala Gly Pro Ser Gly Thr Gly Lys Thr Thr Leu Ala Phe His Ile Ala
        35                  40                  45

Ala Gln Leu Gly Arg Gln Val Val Leu Met His Gly Asp Asp Glu Leu
    50                  55                  60

Gly Ser Ala Asp Leu Val Gly Arg Gly Ala Gly Tyr Arg Arg Ser Arg
65                  70                  75                  80

Val Val Asp Asn Phe Ile His Ser Val Val Lys Thr Glu Gly Glu Met
                85                  90                  95

Thr Thr Thr Trp Ile Asp Asn Arg Leu Thr Thr Ala Cys Gln His Gly
            100                 105                 110

Leu Thr Leu Ile Tyr Asp Glu Phe Asn Arg Ser Arg Pro Glu Ala Asn
        115                 120                 125

Asn Ala Leu Leu Pro Val Leu Ser Glu Gly Ile Leu Asn Leu Pro Asn
    130                 135                 140

Arg Met Thr Gly Ala Gly Tyr Leu Thr Val His Pro Gly Phe Arg Ala
145                 150                 155                 160

Ile Phe Thr Ser Asn Pro Glu Glu Tyr Val Gly Val His Lys Thr Gln
                165                 170                 175

Asn Ala Leu Met Gly Arg Leu Ile Thr Ile Gln Val Gly His Tyr Asp
            180                 185                 190

Arg Glu Thr Glu Val Glu Ile Val Arg Ala Arg Ser Gly Ile Ala Arg
        195                 200                 205
```

Ala Asp Ala Glu Arg Ile Val Asp Leu Thr Arg Arg Leu Arg Asp Ala
    210                 215                 220

Asp Asp Asn Gly His His Pro Ser Ile Arg Ala Ala Ile Ala Leu Ala
225                 230                 235                 240

Arg Ala Leu Ser Tyr Cys Gly Gly Glu Ala Thr Pro Asp Asn Ala Gly
            245                 250                 255

Tyr Val Trp Ala Cys Arg Asp Ile Leu Gly Val Asp Leu Glu Gln Asp
                260                 265                 270

Ala Arg Thr Arg Ser Gln Ala Gly Arg Arg Thr Lys Ala Arg Arg
            275                 280                 285

<210> SEQ ID NO 310
<211> LENGTH: 308
<212> TYPE: PRT
<213> ORGANISM: Chlorobium luteolum DSM 273

<400> SEQUENCE: 310

Met Arg Ala Ala Val Asn Asp Asn Glu Met Asn Thr Val Leu Ala Pro
1               5                   10                  15

Arg Pro Met Ala Asn Phe Val Glu Thr Glu Tyr Ile Arg Asp Ile Thr
            20                  25                  30

Glu Arg Gly Leu Thr Tyr Leu Lys Ala Gly Phe Pro Val His Phe Arg
        35                  40                  45

Gly Pro Ser Gly Thr Gly Lys Thr Thr Val Ala Met His Leu Ala Gly
    50                  55                  60

Lys Ile Gly Arg Pro Val Val Ile His Gly Asp Ser Glu Tyr Lys
65                  70                  75                  80

Thr Ser Asp Leu Ile Gly Ser Glu Gln Gly Tyr Lys Phe Arg Arg Leu
                85                  90                  95

Asn Asp Asn Phe Ile His Ser Val His Lys Tyr Glu Glu Asp Met Ser
            100                 105                 110

Lys Gln Trp Val Asn Asn Arg Leu Ser Ile Ala Ile Lys Lys Gly Phe
        115                 120                 125

Thr Leu Val Tyr Asp Glu Phe Thr Arg Ser Arg Pro Glu Ala Asn Asn
    130                 135                 140

Ile Leu Leu Pro Ile Leu Gln Glu Lys Met Leu Ser Thr Ser Ala Ser
145                 150                 155                 160

Asn Glu Glu Asp Tyr Tyr Met Lys Val His Pro Glu Phe Arg Ala Ile
                165                 170                 175

Phe Thr Ser Asn Pro Glu Glu Tyr Ala Gly Val Asn Arg Thr Gln Asp
            180                 185                 190

Ala Leu Arg Asp Arg Met Val Thr Met Asp Leu Asp Tyr Phe Asp Tyr
        195                 200                 205

Glu Thr Glu Leu Arg Val Thr His Ala Lys Ser Glu Leu Thr Leu Glu
    210                 215                 220

Asp Ser Glu Lys Ile Val Gln Val Val Arg Gly Leu Arg Glu Ser Gly
225                 230                 235                 240

Lys Thr Glu Phe Asp Pro Thr Val Arg Gly Ser Ile Met Ile Ala Arg
                245                 250                 255

Thr Leu His Ile Met Gln Val Arg Pro Glu Lys Thr Asn Asp Ala Val
            260                 265                 270

Arg Lys Val Phe Gln Asp Ile Leu Thr Ser Glu Thr Ser Arg Val Gly
        275                 280                 285

Ser Lys Thr Asn Gln Glu Lys Val Arg Ala Ile Val Asn Asp Leu Ile

```
              290                 295                 300
Glu Ala Tyr Leu
305

<210> SEQ ID NO 311
<211> LENGTH: 273
<212> TYPE: PRT
<213> ORGANISM: Dactylococcopsis salina PCC 8305

<400> SEQUENCE: 311

Met Thr Thr Val Leu His Ala Arg Pro Lys Gly Phe Val Ser Thr Pro
1               5                   10                  15

Thr Ile Asp Arg Ile Ser Gly Arg Ala Trp Arg Tyr Leu Gln Ser Gly
                20                  25                  30

Phe Ser Ile His Leu Arg Gly Pro Ala Gly Thr Gly Lys Thr Thr Leu
            35                  40                  45

Ala Met His Leu Ala Asp Leu Leu Asn Arg Pro Ile Met Leu Leu Tyr
        50                  55                  60

Gly Asp Asp Glu Phe Lys Ser Thr Asp Leu Ile Gly Ser Asn Thr Gly
65                  70                  75                  80

Tyr Thr Arg Lys Lys Val Val Asp Asn Tyr Ile His Ser Val Val Lys
                85                  90                  95

Glu Glu Asp Glu Leu Arg Gln Gln Trp Val Asp Ser Arg Leu Thr Met
            100                 105                 110

Ala Cys Arg Glu Gly Phe Thr Leu Val Tyr Asp Glu Phe Asn Arg Ser
        115                 120                 125

Pro Pro Glu Val Asn Asn Val Leu Leu Ser Ala Leu Glu Glu Lys Leu
130                 135                 140

Leu Val Leu Pro Pro Asp Ser Asn Arg Ser Glu Tyr Val Arg Val Ser
145                 150                 155                 160

Pro Asn Phe Arg Ala Ile Phe Thr Ser Asn Pro Glu Glu Tyr Trp Gly
                165                 170                 175

Val His Gly Thr Gln Asp Ala Leu Leu Asp Arg Val Val Thr Ile Asn
            180                 185                 190

Val Pro Glu Pro Asp Leu Glu Thr Gln Gln Ile Ile Thr Gln Lys
        195                 200                 205

Val Gly Ile Asn Ala Asn Asp Gly Glu Lys Ile Val Asn Phe Val Arg
210                 215                 220

Gln Phe Arg Asp Arg Ala Ala Val Lys Asn Ser Ser Gly Leu Arg Ser
225                 230                 235                 240

Cys Leu Met Ile Ala Gln Val Cys His Gln His Glu Ile Pro Val Gln
                245                 250                 255

Thr Ser Asp Glu Gly Phe Arg Asp Ile Cys Tyr Asp Ile Leu Ser Ser
            260                 265                 270

Arg

<210> SEQ ID NO 312
<211> LENGTH: 316
<212> TYPE: PRT
<213> ORGANISM: Desulfobacterium vacuolatum_DSM 3385

<400> SEQUENCE: 312

Met Ser Ala Ser Met Ser Ser Met Lys Glu Thr Arg Gln Arg Met Ser
1               5                   10                  15

Ala Pro Glu Gln Asp Asn Val Val Pro Glu Ala Gly Ser Asp Phe Val
                20                  25                  30
```

-continued

```
Glu Thr Pro Tyr Val Lys Asp Ile Thr Asp Arg Ala Leu Ala Tyr Leu
             35                  40                  45

His Val Gly Tyr Pro Val His Phe Ser Gly Pro Ala Gly Thr Gly Lys
         50                  55                  60

Thr Thr Leu Ala Phe His Val Ala Ala Lys Leu Lys Arg Thr Val Met
65                  70                  75                  80

Leu Ile His Gly Asp Asp Glu Phe Gly Ser Ser Asp Leu Ile Gly Lys
                 85                  90                  95

Asp Ser Gly Tyr Arg Lys Ala Lys Val Val Asp Asn Tyr Ile His Ser
            100                 105                 110

Val Val Lys Thr Glu Glu Ser Met Asn Thr Val Trp Ala Asp Asn Arg
        115                 120                 125

Leu Thr Ile Ala Cys Gln Gln Gly Cys Thr Leu Val Tyr Asp Glu Phe
    130                 135                 140

Thr Arg Ser Arg Pro Glu Ala Asn Asn Ala Phe Leu Ser Val Leu Glu
145                 150                 155                 160

Glu Lys Ile Leu Asn Ile Pro Ser Leu Arg Asp Ile Asp Gln Gly Tyr
                165                 170                 175

Leu Gln Val His Pro Glu Phe Arg Ala Ile Phe Thr Ser Asn Pro Glu
            180                 185                 190

Glu Tyr Ala Gly Val His Lys Thr Gln Asp Ala Met Met Asp Arg Leu
        195                 200                 205

Ile Thr Ile Thr Leu Asp His Phe Asp Arg Asp Thr Glu Val Gln Val
    210                 215                 220

Thr Met Ser Lys Ser Asp Leu Pro Gln Lys Asp Ala Glu Lys Ile Val
225                 230                 235                 240

Asp Ile Val Arg Lys Leu Arg Lys Thr Gly Val Asn Asn His Arg Pro
                245                 250                 255

Thr Ile Arg Ala Cys Ile Ala Ile Gly Lys Ile Leu Lys His Met Gly
            260                 265                 270

Gly Gly Ala Ser Lys Asp Asn Phe Val Phe Lys Gln Ile Cys Arg Asp
        275                 280                 285

Val Leu Asn Val Asp Thr Thr Lys Val Thr Arg Asp Gly Glu Pro Leu
    290                 295                 300

Leu Pro Arg Lys Ile Asp Glu Leu Ile Asn Ser Leu
305                 310                 315

<210> SEQ ID NO 313
<211> LENGTH: 337
<212> TYPE: PRT
<213> ORGANISM: Desulfomonile tiedjei DSM 6799

<400> SEQUENCE: 313

Met Asn Gly Ala Glu Leu Arg Ile Ala Ser Ile Glu Thr Glu Val Ile
1               5                   10                  15

Thr Ala Asn Asn Glu Asn Ile Val Pro Glu Ala Gly Asp Arg Phe Val
            20                  25                  30

Asn Thr Pro His Val Glu Glu Leu Thr Ala Arg Ala Met Ala Tyr Leu
        35                  40                  45

Glu Val Gly Tyr Ser Val His Phe Ser Gly Val Ala Gly Thr Gly Lys
    50                  55                  60

Thr Thr Leu Ala Phe His Ala Ala Ala Lys Leu Gly Arg Pro Val Ile
65                  70                  75                  80

Leu Val His Gly Asp His Glu Phe Gly Ser Ser Asp Leu Ile Gly Arg
```

```
            85                  90                  95
Asp Ala Gly Tyr Lys Lys Ser Arg Leu Val Asp Asn Phe Ile His Ser
            100                 105                 110
Val Val Lys Thr Glu Glu Met Arg Ser Leu Trp Val Asp Asn Arg
            115                 120                 125
Leu Thr Thr Ala Cys Arg Asp Gly Tyr Thr Leu Ile Tyr Asp Glu Phe
130                 135                 140
Thr Arg Ser Arg Pro Glu Ala Asn Asn Val Leu Leu Ser Ile Leu Glu
145                 150                 155                 160
Glu Lys Ile Leu Asn Leu Pro Ser Leu Arg Arg Thr Gly Glu Gly Tyr
            165                 170                 175
Leu Glu Val His Pro Ser Phe Arg Ala Ile Phe Thr Ser Asn Pro Glu
            180                 185                 190
Glu Tyr Ala Gly Val His Lys Thr Gln Asp Ala Leu Met Asp Arg Ile
            195                 200                 205
Ile Thr Ile Asn Val Asp His Tyr Asp Arg Glu Thr Glu Ile Glu Ile
            210                 215                 220
Thr Arg Ala Lys Ser Gly Val Cys Lys Gln Asp Ala Thr Val Ile Val
225                 230                 235                 240
Asp Ile Ile Arg Glu Leu Arg Leu Leu Gly Val Asn Asn His Arg Pro
            245                 250                 255
Thr Ile Arg Ala Ala Ile Ala Ile Ala Arg Val Leu Ala His Thr Gly
            260                 265                 270
Glu His Ala Asp Gln His Asn Ser Val Phe Gln Trp Leu Cys Lys Asp
            275                 280                 285
Val Leu Ser Thr Asp Thr Val Lys Val Ser Arg Gly Gly Ser Pro Leu
            290                 295                 300
Met Ala Lys Lys Val Glu Glu Val Ile Arg Lys Val Cys Gly Arg Thr
305                 310                 315                 320
Gly Gly Lys Arg Ser Gly Lys Pro Val Gly Ser Lys Glu Glu Thr Ser
            325                 330                 335
Glu

<210> SEQ ID NO 314
<211> LENGTH: 307
<212> TYPE: PRT
<213> ORGANISM: Desulfotomaculum acetoxidans_DSM 771

<400> SEQUENCE: 314

Met Gln Leu Asn Gly Leu Asp Lys Asn Ser Ile Ile Asn Pro Val Val
1               5                   10                  15
Leu Ser Asp Phe Val Val Thr Asp Tyr Ile Ser Asn Val Val Asp Arg
            20                  25                  30
Ala Leu Ala Tyr Ile Lys Ala Gly Phe Ala Ile His Leu Arg Gly Arg
            35                  40                  45
Ser Gly Thr Gly Lys Thr Ser Ile Ala Met Tyr Ile Ser Ser Lys Leu
            50                  55                  60
Asn Arg Pro Thr Leu Val Ile His Gly Asp Glu Glu Phe Arg Thr Ser
65                  70                  75                  80
Asp Leu Ile Gly Gly Arg Tyr Gly Tyr Arg Ile Arg Lys Thr Ile Asp
            85                  90                  95
Asn Phe Val Gln Ser Val Val Lys Val Glu Glu Asp Leu Val Glu Arg
            100                 105                 110
Trp Val Asp Ser Arg Leu Thr Thr Ala Cys Lys Asn Gly Tyr Thr Leu
```

```
            115                 120                 125
Val Tyr Asp Glu Phe Thr Arg Ser Arg Pro Glu Ala Asn Asn Ile Leu
            130                 135                 140

Leu Ser Val Leu Gln Glu Arg Leu Leu Asp Ile Ser Val Ala Arg Gly
145                 150                 155                 160

Ala Glu Glu Gly Tyr Val Lys Val His Pro Asp Phe Thr Ala Ile Phe
                165                 170                 175

Thr Ser Asn Pro Glu Asp Tyr Ala Gly Val Tyr Gly Ser Gln Asp Ala
            180                 185                 190

Leu Arg Asp Arg Met Val Thr Leu Asp Leu Asp Asn Tyr Asp Lys Glu
            195                 200                 205

Thr Glu Ile Ser Ile Ile Lys Ser Lys Ser Lys Leu Ser Arg Glu Asp
            210                 215                 220

Ser Glu Arg Val Val Asn Ile Leu Arg Asp Leu Arg Glu Leu Gly Asp
225                 230                 235                 240

Cys Glu Tyr Gly Pro Thr Ile Arg Gly Gly Ile Met Ile Ala Lys Thr
                245                 250                 255

Leu Gln Val Leu Gly Ala Pro Val Asp Lys Asn Asn Glu Met Phe Arg
            260                 265                 270

Gln Ile Cys Glu Glu Val Leu Ala Ser Glu Thr Ser Arg Ala Gly Asn
            275                 280                 285

Leu Gln Ala Leu Arg Lys Val Arg Lys Val Ile Asn Glu Leu Phe Asn
            290                 295                 300

Lys Tyr Ala
305

<210> SEQ ID NO 315
<211> LENGTH: 352
<212> TYPE: PRT
<213> ORGANISM: Dolichospermum circinale

<400> SEQUENCE: 315

Met Ser Ile Thr Lys Val Asn His Lys Arg Ala Val Leu Arg Leu Arg
1               5                   10                  15

Pro Gly Gln Phe Val Val Thr Pro Ala Ile Glu Arg Val Val Ile Arg
            20                  25                  30

Ala Leu Arg Tyr Leu Arg Ser Gly Phe Pro Ile His Leu Arg Gly Pro
        35                  40                  45

Ala Gly Thr Gly Lys Thr Thr Leu Gly Met His Leu Ala Asn Cys Leu
    50                  55                  60

Asp Arg Pro Val Met Leu Leu Phe Gly Asp Gln Phe Lys Ser Ser
65                  70                  75                  80

Asp Leu Ile Gly Ser Glu Ser Gly Tyr Thr His Lys Lys Leu Leu Asp
                85                  90                  95

Asn Tyr Ile His Ser Val Lys Val Glu Asp Glu Phe Lys Gln Asn
                100                 105                 110

Trp Val Asp Ser Arg Leu Thr Leu Ala Cys Arg Glu Gly Phe Thr Leu
            115                 120                 125

Val Tyr Asp Glu Phe Asn Arg Ser Arg Pro Glu Val Asn Asn Val Leu
            130                 135                 140

Leu Ser Ala Leu Glu Glu Lys Ile Leu Ser Leu Pro Pro Ser Ser Asn
145                 150                 155                 160

Gln Pro Glu Tyr Leu Ser Val Asn Pro Gln Phe Arg Val Ile Phe Thr
                165                 170                 175
```

Ser Asn Pro Glu Glu Tyr Cys Gly Val His Ser Thr Gln Asp Ala Leu
              180                 185                 190

Met Asp Arg Leu Val Thr Ile Asn Met Pro Glu Pro Asp Glu Ile Thr
          195                 200                 205

Gln Thr Glu Ile Leu Ile Gln Lys Thr Asn Ile Gly Arg Glu Ser Ala
    210                 215                 220

Asn Leu Ile Val Arg Leu Val Lys Ser Phe Arg Leu Ala Thr Gly Ala
225                 230                 235                 240

Glu Lys Thr Ser Gly Leu Arg Ser Cys Leu Met Ile Ala Lys Ile Cys
                245                 250                 255

Ala Asp His Asp Ile Pro Ala Ser Thr Glu Asp Leu Asp Phe Arg Glu
            260                 265                 270

Ile Ala Ile Asp Ile Leu Phe Asn Arg Ala Gln Leu Ser Ile Ser Glu
        275                 280                 285

Ser Thr Asp Ile Phe Met Gly Leu Leu Glu Gln Phe Ser Ala Glu Glu
    290                 295                 300

Ile Lys Val Leu Asn Asp Thr His Phe Pro Thr Asp Glu Leu Leu Ile
305                 310                 315                 320

Asn Asn Ser Gln Phe Ile Thr Gln Glu Leu Val Thr Gln Pro Asn Thr
                325                 330                 335

Glu Leu Ala Thr Asp Ile Pro Gln Glu Leu Arg Lys Thr Glu Gln Asn
            340                 345                 350

<210> SEQ ID NO 316
<211> LENGTH: 321
<212> TYPE: PRT
<213> ORGANISM: Enhydrobacter aerosaccus strain ATCC 27094

<400> SEQUENCE: 316

Met Ser Met Asp Gln Ala Glu Glu Ile Gly Val Val Thr Thr Ile Glu
1               5                   10                  15

Pro Arg Pro Arg Ala Asp Phe Val Arg Thr Gln Ser Val Glu Ala Thr
            20                  25                  30

Ala Arg Arg Ala Leu Gly Tyr Leu Asn Ala Gly Phe Ser Val His Phe
        35                  40                  45

Arg Gly Pro Ala Gly Thr Gly Lys Thr Thr Leu Ala Leu His Leu Ala
    50                  55                  60

Ala Leu Leu Gly Arg Pro Met Val Met Ile Thr Gly Asp Glu Glu Met
65                  70                  75                  80

Leu Thr Ser Thr Leu Val Gly Thr Gln His Gly Tyr His Phe Arg Arg
                85                  90                  95

Val Val Asp Arg Phe Ile His Thr Val Thr Lys Thr Glu Glu Thr Ala
            100                 105                 110

Asp Lys Arg Trp Ala Asp His Arg Leu Thr Thr Ala Cys Arg Glu Gly
        115                 120                 125

Tyr Thr Leu Ile Tyr Asp Glu Phe Thr Arg Ser Arg Pro Glu Ala Asn
    130                 135                 140

Asn Val Leu Leu Ser Val Leu Glu Glu Gly Leu Leu Val Leu Pro Ala
145                 150                 155                 160

Gln Asn Gln Asn Glu Pro Tyr Ile Lys Val His Pro Asn Phe Arg Val
                165                 170                 175

Ile Phe Thr Ser Asn Pro Gln Glu Tyr Ala Gly Val His Asp Ala Gln
            180                 185                 190

Asp Ala Leu Gly Asp Arg Ile Val Thr Ile Asp Met Gly His Ala Asp
        195                 200                 205

-continued

```
Arg Glu Leu Glu Leu Ala Ile Ala Ala Ala Arg Ser Gly Leu Pro Pro
    210                 215                 220
Thr Gln Val Ala Pro Ile Val Asp Met Val Arg Glu Phe Arg Glu Thr
225                 230                 235                 240
Gly Glu Tyr Asp Gln Thr Pro Thr Leu Arg Thr Ser Ile Met Ile Cys
                245                 250                 255
Arg Met Met Ser Gln Glu Arg Leu Ala Pro Thr Ile Glu Asp Gln Gln
                260                 265                 270
Phe Val Gln Ile Cys Met Asp Ile Leu Gly Gly Lys Ser Leu Pro Gly
            275                 280                 285
Gly Lys Gly Asp Asn Lys Arg Ala Gln Gln Lys Met Leu Leu Ser
290                 295                 300
Leu Ile Glu His His Cys Pro Ala Arg Ser Phe Thr Ser Val Gly Glu
305                 310                 315                 320
Val
```

<210> SEQ ID NO 317
<211> LENGTH: 345
<212> TYPE: PRT
<213> ORGANISM: Isosphaera pallida_ATCC-43644

<400> SEQUENCE: 317

```
Met Asp Tyr Glu Ser Thr Ala Leu Gln Leu Lys Pro Arg Pro Asp Phe
1               5                   10                  15
Val Ala Thr Pro Trp Val Arg Glu Leu Ala Asp Arg Ala Leu Gly Tyr
                20                  25                  30
Leu Thr Ala Gly Tyr Pro Val His Phe Ser Gly Pro Ala Gly Thr Gly
            35                  40                  45
Lys Thr Thr Leu Ala Met His Leu Ala Ala Leu Val Asn Arg Pro Val
50                  55                  60
Val Leu Leu His Gly Asp Asp Glu Phe Gly Ser Ser Asp Leu Val Gly
65                  70                  75                  80
Asp His Leu Gly Phe Arg Ser Thr Lys Val Val Asp Asn Phe Ile His
                85                  90                  95
Ser Val Val Lys Thr Glu Gln Ser Val Ser Lys Thr Trp Val Asp His
                100                 105                 110
Arg Leu Thr Thr Ala Cys Arg His Gly Phe Thr Leu Ile Tyr Asp Glu
            115                 120                 125
Phe Asn Arg Ser Arg Pro Glu Ala Asn Asn Ile Leu Leu Thr Ile Leu
        130                 135                 140
Glu Glu Arg Leu Leu Glu Leu Pro Pro Ile Ala Gly Gly Arg Asp Gly
145                 150                 155                 160
Ser Gly Pro Leu Arg Val His Pro Glu Phe Arg Ala Ile Phe Thr Ser
                165                 170                 175
Asn Pro Glu Glu Tyr Ala Gly Val His Lys Thr Gln Asp Ala Leu Leu
            180                 185                 190
Asp Arg Met Ile Thr Ile Ser Met Gly Gly His Asp Glu Ala Thr Glu
        195                 200                 205
Thr Glu Ile Thr Ala Ala Lys Ser Gly Leu Ser Arg Asp Glu Ala Ala
    210                 215                 220
Arg Ile Val Glu Leu Ala Arg Ala Val Arg Ala Leu Lys Pro Leu Arg
225                 230                 235                 240
His Pro Pro Thr Ile Arg Ser Cys Leu Met Ile Ala Lys Val Ala Ala
                245                 250                 255
```

```
Leu Arg Lys Val Pro Ile Asp Pro Asn Asp Ala Leu Phe Leu Ala Ile
            260                 265                 270

Cys Arg Asp Val Leu Arg Ile Asp Ala Leu Pro Val Asp Pro Glu
        275                 280                 285

Ala Thr Phe Ala Glu Leu Ile Arg Arg Val Phe Ala Pro Thr Pro Ala
    290                 295                 300

Val Ala Pro Pro Arg Val Pro Thr Thr Gly Phe Ala Ala Asn Arg Val
305                 310                 315                 320

Val Pro Ile Pro Arg Arg Pro Leu Ala Ala Ser Ala Ser Pro Pro Pro
            325                 330                 335

Gly Ala Asn Gly His Ala His Leu Arg
            340                 345

<210> SEQ ID NO 318
<211> LENGTH: 335
<212> TYPE: PRT
<213> ORGANISM: Legionella drancourtii LLAP12

<400> SEQUENCE: 318

Met Met Thr Gln Glu Asn Asn Gly Ser Leu Thr Asp Ser Lys Asn Asn
1               5                   10                  15

Asp Lys Leu Ile Arg Phe Val Asn Asn Arg Ser Asp Asn Ile Leu Leu
            20                  25                  30

Glu Ala Ser Glu Glu Phe Thr Glu Thr Pro His Ile Arg Gly Ile Ser
        35                  40                  45

Glu Arg Ala Leu Ala Tyr Leu Asp Ile Gly Tyr Pro Ile His Leu Leu
    50                  55                  60

Gly Pro Ala Gly Thr Gly Lys Thr Thr Val Ala Leu His Ile Ala Ala
65                  70                  75                  80

Gln Leu Gly Arg Pro Val Ile Leu Ile His Gly Asp Glu Phe Thr
            85                  90                  95

Gly Ala Asp Leu Val Gly Arg Gly Thr Gly Tyr His His Ser Lys Leu
                100                 105                 110

Val Asp Asn Phe Ile His Ser Val Leu Lys Thr Glu Glu Glu Met Thr
            115                 120                 125

Thr Met Trp Thr Asp Asn Arg Leu Thr Thr Ala Cys Glu Gln Gly Tyr
    130                 135                 140

Thr Leu Ile Tyr Asp Glu Phe Asn Arg Ser Arg Ala Glu Ala Asn Asn
145                 150                 155                 160

Ala Leu Leu Ser Val Leu Ser Glu Gly Ile Leu Asn Leu Pro Gly Arg
                165                 170                 175

Arg Glu Arg Asp Gly Ile Gly Tyr Val Asp Val His Ser Asn Phe Arg
            180                 185                 190

Ala Ile Phe Thr Ser Asn Ser Glu Glu Tyr Val Gly Ile His Lys Thr
        195                 200                 205

Gln Asn Ala Leu Ala Asp Arg Leu Ile Ala Ile Lys Met Asp Tyr Pro
    210                 215                 220

Asp Gln Gln Ser Glu Ile Gln Ile Ile Glu Lys Lys Ser Thr Leu Pro
225                 230                 235                 240

Arg Lys Asp Ile Glu Ile Val Asn Leu Ala Arg Glu Leu Arg Leu
                245                 250                 255

Lys Ser Glu Lys Arg Pro Ser Ile Arg Gly Cys Ile Ala Ile Ala Arg
            260                 265                 270

Val Leu Ala Tyr His Asn Arg His Ala His Ala Asp Asp Pro Ile Phe
```

```
                   275                 280                 285
Gln Ala Val Cys Gln Asp Ile Phe Gly Ile Ser Lys Glu Phe Leu Lys
    290                 295                 300

Gln Leu Leu His Pro Met Asp Ser Gly Leu Gln Lys Arg Ser Glu Lys
305                 310                 315                 320

Asn Gln Glu Ser Ile Lys Lys Tyr Lys Thr Lys Asn Gln Lys Leu
                325                 330                 335

<210> SEQ ID NO 319
<211> LENGTH: 421
<212> TYPE: PRT
<213> ORGANISM: Lyngbya confervoides BDU141951

<400> SEQUENCE: 319

Met Ser Thr Val Leu Gln Ala Arg Pro Arg Asn Phe Val Ser Thr Pro
1               5                   10                  15

Ala Val Glu Arg Ile Ala Arg Arg Ala Leu Arg Tyr Leu Gln Ser Gly
                20                  25                  30

Tyr Ser Val His Leu Arg Gly Pro Ala Gly Thr Gly Lys Thr Thr Leu
            35                  40                  45

Ala Leu His Leu Ala Asp Leu Leu Ser Arg Pro Ile Met Leu Val Phe
    50                  55                  60

Gly Asp Asp Glu Phe Lys Thr Ser Asp Leu Ile Gly Asn Gln Ser Gly
65                  70                  75                  80

Tyr Thr Arg Lys Lys Val Val Asp Asn Tyr Ile His Ser Val Val Lys
                85                  90                  95

Val Glu Asp Glu Leu Arg His Asn Trp Val Asp Ser Arg Leu Thr Leu
            100                 105                 110

Ala Cys Arg Glu Gly Phe Thr Leu Val Tyr Asp Glu Phe Asn Arg Ser
        115                 120                 125

Arg Pro Glu Val Asn Asn Val Leu Leu Ser Ala Leu Glu Glu Lys Leu
    130                 135                 140

Leu Val Leu Pro Pro Ser Gly His Arg Pro Glu Tyr Leu Arg Val Asn
145                 150                 155                 160

Pro His Phe Arg Ala Ile Phe Thr Ser Asn Pro Glu Glu Tyr Ala Gly
                165                 170                 175

Val His Gly Thr Gln Asp Ala Leu Leu Asp Arg Leu Ile Thr Ile His
            180                 185                 190

Met Pro Glu Pro Asp Glu Leu Thr Gln Gln Gln Ile Leu Ile Gln Lys
        195                 200                 205

Val Gly Ile Glu Pro Ala Asp Ala Leu Met Ile Val Arg Leu Val Lys
    210                 215                 220

Ala Phe Lys Ser Gln Met Gly Asn His Ser Ala Thr Ser Leu Arg Pro
225                 230                 235                 240

Ser Leu Met Ile Ala Asn Ile Cys His Glu His Gly Val Ala Met Met
                245                 250                 255

Thr Glu Asp Ala Asp Phe Arg Asp Val Cys Ser Asp Val Leu Leu Ser
            260                 265                 270

Arg Val Thr Asn Glu Leu Ser Pro Ala Thr His Thr Leu Trp Asp Leu
        275                 280                 285

Phe Asn Glu Leu Thr Ala Ser Ala Asp Val Leu Gly Pro Glu Ser Asn
    290                 295                 300

Ser Thr Asp Val Ser Pro Gln Pro Glu Ala Asp Lys Pro Val Glu Thr
305                 310                 315                 320
```

```
Lys Gly Ser Lys Gly Lys Ser Thr Thr Lys Ser Lys Ala Lys Glu Ser
                325                 330                 335

Ala Lys Ala Ser Glu Glu Ala Asp Glu Ala Gly Asp Asp Ser Ala Ser
            340                 345                 350

Ala Pro Glu Leu Asp Glu Ile Glu Ser Ser Ile Leu Thr Phe Leu Thr
        355                 360                 365

Ala Arg Glu Ser Ala Ser Leu Ser Glu Ile Glu Ser Glu Leu Ser Leu
    370                 375                 380

Thr Arg Phe Lys Ala Val Asp Ala Leu Arg Ser Leu Val Glu Ala Gly
385                 390                 395                 400

Tyr Leu Gln Lys Gln Asn Gly Ala Gly Lys Pro Ala Ile Tyr Gly Leu
                405                 410                 415

Val Pro Glu Glu Ser
            420

<210> SEQ ID NO 320
<211> LENGTH: 346
<212> TYPE: PRT
<213> ORGANISM: Microcystis aeruginosa NIES-843

<400> SEQUENCE: 320

Met Thr Val Thr Glu Thr Gln Thr Arg Arg Ala Val Leu Ser Leu Arg
1               5                   10                  15

Pro Gly Gln Phe Val Val Thr Pro Ser Ile Asp Gln Ile Ala Thr Arg
            20                  25                  30

Ala Leu Arg Tyr Leu Asn Ser Gly Phe Ser Ile His Leu Cys Gly Pro
        35                  40                  45

Ala Gly Thr Gly Lys Thr Thr Leu Ala Met His Leu Ala Asn Cys Leu
    50                  55                  60

Ala Arg Pro Val Met Leu Ile Phe Gly Asp Asp Phe Thr Ser Ser
65                  70                  75                  80

Asp Leu Ile Gly Ser Gln Ser Gly Tyr Thr His Lys Lys Leu Met Asp
                85                  90                  95

Asn Tyr Ile His Ser Val Leu Lys Val Glu Asp Glu Leu Lys His Asn
            100                 105                 110

Trp Val Asp Ser Arg Leu Thr Met Ala Cys Arg Glu Gly Phe Thr Leu
        115                 120                 125

Val Tyr Asp Glu Phe Asn Arg Ser Arg Pro Glu Val Asn Asn Val Leu
    130                 135                 140

Leu Ser Ala Leu Glu Glu Lys Ile Leu Thr Leu Pro Pro Thr Ser His
145                 150                 155                 160

Gln Pro Asp Tyr Leu Gln Val Asn Ser Gln Phe Arg Ala Ile Phe Thr
                165                 170                 175

Ser Asn Pro Glu Glu Tyr Cys Gly Val His Ala Thr Gln Asp Ala Leu
            180                 185                 190

Met Asp Arg Leu Val Thr Ile Asn Met Pro Glu Pro Asp Gln Leu Thr
        195                 200                 205

Gln Thr Glu Ile Leu Ala Gln Lys Thr Gly Ile Gly Arg Glu Asp Ala
    210                 215                 220

Leu Phe Ile Val Asn Leu Val Lys Thr Phe Arg Val Lys Thr Ala Thr
225                 230                 235                 240

Glu Lys Thr Ser Gly Leu Arg Ser Cys Leu Met Ile Ala Lys Val Cys
                245                 250                 255

Ala Ser His Asp Ile Ala Ala Asn Ser Ala Asp Ser Asp Phe Arg Asp
            260                 265                 270
```

Ile Cys Ala Asp Val Leu Leu Ser Arg Thr Asn Leu Ser Val Asp Lys
            275                 280                 285

Ser Arg Ala Ile Leu Trp Glu Ile Leu Glu Asp Asn Pro Leu Glu Ser
290                 295                 300

Leu Ser Phe Leu Glu Glu Glu Pro Ser Asp Ala Gln Val Ser Thr
305                 310                 315                 320

Ser Glu Pro Ser Thr Gly Asn Gln Ser Leu Lys Ala Ile Gln Ser Leu
                325                 330                 335

Leu Arg Gly Asn Leu Pro Gln Arg Lys Asp
            340                 345

<210> SEQ ID NO 321
<211> LENGTH: 390
<212> TYPE: PRT
<213> ORGANISM: Nostoc punctiforme ATCC 29133

<400> SEQUENCE: 321

Met Thr Thr Val Leu Asn Ala Ser Pro Gln Arg Phe Val Asn Thr Pro
1               5                   10                  15

Ala Val Gln Arg Ile Ala Gln Arg Ala Leu Arg Tyr Leu Gln Ser Gly
            20                  25                  30

Phe Ser Ile His Leu Arg Gly Ala Ala Gly Val Gly Lys Thr Thr Leu
        35                  40                  45

Ala Met His Leu Ala Asp Leu Leu Asn Gln Pro Ile Ile Leu Leu Phe
    50                  55                  60

Gly Asp Asp Glu Phe Lys Thr Ser Asp Leu Ile Gly Asn Gln Leu Gly
65                  70                  75                  80

Tyr Thr Arg Lys Lys Val Val Asp Asn Phe Ile His Ser Val Ile Lys
                85                  90                  95

Val Glu Asp Glu Val Arg Gln His Trp Val Asp Ala Arg Leu Thr Leu
            100                 105                 110

Ala Cys Lys Glu Gly Phe Thr Leu Val Tyr Asp Glu Phe Asn Arg Ser
        115                 120                 125

His Pro Glu Val Asn Asn Val Leu Leu Ser Val Leu Glu Glu Arg Leu
    130                 135                 140

Leu Val Leu Pro Thr Asn Gln His Arg Ala Glu Tyr Ile Arg Val His
145                 150                 155                 160

Pro Gln Phe Arg Ala Ile Leu Thr Ser Asn Pro Gln Glu Tyr Cys Gly
                165                 170                 175

Val His Ala Thr Gln Asp Ala Leu Met Asp Arg Val Ile Thr Ile Asp
            180                 185                 190

Met Pro Thr Pro Asp Glu Leu Ser Gln Gln Glu Ile Val His Lys
        195                 200                 205

Thr Gly Ile Asp Ser Glu Lys Ala Glu Val Ile Val Arg Ile Val Arg
210                 215                 220

Thr Phe Trp Ser Arg Ser Gly Ser Gly Gln Gly Gly Leu Arg Ser
225                 230                 235                 240

Cys Leu Met Ile Ala Lys Ile Cys His Glu His Glu Ile Ser Val Asn
                245                 250                 255

Pro Gly Asp Pro Ser Phe Gln Asp Ile Cys Ala Asp Ile Leu Leu Ser
            260                 265                 270

Arg Thr Asn Gln Pro Leu Ile Glu Ala Thr Arg Leu Leu Glu Glu Val
        275                 280                 285

Leu Ser Glu Phe Tyr His Arg Ile Asn Thr Gln Ser Gln Pro Ser Glu

```
                    290                 295                 300
Ile Ile Pro Asn Asn Gln Asn Gln Ile Val Leu Glu Gln Arg Val Pro
305                 310                 315                 320

Tyr Glu His Glu Val Tyr Asn Tyr Leu Cys Asn Ser Pro Gly Arg Arg
                    325                 330                 335

Phe Ser Glu Leu Ala Val Glu Leu Gly Ile Asp Arg Ser Gln Ile Val
                340                 345                 350

Ala Ala Leu Lys Ser Leu Arg Glu Gln Gly Val Leu Val Gln Met Gln
            355                 360                 365

Gly Asn Ala Glu Ser Pro Ser Ile Ser Gln Thr Val Ala Phe Asp Ser
370                 375                 380

Gly His Leu Ile Asn Lys
385                 390

<210> SEQ ID NO 322
<211> LENGTH: 410
<212> TYPE: PRT
<213> ORGANISM: Nostoc sp. PCC 7120

<400> SEQUENCE: 322

Met Thr Leu Thr Ala Asn Asn Lys Lys Arg Ala Val Leu Arg Val Arg
1               5                   10                  15

Pro Gly Gln Phe Val Val Thr Pro Ala Ile Glu Gln Val Ala Ile Arg
                20                  25                  30

Ala Leu Arg Tyr Leu Thr Ser Gly Phe Ala Ile His Leu Arg Gly Pro
            35                  40                  45

Ala Gly Thr Gly Lys Thr Thr Leu Ala Met His Leu Ala Asn Cys Leu
        50                  55                  60

Asp Arg Pro Ile Met Leu Ile Phe Gly Asp Asp Glu Phe Lys Ser Ser
65                  70                  75                  80

Asp Leu Ile Gly Ser Glu Ser Gly Tyr Thr His Lys Lys Leu Leu Asp
                85                  90                  95

Asn Tyr Ile His Ser Val Leu Lys Val Glu Asp Glu Phe Lys Gln Asn
                100                 105                 110

Trp Val Asp Ser Arg Leu Thr Leu Ala Cys Arg Glu Gly Phe Thr Leu
            115                 120                 125

Val Tyr Asp Glu Phe Asn Arg Ser Arg Pro Glu Val Asn Asn Val Leu
130                 135                 140

Leu Ser Ala Leu Glu Glu Lys Ile Leu Thr Leu Pro Pro Ser Ser Asn
145                 150                 155                 160

Gln Pro Glu Tyr Leu His Val Asn Pro Gln Phe Arg Ala Ile Phe Thr
                165                 170                 175

Ser Asn Pro Glu Glu Tyr Cys Gly Val His Ser Thr Gln Asp Ala Leu
            180                 185                 190

Met Asp Arg Leu Val Thr Ile Asn Met Pro Glu Pro Asp Glu Leu Thr
        195                 200                 205

Gln Thr Glu Ile Leu Ala Gln Lys Thr Ala Leu Asn Arg Ala Asp Ala
210                 215                 220

Leu Leu Ile Val Arg Leu Val Lys Ala Phe Arg Ser Arg Thr Gly Gly
225                 230                 235                 240

Glu Lys Thr Ser Gly Leu Arg Ser Cys Leu Met Ile Ala Lys Val Cys
                245                 250                 255

Ala Glu His Asn Ile Leu Val Ser Pro Gln Ser Ser Asp Phe Arg Glu
            260                 265                 270
```

```
Ile Cys Ala Asp Val Leu Phe Asn Arg Thr Asn Trp Ser Ala Ser Glu
            275                 280                 285

Ala Ala Thr Ile Phe Leu Glu Leu Leu Asn His Leu Asp Leu Gln Gln
290                 295                 300

Ile Glu Glu Phe Lys Asn Ser Ile Ile Pro Glu Asp Thr Asp Ala Ile
305                 310                 315                 320

Ala Glu Gly Gly Phe Pro Thr Ile Ile Asp Ser His Phe Gly Thr Leu
                325                 330                 335

Asp Ser Glu Val Leu Glu Gln Pro Gly Val Asp Ser Ile Pro Phe
            340                 345                 350

Glu Gln Glu Ile Tyr Leu Tyr Leu Gln Gln Tyr Lys Ser Ala Ala Leu
                355                 360                 365

Ala Leu Val Gln Gln Glu Phe Glu Leu Ser Arg Thr Val Ala Thr Asn
            370                 375                 380

Ala Leu Asn Ser Leu Glu Gln Lys Gly Leu Val Ser Lys Asn Asn His
385                 390                 395                 400

Val Tyr Thr Ile Glu Glu Pro Asn Gln Ser
                405                 410

<210> SEQ ID NO 323
<211> LENGTH: 342
<212> TYPE: PRT
<213> ORGANISM: Octadecabacter antarcticus 307

<400> SEQUENCE: 323

Met Asn Ser Asn Leu Arg Ala Thr Asn Ser Gly Gly Pro Asp Ile Ser
1               5                   10                  15

Lys Thr Met Met Pro Glu Ala Arg Glu Asp Phe Val Gln Thr Glu Ser
                20                  25                  30

Val Lys Ser Ile Ser Arg Arg Ala Leu Ala Tyr Ile Asn Ala Gly Tyr
            35                  40                  45

Ser Val His Phe Arg Gly Pro Ala Gly Thr Gly Lys Thr Thr Met Ala
        50                  55                  60

Met His Thr Ala Ala Leu Leu Gly Arg Pro Val Val Leu Ile Thr Gly
65                  70                  75                  80

Asp Glu Glu Met Ile Thr Ser Asn Leu Val Gly Ala Glu Ser Gly Tyr
                85                  90                  95

Asn Tyr Arg Lys Val Thr Asp Asn Tyr Ile His Thr Val Ser Lys Ile
                100                 105                 110

Glu Glu Ser Ser Asp Arg Ser Trp Asn Asp His Arg Leu Thr Thr Ala
            115                 120                 125

Cys Arg Glu Gly Tyr Thr Leu Ile Tyr Asp Glu Phe Thr Arg Ser Arg
        130                 135                 140

Ala Glu Ala Asn Asn Val Leu Leu Ser Val Leu Glu Glu Gly Ile Leu
145                 150                 155                 160

Val Leu Pro Ala Gln Asn Arg Gly Glu Pro Phe Ile Lys Val His Pro
                165                 170                 175

Asn Phe Arg Val Ile Phe Thr Ser Asn Pro Gln Glu Tyr Ala Gly Val
                180                 185                 190

His Glu Ala Gln Asp Ala Leu Ser Asp Arg Ile Val Thr Ile Asp Ile
            195                 200                 205

Gly Glu Ala Asp Arg Glu Leu Glu Val Ser Ile Ala Ser Ser Arg Ser
        210                 215                 220

Gly Leu Glu Val Ala Lys Thr Glu Pro Ile Val Asp Met Val Arg Ala
225                 230                 235                 240
```

```
Phe Arg Asp Thr Gly Glu Tyr Asp Gln Thr Pro Thr Leu Arg Ala Cys
                245                 250                 255

Ile Val Ile Cys Arg Met Val Ala Asn Glu Lys Leu Asn Thr Thr Ile
            260                 265                 270

Asp Asp Pro Phe Phe Val Gln Ile Cys Leu Asp Val Leu Gly Ser Lys
        275                 280                 285

Ser Thr Phe Gly Gly Lys Glu His Asp Lys Arg Thr Gln Gln Arg Lys
    290                 295                 300

Leu Leu Leu Asp Asn Leu Lys His Tyr Cys Pro Ser Lys Val Ser Thr
305                 310                 315                 320

Lys Pro Ser Ala Lys Asp Glu Ser Lys Ser Thr Leu Ile Gln Val
                325                 330                 335

Ser Ser Arg Gly Ser Leu
                340

<210> SEQ ID NO 324
<211> LENGTH: 324
<212> TYPE: PRT
<213> ORGANISM: Octadecabacter arcticus 238

<400> SEQUENCE: 324

Met Met Pro Glu Ala Arg Lys Asp Phe Val Gln Thr Asp Ser Val Lys
1               5                   10                  15

Ser Val Ser Arg Arg Ala Leu Ala Tyr Ile Asn Ala Gly Tyr Ser Val
                20                  25                  30

His Phe Arg Gly Pro Ala Gly Thr Gly Lys Thr Thr Met Ala Met His
            35                  40                  45

Thr Ala Ala Leu Leu Gly Arg Pro Val Val Met Ile Thr Gly Asp Glu
        50                  55                  60

Glu Met Val Thr Ser Asn Leu Val Gly Ala Glu Ser Gly Tyr Asn Tyr
65                  70                  75                  80

Arg Lys Val Thr Asp Asn Tyr Ile His Thr Val Ser Lys Val Glu Glu
                85                  90                  95

Ser Ser Asp Arg Ser Trp Asn Asp His Arg Leu Thr Thr Ala Cys Arg
                100                 105                 110

Glu Gly Tyr Thr Leu Ile Tyr Asp Glu Phe Thr Arg Ser Arg Ala Glu
            115                 120                 125

Ala Asn Asn Val Leu Leu Ser Val Leu Glu Glu Gly Ile Leu Val Leu
        130                 135                 140

Pro Ala Gln Asn Arg Gly Glu Pro Phe Ile Lys Val His Pro Asp Phe
145                 150                 155                 160

Arg Val Ile Phe Thr Ser Asn Pro Gln Glu Tyr Ala Gly Val His Asp
                165                 170                 175

Ala Gln Asp Ala Leu Ser Asp Arg Ile Val Thr Ile Asp Ile Gly Ala
                180                 185                 190

Ala Asp Arg Glu Leu Glu Val Ser Ile Ala Ser Ser Arg Ser Gly Leu
            195                 200                 205

Glu Val Ala Lys Thr Ala Pro Ile Val Asp Met Val Arg Ala Phe Arg
        210                 215                 220

Asp Thr Gly Glu Tyr Asp Gln Thr Pro Thr Leu Arg Ala Cys Ile Met
225                 230                 235                 240

Ile Cys Arg Met Val Ala Asn Glu Lys Leu Asn Pro Thr Ile Asp Asp
                245                 250                 255

Ser Tyr Phe Val Gln Ile Cys Leu Asp Val Leu Gly Ser Lys Ser Met
```

```
                260                 265                 270
Phe Gly Ala Lys Glu Gln Gly Lys Arg Thr Gln Gln Glu Lys Leu Leu
            275                 280                 285

Leu Asp Asn Leu Ser His His Cys Pro Ser Pro Pro Ser Lys Pro
        290                 295                 300

Ser Ala Lys Glu Ala Glu Ala Lys Pro Arg Ser Ile Gln Ala Thr Ser
305                 310                 315                 320

Arg Gly Pro Ala

<210> SEQ ID NO 325
<211> LENGTH: 308
<212> TYPE: PRT
<213> ORGANISM: Pelodictyon phaeoclathratiforme

<400> SEQUENCE: 325

Met Arg Arg Gln Gly Cys Asp Ser Glu Met Asn Thr Val Leu Glu Pro
1               5                   10                  15

Lys Pro Met Pro Asn Phe Val Glu Thr Asp Tyr Ile Arg Asp Ile Thr
            20                  25                  30

Ser Arg Gly Leu Thr Tyr Met Lys Ala Gly Phe Pro Val His Phe Arg
        35                  40                  45

Gly Pro Ser Gly Thr Gly Lys Thr Thr Val Ala Leu His Leu Ala Ser
    50                  55                  60

Lys Ile Gly Arg Pro Val Ile Ile His Gly Asp Ser Glu Tyr Lys
65                  70                  75                  80

Thr Ser Asp Leu Ile Gly Ser Glu Gln Gly Tyr Lys Tyr Arg Arg Leu
                85                  90                  95

Asp Asp Asn Phe Ile His Ser Val His Lys Tyr Glu Glu Asp Met Thr
            100                 105                 110

Lys Gln Trp Val Asn Asn Arg Leu Thr Ile Ala Ile Lys Lys Gly Phe
        115                 120                 125

Thr Leu Val Tyr Asp Glu Phe Thr Arg Ser Arg Pro Glu Ala Asn Asn
    130                 135                 140

Ile Leu Leu Pro Ile Leu Gln Glu Lys Met Met Ser Thr Ser Ser Ser
145                 150                 155                 160

Asn Glu Glu Glu Tyr Tyr Met Lys Val His Pro Glu Phe Arg Ala Ile
                165                 170                 175

Phe Thr Ser Asn Pro Glu Glu Tyr Ala Gly Val Asn Arg Thr Gln Asp
            180                 185                 190

Ala Leu Arg Asp Arg Met Val Thr Met Asp Leu Asp Tyr Phe Asp Tyr
        195                 200                 205

Glu Thr Glu Leu Met Ile Thr His Ala Lys Ser Gly Met Ser Leu Asp
    210                 215                 220

Asp Ala Glu Lys Ile Val Lys Ile Val Arg Gly Leu Arg Glu Ser Gly
225                 230                 235                 240

Lys Thr Glu Phe Asp Pro Thr Ile Arg Gly Ser Ile Met Ile Ala Lys
                245                 250                 255

Thr Leu Asn Val Leu Asn Ala Arg Pro Asp Lys Thr Asn Glu Leu Phe
            260                 265                 270

Lys Lys Val Cys Gln Asp Ile Leu Thr Ser Glu Thr Ser Arg Val Gly
        275                 280                 285

Ser Lys Thr Asn Gln Glu Arg Val Arg Gly Ile Val Asn Glu Leu Ile
    290                 295                 300

Asp Leu His Ser
```

<210> SEQ ID NO 326
<211> LENGTH: 454
<212> TYPE: PRT
<213> ORGANISM: Phormidium tenue NIES-30

<400> SEQUENCE: 326

Met Asn Thr Val Leu Gln Ala Arg Pro Arg Asn Phe Val Ser Thr Pro
1               5                   10                  15

Thr Leu Glu Arg Thr Ser Ile Arg Ala Leu Arg Tyr Leu Gln Ser Gly
            20                  25                  30

Tyr Ser Ile His Leu Lys Gly Pro Ala Gly Thr Gly Lys Thr Thr Leu
        35                  40                  45

Ala Leu His Leu Ala Asp Leu Leu Ala Arg Pro Ile Met Leu Leu Phe
    50                  55                  60

Gly Asp Asp Glu Phe Lys Thr Ser Asp Leu Ile Gly Asn Gln Ser Gly
65                  70                  75                  80

Tyr Thr Arg Lys Lys Val Val Asp Asn Tyr Ile His Ser Val Val Lys
                85                  90                  95

Val Glu Asp Glu Leu Arg His Asn Trp Thr Asp Ser Arg Leu Thr Leu
            100                 105                 110

Ala Cys Arg Glu Gly Phe Thr Met Val Tyr Asp Glu Phe Asn Arg Ser
        115                 120                 125

Arg Pro Glu Val Asn Asn Val Leu Leu Ser Ala Leu Glu Glu Lys Leu
    130                 135                 140

Leu Val Leu Pro Pro Ser Asn Asn Arg Ala Glu Tyr Ile Arg Val Ser
145                 150                 155                 160

Pro His Phe Arg Ala Ile Leu Thr Ser Asn Pro Glu Glu Tyr Cys Gly
                165                 170                 175

Val His Gly Thr Gln Asp Ala Leu Gln Asp Arg Leu Ile Thr Ile Asn
            180                 185                 190

Met Pro Glu Pro Asp Glu Leu Ala Gln Gln Ile Leu Val Gln Lys
        195                 200                 205

Val Gly Ile Asp Ser Ser Ala Leu Gln Ile Val Gln Leu Val Lys
    210                 215                 220

Ala Phe Gln Ser Ala Val Ala Pro Asp Met Val Ser Ser Leu Arg Pro
225                 230                 235                 240

Ser Leu Met Ile Ala Thr Ile Cys His Asp His Asp Ile Leu Pro Leu
                245                 250                 255

Ala Glu Asn Ala Asp Phe Arg Asp Val Cys Ser Asp Ile Leu Leu Ala
            260                 265                 270

Arg Ser Lys Glu Pro Ala Pro Asp Ala Thr Arg His Leu Trp Asn Leu
        275                 280                 285

Phe Asn Arg Phe Val Val Ser Gln Ala Ala Leu Val Asn Asp Leu Ser
    290                 295                 300

Leu Lys Pro Glu Ala His Pro Thr Ala Arg Phe His Gly Glu Glu Glu
305                 310                 315                 320

Asp Asp Ala Pro Leu Gln Pro Leu Glu Ala Leu Val Glu Ser Asp Ile
                325                 330                 335

Asp Asp Val Ala Val Glu Asp Gln Pro Val Ile Gly Pro Gln Asp Leu
            340                 345                 350

Gln Gly Glu Thr Leu Pro Glu Ala Val Ile Pro Glu Pro Gln Gly Glu
        355                 360                 365

```
Thr Val Val Glu Thr Pro Ala Glu Ala Leu Pro Glu Glu Ile
    370             375             380

Ala Arg Val Gln Val Ser Pro Asp Asp Ile Glu Thr Arg Ile Phe Asp
385             390             395             400

Tyr Leu Asp Ala Thr Gly Thr Ala Ser Leu Val Asn Ile Glu Ala Ala
                405             410             415

Leu Asp Leu Asn Arg Phe Gln Ala Val Asn Ala Val Lys Ser Met Leu
            420             425             430

Asp Gln Gly Leu Ile Glu Lys Gln Glu Thr Asp Gly Gln Leu Gln Gly
            435             440             445

Tyr Gln Leu Ser Ser Asn
    450
```

<210> SEQ ID NO 327
<211> LENGTH: 398
<212> TYPE: PRT
<213> ORGANISM: Planktothrix agardhii str. 7805

<400> SEQUENCE: 327

```
Met Thr Thr Val Leu Gln Ala Arg Pro Lys Gly Phe Val Asn Thr Pro
1               5                   10                  15

Thr Ile Glu Gln Leu Thr Ile Arg Ala Leu Arg Tyr Leu Gln Ser Gly
            20                  25                  30

Phe Ser Leu His Leu Arg Gly Pro Ala Gly Thr Gly Lys Thr Thr Leu
        35                  40                  45

Ala Met His Leu Ala Asp Leu Leu Asn Arg Pro Ile Val Leu Ile Phe
    50                  55                  60

Gly Asp Asp Glu Leu Lys Ser Ser Asp Leu Ile Gly Asn Gln Leu Gly
65                  70                  75                  80

Tyr Thr Arg Lys Lys Val Val Asp Asn Phe Ile His Ser Val Val Lys
                85                  90                  95

Leu Glu Asp Glu Leu Arg Gln Asn Trp Ile Asp Ser Arg Leu Thr Leu
            100                 105                 110

Ala Cys Lys Glu Gly Phe Thr Leu Val Tyr Asp Glu Phe Asn Arg Ser
        115                 120                 125

Arg Pro Glu Val Asn Asn Val Leu Leu Ser Ala Leu Glu Glu Lys Leu
    130                 135                 140

Leu Val Leu Pro Pro Asn Asn Ser Arg Ser Glu Tyr Ile Arg Val Asn
145                 150                 155                 160

Pro His Phe Arg Ala Ile Phe Thr Ser Asn Pro Glu Glu Tyr Cys Gly
                165                 170                 175

Val Tyr Gly Thr Gln Asp Ala Leu Leu Asp Arg Leu Ile Thr Ile Asp
            180                 185                 190

Met Pro Glu Pro Asp Asp Glu Thr Gln Gln Glu Ile Leu Ile Gln Lys
        195                 200                 205

Ile Gly Ile Ser Pro Glu Asp Ala Lys Asn Ile Glu Ile Val Lys
    210                 215                 220

Ile Tyr Leu Glu Ile Thr Thr Gln Lys Lys Glu Ile Lys Pro Val Gln
225                 230                 235                 240

Asn Gly Lys Ala Ala Arg Pro His Ile Asp Lys Ala Ser Gly Leu Arg
                245                 250                 255

Pro Gly Leu Ile Ile Ala Lys Ile Cys His Glu His Asp Ile Ser Ile
            260                 265                 270

Gln Glu Asn Asn Gln Asp Phe Ile Lys Val Cys Ala Asp Ile Leu Leu
        275                 280                 285
```

```
Ser Arg Thr Asn Leu Ser Leu Thr Glu Ala Gln Asn Lys Leu Glu Lys
    290                 295                 300

Val Ile Lys Thr Val Leu Thr Asp Gly Asp Thr Ser Asn Asn Ser Phe
305                 310                 315                 320

Leu Pro Pro Ser Glu Thr Gln Leu Thr Glu Asn Asn Ser Leu Glu Ile
                325                 330                 335

Glu Glu Gln Val Tyr Gln Tyr Leu Gln Lys Thr Thr Ser Ala Arg Val
                340                 345                 350

Ser Glu Ile Glu Val Ala Leu Gly Leu Asn Arg Val Gln Thr Thr Asn
                355                 360                 365

Val Leu Arg Ser Leu Leu Lys Gln Gly His Leu Lys Gln Gln Asp Asn
370                 375                 380

Arg Phe Phe Ala Val Asn Lys Gln Gly Glu Leu Ile Gln Pro
385                 390                 395
```

<210> SEQ ID NO 328
<211> LENGTH: 398
<212> TYPE: PRT
<213> ORGANISM: Planktothrix rubescens

<400> SEQUENCE: 328

```
Met Thr Thr Val Leu Gln Ala Arg Pro Lys Gly Phe Val Asn Thr Pro
1               5                   10                  15

Thr Ile Glu Gln Leu Thr Ile Arg Ala Leu Arg Tyr Leu Gln Ser Gly
                20                  25                  30

Phe Ser Leu His Leu Arg Gly Pro Ala Gly Thr Gly Lys Thr Thr Leu
            35                  40                  45

Ala Met His Leu Ala Asp Leu Leu Asn Arg Pro Ile Val Leu Ile Phe
50                  55                  60

Gly Asp Asp Glu Leu Lys Ser Ser Asp Leu Ile Gly Asn Gln Leu Gly
65                  70                  75                  80

Tyr Thr Arg Lys Lys Val Ile Asp Asn Phe Ile His Ser Val Val Lys
                85                  90                  95

Leu Glu Asp Glu Leu Arg Gln Asn Trp Ile Asp Ser Arg Leu Thr Leu
                100                 105                 110

Ala Cys Lys Glu Gly Phe Thr Leu Val Tyr Asp Glu Phe Asn Arg Ser
            115                 120                 125

Arg Pro Glu Val Asn Asn Val Leu Leu Ser Ala Leu Glu Glu Lys Leu
            130                 135                 140

Leu Val Leu Pro Pro Asn Asn Ser Arg Ser Glu Tyr Ile Arg Val Asn
145                 150                 155                 160

Pro His Phe Arg Ala Ile Phe Thr Ser Asn Pro Glu Glu Tyr Cys Gly
                165                 170                 175

Val Tyr Gly Thr Gln Asp Ala Leu Leu Asp Arg Leu Ile Thr Ile Asp
                180                 185                 190

Met Pro Glu Pro Asp Asp Glu Thr Gln Gln Ile Leu Ile Gln Lys
            195                 200                 205

Ile Gly Ile Ser Pro Glu Asp Ala Lys Asn Ile Glu Ile Val Lys
210                 215                 220

Ile Tyr Leu Glu Ile Thr Thr Gln Lys Lys Glu Ile Lys Pro Val Gln
225                 230                 235                 240

Asn Gly Lys Ala Ala Arg Pro His Ile Asp Lys Ala Ser Gly Leu Arg
                245                 250                 255

Pro Gly Leu Ile Ile Ala Lys Ile Cys His Glu His Asp Ile Ser Ile
```

```
                   260                 265                 270
Gln Glu Asn Asn Gln Asp Phe Ile Lys Val Cys Ala Asp Ile Leu Leu
            275                 280                 285

Ser Arg Thr Asn Leu Ser Leu Thr Glu Ala Gln Asn Lys Leu Glu Lys
290                 295                 300

Val Ile Lys Thr Val Leu Thr Asp Gly Asp Thr Ser Thr Asn Ser Phe
305                 310                 315                 320

Leu Pro Leu Ser Glu Thr Gln Leu Thr Glu Asn Asn Ser Leu Glu Ile
            325                 330                 335

Glu Glu Gln Val Tyr Gln Tyr Leu Gln Lys Thr Thr Ser Ala Arg Val
            340                 345                 350

Ser Glu Ile Glu Val Ala Leu Gly Leu Asn Arg Val Gln Thr Thr Asn
            355                 360                 365

Val Leu Arg Ser Leu Leu Lys Gln Gly His Leu Lys Gln Gln Asp Asn
370                 375                 380

Arg Phe Phe Ala Val Asn Lys Gln Gly Glu Leu Ile Gln Pro
385                 390                 395

<210> SEQ ID NO 329
<211> LENGTH: 334
<212> TYPE: PRT
<213> ORGANISM: Psychromonas ingrahamii 37

<400> SEQUENCE: 329

Met Ser Ile Glu Asn Leu Asn Asn Val Ser Glu Ile Lys Ile Glu Gln
1               5                   10                  15

Ser Asp Asp Asp His Ile Tyr Pro Glu Ala Ser Glu Asp Phe Val Glu
            20                  25                  30

Thr Pro Tyr Ile Lys Glu Val Thr Glu Arg Ala Met Leu Tyr Leu Asp
        35                  40                  45

Ala Gly Tyr Pro Val His Phe Ala Gly Pro Ala Gly Thr Gly Lys Thr
    50                  55                  60

Thr Leu Ala Phe His Ile Ala Ala Leu Arg Gln Arg Pro Val Thr Leu
65                  70                  75                  80

Ile His Gly Asn His Glu Phe Gly Thr Ser Asp Leu Ile Gly Lys Glu
                85                  90                  95

Ser Gly Tyr Arg Arg His Arg Val Val Asp Asn Tyr Val His Ser Val
            100                 105                 110

Val Lys Glu Glu Glu Glu Leu Gln Ser Leu Trp Ser Asp Asn Arg Leu
        115                 120                 125

Thr Thr Cys Cys Arg Asn Gly Asp Thr Leu Val Tyr Asp Glu Phe Asn
    130                 135                 140

Arg Ser Thr Pro Glu Ala Asn Asn Val Leu Leu Ser Ile Leu Glu Glu
145                 150                 155                 160

Gly Ile Leu Asn Leu Pro Ser Ser Arg Ser Asp Gly Tyr Leu Glu Val
                165                 170                 175

His Pro Gln Phe Arg Ala Ile Phe Thr Ser Asn Pro Gln Glu Tyr Ala
            180                 185                 190

Gly Thr His Ala Thr Gln Asp Ala Leu Val Asp Arg Met Ile Thr Ile
        195                 200                 205

Met Leu His Tyr Pro Asp Arg His Thr Glu Val Arg Val Ala Ile Ala
    210                 215                 220

Lys Ser Gly Ile Asn Ser Asp Glu Ala Gly Ser Ile Val Asp Ile Val
225                 230                 235                 240
```

```
Asn Glu Phe Arg Glu Leu Cys Gly Ser Lys Ile Val Ser Ser Gly Pro
            245                 250                 255

Lys Thr Met Pro Thr Val Arg Ala Ser Ile Ala Ile Ala Arg Val Leu
        260                 265                 270

Val Gln Lys Gly Glu His Ala Phe Arg Asp Asn Thr Phe Phe His Arg
    275                 280                 285

Ile Cys Arg Asp Val Leu Cys Met Tyr Thr Gln Gln Val Ser Phe Ser
290                 295                 300

Asn Arg Ser Val Leu Asp Lys Gln Leu Glu Asp Leu Ile Met Lys Phe
305                 310                 315                 320

Cys Pro Ala Thr Tyr Lys Ser Ser Gly Ser Lys Ile Arg Ala
                325                 330
```

<210> SEQ ID NO 330
<211> LENGTH: 335
<212> TYPE: PRT
<213> ORGANISM: Psychromonas ingrahamii 37

<400> SEQUENCE: 330

```
Met Ser Ile Asn Asn Leu Asn Ile Ser Thr Ile Lys Ile Glu Gln Pro
1               5                   10                  15

Glu Asn Asp Asn Ile Tyr Pro Glu Ala Ser Ala Glu Phe Val Gln Thr
            20                  25                  30

Pro Tyr Ile Gln Glu Val Thr Glu Arg Ala Leu Leu Tyr Leu Asp Ala
        35                  40                  45

Gly Tyr Pro Val His Phe Ala Gly Pro Ala Gly Thr Gly Lys Thr Thr
    50                  55                  60

Leu Ala Phe His Ile Ala Ala Leu Arg Lys Arg Pro Val Thr Leu Ile
65                  70                  75                  80

His Gly Asn His Glu Phe Gly Ser Ser Asp Leu Ile Gly Lys Glu Ser
            85                  90                  95

Gly Tyr Arg Arg His Arg Leu Val Asp Asn Tyr Val His Ser Val Met
        100                 105                 110

Lys Glu Glu Glu Glu Leu Lys Ser Leu Trp Val Asp Asn Arg Leu Thr
    115                 120                 125

Thr Cys Cys Arg Asn Gly Asp Thr Leu Val Tyr Asp Glu Phe Asn Arg
130                 135                 140

Ser Thr Pro Glu Ala Asn Asn Val Leu Leu Ser Ile Leu Glu Glu Gly
145                 150                 155                 160

Ile Leu Asn Leu Pro Ser Leu Arg Ser Met Gly Asp Gly Tyr Leu Glu
            165                 170                 175

Val His Pro Ser Phe Arg Ala Ile Phe Thr Ser Asn Pro Gln Glu Tyr
        180                 185                 190

Ala Gly Thr His Ala Thr Gln Asp Ala Leu Val Asp Arg Met Ile Thr
    195                 200                 205

Ile Met Leu Asn Tyr Pro Asp Arg Asp Thr Glu Val Arg Val Ala Val
210                 215                 220

Ala Lys Ser Gly Ile Ser Asn Glu Glu Ala Gly Phe Ile Val Asp Ile
225                 230                 235                 240

Val Asn Glu Phe Arg Glu Leu Ser Asn His Lys Ser Leu Ser Ser Gly
            245                 250                 255

Gln Lys Ser Met Pro Thr Val Arg Ala Ser Ile Ala Ile Ser Arg Val
        260                 265                 270

Leu Ile Gln Lys Gly Glu His Ala Phe Arg Asp Asn Val Phe Phe His
    275                 280                 285
```

```
Arg Val Cys His Asp Val Leu Cys Met Tyr Ile Gln Lys Ile Ser Pro
        290                 295                 300

Ser Asn Arg Ser Phe Leu Asp Lys Gln Leu Glu Val Leu Ile Gly Lys
305                 310                 315                 320

Phe Cys Pro Ala Ala Lys Ser Ala Leu Val Pro Lys Val Val Lys
                325                 330                 335
```

<210> SEQ ID NO 331
<211> LENGTH: 305
<212> TYPE: PRT
<213> ORGANISM: Rhodobacter capsulatus SB 1003

<400> SEQUENCE: 331

```
Met Thr Ile Pro Arg Asp Leu Pro Trp Gly Asp Ala Arg Thr Pro Leu
1               5                   10                  15

Phe Glu Asp Glu Glu Leu Arg Ser Leu Leu Asp Arg Ala Glu Ile Tyr
                20                  25                  30

Leu Arg Glu Gly Ile Ala Ile His Phe Arg Gly Pro Ala Gly Val Gly
            35                  40                  45

Lys Thr Thr Leu Ala Leu His Leu Ala Gln Arg Phe Ala Arg Pro Val
50                  55                  60

Thr Phe Phe Val Gly Asn Asp Trp Leu Gly Arg Ala Asp Ile Phe Gly
65                  70                  75                  80

Arg Asp Leu Gly Glu Thr Val Ser Thr Val Gln Asp His Tyr Ile Ser
                85                  90                  95

Ser Val Arg Arg Ala Glu Arg Lys Ser Arg Ile Asp Trp Gln Glu Ala
            100                 105                 110

Pro Leu Ala Arg Ala Met Arg Asp Gly His Val Leu Val Tyr Asp Glu
        115                 120                 125

Phe Ser Arg Ser Arg Pro Glu Ala Asn Ala Ala Leu Leu Ser Val Ile
    130                 135                 140

Glu Glu Gly Val Leu Pro Leu Ser Asp Pro Ala Ala Gly Arg Ser His
145                 150                 155                 160

Ile Val Ala His Pro Asp Phe Arg Val Ile Leu Thr Ser Asn Pro Arg
                165                 170                 175

Asp Tyr Val Gly Val Gln Ala Val Pro Asp Ala Leu Leu Asp Arg Met
            180                 185                 190

Ile Thr Phe Ser Leu Asp Gly Met Ser Phe Glu Thr Glu Val Gly Ile
        195                 200                 205

Val Ala Thr Ala Ala Arg Thr Asp Pro Ala Asp Ala Arg Ala Ile Cys
    210                 215                 220

Ala Leu Ile His Leu Leu Arg Ala Glu Lys Pro Gly Thr Met Glu Ile
225                 230                 235                 240

Ser Met Arg Ser Gly Ile Met Ile Ala Arg Leu Ala Arg Ala Ala Gly
                245                 250                 255

Val Ala Pro Asp Pro Ala Asp Pro Val Phe Val Gln Ile Cys Ala Asp
            260                 265                 270

Val Leu Gly Thr Arg Met Arg Gly Ser Asp Ile Asp Asp Val Met Ala
        275                 280                 285

Leu Leu Leu Arg Pro Asp Pro Ala Pro Ala Ala Cys Ala Gly Gly Ala
    290                 295                 300

Arg
305
```

<210> SEQ ID NO 332
<211> LENGTH: 316
<212> TYPE: PRT
<213> ORGANISM: Rhodobacter sphaeroides 2.4.1

<400> SEQUENCE: 332

Met Thr Val Leu Ser Pro Ser Leu Pro His Ala Ala Gly Ile Asp Ala
1               5                   10                  15

Ala Leu Val Glu Asn Pro Trp Leu Gly Leu Arg Arg Ser Gly Arg Tyr
            20                  25                  30

Phe Gln Asn Ala Glu Thr Glu Ala Leu Phe Ala Arg Ala Leu Gly Tyr
        35                  40                  45

Ala Arg Ala Gly Val Cys Val His Leu Ala Gly Pro Ala Gly Leu Gly
    50                  55                  60

Lys Thr Thr Leu Ala Leu Arg Ile Ala Gln Ala Leu Gly Arg Pro Val
65                  70                  75                  80

Ala Phe Met Thr Gly Asn Glu Trp Leu Gly Ser Arg Asp Phe Ile Gly
                85                  90                  95

Gly Glu Ile Gly Gln Thr Val Thr Ser Val Val Asp Arg Tyr Ile Gln
            100                 105                 110

Ser Val Arg Arg Thr Glu Gln Ser Ala Arg Ile Asp Trp Lys Glu Ser
        115                 120                 125

Ile Leu Gly Gln Ala Met Arg Cys Gly Gln Thr Phe Ile Tyr Asp Glu
    130                 135                 140

Phe Thr Arg Ala Ser Pro Glu Ala Asn Ala Ala Leu Leu Ser Val Leu
145                 150                 155                 160

Glu Glu Gly Val Leu Val Ser Thr Asp Gly Ala Ser Arg His Gln Tyr
                165                 170                 175

Ile Glu Ala His Pro Asp Phe Arg Val Leu Leu Thr Ser Asn Pro His
            180                 185                 190

Glu Tyr Gln Gly Val Lys Ala Ala Pro Asp Ala Leu Ile Asp Arg Met
        195                 200                 205

Val Thr Leu Arg Leu Glu Glu Pro Ser Ala Pro Thr Leu Ala Gly Ile
    210                 215                 220

Val Ala Leu Arg Ser Gly Leu Asp Pro Ala Thr Ala Arg Arg Ile Val
225                 230                 235                 240

Asp Leu Ile Leu Ser Val Gln Arg Ser Gly Glu Met Gln Ala Pro Pro
                245                 250                 255

Ser Met Arg Thr Ala Ile Leu Val Ala Arg Leu Ala Ala Pro Leu Arg
            260                 265                 270

Leu Ala Gly Arg Leu Ser Asp Ala Ala Leu Ala Glu Ile Ala Ala Asp
        275                 280                 285

Val Leu Arg Gly Arg Gly Leu Glu Ala Asp Ala Ala Phe Glu Ala
    290                 295                 300

Lys Leu Ala Ala Pro Thr Pro Gly Glu Thr Ala Arg
305                 310                 315

<210> SEQ ID NO 333
<211> LENGTH: 329
<212> TYPE: PRT
<213> ORGANISM: Serratia sp. ATCC 39006

<400> SEQUENCE: 333

Met Ile Lys Gln Asn Thr Val Ser Gln Tyr Thr Val Asp Asp Leu
1               5                   10                  15

Val Val Pro Glu Ala Ser Glu His Phe Val Ala Thr Ser Tyr Val Asn

```
                20                  25                  30

Asp Ile Ile Glu Arg Ala Leu Val Tyr Leu Arg Ala Gly Tyr Pro Val
                35                  40                  45

His Phe Ala Gly Pro Ser Gly Ile Gly Lys Thr Thr Leu Ala Phe His
 50                  55                  60

Leu Ala Ala Leu Trp Gly Arg Pro Val Thr Met Leu Gln Gly Asn Glu
 65                  70                  75                  80

Glu Phe Val Ser Ser Asp Leu Thr Gly Lys Asp Ile Gly Tyr Arg Lys
                 85                  90                  95

Ser Ser Leu Val Asp Asn Tyr Ile His Ser Val Leu Lys Thr Glu Glu
                100                 105                 110

Gln Met Asn Arg Met Trp Val Asp Asn Arg Leu Thr Thr Ala Cys Arg
                115                 120                 125

Asn Gly Asp Met Leu Ile Tyr Asp Glu Phe Asn Arg Ser Lys Ala Glu
            130                 135                 140

Thr Asn Asn Val Leu Leu Ser Val Leu Ser Glu Gly Ile Leu Asn Leu
145                 150                 155                 160

Pro Gly Leu Arg Gly Val Gly Glu Gly Tyr Leu Asp Val His Pro Glu
                165                 170                 175

Phe Arg Ala Ile Phe Thr Ser Asn Pro Glu Glu Tyr Ala Gly Thr His
                180                 185                 190

Lys Thr Gln Asp Ala Leu Met Asp Arg Met Ile Thr Ile Asn Ile Gly
            195                 200                 205

Leu Val Asp Arg Asp Thr Glu Leu Gln Ile Leu His Ala Arg Ser Glu
210                 215                 220

Leu Glu Leu Lys Glu Ala Ala Tyr Ile Val Asp Ile Ile Arg Glu Leu
225                 230                 235                 240

Arg Gly Asn Glu His Glu Thr Lys His Gly Leu Arg Ala Gly Ile Ala
                245                 250                 255

Ile Ala His Ile Leu His Gln Gln Gly Ile Lys Pro Arg Tyr Gly Asp
            260                 265                 270

Lys Leu Phe His Ala Ile Cys Tyr Asp Val Leu Ser Met Asp Ala Ala
            275                 280                 285

Lys Ile Gln His Ala Gly Arg Ser Ile Tyr Arg Glu Met Val Asp Gly
            290                 295                 300

Val Ile Arg Lys Ile Cys Pro Ile Gly Ser Asp Thr Val Lys Ala
305                 310                 315                 320

Ser Thr Gln Lys Ile Lys Ala Val Glu
                325

<210> SEQ ID NO 334
<211> LENGTH: 364
<212> TYPE: PRT
<213> ORGANISM: Stella vacuolata_ATCC-43931

<400> SEQUENCE: 334

Met Ser Thr Glu Pro Ala Pro Val Met Pro Pro Ser Thr Asp Ile Glu
1               5                   10                  15

Phe Gly Ser Gln Arg Pro Ala Arg Pro Lys Pro Ala Glu Ala Leu Ala
                20                  25                  30

Val Gly Tyr Arg Leu Ser Ala Arg Pro Ala Ala Pro Ser Thr Leu Thr
            35                  40                  45

Leu Arg Pro Arg Ala Asp Phe Val Glu Thr Asp Gln Val Lys Asp Leu
 50                  55                  60
```

Thr Arg Arg Gly Leu Gly Phe Leu Arg Ala Gly Tyr Pro Leu His Phe
 65                  70                  75                  80

Arg Gly Pro Ala Gly Thr Gly Lys Thr Thr Leu Ala Leu His Val Ala
             85                  90                  95

Ala Gln Leu Gly Arg Pro Val Ile Val Ile Thr Gly Asp Asn Glu Leu
         100                 105                 110

Gly Thr Ala Asp Leu Val Gly Ser Gln Arg Gly Tyr His Tyr Arg Lys
     115                 120                 125

Val Val Asp Gln Phe Ile His Asn Val Thr Lys Leu Glu Glu Thr Ala
130                 135                 140

Asn Gln Arg Trp Thr Asp His Arg Leu Thr Thr Ala Cys Arg Glu Gly
145                 150                 155                 160

Tyr Thr Leu Val Tyr Asp Glu Phe Thr Arg Ser Arg Pro Glu Thr His
                165                 170                 175

Asn Val Leu Leu Gly Val Phe Glu Glu Lys Ile Leu Phe Leu Pro Ala
            180                 185                 190

Glu Ala Arg Glu Glu Cys Tyr Ile Arg Val His Pro Asp Phe Arg Ala
        195                 200                 205

Ile Phe Thr Ser Asn Pro Gln Glu Tyr Ala Gly Val His Ala Ser Gln
    210                 215                 220

Asp Ala Leu Ala Asp Arg Leu Ala Thr Ile Asp Val Asp Tyr Pro Asn
225                 230                 235                 240

Arg Ala Met Glu Leu Ala Val Ala Ser Ala Arg Thr Gly Leu Ala Glu
                245                 250                 255

Ala Glu Ala Ala Arg Ile Ile Asp Leu Val Arg Ala Phe Arg Ala Ser
            260                 265                 270

Gly Asp Tyr Gln Gln Thr Pro Thr Met Arg Ala Ser Leu Met Ile Ala
        275                 280                 285

Arg Val Ala Ala Gln Glu Gly Leu Arg Ile Ser Val Asp Asp Pro Gly
    290                 295                 300

Phe Val Gln Leu Cys Met Asp Ala Leu Glu Ser Arg Ile Phe Ser Gly
305                 310                 315                 320

Ala Arg Gln Glu Ala Asp Ala Arg Ala Arg His Arg Val Ala Leu Leu
                325                 330                 335

Gly Leu Leu Ala Thr His Cys Pro Ser Glu Ala Pro Val Ala Arg Val
            340                 345                 350

Ala Thr Val Ala Arg Ala Lys Arg Lys Ser Ala Ser
    355                 360

<210> SEQ ID NO 335
<211> LENGTH: 332
<212> TYPE: PRT
<213> ORGANISM: Thiocapsa rosea strain DSM 235 Ga0242571_11

<400> SEQUENCE: 335

Met Ser Ala Lys Pro Leu Gln Asp Ala Ser Glu Val Ser Ala Leu Asn
1               5                   10                  15

Asn Asp Asn Val Gln Pro Glu Ala Ser Asp Thr Phe Val Cys Thr Pro
            20                  25                  30

Ser Val Glu Ala Leu Ala Glu Arg Ala Ser Ala Tyr Leu Gln Ala Gly
        35                  40                  45

Tyr Pro Val His Leu Ala Gly Pro Ala Gly Thr Gly Lys Thr Thr Leu
    50                  55                  60

Ala Phe His Ala Ala Ala Lys Arg Gly Arg Pro Val Lys Leu Ile His
65                  70                  75                  80

```
Gly Asn Asp Glu Leu Gly Leu Ala Asp Met Val Gly Gln Asp Asn Gly
                 85                  90                  95

Tyr Arg Arg Asn Thr Leu Val Asp Asn Tyr Ile His Ser Val Val Lys
            100                 105                 110

Thr Gln Glu Glu Val Arg Thr Phe Trp Ile Asp Asn Arg Val Thr Thr
        115                 120                 125

Ala Cys Leu Asn Gly Glu Thr Leu Ile Tyr Asp Glu Phe Asn Arg Ser
130                 135                 140

Arg Pro Glu Val Asn Asn Ile Phe Leu Ser Ile Leu Gly Glu Gly Ile
145                 150                 155                 160

Leu Asn Leu Pro Asn Arg Arg His Gln Gly Ala Gly Tyr Leu Glu Val
                165                 170                 175

His Pro Glu Phe Arg Val Ile Phe Thr Ser Asn Pro Glu Glu Tyr Ala
            180                 185                 190

Gly Thr His Lys Thr Gln Asp Ala Leu Met Asp Arg Met Ile Thr Met
        195                 200                 205

Lys Ile Gly His Tyr Asp Arg Glu Thr Glu Ile Arg Val Thr Arg Ala
210                 215                 220

Lys Ser Gly Leu Pro Pro Ser Glu Val Ala Ile Val Asp Ile Val
225                 230                 235                 240

Arg Glu Leu Arg Gly Gln Ser Val Asn His His Arg Pro Thr Leu Arg
                245                 250                 255

Ala Cys Ile Ala Ile Ala Arg Ile Met Ala Asp Arg Arg Ile Ser Ala
            260                 265                 270

Arg Ser Asn Asn Ser Phe Phe Arg Asp Ile Cys Arg Asp Ile Leu Asp
        275                 280                 285

Met Asp Ser Ala Lys Val Arg Arg Asp Gly Asn Ala Leu Gly Glu Ser
290                 295                 300

Pro Val Asp Asp Val Val Ala Ser Ile Ser Ala Arg Ala Arg Arg Pro
305                 310                 315                 320

Lys Ile Val Glu Pro Lys Gly Leu His Lys Glu Ile
                325                 330

<210> SEQ ID NO 336
<211> LENGTH: 348
<212> TYPE: PRT
<213> ORGANISM: Tolypothrix sp. PCC 7601

<400> SEQUENCE: 336

Met Thr Asn Thr Glu Asn His Lys Lys Arg Ala Val Leu Arg Val Arg
1               5                   10                  15

Pro Gly Gln Phe Val Val Thr Pro Ala Ile Glu Lys Val Ala Ile Arg
            20                  25                  30

Ala Leu Arg Tyr Leu Thr Ser Gly Phe Ala Ile His Leu Arg Gly Pro
        35                  40                  45

Ala Gly Thr Gly Lys Thr Thr Leu Ala Met His Leu Ala Asn Cys Leu
    50                  55                  60

Asp Arg Pro Ile Met Leu Ile Phe Gly Asp Asp Glu Phe Lys Ser Ser
65                  70                  75                  80

Asp Leu Ile Gly Ser Glu Ser Gly Tyr Thr His Lys Lys Leu Leu Asp
                85                  90                  95

Asn Tyr Ile His Asn Val Leu Lys Val Glu Asp Glu Leu Lys Gln Asn
            100                 105                 110

Trp Val Asp Ser Arg Leu Thr Leu Ala Cys Arg Glu Gly Leu Thr Leu
```

```
            115                 120                 125
Val Tyr Asp Glu Phe Asn Arg Ser Arg Pro Glu Val Asn Asn Val Leu
130                 135                 140

Leu Ser Ala Leu Glu Glu Lys Ile Leu Thr Leu Pro Pro Ser Ser Asn
145                 150                 155                 160

Gln Pro Glu Tyr Leu His Val His Pro Lys Phe Arg Ala Ile Phe Thr
                165                 170                 175

Ser Asn Pro Glu Glu Tyr Cys Gly Val His Ser Thr Gln Asp Ala Leu
            180                 185                 190

Met Asp Arg Leu Val Thr Ile Asn Met Pro Glu Pro Asp Glu Gln Thr
        195                 200                 205

Gln Ile Glu Ile Leu Thr His Lys Thr Gly Ile His His Glu Tyr Ala
    210                 215                 220

Gln Leu Ile Ala Arg Leu Val Lys Ala Phe Arg Ser Ala Thr Gly Ala
225                 230                 235                 240

Glu Lys Thr Ser Gly Leu Arg Ser Cys Leu Met Val Ala Lys Val Cys
                245                 250                 255

Ala Glu His Asp Ile Leu Val Thr Pro Glu Asn Thr Asp Phe Arg Glu
            260                 265                 270

Ile Cys Ala Asp Val Leu Phe Asn Arg Thr Asn Leu Ser Ala Ser Asp
        275                 280                 285

Ala Thr Thr Leu Phe Leu Glu Leu Leu Asn His Val Gln Val Lys Pro
    290                 295                 300

Val Glu Pro Val Asp Asp Ser Asp Pro Tyr Val Ala Glu Ala Glu
305                 310                 315                 320

Ile Val Gly Ala Ala Glu Pro Gln Thr Asp Ala Ile Ala Glu Pro Val
                325                 330                 335

Thr Leu Asp Glu Ser Leu Leu Ser Asp Gln Pro Asn
            340                 345

<210> SEQ ID NO 337
<211> LENGTH: 311
<212> TYPE: PRT
<213> ORGANISM: Trichodesmium erythraeum IMS101

<400> SEQUENCE: 337

Met Thr Thr Val Leu Asn Val Ser Pro Asp Arg Phe Val Ser Thr Pro
1               5                   10                  15

Gly Val Glu Arg Val Thr Gln Arg Ala Ser Arg Tyr Leu Glu Ser Gly
            20                  25                  30

Tyr Ser Val His Leu Arg Gly Pro Ala Gly Val Gly Lys Thr Thr Leu
        35                  40                  45

Ala Leu His Leu Ala His Leu Arg Gln Gln Pro Ile Phe Leu Met Ile
    50                  55                  60

Gly Asp Asp Glu Phe Lys Thr Ser Asp Leu Ile Gly Asn Lys Ser Gly
65                  70                  75                  80

Tyr Thr Arg Lys Lys Leu Val Asp Asn Tyr Ile His Thr Val Leu Lys
                85                  90                  95

Val Glu Asp Glu Leu Arg Asp Asn Trp Ile Asp Ser Arg Leu Thr Leu
            100                 105                 110

Ala Cys Lys Glu Gly Phe Thr Leu Ile Tyr Asp Glu Phe Asn Arg Ser
        115                 120                 125

Arg Pro Glu Val Asn Asn Val Leu Leu Ser Val Leu Glu Glu Lys Met
    130                 135                 140
```

```
Leu Val Leu Pro Pro Ser Gln Asn Gln Ser Glu Tyr Ile Gln Val His
145                 150                 155                 160

Pro Gln Phe Arg Val Ile Leu Thr Ser Asn Ser Glu Glu Trp Thr Gly
                165                 170                 175

Val His Ala Thr Gln Asp Ala Leu Leu Asp Arg Val Val Thr Ile Gly
                180                 185                 190

Met Glu Gln Pro Asp Ile Ser Thr Glu Gln Asn Ile Val Ile Gln Lys
            195                 200                 205

Thr Gly Ile Asn Pro Leu Lys Ala Glu Val Ile Ile Lys Leu Val Arg
210                 215                 220

Ser Val Arg Gln Arg Val Asp Lys Glu Asp Leu Gly Ser Leu Arg Ser
225                 230                 235                 240

Ala Leu Met Ile Ser Lys Val Cys His Asp His Asp Ile Pro Leu Asp
                245                 250                 255

Gly Lys Asp Ser Ser Phe Ser Asp Leu Cys Ala Asp Ile Leu Ile Ser
                260                 265                 270

Arg Pro Asn Leu Pro Arg Gln Glu Ala Leu Gln Leu Asp Glu Val
                275                 280                 285

Leu Glu Glu Phe Phe Pro Ala Asp Gln Pro Ser Ser Ser Asp Val Gly
290                 295                 300

Leu Glu Lys Glu Gly Ser Leu
305                 310

<210> SEQ ID NO 338
<211> LENGTH: 311
<212> TYPE: PRT
<213> ORGANISM: Trichodesmium erythraeum IMS101

<400> SEQUENCE: 338

Met Thr Thr Val Leu Asn Val Ser Pro Asp Arg Phe Val Ser Thr Pro
1               5                   10                  15

Ser Val Glu Arg Val Thr Gln Arg Ala Ser Arg Tyr Leu Glu Ser Gly
                20                  25                  30

Tyr Ser Val His Leu Arg Gly Pro Ala Gly Val Gly Lys Thr Thr Leu
            35                  40                  45

Ala Leu His Leu Ala His Leu Arg Gln Gln Pro Ile Phe Leu Met Ile
50                  55                  60

Gly Asp Asp Glu Phe Lys Thr Ser Asp Leu Ile Gly Asn Lys Ser Gly
65                  70                  75                  80

Tyr Thr Arg Lys Lys Leu Val Asp Asn Tyr Ile His Thr Val Leu Lys
                85                  90                  95

Val Glu Asp Glu Leu Lys His Asn Trp Ile Asp Ser Arg Leu Thr Leu
            100                 105                 110

Ala Cys Lys Glu Gly Phe Thr Leu Ile Tyr Asp Glu Phe Asn Arg Ser
        115                 120                 125

Arg Pro Glu Val Asn Asn Val Leu Leu Ser Val Leu Glu Glu Lys Met
    130                 135                 140

Leu Val Leu Pro Pro Ser Gln Asn Gln Ser Glu Tyr Ile Gln Val His
145                 150                 155                 160

Pro Gln Phe Arg Val Ile Leu Thr Ser Asn Ser Glu Glu Trp Thr Gly
                165                 170                 175

Val His Ala Thr Gln Asp Ala Leu Leu Asp Arg Val Val Thr Ile Gly
                180                 185                 190

Met Gly Gln Pro Asp Ile Ser Thr Glu Gln Asn Ile Ile Ile Gln Lys
            195                 200                 205
```

```
Thr Gly Ile Asn Pro Leu Lys Ala Glu Val Ile Ile Lys Leu Val Arg
    210                 215                 220

Ser Val Arg Glu Arg Leu Glu Thr Glu Asp Leu Gly Ser Leu Arg Ser
225                 230                 235                 240

Ala Leu Met Ile Ser Lys Val Cys His Asp His Asp Ile Pro Leu Gly
                245                 250                 255

Gly Lys Asp Ser Asn Phe Ser Asp Leu Cys Ala Asp Ile Leu Ile Ser
                260                 265                 270

Arg Ala Asn Leu Pro Arg Gln Glu Ala Leu Lys Gln Leu Asp Glu Val
            275                 280                 285

Leu Glu Glu Leu Phe Pro Ala Asp Gln Leu Ser Ile Ser Asp Ile Gly
        290                 295                 300

Leu Lys Lys Glu Gly Ser Leu
305                 310

<210> SEQ ID NO 339
<211> LENGTH: 114
<212> TYPE: PRT
<213> ORGANISM: Anabaena-flos-aquae

<400> SEQUENCE: 339

Met Ile Lys Asn Ile Gln Val Phe Phe Met Lys Thr Ile Ser Asn Arg
1               5                   10                  15

Ser Ile Ser Arg Ala Lys Ile Ser Thr Met Pro Arg Pro Lys Ser Asp
                20                  25                  30

Ala Ser Ser Gln Leu Asp Leu Tyr Lys Met Val Thr Glu Lys Gln Arg
            35                  40                  45

Ile Gln Arg Asp Met Tyr Ser Ile Lys Glu Arg Met Gly Leu Leu Gln
        50                  55                  60

Gln Arg Leu Asp Ile Leu Asn Gln Gln Ile Glu Ala Thr Glu Lys Thr
65                  70                  75                  80

Ile His Lys Leu Arg Gln Pro His Ser Asn Thr Ala Gln Asn Ile Val
                85                  90                  95

Arg Ser Asn Ile Phe Val Glu Ser Asn Asn Tyr Gln Thr Phe Glu Val
                100                 105                 110

Glu Tyr

<210> SEQ ID NO 340
<211> LENGTH: 105
<212> TYPE: PRT
<213> ORGANISM: Aphanizomenon flos-aquae NIES-81

<400> SEQUENCE: 340

Met Lys Ser Phe Arg His Arg Ser Ile Ile Arg Ala Lys Ile Ser Thr
1               5                   10                  15

Met Pro Arg His Ile Ser Glu Ala Ser Ser Gln Leu Glu Leu Tyr Lys
                20                  25                  30

Met Val Ala Glu Lys Gln Arg Ile Ser Arg Glu Leu Ser Ser Ile Lys
            35                  40                  45

Glu Arg Met Ala Thr Leu Gln Lys Arg Leu Asp Ser Leu Asn Asn Glu
        50                  55                  60

Ile Asp Asn Thr Glu Lys Thr Ile His Lys Leu Arg Gln Pro His Ser
65                  70                  75                  80

Ser Thr Ala Gln Asn Ile Val Arg Ser Lys Asn Val Val Glu Ser Asn
                85                  90                  95
```

```
Asn Tyr Gln Thr Phe Glu Ile Glu Tyr
            100                 105
```

<210> SEQ ID NO 341
<211> LENGTH: 112
<212> TYPE: PRT
<213> ORGANISM: Arthrospira platensis NIES-39

<400> SEQUENCE: 341

```
Met Arg Tyr Lys Tyr His Arg Gln Ile Gln Pro Lys Leu Ser Ala Ile
1               5                   10                  15

Pro Arg Gln Lys Ser Gln Ala Asn Leu Tyr Arg Asn Ser Tyr Leu Leu
            20                  25                  30

Ala Val Glu Lys Lys Arg Leu Thr Glu Glu Leu Glu Val Leu Gln Ser
        35                  40                  45

Arg Ser His Ile Ile Glu Gln Arg Leu Ala Leu Ile Glu Asp Gln Leu
    50                  55                  60

Gly Glu Leu Glu Lys Asp Val Thr Gln Leu Ser Val Pro Pro Ser Pro
65                  70                  75                  80

Lys Pro Gln Asn Asn Leu Pro Val Asn Pro Glu Pro Pro Gln
                85                  90                  95

Ser Asn Pro Thr Asn Ser Ser His Ile Asn Thr Phe Met Val Asp Tyr
            100                 105                 110
```

<210> SEQ ID NO 342
<211> LENGTH: 91
<212> TYPE: PRT
<213> ORGANISM: Burkholderia thailandensis sp. Bp5365 strain MSMB43

<400> SEQUENCE: 342

```
Met Pro Ile Pro Lys Lys Gly Leu His Asp Ile Arg Phe Arg His Ala
1               5                   10                  15

Pro Gly Ala Thr Pro Leu Pro Val His Ser Met Tyr Met Arg Ile Ser
            20                  25                  30

Cys Ile Glu Met Glu Lys Ser Arg Arg Thr Ile Glu Arg Arg Ala Ala
        35                  40                  45

Gln Arg Arg Ile Ala Ala Val Asp Ser Arg Val Ala Asp Leu Glu Arg
    50                  55                  60

Glu Lys Ala Arg Leu Tyr Ala Ala Ile Asp Asn Glu Ala Pro Gln Ala
65                  70                  75                  80

Gly Asp Ile Arg Gly Ser Phe Arg Ile Arg Tyr
                85                  90
```

<210> SEQ ID NO 343
<211> LENGTH: 103
<212> TYPE: PRT
<213> ORGANISM: Desulfobacterium vacuolatum_DSM 3385

<400> SEQUENCE: 343

```
Met Leu Lys Asn Arg Asn Arg Ser Ile Lys Gly Val Gln Asn Ile Lys
1               5                   10                  15

Thr His Ala Gly Lys Val Asp His Val Ser His Pro His Met Ala Tyr
            20                  25                  30

Met Arg Ile Ser Cys Leu Glu Met Glu Lys Ala Arg Lys Asn Lys Glu
        35                  40                  45

Lys Ser Gly Ala Gln Lys Arg Ile Asp Met Ile Asn Gln Arg Leu Met
    50                  55                  60

Glu Ile Glu Lys Glu Lys Ala His Ile Gln Arg Ile Leu Gly Asp Thr
```

```
                65                  70                  75                  80
Ser Ile Ala Leu Glu Ser Ser Asn Val Asp His Asp Ser Glu Ile Lys
                    85                  90                  95

Gly Gly Phe Lys Ile Lys Tyr
            100

<210> SEQ ID NO 344
<211> LENGTH: 106
<212> TYPE: PRT
<213> ORGANISM: Desulfomonile tiedjei DSM 6799

<400> SEQUENCE: 344

Met Asn Ile Arg Met Lys Gly Asn Ser Arg Gly Leu Arg Asp Ile Arg
1               5                   10                  15

Thr His Ser Gly Lys Val Asp Arg Val Gly Leu Pro Tyr Met Ala Tyr
                20                  25                  30

Met Ser Ile Ser Cys Leu Glu Met Glu Lys Ala Arg Arg Glu Lys Glu
            35                  40                  45

Arg Leu Ser Ala Leu Thr Arg Ile Lys Asn Ile Glu Gln Arg Ile Arg
        50                  55                  60

Glu Ile Glu Ala Glu Lys Asp Leu Leu Lys Gly Val Gly Glu Arg
65                  70                  75                  80

Thr Arg Thr Asp Leu Gln Lys Ala Ser Thr Pro Arg Asp Gln Ser Ala
                85                  90                  95

Gln Cys Lys Gly Gly Phe Lys Ile Arg Tyr
            100                 105

<210> SEQ ID NO 345
<211> LENGTH: 105
<212> TYPE: PRT
<213> ORGANISM: Legionella drancourtii LLAP12

<400> SEQUENCE: 345

Met Met Pro Ala Leu Val Lys Gly Leu Arg Asn Ile Lys Thr Met Ser
1               5                   10                  15

Asn Arg Leu Asp Lys Val Gln Ser Pro His Glu Ala Phe Ile Ser Ala
                20                  25                  30

Ala Ala Leu His Arg Glu Lys Gln Arg His Leu Gln Glu Leu Ala Ile
            35                  40                  45

Leu Arg Asn Arg Leu Asp Glu Ile Asn Leu Arg Leu Glu Gln Ile Asn
        50                  55                  60

Glu Gln Gln Asn Gln Val Ala Glu Ala Phe Asp Ile Ser Pro Pro Arg
65                  70                  75                  80

Ala Val Lys Ser Ala Leu Arg Thr Gly Ile Gln Ser Lys Thr Gly Ser
                85                  90                  95

Thr Ser His Gly Phe Lys Ile Lys Tyr
            100                 105

<210> SEQ ID NO 346
<211> LENGTH: 110
<212> TYPE: PRT
<213> ORGANISM: Microcystis aeruginosa NIES-843

<400> SEQUENCE: 346

Met Thr Thr Thr Arg Pro Pro Arg Pro Ile Arg Ser Lys Ile Ser Thr
1               5                   10                  15

Met Pro Arg Lys Gln Ser Glu Ala Asp His Gln Leu Glu Leu Tyr Lys
                20                  25                  30
```

```
Leu Ile Thr Glu Lys Gln Arg Ile Gln Glu Lys Leu Glu Met Met Glu
        35                  40                  45

Arg Gln Ile Gln Gln Leu Lys Asn Arg Leu Thr Phe Val Thr Glu Gln
    50                  55                  60

Ile Glu Thr Thr Glu Gln Ser Ile Gln Asn Leu Arg Thr Ala Asn Pro
65                  70                  75                  80

Pro Ser Val Ala Lys Lys Pro Asp Ser Pro Lys Thr Val Ala His Ser
                85                  90                  95

Ser Asn Asn Ser Ser Asn Phe Gln Thr Phe Tyr Leu Glu Tyr
            100                 105                 110

<210> SEQ ID NO 347
<211> LENGTH: 94
<212> TYPE: PRT
<213> ORGANISM: Nostoc punctiforme ATCC 29133

<400> SEQUENCE: 347

Met His Arg Thr Pro Asn Arg Arg Gln Ile Gln Ala Lys Leu Ser Thr
1               5                   10                  15

Met Pro Pro Gln Arg Ser Gln Ala Thr Val Tyr Leu Asn Ala Tyr Lys
            20                  25                  30

Met Met Leu Glu Lys Glu Arg Leu Glu Glu Leu Glu Lys Leu Glu
        35                  40                  45

Ala Arg Arg His Gln Ile Gln Gln Arg Leu Ala Ile Leu Asn Ser Gln
    50                  55                  60

Thr Ile Pro Glu Glu Asn Met Thr His Gln Gln Ala Asn Thr Asp Leu
65                  70                  75                  80

Glu Asn Asn Thr Pro Lys Phe Asn Thr Leu Thr Leu Glu Tyr
                85                  90

<210> SEQ ID NO 348
<211> LENGTH: 113
<212> TYPE: PRT
<213> ORGANISM: Nostoc sp. PCC 7120

<400> SEQUENCE: 348

Met Leu Ser Ile Ile Gln Val Phe Pro Met Thr Lys Val Arg Asn Arg
1               5                   10                  15

Gly Ile Ile Arg Pro Lys Ile Thr Thr Met Pro Arg Asn Lys Ser Glu
            20                  25                  30

Ala Ser Ser Gln Leu Glu Leu Tyr Lys Leu Val Thr Glu Gln Gln Arg
        35                  40                  45

Ile Lys Gln Glu Leu Ala Phe Ile Glu Gln Arg Thr Val Leu Leu Lys
    50                  55                  60

Gln Arg Leu Ser Thr Leu Lys Thr Gln Ile Glu Gly Thr Glu Arg Ser
65                  70                  75                  80

Ile Asn His Leu Arg His Ser Glu Leu Lys Tyr Ser Arg Ile Ala Leu
                85                  90                  95

Pro Lys Ile Phe Ser Glu Thr Asn Asn Tyr Gln Ala Phe Asp Ile Glu
            100                 105                 110

Tyr

<210> SEQ ID NO 349
<211> LENGTH: 108
<212> TYPE: PRT
<213> ORGANISM: Planktothrix agardhii str. 7805
```

-continued

<400> SEQUENCE: 349

Met Arg Pro Phe Arg Ser Gln Pro Pro Ile Leu Pro Lys Ile Ser Thr
1               5                   10                  15

Met Pro Arg Gln Lys Thr Glu Ala Thr Leu Tyr Arg Ser Leu Tyr Gln
                20                  25                  30

Leu Ala Val Glu Lys Lys Arg Leu Gln Glu Glu Leu Glu Ser Leu Gly
            35                  40                  45

Gln Arg Phe Glu Thr Val Thr Gln Arg Leu Gln Gln Ile Glu Thr Gln
        50                  55                  60

Ile Gln Gly Leu Glu Thr Asp Val Lys Gln Ile Ala Pro Pro Lys Pro
65                  70                  75                  80

Pro Glu Thr Lys Pro Asn Gln Pro Ser Thr Pro Thr Pro Lys Ala
                85                  90                  95

Glu Pro Gly Ser Val Ser Thr Phe Thr Leu Asp Tyr
            100                 105

<210> SEQ ID NO 350
<211> LENGTH: 103
<212> TYPE: PRT
<213> ORGANISM: Psychromonas ingrahamii 37

<400> SEQUENCE: 350

Met Thr Ala Ala Lys Arg Lys Thr Leu Arg Gly Leu Ala Asp Ile Arg
1               5                   10                  15

Thr Ile Ser Ser Cys Gly Thr Ser Gly Gln Glu Ala Tyr Gln Met Tyr
                20                  25                  30

Leu Lys Arg Gly Val Leu Glu Met Glu Lys Leu Arg Arg Gln Lys Glu
            35                  40                  45

Lys Asn Ser Ala Leu Glu Arg Val Thr Asn Ile Asn Arg Arg Leu Met
        50                  55                  60

Ala Ile Asp Thr Asp Ile Asp Phe Leu Cys Gln Ser Leu Lys Val Ile
65                  70                  75                  80

Glu Lys Arg Thr Asn Gln Glu Asn Ser Ile Val Glu Lys Ser Val Ser
                85                  90                  95

Arg Gly Phe Lys Leu Arg Tyr
            100

<210> SEQ ID NO 351
<211> LENGTH: 106
<212> TYPE: PRT
<213> ORGANISM: Psychromonas ingrahamii 37

<400> SEQUENCE: 351

Met Ile Phe Ser Lys Lys Lys Asn Ala Leu Arg Gly Leu Ala Asp Ile
1               5                   10                  15

Arg Thr Leu Ser Gly Cys Gly Thr Ser Gly Gln Glu Ala Tyr Gln Met
                20                  25                  30

Tyr Leu Lys Arg Gly Val Leu Glu Met Glu Lys Leu Arg Arg Gln Lys
            35                  40                  45

Glu Lys Asn Ser Ala Leu Glu Arg Val Arg Asn Ile Asn Tyr Arg Leu
        50                  55                  60

Met Ala Ile Asp Ala Asp Ile Asp Phe Leu Cys Gln Ser Leu Lys Val
65                  70                  75                  80

Ile Glu Glu Arg Thr Asn Lys Glu Asn Ser Ile Ser Asn Glu Ser Val
                85                  90                  95

Thr Tyr Lys Lys Gly Phe Lys Leu Arg Tyr
            100

-continued

```
                100                 105

<210> SEQ ID NO 352
<211> LENGTH: 105
<212> TYPE: PRT
<213> ORGANISM: Serratia sp. ATCC 39006

<400> SEQUENCE: 352

Met Ala Ile Ser Thr Arg Pro Leu Arg Thr Leu Ser Asp Ile Lys Thr
1               5                   10                  15

His Ser Gly Arg Val Ser Gly Glu His Gln Thr Tyr Arg Asp Tyr Phe
            20                  25                  30

Gln Ile Gly Ala Leu Glu Leu Gly Arg Trp Arg Arg Thr Arg Glu Arg
        35                  40                  45

Glu Ala Ala Ser Ser Arg Ile Ala Ser Ile Asp Glu Arg Ile Ala Asp
    50                  55                  60

Ile Asp Lys Glu Lys Ala Ala Leu Leu Ala Asp Ala Thr Ala Ala Ser
65                  70                  75                  80

Ala Val Ala Glu Asn Asn Asp Lys Ser Glu Ala Ala Glu Lys Lys Lys
                85                  90                  95

Lys Ser Ser Gly Leu Arg Ile Lys Tyr
            100                 105

<210> SEQ ID NO 353
<211> LENGTH: 130
<212> TYPE: PRT
<213> ORGANISM: Thiocapsa rosea strain DSM 235 Ga0242571_11

<400> SEQUENCE: 353

Met Ser Lys Phe Thr Gln Pro Ser Arg Ser Val Arg Asp Ile Lys Thr
1               5                   10                  15

Leu Ala Gly Met Ala Asp Asp Val Arg Ala Pro His Lys Met Tyr Met
            20                  25                  30

Arg Leu Phe Ala Leu Glu Thr Glu Arg His Arg Arg Leu Gln Glu Arg
        35                  40                  45

Ala Ser Ala Met Leu Arg Val Asp Asn Ile Asp Ala Arg Cys Ala Glu
    50                  55                  60

Ile Ala Glu Glu Met Glu Gln Leu Leu Gln Ile Leu Gly Val Glu Ala
65                  70                  75                  80

Val Ala Pro Gly Gly Pro Pro Ala Asn Ala Arg Pro Gly Ser Gly Arg
                85                  90                  95

Val Pro Thr Gln Pro His Arg Gly Arg Gly Lys Gly Thr Gly Ala Gly
            100                 105                 110

Arg Gln Thr Thr Ser Gly Glu Thr Ser Val Gly Glu Ala Val Lys Ile
        115                 120                 125

Arg Tyr
    130

<210> SEQ ID NO 354
<211> LENGTH: 226
<212> TYPE: PRT
<213> ORGANISM: Anabaena-flos-aquae

<400> SEQUENCE: 354

Met Glu Leu Glu Asn Leu Tyr Thr Tyr Ala Phe Leu Glu Ile Pro Ser
1               5                   10                  15

Ser Pro Leu Ile Leu Pro Gln Gly Ala Ala Asn Gln Val Val Leu Ile
            20                  25                  30
```

```
Asn Gly Thr Glu Leu Ala Ala Ile Val Glu Pro Gly Ile Phe Leu Glu
         35                  40                  45

Ser Phe Gln Asn Asn Asp Glu Lys Ile Ile Gln Met Ala Leu Ser His
 50                  55                  60

Asp Arg Val Ile Cys Glu Leu Phe Gln Gln Ile Thr Val Leu Pro Leu
 65                  70                  75                  80

Arg Phe Gly Thr Tyr Phe Thr Ser Thr Asn Asn Leu Leu Asn His Leu
                 85                  90                  95

Lys Ser His Glu Lys Glu Tyr Gln Asn Lys Leu Glu Lys Ile Asn Gly
             100                 105                 110

Lys Asn Glu Phe Thr Leu Lys Leu Ile Pro Arg Met Ile Glu Glu Ile
             115                 120                 125

Val Pro Ser Glu Gly Gly Lys Asp Tyr Phe Leu Ala Lys Lys Gln
 130                 135                 140

Arg Tyr Gln Asn Gln Asn Asn Phe Ser Ile Ala Gln Ala Glu Lys
 145                 150                 155                 160

Gln Asn Leu Ile Asp Leu Ile Thr Lys Val Asn Gln Leu Pro Val Val
                 165                 170                 175

Val Gln Glu Gln Glu Gln Ile Gln Ile Tyr Leu Leu Val Ser Cys
             180                 185                 190

Gln Asp Lys Thr Leu Leu Leu Glu Gln Phe Leu Thr Trp Gln Lys Ala
                 195                 200                 205

Cys Pro Arg Trp Asp Leu Leu Leu Gly Asp Cys Leu Pro Pro Tyr His
 210                 215                 220

Phe Ile
225

<210> SEQ ID NO 355
<211> LENGTH: 226
<212> TYPE: PRT
<213> ORGANISM: Aphanizomenon flos-aquae NIES-81

<400> SEQUENCE: 355

Met Glu Leu Glu Asn Leu Tyr Thr Tyr Ala Phe Leu Lys Thr Pro Ser
 1               5                  10                  15

Phe Ser Leu His Leu Pro Gln Gly Ser Thr Thr Ser Val Ile Gln Ile
                 20                  25                  30

Asp Gly Asn Gly Leu Ser Ala Ile Val Glu Pro Gly Ile Ser Leu Asp
         35                  40                  45

Ser Phe Gln Asp Asp Glu Lys Ile Val Gln Met Ala Ile Glu His
 50                  55                  60

Asp Arg Val Ile Cys Asp Ile Phe Arg Gln Ile Thr Val Leu Pro Leu
 65                  70                  75                  80

Arg Phe Gly Thr Tyr Phe Ala Asn Thr Asp Asn Leu Leu Thr His Leu
                 85                  90                  95

Glu Ser Tyr Gly Gln Tyr Leu Asp Lys Leu Glu Lys Ile Asn Cys
             100                 105                 110

Lys Thr Glu Phe Ile Leu Lys Leu Ile Pro Arg Met Ile Thr Glu Glu
             115                 120                 125

Ser Pro Val Leu Glu Ser Gly Arg His Tyr Phe Leu Ala Lys Lys Gln
 130                 135                 140

His Tyr Gln Arg Gln Lys Asn Phe Ile Leu Ala Gln Ala Ser Glu Lys
 145                 150                 155                 160

Glu Ile Leu Ile Asn Phe Ile Ser Lys Ile Asn Gln Ile Pro Val Ile
```

```
                165                 170                 175
Ile Gln Glu Gln Glu Glu Glu Val Arg Ile Tyr Leu Val Asn Tyr
            180                 185                 190

Gln Asp Lys Thr Leu Leu Leu Glu Gln Phe Leu Thr Trp Gln Gln Thr
            195                 200                 205

Cys Pro Arg Trp Asp Leu Phe Leu Gly Glu Gly Ile Pro Pro Tyr His
            210                 215                 220

Phe Ile
225

<210> SEQ ID NO 356
<211> LENGTH: 227
<212> TYPE: PRT
<213> ORGANISM: Arthrospira platensis NIES-39

<400> SEQUENCE: 356

Met Tyr Val Tyr Ala Phe Ile Lys Ser Gln Ser Ile Ser Trp Lys Ser
1               5                   10                  15

Val Gln Gly Ile Tyr Glu Pro Val Val Leu Leu Glu Ala Gly Ala Leu
            20                  25                  30

Ala Ala Val Val Glu Pro Asn Leu Gln Ala Glu Asn Leu Ser Ala Asp
            35                  40                  45

Asn Glu Glu Leu Met Arg Ala Val Leu Thr His Asp Arg Ile Val
50                  55                  60

Cys Gln Ile Phe Glu Glu Thr Thr Val Leu Pro Val Arg Phe Gly Thr
65                  70                  75                  80

Cys Phe Asp Ser Glu Ala Arg Leu Cys Glu His Leu Thr Thr Glu Gly
                85                  90                  95

Asp Arg Tyr Phe Arg Gln Leu Glu Lys Leu Thr Gly Arg Ala Glu Tyr
            100                 105                 110

Leu Leu Glu Ala Ile Pro Gln Pro Phe Asn Gln Glu Lys Pro Ser Ser
            115                 120                 125

Asp Thr Thr Ala Pro Pro Thr Lys Gly Arg Asp Tyr Phe Leu Gln Lys
130                 135                 140

Lys Arg Leu His Gln Gln Arg Leu Asn Phe Glu Gln Gln Gln Glu Gln
145                 150                 155                 160

Gln Trp Gln Asp Phe Ile Asn Ala Ile Ala Ser Lys Tyr Pro Ile Val
                165                 170                 175

Gln Gly Lys Ala Thr Glu Asp Ala Glu Arg Ile Tyr Leu Leu Ile Pro
            180                 185                 190

Arg Ser Gln Glu Val Ala Leu Val Glu Trp Val Ala Gln Gln Gln Gln
            195                 200                 205

Asn Ile Asp Leu Trp Glu Phe Ser Leu Gly Asn Ala Val Pro Ala Tyr
            210                 215                 220

His Phe Leu
225

<210> SEQ ID NO 357
<211> LENGTH: 226
<212> TYPE: PRT
<213> ORGANISM: Dolichospermum circinale

<400> SEQUENCE: 357

Met Lys Leu Glu Asn Phe Tyr Thr Tyr Ala Phe Leu Glu Ile Pro Arg
1               5                   10                  15

Phe Pro Leu Val Leu Pro Gln Gly Ala Ala Ser Gln Val Ile Leu Ile
```

```
              20                  25                  30
Asn Gly Ser Gly Met Ser Ala Ile Val Glu Pro Gly Ile Ser Leu Glu
         35                  40                  45

Ser Phe Gln Asn Asn Asp Glu Lys Ile Ile Gln Met Ala Leu Ser His
 50                  55                  60

Asp Arg Val Ile Cys Glu Leu Phe Gln Gln Val Thr Val Leu Pro Leu
 65                  70                  75                  80

Arg Phe Gly Thr Cys Phe Thr Ser Thr Asn Asn Leu Leu Asn Tyr Leu
                 85                  90                  95

Glu Leu His Arg Gln Glu Tyr Gln Glu Lys Leu Glu Lys Ile Asn Gly
            100                 105                 110

Lys Ile Glu Phe Thr Leu Lys Leu Ile Pro Gln Thr Met Glu Glu Pro
        115                 120                 125

Ala Pro Leu Glu Arg Gly Gly Arg Asp Tyr Phe Leu Ala Lys Lys Gln
130                 135                 140

Arg Tyr Gln Asp Gln Asn Asn Phe Arg Ile Ala Gln Ala Ala Glu Lys
145                 150                 155                 160

Gln Asn Leu Ile Asp Ser Ile Ser Lys Val Asn Gln Leu Pro Phe Val
                165                 170                 175

Ile Gln Glu Lys Glu Glu Val Asn Ile Tyr Leu Leu Val Lys Ser
            180                 185                 190

Glu Asp Lys Thr Leu Leu Leu Glu Gln Phe Leu Asn Trp Gln Lys Ala
        195                 200                 205

Cys Pro Arg Trp Asp Leu Leu Leu Gly Glu Pro Leu Pro Pro Tyr His
    210                 215                 220

Phe Ile
225

<210> SEQ ID NO 358
<211> LENGTH: 227
<212> TYPE: PRT
<213> ORGANISM: Microcystis aeruginosa NIES-843

<400> SEQUENCE: 358

Met Lys Leu Tyr Asn Leu Tyr Thr Tyr Ala Phe Leu Lys Thr Pro Ile
 1               5                  10                  15

Glu Ser Leu Lys Leu Pro Val Gly Met Ala Asn Pro Leu Leu Leu Ile
            20                  25                  30

Thr Gly Gly Glu Leu Ser Ala Val Val Glu Pro Glu Val Gly Leu Asp
         35                  40                  45

Thr Leu Gln Asn Asp Asp Glu Arg Leu Ile Gln Ser Val Leu Cys His
 50                  55                  60

Asp Arg Val Ile Cys Gln Leu Phe Gln Gln Thr Thr Ile Leu Pro Leu
 65                  70                  75                  80

Arg Phe Gly Thr Ser Phe Leu Glu Ala Glu Asn Leu Leu Thr His Leu
                 85                  90                  95

Cys Ser His Gly Gln Glu Tyr Gln Glu Lys Ile Glu Glu Leu Glu Gly
            100                 105                 110

Lys Gly Glu Tyr Leu Leu Lys Cys Ile Pro Arg Lys Pro Glu Glu Pro
        115                 120                 125

Val Leu Phe Ser Glu Ser Lys Gly Arg Gln Tyr Phe Leu Ala Lys Lys
130                 135                 140

Gln Leu Tyr Glu Ala Gln Gln Asp Phe Tyr Thr Leu Gln Gly Ser Glu
145                 150                 155                 160
```

Trp Gln Asn Leu Val Asn Leu Ile Thr Gln Ser Tyr Pro Ser Thr Arg
                165                 170                 175

Ile Ile Thr Ala Pro Gly Thr Glu Ser Arg Ile Tyr Leu Leu Val Asn
            180                 185                 190

Leu Gln Glu Glu Pro Leu Leu Ile Glu Gln Val Leu His Trp Gln Lys
        195                 200                 205

Ala Cys Pro Arg Trp Glu Leu Gln Leu Gly Gln Val Ser Pro Pro Tyr
    210                 215                 220

His Phe Thr
225

<210> SEQ ID NO 359
<211> LENGTH: 229
<212> TYPE: PRT
<213> ORGANISM: Nostoc punctiforme ATCC 29133

<400> SEQUENCE: 359

Met Ser Ile Tyr Ala Tyr Ala Leu Leu Val Pro Thr Ala Ser Pro Leu
1               5                   10                  15

Val Leu Pro Leu Gly Met Glu Arg Asn Thr Glu Leu Val Tyr Ser Ser
            20                  25                  30

Gly Leu Ala Ala Leu Val Glu Pro Glu Ile Ser Leu Glu Ala Ile Gln
        35                  40                  45

Ala Thr Asp Glu Arg Leu Leu Gln Ala Val Leu Asn His Asp His Val
    50                  55                  60

Ile Arg Glu Leu Phe Gln Gln Thr Pro Leu Leu Pro Leu Arg Phe Gly
65                  70                  75                  80

Arg Gly Phe Thr Ser Val Glu Lys Leu Leu Asn His Leu Glu Asn His
                85                  90                  95

Gln Glu Gln Tyr Leu Glu Thr Leu Thr Gln Leu Ala Asp Lys Val Glu
            100                 105                 110

Tyr Ser Val Lys Val Thr Ala Cys Ser Leu Leu Asp Asp Ser Asp Thr
        115                 120                 125

Ile Asp Ala Arg Gly Lys Ala Tyr Leu Leu Ala Lys Lys Gln Arg Tyr
    130                 135                 140

Gln Thr Gln Gln Ala Phe Gln Ala Gln Gln Cys Glu Gln Trp Glu Leu
145                 150                 155                 160

Leu Asn Glu Leu Ile Leu Lys Tyr Thr Asn Val Ile Cys Glu Thr
                165                 170                 175

Arg Gln Ser Asp Val Arg Gln Ile His Phe Leu Ala Gln Arg Asn Asp
            180                 185                 190

Ser Thr Leu Ser Thr Gln Leu Phe Ser Leu Trp Gln Val Gln Cys Ser
        195                 200                 205

His Trp Gln Leu Ala Leu Ser Glu Pro Leu Pro Pro Tyr His Phe Leu
    210                 215                 220

Lys Asn Thr Leu Ile
225

<210> SEQ ID NO 360
<211> LENGTH: 227
<212> TYPE: PRT
<213> ORGANISM: Nostoc sp. PCC 7120

<400> SEQUENCE: 360

Met Arg Ser Pro Asn Phe Tyr Thr Tyr Ala Phe Leu Asn Thr Pro Asp
1               5                   10                  15

Ile Pro Leu Arg Leu Pro Ser Gly Asn Gly Gln Leu Leu Ile
            20              25              30

His Gly His Lys Leu Ser Ala Val Val Glu Pro Gly Ile Ser Leu Glu
            35              40              45

Ser Ser Gln Asn Asn Asp Glu Glu Val Ile Lys Met Val Leu Ala His
 50                  55                  60

Asp Arg Val Ile Cys Glu Leu Ser Gln Gln Thr Thr Val Leu Pro Leu
 65              70                  75                  80

Arg Phe Gly Thr Tyr Phe Asn Ser Glu Thr Leu Leu Asn His Ile
                85                  90                  95

Glu Ser His Ala Gln Glu Tyr Gln Lys Lys Leu Asp His Ile Gln Gly
                100                 105                 110

Lys Thr Glu Tyr Thr Leu Lys Leu Ile Pro Arg Lys Phe Glu Glu Leu
            115                 120                 125

Ala Lys Val Ser Gly Gly Asn Gly Arg Asp Tyr Phe Leu Ala Lys Lys
        130                 135                 140

Leu His Tyr Glu His Gln Lys Asn Phe Ile Gly Asp Gln Asn Arg Glu
145                 150                 155                 160

Lys Asn His Leu Ile Asn Leu Ile Met Asp Val Tyr Arg Ser Ser Ala
                165                 170                 175

Ile Ile Gln Asp Tyr Val Glu Val Arg Leu His Leu Leu Val Asp
                180                 185                 190

Arg His Asp Lys Thr Leu Leu Phe Lys Gln Val Leu Thr Leu Gln Glu
            195                 200                 205

Lys Cys Pro His Trp Asn Leu Ile Leu Gly Pro Leu Pro Pro Tyr
210                 215                 220

His Phe Val
225

<210> SEQ ID NO 361
<211> LENGTH: 88
<212> TYPE: PRT
<213> ORGANISM: Bacillus-megaterium

<400> SEQUENCE: 361

Met Glu Ile Lys Lys Ile Met Gln Ala Val Asn Asp Phe Phe Gly Glu
1               5                   10                  15

His Val Ala Pro Pro His Lys Ile Thr Ser Val Glu Ala Thr Glu Asp
            20                  25                  30

Glu Gly Trp Arg Val Ile Val Glu Val Ile Glu Glu Arg Glu Tyr Met
            35                  40                  45

Lys Lys Tyr Ala Lys Asp Glu Met Leu Gly Thr Tyr Glu Cys Phe Val
 50                  55                  60

Asn Lys Glu Lys Glu Val Ile Ser Phe Lys Arg Leu Asp Val Arg Tyr
 65                  70                  75                  80

Arg Ser Ala Ile Gly Ile Glu Ala
                85

<210> SEQ ID NO 362
<211> LENGTH: 95
<212> TYPE: PRT
<213> ORGANISM: Bacillus-megaterium

<400> SEQUENCE: 362

Met Ser Leu Lys Gln Ser Met Glu Asn Lys Asp Ile Ala Leu Ile Asp
1               5                   10                  15

```
Ile Leu Asp Val Ile Leu Asp Lys Gly Val Ala Ile Lys Gly Asp Leu
             20                  25                  30

Ile Ile Ser Ile Ala Gly Val Asp Leu Val Tyr Leu Asp Leu Arg Val
         35                  40                  45

Leu Ile Ser Ser Val Glu Thr Leu Val Gln Ala Lys Glu Gly Asn His
     50                  55                  60

Lys Pro Ile Thr Ser Glu Gln Phe Asp Lys Gln Lys Glu Glu Leu Met
 65                  70                  75                  80

Asp Ala Thr Gly Gln Pro Ser Lys Trp Thr Asn Pro Leu Gly Ser
                 85                  90                  95

<210> SEQ ID NO 363
<211> LENGTH: 65
<212> TYPE: PRT
<213> ORGANISM: Rhodococcus hoagii 103S

<400> SEQUENCE: 363

Met Ser Ala Thr Pro Asp Arg Arg Ile Ala Leu Val Asp Leu Leu Asp
  1               5                  10                  15

Arg Val Leu Gly Gly Gly Val Val Ala Gly Glu Ile Thr Leu Ser
                 20                  25                  30

Ile Ala Asp Val Asp Met Val His Ile Ser Leu Arg Thr Leu Val Ser
         35                  40                  45

Ser Val Ser Ala Leu Thr Arg Pro Pro Asp Glu Lys Pro Glu Asn Asp
     50                  55                  60

Gly
 65

<210> SEQ ID NO 364
<211> LENGTH: 292
<212> TYPE: PRT
<213> ORGANISM: Bacillus-megaterium

<400> SEQUENCE: 364

Met Ala Thr Glu Thr Lys Leu Asp Asn Thr Gln Ala Glu Asn Lys Glu
  1               5                  10                  15

Asn Lys Asn Ala Glu Asn Gly Ser Lys Glu Lys Asn Gly Ser Lys Ala
                 20                  25                  30

Ser Lys Thr Thr Ser Ser Gly Pro Ile Lys Arg Ala Val Ala Gly Gly
         35                  40                  45

Ile Ile Gly Ala Thr Ile Gly Tyr Val Ser Thr Pro Glu Asn Arg Lys
     50                  55                  60

Ser Leu Leu Asp Arg Ile Asp Thr Asp Glu Leu Lys Ser Lys Ala Ser
 65                  70                  75                  80

Asp Leu Gly Thr Lys Val Lys Glu Lys Ser Lys Ser Ser Val Ala Ser
                 85                  90                  95

Leu Lys Thr Ser Ala Gly Ser Leu Phe Lys Lys Asp Lys Asp Lys Ser
                100                 105                 110

Lys Asp Asp Glu Glu Asn Val Asn Ser Ser Ser Glu Thr Glu Asp
            115                 120                 125

Asp Asn Val Gln Glu Tyr Asp Glu Leu Lys Glu Glu Asn Gln Thr Leu
        130                 135                 140

Gln Asp Arg Leu Ser Gln Leu Glu Glu Lys Met Asn Met Leu Val Glu
145                 150                 155                 160

Leu Ser Leu Asn Lys Asn Gln Asp Glu Glu Ala Glu Asp Thr Asp Ser
                165                 170                 175
```

-continued

```
Asp Glu Glu Glu Asn Asp Glu Asn Asp Glu Asn Asp Glu Asn Glu Gln
            180                 185                 190

Asp Asp Glu Asn Glu Glu Thr Ser Lys Pro Arg Lys Lys Asp Lys
        195                 200                 205

Lys Glu Ala Glu Glu Glu Ser Glu Ser Asp Glu Asp Ser Glu Glu
        210                 215                 220

Glu Glu Glu Asp Ser Arg Ser Asn Lys Lys Asn Lys Lys Val Lys Thr
225                 230                 235                 240

Glu Glu Glu Asp Glu Asp Glu Ser Glu Glu Glu Lys Lys Glu Ala Lys
                245                 250                 255

Pro Lys Lys Ser Thr Ala Lys Lys Ser Lys Asn Thr Lys Ala Lys Lys
            260                 265                 270

Asn Thr Asp Glu Glu Asp Asp Glu Ala Thr Ser Leu Ser Ser Glu Asp
        275                 280                 285

Asp Thr Thr Ala
    290

<210> SEQ ID NO 365
<211> LENGTH: 138
<212> TYPE: PRT
<213> ORGANISM: Bacillus-megaterium

<400> SEQUENCE: 365

Met Ser Thr Gly Pro Ser Phe Ser Thr Lys Asp Asn Thr Leu Glu Tyr
1               5                   10                  15

Phe Val Lys Ala Ser Asn Lys His Gly Phe Ser Leu Asp Ile Ser Leu
            20                  25                  30

Asn Val Asn Gly Ala Val Ile Ser Gly Thr Met Ile Ser Ala Lys Glu
        35                  40                  45

Tyr Phe Asp Tyr Leu Ser Glu Thr Phe Glu Glu Gly Ser Glu Val Ala
    50                  55                  60

Gln Ala Leu Ser Glu Gln Phe Ser Leu Ala Ser Glu Ala Ser Glu Ser
65                  70                  75                  80

Asn Gly Glu Ala Glu Ala His Phe Ile His Leu Lys Asn Thr Lys Ile
                85                  90                  95

Tyr Cys Gly Asp Ser Lys Ser Thr Pro Ser Lys Gly Lys Ile Phe Trp
            100                 105                 110

Arg Gly Lys Ile Ala Glu Val Asp Gly Phe Phe Leu Gly Lys Ile Ser
            115                 120                 125

Asp Ala Lys Ser Thr Ser Lys Lys Ser Ser
        130                 135
```

BURST ULTRASOUND RECONSTRUCTION WITH SIGNAL TEMPLATES AND RELATED METHODS AND SYSTEMS

CROSS REFERENCE TO RELATED APPLICATIONS

The present application claims priority to U.S. Provisional Application No. 62/895,553, entitled "BURST Ultrasound Reconstruction with Signal Templates" filed on Sep. 4, 2019, and U.S. Provisional Application No. 62/789,295, entitled "Mammalian Expression Of Gas Vesicles As Acoustic Reporter Genes" filed on Jan. 7, 2019, all of which are incorporated herein by reference in their entirety. The present application also claims priority to U.S. Provisional Application No. 62/825,612, entitled "Genetically Encodable Nuclei For Inertial Cavitation" filed on Mar. 28, 2019.

The present application is also related to co-pending U.S. application Ser. No. 16/736,683, entitled "Genetically Engineered Gas Vesicle Gene Clusters, Genetic Circuits, Vectors, Mammalian Cells, Compositions, Methods And Systems For Contrast-Enhanced Imaging", filed on Jan. 7, 2020, which is incorporated herein by reference in its entirety.

STATEMENT OF INTEREST

This invention was made with government support under Grant No. EB018975 awarded by the National Institute of Health. The government has certain rights in the invention."

FIELD

The present disclosure relates to gas-filled structures for use in imaging technologies, and related compositions methods and systems to image a target site with particular reference to imaging performed by ultrasound.

BACKGROUND

Ultrasound is among the most widely used biomedical imaging modalities due to its superior spatiotemporal resolution, safety, cost and ease of use compared to other techniques.

In addition to visualizing anatomy and physiology, ultrasound can take advantage of contrast agents to more specifically image blood flow, discern the location of certain molecular targets, and resolve structures beyond its normal wavelength limit via super-localization.

Challenges remain for identifying and developing methods and biocompatible nanoscale contrast agents for ultrasound detection of a target site obtained with high sensitivity and resolution.

SUMMARY

Provided herein are systems and methods to ultrasound image gas vesicles at high sensitivity by creating time-series vectors from successive images during a step function increase in acoustic pressure. The systems and methods allow for high sensitivity imaging even down to imaging a single cell.

According to a first aspect, a method of ultrasound imaging to be used on a target site contrasted with gas vesicles (GVs) having an acoustic collapse pressure threshold, the method comprising: applying ultrasound to the target site at a peak positive pressure less than the acoustic collapse pressure threshold; increasing peak positive pressure (PPP) to above the selective acoustic collapse pressure value as a step function; imaging the target site in successive frames during the increasing; and extracting a time-series vector for each of at least one pixel of the successive frames. This method requires non-collapsed GVs that may be expressed in native or non-native host cells, isolated from prokaryotes, or produced via cell-free expression.

According to a second aspect, a system for imaging a target site contrasted with gas vesicles (GVs) having an acoustic collapse pressure threshold, the system comprising: an ultrasound source capable of producing peak positive pressure both below and above the acoustic collapse pressure threshold; an ultrasound imager configured to capture successive frames from the target site; and a processor configured to: calculate a time-series vector for each of at least one pixel of the successive frames.

The processor can be further configured to perform a signal separation algorithm on the time-series vectors using at least one template vector. The can further comprise a means for introducing the gas vesicles at the target site. Delivering the GVs to the target site can be using an acoustic reporter gene to express the GVs. The acoustic reporter gene can be in a mammalian cell such as a human embryonic kidney cell or a bacterial cell such as *E. coli* or *S. typhimurium*.

The primary advantage of BURST (Burst Ultrasound Reconstruction with Signal Templates) is its improvement in sensitivity of up to 1,000,000-fold compared with conventional B-mode ultrasound. BURST also achieves high specificity by cancelling signal from strong linear scatterers such as biological tissue. Unlike contrast mode ultrasound imaging methods such as amplitude modulation and pulse inversion that rely on linear acoustic wave propagation, the specificity of BURST does not deteriorate at higher acoustic pressures where acoustic wave propagation becomes significantly nonlinear.

The imaging methods and systems herein described can be used in connection with various applications wherein reporting of biological events in a target site is desired. For example, the imaging methods and systems herein described can be used for visualization of biological events, such as a gene expression, proteolysis, biochemical reactions as well as cell location on a target site (e.g. tumor cells inside a host individual, such as mammalian hosts), facilitating for example the study of the mammalian microbiome and the development of diagnostic and therapeutic cellular agents, among other advantages identifiable by a skilled person, in medical applications, as well diagnostics applications. Additional exemplary applications include uses of imaging methods and systems herein described in several fields including basic biology research, neuroscience, applied biology, bio-engineering, bio-energy, medical research, medical diagnostics, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the detailed description and the examples, serve to explain the principles and implementations of the disclosure.

DETAILED DESCRIPTION

Figure 1:
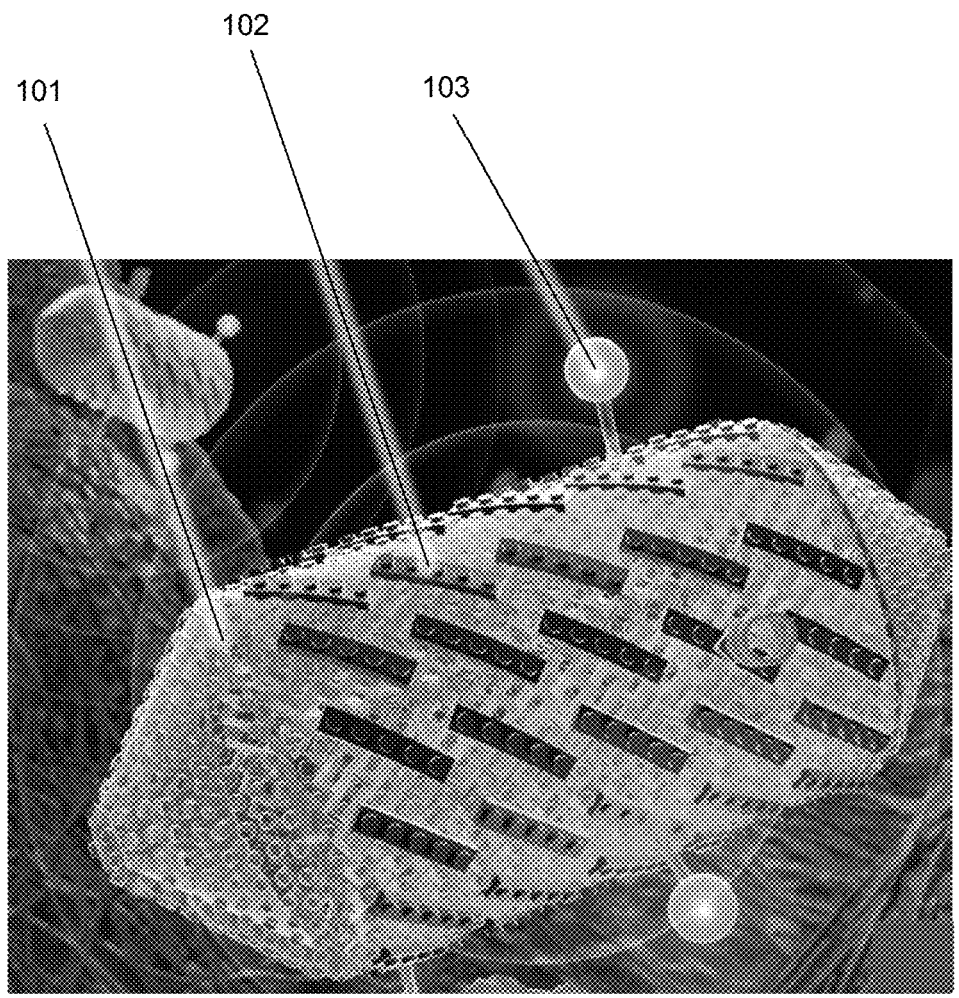
FIG. 1 shows an example of a gas vesicle used for BURST imaging.

Provided herein are gas-filled protein structures, also referred to as "gas vesicles" (GVs), and related compositions methods and systems for use in ultrasound imaging particularly in contrast enhanced ultrasound imaging.

The term "contrast enhanced imaging" or "imaging", as herein indicates a visualization of a target site performed with the aid of a contrast agent administered to the target site to improve the visibility of structures or fluids by devices process and techniques suitable to provide a visual representation of a target site. Accordingly contrast agent is a substance that enhances the contrast of structures or fluids within the target site, producing a higher contrast image for evaluation.

The term "ultrasound imaging" or "ultrasound scanning" or "sonography" as used herein indicate imaging performed with techniques based on the application of ultrasound.

Ultrasound refers to sound with frequencies higher than the audible limits of human beings, typically over 20 kHz. Ultrasound devices typically can range up to the gigahertz range of frequencies, with most medical ultrasound devices operating in the 1 to 18 MHz range. The amplitude of the waves relates to the intensity of the ultrasound, which in turn relates to the pressure created by the ultrasound waves. Applying ultrasound can be accomplished, for example, by sending strong, short electrical pulses to a piezoelectric transducer directed at the target. Ultrasound can be applied as a continuous wave, or as wave pulses as will be understood by a skilled person.

Accordingly, the wording "ultrasound imaging" as used herein refers in particular to the use of high frequency sound waves, typically broadband waves in the megahertz range, to image structures in the body. The image can be up to 3D with ultrasound. In particular, ultrasound imaging typically involves the use of a small transducer (probe) transmitting high-frequency sound waves to a target site and collecting the sounds that bounce back from the target site to provide the collected sound to a computer using sound waves to create an image of the target site. Ultrasound imaging allows detection of the function of moving structures in real-time. Ultrasound imaging works on the principle that different structures/fluids in the target site will attenuate and return sound differently depending on their composition. Ultrasound imaging can be performed with conventional ultrasound techniques and devices displaying 2D images as well as three-dimensional (3-D) ultrasound that formats the sound wave data into 3-D images. In addition to 3D ultrasound imaging, ultrasound imaging also encompasses Doppler ultrasound imaging, which uses the Doppler Effect or signal decorrelation to measure and visualize movement, such as blood flow rates. Types of Doppler imaging includes continuous wave Doppler, where a continuous sinusoidal wave is used and pulsed wave Doppler, which uses pulsed waves transmitted at a constant repetition frequency. Doppler measurements can be imaged using color flow imaging which uses the phase shift between pulses to determine velocity information which is given a false color (such as red=flow towards viewer and blue=flow away from viewer) superimposed on a grey-scale anatomical image, power Doppler which uses the amplitude of Doppler signal to detect moving matter, or some other method. Ultrasound imaging can use linear or non-linear propagation depending on the signal level. Harmonic and harmonic transient ultrasound response imaging can be used for increased axial resolution, as harmonic waves are generated from non-linear distortions of the acoustic signal as the ultrasound waves insonate tissues in the body.

Other ultrasound techniques and devices suitable to image a target site using ultrasound would be understood by a skilled person.

The term "target site" as used herein indicates an environment comprising one or more targets intended as a combination of structures and fluids to be contrasted, such as cells. In particular, the term "target site" refers to biological environments such as cells, tissues, organs in vitro, in vivo or ex vivo that contain at least one target. A target is a portion of the target site to be contrasted against the background (e.g. surrounding matter) of the target site. Accordingly, a target can include any molecule, cell, tissue, body part, body cavity, organ system, whole organisms, collection of any number of organisms within any suitable environment in vitro, in vivo or ex vivo as will be understood by a skilled person. Exemplary target sites include collections of microorganisms, including, bacteria or archaea in a solution in vitro, as well as cells grown in an in vitro culture, including, primary mammalian cells, immortalized cell lines, tumor cells, stem cells, and the like. Additional exemplary target sites include tissues and organs in an ex vivo culture and tissue, organs, or organ systems in a subject, for example, lungs, brain, kidney, liver, heart, the central nervous system, the peripheral nervous system, the gastrointestinal system, the circulatory system, the immune system, the skeletal system, the sensory system, within a body of an individual and additional environments identifiable by a skilled person. The term "individual" or "subject" or "patient" as used herein in the context of imaging includes a single plant or animal and in particular higher plants or animals and in particular vertebrates such as mammals and more particularly human beings. Types of ultrasound imaging of biological target sites include abdominal ultrasound, vascular ultrasound, obstetrical ultrasound, hysterosonography, pelvic ultrasound, renal ultrasound, thyroid ultrasound, testicular ultrasound, and pediatric ultrasound as well as additional ultrasound imaging as would be understood by a skilled person.

In embodiments herein described the ultrasound imaging of target site is performed in connection with the administration to the target site of gas vesicle protein structures.

The wordings "gas vesicles", GV", "gas vesicles protein structure", or "GVPS", refer to a gas-filled protein structure natively intracellularly expressed by certain bacteria or archaea as a mechanism to regulate cellular buoyancy in aqueous environments [1]. In particular, gas vesicles are protein structures natively expressed almost exclusively in microorganisms from aquatic habitats, to provide buoyancy by lowering the density of the cells [1]. GVs have been found in over 150 species of prokaryotes, comprising cyanobacteria and bacteria other than cyanobacteria [2, 3], from at least 5 of the 11 phyla of bacteria and 2 of the phyla of archaea described by Woese (1987) [4]. Exemplary microorganisms expressing or carrying gas vesicle protein structures and/or related genes include cyanobacteria such as *Microcystis aeruginosa, Aphanizomenon flos aquae Oscillatoria agardhii, Anabaena, Microchaete diplosiphon* and *Nostoc*; phototropic bacteria such as *Amoebobacter, T. hiodiclyon, Pelodiclyon*, and *Ancalochloris*; non phototropic bacteria such as *Microcyclus aquaticus*; Gram-positive bacteria such as *Bacillus megaterium* Gram-negative bacteria such as *Serratia*, as well as additional microorganisms identifiable by a skilled person.

In particular, a GV in the sense of the disclosure is an intracellularly expressed structure forming a hollow structure wherein a gas is enclosed by a protein shell, which is a shell substantially made of protein (at least 95% protein). In gas vesicles in the sense of the disclosure, the protein shell is formed by a plurality of proteins herein also indicated as GV proteins or "gvp"s, which form in the cytoplasm a gas permeable and liquid impermeable protein shell configuration encircling gas. Accordingly, a protein shell of a GV is permeable to gas but not to surrounding liquid such as water. In particular, GV protein shells exclude water but permit gas to freely diffuse in and out from the surrounding media [5] making them physically stable despite their usual nanometer size, unlike microbubbles, which trap pre-loaded gas in an unstable configuration.

GV structures are typically nanostructures with widths and lengths of nanometer dimensions (in particular with widths of 45-250 nm and lengths of 100-800 nm) but can have lengths up to 2 μm in prokaryotes or 8 to 10 μm in mammalian cells as will be understood by a skilled person upon reading of the present disclosure. In certain embodiments, the gas vesicles protein structure have average dimensions of 1000 nm or less, such as 900 nm or less, including 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less, or 25 nm or less, or 10 nm or less. For example, the average diameter of the gas vesicles may range from 10 nm to 1000 nm, such as 25 nm to 500 nm, including 50 nm to 250 nm, or 100 nm to 250 nm. By "average" is meant the arithmetic mean.

GVs in the sense of the disclosure have different shapes depending on their genetic origins [5]. For example, GVs in the sense of the disclosure can be substantially spherical, ellipsoid, cylindrical, or have other shapes such as football shape or cylindrical with cone shaped end portions depending on the type of bacteria providing the gas vesicles.

Representative examples of endogenously expressed GVs native to bacterial or archaeal species are the gas vesicle protein structure produced by the Cyanobacterium *Anabaena flos-aquae* (Ana GVs) [1], and the *Halobacterium Halobacterium salinarum* (Halo GVs) [6]. In particular, Ana GVs are cone-tipped cylindrical structures with a diameter of approximately 140 nm and length of up to 2 μm and in particular 200-800 nm or longer. Halo GVs are typically spindle-like structures with a maximal diameter of approximately 250 nm and length of 250-600 nm.

Additional, GVs can be found based on the fact that in bacteria or archaea expressing GVs, the genes (herein also gyp genes) encoding for the proteins forming the GVs (herein also GV proteins), are organized in a gas vesicle gene cluster of 8 to 14 different genes depending on the host bacteria or archaea, as will be understood by a skilled person.

The term "Gas Vesicle Genes Cluster" or "GVGC" as described herein indicates a gene cluster encoding a set of GV proteins capable of providing a GV upon expression within a bacterial or archaeal cell. The term "gene cluster" as used herein means a group of two or more genes found within an organism's DNA that encode two or more polypeptides or proteins, which collectively share a generalized function or are genetically regulated together to produce a cellular structure and are often located within a few thousand base pairs of each other. The size of gene clusters can vary significantly, from a few genes to several hundred genes [7]. Portions of the DNA sequence of each gene within a gene cluster are sometimes found to be similar or identical; however, the resulting protein of each gene is distinctive from the resulting protein of another gene within the cluster. Genes found in a gene cluster can be observed near one another on the same chromosome or native plasmid DNA, or on different, but homologous chromosomes. An example of a gene cluster is the Hox gene, which is made up of eight genes and is part of the Homeobox gene family. In the sense of the disclosure, gene clusters as described herein also comprise gas vesicle gene clusters, wherein the expressed proteins thereof together are able to form gas vesicles.

The term "gene" as used herein indicates a polynucleotide encoding for a protein that in some instances can take the form of a unit of genomic DNA within a bacteria, plant, or other organism.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term polynucleotide includes nucleic acids of any length, and in particular DNA RNA analogs and fragments thereof.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immunoprecipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine (—$NH_2$) to form an amide bond or a "peptide" bond.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—$NH_2$) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In embodiments herein described identification of a gene cluster encoding GV proteins naturally expressed in bacteria or archaea as described herein can be performed for example by isolating the GVs from the bacteria or archaea, isolating the protein for the protein shell of the GV and deriving the related amino acidic sequence with methods and techniques identifiable by a skilled person. The sequence of the genes encoding for the GV proteins can then be identified by methods and techniques identifiable by a skilled person. For example, gas vesicle gene clusters can also be identified by persons skilled in the art by performing gene sequencing or partial- or whole-genome sequencing of organisms using wet lab and in silico molecular biology techniques known to those skilled in the art. As understood by those skilled in the art, gas vesicle gene clusters can be located on the chromosomal DNA or native plasmid DNA of microorganisms. After performing DNA or cDNA isolation from a microorganism, the polynucleotide sequences or fragments thereof or PCR-amplified fragments thereof can be sequenced using DNA sequencing methods such as Sanger sequencing, DNASeq, RNASeq, whole genome sequencing, and other methods known in the art using commercially available DNA sequencing reagents and equipment, and then the DNA sequences analyzed using computer programs for DNA sequence analysis known to skilled persons.

In some embodiments, identification of a gene cluster encoding for GV proteins [6, 8, 9] can also be performed by screening DNA sequence databases such as GenBank, EMBL, DNA Data Bank of Japan, and others. Gas vesicle gene cluster gene sequences in databases such as those above can be searched using tools such as NCBI Nucleotide BLAST and the like, for gas vesicle gene sequences and homologs thereof, using gene sequence query methods known to those skilled in the art. For example, genes of the gene cluster for the exemplary haloarchael GVs (which have the largest number of different gyp genes) and their predicted function and features are illustrated in Example 26 of related U.S. application Ser. No. 15/613,104, filed on Jun. 2, 2017 which is incorporated herein by reference in its entirety.

A GV gene cluster encoding for GV proteins typically comprises Gas Vesicle Assembly (GVA) genes and Gas Vesicle Structural (GVS) genes.

The term Gas Vesicle Structural (GVS) proteins as used herein indicates proteins forming part of a gas-filled protein structure intracellularly expressed by certain bacteria or archaea and can be used as a mechanism to regulate cellular buoyancy in aqueous environments [5]. In particular, GVS shell comprises a GVS identified as gvpA or gvpB (herein also referred to as gyp A/B) and optionally also a GVS identified as gvpC.

In particular gvpB gene is a gene encoding for gas vesicle structural protein B. gvpB genes is highly homologous to gvpA gene encoding for gas vesicle structural protein A. A gyp A/B is a protein of the GV shell that has a higher than 70% identity to the following consensus sequence: SSS-LAEVLDRILDKGXVIDAWARVSLVGIEILTIEARVVI-ASVDTYLR (SEQ ID NO: 1) wherein X can be any amino acid. In particular in a gyp A/B of prokaryotes, the consensus sequence of SEQ ID NO: 1 typically forms a conserved secondary structure having an alpha-beta-beta-alpha structural motif formed by portions of the consensus sequence comprising the amino acids LDRILD (SEQ ID NO:2) having an alpha helical structure, RILDKGXVIDAWARVS (SEQ ID NO:3) wherein X can be any amino acid, having a beta strand, beta strand structure, and DTYLR (SEQ ID NO:4) having an alpha helical structure, as will be understood by a skilled person.

As used herein, "homology", "sequence identity" or "identity" in the context of two nucleic acid or polypeptide sequences makes reference to the nucleotide bases or residues in the two sequences that are the same when aligned for maximum correspondence over a specified comparison window. When percentage of sequence identity or similarity is used in reference to proteins, it is recognized that residue positions which are not identical often differ by conservative amino acid substitutions, where amino acid residues are substituted with a functionally equivalent residue of the amino acid residues with similar physiochemical properties and therefore do not change the functional properties of the molecule.

A functionally equivalent residue of an amino acid used herein typically refers to other amino acid residues having physiochemical and stereochemical characteristics substantially similar to the original amino acid. The physiochemical properties include water solubility (hydrophobicity or hydrophilicity), dielectric and electrochemical properties, physiological pH, partial charge of side chains (positive, negative or neutral) and other properties identifiable to a person skilled in the art. The stereochemical characteristics include spatial and conformational arrangement of the amino acids and their chirality. For example, glutamic acid is considered to be a functionally equivalent residue to aspartic acid in the sense of the current disclosure. Tyrosine and tryptophan are considered as functionally equivalent residues to phenylalanine. Arginine and lysine are considered as functionally equivalent residues to histidine.

A person skilled in the art would understand that similarity between sequences is typically measured by a process that comprises the steps of aligning the two polypeptide or polynucleotide sequences to form aligned sequences, then detecting the number of matched characters, i.e. characters similar or identical between the two aligned sequences, and calculating the total number of matched characters divided by the total number of aligned characters in each polypeptide or polynucleotide sequence, including gaps. The similarity result is expressed as a percentage of identity.

As used herein, "percentage of sequence identity" means the value determined by comparing two optimally aligned sequences over a comparison window, wherein the portion of the polynucleotide sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length protein or protein fragment. A reference sequence can comprise, for example, a sequence identifiable a database such as GenBank™ and UniProt™ and others identifiable to those skilled in the art.

Thus, a gyp A/B protein in a prokaryote of interest can be identified for example by isolating GVs from a prokaryote of interest, isolating the protein from the protein shell of the GV and obtaining the amino acid sequence of the isolated protein. In addition to, or in the alternative to, isolating the GVs and isolating the protein, the method can include obtaining amino acidic sequences of the shell proteins of the GV of the prokaryote of interest from available database. The method further comprises performing a sequence alignment of the obtained amino acidic sequences against the gyp A/B protein consensus sequence of SEQ ID NO:1.

In particular the isolating GVs from a prokaryote of interest can be performed following methods to isolate gas vesicles as described in U.S. application Ser. No. 15/613,104, filed on Jun. 2, 2017. Isolating the protein for the protein shell of the GV and obtaining the related amino acidic sequence can be performed with tandem liquid chromatography mass-spectrometry alone or in combination with obtaining amino acid sequences of the isolated protein with wet lab techniques or from available databases comprising the sequences of the prokaryote of interest as well as additional techniques and approaches identifiable by a skilled person. Obtaining amino acid sequences of GV shell proteins of the prokaryote of interest can be performed by screening available databases of gene and protein sequences identifiable by a skilled person. Performing a sequence alignment of the sequences of the isolated GV proteins or proteins encoded in the genome of a prokaryote of interest can be performed (using Protein BLAST as described herein) against the gyp A/B protein consensus sequence of SEQ ID NO:1. In particular, a sequence alignment can be performed using gyp A/B protein sequences from the closest phylogenetic relative to the prokaryote of interest.

The optional gvpC gene encodes for a gvpC protein which is a hydrophilic protein of a GV shell, including repetitions of one repeat region flanked by an N-terminal region and a C terminal region. The term "repeat region" or "repeat" as used herein with reference to a protein refers to the minimum sequence that is present within the protein in multiple repetitions along the protein sequence without any gaps. Accordingly, in a gvpC multiple repetitions of a same repeat is flanked by an N-terminal region and a C-terminal region. In a same gvpC, repetitions of a same repeat in the gvpC protein can have different lengths and different sequence identity one with respect to another. In performing alignment steps sequence are identified as repeat when the sequence shows at least 3 or more of the characteristics described in U.S. application Ser. No. 15/663,635 published as US 2018/0030501 (incorporated herein by reference in its entirety) which also include additional features of gvpC proteins and the related identification.

In a GVGC, the GVS genes are comprised with Gas Vesicle Assembly genes. The Gas Vesicle Assembly genes are genes encoding for GVA proteins. GVA proteins comprise proteins with various putative functions such as nucleators and/or chaperons as well as proteins with an unknown specific function related to the assembly of the GV.

In a prokaryotic cell GVA genes are all the genes within one or more operons comprising at least one of a gvpN and a gvpF excluding any gyp A/B and gvpC gene possibly present within said one or more operons. Therefore, GVA genes can be identified by identifying an operon in a prokaryote including at least one of a gvpN and a gvpF excluding any gyp A/B and gvpC gene.

Preferably the one or more operons comprising all the GVA genes of a prokaryote can be identified and detected by detecting a gvpN gene encoding for a GVP protein consensus sequence (SEQ ID NO: 5)
RALXYLQAGYXVHXRGPAGTGKTTLAMHLAXXLXRPVMLIXGDDEFXTSD
LIGSESGYXXKKVVDNYIHSVVKVEDELRQNWVDNRLTXACREGFTLVYD
EFNRSRPEXNNVLLSVLEEKILXLP wherein X indicates any amino acid or a sequence of any length having at least 50%, and more preferably 60% or higher, most preferably from 50% to 83% identity.

GvpN genes of various microorganisms have a sequence encoding for a gvpN protein within the consensus SEQ ID NO: 5. In particular, gvpN gene in the sense of the disclosure is gene encoding for sequence (SEQ ID NO: 6)
MTVLTDKRKKGSGAFIQDDETKEVLSRALSYLKSGYSIHFTGPAGGGKTS

LARALAKKRKRPVMLMHGNHELNNKDLIGDFTGYTSKKVIDQYVRSVYKK

DEQVSENWQDGRLLEAVKNGYTLIYDEFTRSKPATNNIFLSILEEGVLPL

YGVKMTDPFVRVHPDFRVIFTSNPAEYAGVYDTQDALLDRLITMFIDYKD

IDRETAILTEKTDVEEDEARTIVTLVANVRNRSGDENSSGLSLRASLMIA

TLATQQDIPIDGSDEDFQTLCIDILHHPLTKCLDEENAKSKAEKIILEEC

KNIDTEEK or a sequence of any length having at least 30% sequence identity with respect to SEQ ID NO:6, preferably at least 50%, and more preferably 60% or higher,
and gvpF gene in the sense of the disclosure is gene encoding for sequence (SEQ ID NO: 7)
MSETNETGIYIFSAIQTDKDEEFGAVEVEGTKAETFLIRYKDAAMVAAEV

PMKIYHPNRQNLLMHQNAVAAIMDKNDTVIPISFGNVFKSKEDVKVLLEN

LYPQFEKLFPAIKGKIEVGLKVIGKKEWLEKKVNENPELEKVSASVKGKS

EAAGYYERIQLGGMAQKMFTSLQKEVKTDVFSPLEEAAEAAKANEPTGET

MLLNASFLINREDEAKFDEKVNEAHENWKDKADFHYSGPWPAYNFVNIRL

KVEEK or a sequence of any length having at least 20% sequence identity with respect to SEQ ID NO:7, preferably at least 50%, more preferably 60%, and at least 70% or higher.

The term "operon" as described herein indicates a group of genes arranged in tandem in a prokaryotic genome as will be understood by a skilled person. Operons typically encode proteins participating in a common pathway are organized together as understood by those skilled in the art. Typically, genes of an operon are transcribed together into a single mRNA molecule referred to as polycistronic mRNA. Polycistronic mRNA comprises several open reading frames (ORFs), each of which is translated into a polypeptide. These polypeptides usually have a related function and their coding sequence is grouped and regulated together in a regulatory region, containing a promoter and an operator. Typically, repressor proteins bound to the operator sequence can physically obstruct the RNA polymerase enzyme from binding the promoter, preventing transcription. An example of a prokaryotic operon is the lac operon, which natively regulates transport and metabolism of lactose in *E. coli* and many other enteric bacteria.

In an operon, each ORF typically has its own ribosome binding site (RBS) so that ribosomes simultaneously translate ORFs on the same mRNA. Some operons also exhibit translational coupling, where the translation rates of multiple ORFs within an operon are linked. This can occur when the ribosome remains attached at the end of an ORF and translocates along to the next ORF without the need for a new RBS. Translational coupling is also observed when translation of an ORF affects the accessibility of the next RBS through changes in RNA secondary structure.

In some embodiments, a GV cluster comprises one of gvpN or gvpF. In several embodiments GV clusters include both gvpN and gvpF as will be understood by a skilled person. Accordingly, for a certain prokaryote, GVA genes in the sense of the disclosure indicate all the genes that are comprised in the one or more operons having at least one of a gvpN and/or a gvpF herein described and excluding any Gas Vesicle Structural (GVS) genes of the prokaryotes possibly comprised within the one or more operons.

Thus, GVA genes comprised in a gas vesicle gene cluster in a prokaryote can be identified for example by obtaining genome sequence of the prokaryote of interest and performing a sequence alignment of the protein sequences encoded in the genome of the prokaryote of interest against a gvpN protein sequence and/or a gvpF protein sequence.

In particular, obtaining the genome sequence of the prokaryote of interest, can be performed either using wet lab techniques identifiable by a skilled person upon reading of the present disclosure, or obtained from databases of gene and protein sequences also identifiable by a skilled person upon reading of the present disclosure. Performing a sequence alignment of the protein sequences encoded in the genome of the prokaryote of interest can per performed using Protein BLAST or other alignment algorithms identifiable by a skilled person. Exemplary gvpN protein sequence and/or a gvpF protein sequence, that can be used in performing the alignment are sequences SEQ ID NO:6 and/or SEQ ID NO:7. In particular, a sequence alignment can be performed using gvpN and/or gvpF protein sequences from the closest phylogenetic relative to the prokaryote of interest. Accordingly, one or more operons that comprise the gvpN and/or gvpF genes can be identified, and any other gyps within the one or more operons can also be identified, wherein the other gyps are comprised in ORFs within the one or more operons, excluding any ORFs encoding gyp A/B or gvpC genes comprised in the one or more operons of the GV gene cluster.

Accordingly, GVA genes can also be identified based on the configuration of operon and Gene Clusters identified through homology, phylogenesis also using the gyp A/B, gvpN and/or gvpF consensus of SEQ ID Nos: 1, 6, and 7 herein provided preferably gyp A/B consensus of SEQ ID NO:1 and gvpN consensus of SEQ ID NO: 5.

GVS genes of a GVGC of the disclosure, identified with methods herein indicated, typically comprise gvpA or gvpB which have similar sequences and are equivalent in their purpose and optionally gvpC. Exemplary sequences for gvpA and gvpB genes of GV gene clusters in the sense of the disclosure, which can also be used to identify additional GVS and GVGC through homology and alignment.

GVA genes of a GVGC of the disclosure, identified with methods herein indicated, typically comprise proteins identified as gvpN, F, G, L, S, K, J, and U. GVA genes and proteins can also comprise gvpR and gvpT (see e.g. *B. megaterium* GVA) gvpV, gvpW (se *Anaboena flos aque* and *Serratia* GVA) and/or gvpX, gvpY and gvpZ (see e.g. *Serratiai* GVA). Exemplary sequences for GVA genes of GV gene clusters in the sense of the disclosure which can also be used to identify additional GVAs and GVGC through homology and alignment.

In GVGC herein described co-expression of the GVS genes and the GVA genes in connection with regulatory sequence capable of operating in a host cell are configured to provide a GV type, with a different GVGC typically resulting in a different GV type.

The wording "GV type" in the sense of the disclosure indicates a gas vesicle having dimensions and shape resulting in distinctive mechanical, acoustic, surface and/or magnetic properties as will be understood by a skilled person upon reading of the present disclosure. In particular, a skilled person will understand that different shapes and dimensions will result in different properties in view of the indications in provided in U.S. application Ser. No. 15/613, 104 and U.S. Ser. No. 15/663,600 and additional indications identifiable by a skilled person. Typically, larger volume results in stronger per-particle scattering, smaller diameter generally results in higher collapse pressure after removal of gvpC, and different dimensions result in different ratios of T2/T2* relaxivity per volume-averaged magnetic susceptibility [12].

Accordingly, in embodiments herein described, GVGC can be selected based on desired properties of the corresponding GV type. In particular, to this extent, a skilled person can use naturally occurring GVGC or can provide modified GVGC wherein some of the naturally occurring gyp genes are omitted, or can provide hybrid GVGC in which GVAs and GVS genes of naturally occurring GVGCs are mixed to provide GV types having the shape and dimensions resulting in the desired properties. Typically, a gene cluster of gyp genes (GVGC) comprises at least gvpF, gvpG, gvpL, gvpS, gvpK, gvpJ, and gvpU. Preferably a gene cluster of gyp genes (GVGC) comprises a gvpN The term "hybrid gene cluster" or "hybrid cluster" as used herein indicates a cluster comprising at least two genes native to different species and resulting in a cluster not natively in any organisms. Typically, a hybrid gene cluster comprises a subset of gas vesicle genes native to a first bacterial species and another subsets of gas vesicle genes native to one or more bacterial species, with at least one of the one or more bacterial species different from the first bacterial specie Accordingly, a hybrid GV gene clusters including a combination of GV genes which is not native in any naturally occurring prokaryotes.

For example, in one exemplary embodiment, all the gyp genes B, N, F, G, L, S, K, J and U are from *B. megaterium*. Mega GVs are typically cone-tipped cylindrical structures with a diameter of approximately 73 nm and length of 100-600 nm, encoded by a cluster of eleven or fourteen different genes, including the primary structural protein, gvpB, and several putative minor components and putative chaperones [10, 11] as would be understood by a person skilled in the art.

FIG. 1 shows a rendition of engineered GVs illustrating gvpA (101) as the main building block of GVs. GvpA is a structural protein that assembles through repeated units to make up the bulk of GVs. GvpC (102) is a scaffold protein with 5 repeat units that assemble on the outer shell of GVs. GvpC can be engineered to tune the mechanical and acoustic properties of GVs as well as act as a handle for appending moieties (103) on to.

A gvpC protein is a hydrophilic protein of a GV shell, which includes repetitions of one repeat region flanked by an N-terminal region and a C terminal region. The term "repeat region" or "repeat" as used herein with reference to a protein refers to the minimum sequence that is present within the protein in multiple repetitions along the protein sequence without any gaps. Accordingly, in a gvpC multiple repetitions of a same repeat is flanked by an N-terminal region and a C-terminal region. In a same gvpC, repetitions of a same repeat in the gvpC protein can have different lengths and different sequence identity one with respect to another.

As indicated above GV structures are typically nanostructures with widths and lengths of nanometer dimensions (in particular with widths of 45-250 nm and lengths of 100-800 nm) but can have lengths up to 2 μm or up to 8-10 μm as will be understood by a skilled person. In certain embodiments, the gas vesicles protein structure have average dimensions of 1000 nm or less, such as 900 nm or less, including 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less, or 25 nm or less, or 10 nm or less. For example, the average diameter of the gas vesicles may range from 10 nm to 1000 nm, such as 25 nm to 500 nm, including 50 nm to 250 nm, or 100 nm to 250 nm. By "average" is meant the arithmetic mean.

GVs in the sense of the disclosure have different shapes depending on their genetic origins. For example, GVs in the sense of the disclosure can be substantially spherical, ellipsoid, cylindrical, or have other shapes such as football shape or cylindrical with cone shaped end portions depending on the type of bacteria or archaea providing the gas vesicles.

In embodiments herein described, GVs in the sense of the disclosure are capable of withstanding pressures of several kPa, but collapse irreversibly at a pressure at which the GV protein shell is deformed to the point where it flattens or breaks irreversibly, allowing the gas inside the GV to escape and subsequently dissolve in surrounding media, herein also referred to as a critical collapse pressure, or acoustic collapse pressure threshold, as there are various points along a collapse pressure profile.

A collapse pressure profile as used herein indicates a range of pressures over which collapse of a population of GVs of a certain type occurs. In particular, a collapse pressure profile in the sense of the disclosure comprise increasing acoustic collapse pressure values, starting from an initial collapse pressure value at which the GV signal/ optical scattering by GVs starts to be erased to a complete collapse pressure value at which the GV signal/optical scattering by GVs is completely erased. The collapse pressure profile of a set type of GV is thus characterized by a mid-point pressure where 50% of the GVs of the set type have been collapsed (also known as the "midpoint collapse pressure"), an initial collapse pressure where 5% or lower of the GVs of the type have been collapsed, and a complete collapse pressure where at least 95% of the GVs of the type have been collapsed. In embodiments herein described a selectable critical collapse pressure (herein also "collapse threshold") can be any of these collapse pressures within a collapse pressure profile, as well as any point between them. The critical collapse pressure profile of a GV is functional to the mechanical properties of the protein shell and the diameter of the shell structure.

The term "acoustic pressure" as used herein indicates the pressure exerted by a sound wave, such as ultrasound wave, propagating through a medium. In ultrasound imaging, this wave is typically generated by an ultrasound transducer, and the pressure resulting at any time and point in the medium is determined by transducer output and patterns of constructive and destructive interference, attenuation, reflection, refraction and diffraction. Ultrasound images are generated by transmitting one or more pulses into the medium and acquiring backscattered signals from the medium, which depend on medium composition, including the presence of contrast agents.

In embodiments herein described, the collapse behavior of GVs under ultrasound exhibits a spectral pattern, as the GVs can collapse over a range or spectra of continuous increasing acoustic collapse pressure values, starting from an initial collapse pressure value at which the GV signal starts to be erased to a complete collapse pressure value at which the GV signal is completely erased. Therefore, for some embodiments of the method, the method begins with applying ultrasound to a target site at a PPP less than the acoustic collapse pressure threshold. The collapse pressure also can vary based on the frequency of the acoustic signal.

The acoustic collapse pressures of a given GV type can be characterized by an acoustic collapse pressure profile, which is a normalized sigmoid function f(p) defined as follows:

$$f(p) = (1 + e^{(p-p_c)/\Delta p})^{-1} \tag{1}$$

where p is the applied pressure, $p_c$ is the collapse mid-point and $\Delta p$ is the variance, the latter two being parameters obtained from fitting with a sigmoid function. The acoustic collapse pressure profile shows normalized ultrasound signal intensities as a function of increasing pressures.

The acoustic collapse pressure profile of a given GV type can be determined by imaging GVs with imaging ultrasound energy after collapsing portions of the given GV type population with a collapsing ultrasound energy (e.g. ultrasound pulses) with increasing peak positive pressure amplitudes to obtain acoustic pressure data point of acoustic pressure values, the data points forming an acoustic collapse curve. The acoustic collapse pressure function f(p) can be derived from the acoustic collapse curve by fitting the data with a sigmoid function such as a Boltzmann sigmoid function.

Accordingly, acoustic collapse pressure profile in the sense of the disclosure include a set of initial collapse pressure values, a midpoint collapse pressure value and a set of complete collapse pressure values. The initial collapse pressures are the acoustic collapse pressures at which 5% or less of the GV signal is erased. A midpoint collapse pressure is the acoustic collapse pressure at which 50% of the GV signal is erased. Complete collapse pressures are the acoustic collapse pressures at which 95% or more of the GV signal is erased.

The initial collapse pressures can be obtained by solving the fitted equations for p such that $f(p) \leq 0.05$. The midpoint collapse pressure can be obtained by solving the fitted equations for p such that $f(p) = 0.5$. The complete collapse pressures can be obtained by solving the fitted equations for p such that $f(p) \geq 0.95$. In some embodiments, the acoustic collapse pressure threshold can be set to either the initial collapse pressure, the midpoint collapse pressure, the complete collapse pressure, or some other value in the collapse profile where collapse occurs. For most practical applications, the acoustic collapse pressure threshold would be set at least as high as the midpoint collapse pressure. If the contrast material is composed of multiple types of GVs, where each type has a different collapse pressure threshold, then the effective collapse pressure threshold for the material can be set to the highest collapse pressure threshold of all of the GV types.

If the imaging is being performed on living tissue, then care must be taken to not have the PPP pressure damage the tissue. This limit on PPP depends on the target site being imaged (and its surrounding tissue).

Since method ultrasound imaging of the instant disclosure are based on the acoustic collapse pressure of a GV type, GV types can be tested to identify an acoustic collapse pressure before the related use. In some embodiments, a GV type can also be modified by engineering the corresponding GVGC to provide a GV detectable in the target cell and having a desired acoustic collapse pressure as will be understood by a skilled person.

Identification of a GVGC corresponding to a GV type and detection of the related acoustic collapse pressure in a target cell can be performed through a testing method which can be performed in the target cell where detection of the GV type is desired or in testing cells having a cell environment equivalent to the cell environment of the target cell in terms of expression of GV genes and GV formation and thus provide a model to verify ability of the gyp genes to provide a GVGC for the target cells. If the GVGC is known, it might be possible to look up its acoustic collapse pressure profile or threshold in a database of GVGC.

In the method, the GVGC cluster can be introduced in the target cell or testing cell using engineered polynucleotide constructs contacted with the target cell or testing cell for a time and under conditions to allow expression of the GVGC and formation of the GV type (e.g. using the methods described in U.S. application Ser. No. 15/663,635 published as US 2018/0030501 incorporated herein by reference). The method further comprises detecting the acoustic collapse pressure of the GV type in the target cell or testing cell. Preferably the testing can be performed in a target cell or testing cell, that have been modified, either chemically or genetically, to have the same cellular turgor pressure as mammalian cells according to methods identifiable by a skilled person.

Additionally, or in the alternative, the GVs can be introduced to the target site pre-formed (e.g. formed in vitro from a bacteria culture) before the detecting.

Several detectable GVGC with one or more detection method of interests have been identified and can be used for production of GV types in various cells through various genetically engineered constructs as will be understood by a skilled person upon reading of the present disclosure and U.S. application Ser. No. 15/663,635 herein incorporated by reference in its entirety.

In some embodiments those GVGC can comprise gyp genes A/B, C and N (gvpB, gvpC and gvpN genes) from a same or different prokaryote. Preferably the GVGC comprises gvpN gene as presence of gvpN protein is known or expected to result in an increased detectability of the related GV type (better signal under ultrasound collapse).

Exemplary gene clusters which have provided to be detectable in mammalian cells and *E. Coli* comprise gyp genes from *B. megaterium* (herein also mega-gyp) and/or *Anabaena flos-aquae* (herein also Ana-gyp), and in particular those summarized in Table 1. The acoustic collapse pressures for the clusters are listed in Table 1 for frequencies between 5 MHz and 20 MHz.

TABLE 1

Exemplary GVGCs

| Type of cluster | gvp genes of the GVGC | Acoustic° Collapse Pressure |
|---|---|---|
| Naturally ooccuring in *B. megaterium* | Mega-gvpB, Mega-gvpN Mega-gvpF, Mega-gvpG, Mega-gvpL Mega-gvpS, Mega-gvpK, Mega-gvpJ, Mega-gvp-R, Mega-gvp-T and Mega-gvpU | 1.9 MPa |
| Engineered | Mega-gvpB, Mega-vpN Mega-gvpF, Mega-gvpG, Mega-gvpL Mega-gvpS, Mega-gvpK, Mega-gvpJ, and Mega-gvpU | 1.9 MPa |
| Naturally ooccuring in *Anabaena flosaquae* | Ana-gvpA, Ana-gvpC, Ana-gvpN, Ana-gvpJ, Ana-gvpK, Ana-gvpF, Ana-gvpG, Ana-gvpV, Ana-gvpW | 0.9 MPa |
| Engineered | Ana-gvpA, Ana-gvpN, Ana-gvpJ, Ana-gvpK, Ana-gvpF, Ana-gvpG, Ana-gvpV, Ana-gvpW | 0.6 MPa |
| Hybrid engineered | Ana-gvpA gen, Mega-gvpR, Mega-gvpN, Mega-gvpF, Mega-gvpG, Mega-gvpL, Mega-gvpS, Mega-gvpK, Mega-gvpJ, gvpT and gvpU | 0.6 MPa |
| Hybrid engineered | Ana-gvpA, Ana-gvpC, Mega-gvpN Mega-gvpF, Mega-gvpG, Mega-gvpL Mega-gvpS, Mega-gvpK, Mega-gvpJ, and Mega-gvpU | 2.2 MPa |
| Hybrid engineered | Ana-gvpA, Ana-gvpC, Mega-gvpN Mega-gvpF, Mega-gvpG, Mega-gvpL Mega-gvpR Mega-gvpS, Mega-gvpT Mega-gvpK, Mega-gvpJ, and Mega-gvpU | 2.2 MPa |
| Hybrid engineered | Ana-gvpA, Ana-gvpC Ana-gvpN; Mega- Mega-gvpF, Mega-gvpG, Mega-gvpL Mega-gvpS, Mega-gvpK, Mega-gvpJ, and Mega-gvpU | 2.2 MPa |
| Hybrid engineered | Ana-gvpA, Ana-gvpC Ana-gvpN; Mega- Mega-gvpF, Mega-gvpG, Mega-gvpL Mega-gvpR, Mega-gvpS, Mega-gvpT, Mega-gvpK, Mega-gvpJ, and Mega-gvpU | 2.2 MPa |

Additional GVGCs can be identified based on the genes and exemplary sequences reported in Example 1 herein described and the related mechanical and acoustic properties such as acoustic collapse pressure of each GV type is also identifiable by a skilled person upon reading of the present disclosure.

Based on the above acoustic collapse pressure values, a standard collapse pressure of 4.3 MPa has been established which will result in the collapse of the GV types reported in Table 1 and is still below 4.6 MPa, a pressure that, according to limits on ultrasound imaging pressure set by the U.S. Food and Drug Administration (USFDA), could be considered damaging to a target site comprising living cells for a longBURST pulse sequence at 6 MHz, assuming peak negative pressure is equal in magnitude to peak positive pressure. In view of known values of acoustic collapse pressure for GVs this standard collapse pressure is expected to work for most GV types and can be used in the testing method to identify acoustic properties of GVs herein described.

Accordingly different GV types can be provided to be used in a method of ultrasound imaging to be used on a target site contrasted with gas vesicles (GVs) having an acoustic collapse pressure threshold, which comprises: applying ultrasound to the target site at a peak positive pressure less than the acoustic collapse pressure threshold; increasing peak positive pressure (PPP) to above the selective acoustic collapse pressure value as a step function; and imaging the target site in successive frames during the increasing; and extracting a time-series vector for each of at least one pixel of the successive frames.

In particular, in methods of the instant disclosure, applying ultrasound refers to sending ultrasound-range acoustic energy to a target. The sound energy produced by the piezoelectric transducer can be focused by beamforming, through transducer shape, lensing, or use of control pulses. The soundwave formed is transmitted to the body, then partially reflected or scattered by structures within a body; larger and smoother structures typically reflecting, and smaller or rougher structures typically scattering. The return sound energy reflected/scattered to the transducer vibrates the transducer and turns the return sound energy into electrical signals to be analyzed for imaging. The frequency and pressure of the input sound energy can be controlled and are selected based on the needs of the particular imaging task and, in some methods described herein, collapsing GVs.

The increasing peak positive pressure (PPP) to above the selective acoustic collapse pressure value as a step function can be performed by implementing an automated pulse sequence on a programmable ultrasound system and transducer in which the voltage applied to the transducer, and thus the PPP, increases during certain successive pulses.

To create images, particularly 2D and 3D imaging, scanning techniques can be used where the ultrasound energy is applied in lines or slices which are composited into an image. The images can be captured in successive frames, showing images at successively different times typically ranging from 100 microseconds to 100 milliseconds between image frames, depending on the amount of motion in the target.

In some embodiments, imaging the target site can be performed by scanning an ultrasound image of the target site in successive frames. In some cases, imaging the target site includes transmitting an imaging ultrasound signal from an ultrasound transmitter to the target site, and receiving a set of ultrasound data at a receiver. The visible image is formed by ultrasound signals backscattered from the target site. The ultrasound data can be analyzed using a processor, such as a processor configured to analyze the ultrasound data and produce an ultrasound image from the ultrasound data. In certain embodiments, the ultrasound data detected by the receiver includes an ultrasound signal reflected by the target site of the subject. The imaging can be any type of ultrasound imaging, including the standard B-mode or a contrast mode sequence such as amplitude modulation (AM) or pulse inversion (PI).

Methods for performing ultrasound imaging are known in the art and can be employed in methods of the current disclosure. In certain aspects, an ultrasound transducer, which comprises piezoelectric elements, transmits an ultrasound imaging signal (or pulse) in the direction of the target site. Variations in the acoustic impedance (or echogenicity) along the path of the ultrasound imaging signal causes backscatter (or echo) of the imaging signal, which is received by the piezoelectric elements. The received echo signal is digitized into ultrasound data and displayed as an ultrasound image. Conventional ultrasound imaging systems comprise an array of ultrasonic transducer elements that are used to transmit an ultrasound beam, or a composite of ultrasonic imaging signals that form a scan line. The ultrasound beam is focused onto a target site by adjusting the relative phase and amplitudes of the imaging signals. The imaging signals are reflected back from the target site and received at the transducer elements. The voltages produced at the receiving transducer elements are summed so that the net signal is indicative of the ultrasound energy reflected from a single focal point in the subject. An ultrasound image is then composed of multiple image scan lines.

In certain embodiments, the ultrasound signal has a transmit frequency of at least 1 MHz, 5 MHz, 10 MHz, 20 MHz, 30 MHz, 40 MHz or 50 MHz. For example, an ultrasound data is obtained by applying to the target site an ultrasound signal at a transmit frequency from 4 to 11 MHz, or at a transmit frequency from 14 to 22 MHz.

In the embodiments herein described, the collapsing ultrasound and imaging ultrasound are selected to have a collapsing pressure and an imaging pressure amplitude based on the acoustic collapse pressure profile of the GV structure type used in the contrast agent. In some instances, the ultrasound pressure, including the collapsing ultrasound pressure and the imaging ultrasound pressure can be referred to as the "peak positive pressure" of the ultrasound pulses. The term "peak positive pressure" refers to the maximum pressure amplitude of the positive pulse of a pressure wave, typically in terms of the difference between the peak pressure and the ambient pressure at the location in the person or specimen that is being imaged.

In some embodiments, the GV contrast agent is detected by burst ultrasound reconstruction with signal templates (BURST), which involves applying an ultrasound step function pressure differential to the location of the GV contrast agent and capturing successive frames of the ultrasound image during the increase of pressure. In some embodiments, the ultrasound step function pressure differential increases the acoustic pressure from a pressure below the collapse threshold of the GVs to an acoustic pressure above the collapse threshold of the GVs. Example step function pressure differentials can include increasing the ultrasound peak positive pressure (PPP) from a value under 1 MPa to a value over 1 MPa, such as 3 MPa or higher, 3.7 MPa or higher, 4 MPa or higher, 4.3 MPa or higher, or other values. BURST allows for an ability to detect smaller number of cells than conventional imaging, and even allows sensitivity down to imaging individual cells in the imaging plane. See e.g. Example 2.

The term "peak positive pressure" (or PPP) as used herein refers to the pressure difference from zero to the highest positive pressure (the peak of the positive part of a pressure wave) of the signal. As used herein, the PPP is measured or calculated at the target site, not at the transducer/source. Some attenuation is expected as the ultrasound permeates matter to reach the target site.

The term "step function" as used herein refers to a strong increase or decrease in value over a short period of time. The BURST step function is an increase of PPP. The strength of the increase does not need to be particularly strong, so long as there is a clear transition from a PPP below the collapse threshold to a PPP above the collapse threshold, such that the collapse rate prior to the step function increase is very low (ex. <5%) and the collapse rate after the step function increase is high (ex. >80%). Typically, an increase of at least 3 MPa is required for most GVs, but the actual value will depend on individual GV collapse sensitivity. Typically, larger pressure increases lead to larger gains in sensitivity. Detection of single cells typically requires a pressure increase of 4 MPa. Because the step function consists of several discrete ultrasound pulses, the speed of the step function transition is equal to the time between ultrasound pulses, which typically matches the time between images frames of 100 microseconds to 100 milliseconds. A step function can include an impulse (a step function increase followed shortly by a step function decrease).

In some embodiments, the detection includes detecting a transient signal from the GV contrast in the time domain of the ultrasound image. An example of a transient signal is an increase in contrast in the image over less than a second. For example, a transient signal might be present over a few hundred microseconds. The transient signal appears as a strong increase in contrast signal during and after the collapse of the GVs.

In some embodiments, the detection of the transient signal can be accomplished by imaging the target site in successive frames during the step function increase of pressure (for example, including frames from before collapse, during collapse, and after collapse) and extracting a time-series vector for each pixel from the successive frames.

The term "time-series vector" as used herein refers to a vector of data taken from multiple points in time for a common pixel location in an image.

In some embodiments, the method can also comprise performing a signal separation algorithm on the time-series vectors using at least one template vector. Signal separation allows for greater sensitivity of imaging against background noise. Signal separation algorithms include template projection and template unmixing. The at least one template vector can include linear scatterers, noise, gas vesicles, or a combination thereof. The successive frames can comprise a frame prior to GV collapse, a frame during GVs collapse, and a frame after GVs collapse.

Signal separation algorithms include template projection and template unmixing. In an embodiment, the method of imaging can include template projection and/or template unmixing of template vectors with the pixel vectors. The signal separation algorithm can be implemented in software or firmware/hardware.

The term "signal separation" as used herein refers to a method of separating the signal from the noise for an image (set of data).

The term "template vector" as used herein refers to a vector obtained from a previously known signal to allow signal separation for a possibly noisy signal under consideration.

The unique temporal responses of GVs, linear scatterers, and non-scattering material to this stimulus allows us to use known signal templates to separate the signal due to GVs from signal due to noise or linear scatterers such as biological tissue. Signal templates can be estimated empirically by averaging pixel time series from regions of interest (ROIs) containing known samples, as exemplified in Example 2 (see FIG. 4), and, in general, BURST can be used with any number of unique signal templates. However, in one problem setting, the physical properties of GVs and biological tissue can be used to specify exact signal templates a priori: a flat function for noise, a step function for linear scatterers, and an impulse function for GVs. Hence, as few as three frames (pre-collapse, collapse, and post-collapse) can be used to distinguish these templates, which would correspond to the following template vectors for:

$$\text{linear scatterers}\left(u_s = \begin{pmatrix} 0 \\ 1 \\ 1 \end{pmatrix}\right), \tag{2}$$

$$\text{noise}\left(u_n = \begin{pmatrix} 1 \\ 1 \\ 1 \end{pmatrix}\right), \text{ and} \tag{3}$$

$$GVs\left(u_g = \begin{pmatrix} 0 \\ 1 \\ 0 \end{pmatrix}\right). \tag{4}$$

In template projection, the final BURST intensity I for each pixel can be a normalized similarity score computed as the projection of the template vector of interest (in our case $u_g$) onto the pixel vector:

$$I = \frac{(u_g^T p)}{\|p\|} \tag{5}$$

Figure 4:
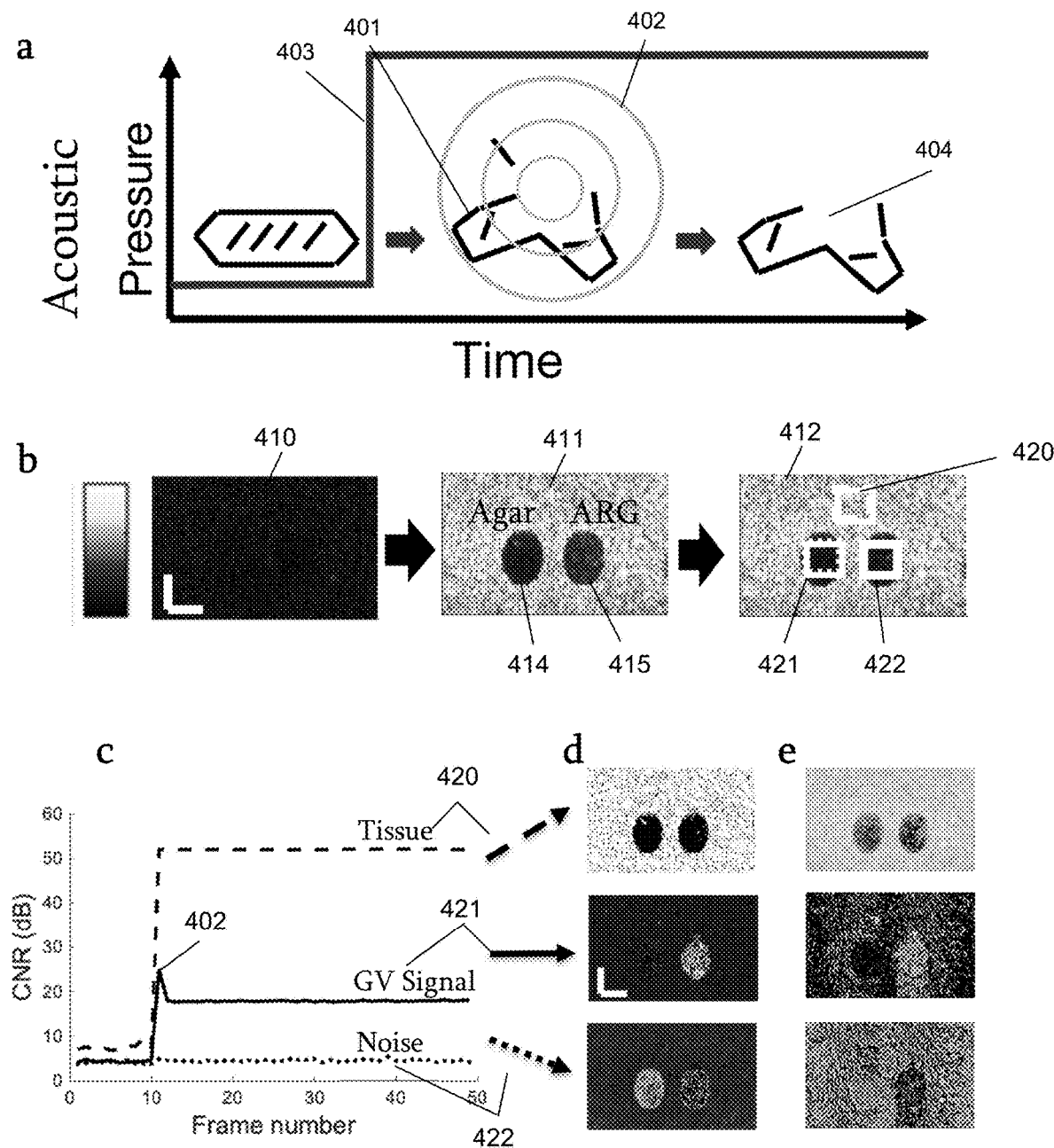
FIG. 4 shows an example of the BURST paradigm. Panel (a) shows an illustration of the GV collapse. Panel (b) shows three consecutive images from the successive images taken during the collapse. Panel (c) shows a contrast-to-noise ratio (CNR) vs. frame number. Panel (d) shows example output of the template projection algorithm. Panel (e) shows example output of the template unmixing algorithm.

Because the template vector can be projected onto the pixel vector, rather than vice versa, template projection is scale-invariant: pixel locations with clear impulse time traces will have the highest intensity in the final BURST image even if the peak intensities of the time traces are orders of magnitude lower in intensity than those corresponding to surrounding linear scatterers, as is the case exemplified in Example 2 (see in particular FIG. 4). In fact, for a given GV signal intensity, stronger scatterer signals will be more efficiently canceled. This contrasts with conventional techniques for improving specificity in ultrasound imaging of contrast agents, which typically improve CTR by an approximately fixed amount that often leaves a visible residual signal in vivo [1]. Moreover, as AM and PI rely on linearity of acoustic scattering, their specificity deteriorates rapidly with increasing acoustic pressures, as observed in the exemplary detection of Example 2 (see in particular FIG. 4).

Despite these advantages, template projection has its limitations. Firstly, its scale invariance means that pixel values in the final template projection image do not always directly correspond to physical quantities, making quantification difficult. Second, the performance of template projection might be compromised in scenarios where GV signal is colocalized with strong linear scatterer signal.

In template unmixing, the colocalization problem can be addressed by modeling each pixel vector as a linear combination of the template vectors. This model can be represented by the linear equation $$Vw=p, \quad (6)$$

where the template vectors are concatenated into the template matrix $$V=[u_s u_n u_g], \quad (7)$$

and w contains the weights for each template. For each pixel vector p, obtain the least squares solution for the template weights by the pseudoinverse:

$$w=(V^T V)^{-1} V^T p \quad (8)$$

Technically, because negative weights have no meaning in this model, a proper estimation of the template weights would require the appropriate constrained linear least squares solution, which is typically two orders of magnitude slower to compute. However, empirically, setting all negative values of the unconstrained solution to zero results in a final image that is not appreciably different from that obtained using the constrained solution.

Template unmixing tends to cancel linear scatterers less efficiently than template projection due to the lack of scale invariance (see Example 2 and in particular FIG. 4, panel (e)), showing that template projection is preferable in scenarios where GVs are known to not be co-localized with linear scatterers. However, because co-localization occurs in many interesting in vivo contexts, and because it is often desired to quantify BURST contrast, template unmixing can be considered the more robust and versatile algorithm generally and it is used for BURST images herein, unless otherwise specified. This method is also applicable in scenarios where a nonlinear signal is produced at the target site. In fact, at high PPP (ex. above 3 MPa), intrinsic nonlinearities in most media result in production of strong nonlinear signal even in the absence of contrast agents. Because the signal separation algorithms employed rely only on detectable changes in the signals generated by GVs, BURST is equally applicable to targets that produce linear signals and those that produce nonlinear signals.

The PPP used to collapse the GV contrast can be divided into two or more regimes. For example, lower pressure can be considered "loBURST" and higher pressure can be considered "hiBURST", separated by what the predominant mechanism is for the signal. See e.g. Example 3. For PPPs in between loBURST and hiBURST, which may be used when a tradeoff between the benefits and drawbacks of each is desired, the generated signal will consist of a mixture of the mechanisms characterizing each regime.

In an embodiment, the PPP is in a loBURST regime (relatively low PPP), where the dominate mechanism of the signal is due to an acoustic wave generated by the collapse of the GV shell and the resulting rapid displacement of fluid volume. The loBURST regime is characterized by a signal composed predominantly of dim sources, dominated by the fundamental and second harmonic peaks. An example of loBURST is a PPP of around 3.7 MPa for a half-cycle duration. The minimum loBURST PPP will depend on the type of GV used, in particular the collapse threshold. The hiBURST PPP can be lower in setups with lower frequencies, larger number of waveform cycles, or less attenuating tissue types, since these factors all contribute to enhancing cavitation.

In an embodiment, the PPP is in a hiBURST regime (relatively high PPP), where the dominant mechanisms include stable cavitation of nanobubbles liberated from the GVs following collapse, and a limited amount of inertial cavitation in some cases. The hiBURST regime is characterized by a signal composed predominately of bright sources, and the emergence of higher (>2) harmonic peaks. An example of hiBURST is a PPP of around 4.3 MPa for 1.5 half-cycles.

Operating in a loBURST or hiBURST regime can depend on what is optimal for a particular use case. In cases where it is desirable to maximize sensitivity or detect single cells, such as with highly scattering tissue or low cell and/or GV concentrations, hiBURST is often optimal. However, because hiBURST results in a greater amount of cavitation, it results in a reduction in viability of GV-expressing bacteria. Thus, in cases where it is desirable to minimize effects on host cells and/or surrounding tissue and where cell and/or GV concentrations are sufficient for detection by loBURST, loBURST is often optimal. The loBURST PPP can be lower in setups with GVs that have a lower collapse threshold. The maximum loBURST PPP will increase with the frequency and decrease with the number of waveform half-cycles. For example, a PPP of 4.3 MPa that would normally define a hiBURST regime with a waveform using the standard 3 half-cycles will instead correspond to loBURST when using a short waveform with only 1 half-cycle. This will also depend on the specific transducer model used and its ability to realize the specified number of half-cycles with minimal ringdown.

Accordingly, in some embodiments, the increasing PPP can be increasing the PPP to a hiBURST regime or increasing the PPP to a loBURST regime. The hiBURST regime can be 4.3 MPa or higher and the loBURST regime can be 3.7 MPa or lower. Other values of hiBURST and loBURST can be used, so long as loBURST is less than hiBURST. The distinction of hiBURST and loBURST is mainly characterized by the differences in the mechanisms behind the signals produced.

Additionally, the duration of the increased PPP can affect the sensitivity of the imaging. For example, the number of half-cycles in the transmit waveform can be divided into two or more regimes. For example, smaller numbers of half-cycles can be considered "shortBURST" and larger numbers of half-cycles can be considered "longBURST", separated by what the predominant mechanism is for the signal. See e.g. Example 10.

In an embodiment, the waveform is in a shortBURST regime (relatively small number of half-cycles), where the dominate mechanism of the signal is due to an acoustic wave generated by the collapse of the GV shell and the resulting rapid displacement of fluid volume. The loBURST regime is characterized by a signal composed predominantly of dim sources, dominated by the fundamental and second harmonic peaks. An example of shortBURST is a waveform with 1 half-cycle with a PPP of 4.3. The loBURST regime coincides with the shortBURST regime since both are defined by the dominant signal generation mechanism.

In an embodiment, the waveform is in a longBURST regime (relatively large number of half-cycles), where the dominant mechanisms include stable cavitation of nanobubbles liberated from the GVs following collapse, and a limited amount of inertial cavitation in some cases. The longBURST regime is characterized by a signal composed predominately of bright sources. An example of longBURST is a waveform with 5 half-cycles with a PPP of 4.3 MPa.

Figure 2:
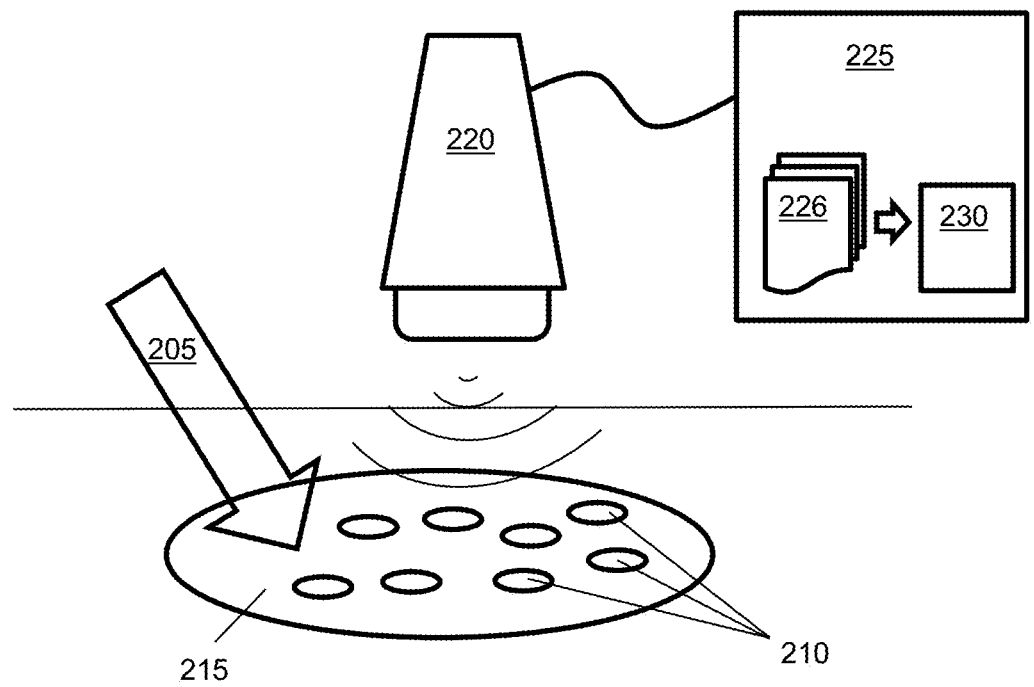
FIG. 2 shows a schematic representation of an exemplary system for implementing BURST detection methods herein described.

The BURST technique can be implemented by a combination of hardware, software, and biotechnology. In an embodiment, an example of which is shown in FIG. 2, a system for imaging a target site (215) can include: a means (205) for introducing GVs (210) to the target site (215), the GVs (210) having a collapse threshold; an ultrasound source (220) capable of producing PPP both below and above the collapse threshold; and an ultrasound imager (225) configured to capture successive frames (226) from the target site (215). A processor (230) can be configured to calculate the pixel vectors from the successive frames (226) and then perform a signal separation algorithm (such as threshold unmixing) on the pixel vectors from a set of template vectors. The processor can be part of the imager (as shown in FIG. 2), or it can be a part of a separate device. The means for introducing GVs to the target site can include techniques such as injecting GVs to the site, introducing cells containing GVs to the site, modifying cells at the site to produce the GVs, modifying cells to produce GVs then introducing those cells to the site, combinations thereof, or any similar technique. The ultrasound source typically needs to be capable of producing the PPP both below and above the collapse threshold in order to perform the step function for the BURST. The ultrasound imager needs to be capable of capturing the successive frames of the image.

The wording "systemic administration" as used herein indicates any route of administration by which the one or more genetically engineered bacterial cell types comprising a GVR genetic circuit is brought in contact with the body of the individual, so that the resulting location of the one or more genetically engineered bacterial cell types comprising a GVR genetic circuit in the body is systemic (not limited to a specific tissue, organ or other body part where the imaging is desired). Systemic administration includes enteral and parenteral administration. Enteral administration is a systemic route of administration where the substance is given via the digestive tract, and includes but is not limited to oral administration, administration by gastric feeding tube, administration by duodenal feeding tube, gastrostomy, enteral nutrition, and rectal administration. Parenteral administration is a systemic route of administration where the substance is given by route other than the digestive tract and includes but is not limited to intravenous administration, intra-arterial administration, intramuscular administration, subcutaneous administration, intradermal administration, intraperitoneal administration, and intravesical infusion.

Figure 3:
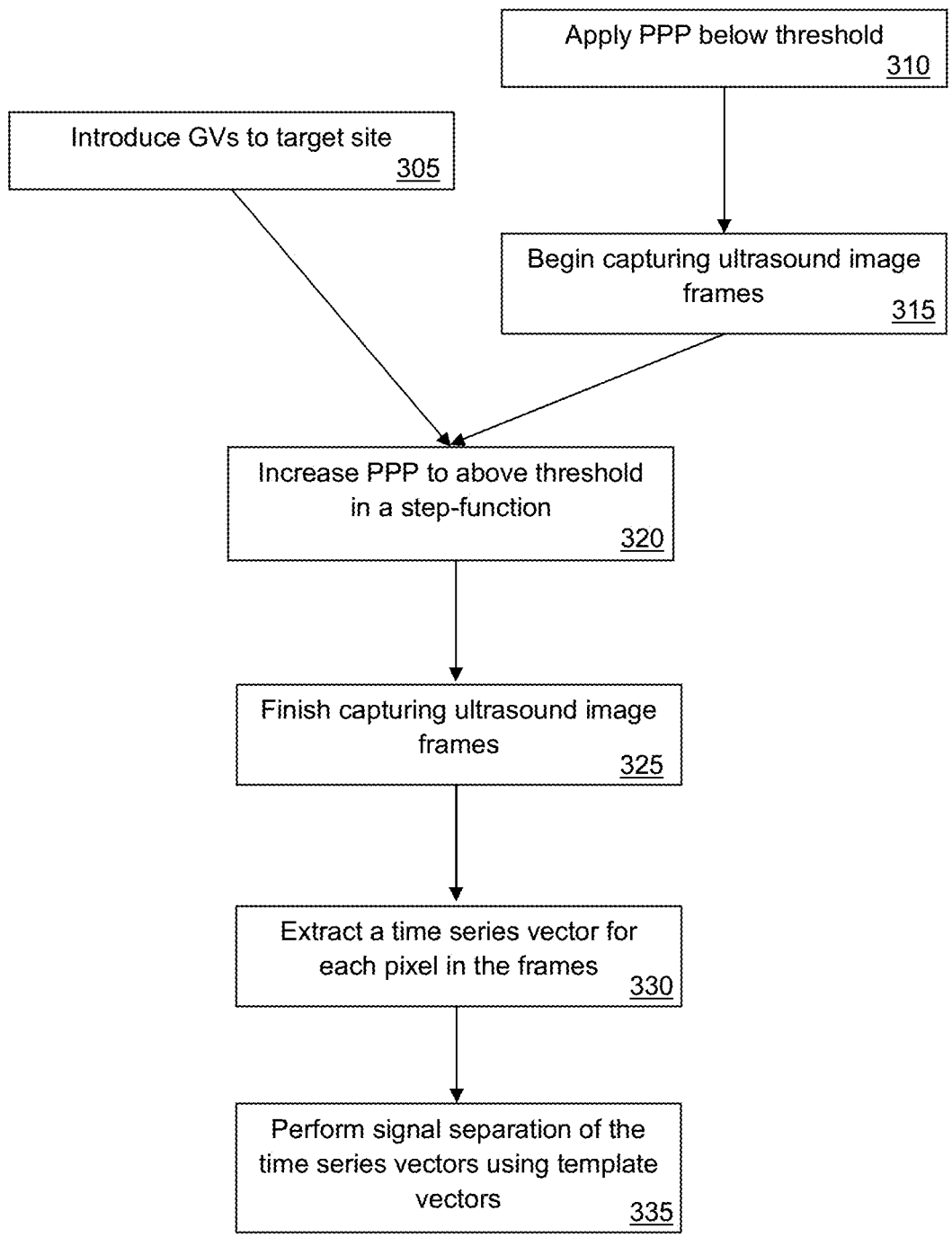
FIG. 3 shows an example method of using BURST for imaging.

FIG. 3 shows an example method of using BURST for imaging. In an embodiment, the process begins with the introduction of GVs to the target site (305). The means for introducing the GVs can vary, including injection of the GVs in solution, injection of GVs in host cells, injection of host cells with acoustic reporter genes (either naturally occurring or engineered cells), or engineering cells at the target site to have acoustic reporter genes. The target site can be in vitro or in vivo.

An example of introducing GVs to a target site is injecting isolated GVs into the tail vein of a mouse. Another example is mixing engineered GV-expressing bacteria with molten agarose and injecting the solution into the colon of an animal model. Another example is gavaging a solution of GV-expressing bacteria into an animal model and waiting for the cells to propagate through the gastrointestinal tract. Another example is growing a tumor on a mouse model where the tumor is grown from mammalian cells with acoustic reporter genes.

An ultrasound PPP below the collapse threshold of the GVs is applied to the target site (310), which can be started before, during, or after the GVs are introduced. Image frames are captured in sequence from the ultrasound image (315). This can be performed before, during, or after the introduction of GVs, but the frames taken prior to the introduction of the GVs might not have any value to the BURST process (but may have other use). Once the GVs are present and images frames are being captured, the ultrasound PPP can be rapidly increased to value over the collapse threshold of the GVs (320), which can be described as a step function change in PPP.

As the PPP is increased, the image frames continue to be captured. Any number of frames can be captured, but at a minimum three frames should be captured—one before the GVs collapse, one during the GVs collapse, and one after the GVs collapse. After the GVs collapse, the capturing of image frames can end (325). For each pixel of the image frames, a time-series vector can be extracted (330). Either all pixels of the frame can have time-series vectors extracted, or only those pixels within a region of interest within the frames can be represented by time-series vectors. When the time-series vectors are found, signal separation can be performed on them using template vectors (335). Signal separation can be performed by any method, such as template projection or template unmixing.

Four mechanisms can contribute to the transient acoustic signal observed with loBURST and/or the much stronger transient signal observed with hiBURST: 1) the same linear scattering that creates contrast when imaging below the collapse threshold of the GV, 2) an acoustic wave generated by the rapid volume change that occurs during GV collapse, 3) stable cavitation of nanobubbles liberated from the GVs following collapse, and 4) inertial cavitation of liberated nanobubbles. In the case of (1), the signal strength is due to an increase in scattering amplitude in proportion to the higher pressures applied, while the signal transience is explained by the collapse of the GVs after the initial scattering event. For (3) and (4), signal transience would result from the sub-millisecond dissolution times of the nanobubbles. While these mechanisms are not mutually exclusive, their fundamental physical differences suggest the resulting signal amplitudes are likely to differ by orders of magnitude. Thus, the transient collapse signal from hiBURST or loBURST can be considered to be due predominately to a single mechanism, and for the dominant mechanism to differ between hiBURST and loBURST.

By imaging ARG-expressing $E.\ coli$ in liquid buffer suspension at $10^5$ cells/ml and recording the frequency spectra and temporal properties of the resulting BURST signal at various pressure levels, this difference can be shown. In order to achieve sufficient frequency resolution to discern higher harmonics from broadband enhancement, acquire data with a pulse sequence using 10 cycles at 5 MHz (see Example 3 and FIG. 5, panels (a), (b), (e), (g)) in addition to the standard BURST sequence using ½ cycle at 6 MHz (see Example 3, FIG. 5 panels (c), (d), (f), (h)), chosen to match the center frequency of our transducer and maximize axial resolution. In a small window of transitional pressure levels just below the hiBURST threshold, the signal tends to be a combination of elongated "bright" sources and a thinner band of lower intensity (see Example 3 and FIG. 5, (d)-(e), top). At lower pressures or concentration, it is apparent that the low-intensity band is composed of smaller, point-like "dim" sources (see Example 3 and FIG. 5, panel (h)). This indicates that the loBURST regime is characterized by a signal composed predominantly of dim sources, while the hiBURST regime signal is composed predominantly of bright sources.

It is observed that there are markedly different temporal properties for these two types of sources. Though both appear transient in the standard BURST pulse sequence with an inter-frame delay on the order of 10 msec, an ultrafast implementation of BURST with an inter-frame delay of 100 µsec shows that many bright sources persist after several high-pressure transmits (see Example 3 and FIG. 5, panel (e)). In contrast, the band of dim sources always vanishes after the first high-pressure frame. Because mechanism (2) depends on an irreversible collapse of the GV shell, it can be ruled out as a cause of the bright sources. Though it is conceivable that the dim sources could result from cavitation of much smaller nanobubbles, this is unlikely because a sample preparation protocol ensures both that there are no free GVs present and that all ARG-expressing cells have similar numbers of GVs, so mechanisms (3) and (4) can be ruled out for the dim sources.

Figure 5:
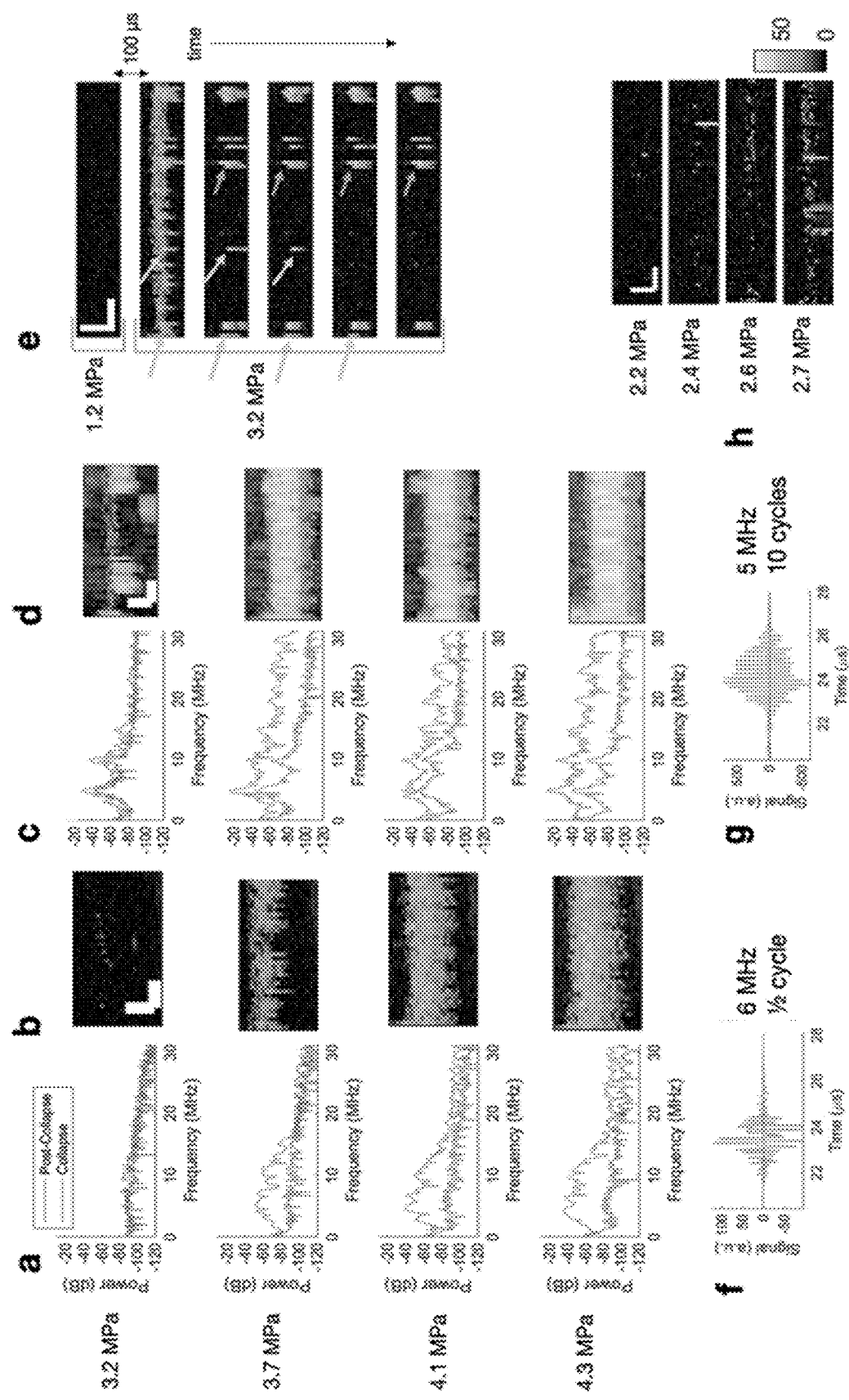
FIG. 5 shows examples of loBURST and hiBURST collapse signal generation. Panels (a) and (c) show the power spectra resulting from BURST acquisitions. Panels (b) and (d) show their corresponding images. Panels (a) and (b) show the power spectra and images acquired using standard BURST imaging parameters. Panels (c) and (d) show the power spectra and images acquired using a 10-cycle pulse at 5 MHz. Panel (e) shows an image time series acquired with an ultrafast version of hiBURST. Panel (f) shows the time domain signal used to generate the power spectrum in panel (a) and panel (g) shows the time domain signal used to generate the power spectrum in panel (c). Panel (h) shows BURST images acquired with the 10-cycle sequence at pressures near the 10-cycle loBURST threshold.

The loBURST mechanism can be narrowed down with the observation that the density of dim sources increases with pressure while their intensity remains relatively constant (see Example 3 and FIG. 5, panel (h)). If the sources were generated by mechanism (1), the opposite would be observed: there should be scattering from all cells in the field of view at an intensity that increases proportionally with incident pressure. Instead, the observations are consistent with a stochastic collapse model in which a given GV collapses with a probability proportional to the peak positive acoustic pressure. Therefore, the loBURST signal is the result of mechanism (2): an acoustic wave generated by the collapse of the GV shell and the resulting rapid displacement of fluid volume.

The hiBURST mechanism can be determined with the signal spectra. Below the hiBURST threshold with the 10-cycle pulse sequence, the spectrum is dominated by the fundamental and second harmonic peaks, which are both also observed in the post-collapse spectra (while all scattering occurs at the fundamental frequency in a linear medium, the intrinsic nonlinearity of water causes significant scattering at the second harmonic at elevated pressure levels). Above the hiBURST threshold, appearance of the bright sources is accompanied by both the emergence of higher harmonic peaks, a characteristic of stable cavitation, and a broadband enhancement in the power spectrum (see Example 3 and FIG. 5, panel (c)), a characteristic of inertial cavitation [2]. Based on the relative amplitude of the broadband and harmonic enhancements, mechanisms (3) and (4) both play a significant role in signal generated by hiBURST with the 10-cycle pulse sequence. It is more difficult to assess the contribution of inertial cavitation to hiBURST signal with the standard ½ cycle pulse sequence because, while a slight enhancement is observed across higher frequencies at pressures above the hiBURST threshold (see Example 3 and FIG. 5, panel (a)), there is not sufficient frequency resolution to distinguish harmonic enhancement from broadband enhancement. However, because the observed enhancement is weak relative to the 10-cycle case, and because inertial cavitation is typically generated by pulses with a large number of cycles, it can be concluded that the hiBURST signal involving few-cycle pulse sequences is predominantly generated by mechanism (3), with the possible presence of a limited amount of inertial cavitation.

In some embodiments, the imaging method herein described can further comprise delivering the GVs to the target site. Delivering the GVs to the target site can include using an acoustic reporter gene to express the GVs. The target site can comprise a mammalian cell with the acoustic reporter gene or a bacterial cell with the acoustic reporter gene.

In methods herein described, administering the contrast agent can be performed in any way suitable to deliver a GV to the target site to be imaged. In some embodiments, the contrast agent can be administered to the target site locally or systemically. The GVs can be delivered by the use of acoustic reporter gene (ARG) engineering.

The term "acoustic reporter gene" (or ARG) as used herein indicates genes used to express GVs in bacterial cells. The term "mammalian acoustic reporter gene" (or mARG) as used herein indicates genes used to express GVs in mammalian cells.

The wording "local administration" or "topic administration" as used herein indicates any route of administration by which a GV is brought in contact with the body of the individual, so that the resulting GV location in the body is topic (limited to a specific tissue, organ or other body part where the imaging is desired). Exemplary local administration routes include injection into a particular tissue by a needle, gavage into the gastrointestinal tract, and spreading a solution containing GVs on a skin surface.

The wording "systemic administration" as used herein indicates any route of administration by which a GV is brought in contact with the body of the individual, so that the resulting GV location in the body is systemic (i.e. non limited to a specific tissue, organ or other body part where the imaging is desired). Systemic administration includes enteral and parenteral administration. Enteral administration is a systemic route of administration where the substance is given via the digestive tract, and includes but is not limited to oral administration, administration by gastric feeding tube, administration by duodenal feeding tube, gastrostomy, enteral nutrition, and rectal administration. Parenteral administration is a systemic route of administration where the substance is given by route other than the digestive tract and includes but is not limited to intravenous administration, intra-arterial administration, intramuscular administration, subcutaneous administration, intradermal, administration, intraperitoneal administration, and intravesical infusion.

Accordingly, in some embodiments of methods herein described, administering a contrast agent can be performed topically or systemically by intradermal, intramuscular, intraperitoneal, intravenous, subcutaneous, intranasal, rectal, vaginal, and oral routes. In particular, a contrast agent can be administered by infusion or bolus injection, by absorption through epithelial or mucocutaneous linings (e.g., oral mucosa, vaginal, rectal and intestinal mucosa, etc.) and can optionally be administered together with other biologically active agents. In some embodiments of methods herein described, administering a contrast agent can be performed by injecting the contrast agent into a subject at the target site of interest, such as in a body cavity or lumen. In some embodiments, it can be performed by spreading a solution containing the contrast agent on a region of the skin.

In some embodiments, the GV are provided by transforming cells within a target site with polynucleotide construct directed to deliver genes encoding for the GP proteins forming one or more gas vesicles type.

GV production in prokaryotes can be natural or engineered. An initial inquiry to determine if a given prokaryote will produce GVs is to determine if there is a gene cluster containing gvpF and gvpN. gvpN is not strictly needed for GV production, but GVs produced with gvpN typically have better acoustic properties (in the case of BURST, a stronger collapse signal). If there is such a gene cluster (determined, for example, by sequencing) and if the prokaryote contains gyp A/B, then the prokaryote will likely produce useful GVs (for BURST) if those genes are expressed.

GVs can also be produced in mammalian cells through engineering (e.g. inserting gyps by means of a plasmid). The gyps for GV production in mammalian cells match those used for prokaryotes. For both prokaryotic and mammalian production, there are a number of permutations of gyps that can produce different GV types (GVs with different structural properties, such as shape, size, collapse threshold, etc.) with gvpF and gyp A/B being the conserved genes (and gvpN being an optional, but useful, gene).

In addition or in the alternative to detecting an acoustic collapse pressure for corresponding GV types, in exemplary embodiments where a GV type is to be used in the BURST (burst ultrasound reconstruction with signal templates) imaging described herein, the method of detection can be performed to further identify the a peak positive pressure (PPP) to be applied in connection with the specific GV type and can comprise imaging with ultrasound a target site comprising the cell following the introduction of the GVGC, over successive frames, at a peak positive pressure (PPP) well below the known or expected collapse threshold pressure for the GVs. While the frames are being taken, increasing the PPP step-wise to a value well over the expected collapse threshold pressure for at least 9 half-cycles. Frames from before, during, and after the application of the increased pressure undergo template unmixing to detect a BURST signal from the collapsing GVs, if present.

Further details concerning the BURST detection, and related methods and systems in accordance with the present disclosure will become more apparent hereinafter from the following detailed disclosure of examples by way of illustration only with reference to an experimental section.

EXAMPLES

The BURST imaging methods and systems herein disclosed are further illustrated in the following examples, which are provided by way of illustration and are not intended to be limiting.

In particular, the following examples illustrate exemplary methods and protocols for methods and systems to perform BURST imaging in accordance with the present disclosure. A person skilled in the art will appreciate the applicability and the necessary modifications to adapt the features described in detail in the present section, to detection of additional gas vesicle structures and related genetic circuits, vectors, genetically engineered mammalian cells, compositions, methods and systems according to embodiments of the present disclosure.

Example 1: Amino Acid Sequences of Exemplary GV Proteins Including GVS and GVA Proteins Several gyp genes and related proteins have been identified and are available in accessible databases.

In particular, Table 2 shows amino acid sequences of exemplary GVS (gyp AB or gvpC) and GVA proteins from several exemplary prokaryotic species. In particular, these exemplary amino acid sequences can be used as reference amino acid sequences in some embodiments for homology-based searches for related GVS and GVA proteins.

TABLE 2

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| gvpA/B | | |
| Ana-family-consensus_gvpA | MAVEKTNSSSSLAEVIDRILDKGIVIDAWVRVSLVGIELLAIEARXV IASVETYLKYAEAVGLTXSAAVPAX | 8 |
| Aphanizomenon-flos-aquae_gvpA | MAVEKTNSSSSLAEVIDRILDKGIVIDAWVRVSLVGIELLAIEARIVI ASVETYLKYAEAVGLTQSAAVPA* | 9 |
| Aphanothece-halophytica_gvpA | MAVEKTNSSSSLGEVVDRILDKGVVVDLWVRVSLVGIELLAVEAR VVVASVETYLKYAEAVGLTSSAAVPAE* | 10 |
| Anabaena-flos-aquae_gvpA | MAVEKTNSSSSLAEVIDRILDKGIVIDAWVRVSLVGIELLAIEARIVI ASVETYLKYAEAVGLTQSAAVPA* | 11 |
| Ancylobacter-aquaticus_gvpA | MAVEKINASSSLAEVVDRILDKGVVVDAWVRVSLVGIELLAVEAR VVVAGVDTYLKYAEAVGLTASAQAA* | 12 |
| Aquabacter-spiritensis_gvpA | MAVEKINASSSLAEVVDRILDKGVVVDAWVRVSLVGIELLAVEAR VVVAGVDTYLKYAEAVGLTAGAQAA* | 13 |
| Arthrospira-sp-PCC-8005_gvpA | MAVEKVNSSSSLAEVIDRILDKGIVIDAWVRVSLVGIELLSVEARV VIASVETYLKYAEAVGLTAQAAVPSV* | 14 |
| Calothrix-sp-strain-PCC-7601_gvpA | MAVEKTNSSSSLAEVIDRILDKGIVVDAWVRVSLVGIELLAIEARIV IASVETYLKYAEAVGLTQSAAVPA* | 15 |
| Dactylococcopsis-salina-PCC-8305_gvpA1 | MAVEKTNSSSSLGEVVDRILDKGVVVDLWVRVSLVGIELLAVEAR VVIASVETYLKYAEAVGLTSSAAVPAE* | 16 |
| Dolichospermum-circinale-AWQC131C_gvpA | MAVEKTNSSSSLAEVIDRILDKGIVIDAWVRVSLVGIELLAIEARIVI ASVETYLKYAEAVGLTQSAAVPA* | 17 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Dolichospermum-lemmermannii_gvpA | MAVEKTNSSSSLAEVIDRILDKGIVIDAWVRVSLVGIELLAIEARIVI ASVETYLKYAEAVGLTQSAAVPA | 18 |
| Enhydrobacter-aerosaccus_gvpA1 | MAVEKMNASSSLAEVVDRILDKGIVIDAWVRVSLVGIELLAVEAR VVVAGVDTYLKYAEAVGLTAGAEAA* | 19 |
| Lyngbya-confervoides-BDU141951_gvnA | MAVEKVNSSSSLAEVVDRILDKGIVVDAWVRVSLVGIELLAIEAR VVIASVETYLKYAEAVGLTAQAAVPAS* | 20 |
| Nostoc-punctiforme-PCC-73102_gvpA | MAVEKVNSSSSLAEVIDRILDKGIVIDAWVRVSLVGIELLSIEARIVI ASVETYLRYAEAVGLTSQAAVPSAA* | 21 |
| Nostoc-sp-PCC-7120_gvpA | MAVEKTNSSSSLAEVIDRILDKGIVVDAWVRVSLVGIELLAIEARIV IASVETYLKYAEAVGLTQSAAMPA* | 22 |
| Microchaete-diplosiphon_gvpA | MAVEKTNSSSSLAEVIDRILDKGIVVDAWVRVSLVGIELLAIEARIV IASVETYLKYAEAVGLTQSAAVPA* | 23 |
| Microcystis-aeruginosa-NIES-843_gvpA1 | MAVEKTNSSSSLAEVIDRILDKGIVIDAWARVSLVGIELLAIEARVV IASVETYLKYAEAVGLTQSAAVPA* | 24 |
| Microcystis-aeruginosa-NIES-843_gvpA2 | MAVEKTNSSSSLAEVIDRILDKGIVIDAWARVSLVGIELLAIEARVV IASVETYLKYAEAVGLTQSAAVPA* | 25 |
| Microcystis-aeruginosa-NIES-843_gvpA3 | MAVEKTNSSSSLAEVIDRILDKGIVIDAWARVSLVGIELLAIEARVV IASVETYLKYAEAVGLTQSAAVPA* | 26 |
| Microcystis-flos-aquae-TF09_gvpA | MAVEKTNSSSSLAEVIDRILDKGIVIDAWARVSLVGIELLAIEARVV IASVETYLKYAEAVGLTQSAAVPA* | 27 |
| Phormidium-tenue-NIES-30_gvpA | MAVEKVNSSSSLAEVVDRILDKGIVIDAWVRVSLVGIELLAIEARV VIASVDTYLKYAEAVGLTAQAAVPAA* | 28 |
| Planktothrix-agardhii_gvpA | MAVEKVNSSSSLAEVIDRILDKGIVIDAWVRVSLVGIELLSIEARIVI ASVETYLKYAEAVGLTAQAAVPSV | 29 |
| Planktothrix-rubescens_gvpA | MAVEKVNSSSSLAEVIDRILDKGIVIDAWVRVSLVGIELLSIEARIVI ASVETYLKYAEAVGLTAQAAVPSV* | 30 |
| Pseudanabaena-galeata-PCC-6901_gvpA | MAVEKVNSSSSLAEVIDRILDKGIVIDAWVRVSLVGIELLSIEARVV IASVETYLKYAEAVGLTASAAVPAA | 31 |
| Stella-vacuolata_gvpA | MAVEKINASSSLAEVVDRILDKGVVVDAWVRVSLVGIELLAVEAR VVVAGVDTYLKYAEAVGLTAGAQTA* | 32 |
| Trichodesmium-erythraeum-IMS101_gvpA3 | MAVEKVNSSSSLAEVIDRILDKGVVVDAWIRLSLVGIELLTIEARIV VASVETYLKYAEAVGLTTLAAAPGEAAA* | 33 |
| Trichodesmium-erythraeum-IMS101_gvpA4 | MAVEKVNSSSSLAEVIDRILDKGVVVDAWVRLSLVGIELLTIEARI VIASVETYLKYAEAVGLTTLAAEPAA* | 34 |
| Tolypothrix-sp.-PCC-7601_gvpA1 | MAVEKTNSSSSLAEVIDRILDKGIVVDAWVRVSLVGIELLAIEARIV IASVETYLKYAEAVGLTQSAAVPA* | 35 |
| Tolypothrix-sp.-PCC-7601_gvpA2 | MAVEKTNSSSSLAEVIDRILDKGIVVDAWVRVSLVGIELLAIEARIV IASVETYLKYAEAVGLTQSAAVPA* | 36 |
| Halo-family-consensus_gvpA | MAQPDSSSLAEVLDRVLDKGVVVDVWARXSLVGIEILTVEARVV AASVDTFLHYAELIAKIEQAELTAGAEA-XPAPEA | 37 |
| Halobacterium-salinarum_gvpA1 | MAQPDSSGLAEVLDRVLDKGVVVDVWARVSLVGIEILTVEARVV AASVDTFLHYAELIAKIEQAELTAGALAAPEA | 38 |
| Halobacterium-salinarum_gvpA2 | MAQPDSSSLAEVLDRVLDKGVVVDVWARISLVGIEILTVEARVVA ASVDTFLHYAELIAKIEQAELTAGAEAEAPEPAPEA | 39 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Halobacterium-salinarum-NRC-1_gvpA1 | MAQPDSSGLAEVLDRVLDKGVVVDVWARVSLVGIEILTVEARVV AASVDTFLHYAELIAKIEQAELTAGALAAPEA* | 40 |
| Halobacterium-salinarum-NRC-1_gvpA2 | MAQPDSSSLAEVLDRVLDKGVVVDVWARISLVGIEILTVEARVVA ASVDTFLHYAEEIAKIEQAELTAGAEAPEPAPEA* | 41 |
| Haloferax-mediterranei-ATCC-33500_gvpA | MVQPDSSSLAEVLDRVLDKGVVVDVWARISLVGIEILTVEARVVA ASVDTFLHYAEEIAKIEQAELTAGAEAAPTPEA* | 42 |
| Halogeometricum-borinquense-DSM-11551_gvpA | MAQPDSSSLAEVLDRVLDKGVVVDVWARVSLVGIEILTVEARVV AASVDTFLHYAEEIAKIEQAELTATAEAAPTPEA* | 43 |
| Halopenitus-persicus-strain-DC30_gvpA | MAQPDSSGLAEVLDRVLDKGVVVDVWARVSLVGIEILTVEARVV AASVDTFLHYAEEIAKIEQAELTAGAEAAPEA | 44 |
| Haloquadratum-walsbyi-C23_gvpA | MAQPDSSSLAEVLDRVLDKGIVVDTFARISLVGIEILTVEARVVVA SVDTFLHYAEEIAKIEQAELTAGAEA* | 45 |
| Halorubrum-vacuolatum-strain-DSM-8800_gvpA | MAQPDSSSLAEVLDRVLDKGVVVDVYARLSLVGIEILTVEARVVA ASVDTFLHYAEEIAKIEQAELTAGAEAAPTPEA* | 46 |
| Halopiger-xanaduensis_gvpA1 | MAQPQRRPDSSSLAEVLDRILDKGVVIDVWARISVVGIELLTIEAR VVVASVDTFLHYAEEIAKIEQATAEGDLEELEELEVEPRPESSPQSA AE* | 47 |
| Natrialba-magadii-ATCC-43099_gvpA | MAQPQRRPDSSSLAEVLDRVLDKGVVIDIWARVSVVGIELLTVEA RVVVASVDTFLHYAEEIAKIEQATAEGDLEDLEELEVEPRPESSPKS ATE* | 48 |
| Natrinema-pellirubrum-DSM-15624_gvpA1 | MAQPQRRPDSSSLAEVLDRVLDKGVVIDVWARVSVVGIELLTIEAR VVVASVDTFLHYAEEIAKIEQATAEGDLELEELEVEPRPESSPKS AE* | 49 |
| Natronobacterium-gregoryi-SP2_gvpA1 | MAQPQRRPDSSSLAEVLDRILDKGVVIDVWARVSVVGIELLTIEAR VVVASVDTFLHYAEEIAKIEQATAEGDLEDLEELEVEPRPESSPQS ATE* | 50 |
| Methanosaeta-thermophila_gvpA1 | MVTSTPDSSSLAEVLDRILDKGIVVDVWARVSLVGIEILTVEARVV VASVDTFLHYSEEMAKIEQAAIAAAPSA* | 51 |
| Methanosaeta-thermophila_gvpA2 | MVTSTPDSSSLAEVLDRILDKGIVVDVWARVSLVGIEILTVEARVV VASVDTFLHYSEEMAKIEQAAIAAAPGVPA* | 52 |
| Methanosarcina-barkeri-3_gvpA1 | mvSQSPDSSSLAEVLDRILDKGIVVDVWARVSLVGIEILAIEARVV VASVDTFLHYAEEITKIEIAAKEEKPAIAA* | 53 |
| Methanosarcina-vacuolata_gvpA1 | mvSQSPDSSSLAEVLDRILDKGIVVDTWARVSLVGIEILAIEARVV VASVDTFLHYAEEITKIEIAAREEKPVIAA* | 54 |
| Methanosarcina-vacuolata_gvpA2 | mvSQSPDCSSLAEVLDRILDKGIVVDTWARVSLVGIEILMEARVV VASVDTFLHYAEEITKIEIAAREEKPVIAA* | 55 |
| Haladaptatus-paucihalophilus-DX253_gvpA | MVQAEPNSSSLADVLDRILDKGVVIDVWARISVVGIEVETVEARV VVASVDTFLHYAKEMAKLERASSEDEIDFEQVEVASPEASTS* | 56 |
| Mega-family-consensus_gvpA | MSIQKSTXSSSLAEVIDRILDKGIVIDAFARVSXVGIEILTIEARVVIA SVDTWERYAEAVGLL-D-VEE-GLP-RX- | 57 |
| Bacillus-megaterium_gvpA | MSIQKSTDSSSLAEVIDRILDKGIVIDAFARVSLVGIEILTIEARVVIA SVDTWLRYAEAVGLLTDKVEEEGLPGRTEERGAGLSF* | 58 |
| Bacillus-megaterium_gvpB | MSIQKSTNSSSLAEVIDRILDKGIVIDAFARVSVVGIEILTIEARVVIA SVDTWLRYAEAVGLLRDDVEENGLPERSNSSEGQPRFSI* | 59 |
| Serratia-family-consensus | MAKVQKSTDSSSLAEVVDRILDKGIVIDAWXKVSLVGIELLSIEAR VVIASVETYLKYAEAIGLTAXAAAPA* | 60 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Burkholderia-sp-Bp5365_gvpA1 | MAKVQKSTDSSSLAEVVDRILDKGIVIDVWAKVSLVGIELLSIEAR VVIASVETYLKYAEAIGLTATAAAPTA* | 61 |
| Desulfobacterium-vacuolatum-DSM-3385_gvpA | MAKVQKTTDSSSLAEVVDRILDKGIVVDAWAKISLVGIELISIEAR VVIASVETYLKYAEAIGLTAAAAPA* | 62 |
| Desulfomonile-tiedjei-DSM-6799_gvpA1 | MAKIAKSTDSSSLAEVVDRILDKGIVIDAWAKVSLVGIELLSVEAR VVIASVETYLKYAEAIGLTASAAAPA* | 63 |
| Isosphaera-pallida-ATCC-43644_gvpA1 | MAKVTKSTDSSSLAEVVDRILDKGIVIDAFAKVSLVGIELLSVEAR VVIASVETYLKYAEAIGLTASAATPA* | 64 |
| Lamprocystis-purpurea-DSM-4197_gvpA1 | MAKVANSTDSSSLAEVVDRILDKGIVIDAWIKVSLVGIELLAIEARI VIASVETYLKYAEAIGLTAPAAAPA* | 65 |
| Lamprocystis-purpurea-DSM-4197_gvpA2 | MAKVANSTDSSSLAEVVDRILDKGIVIDAWLKVSLVGIELLAVEA RVVIASVETYLKYAEAIGLTAPAAAPA* | 66 |
| Legionella-drancourtii-LLAP12_gvpA1 | MAKVQKSTDSSSLAEVIDRILDKGIVIDVWAKVSLVGIELLSIEARV VIASVETYLKYAEAIGLTATASHPA* | 67 |
| Psychromonas-Ingrahamii_gvpA1 | MANVQKTTDSSGLAEVIDRILDKGIVIDAFVKVSLVGIELLSIEARV VIASVETYLKYAEAIGLTASAATPA* | 68 |
| Psychromonas-Ingrahamii_gvpA4 | MANVQKSTDSSGLAEVVDRILEKGIVIDAFVKVSLVGIELLSIEARV VIASVETYLKYAEAIGLTASAATPA* | 69 |
| Serratia-39006_gvpA1 | MAKVQKSTDSSSLAEVVDRILDKGIVIDAWVKVSLVGIELLSIEAR VVIASVETYLKYAEAIGLTASAATPA* | 70 |
| Thiocapsa-rosea-strain-DSM-235-Ga0242571-11_gvpA1 | MAKVANSTDSSSLAEVVDRILDKGIVIDAWVKVSLVGIELLAIEAR VVIASVETYLKYAEAIGLTAPAAAPA* | 71 |
| Other gvpAs | | |
| Bradyrhizobium-oligotrophicum-S58_gvpA1 | MAIEKATASSSLAEVIDRILDKGVVIDAFVRVSLVGIELLSIELRAV VASVETWLKYAEAIGLVAQPMPA* | 72 |
| Desulfotomaculum-acetoxidans-DSM-771_gvpA1 | MAVKHSVASSSLVEVIDRILEKGIVIDAWARVSLVGIELLAIEARV VVASVDTFLKYAEAIGLTKFAAVPA* | 73 |
| Octadecabacter-antarcticus-307_gvpA1 | MAVNKMNSSSSLAEVVDRILDKGVVIDAWVRVSLVGIELIAVEAR VVIAGVDTYLKYAEAVGLTAEA* | 74 |
| Octadecabacter-arcticus-238_gvpA1 | MAVSKMNSSSSLAEVVDRILDKGVVIDAWVRVSLVGIELIAVEAR VVIAGVDTYLKYAEAVGLTAEA* | 75 |
| Pelodictyon-luteolum-DSM-273_gvpA1 | MAVEKTIGSSSLVEVIDRILDKGVVVDAWVRMSLVGIELLAIEARV VVASVETYLKYAEAIGLTAKAA* | 76 |
| Pelodictyon-luteolum-DSM-273_gvpA2 | MAVEKTIGSSSLVEVIDRILDKGVVVDAWVRVSLVGIELLAIEARV VVASVETYLKYAEAIGLTAKAA* | 77 |
| Pelodictyon-phaeo-clathratiforme_gvpA1 | MSVEKTIGSSSLVEVIDRILDKGVVVDAWVRVSLVGIELLAIEARV VVASVETYLKYAEAIGLTAKAA* | 78 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Rhodobacter-capsulatus-SB-1003_gvpA1 | MAIEKSLASASIAEVIDRVLDKGIVVDAFVRISLVGIELLAIELRAV VASVETWLKYAEAIGLTVDPQTP* | 79 |
| Rhodobacter-sphaeroides_gvpA1 gvpF | MAIEKSVASASIAEVIDRILDKGVVIDAFVRVSLVGIELIAIEVRAVV ASIETWLKYAEAVGLTVDPATT* | 80 |
| Anabaena-i-aquae_gvpF | MSIPLYLYGIFPNTIPETLELEGLDKQPVHSQVVDEFCFLYSEARQE KYLASRRNLLTHEKVLEQTMHAGFRVLLPLRFGLVVKDWETIMS QLINPHKDQLNQLFQKLAGKREVSIKIFWDAKAELQTMMESHQDL KQQRDNMEGKKLSMEEVIQIGQLIEINLLARKQAVIEVFSQELNPF AQEIVVSDPMTEEMIYNAAFLIPWESESEFSERVEVIDQKFGDRLRI RYNNFTAPYTFAQLDS* | 81 |
| Ancylobacter aquaticus strain UV5_gvpF | MSATLSAPGTANVAVEATAAADGKYLYGIIEAPAPATFDVPAIGG RGDVVHTIALGRLAAVVSNSPRIDYDNSRRNMLAHTKVLEAVMA RHTLLPVCFGTVGSDAEVIIEKILRERRDELAGLLGQMHGRMELGL KASWREEIIFEEVLAENPAIRKLRDALVGRSPDQSHYERIQLGERIG QALQRKRQDDEERILERVRPFVHKTRLNKLIGDRMVINAAFLVDA AVESRLDASIRAMDEEWGGRLAFKYVGPVPPYNFVTITIHW* | 82 |
| Aphanizomenon flos-aquae NIES-81_gvpF | MNTGLYLYGIFPDPIPETVDLQGLDKQSVHSQVVDGFSFLYSDAC QEKYLASRRNLLTHEKVLEQAMHEGFHVLLPLRFGLVVKDWETI QKQLIEPYKEQLNELFQKLAGQREVSIKILWDSKSELQAMMESNQ DLKQQRDNMEGKKLKMEEIIQIGQLIESNLAARKQTVIQEFFNNLH PLAKEIIESEPMTEEMIYNAAFLIPWETESVFSERVEAIDRKFGDRL RIRYNNFTAPYTFAQLAS* | 83 |
| Aphanothece halophytica (strain PCC 7418)_gvpF | MAEGFYLYGIFPPPGPQTIAVQGLDKQPIFSHTVEGFTFLYSEAQQS RYLASRRNLITHTKVLEEAMEQGFRTLLPLPQFGLVVPDWESVSQD LLQHQSETLQLLFQRLEGKREVSLKIYWETDAELNALLEENPDLK ARRDNLEGKNLSMDEVIQIGQALEQAMERRKQEVITRFEDALIPFA VETQENDVETETMIYNTAFLIPWESEPEFGEAVETVDAEFAPREKI RYNNFTPPYNFVELRE* | 84 |
| Aquabacter spiritensis strain DSM 9035_gvpF | MMQTDTLAPAETVAEGKYLYCLIDAPAPDTFASPGIGGRGDVVHT ITVGRLAAVVSDSPRIEYENSRRNMMAHTKVLEEVMARHTMLPV CFGTVATGPDPISGKILEGRRDELVGLLEQMRGRLELGLKATWRE DVIFAEILQENPAIAKERDSLVGRSPEKSHFERIRLGEMIGQAMERK RRDDEERILERVRPFVHKTKLNKPIGDRMILNAAVEVEAAREAGL DQAVRQMDAEWGARLSFKYVGPVPPYNFVTITIHW* | 85 |
| Bacillus-megaterium_gvpF | MSETNETGIYIFSAIQTDKDEEFGAVEVEGTKAETFLIRYKDAAMV AAEVPMKIYHPNRQNLLMHQNAVAAIMDKNDTVIPISFGNVFKSK EDVKVLLENLYPQFEKLFPAIKGKIEVGLKVIGKKEWLEKKVNEN PELEKVSASVKGKSEAAGYYERIQLGGMAQKMFTSLQKEVKTDV FSPLEEAAEAAKANEPTGETMLLNASFLINREDEAKFDEKVNEAH ENWKDKADPHYSGPWPAYNFVNIRLKVEEK* | 86 |
| Bradyrhizobium oligotrophicum S58_gvpF | MSNQPIYVYGLIRAEDHQPLAVRAVGDSEQPVNIIGSGNVAALVST IDLPEIMPTRRHMLAHTKVLEAAMANGPVLPMRFGIIVPNPATLER VIGFRHQELRARLDEIDGRIEVALKASWDEQFMWRQLASEHPDLA vSGRTMMGRGEQQSYYDRIELGRAIGAALEERRTAARLQLLQTVT PFAVQVKELTPVDDAMFAHLALLVEKGAEPSLYQTVEALERSNDS GLKFRYVAPIPPYNFVAVTLDWEQHEQAPRR* | 87 |
| Burkholderia thailandensis sp. Bp5365 strain MSMB43_gvpF | MNSRNGARYLYAVQHARDVPASLPAGIGGAAVRALTDGDVAAIV SDTGLAKVRPERRHLLAHHTVIQSLAAAGTVLPVAFGTIATSEVAL RRMERKHRNALAGELARLVDHVEMSVRENWDVTDEFRHLIDVRP DLKAARDAMLALGSAVTRDDKIELGSRFERVLNEERARHAALVD EALDACCKEIRRDPPRHETEILHLTCLVRHAELGRFESGVAAASRE LDDSLVLKYSGPCPPHHFVNLNMSL* | 88 |
| Chlorobium luteolum DSM 273_gvpF1 | MERDGKYIYCIIGADCECDFGPIGIGGRGDLVSTIGFEGISMVVSDH PLNRFVVDPDGILAHQRVIEAVMKEHESVIPVRFGTVAATPDEIRN LLDRRYGELSELLERERNKVEFNVTGRWHDMAAIYKEVERTHPEI KEQRARIESMRDGDGEALKQSLILDTGHQIEAALEVMKEEKFDAV ASLFRKTAMASKMNRTTSPDMFMNAAFLIDRGREVEFDGIMEILG QKDADRCDYRYSGPLAIFNFVDLRILPEKWEL* | 89 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Chlorobium luteolum DSM 273_gvpF2 | MAHEAAEQDGLYIYGIINNSGELDFGPIGIGGREERVYAVIHNDIA AVVSRTVVKEFEPRRANMIAHQKVLEAVMVSHAVLPVRFSTVSPG HDDMKVEKILEEDYLREKKELVKMEGKKEMGEKVMANEEKVYE SIITGYDNIRYLRDKLINLPPEKTHYQRVKIGELVAAALEKEVGTY KDAVLDALSPIAEEVKVNDSYGSMMVLNAAFLIRTAREEEFDRAV NALDDRYHDMMTFKYVGTLPPYNFVNISINIKGR* | 90 |
| Chlorobium luteolum DSM 273_gvpF3 | MNQSIYIYGIVNEPALAASFVETDPDIYAVASMGCSAIVENRPAIDL GELDRESLARMLLQHQQTLERLMESGMQLIPLKLGTFVSSAADAA CIIEDGYNLIERIFRETEDAHELEVVVKWSSFADLLQEVVSEGDVQ ELKREVEARQSSSTEDAIAVGRLIKEKIDRRNAALSASVLRQLGER ASQSKRHETMDDEMVLNAAFLVNRGDVDAFVATVEALDSQYLN ALHFRIVGPLPCYSFYTLEVTALFEEFIAEKRAVEGLDARSCEADV KKAYHAKAKVAHPDVHVPAGANNGADFTVLNEAYMTLHDYYS ALRNSASSRHGHEGQDSSSVVFSVKILN* | 91 |
| Dactylococcopsis salina PCC 8305_gvpF | MTEGFYLYGIFPPPGPKTIETQGLDKQPIFSHTVEGFTFLYSEAQQS RYLASRRNLITHTKVLEEAMENGSRTELPLQFGLIVPDWETVVQD LLQHQAESLHFFLEKLEGKREVSLKIYWETNAELNALLEENPALK ARRDNLEGKQLSMDEVIQIGQALEQEMEGRKQDIISRFEEVLIPFAF EIKENDVETETMIYNTAFLINWDAESDFGEQLEAIDAEFSPREKIRY NNFTPPYNFVELRE* | 92 |
| Desulfobacterium vacuolatum_DSM 3385_gvpF | MSKKNLKRNGRYLYAIIEASEEKTFGSIGMDGSDVYLIVEDKTAA VVSDVPNKKIRPQRKNIAAHHAVLNKIMEEITPLPMAFGIIADGEQ AIRKILADNRDVFREQFATVSGKVEMGMRISYDVPNIFEYFISTDSE IRAARDQYFGGNREPSQEAKLELGRMFNRQLNANREEYTNQVIEI LDDYCDDIKENKCRNEQEVTSLACLINRSDQKRFEEGVFESARHFD NNFSFEYNGPWSPHNFVNILIEL* | 93 |
| Desulfomonile tiedjei DSM 6799_gvpF | MEKATIKTTGSNGRYLYAVVPGSQERVYGCLGINGGNVYTIAAKD VAAVVSDVPHQKIRPERRHFAAHQAVEKRVMEDGDELPMSFGIIS QGPKAVRAILSRNNKSVQQQLKRISGKAEMGIKVTWDVPNIFEYFI DVNRELREARNKLVQPNYLPTQQEKIEIGRMFEEILNLERERHTKQ VERVMSKRCSEIKRSKCRTEIEVMNESCLVDRTLESDFEAGVLEAA SHFDDSFAFDFNGPWAPHNFVDLEIDV* | 94 |
| Desulfotomaculum acetoxidans DSM 771_gvpF1 | MSTGRYVYCVINSIEPLTFMSGPVGNEPEGVFTVHYKELAAVVSQ SSEEKYNVCRENTIAHQKVLEEVLVSHPLLPVRFGTVAQNEEIVKK FLLQERYAELRSMEHNVTGKVQMGEKVEWTDMKTVYQEIVEENP QIKNEKKKLESKPAETIHYEMIDLGQMVNQALLRKKEKQKEMVL KPLQKIALETKESFLYGDQMFVNADFLISRSSLDDFNAKVNELGEF FNEQALFKYIGPLPPYNFVTLYVNF* | 95 |
| Desulfotomaculum acetoxidans DSM 771_gvpF2 | MVKNHNTDHLKELYIYGLIGGTPFKDELEKISVIQENTPIYGVWHK NIGFAVSAAPDYPLKDLSKESIIQLFVDHQQVLECLRQKFSLIPVKL GTVLESVTEAAAVLANNEEKFNDLLNYLKDKVELNLSVSWNDLN EVVAKIGEEDEVKKLKQSLLAQEQVSQEDLIKIGKIISFQMQQKKQ AAREYIISELRNLWEDYFINEVVDENSILNLTLLAITGKVDDVNKKI EYLNQIYRDSLDFSLTKSLLPQGFSTVSIKKITMDQLLLAKDILKLP DTASLQDINAARRALLHCYHPDKNDHAAVNKVQEINAAYKLLEE YCQENSSDFNVDLITDYYIMKVIKADKSNVNSMNME* | 96 |
| Dolichospermum circinale_gvpF | MNTDLAHKNFGLYLYGIFPDTIPETLEIKGLDGKSVHSQVVDGFTF LYSQACQEKYLASRRNLLAHERVLEQTMHEGFHVLLPLRFGLVV KDWETIMSQLINPHKEQLHKLFEKLAGQREVSIKILWDAKAELQA MMESNHDLRQQRDNMEGKKLSMEEVIQIGQLIESNLQARKQAVIE VFTRELNPLAQEIVVSEPMTEEMIYNAAFLIPWDSEPLFSERVESID QKFGNRLRIRYNNFTAPYTFALLDS* | 97 |
| Enhydrobacter aerosaccus strain ATCC 27094_gvpF | MNPPEAYIAGRTAAKSVEDRKARPQDLAEGKYVYAIIACDEPREF KNRGIGERGDKVHTINHRQMAAVVSDSPTIDYERSRRNMMAHTV VLEEVMKEFDLLPLRFGTVASSAESVERQLLVPRYGELSAMLEKM RGRSEFGLKAFWHEGVAFGEIVRENARVRKLRDALQGRSLEESYY QRIQLGEEVEKALTAIRARDEELILSRLRPFMRDIRTNKIIISDRMVL NAAFLVERGDVPALDEAIRQLDQEFSERLMFKYVGPVPPYNFVNI AINWER* | 98 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| *Isosphaera pallida* ATCC-43644_gvpF | MRNAPPTRPGSVTPASPGKPVIDGPARYLYAFTHDLPEGPLADLEG LPGARVVVVADGRVAAVVSPCPLGKVRPERQRVAGHHHVLKHL QDTLGKAILPASFGMVADSEEDLRALLRHHSAAIAEGLVRVQGKV EMTVKLRWAPDNVAQAVLGRDPELRQLRDQLYSNGQTPTRDQSL DLGRRFHHALERQRDHYAAYLRAALSPLLSELVEEDLRDERDLVH WACLIENQRRAGFEAALDRLAEELEDDLVLELTGPWPPHHFVDLD LDDDHDDDEEE* | 99 |
| *Legionella drancourtii* LLAP12_gvpF | MDSTSKKPAASNLYLYAIASVNENQEPISFHGIEEQPIDLVPYKDIM LVVSNLSKKKVRPERKNVAVHHAVLNHLMKHNTSMLPIRFGMIA DNRKEVQRLLTINYDMLHTKLKMMAGRVEMGVSLSWDVPNIFEY LLNRHSQLRETRDKLLANPAHEPSRDEKIEIGALFSQILDEEREVYT DTILSLLSPVCCDVVKSTYRNDTEIMNIFCLISAARRDEFEEKIIEAS TILDDNFVIKYTGPWPPHNFSKLNLSLE* | 100 |
| *Lyngbya confervoides* BDU141951_gvpF | MPQLLYLYGIFPAPGPQDLEVQGLDQQPIHTHIIDEFVFLYSVAQQE RYLASRKNLLGHERVLEAAMKVGYRTLLPLQFGLIIETWDRVIKE LITPRGDALKRLFAKLEGRREVSVKLLWGPDAELNQLMEEDAGLR AERDRLEGQQLSMDQIVDIGQAIETAMTERKDDVINAFRQRLNAL AIEVLENDPLTDAMIYNTAYLIPWEDEVKFSQAIEELDEQFEDRLRI RYNNFTAPYNFAQLDQLS* | 101 |
| *Microcystis aeruginosa* NIES-843_gvpF | MTVGLYLYGIFPEPVPDGLVLQGIDNEPVHSEMIEGFSFLYSAAHK EKYLASRRYLICHEKVLETVMEAGFTTLLPLRFGLVIKTWESVTEQ LISPYKTQLKELFAKLSGQREVSIKIFWDNQWELQAALESNPKLKQ ERDAMMGKNLNMEEIIHIGQLIEATVLQRKQDIIQVFRDQLNHRA QEVIESDPMTDDMIYNAAYLIPWEQEPEFSQNVEAIDQQFGDRLRI RYNNLTAPYTFAQLV* | 102 |
| *Nostoc punctiforme* ATCC 29133_gvpF | MSFYIYGILTLPAPQNLNLEGLDRQPVQIKILDDFAVIYSEAQQERY LASRRNLLSHEKVLEEIMQAGDRYLLPVQFGLLVSSWETVSQQLIR PHQEELTQLLAKLSGCREVSVKVFWDTEAEIQGLLAEHPNLKVE DKLVGQPLSMERVIQIGQVIEQGMSDRKQGIIDVFKGTLNSIAIEVV ENTPQVDTMIYNSAYLIPWEAESQFSEHVESLDRQFENRLRIRYNN FTAPYNFARLRLTTSN* | 103 |
| *Nostoc* sp. PCC 7120_gvpF | MSSGLYLYGIFPDPIPETVTLQGLDSQLVYSQIIDGFTFLYSEAKQE KYLASRRNLISHEKVLEQAMHAGFRTLLPLRFGLVVKNWETVVT QLLQPYKAQLRELFQKLAGRREVSVKIFWDSKAELQAMMDSHQD LKQKRDQMEGKALSMEEVIHIGQLIESNLLSRKESIIQVFFDELKPL ADEVIESDPMTEDMIYNAAFLIPWENESIFSQQVESIDHKFDERLRI RYNNFTAPYTFAQIS* | 104 |
| *Octadecabacter antarcticus* 307_gvpF1 | MKREVVRMTDENTINSKYLYAIIKCREQREFIARGIGERGDAVHTI AYKGLAAVVSDSPVMEYDQSRRNMMAHTAVLEELMEEFTLLPVR FNTVAPEAGAIEERLLVPRHEEFTQLLGQIDKRVELGIKAFWHDG MIFEEVLRENDSIRKMRDALEGKSVDGSYYERIQLGEKIEQAMIKK RVEDEEIILSRIRQHVHKSRSNKTIGDRMVLNGAFLVDANKESDFD KAVQLLDQDLGNRLMFKYVGPVPPYNFVNIVVNWGVV* | 105 |
| *Octadecabacter antarcticus* 307_gvpF2 | MTVVAEENMTGSVGLYVCAIVAEWESNSALIKCANEAQGEIQLIG QGGITAVVMVPPEDQPVSRDRQELVRQLLVHQQLVERFTEIAPVL PVKFGTLAPDRESVELGLERGREKFFTAFGGLSGKTQFEITVTWDV ADVFAKIAKLPAVVKLKVDLVATSESDRPINLDRVGRLVKETLDH QRAQTGKVLLDALLPLGVDSIVNPILNDSIVLNLALLVDTDQADAL DRCLDELDSTFHGALSFRCVGPMPPHSFATVEINYIEPTQVSHACC VLELDAAHNFEEIRSAYHRLARQTQQDIAPDVVVDNKSSSVGIAV LNDAYKTLLSFVDAGGPVVVSVQRQEDAYATDIPSSGG* | 106 |
| *Octadecabacter arcticus* 238_gvpF1 | MTDEKKVNSKYLYAIIQCREPRELKARGIGERGDVVHTVVHKGLA AVVSDSPVMEYDQSRRNMMAHTAVLEELMEEFTLLPVRFNTVAP EAVAIEERLLVPRHDEFTQLLGQIDKRVELGLKAFWHDGMIFGEV LRENDSIRKMRDSLKGQSVDGSYYERIQLGEKIEKALTEKRLEDEE MILSRIRPHVHKSRSNKTIGDRMVLNGAFLVDAEKESKFDEAVQSL DQDLSDRLMFKYVGPVPPYNFVNIVVNWGES* | 107 |
| *Octadecabacter arcticus* 238_gvpF2 | MRAQKVIPAAEENISGNVGLYVCAIVAERVSCSALIQCANDAPGEI QLIGHGDFTAVVMVPEKDQLVSPDRKELMQQLLVHQQLIEKFMEI APVLPVKFATLAPNRESVELGLEVGSEKFSAAFNSLSGKVQFEVIV TWDVALVFALIAKEPAVAKLKVDLAAMPESYGSVSLEQLGKLVK ETLELRRAETGKVLLDALVQVGVDNVVNSILNDSIILNLALLVEAK RADAFDRCLDELDSTYHGALTFRCVGPLPPHSFATVEITYLEPAKV TEACDILELDVARSTEEVRSAYHRLARKSHPDIVPDVAVGETASVS MAVLTDAYKTLLSFVGAGGSVVVSVQRQEASYAADIISSAG* | 108 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Pelodictyon phaeo-clathratiforme_gvpF1 | MDIETTKEGRYIYGIIRNSEFIDFGQIGIGKRNDRVYGVIYKDICAV VSSTPIIQYEARRANMIAHQKVLEEVMKRFNVLPVRFSTISPHDND DAIIKILITDYSRFDELLIKMKGKKELGLKVMADETRIYENIIQKYD NIRSLRDKLLNQPADKIHYQRVKIGEMVADALKKEIESYKQQILDI LSPIAEDIKITDNYGNLMILNAAFLIKEVKESEFDDSVNKLDEKYGN IMTFKYVGTLPPYNFVNLSINTKGV* | 109 |
| Pelodictyon phaeo-clathratiforme_gvpF2 | MEKDGKYVYCIIASTYECNFGAIGIGGRGDLVNTIGFQGLSMVVSD HPLNHFVLNPDNILAHQRVIEVVMSQFNSVIPVRFGTVAATPDEIR NLLDRRYGELSELLERFENKVEYNLKASWRCMIDIYKEIDKEHVE LKQLRREIEGLKDEEKRKLLIVEAGHIIENELQKKKEVEAYEIVTYL RKTVVAHKHNKTTGEAMFMNTAFLLNKGREVEFDNIMNDLGEQ YKDRSDYYYTGPLPIFNFIDLRILPEKWEL* | 110 |
| Pelodictyon phaeo-clathratiforme_gvpF3 | MDRQGIYIYGFIPNHYLTDIKTILIESGIYSIEYGSIAALVSDTMVDDI EYLNREDLAYLLVDHQKKIELIMSTGCSTIIPMQLGTIVNSGNDVIK IVKNGLRIIINKTFDDIADIQEFDLVVMWNNFPDLIKKISDTPQIRIMK EEIANKGSYDQADSINIGKIIKKKIDEKNSKVNLDIMNSLSSLCICVK KHESMNDEMPLNSAFLIKKDKENSFIEMVNQLDIKYENLLRYKIV GPLPCYSFYTLESKLLNKKEIEKAEKILGIDAYKSESDIKKAYRAKA AHAHPDKNNTISAIDNDDFIEINKAYQILLEYSSVFKDSPDHKPDEP FYLVKIKK* | 111 |
| Phormidium tenue NIES-30_gvpF | MADRYYLYGIFPAPGPAELPLMGLDEQVVQAQQLGDFTFLYSLAC QKRYLSSRKNLLGHEKVLEAAMEQGHRTLLPLQFGLIVESWNQV QEDLVTPYAEDLTQLFGRLNGCREVSIKVQWEPSTELEMMMAEN ADLRAQRDQLEGTQLGMEQVIFIGQQIESALEERKQGIVDQFRQAL SPLAKDVLENAPQTDVMIYNAAFLIPWESEAEFSQAVDAIDSTFGD RLRIRYNNFTAPYNFAQLN* | 112 |
| Planktothrix agardhii str. 7805_gvpF | MGNGLYLYGILPTNRVRPLALHGLDKPIQTHPVDEFSFLYSETQQ ERYLASRRNLLGHEDVLEKVMQHGYRSVLPLQFGLIVKDWDHVK AQLIIPYQDRLKELFHKLEGKREVGVKIFWEETEELDLLMTENQEL REKRDSLEGKRLSMDEIIGIGQEIERAMQDRQQGIIDKFQQILNPLA QEIVENDNLTSAMIYNAAYLIPWDIEPQFGDKIEELDHHFNNRLRIR YNNFTAPFNFAQLNP* | 113 |
| Psychromonas ingrahamii 37_gvpF | MAENKKKVRKSSSKVIAKPKVIYAITAGGLQDLGNLVGINKSDIYT IEKESISFVVSDLSPSSPRPRPDRRNIMAHNEILKQLMSKTSVLPVRF GTVATGERAVNRFCSQYNAQLLEQLDRVQDRVEMGIKVTWNVP NIYDYFVDNHSELREERDRVYDGNKNPRRDDRINLGHMYDALVT EARLSHQTDLEEIILPGCDEIHSIPPKDEKVVVNLACLVQRADLEVF EERVVEAGKTLDNTYDIELNGPWAPHNFVELDLKTMTGRR* | 114 |
| Serratia sp. ATCC 39006_gvpF | MMSIDKSRNHRAKVLYALCVSDDSTPNYKIRGLEAAPVYSIDQDG LRAVVSDTLSTRLRPERRNITAHQAVLHKLTEEGTVLPMRFGVIAR NAEAVKNLLVANQDTIREHFERLDGCVEMGLRVSWDVTNIYEYF VATYPVLSETRDEIWNGNSNANNHREEKIRLGNLYESLRSGDRKE STEKVKEVLLDYCEEIIENPVKKEKDVMNLACLVARERMDEFAKG VFEASKLFDNVYLFDYTGPWAPHNFVTLDLHAPTAKKKTLTRAG TLSD* | 115 |
| Stella vacuolata_ATCC-43931_gvpF | MQTEALAPAAVAAEGKYLYCIIDAPAPATFASPGIGGRGDVVHTL AVGRLAAVVSDTPRIEYENSRRNMMAHTKVLEEVMAHHTLLPVC FGTVGSGDDVIAEKILEGRREELSRLLEEMRGRVELGLKATWREE VIFAEVLDEDPAVRKLRDSLVGRSPEKSHFERIRLGELIGQALLRKR RDEEERILDRVRPFVRKTKLNKPIGDRMILNAAFLVETAREAALDQ SVREMDADWGARLSFKYVGPVPPYNFVTITIHW* | 116 |
| Thiocapsa rosea strain DSM 235 Ga0242571_11_gvpF | MQQAKRQDVAAGRYIYAIIPDRGDHSLGRIGLDESEVYTIGDGRV AAVVSDLSGGRIRPQRRNMAAHQEVLKQVLREVSPLPAAFGLMA DDEAAIIRILKDNQDAFLNQLERVDGSLEMGLRMSWDVPNIFEYF VGAHPELQELRDDFFRDGSNLTQDQMITLGRSFERLLEQDREEYTE QVESVMRSCCREIKRNKCRTEKEVLHLACLVDRDAAGRFEQVVL QAARPFDNNYAFDFNGPWAPHNFVEMDIHV* | 117 |
| Tolypothrix sp. PCC 7601_gvpF | MDAGLYLYGIFSDPIPPTVSLKGLDSQPVYSQVIEGFTFLYSDAKQE KYLASRRNLISHEKVLEQAMQEGFRTLLPRFGLVVKNWETVISQ LIQPCERQLRDLFQKLAGKREVSVKILWDTKAELQAMMQSNPDL KQKRDQMEGKNLSMEEVIEIGQLIESNLQQRKEAVIKTFFDELKPL AEEVVESEPMMEEMIYNAAFLIPWDQEALFSQRVEAIDKKFGDRL RIRYNNFTAPYTFAQIS* | 118 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Trichodesmium erythraeum IMS101_gvpF | MEFGFYVYGLIQEKGKMDESKDESKNGLKGSNESKDELKGLDKE DVKIQDVDEFAVLYSIAKKERYLASRRNLITHEKVLESAMEAGYR NLLPMQFGLVVSEWEKFSQDFTKPCEQQIHDLFTKLKNNREVGIKI YWEPDAELEKLLENDKDLKEERDSLKDKKLTMDQVIDIGQKIEQG MNERKQNIIEIFQETLNKMAIEVIENEVQTEKMIYNAAYLIPWDQE EDFGEKVETIDSKLCERGNFTIRYNSFTAPYNFARIRQQD* | 119 | gvpF/L

| Species, protein | Amino acid sequence | SEQ ID NO.: |
|---|---|---|
| Ancylobacter aquaticus strain UV5_gvpFL1 | MTDLLVFAVVPADRFDPAILAEGDGLPPGLRAIAAGPLAAVVGAA PEGGLKGRERSALLPWLLASQKVMERLLANAPVLPVALGTVVED EGRVRHMLDAGAAILGEGFQAVGDGIEMNLSVLWHLDTVVARLL PGVAPELRQAAAGGDAIERQALGVVLAGLVSAERRRARARVIEAL QAVTRDFAIGEPTEPGGVVNLALLVDRAAEEALGAALEALDAEFD GALTFRLVGPLPPYSFASVQVHLSPAAAVCGARAALGVEPDASPE TVKAAYRRAARETHPDLVPMGGEDEEAPEATADETSRFVVLSDA YRVLEGEHAPVSLRRLDSVLTE* | 120 |
| Ancylobacter aquaticus strain UV5_gvpFL2 | MLYVYAITADYAAGANHLLPAKGIVPGVPVQRFGTGALGAVASP VPVTVFGKEALHALLDDADWTRARILAHQRVVSSLLPLATVLPLK FGTLVAGEASLAAALTSQHDALDATVARLRGAREWGVKLFFEAP TRTIRAEEPVGAGAGLAFFRRKKEEQETRAAAEAALDRCVAASHR RLASHARAAVANPLQPPELHGHPGTMGLNGAYLVAAENEAAWR VCFSELEQAYAALGARYVRTGPWAAYNFTGGGLV* | 121 |
| Aquabacter spiritensis strain DSM 9035_ppFL1 | MSGLLVFAIVPADRIEPGLLAPAEGLPPGLETVVAAGFAAIVGTAP EGGLKGRDRGSLLPWLLASQKVIERLMARGPVLPAALGSVLEDES RVRHMLVCGQAALAAAFETLNGCWQTDLSVRWDLSRTVAHLMT ELPPGLRAAAETGDETARRSLGAALAGLVAGERRRIQSRIGAVLG AVARDLIVSDPVEPEGVVGVALLVDAPASAQVDAALDRLDGEFE GRLTFRLVGPLAPYSFATVQIHLGPAAGLAGAHAELGLEAGAPLE AVKAAYHRLIVGLHPDLVPHGSPGDDADDAASGKGGRAARFAAV TAAYRTLQAEHAPVSLRRQDGLSPG* | 122 |
| Aquabacter spiritensis strain DSM 9035_gvpFL2 | MLYVYAITADHPGPHDAGSLPGEGIVPGAPVRLLPFGDLAAAVSP VSAVDFGPEALPARLQDVDWTGQRVLAHQRVVDSLVDVATVLP MKFCTLFSGAAALRAALADNRAALEATVVRLRGAREWGVKLFW EAPPAEPAPVERGPGAGAAFFQRKRDAQRLRAEAEAALAHGVAE SHRRLAARARAAVANPVQPAAVHRRRGEMALNGAYLVPRADEA AWRESLAELERTYAGAGIRYELTGPWGPYNFTGGGLAGS* | 123 |
| Bradyrhizobium oligotrophicum S58_gvpFL1 | MTMNLVGITTPDVAGAIAAAGGRLADVETRAVEAGGLVALLALS KAPFWHVLRRSRTALRSMLTAQRILEAAAVYGPLLPARPGTLIRN DAEACMLLRSQCRHLAEGLRLHGTSRQYQITISWDPVAALAARRD HQDLVEAAAASADGAADKAASMIQRFMSDQQARFEAEAMRALA AVAEDVITLPVNQPDMLMNAVVLLAPGAEPELERVLEALDRGLR GKNLIRLIGPLPPVSFAAVSIERPGRQRIAAARRLLGIGEATRTCDLR RAYLDKAHAHHPDTGGHAADASIVGAAAEAFRLLARVAEARASA GQDDVILVDIRRQDQQRSLST* | 124 |
| Bradyrhizobium oligotrophicum S58_gvpFL2 | MSKANLGIGLVHGVVTAQSAALLPQIVDAFDATEIIVVNTEQQALL ISDIPQYLRGHVEADTLFSDPARISTLAMKHHRILQAAAVVTDVVP VRLGTLVRGPSGARDLLNREAVRFAGHLVTIHNALEFSVRILPTEQ PSRRVARPVPSSGRDYLRIRRDERCGQRPAVVDITLQELASRAVAI RERQSASRSGGRTPALAEAAFLVDRHALAAFDDCAGRIERQIAEN GLALDIFGPWPAYSFVDGARENLG* | 125 |
| Bradyrhizobium oligotrophicum S58_gvpFL3 | MSSPRLIGLLAADDVPADLADQIMSCGPVAAAIRFAPAAASSSESL DHHAAVVAWCRRAAFLPSRAGIPISPELLQSIARSAWYHRSTIEHIE GRVEISVELERRDGVRDGGIDGGGRAYLRATAHDLRACEVGVAT AANLLAMYSERADADLIARTAPLPAIRLRASVLVRRAVAPRLARQ FDSMLSAISDRLVCRVTGPWPPYSFSTIREPS* | 126 |
| Burkholderia thailandensis sp. Bp5365 strain MSMB43_gvpFL | MVWLTYAVLTPKRSITLPPGVAGARLEIVDGAHLRTIVSEHPRAPS ATIPSALDFGQTVAALFRHGAIVPMRFPTCLDSKQAVRDWLDDES DMYRDLLQRIDGCVEMGLRFRLPEAPRAQPRPQAGGPGHAYLAA RGAPNSVARSHGERIAAVLRNLYRDWRFDGLVEGFVSLSFLVRQT TLDDFVDRCRQAARETAFPLYMSGPWPPYSFATDERSSAPEPHRA LRLMRRPSTAVSISANVAAPEKKDSAR* | 127 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| *Desulfobacterium vacuolatum*-DSM 3385_gvpFL | MTLHLLYCVFSSGEMEKTRKLVPPGIDGEPVHEICSNKISGVVSTL GKPPDTHVKSLLAYHGVIDSYHQNRTVIPMRFAAVFRTYAHMITA LNNNEKSYLLQLKRLHDCTEMCVRFISNSPCCVKKKEPAISPKKIS GTTFLQQRKAMYEQQNRLPPEIHEKTRDILQHFRGLYMEFKQESQ PLEKDCPSLSLQGAEKTDGNALLISLFFLISKKNISLFRSRFQNICGS SSGRHMMNGPWPPFNFINTESNLTDPS* | 128 |
| *Desulfomonile tiedjei* DSM 6799_gvpFL | MLGSLAAIQFLSISSYGADEMKFLMYCIFTENSIEPPHSLVGVNRSP VRIISCDGLAAAVSVITQKEIPRDPATGLDYHKVIQWFHERIGVIPL RLGTCLGHESDVVQLLHSHGARYKSLLKELDGCVEMGIRVIHDRP GPQELASKSPFISRFNGTESGTDYLMRRKVLFDADEFAISRNREIVE RYHSPFTGLYVSFKAQTSKFSPLGTDRNSVLTSLYFLIPRQSADSFR AIYGDLRSGLHERIMLSGPWPPYNFVLPEDCL* | 129 |
| *Enhydrobacter aerosaccus* strain ATCC 27094_gvpFL | MEGHRIYIYGIVRDAADGGPAPVPPVAGLDGGALRAIAGYGLAAI ASAVDLSKAGIPFEEQLKDPDRATALVLEHHRVLQQAIDAQTVLP MRFGALFQDDRGVTDALEKNRCGLMDALGRIDGAREWGVKIFCD RAVAARQLSATSAVVQAAEKELSGLAEGRAFFLRRRLERLRTEET DRAVAHEVDSRQALCELARASAPLKLQPAAVHGRGEDMVVNG AFLVPRSGEERFLSRLEVVVQSRSDLGLHYEVTGPWPPFSFVDGQL EGGGDACPDGA* | 130 |
| *Octadecabacter antarcticus* 307_gvpFL | MRSATSIVYAYGVLTNCSDIALDMPRSDLAGLVKNGPLRILPFGNI AAVVCDFVLPNGSDLETLLEDSRSAERLILNHHQVLSYIVSQHTILP LRFGAAFTEDAGVIAALGGRCSELQKALGRIDGALEWGVKTFCDR KLLKQRVRGTGSEISDLESEIAKQGEGKAFFLRRRKERLILEEVELI LEQCVVGTQEQLEPSVIEEALVKLQPPTVHGHEHDMLSNISYLIAR GTEDAFMQSLEDLRLAHAPYGLEYQMNGPWPAYSFSDQQLEGGV NDQ* | 131 |
| *Octadecabacter arcticus* 238_gvpFL | MSSATSIVYVYGVLTNCSDLVLDFPPGDLAGIVESGPLRILPFGDIG ALVCDFILPDGSDLKTILEDSRSAERMILNHHLVLADMVSRYTILPL RFGAVFAEDAGVIAALGGRYSTLQKELDRIDGAIEWGVKSFCNRK MFSECVAETVSEISVLEKEIADQGEGKAFFLRRRIQRLILDEVEKTL EQCLVGAQDQLKSRAIEETLVKLQPPTVHGHKHEMVSNRSYLIAR GAEDAFMQSLDDLRVVYAPFGFDYQINGPWPAYSFSDQQLGGGV NDK* | 132 |
| *Rhodobacter capsulatus* SB 1003_gvpFL1 | MGHYLYGLLAPPARGTLAQMQAAAAGVTSLGGPVALSAVEGML LVHCPCDLAEISQTRRNMLAHTRMLEALMPLATCLPVRFGVIAQD LAEVARMIHERRAELVGHAQRLLDPVEIGLRVRFPRDRALAQLMA ETPDFVAERDRLMGQGAGAHFARADFGRRLAEALDARRTRDQKR LLAALRPHVRDHVLRAPEEDVEVLRAEFLIPAAGVDAFSRIAHDLA AALGFAGAAEPELQVIGPAPPYHFLSLSLAFDNTSEAA* | 133 |
| *Rhodobacter capsulatus* SB 1003_gvpFL2 | MAHEIIAILPCEAAQLPSGLTGVVGRGATAVLAPAPGWAERLTGG PKQTAVRHHSRLEALMAMGSVLPFAAGIACTPEEAALLLRLDAPLI ARLAAEIGPRRHFQLALDWDESRVLAAFRDSPELAPLFSGAAVTPE ALRQAITALADRLSATALRLLDPVAEDPVEQPRAPGCLLNLVFLLR PEDEPRLDAALQAIDALWSEGLRLRLIGPSAPISHALVDIDRADVA ALAAAADLLKVAPEAGPEAVTEAAKAALRSPDLAANAAEQIRAA ARLLLRAGDIAALGLSGAATLPHLVHLRPGGRKSGLTSSGEAA* | 134 |
| *Rhodobacter capsulatus* SB 1003_gvpFL3 | MTGLALHGFVSPDGWSAAAAPPARCAVVLGGVAALVSEAGDAL DTPETAQAAALAHHALISAWHRRGPVLPVRLGTVFSSQAALQTAL APKAAQLRAALDALADKEEMVLTIVPAARPPDLPPPAATGADWL RARKAVRDRGQARQTDRQQTLAGLQDALRAQGVASLAAPAPRE GGSRWHLLIARDDGAGLDRWLAAQADRFDAAGLDLTLDGPWPP YRFAAEILEALDG* | 135 |
| *Rhodobacter capsulatus* SB 1003_gvpFL4 | MSEPRISGLAPWRADLPDVIGCHGGWVLMGAAADETPEARLRRQ VGWCRAAVDVLPLSPRLAPTRAEAERLVATRGPDLERAHRHIRGR LQVIVQLEMCRTDLGLVRREISGGRSWLQDRAERATREARANADF EAQVRRVVRALFPREGQVVTLAPSGTAGQLRLRRAVLVPRAGLQ AFAAALSADLRDRGRGGLWDVIAPLPPLAFAALEAGPGGAVT* | 136 |
| *Rhodobacter sphaeroides* 2.4.1_gvpFL1 | MIYLYGLLEEPASGHEVLAGMAGVTGPIALARLPGGILIYSSATEA DILPRRRLLLAHTRVLEAAAWFGNLLPMRFGMMASTLAEVAAML ASRLTELCAAFDVRGRVELGLRLSFPREPALAATLATAPDLAAER ARLLALRRPDPMAQAEFGRRLAERLDARRGETQRLLFQSLRPLWV DHRLRVPDSDVQVIAVDVLVEDGAQDRLAAALVKAAADCSFAPT ALPSVRVIGPVPLFNFVDLVLSPRREEVA* | 137 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Rhodobacter sphaeroides 2.4.1_gvpFL2 | MRLREVVAVLEGHPPSVLPEGTEAICEAGLTAILGMPPGLLSGRRA LLEHAACRQAVLERLMAFGTVLPVLTGNCLTPAEAAAALAANSP RLRQELRRLAGRVQFQVLVQWHAALVPKRTDPDETAEDLRLRFT HRIADALARVAERHVNLPLREDMLANQALLLLQTRTDDLDRSLEQ IDALWTEGLRIRRIGPSPPVSFASLNFRRVSSAAIRRARHRFDLEGP VDPIRLRALRRDLLLRASEAERAEILAAAAVLDLLTRCAASGGDLH LVRIWSEGQAVPSDLEDAA* | 138 |
| Rhodobacter sphaeroides 2.4.1_gvpFL3 | MSGLLLLLGVVSGLGISPAITSPHLRLDGDGYAAILLSLDRLPPDPAS PDWAVQAALAQNAILSAYAATEDVLPVALGAAFTGIAAVKRHLD AERATLDAGMERLAGRAEYVAQLIAEQVADGAAPAPASGSAFLK ARSARHEQRRHLARERTGFARATAEELASLSCSASARPLKPDGPLL DLSLLVARDRVPGLLEAAEASSRAGSRLALSVRLIGPCAPFSFLPET RGHD* | 139 |
| Rhodobacter sphaeroides 2.4.1_gvpFL4 | MAGDARSRVRLHLAAMRDCETFLPFPPAATIAVDEAIAWCGRRTN ALAELIDRFSRQRQLTVSARLIAPLLPDAAASGAGWLRARRDASA HQARLRTVLMQIMSLLGEVRCIPGRLQDEVQVNLLVPAAETHPVL HELRERLRVGDALWSACTVTGPWPPYAFISWETA* | 140 |
| Rhodococcus hoagii 103S_gvpFL1 | MSEQESAPDGGGPVVYVYGLVPADVEVKEDATGIGSPPRPLKIVH HEDVAALVSEIDPDTPLGSSDDLRAHAAVLDSTATVAPVLPLRFG AVLTDTDAVVAELLEPYRDEFHEALEQLEGKVEFVVKGKYVEDAI LREILADDPEAARLRDVVREQPEDTTRDERLALGERISQALTAKRE QDTGRIVEALQPAATAVAPREPTDDELAGSVAVLISADGVDELDK AVARLIDDWQGRVEVTVTGPLAAYDFVKTRAPGT* | 141 |
| Rhodococcus hoagii 103S_gvpFL2 | MTPDDGVWVYAVTGDGSFPGGISGIRGVAGEELRTVTDSGFTAVV GTVRLDTFGEEALRRNLEDLDWLADTARRHDAVVAAICAGGATV PLRLATVYFDDDRVRTMLRDNAEQLGEALQQIADRSEWGVRAYL ERPRSEPRDAREKTGRPSGTAYLMQRRAQVAAREQAESAAGRRA DEIFAELARWAVAGVRQPPSPPDLAGRRSQEILNTSFLVDNGRHRE FVTAVEELDARLSDVDLVLTGPWPPYSFTSVEASAR* | 142 |
| Serratia sp. ATCC 39006_gvpFL | MSLLLYGIVAEDTQLALEPDGSPHAGEEPMQLVKAATLAALVKPC EADVSREPAAALAFGQQIMHVHQQTTIIPIRYGCVLADEDAVTQH LLNHEAHYQTQLVELENCDEMGIRLSLASAEDNAVTTPQASGLDY LRSRKLAYAVPEHAERQAALLNNAFTGLYRRHCAEISMFNGQRTY LLSYLVPRTGLQAFRDQFNTLANNMTDIGVISGPWPPYNFAS* | 143 |
| Stella vacuolata- ATCC- 43931_gvpFL1 | MSGLLVFAIVPADGIEPGILAPREELPANLRAVAADGFAAVVGAAP EGGLKGRDRSVLLPRLLASQKVIERLMARGPVLPVTLGTVLEDEA RVRHMLAAGAPMLEAAFGTLGDCWQMDLSVRWDLNQVVARLM GEVPGDVRAAAGSGDEAARRLALGEALAGLAAGERRRVQSRLAA ALRDVARDLIVSEPVEPESVVDIAILVERPALAEVEAALDRLDAEF EGRLKFRLVGPLAPHSFATVQVHLAPEAALAGACAELGVERGAGL QDVKVAYHRALVRFHPDLAPHGDDGGPEDEHDGGEGRASRLLTV TAAYRALQAEHAPISLRRQDGIAVNQEQDASAAMGQQRGIVPGRE LQALRM* | 144 |
| Stella vacuolata- ATCC- 43931_gvpFL2 | MLYVYAIAADHPDPDNAMFGGEGIVPDAPVRLLQLGDLAVAASL vSAADFAADALRAHLEDARWTALRVLAHQRVVDSLLPHATVLP MKFCTLFSGEAALKQALAHNRAALQATVERLRGAREWGVKLYW EAPRNPAPPSAGQGEAGAGAAFFQRKRDQQRQRAEAEAAVARCV AASHRRLADAARAAVANPVQPPAVHRQPGEMALNGAYLVARAA EPAWREVLAELERTHADGGIRYELTGPWGPYNFTGSGLVGS* | 145 |
| Thiocapsa rosea strain DSM 235 Ga0242571- 11_gvpFL | MSDRPRPMLHCILRSPPGSIARAEAGLRWIERDGLAALVADREPSE IAGASSVGLQRYADIVAEIHACAAVIPVRFGCLLAGDEAVGKLLHR SRDRLHGLLDQVGDCLEFGIRLLLPADAPAATDDDAAPRLHANAP SDPRADPDMGPGLSHLLAIRHRLDVEASLAARAREAREVIKGRVA GRFREVREELGQIDGRSLLSLYFLVPREQGEHFVECLRQDASSLRG TGLLTGPWPPYNFVGAIDDDIRSLD* | 146 |
| gvpG |
| Anabaena-flos- aquae_gvpG | MLTKLLLLPIMGPLNGVVWIAEQIQERTNTEFDAQENLHKQLLSL QLSFDIGEIGEEEFEIQEEEILLKIQALEEEEARLELEAEQEEARLELEA EQEDFEYPPQFTAEVNKDQHLVLLP* | 147 |
| Bacillus- megaterium_gvpG | VLHKLVTAPINLVVKIGEKVQEEADKQLYDLPTIQQKLIQLQMMF ELGEIPEEAFQEKEDELLMRYEIAKRREIEQWEELTQKRNEES* | 148 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
| --- | --- | --- |
| Ancylobacter aquaticus strain UV5_gvpG | MGMLTDVVFAPAVGPLKGVLWLARIIAEQAERTLYDEGVIRAALL DLEQQLEAGEIDEDAYETQETVLLERLKIARERMRSGL* | 149 |
| Aphanizomenon flos-aquae NIES-81_gvpG | MLTKLLLLPIMGPLNGLVWIGEQIQERTNTEFDAQENLHKQLLNL QLSFDIGEISEEDFEIQEEELLLKIQALEEEARLELELAEEEARLELEL EQEEEEDFVVKPQLTTEIDRDKDLVLLP* | 150 |
| Aphanothece halophytica (strain PCC 7418)_gvpG | MVFKLLLLPITGPIEGVTWLGEQILERANQELDEKENLNKRLLSLQ LSLDLGEISEEEYDEQEEEILLAMQAMEDEENNQAEEETD* | 151 |
| Aquabacter spiritensis strain DSM 9035_gvpG | MSLVTDVLFAPAVGPLKGVLWLARLIAEQAERTLYDEDVLRAAL LDLEQRFEAGEISEADYETEEDILLARLKIARERMRSGL* | 152 |
| Bradyrhizobium oligotrophicum S58_gvpG | MLFQILTSPVSGPFRMVSWIGGAIRDAVDTKMNDPAEIKRALAAL EQQLEAGSLSEQDYERMEMELIERLQSSLRHGSGNGG* | 153 |
| Burkholderia thailandensis sp. Bp5365 strain MSMB43_gvpG | MFILDNLLAAPIKGMFWIFEEIAQAAEEETIADIEMIKAALVELYRE LESGQIDETEFETRERALLDRLDSLETS* | 154 |
| Chlorobium luteolum DSM 273_gvpG | MFILDDDILLAPLSGMVFLGRKINEIVQNEMSDEGAVKEQLMKLQF RFEMDELSEEEYDRLEDELLSTLAEIRAQKENR* | 155 |
| Dactylococcopsis salina PCC 8305_gvpG | MVFKLELLPITGPIEGITWEGEQILERADQELDSKENLNKRELSEQL SLDLGEISEEEYDEQEEEILLAMQAMEDEENEEEES* | 156 |
| Desulfobacterium vacuolatum_DSM 3385_gvpG | MFLVDDILFFPAKSLVWVFRELHNAVQQEKTNESDALTTELSELY MMLETGKITEEEFDEREEQILDRLDEIQERDQ* | 157 |
| Desulfomonile tiedjei DSM 6799_gvpG | MERYTMFLEDDILFLPMNGVLWICNEIHDAAEQELHNESDAITAQ LQKLYTLLEAGDIGESEFDVLEAELLDRLDAIQERGALLEA* | 158 |
| Desulfotomaculum acetoxidans_DSM 771_gvpG | MEGKELLSPILGPVMGVKFIAEKIKQQADQELYDKSKIKQDLMEL QIKLELEEITEEYYLQREEELLVRLDELASMETEEEEV* | 159 |
| Dolichospermum circinale_gvpG | METQLELLPIMGPLNGVVWIAEQIQERTNTEFDAQENLHKQLLSL QLSFDIGEISEEEFEIQEEEILLKIQALEEEARLELEAEQEEARLELEA EQEQARLELEAEQEELENQPQLTPKIDTYRHLVKL* | 160 |
| Enhydrobacter aerosaccus strain ATCC 27094_gvpG | MGMLARLLTLPVSAPVGGVLWIARKIEEEANAERWDRNKITGALS ELELELDLGAIDVEEYDAREAVELQKLKELQEVEND* | 161 |
| Isosphaera pallida_ATCC-43644_gvpG | MFLVDDILLAPAHSLMFLLREIHQAALEELRRDAQKVREELAECY RALETGALTDEEFASLETDLLDRLDALEELARFNSDEDDDPEDED WDVEDDDPAEAVW* | 162 |
| Legionella drancourtii LLAP12_gvpG | MLLLGSILMAPVHGLMAIFEKIKEAVDEEKQHDIERIKSELMALYT KLESGELSEADFEKQEKILLDKLDSLEDEDD* | 163 |
| Microcystis aeruginosa NIES-843_gvpG | MFLDLLFLPVTGPIGGLIWIGEKIQERADIEYDEAENLHKLLLSLQL SYDMGNISEEEFEIQEEELLLKIQALEELEAENESESSL* | 164 |
| Nostoc punctiforme ATCC 29133_gvpG | MVLRFLLLPITGPLMGVTWLGEKILEQASTEIDDKENLSKQLLALQ LAFDMGEIPEEEFEIQLEALLLAILEAEQEERDQTQEY* | 165 |
| Nostoc sp. PCC 7120_gvpG | MLGKILLLPVMGPINGLMWIGEQIQERTNTEFDAQENLHKQLLSL QLKFDMGEISEEEFDIQEEEILLKIQALEALERLNAESEEDDDLDVQ PIFILASEENPVYQDQSRFSEEYEDKEDLVLSP* | 166 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Octadecabacter antarcticus 307_gvpG | MGIILNTLMSPLIGPMKGVFWVALQIKDQTDAEIYDDSKILVELSE LELLLDLEKIELKDFEAKEDVLLKRLQEIRKAKKNDSV* | 167 |
| Octadecabacter arcticus 238_gvpG | MSIILNTLMGPLIGPMKGLLWVAEQIKDQADAELYDDSKILVALSE LELSFDLEQIELKEFEAQEDVLLQRLQAIRKAKQNDTD* | 168 |
| Pelodictyon phaeo-clathratiforme_gvpG | MFILDDILFAPLNGLIFIAKKINDVVEKETSDEGVVKERLMALQLRF ELDEIDEVEYDREEDELLQKLERIRLNKQNQ* | 169 |
| Phormidium tenue NIES-30_gvpG | MLFKLLFAPVLGPIEGISWVANKLLEQADVPTNDLESLQKQLLAL QLAFDMGEVAEADFLIQEEEILLAIQAIEDEEDEDE* | 170 |
| Planktothrix agardhii str. 7805_gvpG | MILRELLSPITAPFEGVIWIGEQLLERAEAELDDKENEGKRELALQL AFDMGDIPEEDFEVQEEELLLQIQALEDEANQENDEID* | 171 |
| Psychromonas ingrahamii 37_gvpG | MFILDDILLAPYSGIKWLFKEIQRQAQEELDGEADRITTDLTNLYR QFESNEITEQEFEERETVELDRLDELQEESNELDEEYDEEYEDDDE EYEDDDEEYEDDDEEYEDDDEEYEDDDKNDKDKNDDHDNDDDD ENKDENDKYNDEER* | 172 |
| Rhodobacter capsulatus SB 1003_gvpG | MGLERKELLAPVELPITGALWIVEKIAETAESELTDPGTVRRLERG LEQQLEAGEITEEEYEFAEEILLDRLKRGQAAEARSGGP* | 173 |
| Rhodobacter sphaeroides 2.4.1_gvpG | MGELTSLLTLPFRGPFDGTLWIAARIGEAAEQSWNDPAALRAALV EAERQLLAGELSEETYDAIELDLLERLKGTAR* | 174 |
| Rhodococcus hoagii 103S_gvpG | MGLFSAIFGLPLAPVRGVVWIGEVVRRQVEEETTSPAAMRRDLEAI EEGRRSGEISEDEAAQAEDEILHRVTRRRDAGASGEE* | 175 |
| Serratia sp. ATCC 39006_gvpG | MLLIDDILFSPVKGVMWIFRQIHELAEDELAGEADRIRESLTDLYM LLETGQITEDEFEQQEAVELDRLDALDEEDDMEGDEPGDDEDDEY EEDDDEEDDDEEDDDDEDDDDEDDDDEEDDDDDEDDDDEDEPE GTTK* | 176 |
| Stella vacuolata_ATCC-43931_gvpG | MGLVTNVAFAPVVGPLKGVEWLARLIADQAERTLYDEDEVRAAL LDLEQRLDAGQISEADYDAEEEILLARLKIARERMRSGL* | 177 |
| Thiocapsa rosea strain DSM 235 Ga0242571_11_gvpG | MLIVDDLLAAPFKGIIWVFEEIHKSATAEQRARRDEIMAALSALYR ALEQGEITDDTFDTREQALLDELDALDAREDANELGSDEDEDDLD GAGEDAS* | 178 |
| Tolypothrix sp. PCC 7601_gvpG | MEVMIMEGKILLFPVMGPISGLMWIGEQIQERTDTEFDAQENLHK QLLSLQLSFDIGEISEEDFEEQEEELLLKIQALEEEKARLEAESIEDE EDEVEPTYFIAEVEEDKVLAEAFRGNKKYEDNENLVLSP* | 179 |
| Trichodesmium erythraeum IMS101_gvpG | MLLRLLTLPISGPLEGVTWLGKKLQEQVDTEIDETENLSKKLLTLQ LAFDMGEISEEDFEDQEEELLLAIQALEEQKLKEEEEDA* | 180 | gvpJ

| Anabaena-flos-aquae_gvpJ | MLPTRPQTNSSRTINTSTQGSTLADILERVLDKGIVIAGDISISIASTE LVHIRIRLLISSVDKAKEMGINWWESDPYLSTKAQRLVEENQQLQ HRLESLEAKLNSLTSSSVKEEIPLAADVKDDLYQTSAKIPSPVDTPI EVLDFQAQSSGGTPPYVNTSMEILDFQAQTSAESSSPVGSTVEILDF QAQTSEESSSPVVSTVEILDFQAQTSEESSSPVGSTVEILDFQAQTSE LIPSSVDPAIDV* | 181 |
| Bacillus-megaterium_gvpJ | MAVEHNMQSSTIVDVLEKILDKGVVIAGDITVGIADVELLTIKIRLI VASVDKAKEIGMDWWENDPYLSSKGANNKALEEENKMLHERLK TLEEKIETKR* | 182 |
| Ancylobacter aquaticus strain UV5_gvpJ1 | MNEQRMEHSLQAVGLADILERVLDKGIVIAGDITISLVEVELLNIRL RLVVASVDRAMSMGINWWQSDPHLNSHARELAEENKLLRERLDR LEAAVVPSALPADAALEPSLAGEDARHGG* | 183 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Ancylobacter aquaticus strain UV5_gvpJ2 | MPSRHSGEIAVADLLDRALHKGLVVWGEATISVAGVDLVYLGLK LLLTSTDTVNRMREAANAPPDERHLHAD* | 184 |
| Aphanizomenon flos-aquae NIES-81_gvpJ | VTSTPILPTRPQTNSSRAINTSTQGSTLADILERVLDKGIVIAGDISISI ASTELIHIRIRLLIASVDKAKEMGINWWETDPYLSTKAQRLVEENQ QLQNRLENLESQINLLTSAKVQEQISLVETTEDNTHQTTEDNTHQT HEESIPLPIDSQLDV* | 185 |
| Aphanothece halophytica (strain PCC 7418)_gvpJ | MVNPNTNKPKSYQSKGITNSTQSSSLADILERVLDKGIVIAGDITVS VGSTELLSIRIRLLVSSVDKARELGINWWEGDPYLSSQANLLKEEN QALQNRLENMEAELRRLKGETNPEPSFLSESEDNS* | 186 |
| Aquabacter spiritensis strain DSM 9035_gvpJ1 | MSEQRMEHSLQAVGLADILERVLDKGIVIAGDISISLVEVDLLNIRL RLVVASVDRAMSMGINWWQSDPHLNSHARQLEEENRLLRERLDR LEAALAPPEGGMLRAEVEVAHGG* | 187 |
| Aquabacter spiritensis strain DSM 9035_gvpJ2 | MPDPEPIIPRTSGDVALADLLDRALHKGLVLWGEATISVAGVDLV YLGLKVLLASTDTANRMRDAAAASAAGSHLPGG* | 188 |
| Arthrospira platensis NIES-39_gvpJ | MTLQSRSSSPQRGVPMSTSGSSLADILERVLDKGIVIAGDISVSVGS TELLSIRIRLLIASVDKAKEIGINWWESDPYLSSQAQQLSQSNQQLL EEVKRLQEEVRSLKALTSQSSQPVTPPNSENDD* | 189 |
| Bradyrhizobium oligotrophicum S58_gvpJ1 | MTFTVHQPTGGDRLADILERVLDKGIVVAGDVTISLVGIELLNIKIR LIVATVDRALELGINWWEADPRLTTRASELSVENEELKKRLALLE ADAGRNQPRPRKRRVRSIAATSGASHER* | 190 |
| Bradyrhizobium oligotrophicum S58_gvpJ2 | MTYRADLDYLEPAASSEGSLLELLDHLLDRGVLLWGELRISVADV ELIEVGLKLMLASARTADRWRQTTTQRASIAPGDCP* | 191 |
| Burkholderia thailandensis sp. Bp5365 strain MSMB43_gvpJ1 | MRSADGEPVSAELAQRLSLCESLDRILNKGAVISAQVVVSVADVD LLYLHLRLLLTSVETALVGRAMPREEASR* | 192 |
| Burkholderia thailandensis sp. Bp5365 strain MSMB43_gvpJ2 | MADLLERVLDKGVVITGDIRINLVDVELLTIRIRLLVCSVDKAKEL GIDWWNADTFFLGPDRGQSALPGRASAVDVAAGSAVHADAAHR* | 193 |
| Chlorobium luteolum DSM 273_gvpJ1 | MPELKHAVNATGLADILERVLDKGIVIAGDIKIQIADIDLLTIKIRL MVASVDKAIEMGINWWQEDPYLSTGAKTSEQTRLLGEINQRIEKL ESINR* | 194 |
| Chlorobium luteolum DSM 273_gvpJ2 | MQEDLYTANRQVTLLDILDRVLNKGVVISGDIIISVAGIDLVYVGL RVLLSSVETMERLDAARAEGLQQ* | 195 |
| Chlorobium luteolum DSM 273_gvpJ3 | MAVEKTIGSSSLVEVIDRILDKGVVVDAWVRVSLVGIELLAIEARV VVASVETYLKYAEAIGLTAKAA* | 196 |
| Chlorobium luteolum DSM 273_gvpJ4 | MAVEKTIGSSSLVEVIDRILDKGVVVDAWVRVSLVGIELLAIEARV VVASVETYLKYAEAIGLTAKAA* | 197 |
| Dactylococcopsis salina PCC 8305_gvpJ | MVNSNTNQPKSYQSKGITNSTQSSSLADILERVLDKGIVIAGDISVS VGSTELLTIRIRLLISSVDRAREIGINWWESDPYLSSQAHLMKEENQ ALQSRLENMEAELRRLKGETNLDQSSLGESDQRSLQ* | 198 |
| Desulfobacterium vacuolatum_DSM 3385_gvpJ1 | MAYIDIDNDASKQISICEALDRVLNKGAVITGELTISVADIDLIYLSL QAVLTSVETARHMFDSQINDAVKEVK* | 199 |
| Desulfobacterium vacuolatum_DSM 3385_gvpJ2 | MPIQRTAQHSIESTNIADLLERVLDKGIVIAGDIKISLVDIELLSIQLR LVICSVDKAKEMGMDWWVNNPVFMPNKGTQNDEIADTLTKINSR LEHLEKATISGS* | 200 |
| Desulfomonile tiedjei DSM 6799_gvpJ1 | MMDEEEHVSLCEALDRVLNKGAVIAGEVTISVANVDLIYLGLQVV LASVDTIRGKRNELLRHDVGLHLTADNA* | 201 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| *Desulfomonile tiedjei* DSM 6799_gvpJ2 | MSIQASTRHSIQSTNLADLLERVLDKGVVIAGDIKIKLVDVELLTIQ IRLVVCSVDKAKEMGMDWWTNNPAFQPALAQISE* | 202 |
| *Desulfotomaculum acetoxidans*_DSM 771_gvpJ1 | MGPQMGPIKSTGNLSLLDVIDRILDKGLVINADISVSIVGVELLGIKI KAAVASFETAAKYGLQFPTGTEINEKVSEAAKQLKEICPECGKKSG RDELLHEGCPWCGWISARALRLETEHSQR* | 203 |
| *Desulfotomaculum acetoxidans*_DSM 771_gvpJ2 | MLPIREERATLTDLLDRVLDKGLLLNADILISVAGVPLIGITLKAAI AGMETMKKYGLLIDWDQESRLAERRLRSSRH* | 204 |
| *Enhydrobacter aerosaccus* strain ATCC 27094_gvpJ1 | MAVTNGRMEHSIQGSSLADILDRILDKGIVIAGDVTISLVGVELLNI RLRLLVASVDKAIEMGINWWEADPYLTSQTKASSEQTELLQQRLE RIEGLLAGQATKEQPL* | 205 |
| *Enhydrobacter aerosaccus* strain ATCC 27094_gvpJ2 | MPVQTAHDGELALADLLDRALNKGVVLWGDATISLAGVELVYV GLRVLVASCSTMEKYRSSPRKGSMPIARGES* | 206 |
| *Isosphaera pallida*_ATCC-43644_gvpJ1 | MIVCSSSTPERIGPPMNLPPPHHAPWCYDSPDLETLPLDPAERIALC EVLDRVLNKGVVIHGEITISVAGVDLVYLGLNLLLTSVETAQSWK FRGMIE* | 207 |
| *Isosphaera pallida*_ATCC-43644_gvpJ2 | MAITRSSRPDVTHSTSGATLADVLERVLDKGLVIAGDIKIKLVDVE LLTIQIRLVVASVDKAREMGLDWWTRSPELSSLAATTCPALTPPKQ EATPPATRIQAPTESAQTTPDQSHPSDPSASNIDEVAELRRHIELMQ LRDEARQRAHREELAALRAQLTRLTELLDSPR* | 208 |
| *Legionella drancourtii* LLAP12_gvpJ1 | MIIEDKPVSLCETLDRVLNKGVVVAGTVTISVADVDLLYLDLHCL LSSMKGMNLIGSERER* | 209 |
| *Legionella drancourtii* LLAP12_gvpJ2 | MELQKSPTHSIGSTTIADLLERILDKGIVIAGDIKVNLVQVELLTIQI RLLICSVDKAKEIGMDWWTHQNDVQSKNGSMPIQEYVTQMEERL KNLENTLASSKNAI* | 210 |
| *Lyngbya confervoides* BDU141951_gvpJ | MTGQSLSRSSSANRQMATATQGSTLVDVLERVLDKGIVIAGDISVS VGSTELLTIRIRLLVASVDKAREMGINWWENDPYLSARSQELLTA NEQLQSRIESLEQELKSLRSQED* | 211 |
| *Microcystis aeruginosa* NIES-843_gvpJ | MTSSTFAGSLRNQSNNSLKTATQGSSLADILERVLDKGIVIAGDISV SIASTELINIRIRLLIASVDKAREMGINWWEGDPYLHSQSQALLAEN RELSLRLQTLETELETLKSLTQLSAMESHDTSPNDEAHSSDA* | 212 |
| *Nostoc punctiforme* ATCC 29133_gvpJ | MSTNTNRGAITTSTQGSTLADILERVLDKGIVIAGDISISVGSTELLN IRIRLLISSVDKAKEIGINWWESDPYLNSQTRTLLATNQQLQERLAS LETELQSLKALNPINHQNAGD* | 213 |
| *Nostoc* sp. PCC 7120_gvpJ | MTTTPIHPTRPQTNSNRVIPTSTQGSTLADILERVLDKGIVIAGDISIS IASTELIHIRIRLLISSVDKAREMGINWWENDPYLSSKSQRLVEENQ QLQQRLESLETQLRLLTSAAKEETTLTANNPEDLQPMYEVNSQEG DNSQLEA* | 214 |
| *Octadecabacter antarcticus* 307_gvpJ1 | MNDGKMEHSLNATNLADILERVLDKGIVIAGDVTISLVGVELLNIK LRLLIASVDKAMEMGINWWAHDPFLTAGAQAPAVADPAMLERM DRLEAALATALASNQTTPMKGHK* | 215 |
| *Octadecabacter antarcticus* 307_gvpJ2 | MTNKAQGGQDLALADLLDRALSTGVVIWGEATISLAGVDLVYVG LKVLVASVDAAERMKAASLVDRPTDRGQQI* | 216 |
| *Octadecabacter arcticus* 238_gvpJ1 | MNNGKMEHSLDATNLADILERVLDKGIVIAGDVTISLVGVELLNIK LRLLIASVDKAMEMGINWWAHDPYLTAGAQAPVGVDPAMLERM DRLEAALAKALASNQTTPAEGQSS* | 217 |
| *Octadecabacter arcticus* 238_gvpJ2 | MTNETQGGQDLALADLLDRALSTGVVIWGEATISLAGVDLVYVG LKVLVASVDAAQRMKDASLVDRPTDGGQ* | 218 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| *Pelodictyon phaeo-clathratiforme*_gvpJ1 | MPELKHAVNATGLADILERVLDKGIVIAGDIKIQIADIDLLTIKIRLL IASVDKAMEMGINWWQEDTYLSTKAKDKEQQLLRDDLQQRIEKL EALTKIT* | 219 |
| *Pelodictyon phaeo-clathratiforme*_gvpJ2 | MQDEFYSKNKEITILDVLDRVLTKGVVITGDIVISVADIDLVYVGL RLLLSSVETMEKNKQNSIKM* | 220 |
| *Phormidium tenue* NIES-30_gvpJ | MATATQGSSLVDVIERVLDKGIVIAGDISVSVGSTELLSIRIRLIISSV DKAREIGINWWESDPYLSSRTNELLEANQQLQSRLETLEAELKALR SAEPVS* | 221 |
| *Planktothrix agardhii* str. 7805_gvpJ | MNSQQLPSNIQRGVPTSTQGSSLADILERVLDKGIVIAGDISVSVGS TELLNIRIRLLIASVDKAREIGINWWESDPYLSSQTKVLTESNQQLL EQVKFLQEEVKALKALLPQENQPNPISDPHK* | 222 |
| *Planktothrix rubescens*_gvpJ | MNSQQRPSNIQRGVPTSTQGSSLADILERVLDKGIVIAGDISVSVGS TELLNIRIRLLIASVDKAREIGINWWESDPYLSSQTKVLTESNQELL EQVKLLQEEVKALKALLPQENQPKEME* | 223 |
| *Psychromonas ingrahamii* 37_gvpJ1 | MANVQKSTDSSGLAEVVDRILEKGIVIDAFVKVSLVGIELLSIEARV VIASVETYLKYAEAIGLTASAATPA* | 224 |
| *Psychromonas ingrahamii* 37_gvpJ2 | MPMANVSINPELTAQECEKISLCDALDRIINKGVVIHGEITISVANV DLISLGVRLILSNVETREQSNTPKEEV* | 225 |
| *Psychromonas ingrahamii* 37_gvpJ3 | MATGKPQSMTHSVKSTTVADLLERILDKGIVVTGDIKIKLVDVELL TVELRLVICSVDKAVEMGMDWWNNNPAFAPQAPAQEGELSSIEK RLEKIEKALVK* | 226 |
| *Rhodobacter capsulatus* SB 1003_gvpJ1 | MGYRSASQPEGLADVLERILDKGIVIAGDVSVSLVGIELLTIRLRLL IATVDKAREMGIDWWSHDPYLNGRLRPGEPAPETETETAALRDRL AQLEAQLSALGAQVGAAPALAEPALRGLAAAGSSALCAAPEASSA DVVQPVFRRYKEAP* | 227 |
| *Rhodobacter capsulatus* SB 1003_gvpJ2 | MDDRFSLRLFGPEEVFDAPSGGLADLLLDGLLGHGIVLHGDLWLTV ADVELVYVGLSAVLASPEALRSHE* | 228 |
| *Rhodobacter sphaeroides* 2.4.1_gvpJ1 | MSFQMQSPLQQDSLADVLERILDKGIVIAGDISISLVGIELLTIRLRL LVATVDKAREMGINWWESDPRLCITQAPASDGSAALLDRLERIET QIGQLAAAREG* | 229 |
| *Rhodobacter sphaeroides* 2.4.1_gvpJ2 | MTDSAPTLQFATAEEALQSSETRLVDVVDALLSQGIAIRGELWLTI ADVDLVFLGLDLLLANPDRLQCRVPDAA* | 230 |
| *Rhodococcus hoagii* 103S_gvpJ | MTRSGSGANYPQQYSQGLGGAGHEPANLGDILERVLDKGIVIAGD IRVNLLDIELLTIKLRLVIASLETAREVGIDWWEHDPWLSGNNRDL ELENERLRARIEALESGERRVADVTDPHRAVQPAESPAAEVRDDD A* | 231 |
| *Serratia* sp. ATCC 39006_gvpJ1 | MPVNKQYQDEQQQVSLCEALDRVLNKGVVIVADITISVANIDLIYL SLQALVSSVEAKNRLPGRE* | 232 |
| *Serratia* sp. ATCC 39006_gvpJ2 | MSGNKKLTHSTDSTTVADLLERLLDKGVVISGDIRIRLVEVELLTL EIRLLICSVDKAVEMGLDWWSGNPAFDSRARVSSSAPAPELEERL QRLEARLEAAPSVIEETHL | 233 |
| *Stella vacuolata*_ATCC-43931_gvpJ1 | MSGQRMEHSVQAVGLADILERVLDKGIVIAGDISISLVEVELLTIRL RLVVASVDRAMSMGINWWQSDPNLNSHARQLEEDNRLLRERLDR LEAALALPEMAGERLADAGQGGGAEQGVTHGR* | 234 |
| *Stella vacuolata*_ATCC-43931_gvpJ2 | MSDPEPIIPRTSGDIALADLLDRALHKGLVLWGEATISVAGVDLVY LGLKVLVASTETADRMRAAAASQSADPKVRAG* | 235 |
| *Thiocapsa rosea* strain DSM 235 Ga0242571_11_gvpJ1 | MMLAIGEHPDCPEEIQRVSLCEALDRILNKGAVVSGELTIAVANVD LLYLSLQLVITSVETAKREMLYVRH* | 236 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Thiocapsa rosea strain DSM 235 Ga0242571_11_gvpJ2 | MSVQRSTLTHSTNSTSVADLLERVLDKGIVIAGDIRIKLVDIELLTIQ LRLVICSVDKAREMGIDWWSDNAMFKGLSSQASAASLPGTAAAS GIEDRLARLESLLVKQSAAAETVL* | 237 |
| Tolypothrix sp. PCC 7601_gvpJ | MADILERVLDKGIVIAGDISVSIASTELLHIRIRLLISSVDKAKELGIN WWENDPYLSSKSQRLVEENQQLQQRLESLEAQLRSLTAAKINNPE LFPVNAEDNGQSDEENVPLPMNYQPND* | 238 |
| Trichodesmium erythraeum IMS101_gvpJ1 | MFIRVDFLLDKGVIVDAWVRLSLVVIELLTIEAKIVIASVEAYLKYS EAFCFNY* | 239 |
| Trichodesmium erythraeum IMS101_gvpJ2 | MAVEKVNSSSSLAEVIDRILDKGVVVDAWIRLSLVGIELLTIEARIV VASVETYLKYAEAVGLTTLAAAPGEAAA* | 240 |
| Trichodesmium erythraeum IMS101_gvpJ3 | MAVEKVNSSSSLAEVIDRILDKGVVVDAWVRLSLVGIELLTIEARI VIASVETYLKYAEAVGLTTLAAAEPAA* | 241 |
| Trichodesmium erythraeum IMS101_gvpJ4 | MKTSANIATSASGNGLADVLERVLDKGVVIAGDISVSIASTELLNI KIRLLISSVERAKEIGINWWESDPYFSSQNNSLVQANEKLLERVASL ESEIKALRSN* | 242 |
| Trichodesmium erythraeum IMS101_gvpJ5 | MKTSANIAKSAGGDSLADVLERVLDKGIVIAGDISVSIASTELLNIK IRLLISSVERAKEIGINWWESDPSLSSQNNSLVQVNQKLLERVASLE SEIEALKYSQ* | 243 |
| gvpK | | |
| Anabaena-flos-aquae_gvpK | MVCTPAENFNNSLTIASKPKNEAGLAPLLLTVLELVRQLMEAQVIR RMEEDLLSEPDLERAADSLQKLEEQILHLCEMFEVDPADLNINLGE IGTLLPSSGSYYPGQPSSRPSVLELLDRLLNTGIVVDGEIDLGIAQID LIHAKLRLVLTSKPI* | 244 |
| Bacillus-megaterium_gvpK | MQPVSQANGRIHLDPDQAEQGLAQLVMTVIELLRQIVERHAMRR VEGGTLTDEQIENLGIALMNLEEKMDELKEVFGLDAEDLNIDLGPL GSLL* | 245 |
| Ancylobacter aquaticus strain UV5_gvpK | MTAPCTAETLENALRGRIDIDPEKVEQGLVKLVLMLVETVRQVVE RQAIRRVEGGTLTEEETERLGLALMRLEEKMAELRLHFGLEDGDL DLKLQLPLGEL* | 246 |
| Aphanizomenon flos-aquae NIES-81_gvpK | MVYSPVENSNDFLNVIPVENSNEFLNTSPKKKSNSETGLAPLLLTV LELIRQLMEAQIIRRMEEDLLSESDLERTAESLQKLEEQILNLCQIFD IDPADLNINLGDFGSLLPASGSYYPGETGNRPSILELLDRLLNTGIV VDGEIDIGVAQLDLIHAKLRLVLTSKPI* | 247 |
| Aphanothece halophytica (strain PCC 7418)_gvpK | MSADESNLSQVNLNPATSNSDAGLAPLLLTVTELIRQLMEAQVIRR MDGGLLNEEELDRAGDSLQRLEAEIIRLCEIFEIDPKDLNVDLGELG TLMPKNGGYYPGESSDDPSILELLDRILHKGVVIDGNLDLGIAQLS LIQARLHLVLTSQPINGK* | 248 |
| Aquabacter spiritensis strain DSM 9035_gvpK | MTGFAGGPAVTETLESVLQGRVDIDPERVEQGLVKLVLMVVETLR QVIERQAIRRVEAGALTDEEIERLGLTLLRLEEKMAELRVQFNLSE ADLSLKLRLPLGEL* | 249 |
| Bradyrhizobium oligotrophicum S58_gvpK | MSASSHSEAPGLRLQLGDLDTALAAVFTDAAPNGSINLDPDKIEHD LARLVLTLIEFLRRLLELQAIRRMEANELSEDEEERVGLALMRAAA QVSRLARELGVDPRELNLQLGPLGRLL* | 250 |
| Burkholderia thailandensis sp. Bp5365 strain MSMB43_gvpK | MNAPHAAAVSDAAALAAALEQALAQQQAPPPRATQRFDVATAS AGNGLAKLVLALMKLLHELLERQALRRIEAGSLNDDEIERLGLAL MRQAEEIERLAAQFGFTDADLNLDLGPLGRLF* | 251 |
| Chlorobium luteolum DSM 273_gvpK | MHEDKVQFQASSVEEALRQLEGMKQGKESRIEANPDNVESGLAR LVLTLIELLRKLMEKQAMRRIDGGSLDEAQIDELGETLMKLEMKM DELKKTFNLTDSDLNLNLGPLGDLM* | 252 |
| Dactylococcopsis salina PCC 8305_gvpK | MSEEESNLSRVDLNPASSNSDAGLAPLLLTVTELIRQLMEAQVIRR MDAELLTEAELDRAGESLQRLEEEILRLCEIFDVDPADLNVHLGEL GTLLPKEGGYYPGETSDQPSILELLDRVLHTGVVIDGNLDLGIAQL NLIQAKLHLVLTSQPINN* | 253 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Desulfobacterium vacuolatum_DSM 3385_gvpK | MIKDPEAKDFKIESDSIDAFARVMHADTSSCSSSSVTAGQRQQRLK IDEENIKNGLAQLVMTLIKLLHELLERQAIRRIESGSLDDDQIERLG LTLMQQCEEIDRLRKLFDLEEEDLNLDLGPLGKLL* | 254 |
| Desulfomonile tiedjei DSM 6799_gvpK | MNPMNIAKVESDSLGDFAEIMQTDWISSLHSDKEEKRLNLNQDSV KNGLGQLVLTLVKLLHDLLERQAIRRMEAGTLTDTEIDRLGTTLM MQAQEIERLRSEFGLEEEDLNLDLGPLGKLL* | 255 |
| Desulfotomaculum acetoxidans_DSM 771_gvpK | MYIDISEGSLKQGVLGLLLALVEIIKDALKIQALKRIEGDSLTEDEIE RLGNALHELEEALVEIEMEHNLQNVVQNIREGLDNVVNEVVDTFN PERWIAENEFN* | 256 |
| Dolichospermum circinale_gvpK | MLSTPADNFDESLTTVSKSKNEAGLAPLLLTVLELLRQLMEAQVIR RMEDNLLSESELERAADSIQKLEEQILHLCETFEVDPAELNINLGDF GTLLPQSGSYYPGETGSRPSVLELLDRLLNTGVVLDGEIDLGLAQL DLIHAKLRLVLTSKPI* | 257 |
| Enhydrobacter aerosaccus strain ATCC 27094_gvpK | MTKLLEAKTVDPDKAGDDLVKLVLALVETLRQLVERQAIRRVDS GVLNDDEVERLGLALLRLEEKMSELKAHFGFGDEELTLKLGSLGE LARDV* | 258 |
| Isosphaera pallida_ATCC-43644_gvpK | MSDSLFEVRSPSAAPPSPVNPGVADEWTAVLKDWDTLTAQLRQA TAPPNAENSARSHATTGRIDLDPEQVGDGLAKLVLTLLELIRQLLE RQAIRRLDAGSLDHEQTERLGLTLMRLAQRMEELKTHFGLQGEDL NLDLGPLGKLL* | 259 |
| Legionella drancourtii LLAP12_gvpK | MNDKREEDNALPQRINLQPDDVKNGLGKLVLILIQLIHELLERQAI GRIEAGDLSDEQIDRLGITLMKQAELIDKLREVFGLTQEDLNLDLG PLGKLL* | 260 |
| Microcystis aeruginosa NIES-843_gvpK | MTLACTPYDSDNQALLTRPESNSQAGLAPLLLTVVELVRQLLEAQI IRRMEKGVLSESDLDRAAESIQKLQEQILYLCEIFEVEPEELNVHLG EFGTLLPEAGSYYPGEEGIKPSVLELVDRLLNTGVVEGNVDLGL AQLDLIHLKLRLVLTSQPV* | 261 |
| Nostoc punctiforme ATCC 29133_gvpK | MQAISKSKGSDSGLAPLLLLTVVELIRQLMEAQVIRRMDAGTLNDS ELDRAAESLQKLEQQVVQLCEIFDIDPADLNINLGEMGNLLPQSGG YYPGETSSQPSILELLDRLLNTGVVEGDLDLGLAQLSLVHAKLRL VLTSKPL* | 262 |
| Nostoc sp. PCC 7120_gvpK | MVCTPVEKSPNLLPTTSKANSKAGLAPLLLTVVELIRQLMEAQVIR RMEQDCLSESELEQASESLQKLEEQVLNLCHIFEIEPADLNINLGDV GTLLPSPGSYYPGEIGNKPSVLELLDRLLNTGIVVDGEIDLGLAQLN LIHAKLRLVLTSRPL* | 263 |
| Octadecabacter antarcticus 307_gvpK | MKTTSDSQFDSMKKILTDSSKEDSASCDPTDLLPNKSLPPSLSTSPE TAADDLVKLVLAVIDTVRQVMEKQAIRRVESGALAEAEIERLGLT LMRLEARMVELKSHFGLSNEDLNLHFGTVQDLKDILNDEE* | 264 |
| Octadecabacter arcticus 238_gvpK | MKTQNDTQFDSMKKILTDSGGGDPNPNGSPDQTQHASLPSNLSTD PETAADDLVKLVLAVIDTVRQVMERQAIRRVDSGALADEEIERLG LTLMRLEERMADLKSHFGLSNEDLNLNFGTVQDLKDILNDEE* | 265 |
| Pelodictyon phaeo-clathratiforme_gvpK | MDSDKILYYAGSADEIIEELEKLKPGIQGRINATPDNVESGLAKLVL TLIELIRKLIEKQAMRRIDGNSLSESQIEELGETLMKLEKKMEELKG IFNLTDKDLNLNLGPLGDLM* | 266 |
| Phormidium tenue NIES-30_gvpK | MTSENAEPDLSTTLALQPPAKTDAGLAPLLLTVIELVRQLMEAQVI RRMESGDLDDNDLERAADSLRKLEEQVVSMCEIFDVDPADLNIDL GEIGTLLPKEGNYYPGQKNQNPTILELLDRLLDTGVVVEGDVDLG MAQLNLIHAKLRLVLTSKPI* | 267 |
| Planktothrix agardhii str. 7805_gvpK | MSSSEPSIETIITPKSSRKDAGLAPLVLTLVELIRQLMEAQVIRRMEG NTLSEEELDRAAQSLQQLEIQVLKLCEIFEIDPTDLNIELSEFGTLLP KSGSYYPGENTQNPSILELLDRLMNTGIVVEGSVDLGLAQLNLIHA KLRLVLTSKPL* | 268 |
| Psychromonas ingrahamii 37_gvpK | MPFEHFKSNNQADVNSDTKPAASVGGLNLESDDLKNGLGRLVLT LVKLLHELLERQALRRMDAGSLQDDEIERLGLAFMKQAELIDRLR KEFGLEVEDLNLDLGPLGRLL* | 269 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Rhodobacter capsulatus SB 1003_gvpK | MSAAMHLELGDVDAVLSQAARSLAAGGRLTLDPERVEQDLARLV LGIVELLRKLMELQAIRRMEAGSLTPEQEETLGLTLMRAEAALHE VAAKFGLQPADLILDLGPLGRSV* | 270 |
| Rhodobacter sphaeroides 2.4.1_gvpK | MTYPFPPLLLRDDRLPPTEAPVTAPRIALDPDRLEHDLARILLGLME MLRQIMELQAIRRMEAGSLSESQQEQLGTTLMRAEAAIHEMAARF GLTPADLSLDLGPLGRTI* | 271 |
| Rhodococcus hoagii 103S_gvpK | MRRRIDSDPESVERGLVALVLTLVELLRQLMERQALRRVDAGDLS DDQIERIGTTLMLLEEKMEELREHFGLEPEDLNIDLGPLGPLLAED* | 272 |
| Serratia sp. ATCC 39006_gvpK | MTTNQLSHHSPVFGPTSPAIQRPITEANRHKIDIDGERVRDGLAQL VLTLVKLLHELLERQAIRRMDSGSLSDEEVERLGLALMRQAEELT HLCDVFGFKDDDLNLDLGPLGRLL* | 273 |
| Stella vacuolata_ATCC-43931_gvpK | MTGFLNGPADVETLETALRGRVDIDPERVEQGLVKLVLMVVETLR QVIERQAIRRVESGSLTDDEVERLGLTLMRLEEKMDQLRRQFDLG EEDLSMRLRLPLQEL* | 274 |
| Thiocapsa rosea strain DSM 235 Ga0242571_11_gvpK | MSDTRTGTAPSSAASAAPDTSTLQRANLLADLLETKVAAAGRRIDI DPERVQRGLGQLVLTVVKLLHVLLERQAIRRVDGGDLDEDEIEQL GLALMRQSEEIERLRRLLGLEEQDLNLDLGPLGKLF* | 275 |
| Tolypothrix sp. PCC 7601_gvpK | MAMVCTPSENSNDLLATNSKANNQAGLVPLLLTVVELIRQLMEA QVIRRMEEECLSESDLERAAESLQKLEEQVLNLCQIFEIDPADLNIH LGELGSLLPAAGSYYPGETGNTPSVLELLDRLLNTGVVVDGELDL GVAQLNLIHAKLRLVLTSKPLNTK* | 276 |
| Trichodesmium erythraeum IMS101_gvpK | MSLENSPEESLIVPIDKSKSNPEAGLAPLLLTVIELLRELMQAQVIR RMDAGILSDEQLERAAEGLRQLEEQVIKLCKVFDIPTEDLNLDLGE IGTLLPKSGEYYPGEKSENPSVLELLDRILNTGVVLDGTVDLGLAE LDLIHARLRLVLTA* | 277 |
| gvpL | | |
| Ancylobacter aquaticus strain UV5_gvpL | MLYLYAILESPPPQKPLPPGIGGAAPLFVESHALVCAASEAADAAI AREPSQIWRHQEVVAALMEGRPVLPLRFGTVVEDSAACLRLLARH HAELSAQLDRVRHCVEFALRVAGLSELADPGLDPNATPAGLGPGA SHLRTLVRRERGWPVSSAAFPHDTLTAHAASRLLWARSPSQPDLR ASFLVQRRSASAFLDDVNALQRLRPDLGITVTGPWPPYSFSDPDLS GGRE* | 278 |
| Aphanothece halophytica (strain PCC 7418)_gvpL | MLYTYCFLFSPEKTLSLPQGFKGDLQMIEKGAIAAVVEPNLPKAEL EEDDQKLVQAVVHHDWVICELFRGLTVLPLRFGTYFRGEADLRSH LAAYEESYQQKLTALTGKVEVTLKLTPIPFSEEGSSSTAKGKAYLQ AKKQRYQQQSNYQTQQQEALEKLQEEIKKTYPQLIHDEPKENTER FYLLIDSHSFSVFGEKMEQWKQFLSSWSILISDPLPPYHFL* | 279 |
| Aquabacter spiritensis strain DSM 9035_gvpL | MLYLYAVLEAPPPARSLPPGIGGGAPHFIEAFELVCAASETPNRSV APEPAEVWRHQQVVEALIDRAPALPLRFGTLVEDASACRRLLTRH RDALGAQLGRVRHCVEFALRVSGLPEEVAPDPGIGGGPGTSYLRT LARREAGWPPSTAVFPHDGLAAHAAERLLWARSTSQPDLRASFLV RKPNVAAFLADVSALQRVRPDLGITCTGPWPPYSFSDPDLSGVSP* | 280 |
| Bacillus-megaterium_gvpL | MGELLYLYGLIPTKEAAAIEPFPSYKGFDEHSLYPIAFDQVTAVV SKLDADTYSEKVIQEKMEQDMSWLQEKAFHHHETVAALYEEFTII PLKFCTIYKGEESLQAAIEINKEKIENSLTLLQGNEEWNVKIYCDDT ELKKGISETNESVKAKKQEISHLSPGRQFFEKKKIDQLIEKELELHK NKVCEEIHDKLKELSLYDSVKKNWSKDVTGAAEQMAWNSVFLLP SLQITKFVNEIEELQQRLENKGWKFEVTGPWPPYHFSSFA* | 281 |
| Burkholderia thailandensis sp. Bp5365 strain MSMB43_gvpL | MNDALYLFCFARAEPLAPAWAKRAPGEPRLQLLHEGNLAAVLCD VSRSEFAGADAERRLADPAWIAGRVAVHAAAIEWTMRYSPVIPAQ FGTLFSGAGRVIALMESCHAHIGRVLDHVEGKTEWAVKGWLDRQ AAADSQAALLRADEPESAARTAGARYLRERQLQARAGQNLRDW LEQSVPPISARLQRHAVEMCSRPCRASDSEHEIVANWAFLVRNRD VPAFRRQAEAIDAEFATWGLHFDFSGPWPPYSFCAPLTEETTWSG* | 282 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
| --- | --- | --- |
| *Chlorobium luteolum* DSM 273_gvpL | MPCRLTVTWKSLRTAGLLPTAKGIQGRTERMAQNILYVYCIVRQL PGADIVARYPDLVFIEAGSAYVAAKYVSPLEYSDASMKLKLADEE WLDRNAREHLSVNVMIMAQQTIIPFNFGTIFKSRESLSGFLGDYGR KLDESFDALEGREEWAVKAYCNESFLLKNLHLESPAIAAIEQEIQA ASPGKAYLLKKKEAMSASALEGVHQGHAKAVWGELAALSKEH VLNRLIPEDVSGVDGRMIVNGVFLIANTDVGAFIRTTEDLGERYRD AGVFLDVTGPWPPYDFVDIPY* | 283 |
| *Dactylococcopsis salina* PCC 8305_gvpL | MLYTYCLIASSPSALSLPSGFRGELQLIKQGAIAAIVEAELPLEELEE NDQKLIQAVIHHDAVICEIFQQIPLLPLRFGTYFPTEKDLLEHLDFK AEKYQKKLQEIQDKVELTLKLTPLPFSTENASPMEKQGKNYLKAK KQRYQEQTNYQSQQQAELNQLQTQINQDYPQFIHGEPKENIERFY LLIKERDRSVFSEQLEQWKKDFPTWTIEVSDPLPPYHFIE* | 284 |
| *Desulfobacterium vacuolatum*-DSM 3385_gvpL | MEKKKAVYLYCVTRANKFNAPGITGIDANTPVCFEHLENFVAVY NIIPLNTFVGTSAEENMKNIDWIGPRAMRHENVIERMMQESSVYPA RFATLFSSMENLRETLHLKSGLISRFLNQTQHKCEYSLKGFINRKQ LLEFLIKTKFKQEKKQLDGLSPGKKYFAQHQFNKKVETGINQWIK RRCGIFLDHLTKRNPEVSPRELFTEKTEKNNLEMMFNLAFLIHNDS KSAFLQEISQAEKEFSQTGISLVVSGPWAPYSFCKTTRGEGL* | 285 |
| *Desulfomonile tiedjei* DSM 6799_gvpL | MSNVLYLFCLARTGLVDHIEGTGITGTEDLILKNFSGVTAVTCEVP EDDFSGESALIKLQDLAWVGPRAVRHDRIIEEIMQYSPVFPAPFGSL FSSEKRLGTLIESNIDAIREFLDHTADKQEWSVKGLVCKSKAVDEIF TGKLKILSETLSSSPAGMRYFKERQMRSEAEKELSGKVKAACTVV GEKLLACSNNFRQRKNISFGKAEGDKQLVVNWAFLVDHSRISYFL DQVEHANSNYQAGGLAFECSGPWPPYSFCPSLHMEPTR* | 286 |
| *Desulfotomaculum acetoxidans*-DSM 771_gvpL | MNLIDDCKAKYIYCIGENPGNWPSEVMGVEGSLVYHVVYRDIAA VVHDCAEQPYNSDDNNKVIDWVLGHQLVVDKACSCYSSVLPFTF NSIVKGKEDLSSHEILVNWLEDNYDNFKLKLGKIKGKKEYSVQLF LDKQVSLSLLQSESDILELQVELLGSAKGKAYFVQEKINKKIGELM ANRADSYCRQFYHEISSVVSECKLCKLKQAGRNEIMIINLVCLAGD NEVEVLGDVLEKIKSNDIAIKIKFSGPWPAYSFV* | 287 |
| *Enhydrobacter aerosaccus* strain ATCC 27094_gvpL | MLYVYGIADNAFEVLRGAGLLNSDVFAVPAGCLAAAASKLAQGG IETTPQGVWRHEQVLRQLMQDHAVLPLRFGTICRDRETLTDRLME ASDDLVRGLGRVRGKVEIALRIVDEREHEAHPVPSETPTVDAIGGG RGTAYLRARRRHHAAEMGREARAERVGKMLSAYIDVGAEDLVC SVAPEGDHAVSVSCLLGRDQLATLQAALERFQSDHPAIGLSWTGP WTPYSFVAPSLFGVGLP* | 288 |
| *Legionella drancourtii* LLAP12_gvpL | MNKALYLFCLTPASDLPMMEGELLPNFSPLFIHPFQTFNAILSWVP AKEYQEQSTDSNLINTEEFMQRVFFHELVVEKIMRDEAVFPIGFGT LFSSIASLEEQILTHQTLISSCLANLNQKDEYAVRVYLNQDKALESL LSVMLQERESSWASSSPGVQYLKKQQLHNEIQRNLNQHLGGMLD EVLSMFQRHATDFKSRENTAQSSDIHGTSILHWAFLIPRVVSSIFKE QVDLMNAKYNPFGLHFVLTGPWPAYSFCTLQSVEAP* | 289 |
| *Lyngbya confervoides* BDU141951_gvpL | MRWHRSEAVISYCDLSMIYLYALCPNSTETNNLPEGIGTAQVEVLT VGTLGAVIERDVDIAQIQKDDAQLMAAVLAHDRILSHLFTYSPLLP LRFGTQFSNSEAVTTFLKTQGETYRQKLSHLQDRAEYLVKLIPQPL DLPAIASDLKGREYFLAKKQRLQDHTAALNQQADELQTFLTDLAT QDIPLVRSAPQDHEERLHVLLSRDTDTTEQVIMTWQEQLPNWQVV CSEPLPPYHFAA* | 290 |
| *Octadecabacter antarcticus* 307_gvpL | MKRLYVYGIVGATSFDDPLPNGHDEASVFALVSGDIAVAVSFVER SAVEASAANVWLHDNVLSALMTRYAVLPMRFGTIAVGATQLLEG IVKRQKQLMKDLMRLNENVEIALHISGKNWEKVNQKVTKKNTDQ AITQGTAYLLGRQQSLYGSDKTQLLVQNVRRAIRSGLDPLMKDVI WPIDKPQALPFKASCLINRNDVASFVQIVNDIAAQNLDARVTCTGP WAPYSFVGKSGVEGET* | 291 |
| *Octadecabacter arcticus* 238_gvpL | MTKLYVYGIVGATHFDVKLPNGHDEAPVFAIVSGDLAVAVSSLER SAVEASAANVWLHENVLSALMEGHAVLPMRFGTIATGAAQLLGD IVKRRGQLMKDLTRLDGKVEIALRISGKNREKVEQRIAGQIVDTNV TQGVAYLQEKQQNLYGSFYTQSSVQCARRAIRSQLDPFIVEAIWPT DEPQMLPFRASCLIKKGDIARFVQTVDDVVVKVSDIRVTCTGPWA PYSFVGQSGSEAET* | 292 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Pelodictyon phaeo-clathratiforme_gvpL1 | MVAIQERLIYIFCVTSEPPLLQQYQLQKGICVVDVDGLFVTTMDVT DNDPAENQLQSNLSDVVWLDTKVREHLDVITSIMQHVKSLIPFNF GTLYKSESSLMQFIIKYALEFKKNLVYLEEKEEWAVKLYCNKNKI VENITHLSKKVSDINALIQNSSIGKAYILGKKKNEIIENEIINIYNTYS KKIFTKFSILSEEFRFNPIPNNETLEKEDDMILNVVLLLNKANVESFI ETSDQLIIQHQNIGLNIEITGPWPCYSFINISH* | 293 |
| Pelodictyon phaeo-clathratiforme_gvpL2 | MPLIIYAIFDSINYIDSFSSYVDAISLKSKIKLEIISTSTLSAIVSRTTDE KKQACQNDVMIYATIIGDIAAKYSILPMRYGSIVSSPFDVTELLKN HNETFVTIIKKITDKEEYSLRILYSHQDKEKNNIEDLFDLPQNVPDIL HGNTDSKKYLLNKYIKHLSEEKRLQYIDKIQSIVACNLQKITDLIVY NKQTTTGFIVDAVFMIERSKKSELLDLVIQMQTLFSEHNVVLSGPW PPYNFSNINIG* | 294 |
| Psychromonas ingrahamii 37_gvpL1 | MKNSNHSGLDPNQALYLYCFVHADSIQSVTSQAIEKDSPVFIYQW QDIAAVLSHVPTSYFTGYDDEEPEQTIARILPRTQLHEQVIEEVMRQ SPVFPAQFGTLFSSQESLEQEISQQYLAITHTLKEVSGSVEWAVKG VLDRGVAEKALYSQQLTEQQNSLSSSPGMRHLQEQRLRRETQSKL NSWLHQLYTDIATPLSELSGDFFQRKIPSSIEEGKEVILNWAFLVPE SAGDDFHAQIDKLNQRLNSFGLVIQCSGPWPPYSFCNQSS* | 295 |
| Psychromonas ingrahamii 37_gvpL2 | MKNSNHSGLDPNQALYLYCFVHADSIQSVTSQAIEKDSPVFIYQW QDIAAVLSHVPTSYFTGYDDEEPEQTIARILPRTQLHEQVIEEVMRQ SPVFPAQFGTLFSSQESLEQEISQQYLAITHTLKEVSGSVEWAVKG VLDRGVAEKALYSQQLTEQQNSLSSSPGMRHLQEQRLRRETQSKL NSWLHQLYTDIATPLSELSGDFFQRKIPSSIEEGKEVILNWAFLVPE SAGDDFHAQIDKLNQRLNSFGLVIQCSGPWPPYSFCNQSS* | 296 |
| Serratia sp. ATCC 39006_gvpL | MTMNTEAQTEQAIYLYGLTLPDLAAPPILGVDNQHPINTHQCAGL NAVISPVALSDFTGEKGEDNVQNVTWLTPRICRHAQIIDSLMAQGP VYPLPFGTLFSSQNALEQEMKSRATDVFVSLRRITGCQEWALEATL DRKQAVDVLFTEGLDSGRFCLPEAIGRRHLEEQKLRRRLTTELSD WLAHALTAMQNELHPLVRDFRSRRLLDDKILHWAYLLPVEDVAA FQQQVADIVERYEAYGFSFRVTGPWAAYSFCQPDES* | 297 |
| Stella vacuolata-ATCC-43931_gvpL | MLYLYAVLEALPAARTLPAGIGGGELLFVEAFELVCAASETPERAI APEPTQVWRHQQVVEALIDCAAALPLRFGTLVEDAVACRRLLTRH REALCAQLDRVRHCVEFALRVSGLREEVGSDHVIGGGPGVSYMR ALARREASWPPSTGTFPHDGLAAHAADRLLWSRSASQPDLRASFL VLKPNVAAFLADVSALQRMRPDLGITCTGPWPPYSFSDPDLSGMS P* | 298 |
| Thiocapsa rosea strain DSM 235 Ga0242571-11_gvpL | MDAFYCFCFAPACLASDLRFDDCGWEDPIEIRRLAGLDVILSRVPL GRFAGAEAEQRLADLEWLVPRAQAHDRVITRTMERSTVFPLTFAT LFSSLPALALEVAARRRALLDFFERMAGREEWAVKVSMDRERVIA TRMQSLYPEGGDVPAGGRGYLLKQRRRGEAEQAIGPWLKGQIGC LDEALRPSCETLLIRPLRDEMVASRACLVARDLGPSLSEAIERSREA FADQGLDLHCSGPWPLYSFCGTP* | 299 |
| Trichodesmium erythraeum IMS101_gvpL gvpN | MSYYVYGFLYLPESCLALPKGMEKEVELVPYQNIAAVVEANVSIE AIQETEEKLLEAILAHDRVVREIFQQVSMLPLRFGNAFALRENIIND LQNNQQQYLNILTKLQQQAEYTITFTPVSYPSTLEVSKVRGKAYLL AKKQQFEQQQAFQTKQRQQWENIRQLIFKNYPKAVFRDSTESKIK QVHLLANRDARVITTEELSTWQTECSYWQITLSEQLPPYHFV* | 300 |
| Anabaena-flos-aquae_gvpN | MTTTKVNHKRAVLRLRPGQFVVTPAIERVAIRALRYLKSGFPVHL RGPAGTGKTTLAMHLANCLDRPVMLLFGDDQFKSSDLIGSESGYT HKKVLDNYIHSVVKLEDEFKQNWVDSRLTLACREGFTLVYDEFN RSRPEVNNVLLSALEEKILSLPPSSNQPEYLSVNPQFRVIFTSNPEEY AGVHSTQDALMDRLVTISMPEPDEITQTEILIQKTNIDRESANFIVR LVKSFRLATGAEKTSGLRSCLMIAKVCADNNIPVTTESLDFPDIAID ILFNRSHLSMSESTNIFLELLDKFSAELLEILNNRVTGDNDFLIDNSQ FVSQQLAGQPN* | 301 |
| Ancylobacter aquaticus strain UV5_gvpN | MTSEAASKDPISLLSGFGAGAASSGPKAGGRSTPSALTPRPRTGFV EAEQVRDLTRRGLGFLNAGYPLHFRGPAGTGKTTLALHVAAQLG RPVIIITGDNELGTADLVGSQRGYHYRKVVDQFIHNVTKLEETANQ HWTDHRLTTACREGFTLVYDEFTRSRPETHNVLLGVFEERMLFLP AQAREECYIKVHPEFRAIFTSNPQEYAGVHASQDALADRLATIDVD YPDRAMELAVASARTGMPEASAARIIDLVRAFRASGDYQQTPTMR AGLMIARVAAQEGFEVSVDDPRFVQLCSDALESRIFSGQRALEVA REQRRAALHALIDTHCPSAAKPRARRAGGAVRASIEGAQS* | 302 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Aphanizomenon flos-aquae NIES-81_gvpN | MTKTNHKRAVLRVRPGQFVVTPAIEQVAIRALLYLKSGFPIHLRGP AGTGKTTLALHLAHCLDRPVMLLFGDDEFKSSDLIGSESGYTHKK LLDNYIHSVVKVEDEFKQNWVDSRLTLACREGFTLVYDEFNRSRP EVNNVLLSALEEKILSLPPSSNQPEYLSVSPQFRAIFTSNPLEYCGV HSTQDALMDRLVTINMPEPDEITQTEILIQKTNIQKESAHLIVRLVK SFRIATGAEKTSGLRSCLMIAKVCADNNLVAEPENSFFQEIAMEILS NRTHLSVNESTDIFLDVISQFSNKEIEILNDAELGSLPTMDTLANTD LGNDVPLEKEASDYVIQQKNNEFKGFQKPSTKVLN* | 303 |
| Aphanothece halophytica (strain PCC 7418)_gvpN | MTTVLHARPKGFVSTPTIDRISRRAWRYLQSGFSIHLRGPAGTGKT TLAMHLADLLNRPIMLLYGDDEFKSTDLIGSNTGYTRKKVVDNYI HSVVKEEDELRQQWVDSRLTMACREGFTLVYDEFNRSPPEVNNV LLSALEEKLLVLPPDSHRSEYVRVSPNFRAIFTSNPEEYWGVHGTQ DALLDRVVTINVPEPDLETQREIIVQKVGINADDGDMIVNFVRNFR DRAEMENSSGLRSCLMIAQVCHQHEIPVQTSNEDFQDICYDILTSR CPLSTQESISLLEQLFREYELELVVEDEDEDVPSVIVEGETEDLSSDE KPHLRLSHPFGNTEND* | 304 |
| Aquabacter spiritensis strain DSM 9035_gvpN | MSTEPAPLVSPSQDVETTPQRPARPEPAEALAVGYRLSARPASPAT LTPRPRADFVETDQVKDLTRRGLGFLRAGYPLHRGPAGTGKTTL ALHVAAQLGRPVIVITGDNELGTADLVGSQRGYHYRKVVDQFIHN VTKLEETANQRWTDHRLTTACREGYTLVYDEFTRSRPETHNVLLG VFEEKILFLPAQAREECYIRVHPDFRAIFTSNPQEYAGVHASQDAL ADRLTATIDVDYPDRGMELAVASARTGLGETEAARIIDLVRAFRAS GDYQQTPTMRASLMIARVAAQEGLRVSIDDPGFVQLCMDALESR MFSGARLEAATRETSRAALLALLAVHCPSEAPIVRVTAARRAKKA DAS* | 305 |
| Arthrospira platensis NIES-39_gvpN | MTTVLRAVPKGFVNTPAIERITVRALRYLQSGFSVHLRGPAGTGKT TLALHLADLLNRPIMLIFGDDELKSSDLMIGNQTGYTRKKVVDNFIH SVVKLEDSLKQNWIDSRLTACREGFTLVYDEFNRSRPEVNNVLL SALEEKLLVLPPNNSRSEYIRVNPHFRAIFTSNPLEYCGVYSTQDAL LDRLITMNMPEPDEATQQEILIQKVAVTPEEAQTIVTLVQQFREAT HAIAPSKIQTVARQQTNADKASGLRPSLMLARICQEHNIPIVPIDPD FQEVCRDILLSRAIGDITELESRLHQIFDHLSGLENDQIIALPPREELT TSSVPNNLSDTEQKIYTYIKDSDGARVSEIEIALGLNRVQTTDALRS LLRKSYLTQQDNRLFVVYEGD* | 306 |
| Bacillus-megaterium_gvpN | MTVLTDKRKKGSGAFIQDDETKEVLSRALSYLKSGYSIHFTGPAG GGKTSLARALAKKRKRPVMLMHGNHELNNKDLIGDFTGYTSKKV IDQYVRSVYKKDEQVSENWQDGRLLEAVKNGYTLIYDEFTRSKPA TNNIFLSILEEGVLPLYGVKMTDPFVRVHPDFRVIFTSNPAEYAGV YDTQDALLDRLITMFIDYKDIDRETAILTEKTDVEEDEARTIVTLVA NVRNRSGDENSSGLSLRASLMIATLATQQDIPIDGSDEDFQTLCIDI LHHPLTKCLDEENAKSKAEKIILEECKNIDTEEK* | 307 |
| Bradyrhizobium oligotrophicum S58_gvpN | MLRSDRAAIAGGQRGSRAQGDAVARNDAAAGSRAAIAQISPRPD ADNAALSPAPRTDLFENPQLASMAARALTYLNAGIPVHLRGPAGT GKTTMAMQLAARLGRPVVLLTGDDGLTAAHLVGREIGTKSRQVV DRYVHSVRRVETETSSMWCDAVLAQAVVEGLTFVYDEFTRSPPQ ANNPLLSVVEERILIFPAGSRKERLVHAHPEFRAILTSNPEEYAGVS RPQDALLDRLITFDLDDYDRETEIGIVSNRTGLAYAEAGVIVDLVR GVRRWPKAHHPPSMRSAIMIARIVARELITPSVDDPRFVRLCLDVL AAKAKPTDRDDRDRFAATLLRLMNNHCPAGAIDGG* | 308 |
| Burkholderia thailandensis sp. Bp5365 strain MSMB43_gvpN | MEASAEFVQTPAVRNLTERALTYLGAGYGVHLAGPSGTGKTTLA FHIAAQLGRQVVLMHGDDELGSADLVGRGAGYRRSRVVDNFIHS VVKTEEEMTTTWIDNRLTTACQHGLTLIYDEFNRSRPEANNALLP VLSEGILNLPNRMTGAGYLTVHPGFRAIFTSNPEEYVGVHKTQNA LMGRLITIQVGHYDRETEVEIVRARSGIARADAERIVDLTRRLRDA DDNGHHPSIRAAIALARALSYCGGEATPDNAGYVWACRDILGVDL EQDARTRSQAGRRTKARR* | 309 |
| Chlorobium luteolum DSM 273_gvpN | MRAAVNDNEMNTVLAPRPMANFVETEYIRDITERGLTYLKAGFPV HFRGPSGTGKTTVAMHLAGKIGRPVVVIHGDSEYKTSDLIGSEQG YKFRRLNDNFIHSVHKYEEDMSKQWVNNRLSIAIKKGFTLVYDEF TRSRPEANNILLPILQEKMLSTSASNEEDYYMKVHPEFRAIFTSNPE EYAGVNRTQDALRDRMVTMDLDYFDYETELRVTHAKSELTLEDS EKIVQVVRGLRESGKTEFDPTVRGSIMIARTLHIMQVRPEKTNDAV RKVFQDILTSETSRVGSKTNQEKVRAIVNDLIEAYL* | 310 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Dactylococcopsis salina PCC 8305_gvpN | MTTVLHARPKGFVSTPTIDRISGRAWRYLQSGFSIHLRGPAGTGKT TLAMHLADLLNRPIMLLYGDDEFKSTDLIGSNTGYTRKKVVDNYI HSVVKEEDELRQQWVDSRLTMACREGFTLVYDEFNRSPPEVNNV LLSALEEKLLVLPPDSNRSEYVRVSPNFRAIFTSNPEEYWGVHGTQ DALLDRVVTINVPEPDLETQQEIITQKVGINANDGEKIVNFVRQFR DRAAVKNSSGLRSCLMIAQVCHQHEIPVQTSDEGFRDICYDILSSR | 311 |
| Desulfobacterium vacuolatum_DSM 3385_gvpN | MSASMSSMKETRQRMSAPEQDNVVPEAGSDFVETPYVKDITDRA LAYLHVGYPVHFSGPAGTGKTTLAFHVAAKLKRTVMLIHGDDEF GSSDLIGKDSGYRKAKVVDNYIHSVVKTEESMNTVWADNRLTIAC QQGCTLVYDEFTRSRPEANNAFLSVLEEKILNIPSLRDIDQGYLQV HPEFRAIFTSNPEEYAGVHKTQDAMMDRLITITLDHFDRDTEVQVT MSKSDLPQKDAEKIVDIVRKLRKTGVNNHRPTIRACIAIGKILKHM GGGASKDNFVFKQICRDVLNVDTTKVTRDGEPLLPRKIDELINSL* | 312 |
| Desulfomonile tiedjei DSM 6799_gvpN | MNGAELRIASIETEVITANNENIVPEAGDRFVNTPHVEELTARAMA YLEVGYSVHFSGVAGTGKTTLAFHAAAKLGRPVILVHGDHEFGSS DLIGRDAGYKKSRLVDNFIHSVVKTEEEMRSLWVDNRLTTACRD GYTLIYDEFTRSRPEANNVLLSILEEKILNLPSLRRTGEGYLEVHPSF RAIFTSNPLEYAGVHKTQDALMDRIITINVDHYDRETEIEITRAKSG VCKQDATVIVDIIRELRLLGVNNHRPTIRAAIAIARVLAHTGEHAD QHNSVFQWLCKDVLSTDTVKVSRGGSPLMAKKVEEVIRKVCGRT GGKRSGKPVGSKEETSE* | 313 |
| Desulfotomaculum acetoxidans_DSM 771_gvpN | MQLNGLDKNSIINPVVLSDFVVTDYISNVVDRALAYIKAGFAIHLR GRSGTGKTSIAMYISSKLNRPTLVIHGDEEFRTSDLIGGRYGYRIRK TIDNFVQSVVKVEEDLVERWVDSRLTTACKNGYTLVYDEFTRSRP EANNILLSVLQERLLDISVARGALEGYVKVHPDFTAIFTSNPEDYA GVYGSQDALRDRMVTLDLDNYDKETEISIIKSKSKLSREDSERVVN ILRDLRELGDCEYGPTIRGGIMIAKTLQVLGAPVDKNNEMFRQICE EVLASETSRAGNLQALRKVRKVINELFNKYA* | 314 |
| Dolichospermum circinale_gvpN | MSITKVNHKRAVLRLRPGQFVVTPAIERVVIRALRYLRSGFPIHLR GPAGTGKTTLGMHLANCLDRPVMLLFGDDQFKSSDLIGSESGYTH KKLLDNYIHSVVKVEDEFKQNWVDSRLTACREGFTLVYDEFNRS RPEVNNVLLSALEEKILSLPPSSNQPEYLSVNPQFRVIFTSNPLEYCG VHSTQDALMDRLVTINMPEPDEITQTEILIQKTNIGRESANLIVRLV KSFRLATGAEKTSGLRSCLMIAKICADHDIPASTEDLDFREIAIDILF NRAQLSISESTDIFMGLLEQFSAELIKVLNDTHFPTDELLINNSQFIT QELVTQPNTELATDIPQELRKTEQN* | 315 |
| Enhydrobacter aerosaccus strain ATCC 27094_gvpN | MSMDQAEEIGVVTTIEPRPRADFVRTQSVEATARRALGYLNAGFS VHFRGPAGTGKTTLALHLAALLGRPMVMITGDEEMLTSTLVGTQ HGYHFRRVVDRFIHTVTKTEETADKRWADHRLTTACREGYTLIYD EFTRSRPEANNVLLSVLEEGLLVLPAQNQNEPYIKVHPNFRVIFTSN PQEYAGVHDAQDALGDRIVTIDMGHADRELELAIAAARSGLPPTG VAPIVDMVREFRETGEYDQTPTLRTSIMICRMMSQERLAPTIEDQQ FVQICMDILGGKSLPGGKGDNKRAQQQKMLLSLIEHHCPARSFTS VGEV* | 316 |
| Isosphaera pallida_ATCC-43644_gvpN | MDYESTALQLKPRPDFVATPWVRELADRALGYLTAGYPVHFSGP AGTGKTTLAMHLAALVNRPVVLLHGDDEFGSSDLVGDHLGFRST KVVDNFIHSVVKTEQSVSKTWVDHRLTTACRHGFTLIYDEFNRSR PEANNILLTILEERLLELPPIAGGRDGSGPLRVHPEFRAIFTSNPEEY AGVHKTQDALLDRMITISMGGHDEATETEITAAKSGLSRDEAARI VELARAVRALKPLRHPPTIRSCLMIAKVAALRKVPIDPNDALFLAI CRDVLRIDALPVDDPEATFAELIRRVFAPTPAVAPPRVPTTGFAAN RVVPIPRRPLAASASPPPGANGHAHLR* | 317 |
| Legionella drancourtii LLAP12_gvpN | MMTQENNGSLTDSKNNDKLIRFVNNRSDNILLEASEEFTETPHIRGI SERALAYLDIGYPIHLLGPAGTGKTTVALHIAAQLGRPVILIHGDDE FTGADLVGRGTGYHHSKLVDNFIHSVLKTEEEMTTMWTDNRLTT ACEQGYTLIYDEFNRSRAEANNALLSVLSEGILNLPGRRERDGIGY VDVHSNFRAIFTSNSEEYVGIHKTQNALADRLIAIKMDYPDQQSEI QIIEKKSTLPRKDIEIIVNLARELRLKSEKRPSIRGCIAIARVLAYHNR HAHADDPIFQAVCQDIFGISKEFLKQLLHPMDSGLQKRSEKNQESI KKYKTKNQKL* | 318 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Lyngbya confervoides BDU141951_gvnN | MSTVLQARPRNFVSTPAVERIARRALRYLQSGYSVHLRGPAGTGK TTLALHLADLLSRPIMLVFGDDEFKTSDLIGNQSGYTRKKVVDNYI HSVVKVEDELRHNWVDSRLTACREGFTLVYDEFNRSRPEVNNV LLSALEEKLLVLPPSGHRPEYLRVNPHFRAIFTSNPEEYAGVHGTQ DALLDRLITIHMPEPDELTQQQILIQKVGIEPADALMIVRLVKAFKS QMGNHSATSLRPSLMIANICHEHGVAMMTEDADFRDVCSDVLLS RVTNELSPATHTLWDLFNELTASADVLGPESNSTDVSPQPEADKP VETKGSKGKSTTKSKAKESAKASEEADEAGDDSASAPELDEIESSI LTFLTARESASLSEIESELSLTRFKAVDALRSLVEAGYLQKQNGAG KPAIYGLVPEES* | 319 |
| Microcystis aeruginosa NIES-843_gvpN | MTVTETQTRRAVLSLRPGQFVVTPSIDQIATRALRYLNSGFSIHLCG PAGTGKTTLAMHLANCLARPVMLIFGDDDFTSSDLIGSQSGYTHK KLMDNYIHSVLKVEDELKHNWVDSRLTMACREGFTLVYDEFNRS RPEVNNVLLSALEEKILTLPPTSHQPDYLQVNSQFRAIFTSNPLEYC GVHATQDALMDRLVTINMPEPDQLTQTEILAQKTGIGREDALFIVN LVKTFRVKTATEKTSGLRSCLMIAKVCASHDIAANSADSDFRDICA DVLLSRTNLSVDKSRAILWEILEDNPLESLSFLEEEEPSDAQVSTSE PSTGNQSLKAIQSLLRGNLPQRKD* | 320 |
| Nostoc punctiforme ATCC 29133_gvpN | MTTVLNASPQRFVNTPAVQRIAQRALRYLQSGFSIHLRGAAGVGK TTLAMHLADLLNQPIILLFGDDEFKTSDLIGNQLGYTRKKVDNFI HSVIKVEDEVRQHWVDARLTLACKEGFTLVYDEFNRSHPEVNNV LLSVLEERLLVLPTNQHRAEYIRVHPQFRAILTSNPQEYCGVHATQ DALMDRVITIDMPTPDELSQQEIVVHKTGIDSEKAEVIVRIVRTFWS RSGSGQGGGLRSCLMIAKICHEHEISVNPGDPSFQDICADILLSRTN QPLIEATRLLEEVLSEFYHRINTQSQPSEIIPNNQNQIVLEQRVPYEH EVYNYLCNSPGRRFSELAVELGIDRSQIVAALKSLREQGVLVQMQ GNAESPSISQTVAFDSGHLINK* | 321 |
| Nostoc sp. PCC 7120_gvpN | MTLTANNKKRAVLRVRPGQFVVTPAIEQVAIRALRYLTSGFAIHLR GPAGTGKTTLAMHLANCLDRPIMLIFGDDEFKSSDLIGSESGYTHK KLLDNYIHSVLKVEDEFKQNWVDSRLTLACREGFTLVYDEFNRSR PEVNNVLLSALEEKILTLPPSSNQPEYLHVNPQFRAIFTSNPLEYCG VHSTQDALMDRLVTINMPEPDELTQTEILAQKTALNRADALLIVRL VKAFRSRTGGEKTSGLRSCLMIAKVCAEHNILVSPQSSDFREICAD VLFNRTNWSASEAATIFLELLNHLDLQQIEEFKNSIIPEDTDAIAEG GFPTIIDSHFGTLDSEVLEQPGVEDSIPFEQEIYLYLQQYKSAALAL | 322 |
| Octadecabacter antarcticus 307_gvpN | VQQEFELSRTVATNALNSLEQKGLVSKNNHVYTIEEPNQS* MNSNLRATNSGGPDISKTMMPEAREDFVQTESVKSISRRALAYINA GYSVHFRGPAGTGKTTMAMHTAALLGRPVVLITGDEEMITSNLVG AESGYNYRKVTDNYIHTVSKIEESSDRSWNDHRLTTACREGYTLIY DEFTRSRAEANNVLLSVLEEGILVLPAQNRGEPPFIKVHPNFRVIFTS NPQEYAGVHEAQDALSDRIVTIDIGEADRELEVSIASSRSGLEVAK TEPIVDMVRAFRDTGEYDQTPTLRACIVICRMVANEKLNTTIDDPF FVQICLDVLGSKSTFGGKEHDKRTQQRKLLLDNLKHYCPSKVSTK PSAKDDESKSTLIQVSSRGSL* | 323 |
| Octadecabacter arcticus 238_gvpN | MMPEARKDFVQTDSVKSVSRRALAYINAGYSVHFRGPAGTGKTT MAMHTAALLGRPVVMITGDEEMVTSNLVGAESGYNYRKVTDNYI HTVSKVEESSDRSWNDHRLTTACREGYTLIYDEFTRSRAEANNVL LSVLEEGILVLPAQNRGEPPFIKVHPDFRVIFTSNPQEYAGVHDAQD ALSDRIVTIDIGAADRELEVSIASSRSGLEVAKTAPIVDMVRAFRDT GEYDQTPTLRACIMICRMVANEKLNPTIDDSYFVQICLDVLGSKSM FGAKEQGKRTQQEKLLLDNLSHHCPSPPPSKPSAKEAEAKPRSIQA TSRGPA* | 324 |
| Pelodictyon phaeo-clathratiforme_gvpN | MRRQGCDSEMNTVLEPKPMPNFVETDYIRDITSRGLTYMKAGFPV HFRGPSGTGKTTVALHLASKIGRPVVIIHGDSEYKTSDLIGSEQGYK YRRLDDNFIHSVHKYEEDMTKQWVNNRLTIAIKKGFTLVYDEFTR SRPEANNILLPILQEKMMSTSSSNEELYYMKVHPEFRAIFTSNPLEY AGVNRTQDALRDRMVTMDLDYFDYETELMITHAKSGMSLDDAE KIVKIVRGLRESGKTEFDPTIRGSIMIAKTLNVLNARPDKTNELFKK VCQDILTSETSRVGSKTNQERVRGIVNELIDLHS* | 325 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| *Phormidium tenue* NIES-30_gvpN | MNTVLQARPRNFVSTPTLERTSIRALRYLQSGYSIHLKGPAGTGKT TLALHLADLLARPIMLLFGDDEFKTSDLIGNQSGYTRKKVVDNYIH SVVKVEDELRHNWTDSRLTLACREGFTMVYDEFNRSRPEVNNVL LSALEEKLLVLPPSNNRALYIRVSPHFRAILTSNPLEYCGVHGTQD ALQDRLITINMPEPDELAQQQILVQKVGIDSSAALQIVQLVKAFQS AVAPDMVSSLRPSLMIATICHDHDILPLAENADFRDVCSDILLARS KEPAPDATRHLWNLFNRFVVSQAALVNDLSLKPEAHPTARFHGEE EDDAPLQPLEALVESDIDDVAVEDQPVIGPQDLQGETLPEAVIPEP QGETVVETPAEAEALPEEIARVQVSPDDIETRIFDYLDATGTASLV NIEAALDLNRFQAVNAVKSMLDQGLIEKQETDGQLQGYQLSSN* | 326 |
| *Planktothrix agardhii* str. 7805_gvpN | MTTVLQARPKGFVNTPTIEQLTIRALRYLQSGFSLHLRGPAGTGKT TLAMHLADLLNRPIVLIFGDDELKSSDLIGNQLGYTRKKVVDNFIH SVVKLEDELRQNWIDSRLTLACKEGFTLVYDEFNRSRPEVNNVLL SALEEKLLVLPPNNSRSEYIRVNPHFRAIFTSNPLEYCGVYGTQDAL LDRLITIDMPEPDDETQQEILIQKIGISPEDAKNIIEIVKIYLEITTQKK EIKPVQNGKAARPHIDKASGLRPGLIIAKICHEHDISIQENNQDFIKV CADILLSRTNLSLTEAQNKLEKVIKTVLTDGDTSNNSFLPPSETQLT ENNSLEIEEQVYQYLKTTSARVSEIEVALGLNRVQTTNVLRSLLK QGHLKQQDNRFFAVNKQGELIQP* | 327 |
| *Planktothrix rubescens*_gvpN | MTTVLQARPKGFVNTPTIEQLTIRALRYLQSGFSLHLRGPAGTGKT TLAMHLADLLNRPIVLIFGDDELKSSDLIGNQLGYTRKKVIDNFIHS VVKLEDELRQNWIDSRLTLACKEGFTLVYDEFNRSRPEVNNVLLS ALEEKLLVLPPNNSRSEYIRVNPHFRAIFTSNPLEYCGVYGTQDAL LDRLITIDMPEPDDETQQEILIQKIGISPEDAKNIIEIVKIYLEITTQKK EIKPVQNGKAARPHIDKASGLRPGLIIAKICHEHDISIQENNQDFIKV CADILLSRTNLSLTEAQNKLEKVIKTVLTDGDTSNSFLPLSETQLT ENNSLEIEEQVYQYLKTTSARVSEIEVALGLNRVQTTNVLRSLLK QGHLKQQDNRFFAVNKQGELIQP* | 328 |
| *Psychromonas ingrahamii* 37_gvpN1 | MSIENLNNVSEIKIEQSDDDHIYPEASEDFVETPYIKEVTERAMLYL DAGYPVHFAGPAGTGKTTLAFHIAALRQRPVTLIHGNHEFGTSDLI GKESGYRRHRVVDNYVHSVVKEEEELQSLWSDNRLTTCCRNGDT LVYDEFNRSTPEANNVLLSILLEGILNLPSSRSDGYLEVHPQFRAIFT SNPQEYAGTHATQDALVDRMITIMLHYPDRHTEVRVAIAKSGINS DEAGSIVDIVNEFRELCGSKIVSSGPKTMPTVRASIAIARVLVQKGE HAFRDNTFFHRICRDVLCMYTQQVSFSNRSVLDKQLEDLIMKFCP ATYKSSGSKIRA* | 329 |
| *Psychromonas ingrahamii* 37_gvpN2 | MSINNLNISTIKIEQPENDNIYPEASAEFVQTPYIQEVTERALLYLDA GYPVHFAGPAGTGKTTLAFHIAALRKRPVTLIHGNHEFGSSDLIGK ESGYRRHRLVDNYVHSVMKEEEELKSLWVDNRLTTCCRNGDTLV YDEFNRSTPEANNVLLSILLEGILNLPSLRSMGDGYLEVHPSFRAIF TSNPQEYAGTHATQDALVDRMITIMLNYPDRDTEVRVAVAKSGIS NEEAGFIVDIVNEFRELSNHKSLSSGQKSMPTVRASIAISRVLIQKG EHAFRDNVFFHRVCHDVLCMYIQKISPSNRSFLDKQLEVLIGKFCP AAKSALVPKVVK* | 330 |
| *Rhodobacter capsulatus* SB 1003_gvpN | MTIPRDLPWGDARTPLFEDEELRSLLDRAEIYLREGIAIHFRGPAGV GKTTLALHLAQRFARPVTFFVGNDWLGRADIFGRDLGETVSTVQD HYISSVRRAERKSRIDWQEAPLARAMRDGHVLVYDEFSRSRPEAN AALLSVIEEGVLPLSDPAAGRSHIVAHPDFRVILTSNPRDYVGVQA VPDALLDRMITFSLDGMSFETEVGIVATAARTDPADARAICALIHL LRAEKPGTMEISMRSGIMIARLARAAGVAPDPADPVFVQICADVL GTRMRGSDIDDVMALLLRPDPAPAACAGGAR* | 331 |
| *Rhodobacter sphaeroides* 2.4.1_gvpN | MTVLSPSLPHAAGIDAALVENPWLGLRRSGRYFQNAETEALFARA LGYARAGVCVHLAGPAGLGKTTLALRIAQALGRPVAFMTGNEWL GSRDFIGGEIGQTVTSVVDRYIQSVRRTEQSARIDWKESILGQAMR CGQTFIYDEFTRASPEANAALLSVLEEGVLVSTDGASRHQYIEAHP DFRVLLTSNPHEYQGVKAAPDALIDRMVTLRLEEPSAPTLAGIVAL RSGLDPATARRIVDLILSVQRSGEMQAPPSMRTAILVARLAAPLRL AGRLSDAALAEIAADVLRGRGLEADAAAFEAKLAAPTPGETAR* | 332 |
| *Serratia* sp. ATCC 39006_gvpN | MIKQNTVSQYTVDDDLVVPEASEHFVATSYVNDIIERALVYLRAG YPVHFAGPSGIGKTTLAFHLAALWGRPVTMLQGNEEFVSSDLTGK DIGYRKSSLVDNYIHSVLKTEEQMNRMWVDNRLTTACRNGDMLI YDEFNRSKAETNNVLLSVLSEGILNLPGLRGVGEGYLDVHPEFRAI FTSNPEEYAGTHKTQDALMDRMITINIGLVDRDTELQILHARSELE LKEAAYIVDIIRELRGNEHETKHGLRAGIAIAHILHQQGIKPRYGDK LFHAICYDVLSMDAAKIQHAGRSIYREMVDGVIRKICPPIGSDTVK ASTQKIKAVE* | 333 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Stella vacuolata_ATCC-43931_gvpN | MSTEPAPVMPPSTDIEFGSQRPARPKPAEALAVGYRLSARPAAPST LTLRPRADFVETDQVKDLTRRGLGFLRAGYPLHFRGPAGTGKTTL ALHVAAQLGRPVIVITGDNELGTADLVGSQRGYHYRKVVDQFIHN VTKLEETANQRWTDHRLTTACREGYTLVYDEFTRSRPETHNVLLG VFEEKILFLPAEAREECYIRVHPDFRAIFTSNPQEYAGVHASQDALA DRLATIDVDYPNRAMELAVASARTGLAEAEAARIIDLVRAFRASG DYQQTPTMRASLMIARVAAQEGLRISVDDPGFVQLCMDALESRIF SGARQEADARARHRVALLGLLATHCPSEAPVARVATVARAKRKS AS* | 334 |
| Thiocapsa rosea strain DSM 235 Ga0242571_11_gvpN | MSAKPLQDASEVSALNNDNVQPEASDTFVCTPSVEALAERASAYL QAGYPVHLAGPAGTGKTTLAFHAAAKRGRPVKLIHGNDELGLAD MVGQDNGYRRNTLVDNYIHSVVKTQEEVRTFWIDNRVTTACLNG ETLIYDEFNRSRPEVNNIFLSILGEGILNLPNRRHQGAGYLEVHPEF RVIFTSNPEEYAGTHKTQDALMDRMITMKIGHYDRETEIRVTRAK SGLPPSEVAIVVDIVRELRGQSVNHHRPTLRACIAIARIMADRRISA RSNNSFFRDICRDILDMDSAKVRRDGNALGESPVDDVVASISARAR RPKIVEPKGLHKEI* | 335 |
| Tolypothrix sp. PCC 7601_gvpN | MTNTENHKKRAVLRVRPGQFVVTPAIEKVAIRALRYLTSGFAIHLR GPAGTGKTTLAMHLANCLDRPIMLIFGDDEFKSSDLIGSESGYTHK KLLDNYIHNVLKVEDELKQNWVDSRLTLACREGLTLVYDEFNRS RPEVNNVLLSALEEKILTLPPSSNQPEYLHVHPKFRAIFTSNPLEYC GVHSTQDALMDRLVTINMPEPDEQTQIEILTHKTGIHHEYAQLIAR LVKAFRSATGAEKTSGLRSCLMVAKVCAEHDIVTPENTDFREICA DVLFNRTNLSASDATTLFLELLNHVQVKPVEPVDDSDPYDVAEAE IVGAAEPQTDAIAEPVTLDESLLSDQPN* | 336 |
| Trichodesmium erythraeum IMS101_gvpN1 | MTTVLNVSPDRFVSTPGVERVTQRASRYLESGYSVHLRGPAGVGK TTLALHLAHLRQQPIFLMIGDDEFKTSDLIGNKSGYTRKKLVDNYI HTVLKVEDELRDNWIDSRLTLACKEGFTLIYDEFNRSRPEVNNVLL SVLEEKMLVLPPSQNQSEYIQVHPQFRVILTSNSEEWTGVHATQDA LLDRVVTIGMEQPDISTEQNIVIQKTGINPLKAEVIIKLVRSVRQRV DKEDLGSLRSALMISKVCHDHDIPLDGKDSSFSDLCADILISRPNLP RQEALQQLDEVLEEFFPADQPSSSDVGLEKEGSL* | 337 |
| Trichodesmium erythraeum IMS101_gvpN2 | MTTVLNVSPDRFVSTPSVERVTQRASRYLESGYSVHLRGPAGVGK TTLALHLAHLRQQPIFLMIGDDEFKTSDLIGNKSGYTRKKLVDNYI HTVLKVEDELKHNWIDSRLTLACKEGFTLIYDEFNRSRPEVNNVLL SVLEEKMLVLPPSQNQSEYIQVHPQFRVILTSNSEEWTGVHATQDA LLDRVVTIGMGQPDISTEQNIIIQKTGINPLKAEVIIKLVRSVRERLE TEDLGSLRSALMISKVCHDHDIPLGGKDSNFSDLCADILISRANLPR QEALKQLDEVLEELFPADQLSISDIGLKKEGSL* | 338 |
| gvpV | | |
| Anabaena-flos-aquae_gvpV | MIKNIQVFFMKTISNRSISRAKISTMPRPKSDASSQLDLYKMVTEK QRIQRDMYSIKERMGLLQQRLDILNQQIEATEKTIHKLRQPHSNTA QNIVRSNIFVESNNYQTFEVEY* | 339 |
| Aphanizomenon flos-aquae NIES-81_gvpV | MKSFRHRSIIRAKISTMPRHISEASSQLELYKMVAEKQRISRELSSIK ERMATLQKRLDSLNNEIDNTEKTIHKLRQPHSSTAQNIVRSKNVVE SNNYQTFEIEY* | 340 |
| Arthrospira platensis NIES-39_gvpV | MRYKYHRQIQPKLSAIPRQKSQANLYRNSYLLAVEKKRLTEELEV LQSRSHIIEQRLALIEDQLGELEKDVTQLSVPPSPKPQNNLPVNNPE PPPQSNPTNSSHINTFMVDY* | 341 |
| Burkholderia thailandensis sp. Bp5365 strain MSMB43_gvpV | MPIPKKGLHDIRFRHAPGATPLPVHSMYMRISCIEMEKSRRTIERRA AQRRIAAVDSRVADLEREKARLYAAIDNEAPQAGDIRGSFRIRY* | 342 |
| Desulfobacterium vacuolatum_DSM 3385_gvpV | MLKNRNRSIKGVQNIKTHAGKVDHVSHPHMAYMRISCLEMEKAR KNKEKSGAQKRIDMINQRLMEIEKEKAHIQRILGDTSIALESSNVD HDSEIKGGFKIKY* | 343 |
| Desulfomonile tiedjei DSM 6799_gvpV | MNIRMKGNSRGLRDIRTHSGKVDRVGLPYMAYMSISCLEMEKAR REKERLSALTRIKNIEQRIREILAEKDLLLKGVGERTRTDLQKASTP RDQSAQCKGGFKIRY* | 344 |
| Legionella drancourtii LLAP12_gvpV | MMPALVKGLRNIKTMSNRLDKVQSPHEAFISAAALHREKQRHLQ ELAILRNRLDEINLRLEQINEQQNQVAEAFDISPPRAVKSALRTGIQ SKTGSTSHGFKIKY* | 345 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Microcystis aeruginosa NIES-843_gvpV | MTTTRPPRPIRSKISTMPRKQSEADHQLELYKLITEKQRIQEKLEM MERQIQQLKNRLTFVTEQIETTEQSIQNLRTANPPSVAKKPDSPKT VAHSSNNSSNFQTFYLEY* | 346 |
| Nostoc punctiforme ATCC 29133_gvpV | MHRTPNRRQIQAKLSTMPPQRSQATVYLNAYKMMLEKERLEEEL EKLEARRHQIQQRLAILNSQTIPEENMTHQQANTDLENNTPKFNTL TLEY* | 347 |
| Nostoc sp. PCC 7120_gvpV | MLSIIQVFPMTKVRNRGIIRPKITTMPRNKSEASSQLELYKLVTEQQ RIKQELAFIEQRTVLLKQRLSTLKTQIEGTERSINHLRHSELKYSRIA LPKIFSETNNYQAFDIEY* | 348 |
| Planktothrix agardhii str. 7805_gvpV | MRPFRSQPPILPKISTMPRQKTEATLYRSLYQLAVEKKRLQEELESL GQRFETVTQRLQQIETQIQGLETDVKQIAPPKPPETKPNQPSTPTPT KAEPGSVSTFTLDY* | 349 |
| Psychromonas ingrahamii 37_gvpV1 | MTAAKRKTLRGLADIRTISSCGTSGQEAYQMYLKRGVLEMEKLR RQKEKNSALERVTNINRRLMAIDTDIDFLCQSLKVIEKRTNQENSIV EKSVSRGFKLRY* | 350 |
| Psychromonas ingrahamii 37_gvpV2 | MIFSKKKNALRGLADIRTLSGCGTSGQEAYQMYLKRGVLEMEKL RRQKEKNSALERVRNINYRLMAIDADIDFLCQSLKVIEERTNKENS ISNESVTYKKGFKLRY* | 351 |
| Serratia sp. ATCC 39006_gvpV | MAISTRPLRTLSDIKTHSGRVSGEHQTYRDYFQIGALELERWRRTR EREAASSRIASIDERIADIDKEKAALLADATAASAVAENNDKSEAA EKKKKSSGLRIKY* | 352 |
| Thiocapsa rosea strain DSM 235 Ga0242571_11_gvpV | MSKFTQPSRSVRDIKTLAGMADDVRAPHKMYMRLFALETERHRR LQERASAMLRVDNIDARCALIALEMEQLLQILGVEAVAPGGPPAN ARPGSGRVPTQPHRGRGKGTGAGRQTTSGETSVGEAVKIRY* | 353 |
| gvpW | | |
| Anabaena-flos-aquae_gvpW | MELENLYTYAFLEIPSSPLILPQGAANQVVLINGTELAAIVEPGIFLE SFQNNDEKIIQMALSHDRVICELFQQITVLPLRFGTYFTSTNNLLNH LKSHEKEYQNKLEKINGKNEFTLKLIPRMIEEIVPSEGGGKDYFLA KKQRYQNQNNFSIAQAAEKQNLIDLITKVNQLPVVVQEQEEQIQIY LLVSCQDKTLLLEQFLTWQKACPRWDLLLGDCLPPYHFI* | 354 |
| Aphanizomenon flos-aquae NIES-81_gvpW | MELENLYTYAFLKTPSFSLHLPQGSTTSVIQIDGNGLSAIVEPGISLD SFQDDDEKIVQMAIEHDRVICDIFRQITVLPLRFGTYFANTDNLLTH LESYGQEYLDKLEKINCKTEFILKLIPRMITEESPVLESGRHYFLAK KQHYQRQKNFILAQASEKEILINFISKINQIPVIIQEQEEEVRIYLLVN YQDKTLLLEQFLTWQQTCPRWDLFLGEGIPPYHFI* | 355 |
| Arthrospira platensis NIES-39_gvpW | MYVYAFIKSQSISWKSVQGIYEPVVLLEAGALAAVVEPNLQAENL SADNEEELMRAVLTHDRIVCQIFEETTVLPVRFGTCFDSEARLCEH LTTEGDRYFRQLEKLTGRAEYLLEAIPQPFNQEKPSSDTTAPPTKG RDYFLQKKRLHQQRLNFEQQQEQQWQDFINAIASKYPIVQGKATE DAERIYLLIPRSQEVALVEWVAQQQQNIDLWEFSLGNAVPAYHFL* | 356 |
| Dolichospermum circinale_gvpW | MKLENFYTYAFLEIPRFPLVLPQGAASQVILINGSGMSAIVEPGISLE SFQNNDEKIIQMALSHDRVICELFQQVTVLPLRFGTCFTSTNNLLN YLELHRQEYQEKLEKINGKIEFTLKLIPQTMEEPAPLERGGRDYFL AKKQRYQDQNNFRIAQAAEKQNLIDSISKVNQLPFVIQEKEEEVNI YLLVKSEDKTLLLEQFLNWQKACPRWDLLLGEPLPPYHFI | 357 |
| Microcystis aeruginosa NIES-843_gvpW | MKLYNLYTYAFLKTPIESLKLPVGMANPLLLITGGELSAVVEPEVG LDTLQNDDERLIQSVLCHDRVICQLFQQTTILPLRFGTSFLEAENLL THLCSHGQEYQEKIEELEGKGEYLLKCIPRKPEEPVLFSESKGRQYF LAKKQLYEAQQDFYTLQGSEWQNLVNLITQSYPSTRIITAPGTESRI YLLVNLQEEPLLIEQVLHWQKACPRWELQLGQVSPPYHFT* | 358 |
| Nostoc punctiforme ATCC 29133_gvpW | MSIYAYALLVPTASPLVLPLGMERNTELVYSSGLAALVEPEISLEAI QATDERLLQAVLNHDHVIRELFQQTPLLPLRFGRGFTSVEKLLNHL ENHQEQYLETLTQLADKVEYSVKVTACSLLDDSDTIDARGKAYLL AKKQRYQTQQAFQAQQCEQWELLNELILKTYTNVICETRQSDVR QIHFLAQRNDSTLSTQLFSLWQVQCSHWQLALSEPLPPYHFLKNTL I* | 359 |

TABLE 2-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein | Amino acid sequence | SEQ ID NO.: |
|---|---|---|
| Nostoc sp. PCC 7120_gvpW | MRSPNFYTYAFLNTPDIPLRLPSGNLGQLLLIHGHKLSAVVEPGISL ESSQNNDEEVIKMVLAHDRVICELSQQTTVLPLRFGTYFNSEETLL NHIESHAQEYQKKLDHIQGKTEYTLKLIPRKFEELAKVSGGNGRD YFLAKKLHYEHQKNFIGDQNREKNHLINLIMDVYRSSAIIQDYVEE VRLHLLVDRHDKTLLFKQVLTLQEKCPHWNLILGEPLPPYHFV* | 360 |
| | gvpR | |
| Bacillus-megaterium_gvpR | MEIKKIMQAVNDFFGEHVAPPHKITSVEATEDEGWRVIVEVIEERE YMKKYAKDEMLGTYECFVNKEKEVISFKRLDVRYRSAIGIEA* | 361 |
| | gvpS | |
| Bacillus-megaterium_gvpS | MSLKQSMENKDIALIDILDVILDKGVAIKGDLIISIAGVDLVYLDLR VLISSVETLVQAKEGNHKPITSEQFDKQKEELMDATGQPSKWTNP LGS* | 362 |
| Rhodococcus hoagii 103S_gvpS | MSATPDRRIALVDLLDRVLGGGVVVAGEITLSIADVDMVHISLRTL VSSVSALTRPPDEKPENDG* | 363 |
| | gvpT | |
| Bacillus-megaterium_gvpT | MATETKLDNTQAENKENKNAENGSKEKNGSKASKTTSSGPIKRA VAGGIIGATIGYVSTPENRKSLLDRIDTDELKSKASDLGTKVKEKS KSSVASLKTSAGSLFKKDKDKSKDDEENVNSSSSETEDDNVQEYD ELKEENQTLQDRLSQLEEKMNMLVELSLNKNQDEEAEDTDSDEEE NDENDENDENEQDDENEEETSKPRKKDKKEAEEEESESDEDSEEE EEDSRSNKKNKKVKTEEEDEDESEEEKKEAKPKKSTAKKSKNTKA KKNTDEEDDEATSLSSEDDTTA* | 364 |
| | gvpU | |
| Bacillus-megaterium_gvpU | MSTGPSFSTKDNTLEYFVKASNKHGFSEDISENVNGAVISGTMISA KEYFDYLSETFEEGSEVAQALSEQFSLASEASESNGEAEAHFIHLK NTKIYCGDSKSTPSKGKIFWRGKIAEVDGFFLGKISDAKSTSKKSS* | 365 |

The exemplary GVGC cluster formed by Ana-gvpA, Ana-gvpC, Mega-gvpN Mega-gvpF, Mega-gvpG, Mega-gvpL Mega-gvpR Mega-gvpS, Mega-gvpT Mega-gvpK, Mega-gvpJ, and Mega-gvpU was used as ARG in the experiments summarized in the following Examples.

Example 2: BURST Signals

FIG. 4 shows an example of the BURST paradigm. Panel (a) shows an illustration of the GV collapse (401) in response to a step increase in acoustic pressure (402), along with the transient acoustic signal created (403). Shortly after the collapse (401), the signal is diminished with the GV in a collapsed state (404). Panel (b) shows three consecutive images from the successive images taken during the collapse. In this example, these are images ten (410), eleven (411), and twelve (412) of a 50-frame sequence. The frames were taken for a BURST sequence applied to a tissue-mimicking phantom with wells containing plain 1% agarose (414) or 10^8 cells/ml ARG-expressing E. coli embedded in 1% agarose (415). The acoustic pressure is ramped from 0.27 MPa in the first 10 frames, including frame ten (410) to 3.2 MPa for the remaining 40 frames, including frames eleven (411) and twelve (412). Scale bar: 1 mm. Panel (c) shows a contrast-to-noise ratio (CNR) vs. frame number, showing the qualitative differences in the temporal dynamics of mean pixel intensity for different materials, corresponding to the regions of interest (420, 421, 422) identified in panel (b). Panel (d) shows example output of the template projection algorithm, showing selective enhancement of tissue signal (420), GV signal (421), and noise (422). Panel (e) shows example output of the template unmixing algorithm, showing estimated contribution of tissue signal (420), GV signal (421), and noise (422) to every pixel. In this example, the noise (422) and tissue (420) signal levels are fairly constant over time, but BURST can also be used where the signals change over time.

The following protocol was used to obtain the results illustrated in FIG. 4. Plasmids encoding ARGs were transformed into chemically competent E. coli BL21(A1) cells (Thermo Fisher Scientific™) and grown in 5 ml starter cultures in LB medium with 50 μg ml-1 kanamycin, 1% glucose for 16 h at 37° C. Large-scale cultures in LB medium containing 50 μg ml-1 kanamycin and 0.2% glucose were inoculated at a ratio of 1:100 with the starter culture. Cells were grown at 37° C. to OD600 nm=0.5, then induced with 0.5% I-arabinose and 0.4 mM Isopropyl β-d-1-thiogalactopyranoside IPTG for 22 h at 30° C.

Ultrasound imaging was performed using a Verasonics Vantage™ programmable ultrasound scanning system and an L22-14 v 128-element linear array transducer (Verasonics™) Image acquisition was performed using a custom imaging script with a 64-ray-lines protocol with a synthetic aperture to form a focused excitation beam. An aperture of 65 elements was used. The transmit waveform was set to a frequency of 15.625 MHz for the L22 transducer, 67% intra-pulse duty cycle, and a 3/2-cycle pulse.

Phantoms for imaging were prepared by melting 1% (w/v) agarose in phosphate buffered saline (PBS) and casting wells using a custom 3D-printed template that included a pair of 2 mm diameter wells. E. coli cells at 2x the final concentration at 25° C. were mixed in a 1:1 ratio with molten agarose or molten TMM (at 56° C.) and immediately loaded into the phantom. The concentration of cells was determined before loading by measuring their OD600 nm. An arbitrary number of additional signal categories and corresponding templates can be used in the signal unmixing algorithms, including templates for different types of GVs, though the quality of the signal unmixing will tend to degrade as the number of signal categories increases. However, the three original signal templates were included for any version of BURST since they each model signal components that will be present to some degree in all setups.

Because the results found in FIG. 4 are intended primarily to illustrate the BURST method, the protocol described above need not be followed exactly to obtain similar results. For instance, purified GVs or GVs expressed in a different type of cell could be used, different pressure levels could be applied as long as they are above the collapse threshold, and higher or lower concentrations of GVs could be used as long as they allow for detectable signal.

The GV template represents transient signal produced by GV collapse, the tissue template represents persistent signal that varies in proportion to the pressure applied, and the noise template represents persistent signal that does not vary in response to pressure applied. There are no limitations on the linearity of the signals, as mentioned earlier. The unmixing results will remain valid for all relative signal amplitudes, though GV signal may become undetectable in practice if the relative amplitudes of the noise and tissue signals are sufficiently large. Thermal noise, electronic noise, and many other mechanisms can contribute to the overall noise levels.

An arbitrary number of additional signal categories and corresponding templates can be used in the signal unmixing algorithms, including templates for different types of GVs, though the quality of the signal unmixing will tend to degrade as the number of signal categories increases. However, the three original signal templates can be included in any version of BURST since they each model signal components that will be present to some degree in all setups. The GV template represents transient signal produced by GV collapse, the tissue template represents persistent signal that varies in proportion to the pressure applied, and the noise template represents persistent signal that does not vary in response to pressure applied. There are no limitations on the linearity of the signals, as mentioned earlier. The unmixing results will remain valid for all relative signal amplitudes, though GV signal may become undetectable in practice if the relative amplitudes of the noise and tissue signals are sufficiently large. Thermal noise, electronic noise, and many other mechanisms can contribute to the overall noise levels.

Example 3: BURST at Different Pressure Values

FIG. 5 shows examples of loBURST and hiBURST collapse signal generation (0-80° dB, 2 mm scalebars). Panels (a) and (c) show the power spectra resulting from BURST acquisitions with liquid buffer suspension of intact acoustic reporter gene (ARG) *E. coli* Nissle at 10^4 cells/ml, with PPP ranging from 3.2 MPa to 4.3 MPa. Panels (b) and (d) show their corresponding images, with the brighter pixels indicating higher dB. Panels (a) and (b) show the power spectra and images acquired using standard BURST imaging parameters: ½-cycle pulse at 6 MHz. Panels (c) and (d) show the power spectra and images acquired using a 10-cycle pulse at 5 MHz to increase frequency resolution and ensure the second harmonic peak is inside the bandwidth of the transducer. Panel (e) shows an image time series acquired with an ultrafast version of hiBURST, showing that many of the single sources observed in liquid buffer ARG-expressing cell suspension persist for several hundred microseconds (arrows). Panel (f) shows the time domain signal used to generate the power spectrum in panel (a) and panel (g) shows the time domain signal used to generate the power spectrum in panel (c), both at 4.3 MPa (hiBURST). Panel (h) shows BURST images acquired with the 10-cycle sequence at pressures near the 10-cycle loBURST threshold, showing the emergence of single dim sources.

The following protocol was used to obtain the results illustrated in FIG. 5. Plasmids encoding ARGs were transformed into electro-competent *E. coli* Nissle 1917 (Ardeypharm GmbH) and grown in 5 ml starter cultures in LB medium with 50 µg ml-1 kanamycin, 1% glucose for 16 h at 37° C. Large-scale cultures in LB medium containing 50 µg ml-1 kanamycin and 0.2% glucose were inoculated at a ratio of 1:100 with the starter culture. Cells were grown at 37° C. to OD600 nm=0.3, then induced with 3 µM IPTG for 22 h at 30° C.

An L11-4 v transducer (Verasonics™) was mounted on a computer-controlled 3D translatable stage (Velmex™) above a 4 L bucket containing 3.8 L water that had been circulated through a water conditioner for 1 hour to remove air bubbles. 200 ml of 20×PBS was then gently added to the water, with the mouth of the PBS-containing bottle at the level of the surface of the water to avoid creating bubbles. A piece of acoustic absorber material was placed at the bottom of the bucket to reduce reflections. A MATLAB™ script was written to control the Verasonics system in tandem with the Velmex stage, which was programmed to move 1 cm after each of 5 replicate BURST pulse sequences. Intact Nissle cells were added to the bucket for a final concentration of 10^4 cells/ml. After each set of replicate acquisitions, the bucket was stirred gently with a glass rod and another set of acquisitions were made at the next pressure level.

Example 4: Comparison of BURST with Previous Techniques

To compare the performance of BURST with existing techniques under a range of well-controlled conditions, several concentrations of ARG-expressing Nissle *E. coli* in an agarose phantom were imaged using various imaging techniques (see e.g. Example 3 and FIG. 5). The phantom consisted of a rectangular block of agarose gel with several pairs of cylindrical wells that were filled with ARG-expressing Nissle *E. coli* embedded in phantom material. In each pair, the well on the left contained cells whose GVs had been hydrostatically collapsed to serve as a control, while the well on the right contained cells with intact GVs. In half the well pairs, the cells were embedded in plain 1% agarose. In the other half, the cells were embedded in tissue-mimicking material (TMM)[3] to emulate the challenges of in vivo imaging. Cell concentrations ranged from 10^9 cells/ml to 10^3 cells/ml. For each phantom material and concentration, images were acquired using four different ultrasound imaging techniques: 1) standard B-mode, 2) pre-collapse/post-collapse difference, 3) loBURST, and 4) hiBURST. For consistency and quantifiability, template unmixing was used to process all BURST images.

Figure 6:
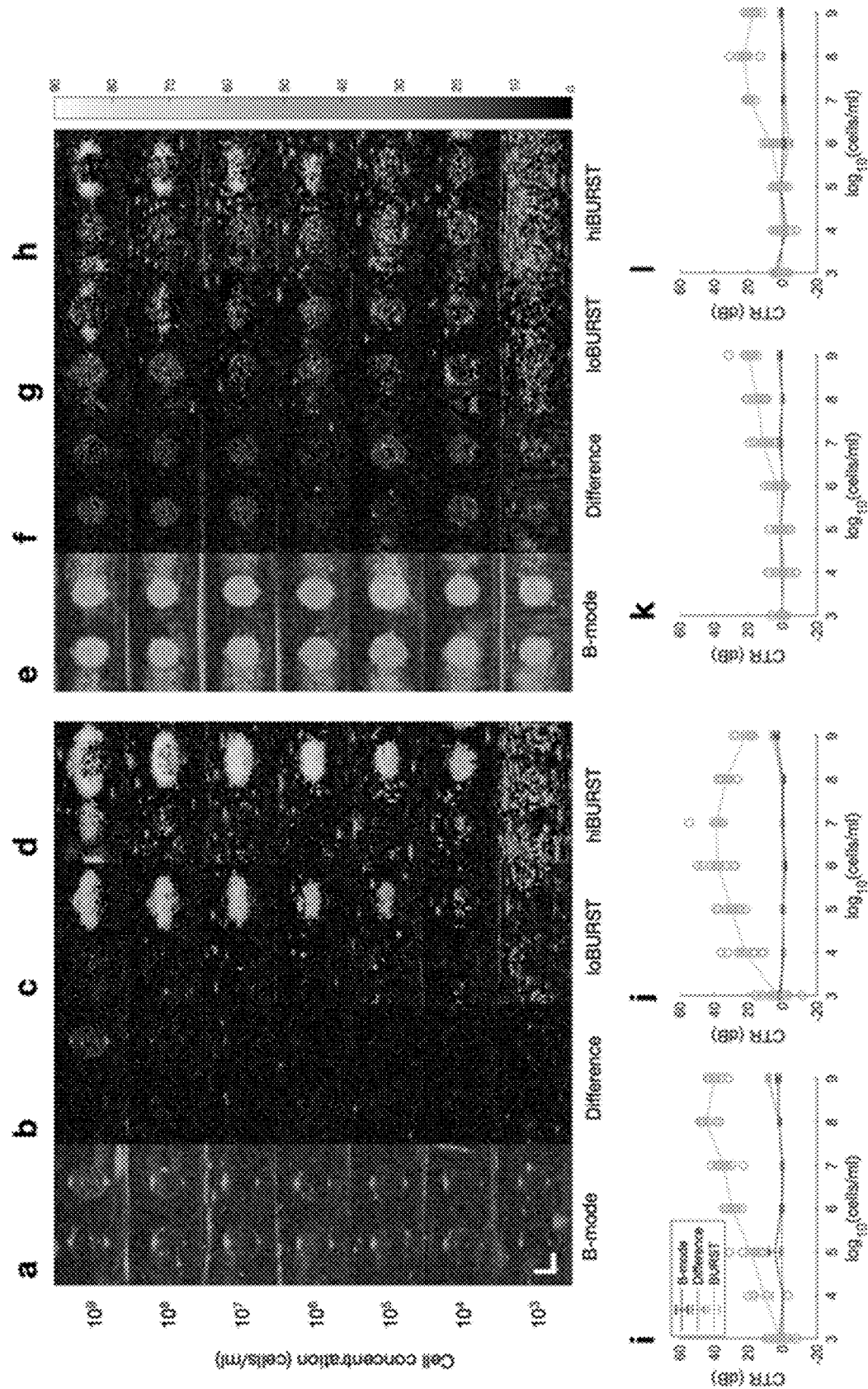
FIG. 6 shows an example of in vitro BURST imaging. Panels (a)-(d) show an array of ultrasound images of a cross section of cylindrical wells containing acoustic reporter gene (ARG)-expressing Nissle E. coli embedded in non-scattering agarose. Panels (e)-(h) show ultrasound images of the same conditions as panels (a)-(d), but with the cells embedded in tissue-mimicking material (TMM) inside the wells. Panels (i)-(l) show contrast-to-tissue ratio (CTR) vs log cell concentration for loBURST and hiBURST. Panel (i) shows loBURST on agar-embedded cells. Panel (j) shows hiBURST on agar-embedded cells. Panel (k) shows loBURST on TMM-embedded cells. Panel (l) shows hiBURST on TMM-embedded cells.

The following protocol was used to obtain the results illustrated in FIG. 6. Plasmids encoding ARGs were transformed into electro-competent *E. coli* Nissle 1917 (Ardeypharm GmbH) and grown in 5 ml starter cultures in LB medium with 50 µg ml-1 kanamycin, 1% glucose for 16 h at 37° C. Large-scale cultures in LB medium containing 50 μg ml-1 kanamycin and 0.2% glucose were inoculated at a ratio of 1:100 with the starter culture. Cells were grown at 37° C. to OD600 nm=0.3, then induced with 3 μM IPTG for 22 h at 30° C.

FIG. 6 shows an example of in vitro BURST imaging. Panels (a)-(d) show an array of ultrasound images of a cross section of cylindrical wells containing ARG-expressing Nissle E. coli embedded in non-scattering agarose, within an agarose phantom. Each image contains a pair of wells, the left well containing cells with collapsed GVs and the right well containing cells with intact GVs. Rows correspond to cell concentrations, which range over seven orders of magnitude. Columns correspond to different image processing techniques, as indicated by the bottom labels. The top edge of each image corresponds to a depth of 16 mm, the bottom to a depth of 23 mm. The left edge of each image corresponds to a lateral coordinate of −7 mm, the right to +7 mm. Scalebars: 2 mm. Panels (e)-(h) show ultrasound images of the same conditions as panels (a)-(d), but with the cells embedded in tissue-mimicking material (TMM) inside the wells. Panels (i)-(l) show CTR vs log cell concentration for loBURST and hiBURST. Panel (i) shows loBURST on agar-embedded cells. Panel (j) shows hiBURST on agar-embedded cells. Panel (k) shows loBURST on TMM-embedded cells. Panel (l) shows hiBURST on TMM-embedded cells.

In line with previously reported results, ARG contrast in B-mode images was clearly detectable at $10^9$ cells/ml in non-scattering agarose and only marginally detectable at $10^8$ cells/ml (FIG. 6, panel (a)). Clutter is reduced in difference images relative to B-mode, but this technique did not improve upon the B-mode detection limit (FIG. 6, panel (b)). In the TMM conditions, ARG contrast was not detectable in either B-mode or difference images for any cell concentration (FIG. 6, panels (e)-(f)). The residual signal observed in TMM control wells in FIG. 6, panels (f)-(h) supports the conclusion that this condition was made more challenging by the presence of microscopic air bubbles inadvertently introduced during mixing of cell samples with molten TMM, which has a significantly higher viscosity than plain 1% agarose.

Both hiBURST and loBURST improved these detection limits to $10^4$ cells/ml in plain agarose (FIG. 6, panels (i)-(j)) and $10^6$ cells/ml in TMM (FIG. 6, panels (k)-(l)). Moreover, loBURST CTR appears to be linearly proportional to cell concentration in all conditions except $10^9$ cells/ml in plain agarose, demonstrating its potential for quantifying ARG-expressing cell concentration across at least five orders of magnitude.

At $10^9$ and $10^8$ cells/ml in plain agarose, hiBURST had suboptimal CTR relative to both the same concentrations with loBURST and even some lower concentrations with hiBURST (FIG. 6, panels (c)-(d), (i)-(j)). This counterintuitive result is mostly due to the generation of cavitation events in the control wells from collapsed GVs, which are known to act as weak cavitation nuclei [2]. There also appears to be amplitude-dependent acoustic shielding, in which acoustic energy is absorbed by cavitation events caused by the higher-pressure pulse in the top portion of the well, shielding the interior. hiBURST also did not significantly improve the detection limit relative to loBURST, mostly due to the presence of microbubbles in the wells that cause confounding transient signal at the higher pressures as well as amplitude-dependent attenuation of the transmitted pulse. Because such microbubbles are not present in biological tissue, hiBURST will likely still offer advantages in certain in vivo imaging contexts.

These results demonstrate the potential of BURST to image ARG-expressing cells co-localized with strong scatterers at $10^6$ cells/ml, which are relevant conditions for imaging rare gut microbial species.

Example 5: BURST Imaging of In Vivo Gut Microbe Distribution

To test the in vivo specificity and robustness of BURST under a protocol used in previous work on GV imaging in vivo, probiotic ARG-expressing E. coli Nissle cells in agarose gel were imaged within the colon of an anesthetized mouse at $10^7$ cells/ml, an order of magnitude lower than the previous in vitro detection limit (see FIG. 6, panel (a)). To demonstrate the maximum contrast to tissue ration (CTR) achievable with conventional imaging in this setting, an AM image of the gel-filled colon at the moment of collapse is shown in FIG. 5, panel (b). Template projection of this image together with the other frames in the time series resulted in a BURST image with 40 dB higher CTR (FIG. 7B, panel (c)). This result demonstrates the in vivo robustness of BURST and its orders-of-magnitude improvement in CTR relative to conventional imaging methods.

All in vivo experiments were performed on mice, under a protocol approved by the Institutional Animal Care and Use Committee of the California Institute of Technology. No randomization or blinding were necessary in this study. Mice were anesthetized with 1-2% isoflurane, maintained at 37° C. on a heating pad, depilated over the imaged region, and imaged using an L11-4 v transducer attached to a manipulator. For colon imaging, an L22-14 v transducer was used. For imaging of gavaged Salmonella typhimurium in the gastrointestinal tract, mice were placed in a supine position, with the ultrasound transducer positioned over the upper abdomen such that the transmit focus of 12 mm was close to the top of the abdominal wall. Two hours prior to imaging, mice were gavaged with 200 μl of buoyancy-enriched Salmonella typhimurium at a concentration of $10^9$ cells/ml.

Because BURST amplifies changes in pixels across frames, any tissue motion in the timeseries may confound the final image. To mitigate this during in vivo imaging, we implemented a custom BURST script that transmits and acquires three 32-aperture focused beams at a time, improving the frame rate by a factor of 3. The smaller aperture meant that hiBURST pressures could not be achieved, so all in vivo images were acquired using loBURST.

After each acquisition, the manipulator was used to translate the transducer 1 mm forward to the next image plane. An attempt was made to time each acquisition to coincide with the part of the mouse's breathing cycle with the least motion.

Prior to processing with template unmixing, a 2×2 median filter followed by a gaussian blur filter with a=1 was applied to each 2D image frame of each image plane of each mouse. Template unmixing was applied using 1 low-pressure frame (frame 5) and 2 high-pressure frames (frames 6-7). The images output from template unmixing were then concatenated into a 3D array to which a 1×1×2 3 D median filter was applied to remove isolated motion artifacts. The resulting 2D BURST images were then dB scaled and overlaid on the square-root-scaled B-mode image representing frame 1 in the corresponding timeseries. The BURST images were overlaid in locations where the BURST image pixel values exceeded a threshold of 105 dB, which was chosen as the minimum threshold at which no residual motion artifacts were visible in the lower abdomen, where no BURST signal was expected. BURST images were pseudo-colored with the hot colormap and B-mode images with the gray colormap. Quantification was performed by manually drawing ROIs conservatively covering the upper half of the abdominal cavity in each image plane for each mouse.

Figure 7A:
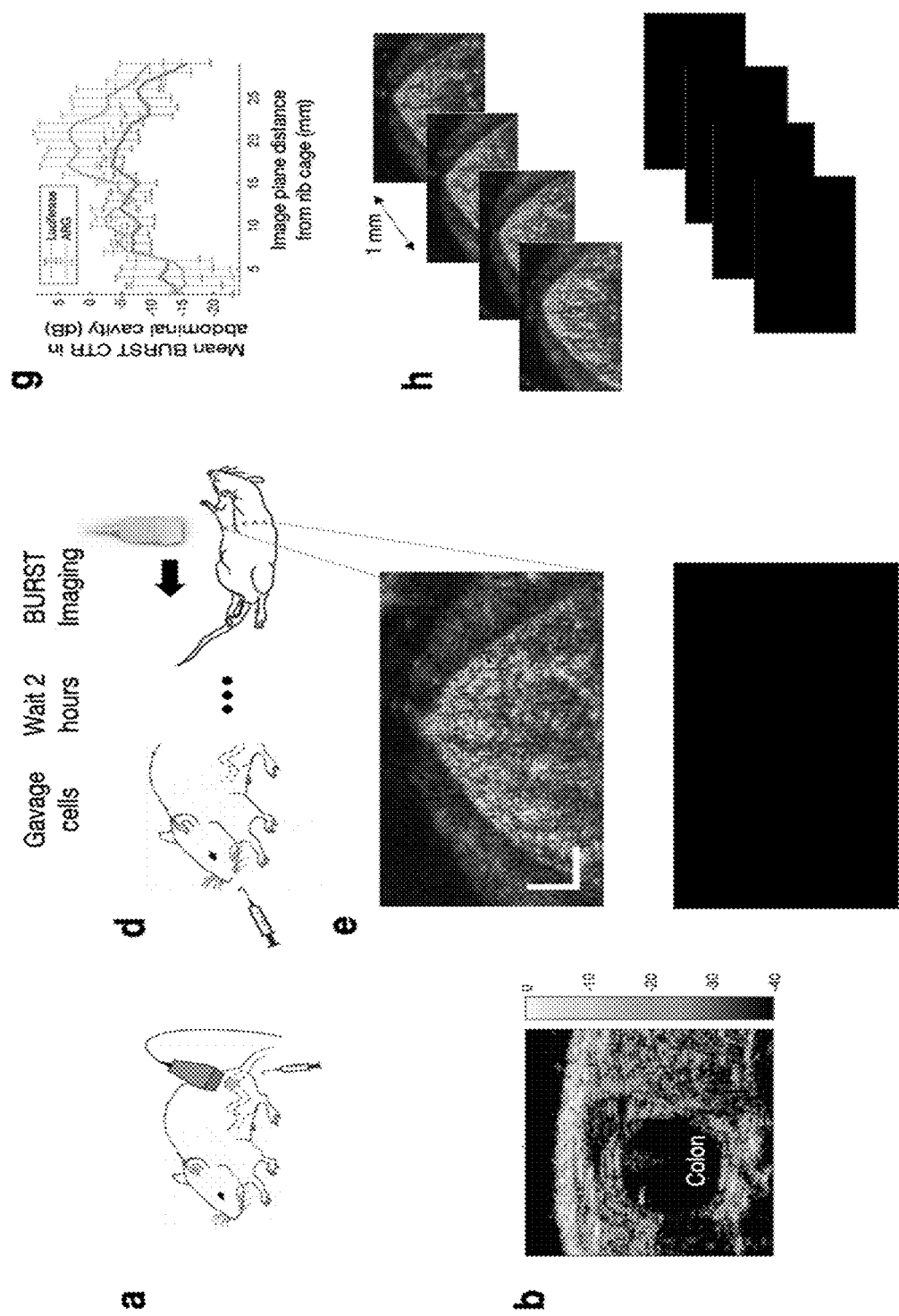
FIGS. 7A and 7B show an example of in vivo BURST imaging. Panel (a) is an illustration of a colon injection experiment. Panel (b) shows a collapse frame AM image of the mouse colon filled with probiotic ARG-expressing E. coli Nissle. Panel (c) shows a BURST image with template projection. Panel (d) is an illustration of an oral gavage experiment. Panels (e)-(f) show B-mode and BURST images of a coronal cross section of the mouse abdominal cavity. Panel (e) shows control gavage of luciferase-expressing Salmonella, with the BURST image displayed below the corresponding B-mode image. Panel (f) shows gavage of ARG-expressing Salmonella, with the BURST image displayed below the corresponding B-mode image. Panel (g) shows a plot of mean BURST CTR in the abdominal cavity vs distance of the image plane in the caudal direction from the rib cage for mice gavaged with ARG-expressing Salmonella and for mice gavaged with luciferase-expressing Salmonella. Panels (h)-(i) show four image planes following those in panels (e) and (f). Panel (h) shows spatial sequence frames for a control mouse, with the BURST images displayed below the corresponding B-mode images. Panel (i) shows spatial sequence frames for a mouse with ARG-expressing Salmonella, with the BURST images displayed below the corresponding B-mode images.
Figure 7B:
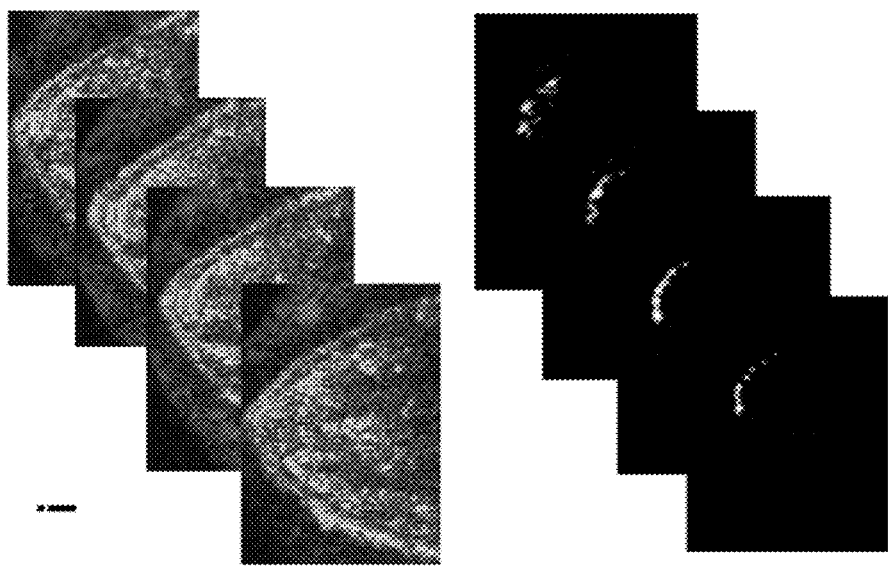
Figure 7B:
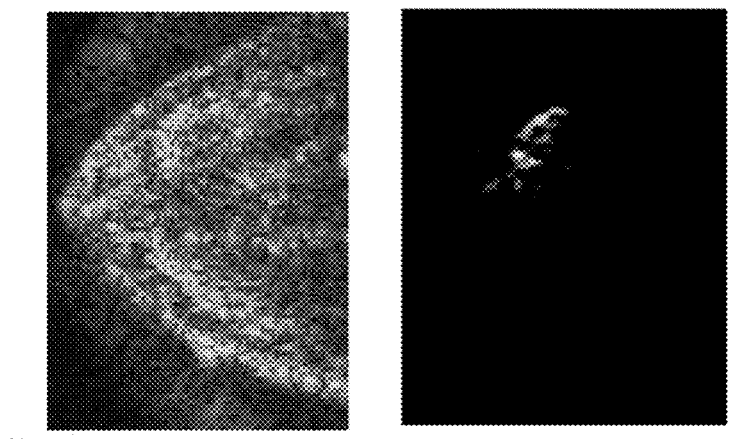
Figure 7B:
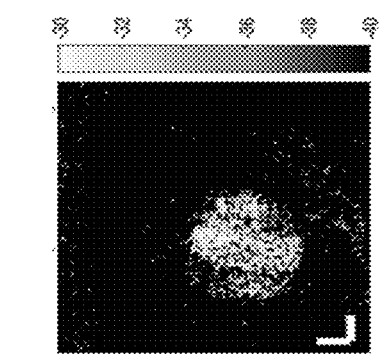

FIGS. 7A and 7B show an example of in vivo BURST imaging. Panel (a) is an illustration of a colon injection experiment. Panel (b) shows a collapse frame AM image of the mouse colon filled with probiotic ARG-expressing *E. coli* Nissle at 10^7 cells/ml. Panel (c) shows a BURST image with template projection, generated from an image time series. Scalebars=1 mm. Panel (d) is an illustration of an oral gavage experiment. Panels (e)-(f) show B-mode images (PPP=0.93 MPa) of a coronal cross section of the mouse abdominal cavity 17 mm caudal to the rib cage, acquired 2 hours post-gavage. A heatmap of the corresponding BURST image is overlaid in locations where the BURST CNR exceeds 105 dB. Panel (e) shows control gavage of luciferase-expressing *Salmonella*. Panel (f) shows gavage of ARG-expressing *Salmonella*. Panel (g) shows a plot of mean BURST CTR in the abdominal cavity vs distance of the image plane in the caudal direction from the rib cage for mice gavaged with ARG-expressing *Salmonella* and luciferase-expressing *Salmonella*. Error bars: SEM, n=4. Panels (h)-(i) show four image planes following those in panels (e) and (f) (18 mm to 21 mm) from the same representative mice with the same display settings. Panel (h) shows spatial sequence frames (1 mm spacing) for a control mouse (luciferase-expressing *Salmonella*), displaying no signal. Panel (i) shows spatial sequence frames (1 mm spacing) for a mouse with ARG-expressing *Salmonella*, the frames displaying a BURST signal.

BURST was used to noninvasively image the spatial distribution of a pathogenic bacteria propagating naturally through the GI tract of a mammalian host, a procedure that could not be performed using previous techniques. An attenuated strain of *Salmonella* was used as a model pathogen for the mouse GI tract. Two groups of four mice were gavaged with 10^9 cells in 200 μl 2 hours prior to anesthetization and imaging. The experimental group was gavaged with buoyancy-enriched ARG-expressing *Salmonella* and the control group with luciferase-expressing *Salmonella*. No fasting, bicarbonate administration, or other pretreatments were used. Because the 3D spatial distribution of cells was not known a priori, loBURST data was acquired for the entire abdominal cavity of each mouse in 20-30 transverse image planes with 1 mm spacing (see FIG. 7A, panel (d)). Display images were generated by overlaying grayscale low-pressure B-mode images with heatmaps of all BURST image pixels exceeding a CNR threshold of 105 dB (FIGS. 7A and 7B, panels (e)-(f)).

In all but one experimental mouse, contiguous patches of supra-threshold BURST signal, approximately 2 mm×1 mm, were observed spanning several contiguous frames in the middle of the abdomen 1 mm below the abdominal wall (FIG. 5, panel (i)), the expected location of the small intestine. No supra-threshold BURST signal was observed in the abdominal cavities of control mice (FIG. 5, panel (h)). Aggregating mean BURST CTR in the upper half of the abdominal cavity in each image plane for all mice, there is a statistically significant enhancement of BURST CTR in the experimental group for all image planes between 16 mm and 22 mm, inclusive. These results demonstrate the capability of BURST to noninvasively image gene expression of cells co-localized with strong scatterers in a live animal host with no prior knowledge of their spatial distribution.

Example 6: Single Cell Imaging

An advantage of BURST is the ability to resolve imaging to detect contrast at the individual cell level. An example of this is imaging in degassed liquid buffer a linear range of concentrations of ARG-expressing Nissle, on the order of 10^2-10^3 cells/ml, as well as pre-collapsed controls. Based on hydrophone measurements of the pressure profile of the ½ cycle BURST pulse sequence and the observed loBURST pressure threshold, it is estimated that all ARG-expressing cells in a 1 mm×19.5 mm×1 mm field of view (FOV) experience sufficient pressure to generate collapse signal by either the loBURST or hiBURST mechanism. This value can be used to estimate the expected number of sources in each BURST image for each cell concentration. Both bright and dim sources can be counted as a single source.

The following protocol was used to obtain the results illustrated in FIG. 5. Plasmids encoding ARGs were transformed into electro-competent *E. coli* Nissle 1917 (Ardeypharm GmbH) and grown in 5 ml starter cultures in LB medium with 50 μg ml-1 kanamycin, 1% glucose for 16 h at 37° C. Large-scale cultures in LB medium containing 50 μg ml-1 kanamycin and 0.2% glucose were inoculated at a ratio of 1:100 with the starter culture. Cells were grown at 37° C. to OD600 nm=0.3, then induced with 3 μM IPTG for 22 h at 30° C.

For validation of single-cell detection, an L11-4 v transducer (Verasonics) was mounted on a computer-controlled 3D translatable stage (Velmex) above a 4 L bucket containing 3.8 L water that had been circulated through a water conditioner for 1 hour to remove air bubbles. 200 ml of 20×PBS was then gently added to the water, with the mouth of the PBS-containing bottle at the level of the surface of the water to avoid creating bubbles. A piece of acoustic absorber material was placed at the bottom of the bucket to reduce reflections. A MATLAB script was written to control the Verasonics system in tandem with the Velmex stage, which was programmed to move 1 cm after each of 10 replicate BURST pulse sequences. After each set of BURST acquisitions (starting with plain PBS), 30 μl of 10^6 cells/ml intact Nissle cells were added to the bucket, which was gently stirred with a glass rod. A separate bucket with freshly conditioned water and buffer was used for the collapsed control cells. A MATLAB script was used to display a 1 mm×19.5 mm segment, centered at the point of highest average intensity, of all BURST images (all replicates, all concentrations, and collapsed vs. intact cells) in a random order, blinding the experimenter to the condition when performing source counting.

Comments for replicating results: One should use the following guidelines for accurate counting:
- If a bright signal that spans 2 or 3 columns is observed, with the intensity decreasing from left to right, then that counts as one source.
- However, if the intensity increases from left to right, usually that should count as two, with the logic being that it is more likely two separate sources or one source that coalesced with another one. Also, if the source spans more than three columns, that is counted as two as well.
- Err on the side of false positives when looking at very weak sources that only slightly stand out from the noise. Sources from bubbles tend to be very bright, and weak sources also don't have the problem of spanning more than one column, so they are what can most confidently be classified as single cells.

If a bright source with chunks of black pixels in it is observed, that corresponds to a persistent bubble that moved slightly between collapse frames and was partially cancelled, and so should not be counted as a source.

If the source is partially outside of the frame, it still counts as long as its brightest point seems to be inside the frame.

Figure 8:
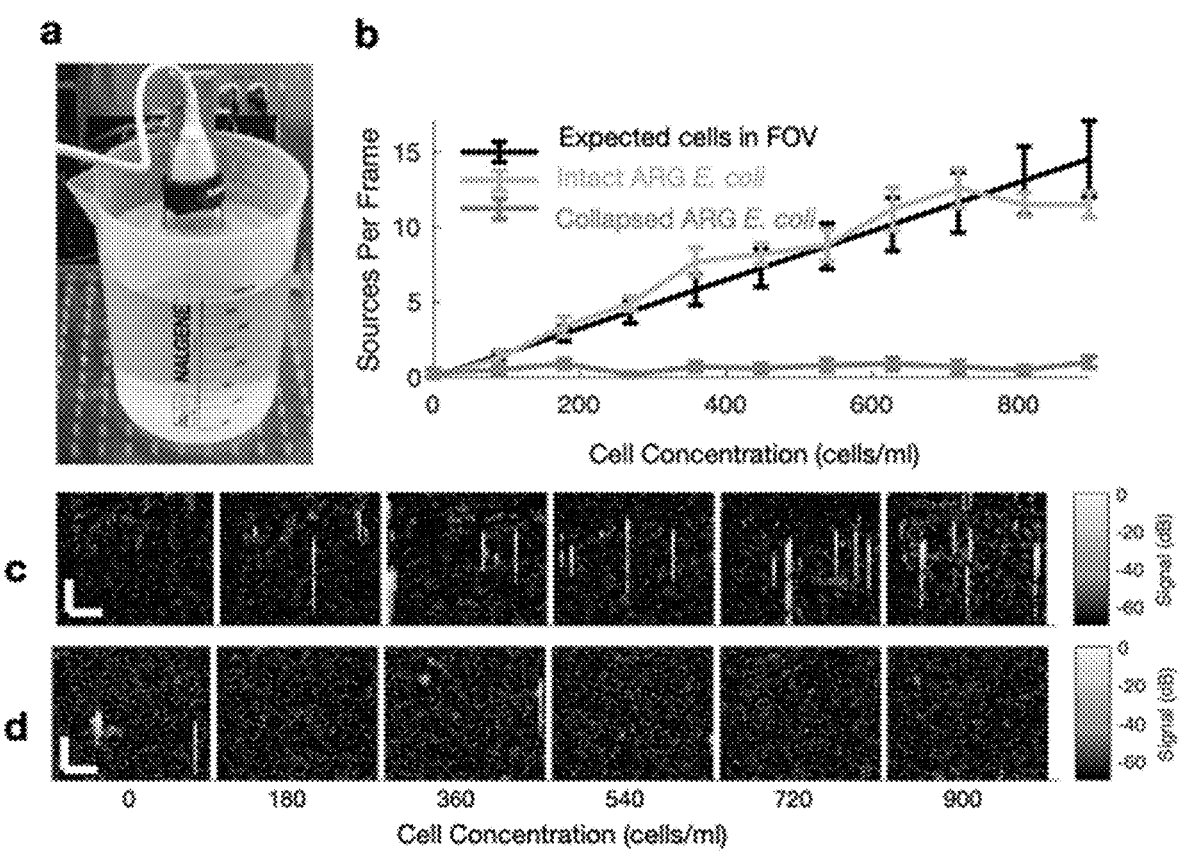
FIG. 8 shows an example of single cell detection compared to a control. Panel (a) shows a picture of the example experimental setup. Panel (b) shows a plot of the average number of single sources counted in images acquired with hiBURST vs cell concentration. Panel (c) shows representative images acquired with hiBURST showing single sources in liquid buffer suspension. Panel (d) shows representative images of liquid buffer suspension with collapsed ARG-expressing E. coli Nissle.

FIG. 8 shows an example of single cell detection compared to a control. Panel (a) shows a picture of the example experimental setup. FIG. 8 Panel (b) shows a plot of the average number of single sources counted in images acquired with hiBURST vs cell concentration for both intact and collapsed ARG-expressing *E. coli* Nissle for the example. The expected number of cells in the transducer's field of view, based on cell counting by fluorescence microscopy and hydrophone measurements of the transducer's peak pressure profile, is also plotted for comparison. Panel (c) shows, for the example, representative images acquired with hiBURST showing single sources in liquid buffer suspension of intact ARG-expressing *E. coli* Nissle, and the number of sources increasing with cell concentration. Panel (d) shows, for the example, representative images of liquid buffer suspension with collapsed ARG-expressing *E. coli* Nissle.

In images of buffer containing cells with intact GVs, the number of sources was found to increase linearly with cell concentration (FIG. 8, panel (c)). In images of buffer containing cells with collapsed GVs, the average number of sources had no significant dependence on cell concentration and the global average for the collapsed condition was 0.65±0.95 (FIG. 8, panel (d)). This establishes intact GVs as the causal agent for the observed sources, demonstrating that few or no observed sources are generated by causes other than the collapse of intact GVs expressed in single cells.

Most significantly, the number of sources observed in images of cells with intact GVs closely tracks the expected number (FIG. 8, panel (b)), with SEM error bars overlapping at all concentrations. The number of sources begins to level off at concentrations above 720 cells/ml, but this is an expected consequence of increased probability of overlapping sources at higher concentrations, demonstrating that most or all single cells expressing intact GVs generate observable sources when exposed to BURST, and each ARG-expressing cell generates one and only one source.

These results demonstrate the ability of BURST to reliably image gene expression in single cells with high sensitivity and specificity.

Example 7: In Vitro Ultrasound Imaging in Mammalian Cell

To create phantoms for in vitro ultrasound imaging, wells were casted with molten 1% w/v agarose in PBS using a custom 3D-printed template. ARG-expressing and mCherry-only control cells were allowed to express gas vesicles using the specified inducer concentrations and expression duration. They were then trypsinized and counted via disposable hemocytometers in bright field microscopy. Next, cells were mixed at a 1:1 ratio with 50° C. agarose and loaded into the wells before solidification. The volume of each well is 60 µl and contain 6×10^6 cells. The phantoms were submerged in PBS, and ultrasound images were acquired using a Verasonics Vantage programmable ultrasound scanning system and L22-14 v 128-element linear array transducer with a 0.10-mm pitch, an 8-mm elevation focus, a 1.5-mm elevation aperture, and a center frequency of 18.5 MHz with 67%-6 dB bandwidth (Verasonics). Each frame was formed from 89 focused beam ray lines, each with a 40-element aperture and 8 mm focus. A 3-half-cycle transmit waveform at 17.9 MHz was applied to each active array element. For each ray line, the AM code is implemented using one transmit with all elements in the aperture active followed by 2 transmits in which the odd- and then even-numbered elements are silenced. Each image contains a circular cross-section of a well with a 4 mm diameter and center positioned at a depth of 8 mm. In AM mode, signal was acquired at 0.9 MPa (2V) for 10 frames and the acoustic pressure was increased to 4.3 MPa (12V) to collect 46 frames. There after the acoustic pressure was increased to 8.3 MPa (25V) to ensure complete collapse of gas vesicles. Gas vesicle-specific signal was determined by subtracting the area under the curve of the first sequence by the post-collapse imaging sequence.

Figure 9:
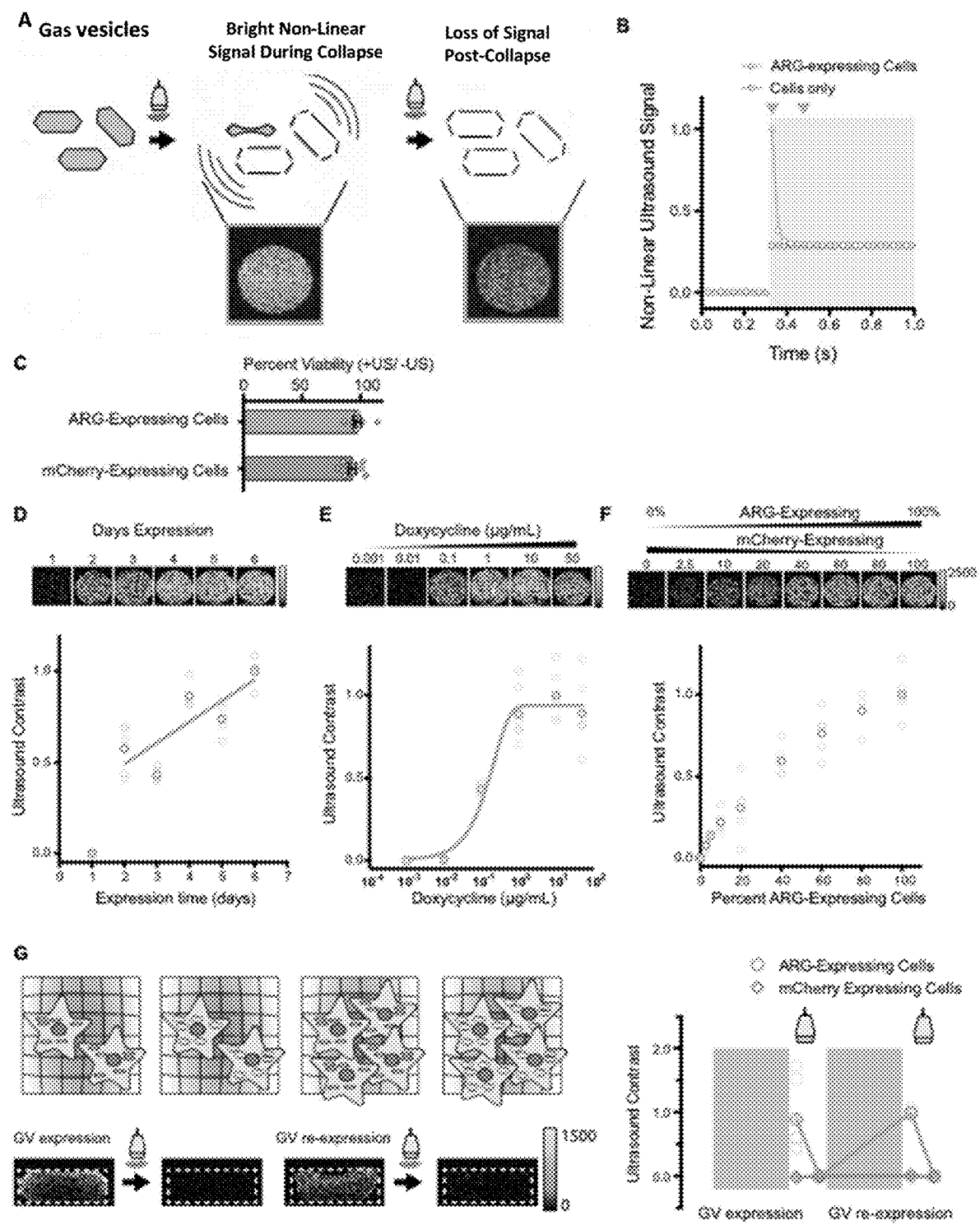
FIG. 9 shows an example of in vitro ultrasound imaging of gene expression. Panel (A) illustrates an ultrasound paradigm used to extract gas vesicle-specific ultrasound image from ARG-expressing cells. Panel (B) shows representative non-linear echoes received during this ultrasound imaging paradigm. Panel (C) shows cellular viability after being insonated under 8.3 MPa acoustic pressures. Panel (D) shows ultrasound imaging of ARG-expressing cells as a function of expression duration. Panel (E) shows example ultrasound imaging of ARG-expressing cells as a function of doxycycline induction concentrations. Panel (F) shows example ultrasound imaging of ARG-expressing cells mixed with mCherry-only control cells in varying proportions Panel (G) illustrates that ARG-expressing cells can re-express gas vesicles after acoustic collapse.

FIG. 9 shows an example of in vitro ultrasound imaging of gene expression. Panel (A) illustrates an ultrasound paradigm used to extract gas vesicle-specific ultrasound image from ARG-expressing cells. Panel (B) shows representative non-linear echoes received during this ultrasound imaging paradigm. Insonated acoustic pressures in the white region are 0.9 MPa and within the grey box are 4.3 MPa. Panel (C) shows cellular viability after being insonated under 8.3 MPa acoustic pressures. Panel (D) shows ultrasound imaging of ARG-expressing cells as a function of expression duration. Cells were induced with 1 µg/mL of doxycycline and 5 mM sodium butyrate. Panel (E) shows example ultrasound imaging of ARG-expressing cells as a function of doxycycline induction concentrations. Cells were allowed to express gas vesicles for 72 hours in the presence of 5 mM sodium butyrate. Panel (F) shows example ultrasound imaging of ARG-expressing cells mixed with mCherry-only control cells in varying proportions. Cells were induced with 1 µg/mL of doxycycline and 5 mM sodium butyrate for 72 hours prior to imaging. Panels (D)-(F) show representative ultrasound images of cells embedded in agarose phantoms. To generate each image, a set of nonlinear ultrasound images are acquired (55 frames totaling 1.65 seconds), the cells are insonated with 8.3 MPa ultrasound and a set of nonlinear ultrasound images are re-acquired for the background. The total ultrasound signal from each series is calculated and the square-root of the difference is displayed (top). Region of interest quantification for each replicate is shown as a shaded circle with the mean shown as a dark circle (bottom). Panel (G) illustrates that ARG-expressing cells can re-express gas vesicles after acoustic collapse. Representative ultrasound image of ARG-expressing cells mixed in Matrigel that were induced with 1 µg/mL of doxycycline and 5 mM sodium butyrate for 72 hours (before and after 8.3 MPa acoustic insonation). The ARG-expressing cells laden in Matrigel are induced for an additional 72 hours and imaged using ultrasound (bottom left). Images are generated from the square-root of the different between the nonlinear ultrasound signal at the moment of gas vesicle collapse (frame 11) from the nonlinear ultrasound signal at frame 15. Region of interest quantification for each replicate is shown as a shaded circle with the mean shown as a dark circle.

Example 8: longBURST and shortBURST Characterization

Figure 10:
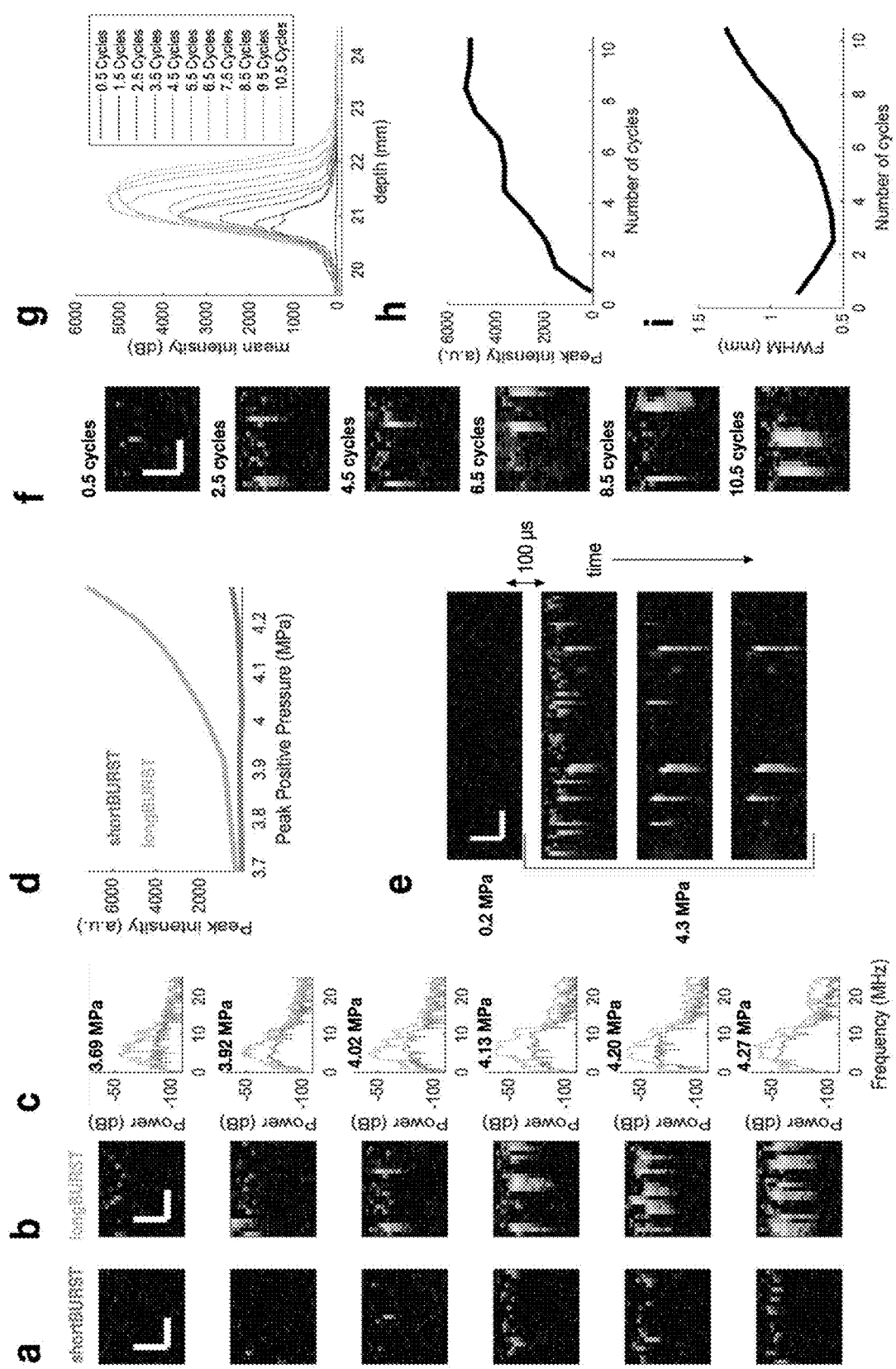
FIG. 10 shows examples of shortBURST and longBURST signal generation and illustrates how the signal properties change with number of transmit waveform cycles. Panel (a) shows representative echoes received following the application of shortBURST at varying pressure levels, indicated by the text in the corresponding rows of panel (c). Panel (b) shows representative echoes received following the application of longBURST at varying pressure levels, indicated by the text in the corresponding rows of panel (c). Panel (c) shows the power spectra of shortBURST (dark gray) and longBURST (light gray) at each pressure level, obtained by averaging the time-domain signals over the 64 ray lines in each of the 10 replicates. Panel (d) shows the peak intensity observed in the shortBURST and longBURST images as a function of peak positive pressure (PPP). Panel (e) shows the persistence and gradual disappearance of several bright sources generated by longBURST. Panel (f) shows representative images of obtained by applying hiBURST with varying numbers of waveform cycles. Panel (g) shows the mean intensity of the hiBURST images (average over 10 replicates) as a function of depth for different numbers of waveform cycles. Panel (h) shows the peak mean intensity as a function of number of waveform cycles. Panel (i) shows the full-width at half maximum (FWHM) of the mean intensity vs. depth profiles as a function of number of waveform cycles.

The results illustrated in FIG. 10 were obtained by the same protocol used in Example 3, except that 10 replicates were used instead of 5.

FIG. 10 shows examples of shortBURST and longBURST signal generation and illustrates how the signal properties change with varying pressure levels and number of transmit waveform cycles. Panel (a) shows representative echoes received following the application of shortBURST at varying pressure levels, indicated by the text in the corresponding rows of panel (c). The number of sources increases with the PPP, and all of the sources are small and dim. Panel (b) shows representative echoes received following the application of longBURST at varying pressure levels, indicated by the text in the corresponding rows of panel (c). The number of sources increases with the PPP and start out with only dim sources being observed at lower PPP. However, unlike with shortBURST, elongated bright sources begin to appear as the PPP is increased. Panel (c) shows the power spectra of shortBURST (dark gray, lower curve) and longBURST (light gray, upper curve) at each pressure level, obtained by averaging the time-domain signals over the 64 ray lines in each of the 10 replicates. The spectral resolution is not sufficient to identify harmonic peaks, but there appears to be a slight broadband enhancement observed in higher frequencies in the longBURST spectra at higher pressure levels. Panel (d) shows the peak intensity observed in the shortBURST and longBURST images as a function of peak positive pressure (PPP). While the shortBURST peak intensity does not increase with pressure, the peak intensity for longBURST, which is dominated by the bright sources, increases significantly with pressure. This is further evidence that the dim sources are produced by the GV collapse event, whose intensity is independent of PPP after the PPP exceeds the collapse threshold. Panel (e) shows the persistence and gradual disappearance of several bright sources generated by longBURST with an ultrafast acquisition script. Dim sources are evident in the first high-pressure frame but disappear completely after 100 μs. 10 bright sources are observed in the first high-pressure frame, 5 are observed after 100 μs, and 3 are observed after 200 μs. This provides evidence that the bright sources are produced by nanobubbles liberated from collapsed GVs. Panel (f) shows representative images obtained by applying hiBURST with varying numbers of waveform cycles. Panel (g) shows the mean intensity of the hiBURST images (average over 10 replicates) as a function of depth for different numbers of waveform cycles (0.5 cycles being the lowest curve, 8.5-10.5 cycles being the highest curves). Panel (h) shows the peak mean intensity as a function of number of waveform cycles, demonstrating that an increase in the number of cycles increases signal intensity, which would be expected if the signal were partially produced by inertial cavitation. Panel (i) shows the full-width at half maximum (FWHM) of the mean intensity vs. depth profiles as a function of number of waveform cycles, providing further evidence for the cavitating bubble mechanism of signal generation.

Example 9: Hypothetical

For a hypothetical example, suppose that you have a new bacteria strain, we will call A. Hypothetica, and you suspect that it can produce GVs. In an initial step, the proteins from A. Hypothetica are sequenced and it is determined that they have a sequence in a gene cluster that is a close match to gvpF. To verify, the GVs are expressed and isolated, via lysing, as a contrast agent. As a control, a portion of these isolated GVs are collapsed using a hydrostatic pressure well above the hydrostatic collapse threshold of all known GVs—in this example, 12 MPa. The contrast agent is injected into a target site of a known signal attenuation for ultrasound at a selected frequency—in this example, approximately 3 dB/cm at 3.5 MHz. The target site is imaged at a starting PPP of 0.5 MPa, calculated using the known attenuation and depth of the target site. While frames are captured, the PPP is suddenly increased to a hiBURST level (e.g. 4.3 MPa) for a longBURST duration (e.g. 8 half-cycles). The frames from before, during, and after the step increase of PPP undergo template unmixing to discern a BURST signal against the background signals. The injection and imaging procedure is repeated with the collapsed control sample. If the signal observed in the target site containing contrast agent is significantly greater than the signal observed in the target site containing the control sample then GVs were present. Additional tests at different increased PPP levels can be performed on new batches of GVs to determine an acoustic collapse profile of the GVs, with the point where approximately 50% of GVs collapsing (profile midpoint) being selected as the acoustic collapse threshold of the GVs.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified methods and arrangements to additional gas vesicles, related components, genetic or chemical variants, as well as in compositions, methods and systems herein described, in according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P2443-US-2020-04-10-Sequence-Listing-ST25.txt, created on Apr. 10, 2020, is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible sub-combinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Walsby, A. E., *Gas vesicles*. Microbiol. Rev., 1994. 58(1): p. 94-144.
2. Walsby, A. E., *Gas-vacuolate bacteria (apart from cyanobacteria)*, in *The Prokaryotes*. 1981, Springer. p. 441-447.
3. Walsby, A. E., *Cyanobacteria: planktonic gas-vacuolate forms*. The Prokaryotes, a Handbook on Habitats, Isolation, and Identification of Bacteria, 2013. 1: p. 224-235.
4. Woese, C. R., *Bacterial evolution*. Microbiological reviews, 1987. 51(2): p. 221.
5. Walsby, A. E., *Gas vesicles*. Microbiol Rev, 1994. 58(1): p. 94-144.
6. Pfeifer, F., *Distribution, formation and regulation of gas vesicles*. Nat. Rev. Microbiol., 2012. 10(10): p. 705-15.
7. Yi, G., S.-H. Sze, and M. R. Thon, *Identifying clusters of functionally related genes in genomes*. Bioinformatics, 2007. 23(9): p. 1053-1060.
8. Hayes, P. and R. Powell, *The gvpA/C cluster of Anabaena flos-aquae has multiple copies of a gene encoding GvpA*. Archives of microbiology, 1995. 164(1): p. 50-57.
9. Kinsman, R. and P. Hayes, *Genes encoding proteins homologous to halobacterial Gvps N, J, K, F & L are located downstream of gvpC in the cyanobacterium Anabaena flos-aquae*. DNA Sequence, 1997. 7(2): p. 97-106.
10. Pfeifer, F., *Distribution, formation and regulation of gas vesicles*. Nat Rev Microbiol, 2012. 10(10): p. 705-15.
11. Li, N. and M. C. Cannon, *Gas vesicle genes identified in Bacillus megaterium and functional expression in Escherichia coli*. J Bacteriol, 1998. 180(9): p. 2450-8.

The invention claimed is:

1. A method of ultrasound imaging to be used on a target site contrasted with gas vesicles (GVs) having an acoustic collapse pressure threshold, the method comprising:
   applying ultrasound to the target site at a peak positive pressure less than the acoustic collapse pressure threshold;
   increasing peak positive pressure (PPP) to above the selective acoustic collapse pressure value threshold as a step function;
   imaging the target site in successive frames during the increasing;
   extracting a time-series vector for each of at least one pixel of the successive frames; and
   detecting from the time-series vectors a transient signal from, due to the increasing PPP, fluid displacement from collapsing of the GVs or cavitating bubbles released from the GVs, the detecting being in a time domain of the successive frames, the transient signal providing an increase in contrast signal in the ultrasound imaging.

2. The method of claim 1, further comprising performing a signal separation algorithm separating a signal due to the GVs from other signals on the time-series vectors using at least one template vector estimated by averaging pixel time series from regions of interest containing known samples.

3. The method of claim 2, wherein the signal separation algorithm includes template projection.

4. The method of claim 2, wherein the signal separation algorithm includes template unmixing.

5. The method of claim 4, wherein the at least one template vector is based on data from linear scatterers, noise, gas vesicles, or a combination thereof.

6. The method of claim 1, wherein the successive frames comprise a frame prior to GVs collapse, a frame during GVs collapse, and a frame after GVs collapse.

7. The method of claim 1, further comprising delivering the GVs to the target site.

8. The method of claim 7, wherein the delivering the GVs to the target site comprises using an acoustic reporter gene to express the GVs.

9. The method of claim 8, wherein the target site comprises a mammalian cell with the acoustic reporter gene.

10. The method of claim 1, wherein the increasing includes increasing the PPP to a hiBURST regime.

11. The method of claim 10, wherein the PPP in hiBURST regime is 4.3 MPa or higher.

12. The method of claim 1, wherein the increasing includes increasing the PPP to a loBURST regime.

13. The method of claim 12, wherein the PPP in loBURST regime is no higher than 3.7 MPa.

14. A system for imaging a target site contrasted with gas vesicles (GVs) having an acoustic collapse pressure threshold, the system comprising:
an ultrasound source capable of producing peak positive pressure both below and above the acoustic collapse pressure threshold;
an ultrasound imager configured to capture successive frames from the target site; and
a processor configured to:
calculate a time-series vector for each of at least one pixel of the successive frames and
detect from the time-series vectors a transient signal from, due to the increasing PPP, fluid displacement from collapsing of the GVs or cavitating bubbles released from the GVs, the detecting being in a time domain of the successive frames, and the transient signal providing an increase in contrast signal in the imaging.

15. The system of claim 14, wherein the processor is further configured to perform a signal separation algorithm separating a signal due to the GVs from other signals on the time-series vectors using at least one template vector estimated by averaging pixel time series from regions of interest containing known samples.

16. The system of claim 15, wherein the signal separation algorithm includes template projection.

17. The system of claim 15, wherein the signal separation algorithm includes template unmixing.

18. The system of claim 17, wherein the at least one template vector is based on data from linear scatterers, noise, gas vesicles, or a combination thereof.

19. The system of claim 14, wherein the successive frames comprise a frame prior to GVs collapse, a frame during GVs collapse, and a frame after GVs collapse.

20. The system of claim 14, further comprising a means for introducing the gas vesicles at the target site.

21. The system of claim 20, wherein the delivering the GVs to the target site comprises using an acoustic reporter gene to express the GVs.

22. The system of claim 21, wherein the acoustic reporter gene is in a mammalian cell.

* * * * *